US011851690B2

(12) United States Patent
Gori et al.

(10) Patent No.: US 11,851,690 B2
(45) Date of Patent: Dec. 26, 2023

(54) SYSTEMS AND METHODS FOR THE TREATMENT OF HEMOGLOBINOPATHIES

(71) Applicant: EDITAS MEDICINE, INC., Cambridge, MA (US)

(72) Inventors: Jennifer Leah Gori, Jamaica Plain, MA (US); Luis A. Barrera, Somerville, MA (US); Edouard Aupepin De Lamothe-Dreuzy, Boston, MA (US); Jack Heath, Boston, MA (US)

(73) Assignee: EDITAS MEDICINE, INC., Cambridge, MA (US)

( * ) Notice: Subject to any disclaimer, the term of this patent is extended or adjusted under 35 U.S.C. 154(b) by 748 days.

(21) Appl. No.: 16/569,336

(22) Filed: Sep. 12, 2019

(65) Prior Publication Data

US 2020/0157515 A1 May 21, 2020

Related U.S. Application Data

(63) Continuation of application No. PCT/US2018/022516, filed on Mar. 14, 2018.

(60) Provisional application No. 62/471,342, filed on Mar. 14, 2017.

(51) Int. Cl.

| | |
|---|---|
| ***C07H 21/02*** | (2006.01) |
| ***C12N 9/22*** | (2006.01) |
| ***C12N 15/11*** | (2006.01) |
| ***A61K 31/7105*** | (2006.01) |
| ***A61K 38/46*** | (2006.01) |

(52) U.S. Cl.

CPC ............ *C12N 9/22* (2013.01); *A61K 31/7105* (2013.01); *A61K 38/465* (2013.01); *C12N 15/111* (2013.01); *C12N 2310/20* (2017.05); *C12N 2320/30* (2013.01)

(58) Field of Classification Search

CPC .............................. C12N 9/22; C12N 2310/20

See application file for complete search history.

(56) References Cited

U.S. PATENT DOCUMENTS

| | | | |
|---|---|---|---|
| 6,413,540 | B1 | 7/2002 | Yaacobi |
| 6,586,240 | B1 | 7/2003 | Singer et al. |
| 8,697,359 | B1 | 4/2014 | Zhang |
| 8,771,945 | B1 | 7/2014 | Zhang |
| 8,795,965 | B2 | 8/2014 | Zhang |
| 8,865,406 | B2 | 10/2014 | Zhang et al. |
| 8,871,445 | B2 | 10/2014 | Cong et al. |
| 8,889,356 | B2 | 11/2014 | Zhang |
| 8,889,394 | B2 | 11/2014 | Chalasani et al. |
| 8,889,418 | B2 | 11/2014 | Zhang et al. |
| 8,895,308 | B1 | 11/2014 | Zhang et al. |
| 8,906,616 | B2 | 12/2014 | Zhang et al. |
| 8,932,814 | B2 | 1/2015 | Cong et al. |
| 8,945,839 | B2 | 2/2015 | Zhang |
| 8,993,233 | B2 | 3/2015 | Zhang et al. |
| 8,999,641 | B2 | 4/2015 | Zhang et al. |
| 9,322,037 | B2 | 4/2016 | Liu et al. |
| 9,499,847 | B2 | 11/2016 | Porter et al. |
| 2003/0186238 | A1 | 10/2003 | Allawi et al. |
| 2007/0020627 | A1 | 1/2007 | Barbas |
| 2010/0055793 | A1 | 3/2010 | Chandrasegaran et al. |
| 2010/0055798 | A1 | 3/2010 | Battersby |
| 2010/0076057 | A1 | 3/2010 | Sontheimer et al. |
| 2011/0059502 | A1 | 3/2011 | Chalasani |
| 2011/0189776 | A1 | 8/2011 | Terns et al. |
| 2011/0223638 | A1 | 9/2011 | Wiedenheft et al. |
| 2011/0236894 | A1 | 9/2011 | Rao et al. |
| 2011/0301073 | A1 | 12/2011 | Gregory et al. |
| 2012/0270273 | A1 | 10/2012 | Zhang et al. |
| 2013/0130248 | A1 | 5/2013 | Haurwitz et al. |
| 2013/0253040 | A1 | 9/2013 | Miller et al. |
| 2014/0068797 | A1 | 3/2014 | Doudna et al. |
| 2014/0179770 | A1 | 6/2014 | Zhang et al. |
| 2014/0242699 | A1 | 8/2014 | Zhang |
| 2014/0309177 | A1 | 10/2014 | Perez-Pinera et al. |
| 2014/0315985 | A1 | 10/2014 | May et al. |
| 2014/0335620 | A1 | 11/2014 | Zhang et al. |
| 2014/0342456 | A1 | 11/2014 | Mali et al. |
| 2014/0342457 | A1 | 11/2014 | Mali et al. |
| 2014/0342458 | A1 | 11/2014 | Mali et al. |
| 2014/0356958 | A1 | 12/2014 | Mali et al. |
| 2015/0056705 | A1 | 2/2015 | Conway et al. |
| 2015/0132269 | A1 | 5/2015 | Orkin et al. |
| 2015/0232833 | A1 | 8/2015 | Mali et al. |
| 2015/0259704 | A1 | 9/2015 | Church et al. |
| 2016/0153005 | A1 | 6/2016 | Zhang et al. |

(Continued)

FOREIGN PATENT DOCUMENTS

| | | | |
|---|---|---|---|
| WO | 2002/089767 | A1 | 11/2002 |
| WO | 2003/072788 | A1 | 9/2003 |

(Continued)

OTHER PUBLICATIONS

Traxler et al. (Nature Medicine, 22, 9, 2016, 987-991).*

Kim, D., et al., "Genome-wide analysis reveals specificities of Cpf1 endonucleases in human cells," Nat. Biotechnol. 34(8):863-868 (2016).

Kleinstiver, B.P., et al., "Genome-Wide Specificities of CRISPR-Cas Cpf1 Nucleases in Human Cells," Nat. Biotechnol. 34(8):869-874 (2016).

Sakuma, T., et al., "Multiplex Genome Engineering in Human Cells Using All-in-One CRISPR/Cas9 Vector System," Sci. Rep. 4(5400):1-6 (2014).

(Continued)

*Primary Examiner* — Amy H Bowman

(74) *Attorney, Agent, or Firm* — Perkins Coie LLP; Courtney Prochnow

(57) ABSTRACT

Genome editing systems, guide RNAs, and CRISPR-mediated methods are provided for altering portions of the HBG1 and HBG2 loci, portions of the erythroid specific enhancer of the BCL11A gene, or a combination thereof, in cells and increasing expression of fetal hemoglobin.

12 Claims, 27 Drawing Sheets

Specification includes a Sequence Listing.

(56) References Cited

U.S. PATENT DOCUMENTS

| | | | |
|---|---|---|---|
| 2016/0281111 | A1 | 9/2016 | Cotta-Ramusino et al. |
| 2016/0289675 | A1 | 10/2016 | Ryan et al. |
| 2016/0324987 | A1 | 11/2016 | Wang et al. |
| 2016/0340661 | A1 | 11/2016 | Cong et al. |
| 2017/0058298 | A1 | 3/2017 | Kennedy et al. |
| 2018/0273609 | A1 | 9/2018 | Porteus et al. |
| 2018/0291370 | A1 | 10/2018 | Gersbach et al. |
| 2019/0010495 | A1 | 1/2019 | Boitano et al. |
| 2019/0241911 | A1 | 8/2019 | Dong et al. |
| 2020/0299661 | A1 | 9/2020 | Gori et al. |
| 2020/0299689 | A1 | 9/2020 | Lee |

FOREIGN PATENT DOCUMENTS

| | | | |
|---|---|---|---|
| WO | 2008/108989 | A2 | 9/2008 |
| WO | 2010/054108 | A9 | 5/2010 |
| WO | 2011/143124 | A2 | 11/2011 |
| WO | 2011/146121 | A1 | 11/2011 |
| WO | 2012/145601 | A2 | 10/2012 |
| WO | 2012/164565 | A8 | 12/2012 |
| WO | 2013/012674 | A1 | 1/2013 |
| WO | 2013/066438 | A2 | 5/2013 |
| WO | 2013/082519 | A2 | 6/2013 |
| WO | 2013/098244 | A1 | 7/2013 |
| WO | 2013/126794 | A1 | 8/2013 |
| WO | 2013/141680 | A1 | 9/2013 |
| WO | 2013/142578 | A1 | 9/2013 |
| WO | 2013/163628 | A2 | 10/2013 |
| WO | 2013/176772 | A1 | 11/2013 |
| WO | 2013/181228 | A1 | 12/2013 |
| WO | 2014/018423 | A8 | 1/2014 |
| WO | 2014/022702 | A2 | 2/2014 |
| WO | 2014/036219 | A2 | 3/2014 |
| WO | 2014/059255 | A1 | 4/2014 |
| WO | 2014/065596 | A1 | 5/2014 |
| WO | 2014/085593 | A1 | 6/2014 |
| WO | 2014/089290 | A1 | 6/2014 |
| WO | 2014/093479 | A1 | 6/2014 |
| WO | 2014/093595 | A1 | 6/2014 |
| WO | 2014/093622 | A8 | 6/2014 |
| WO | 2014/093635 | A9 | 6/2014 |
| WO | 2014/093655 | A2 | 6/2014 |
| WO | 2014/093661 | A2 | 6/2014 |
| WO | 2014/093694 | A1 | 6/2014 |
| WO | 2014/093709 | A1 | 6/2014 |
| WO | 2014/093712 | A1 | 6/2014 |
| WO | 2014/093718 | A1 | 6/2014 |
| WO | 2014/099744 | A1 | 6/2014 |
| WO | 2014/099750 | A2 | 6/2014 |
| WO | 2014/124284 | A1 | 8/2014 |
| WO | 2014/144288 | A1 | 9/2014 |
| WO | 2014/144592 | A2 | 9/2014 |
| WO | 2014/144761 | A2 | 9/2014 |
| WO | 2014/152432 | A2 | 9/2014 |
| WO | 2014/186585 | A2 | 11/2014 |
| WO | 2014/197568 | A2 | 12/2014 |
| WO | 2014/197748 | A2 | 12/2014 |
| WO | 2014/204578 | A1 | 12/2014 |
| WO | 2014/204725 | A8 | 12/2014 |
| WO | 2015/006290 | A1 | 1/2015 |
| WO | 2015/006294 | A2 | 1/2015 |
| WO | 2015/006498 | A2 | 1/2015 |
| WO | 2015/013583 | A8 | 1/2015 |
| WO | 2015/021353 | A1 | 2/2015 |
| WO | 2015/027134 | A1 | 2/2015 |
| WO | 2015/035136 | A8 | 3/2015 |
| WO | 2015/035139 | A2 | 3/2015 |
| WO | 2015/035162 | A2 | 3/2015 |
| WO | 2015/048577 | A2 | 4/2015 |
| WO | 2015/048690 | A1 | 4/2015 |
| WO | 2015/070083 | A1 | 5/2015 |
| WO | 2015/071474 | A9 | 5/2015 |
| WO | 2015/077290 | A2 | 5/2015 |
| WO | 2015/077318 | A1 | 5/2015 |
| WO | 2015/089406 | A1 | 6/2015 |
| WO | 2015/089462 | A1 | 6/2015 |
| WO | 2015/099850 | A1 | 7/2015 |
| WO | 2015/138510 | A8 | 9/2015 |
| WO | 2015/148860 | | 10/2015 |
| WO | 2015/148863 | A2 | 10/2015 |
| WO | 2015/188056 | A1 | 12/2015 |
| WO | 2015/195621 | A1 | 12/2015 |
| WO | 2016/011080 | A2 | 1/2016 |
| WO | 2016/022363 | A9 | 2/2016 |
| WO | 2016/073990 | A2 | 5/2016 |
| WO | 2016/094872 | A1 | 6/2016 |
| WO | WO 2016/094872 | A1 * | 6/2016 ......... C12N 2310/20 |
| WO | 2016/135557 | A2 | 9/2016 |
| WO | 2016/135558 | A2 | 9/2016 |
| WO | 2016/182959 | A1 | 11/2016 |
| WO | 2016/186772 | A2 | 11/2016 |
| WO | 2016/205613 | A1 | 12/2016 |
| WO | 2016/205749 | A1 | 12/2016 |
| WO | 2017/035416 | A2 | 3/2017 |
| WO | 2017/077394 | A2 | 5/2017 |
| WO | 2017/106657 | A1 | 6/2017 |
| WO | 2017/160890 | A1 | 9/2017 |
| WO | 2017/184768 | | 10/2017 |
| WO | 2017/191503 | A1 | 11/2017 |
| WO | 2018/017754 | A1 | 1/2018 |
| WO | 2018/126176 | A1 | 7/2018 |
| WO | 2018/142364 | A1 | 8/2018 |
| WO | 2018/170184 | A1 | 9/2018 |
| WO | 2018/209158 | A2 | 11/2018 |
| WO | 2019/118516 | A1 | 6/2019 |
| WO | 2019/178416 | A1 | 9/2019 |
| WO | 2019/178426 | A1 | 9/2019 |
| WO | 2021/119040 | A1 | 6/2021 |

OTHER PUBLICATIONS

Ding, Q., et al., "Enhanced Efficiency of Human Pluripotent Stem Cell Genme Editing through Replacing TALENs with CRIPSRs," Cell Stem Cell 12:393-394 (2013).

Heintze, J., et al., "A CRISPR CASe for High-Throughput Silencing," Front. Genet. 4(193):1-6 (2013).

Mukherjee-Clavin, B., et al., "Current Approaches for Efficient Genetic Editing in Human Pluripotent Stem Cells," Front. Biol. 8(5):461-467 (2013).

Bothmer, A., et al., "Detection and Modulation of DNA Translocations During Multi-Gene Genome Editing in T Cells," The CRISPR Journal 3(3):177-187 (2020).

Cost, G. J., et al., Geneseq Accession No. BBD49192 (2014), 2 pages.

Fu, B. X. H., et al., "Landscape of Target: Guide Homology Effects on Cas9-Mediated Cleavage," Nucl. Acids Res. 42(22):13778-13787 (2014).

Giannoukos, G., et al., "UDiTaS™, a genome editing detection method for indels and genome rearrangements," BMC Genomics 19:212 (2018).

Giarratana, M. C., et al., "Ex vivo generation of fully mature human red blood cells from hematopoietic stem cells," Nat. Biotechnol. 23(1):69-74 (2005).

Hu, X., "CRISPR/Cas9 System and Its Applications in Human Hematopoietic Cells," Blood Cells, Molecules & Diseases 62:6-12 (2016).

Kleinstiver, B. P., et al., "Engineered CRISPR-Cas12a variants with increased activities and improved targeting ranges for gene, epigenetic and base editing," Nat. Biotechnol. 37(3):276-282 (2019).

Kosicki, M., et al., "Repair of Double-Strand Breaks Induced by CRISPR-Cas9 Leads to Large Deletions and Complex Rearrangements," Nat. Biotechnol. 36(8):765-771 (2018).

Krieg, A. M., et al., GeneSeq Accession No. BAY71542 (2013).

Masala, B., et al., "Detection of Globin Chains By Reversed-Phase High-Performance Liquid Chromatography," Methods Enzymol. 231:21-44 (1994).

Metais, J.Y., et al., "Genome Editing of HBG1 and HBG2 to Induce Fetal Hemoglobin," Blood Adv. 3(21):3379-92 (2019).

Pausch, P., et al., "CRISPR-Casϕ from Huge Phages is a Hypercompact Genome Editor," Science ;369(6501):333-337 (2020).

(56) References Cited

OTHER PUBLICATIONS

Reeks, J., et al., "Structure of a Dimeric Crenarchaeal Cas6 Enzyme with an Atypical Active Site for CRISPR RNA Processing," Biochem. J. 452:223-230 (2013).
Strohkendl, I., et al., "Kinetic Basis for DNA Target Specificity of CRISPR-Cas 12a," Mol Cell. 71(5):816-824 (2018).
Swarts, D. C., et al., "Cas9 Versus Cas 12a/Cpf1: Structure-Function Comparisons and Implications for Genome Editing," WIREs RNA 9:e1481 (2018).
Weber, L., et al., "Editing a y-Globin Repressor Binding Site Restores Fetal Hemoglobin Synthesis and Corrects the Sickle Cell Disease Phenotype," Sci. Adv. 6:eaay9392 (2020).
Vidigal, J. A., et al., "Rapid and Efficient One-Step Generation of Paired gRNA CRISPR-Cas9 Libraries," Nat. Commun. 6:8083 (2015).
European Patent Office, International Search Report and Written Opinion dated Mar. 6, 2020 for PCT/US2019/063766, 12 pages.
Cramer, M. L., et al., "Induction of T-Cell Infiltration and Programmed Death Ligand 2 Expression by Adeno-Associated Virus in Rhesus Macaque Skeletal Muscle and Modulation by Prednisone," Hum. Gene Ther. 28(6):493-509 (2017).
Kumar, S. R.P., et al., "Clinical development of gene therapy: results and lessons from recent successes," Mol. Ther. Methods Clin. Dev. 3:16034 (2016).
Sobrevals, L., et al., "AAV Vectors Transduce Hepatocytes In Vivo as Efficiently in Cirrhotic as in Healthy Rat Livers," Gene Ther. 19:411-417 (2012).
Zetsche, B., et al., "Multiplex Gene Editing by CRISPR-Cpf1 Through Autonomous Processing of a Single crRNA Array," Nat. Biotechnol. 35(1):31-34 (2017).
U.S. Appl. No. 61/652,086, filed May 25, 2012, Jinek et al.
U.S. Appl. No. 61/716,256, filed Oct. 19, 2012, Jinek et al.
U.S. Appl. No. 61/734,256, filed Dec. 6, 2012, Chen et al.
U.S. Appl. No. 61/736,527, filed Dec. 12, 2012, Zhang et al.
U.S. Appl. No. 61/738,355, filed Dec. 17, 2012, Church et al.
U.S. Appl. No. 61/758,624, filed Jan. 30, 2013, Chen et al.
U.S. Appl. No. 61/761,046, filed Feb. 5, 2013, Knight et al.
U.S. Appl. No. 61/779,169, filed Mar. 13, 2013, Mali et al.
Ahern, E.J., et al., "The Prevalence of the Rarer Inherited Haemoglobin Defects in Adult Jamaicans," Br. J. Haematol. 25(4):437-444 (1973).
Akinbami, A.O., et al., "Hereditary Persistence of Fetal Hemoglobin Caused by Single Nucleotide Promoter Mutations in Sickle Cell Trait and Hb SC Disease," Hemoglobin 40(1):64-65 (2016).
Al-Attar, S., et al., "Clustered Regularly Interspaced Short Palindromic Repeats (CRISPRs): The Hallmark of an Ingenious Antiviral Defense Mechanism in Prokaryotes," Biol. Chem. 392:277-289 (2011).
Aliyu, Z.Y., et al., "Sickle Cell Disease and Pulmonary Hypertension in Africa: A Global Perspective and Review of Epidemiology, Pathophysiology, and Management," Am. J. Hematol. 83(1):63-70 (2008).
Altschul, S. F., et al., "Gapped BLAST and PSI-BLAST: A New Generation of Protein Database Search Programs," Nucleic Acids Res. 25(17):3389-3402 (1997).
Altschul, S. F., et al., "Basic Local Alignment Search Tool," J. Mol. Biol. 215(3):403-410 (1990).
Amrani, N., et al., "NmeCas9 is an Intrinsically High-Fidelity Genome-Editing Platform," Genome Biol. 19:214 (2018).
Anders, C., et al., "Structural Basis of PAM-Dependent Target DNA Recognition by the Cas9 Endonuclease," Nature 513(7519):569-573 (2014).
Andreas, S., et al., "Enhanced Efficiency Through Nuclear Localization Signal Fusion on Phage PhiC31-Integrase: Activity Comparison with Cre and FLPe Recombinase in Mammalian Cells," Nucleic Acids Res. 30(11):2299-2306 (2002).
Angastiniotis, M., et al., "Global Epidemiology of Hemoglobin Disorders," Ann. N.Y. Acad. Sci. 850:251-269 (1998).
Anonymous, Third Party Observation for EP13818570.7, Oct. 1, 2014, 15 pages.
Anonymous, Third Party Observation for EP13824232.6, Sep. 8, 2014, 48 pages.
Anonymous, Third Party Observation for EP13824232.6, Sep. 22, 2014, 19 pages.
Anonymous, Third Party Observation for EP13824232.6, Oct. 22, 2014, 7 pages.
Bae, S., et al., "Cas-OFFinder: A Fast and Versatile Algorithm that Searches for Potential Off-Target Sites of Cas9 RNA-Guided Endonucleases," Bioinformatics 30(10):1473-1475 (2014).
Baker, M., "Gene Editing at CRISPR Speed," Nat. Biotechnol. 32(4):309-312 (2014).
Barbosa, C.G., et al., "Promoter Region Sequence Differences in the A and G Gamma Globin Genes of Brazilian Sickle Cell Anemia Patients," Braz. J. Med. Biol. Res. 43(8):705-711 (2010).
Barker, C. S., et al., "Increased DNA Microarray Hybridization Specificity Using sscDNA Targets," BMC Genomics 6:57 (2005).
Baron-Benhamou, J., et al., "Using the LambdaN Peptide to Tether Proteins to RNAs," Methods Mol. Biol. 257:135-153 (2004).
Barrangou, R., "RNA-Mediated Programmable DNA Cleavage," Nat. Biotechnol. 30(9):836-838 (2012).
Barretina, J., et al., "The Cancer Cell Line Encyclopedia Enables Predictive Modeling of Anticancer Drug Sensitivity," Nature 483(7391):603-607 (2012).
Bassett, A. R., et al., "CRISPR/Cas9 and Genome Editing in *Drosophila*," J. Genet. Genom. 41:7-19 (2014).
Bauer, D. E., et al., "An Erythroid Enhancer of BCL11A Subject to Genetic Variation Determines Fetal Hemoglobin Level," Science 342(6155):253-257 (2013).
Beerli, R. R., et al., "Toward Controlling Gene Expresion at Will: Specific Regulation of the erbB-2/HER-2 Promoter by Using Polydactyl Zinc Finger Proteins Constructed from Modular Building Blocks," Proc. Natl. Acad. Sci. 95:14628-14633 (1998).
Bhaya, D., et al., "CRISPR-Cas Systems in Bacteria and Archaea: Versatile Small RNAs for Adaptive Defense and Regulation," Annu. Rev. Genet. 45:273-297 (2011).
Bikard, D., et al., "Programmable Repression and Activation of Bacterial Gene Expression Using an Engineered CRISPR-Cas System," Nucl. Acids Res. 41(15):7429-7437 (2013).
Bitinaite, J., et al., "FokI Dimerization is Required for DNA Cleavage," Proc. Natl. Acad. Sci. 95:10570-10575 (1998).
Boch, J., et al., "Breaking the Code of DNA Binding Specificity of TAL-Type III Effectors," Science 326(5959):1509-1512 (2009).
Boch, J., et al., "Xanthomonas AvrBs3 Family-Type III Effectors: Discovery and Function," Annu. Rev. Phytopathol. 48:419-436 (2010).
Bothmer, A., et al., "Characterization of the Interplay Between DNA Repair and CRISPR/Cas9-Induced DNA Lesions at an Endogenous Locus," Nat. Commun. 8:13905 (2017).
Bouva, M. J., et al., "Known and New Delta Globin Gene Mutations and Their Diagnostic Significance," Haematologica 91(1):129-132 (2006).
Briner, A.E., et al., "Guide RNA Functional Modules Direct Cas9 Activity and Orthogonality," Mol. Cell 56(2):333-339 (2014).
Broad Institute, Communication Forwarding Declaration of Feng Zhang for U.S. Appl. No. 14/256,912, filed Nov. 24, 2014, 5 pages.
Broad Institute, Information Disclosure Statement submitted for U.S. Appl. No. 14/256,912, citing Electronic Mail from T. Kowalski which references Briner et al., Nov. 3, 2014, 8 pages.
Broad Institute, Request for Oral Examination for EP13818570.7, Oct. 27, 2014, 3 pages.
Broad Institute, Response to EP Examination Report for EP13824232.6, dated Dec. 31, 2014, 44 pages.
Broad Institute, Response to Third Party Observations and Request for Oral Hearing for EP13824232.6, Oct. 27, 2014, 9 pages.
Broad Institute, Response to Third Party Observations, with redlined and clean amended claims, for EP13818570.7, Oct. 16, 2014, 30 pages.
Broad Institute, Response to Third Party Observations, with redlined and clean amended claims, for EP13824232.6, Oct. 2, 2014, 16 pages.
Brousseau, D.C., et al., "The Number of People with Sickle-Cell Disease in the United States: National and State Estimates," Am. J. Hematol. 85(1):77-78 (2010).

(56) References Cited

OTHER PUBLICATIONS

Brummelkamp, T. R., et al., "A System for Stable Expression of Short Interfering RNAs in Mammalian Cells," Science 296(5567):550-553 (2002).
Burstein, D., et al., "New CRISPR-Cas Systems from Uncultivated Microbes," Nature 542(7640):237-241 (2017).
Caldecott, K.W., "Single-Strand Break Repair and Genetic Disease," Nat. Rev. Genet. 9(8):619-631 (2008).
Canver, M. C., "Evaluation of the Clinical Success of Ex Vivo and In Vivo Gene Therapy," Journal of Young Investitgators, http://www.hyi.org/issue/evaluation-of-the-clinical-success-of-ex-vivo-and-in-vivo-gene-therapy/, 9 pages (2009).
Canver, M. C., et al., "BCL11A Enancer Dissection by Cas9-Mediated In Situ Saturating Mutagenesis," Nature 527(7577):192-197 (2015).
Carroll, D., "A CRISPR Approach to Gene Targeting," Mol. Ther. 20(9):1658-1660 (2012).
Cassini, A., et al., "A Highly Specific SpCas9 Variant is Identified by In Vivo Screening in Yeast," Nat. Biotechnol. 36(3):265-271 (2018).
Cathomen, T., et al., "Zinc-Finger Nucleases: The Next Generation Emerges," Mol. Ther. 16:1200-1207 (2008).
Cermak, T., et al., "Efficient Design and Assembly of Custom TALEN and Other TAL Effector-Based Constructs for DNA Targeting," Nucl. Acids Res. 39(12):e82 (2011).
Chandrakasan, S., et al., "Gene Therapy for Hemoglobinopathies: The State of the Field and the Future," Hematol. Oncol. Clin. North Am. 28(2):199-216 (2014).
Chang, K.H., et al., "Long-Term Engraftment and Fetal Globin Induction upon BCL11A Gene Editing in Bone-Marrow-Derived CD34+ Hematopoietic Stem and Progenitor Cells," Mol. Ther. Methods Clin. Dev. 4:137-148 (2017).
Chassanidis, C., et al., "The Hellenic Type of Nondeletional Hereditary Persistence of Fetal Hemoglobin Results from a Novel Mutation (g.-109G>T) in the HBG2 Gene Promoter," Ann. Hematol. 88(6):549-555 (2009).
Chen, X., et al., "Fusion Protein Linkers: Property, Design and Functionality," Adv. Drug Deliv. Rev. 65(10):1357-1369 (2013).
Chen, F., et al., "Targeted Activation of Diverse CRISPR-Cas Systems for Mammalian Genome Editing Via Proximal CRISPR Targeting," Nat. Commun. 8:14958 (2017).
Chen, J. S., et al., "Enhanced Proofreading Governs CRISPR-Cas9 Targeting Accuracy," Nature 550(7676):407-410 (2017).
Cho, S. W., et al., Supplementary Information: Targeted Genome Engineering in Human Cells With the Cas9 RNA-Guided Endonuclease, Nature Biotechnology (Mar. 2013) vol. 31, No. 3, 11 pages.
Cho, S. W., et al., "Targeted Genome Engineering in Human Cells with the Cas9 RNA-Guided Endonuclease," Nat. Biotechnol. 31(3):230-232 (2013).
Christian, M., et al., "Targeting DNA Double-Strand Breaks With TAL Effector Nucleases," Genetics 186:757-761 (2010).
Christian, M., et al., "Targeting DNA Double-Strand Breaks With TAL Effector Nucleases," Genetics Supporting Information, 1SI-8SI (2010).
Chylinski, K., et al., "The TrackRNA and Cas9 Families of Type II CRISPR-Cas Immunity Systems," RNA Biol. 10(5):726-737 (2013).
Cong, L., et al., "Multiplex Genome Engineering Using CRISPR/Cas Systems," Science 339(6121):819-823 (2013).
Cong, L. et al., "Supplementary Material: Multiplex Genome Engineering Using CRISPR-Cas Systems," Science Express (Jul. 5, 2012).
Cong, L. et al., "Supplementary Material: Multiplex Genome Engineering Using CRISPR-Cas Systems," Science Express (Jan. 3, 2013).
Cornish-Bowden, A., "Nomenclature for Incompletely Specified Bases in Nucleic Acid Sequences: Recommendations 1984," Nucleic Acids Res. 13(9):3021-3030 (1985).
Cradick, T. J., et al., "CRISPR/Cas9 Systems Targeting Beta-Globin and CCR5 Genes Have Substantial Off-Target Activity," Nucleic Acids Res. 41(20):9584-9592 (2013).
Datsenko, K. A., et al., "Molecular Memory of Prior Infections Activates the CRISPR/Cas Adaptive Bacterial Immunity System," Nat. Commun. 3:945 (2012).
Davis, L., et al., "Homology-Directed Repair of DNA Nicks Via Pathways Distinct from Canonical Double-Strand Break Repair," PNAS 111(10):E924-932 (2014).
Deltcheva, E., et al., CRISPR RNA Maturation by Trans-Encoded Small RNA and Host Factor RNase III, Nature 471:602-607 (2011).
Deltcheva, E., et al., Supplementary Figures: CRISPR RNA Maturation by Trans-Encoded Small RNA and Host Factor RNase III. Downloaded from www.nature.com/nature, p. 1-35, 2011.
Deveau, H., et al., "Phage Response to CRISPR-Encoded Resistance in *Streptococcus thermophilus*," J. Bacteriol. 190(4):1390-1400 (2008).
Dever, D. P., et al., "CRISPR/Cas9 Beta-Globin Gene Targeting in Human Haematopoietic Stem Cells," Nature 539:384-389 (2016).
Dicarlo, J. E., et al., "Genome Engineering in *Saccharomyces cerevisiae* Using CRISPR-Cas Systems," Nucl. Acids Res. 41(7):4336-43 (2013).
Dingwall, C., et al., "A Polypeptide Domain That Specifies Migration of Nucleoplasmin Into the Nucleus," Cell 30:449-458 (1982).
Dreszer, T. R., et al., "The UCSC Genome Browser Database: Extensions and Updates 2011," Nucl. Acids Res. 40:D918-D923 (2012).
Esvelt, K.M., et al., "A System for the Continuous Directed Evolution of Biomolecules," Nature 472(7344):499-503 (2011).
Esvelt, K. M., et al., "Orthogonal Cas9 Proteins for RNA-Guided Gene Regulation and Editing," Nat. Methods 10(11):1116-1121 (2013).
Fine, E.J., et al., "Trans-Spliced Cas9 Allows Cleavage of HBB and CCR5 Genes in Human Cells Using Compact Expression Cassettes," Sci. Rep. 5:10777 (2015).
Fonfara, I., et al., "Phylogeny of Cas9 Determines Functional Exchangeability of Dual-RNA and Cas9 Among Orthologous Type II CRISPR-Cas Systems," Nucl. Acids Res.42(4):2577-2590 (2014).
Friedland, A.E., et al., "Characterization of *Staphylococcus aureus* Cas9: A Smaller Cas9 for All-in-One Adeno-Associated Virus Delivery and Paired Nickase Applications," Genome Biol. 16:257 (2015).
Frit, P., et al., "Alternative End-Joining Pathway(s): Bricolage at DNA Breaks," DNA Repair (Amst) 17:81-97 (2014).
Fu, Y., et al., "High-Frequency Off-Target Mutagenesis Induced by CRISPR-Cas Nucleases in Human Cells," Nat. Biotechnol. 31:822-826 (2013).
Fu, Y., et al., "Targeted Genome Editing in Human Cells Using CRISPR/Cas Nucleases and Truncated Guide RNAs," Methods Enzymol. 546:21-45 (2014).
Fu, Y., et al., "Improving CRISPR-Cas Nuclease Specificity Using Truncated Guide RNAs," Nat. Biotechnol. 32(3):279-284 (2014).
Gabriel, R., et al., "An Unbiased Genome-Wide Analysis of Zinc-Finger Nuclease Specificity," Nat. Biotechnol. 29:816-823 (2011).
Gao, L., et al., "Engineered Cpf1 Variants with Altered PAM Specificities Increase Genome Targeting Range," Nat. Biotechnol. 35(8):789-792 (2017).
Garneau, J. E., et al., "The CRISPR-Cas Bacterial Immune Systems Cleaves Bacteriophage and Plasmid DNA," Nature 468:67-71 (2010).
Gasiunas, G., et al., "Cas9-crRNA Ribonucleoprotein Complex Mediates Specific DNA Cleavage for Adaptive Immunity in Bacteria," Proc. Natl. Acad. Sci. 109(39):E2579-E2586 (2012).
Giarratana, M. C., et al., "Proof of Principle for Transfusion of In Vitro-Generated Red Blood Cells," Blood 118(19):5071-5079 (2011).
Gilbert, L. A., et al., "CRISPR-Mediated Modular RNA-Guided Regulation of Transcription in Eukaryotes," Cell 154(2):442-451 (2013).
Goldfarb, D. S., et al., "Synthetic Peptides as Nuclear Localization Signals," Nature 322:641-644 (1986).
Gratz, S. J., et al., "Genome Engineering of *Drosophila* with the CRISPR RNA-Guided Cas9 Nuclease," Genetics 194(4):1029-1035 (2013).
Grieger, J. C., et al., "Production and Characterization of Adeno-Associated Viral Vectors," Nat. Protoc. 1(3):1412-1428 (2006).

(56) References Cited

OTHER PUBLICATIONS

Guilinger, J. P., et al., "Fusion of Catalytically Inactive Cas9 to Fokl Nuclease Improves the Specificity of Genome Modification," Nat Biotechnol. 32(6):577-583 (2014).
Guo, X., et al., "RNA-Dependent Folding and Stabilization of C5 Protein During Assembly of the *E. coli* Rnase P Holoenzyme," J. Mol. Biol. 360:190-203 (2006).
Guo, Q., et al., "'Cold shock' increases the frequency of homology directed repair gene editing in induced pluripotent stem cells," Sci. Rep. 8(1):2080 (2018).
Gustafsson, C., et al., "Codon Bias and Heterologous Protein Expression," Trends Biotechnol. 22(7):346-353 (2004).
Haft, D. H., et al., "A Guild of 45 CRISPR-Associated (Cas) Protein Families and Multiple CRISPR/Cas Subtypes Exist in Prokaryotic Genomes," PLoS Comput. Biol. 1(6):e60 (2005).
Hale, C. R., et al., "Essential Features and Rational Design of CRISPR RNAs That Function With the Cas RAMP Module Complex to Cleave RNAs," Mol. Cell 45(3):292-302 (2012).
Hatoum-Aslan, A., et al. "Mature Clustered Regularly Interspaced, Short Palindromic Repeats RNA 5,9,14 (crRNA) Length is Measured by a Ruler Mechanism Anchored at the Precursor Processing Site," Proc. Natl. Acad. Sci. 108(52):21218-21222 (2011).
Heigwer, F., et al., "E-CRISP: Fast CRISPR Target Site Identification," Nat. Methods 11(2):122-123 (2014).
Hinz, J. M., et al., "Nucleosomes Selectively Inhibit Cas9 Off-Target Activity at a Site Located at the Nucleosome Edge," J. Biol. Chem. 291(48):24851-24856 (2016).
Hoban, M. D., et al., "A genome editing primer for the hematologist," Blood 127(21):2525-2535 (2016).
Hockemeyer, D., et al., "Efficient Targeting of Expressed and Silent Genes in Human ESCs and iPSCs Using Zinc-Finger Nucleases," Nat. Biotechnol. 27(9):851-857 (2009).
Hockemeyer, D., et al., "Genetic Engineering of Human luripotent Cells Using TALE Nucleases," Nat. Biotechnol. 29:731-734 (2011).
Holt, N, et al., "Zinc Finger Nuclease-Mediated CCR5 Konockout Hematopoietic Stem Cell Transplantation Controls HIV-1 In Vivo," Nat. Biotechnol. 28(8):839-847 (2010).
Horvath, P., et al., "CRISPR/Cas, The Immune System of Bacteria and Archaea," Science 327(5962):167-170 (2010).
Horvath, P., et al., "RNA-Guided Genome Editing A La Carte," Cell Res. 23:733-734 (2013).
Hou, Z., et al., "Efficient Genome Engineering in Human Pluripotent Stem Cells Using Cas9 from Neisseria Meningitidis," Proc. Natl. Acad. Sci. U.S.A. 110(39):15644-15649 (2013).
Hsu, P.D., et al., "DNA Targeting Specificity of RNA-Guided Cas9 Nucleases," Nat. Biotechnol. 31(9):827-832 (2013).
Huang, X., et al., "Production of Gene-Corrected Adult Beta Globin Protein in Human Erythrocytes Differentiated from Patient iPSCs After Genome Editing of the Sickle Point Mutation," Stem Cells 33:1470-1479 (2015).
Hwang, W. Y., et al., "Heritable and Precise Zebrafish Genome Editing Using a CRISPR-Cas System," PLOS One 8(7):e68708 (2013).
Hwang, W. Y., et al., "Efficient Genome Editing in Zebrafish Using a CRISPR-Cas System," Nat. Biotechnol. 31(3):227-229 (2013).
Hyun, P. S., et al., "Therapeutic CRISPR/Cas9 Genome Editing for Treating Sickle Cell Disease," Blood 128(22):4703 (2016).
Iyama, T., et al., "DNA Repair Mechanisms in Dividing and Non-Dividing Cells," DNA Repair (Amst.) 12(8):620-636 (2013).
Iyer, L. M., et al., "Prediction of Novel Families of Enzymes Involved in Oxidative and Other Complex Modifications of Bases in Nucleic Acids," Cell Cycle 8(11):1698-1710 (2009).
Jiang, W., et al., "RNA-Guided Editing of Bacterial Genomes Using CRISPR-Cas Systems," Nat. Biotechnol. 31(3):233-239 (2013).
Jinek, M., et al., "A Programmable Dual-RNA-Guided DNA Endonuclease in Adaptive Bacterial Immunity," Science 337(6096):816-821 (2012).
Jinek, M., et al., "Structures of Cas9 Endonucleases Reveal RNA-Mediated Conformational Activation," Science 343(6176):1247997 (2014).
Jinek, M., et al., "RNA-Programmed Genome Editing in Human Cells," eLife 2:e00471 (2013).
Joung, J., et al., "Genome-Scale CRISPR-Cas9 Knockout and Transcriptional Activation Screening," Nat. Protoc. 12(4):828-863 (2017).
Kaiser, J., "The Gene Editor CRISPR Won't Fully Fix Sick People Anytime Soon. Here's Why," (May 3, 2016), Biol., Technol, CRISPR, DOI: 10.1126/science.aaf5689, 5 pages.
Karolchik, D., et al., "The UCSC Table Browser Data Retrieval Tool," Nucleic Acids Research 32:D493-496 (2004).
Karvelis, T., et al., "crRNA and tracrRNA Guide Cas9-Mediated DNA Interference in *Streptococcus thermophilus*," RNA Biol. 10(5):841-851 (2013).
Kent, W. J., et al., "The Human Genome Browser at UCSC," Genome Research 12:996-1006 (2002).
Keryer-Bibens, C., et al., "Tethering of Proteins to RNAs by Bacteriophage Proteins," Biol. Cell, 100:125-138 (2008).
Khalil, A. S., et al., "Synthetic Biology: Applications Come of Age," Nat. Rev. Genet. 11(5):367-379 (2010).
Kim, H.S., et al., "Problems Encountered in Detecting a Targeted Gene by the Polymerase Chain Reaction," Gene 103:227-233 (1991).
Kim, Y.G., et al., "Hybrid Restriction Enzymes: Zinc Finger Fusions to Fok I Cleavage Domain," Proc. Natl. Acad. Sci. USA 93:1156-1160 (1996).
Kim, E., et al., "In Vivo Genome Editing with a Small Cas9 Orthologue Derived from Campylobacter Jejuni," Nat. Commun. 8:14500 (2017).
King, N. M.P., et al., "En Route to Ethical Recommendations for Gene Transfer Clinical Trials," Mol. Ther. 16(3):432-438 (2008).
Kleinstiver, B.P., et al., "Broadening the Targeting Range of *Staphylococcus aureus* CRISPR-Cas9 by Modifying PAM Recognition," Nat. Biotechnol. 33(12):1293-1298 (2015).
Kleinstiver, B.P., et al., "Engineered CRISPR-Cas9 Nucleases with Altered PAM Specificities," Nature 523(7561):481-485 (2015).
Kleinstiver, B.P., et al., "High-Fidelity CRISPR-Cas9 Nucleases with No Detectable Genome-Wide Off-Target Effects," Nature 529(7587):490-495 (2016).
Koike-Yusa, H., et al., "Genome-Wide Recessive Genetic Screening in Mammalian Cells with a Lentiviral CRISPR-Guide RNA Library," Nat. Biotechnol. 32(3):267-273 (2014).
Komor, A.C., et al., "Programmable Editing of a Target Base in Genomic DNA Without Double-Stranded DNA Cleavage," Nature 533(7603):420-424 (2016).
Kosuri, S., et al., "A Scalable Gene Synthesis Platform Using High-Fidelity DNA Microchips," Nat. Biotechnol. 28(12):1295-1299 (2010).
Kurita, R., et al., "Establishment of Immortalized Human Erythroid Progenitor Cell Lines Able to Produce Enucleated Red Blood Cells," PLoS One 8(3):e59890 (2013).
Lambowitz, A. M., et al., "Group II Introns: Mobile Ribozymes that Invade DNA," Cold Spring Harb. Perspect. Biol. 3:a003616 (2011).
Langmead, B., et al., "Ultrafast and Memory-Efficient Alignment of Short DNA Sequences to the Human Genome," Genome Biology 10(3):R25 (2009).
Lederer, C. W., et al., "Beta Testing: Preclinical Genome Editing in Beta-Globin Disorders," Cell Gene Therapeutic Insights 1(2):231-242 (2015).
Lee, J.H., et al., "A Robust Approach to Identifying Tissue-Specific Gene Expression Regulatory Variants Using Personalized Human Induced Pluripotent Stem Cells," PLoS Genetics 5(11):e1000718 (2009).
Lee, J., et al., "Non-Endocytic Delivery of Functional Engineered Nanoparticles into the Cytoplasm of Live Cells Using a Novel, High-Throughput Microfluidic Device," Nano Lett. 12(12):6322-6327 (2012).
Lee, J. K., et al., "Directed evolution of CRISPR-Cas9 to Increase Its Specificity," Nat. Commun. 9:3048 (2018).
Li, G.M., "Mechanisms and Functions of DNA Mismatch Repair," Cell Res. 18(1):85-98 (2008).
Li, T., et al., "TAL Nucleases (TALNs): Hybrid Proteins Composed of TAL Effectors and Fokl DNA-Cleavage Domain," Nucl. Acids Res.39(1): 359-372 (2011).

(56) References Cited

OTHER PUBLICATIONS

Li, H., et al., "In Vivo Genome Editing Restores Hemostasis in a Mouse Model of Hemophilia," Nature 475(7355):217-221 (2011).
Li, T., et al., "Modularly Assembled Designer TAL Effector Nucleases for Targeted Gene Knockout and Gene Replacement in Eukaryotes," Nucl. Acids Res. 39(14):6315-6325 (2011).
Liang, P., et al., "CRISPR/Cas9-Mediated Gene Editing in Human Tripronuclear Zygotes," Protein Cell 6(5):363-372 (2015).
Lidonnici, M. R., et al., "Gene Therapy and Gene Editing Strategies for Hemoglobinopathies," Blood Cells, Molecules & Diseases 70:87-101 (2018).
Lombardo, A., et al., "Gene Editing in Human Stem Cells Using Xinc Finger Nucleases and Integrase-Defective Lentiviral Vector Delivery," Nat. Biotechnol. 25(11):1298-1306 (2007).
Lorenz, R., et al., "ViennaRNA Package 2.0," Algorithms for Molecular Biology 6:26 (2011).
Maeder, M. L., et al., "CRISPR RNA-Guided Activation of Endogenous Human Genes," Nat. Methods 10:977-979 (2013).
Maeder, M. L., et al., "Rapid "Open-Source" Engineering of Customized Zinc-Finger Nucleases for Highly Efficient Gene Modification," Mol. Cell 31(2):294-301 (2008).
Makarova, K. S., et al., "A Putative RNA-Interference-Based Immune System in Prokaryotes: Computational Analysis of the Predicted Enzymatic Machinery, Functional Analogies with Eukaryotic RNAi, and Hypothetical Mechanisms of Action," Biol. Direct. 1:7 (2006).
Makarova, K. S., et al., "Unification of Cas Protein Families and a Simple Scenario for the Origin and Evolution of CRISPR-Cas Systems," Biol. Direct 6:38 (2011).
Makarova, K.S., et al., "Evolution and Classification of the CRISPR-Cas Systems," Nat. Rev. Microbiol. 9(6):467-477 (2011).
Mali, P., et al., "CAS9 Transcriptional Activators for Target Specificity Screening and Paired Nickases for Cooperative Genome Engineering," Nat. Biotechnol. 31:833-838 (2013).
Mali, P., et al., "Cas9 as a Versatile Tool for Engineering Biology," Nat. Methods 10(10):957-963 (2013).
Mali, P., et al., "RNA-Guided Human Genome Engineering Via Cas9," Science 339(6121):823-826 (2013).
Mantovani, R., et al., "The Effects of HPFH Mutations in the Human Gamma-Globin Promoter on Binding of Ubiquitous and Erythroid Specific Nuclear Factors," Nucleic Acids Res. 16(16):7783-7797 (1988).
Marteijn, J.A., et al., "Understanding Nucleotide Excision Repair and Its Role in Cancer and Ageing," Nat. Rev. Mol. Cell Biol. 15(7):465-481 (2014).
Martyn, G.E., et al., "The Regulation of Human Globin Promoters by CCAAT Box Elements and the Recruitment of NF-Y," Biochim. Biophys. Acta 1860(5):525-536 (2017).
Mathews, D. H., et al., "Expanded Sequence Dependence of Thermodynamic Parameters Improves Prediction of RNA Secondary Structure," J. Mol. Biol. 288:911-940 (1999).
Miller, J. C., et al., "An Improved Zinc-Finger Nuclease Architecture for Highly Specific Genome Editing," Nat. Biotechnol. 25:778-785 (2007).
Miller, J. C., et al., "A Tale Nuclease Architecture for Efficient Genome Editing," Nat. Biotechnol. 29(2):143-150 (2011).
Miyagishim M., et al., "U6 Promoter-Driven siRNAs with Four Uridine 3' Overhangs Efficiently Suppress Targeted Gene Expression in Mammalian Cells," Nat. Biotechnol. 20(5):497-500 (2002).
Moscou, M. J., et al., "A Simple Cipher Governs DNA Recognition by TAL Effectors," Science 326(5959):1501 (2009).
Myers, E. W., et al., "Optimal Alignments in Linear Space," Comput. Appl. Biosci. 4(1):11-17 (1988).
Nakamura, Y., et al., "Codon Usage Tabulated From International DNA Sequence Databases: Status for the Year 2000," Nucl. Acids Res. 28(1):292 (2000).
Needleman, S. B., et al., "A General Method Applicable to the Search for Similarities in the Amino Acid Sequence of Two Proteins," J. Mol. Biol. 48(3):443-453 (1970).
Nishimasu, H., et al., "Crystal Structure of Cas9 in Complex with Guide RNA and Target DNA," Cell 156(5):935-949 (2014).
Nishimasu, H., et al., "Crystal Structure of *Staphylococcus aureus* Cas9," Cell 162:1113-1126 (2015).
Nishimasu, H., et al., "Engineered CRISPR-Cas9 Nuclease with Expanded Targeting Space," Science 361(6408):1259-1262 (2018).
Notta, F., et al., "Isolation of Single Human Hematopoietic Stem Cells Capable of Long-Term Multilineage Engraftment," Science 333(6039):218-221 (2011).
Ou, Z., et al., "The Combination of CRISPR/Cas9 and iPSC Technologies in the Gene Therapy of Human Beta-Thalassemia in Mice," Scientific Reports 6(1):32463 (2016).
Paix, A., et al., "Precision Genome Editing Using CRISPR-Cas9 and Linear Repair Templates in C. Elegans," Methods 121-121:86-93 (2017).
Pattanayak, V., et al., "High-Throughput Profiling of Off-Target DNA Cleavage Reveals RNA-Programmed Cas9 Nuclease Specificity," Nat. Biotechnol. 31:839-843 (2013).
Pattanayak, V., et al., "Revealing Off-Target Cleavage Specificities of Zinc-Finger Nucleases by In Vitro Selection," Nat. Methods 8:765-770 (2011).
Patterson, S. S., et al., "Codon Optimization of Bacterial Luciferase (lux) for Expression in Mammalian Cells," J. Ind. Microbio. Biotechnology 32:115-123 (2005).
Pearson, W. R., et al., "Improved Tools for Biological Sequence Comparison," Proc. Natl. Acad. Sci. U.S.A. 85(8):2444-2448 (1988).
Pellissier, L. P., et al., "Specific Tools for Targeting and Expression in Muller Glial Cells," Mol. Ther. Methods Clin. Dev. 1:14009 (2014).
Peng, R., et al., "Potential Pitfalls of CRISPR/Cas9-Mediated Genome Editing," Febs J. 283:1218-1231 (2016).
Perez, E. E., et al., "Establishment of HIV-1 Resistance in CD4+ T Cells by Genome Editing Using Zinc-Finger Nucleases," Nat. Biotechnol. 26:808-816 (2008).
Porteus, M. H., et al., "Gene Targeting Using Zinc Finger Nucleases," Nat. Biotechnol. 23(8):967-973 (2005).
Pougach, K., et al., "Transcription, Processing and Function of CRISPR Cassettes in *Escherichia coli*," Mol. Microbiol. 77(6):1367-1379 (2010).
Pride, D. T., et al., "Analysis of Streptococcal CRISPRs from Human Saliva Reveals Substantial Sequence Diversity Within and Between Subjects Over Time," Genome Res. 21:126-136 (2011).
Purnick, P. E. M., et al., "The Second Wave of Synthetic Biology: From Modules to Systems," Nat. Rev. Mol. Cell Biol. 10(6):410-422 (2009).
Qi, L. S., et al., "Repurposing CRISPR as an RNA-Guided Platform for Sequence-Specific Control of Gene Expression," Cell 152:1173-1183 (2013).
Qi, L., et al., "RNA Processing Enables Predictable Programming of Gene Expression," Nat. Biotechnol. 30(10):1002-1007 (2012).
Quinlan, A. R., et al., "BEDTools: A Flexible Suite of Utilities for Comparing Genomic Features," Bioinformatics 26(6):841-842 (2010).
Ran, F.A., et al., "Double Nicking by RNA-Guided CRISPR Cas9 for Enhanced Genome Editing Specificity," Cell 154(6):1380-1389 (2013).
Ran, F. A., et al., "In Vivo Genome Editing Using *Staphylococcus aureus* Cas9," Nature 520(7546):186-191 (2015).
Rand, T. A., et al., "Argonaute2 Cleaves the Anti-Guide Strand of siRNA During RISC Activation," Cell 123:621-629 (2005).
Raymond, C. S., et al., "High-Efficiency FLP and PhiC31 Site-Specific Recombination in Mammalian Cells," PLoS One 2(1):e162 (2007).
Rebar, E. J., et al., "Zinc Finger Phage: Affinity Selection of Fingers with New DNA-Binding Specificities," Science 263(5147):671-673 (1994).
Rebar, E. J., et al., "Induction of Angiogenesis in a Mouse Model Using Engineered Transcription Factors," Nat. Med. 8(12):1427-1432 (2008).
Recht, M. I., et al., "Monitoring Assembly of Ribonucleoprotein Complexes by Isothermal Titration Calorimetry," Methods in Mol. Biol. 488:117-127 (2008).
Regalado, A., "Who Owns the Biggest Biotech Discovery of the Century?," MIT Technology Review, Dec. 4, 2014, http://www.technologyreview.com/featuredstory/532796/who-owns-the-biggest- -biotech-discovery-of-the-century/.

(56) References Cited

OTHER PUBLICATIONS

Reyon, D., et al., "FLASH Assembly of TALENs for High-Throughput Genome Editing," Nat. Biotech. 30:460-465 (2012).
Rho, M., et al. "Diverse CRISPRs Evolving in Human Microbiomes." PLoS Genetics 8(6):e1002441 (2012).
Richardson, C. D., et al., "Enhancing Homology-Directed Genome Editing by Catalytically Active and Inactive CRISPR-Cas9 Using Asymmetric Donor DNA," Nat. Biotechnol. 34(3):339-344 (2016).
Sander, J. D., et al., "Zinc Finger Targeter (ZiFiT): An Engineered Zinc Finger/Target Site Design Tool," Nucleic Acids Res. 35:W599-W605 (2007).
Sander, J. D., et al., "ZiFiT (Zinc Finger Targeter): An Updated Zinc Finger Engineering Tool," Nucleic Acids Res. 38:W462-468 (2010).
Sander, J. D., et al., "CRISPR-Cas Systems for Editing, Regulating and Targeting Genomes," Nat. Biotechnol. 32(4):347-355 (2014).
Sanders, R., "Cheap and Easy Technique to Snip DNA Could Revolutionize Gene Therapy", Berkeley News Online, pp. 1-3 (Jan. 7, 2013).
Sanjana, N. E., et al., "A Transcription Activator-Like Effector (TALE) Toolbox for Genome Engineering," Nat. Protoc. 7(1):171-192 (2012).
Sankaran, V. G., et al., "Human Fetal Hemoglobin Expression is Regulated by the Developmental Stage-Specific Repressor BCL11A," Science 322(5909):1839-1842 (2008).
Sapranauskas, R., et al., "The *Streptococcus thermophilus* CRISPR-Cas System Provides Immunity in *Escherichia coli*," Nucl. Acids Res.39:9275-9282 (2011).
Sather, B. D., et al., "Efficient Modification of CCR5 in Primary Human Hematopoietic Cells Using a Mega TAL Nuclease and AAV Donor Template," Sci. Trans. Med. 7(307):307ra156 (2015).
Schramm, L., et al., "Recruitment of RNA Polymerase III to Its Target Promoters," Genes Devel. 16:2593-2620 (2002).
Selleck, W., et al., "Biophysical Characterization and Direct Delivery of *S. pyogenes* Cas9 Ribonucleoprotein Complexes," Editas Medicine, Apr. 27, 2015, retrieved from URL http://www.editasmedicine.com/documents/ASGCT_poster_2015_Will.pdf.
Shalem, O., et al., "Genome-Scale CRISPR-Cas9 Knockout Screening in Human Cells," Science 343:84 (2014).
Shanks, P., "CRISPR Opportunities . . . For What? And for Whom?," Biopolitical Times, Dec. 4, 2014, http://www.biopoliticaltimes.org/article.php?id=8235.
Sharma, R., et al., "In Vivo Genome Editing of the Albumin Locus as a Platform for Protein Replacement Therapy," Blood 126(15):1777-1784 (2015).
Shayakhmetov, D. M., et al., "Analysis of Adenovirus Sequestration in the Liver, Transduction of Hepatic Cells, and Innate Toxicity after Injection of Fiber-Modified Vectors," J. Virol. 78(10):5368-5381 (2004).
Shen, B., et al., "Generation of Gene-Modified Mice via Cas9/RNA-Mediated Gene Targeting," Cell Res. 23:720-723 (2013).
Shmakov, S., et al., "Discovery and Functional Characterization of Diverse Class 2 CRISPR-Cas Systems," Mol. Cell 60(3):385-397 (2015).
Smith, C., et al., "Efficient and Allele-Specific Genome Editing of Disease Loci in Human iPSCs," Mol. Ther. 23(3):570-577 (2015).
Smith, T. F., et al., "Comparison of Biosequences," Adv. Appl. Math. 2(4):482-489 (1981).
Song, B., et al., "Improved Hematopoietic Differentiation Efficiency of Gene-Corrected Beta-Thalassemia Induced Pluripotent Stem Cells by CRISPR/Cas9 System," Stem Cells Devel. 24(9):1053-1065 (2015).
Sontheimer, E., "Project 7: Establishing RNA-Directed DNA Targeting in Eukaryotic Cells; Project dates: Nov. 16, 2011 to Dec. 31, 2012," Physical Sciences—Oncology Center (Feb. 4, 2012).
Sternberg, S.H., et al., "DNA Interrogation by the CRISPR RNA-Guided Endonuclease Cas9," Nature 507(7490):62-67 (2014).
Strecker, J., et al., "Engineering of CRISPR-Cas12b for Human Genome Editing," Nat. Commun. 10:212 (2019).
Sugimoto, N., et al., "Thermodynamic Parameters to Predict Stability of RNA/DNA Hybrid Duplexes," Biochem. 34:11211-11216 (1995).
Sugimoto, N., et al., "Thermodynamics-Structure Relationship of Single Mismatches in RNA/DNA Duplexes," Biochem. 39(37):11270-11281 (2000).
Superti-Furga, G., et al., "The -117 Mutation in Greek HPFH Affects the Binding of Three Nuclear Factors to the CCAAT Region of the Gamma-Globin Gene," EMBO J. 7(10):3099-3107 (1988).
Szczepek, M., et al., "Structure-Based Redesign of the Dimerization Interface Reduces the Toxicity of Zinc-Finger Nucleases," Nat. Biotechnol. 25:786-793 (2007).
Tang, L., et al., "CRISPR/Cas9-Mediated Gene Editing in Human Zygotes Using Cas9 Protein," Mol. Genet. Genom. 292(3):525-533 (2017).
Teng, F., et al., "Repurposing CRISPR-Cas12b for Mammalian Genome Engineering," Cell Discov. 4:63 (2018).
Terns, M. P., et al., "CRISPR-based Adaptive Immune Systems," Curr. Opin. Microbiol. 14:321-327 (2011).
Thein, S.L., et al., "Control of Fetal Hemoglobin: New Insights Emerging from Genomics and Clinical Implications," Hum. Mol. Genet. 18(R2):R216-R223 (2009).
Thorpe, S. J., et al., "Immunochemical Estimation of Haemoglobin Types in Red Blood Cells by FACS Analysis," Br. J. Haematol. 87:125-132 (1994).
Thurman, R. E., et al., "The Accessible Chromatin Landscape of the Human Genome," Nature 489(7414):75-82 (2012).
Tolia, N. H., et al., "Slicer and the Argonautes," Nat. Chem. Biol. 3(1):36-43 (2007).
Tolpin, Thomas W., Third Party Observation for EP13793997.1, Jan. 6, 2015, 50 pages.
Traxler, E., et al., "Genome Editing Recreates Hereditary Persistence of Fetal Hemoglobin in Primary Human Erythroblasts," Blood J. 126(23):640 (2015).
Traxler, E. A., et al., "A Genome-Editing Strategy to Treat Beta-Hemoglobinopathies that Recapitulates a Muation Associated with a Benign Genetic Condition," Nat. Med. 22(9):987-990 (2016).
Truong, L. N., et al., "Microhomology-Mediated End Joining and Homologous Recombination Share the Initial End Resection Step to Repair DNA Double-Strand Breaks in Mammalian Cells," PNAS 110(19):7720-7725 (2013).
Tsai, S. Q., et al., "Dimeric CRISPR RNA-Guided FokI Nucleases for Highly Specific Genome Editing," Nat. Biotechnol. 32(6):569-576 (2014).
Tsai, S.Q., et al., "Open-Source GuideSeq Software for Analysis of GUIDE-Seq Data," Nat. Biotechnol. 34(5):483 (2016).
Urnov, F. D., et al., "Highly Efficient Endogenous Human Gene Correction Using Designed Zinc-Finger Nucleases," Nature 435:646-651 (2005).
Van Der Oost, J., "New Tool for Genome Surgery," Science 336:768-768 (2013).
Van Der Ploeg, J. R., "Analysis of CRISPR in *Streptococcus* Mutans Suggests Frequent Occurrence of Acquired Immunity Against Infection by M102-Like Bacteriophages," Microbiology 155:1966-1976 (2009).
Van Overbeek, M., et al., "DNA Repair Profiling Reveals Nonrandom Outcomes at Cas9-Mediated Breaks," Mol. Cell 63:633-646 (2016).
Waber, P.G., et al., "Concordance of a Point Mutation 5' to the A Gamma-Globin Gene with A Gamma Beta + Hereditary Persistence of Fetal Hemoglobin in Greeks," Blood 67(2):551-554 (1986).
Wang, H., et al., "One-Step Generation of Mice Carrying Mutations in Multiple Genes By CRISPR/Cas-Mediated Genome Engineering," Cell 153(4):910-918 (2013).
Wang, J., et al., "Homology-Driven Genome Editing in Hematopoietic Stem and Progenitor Cells Using ZFN mRNA and AAV6 Donors," Nat. Biotechnol. 33(12):1256-1263 (2015).
Wang, J., et al., "Highly Efficient Homology-Driven Genome Editing in Human T Cells by Combining Zinc-Finger Nuclease mRNA and AAV6 Donor Delivery," Nucleic Acids Res. 44(3):e30 (2016).
Wang, T., et al., "Genetic Screens in Human Cells Using the CRISPR-Cas9 System," Science 343(6166):80-84 (2013).

(56) References Cited

OTHER PUBLICATIONS

Wang, J., et al., "xCas9 Expands the Scope of Genome Editing with Reduced Efficiency in Rice," Plant Biotechnol. J. 17:709-711 (2019).
Wiedenheft, B., et al., "RNA-Guided Genetic Silencing Systems in Bacteria and Archaea," Nature 482:331-338 (2012).
Wu, X., et al., "Genome-Wide Binding of the CRISPR Endonuclease Cas9 in Mammalian Cells," Nat. Biotechnol. 32(7):670-676 (2014).
Wu, Y., et al., "Correction of a Genetic Disease in Mouse via Use of CRISPR-Cas9," Cell Stem Cell 13(6):659-662 (2013).
Wu, Y., et al., "Highly Efficient Therapeutic Gene Editing of Human Hematopoietic Stem Cells," Nat. Med. 25(5):776-783 (2019).
Xiao, A., et al., "CasOT: A Genome-Wide Cas9/gRNA Off-Target Searching Tool," Bioinformatics 30(8):1180-1182 (2014).
Xu, Q., et al., "Design of 240,000 Orthogonal 25mer DNA Barcode Probes," Proc. Natl. Acad. Sci. 106(7):2289-2294 (2009).
Xu, J., et al., "Transcriptional Silencing of {Gamma}-Globin by BCL11A Involves Long-Range Interactions and Cooperation with SOX6," Genes Dev. 24(8):783-798 (2010).
Yamano, T., et al., "Crystal Structure of Cpf1 in Complex with Guide RNA and Target DNA," Cell 165(4):949-962 (2016).
Yan, W. X., et al., "Functionally Diversse Type V CRISPR-Cas Systems," Science 363:88-91 (2019).
Yang, H., et al., "One-Step Generation of Mice Carrying Reporter and Conditional Alleles by CRISPR/Cas-Mediated Genome Engineering," Cell 154(6):1370-1390 (2013).
Zetsche, B., et al., "A Split-Cas9 Architecture for Inducible Genome Editing and Transcription Modulation," Nat. Biotechnol. 33(2):139-142 (2015).
Zetsche, B., et al., "Cpf1 Is a Single RNA-Guided Endonuclease of a Class 2 CRISPR-Cas System," Cell 163(3):759-771 (2015).
Zou, J., et al., "Gene Targeting of a Disease-Related Gene in Human Induced Pluripotent Stem and Embryonic Stem Cells," Cell Stem Cell 5(1):97-110 (2009).
Zou, J., et al., "Site-Specific Gene Correction of a Point Mutation in Human iPS Cells Derived from an Adult Patient with Sickle Cell Disease," Blood 118(17):4599-4608 (2011).
European Patent Office, International Search Report and Written Opinion dated Jun. 24, 2015 for PCT/US2015/019064.
European Patent Office, International Search Report and Written Opinion dated Jul. 1, 2015 for PCT/US2015/019790.
European Patent Office, International Search Report and Written Opinion dated Sep. 28, 2015 for PCT/US2015/022856.
European Patent Office, International Search Report and Written Opinion dated Jul. 31, 2015 for PCT/US2015/022851.
European Patent Office, International Search Report and Written Opinion dated Aug. 10, 2015 for PCT/US2015/023906.
European Patent Office, International Search Report and Written Opinion dated Jun. 12, 2017 for PCT/US2017/024163.
European Patent Office, International Search Report and Written Opinion dated Jul. 28, 2016 for PCT/US2016/029252.
European Patent Office, International Search Report and Written Opinion dated May 29, 2017 for PCT/US2017/022377.
European Patent Office, International Search Report and Written Opinion dated Aug. 20, 2018 for PCT/US2018/022516.
European Patent Office, International Search Report and Written Opinion dated Dec. 3, 2018 for PCT/US2018/032172.
European Patent Office, International Search Report and Written Opinion dated Mar. 13, 2019 for PCT/US2018/059700.
European Patent Office, International Search Report and Written Opinion dated Jul. 1, 2019 for PCT/US2019/022360.
United States Patent and Trademark Office, International Search Report and Written Opinion for PCT/US2013/075317, dated Apr. 15, 2014, 12 pages.
United States Patent and Trademark Office, International Search Report and Written Opinion for PCT/US2013/075326, dated Aug. 22, 2014, 13 pages.
United States Patent and Trademark Office, International Search Report and Written Opinion for PCT/US2014/027335, dated Jul. 16, 2014, 13 pages.
United States Patent and Trademark Office, International Search Report and Written Opinion for PCT/US2014/028630, dated Jul. 24, 2014, 9 pages.
De Dreuzy, E., et al., "EDIT-301: An Experimental Autologous Cell Therapy Comprising Cas12a-RNP Modified mPB-CD34+ Cells for the Potential Treatment of SCD," Blood 134(Suppl. 1):4636 (2019).
De Dreuzy, E., et al., "Robust Pre-Clinical Results and Large-Scale Manufacturing Process for Edit-301: An Autologous Cell Therapy for the Potential Treatment of SCD," Blood 136(Suppl. 1):45-46 (2020).
Heath, J., et al., "EDIT-301: An Autologous Cell Therapy to Promote Fetal Hemoglobin Expression for the Potential Treatment of Sickle Cell Disease," Hemasphere 4(S1):S292 (2020).
European Patent Office, International Search Report and Written Opinion dated Apr. 13, 2021 for PCT/US2020/063854, 18 pages.
Bernaudin, F., et al., "Long-Term Results of Related Myeloablative Stem-Cell Transplantation to Cure Sickle Cell Disease," Blood 110(7):2749-2756 (2007).
Steinberg, M. H., et al., "Fetal Hemoglobin in Sickle Cell Anemia: A Glass Half Full?" Blood 123(4):481-485 (2014).
Van Diemen, F. R., et al., "CRISPR/Cas9, A Powerful Tool to Target Human Herpesviruses," Cell. Microbiol. 19:e12694 (2017).
Walters, M. C., et al., "Bone Marrow Transplantation for Sickle Cell Disease," New Engl. J. Med. 335(6):369-376 (1996).
European Patent Office, International Search Report and Written Opinion dated Nov. 22, 2022 for PCT/US2022/039192, 13 pages.

* cited by examiner

SEQ ID NO: 996

SEQUENCE LISTING

```
<160> NUMBER OF SEQ ID NOS: 996

<210> SEQ ID NO 1
<211> LENGTH: 1345
<212> TYPE: PRT
<213> ORGANISM: Streptococcus mutans
<220> FEATURE:
<221> NAME/KEY: misc_feature
<222> LOCATION: (10)..(21)
<223> OTHER INFORMATION: N-terminal RuvC-like domain
<220> FEATURE:
<221> NAME/KEY: misc_feature
<222> LOCATION: (759)..(766)
<223> OTHER INFORMATION: RuvC-like domain
<220> FEATURE:
<221> NAME/KEY: misc_feature
<222> LOCATION: (837)..(863)
<223> OTHER INFORMATION: HNH-like domain
<220> FEATURE:
<221> NAME/KEY: misc_feature
<222> LOCATION: (982)..(989)
<223> OTHER INFORMATION: RuvC-like domain

<400> SEQUENCE: 1

Met Lys Lys Pro Tyr Ser Ile Gly Leu Asp Ile Gly Thr Asn Ser Val
1               5                   10                  15

Gly Trp Ala Val Val Thr Asp Asp Tyr Lys Val Pro Ala Lys Lys Met
            20                  25                  30

Lys Val Leu Gly Asn Thr Asp Lys Ser His Ile Glu Lys Asn Leu Leu
        35                  40                  45

Gly Ala Leu Leu Phe Asp Ser Gly Asn Thr Ala Glu Asp Arg Arg Leu
    50                  55                  60

Lys Arg Thr Ala Arg Arg Arg Tyr Thr Arg Arg Arg Asn Arg Ile Leu
65                  70                  75                  80

Tyr Leu Gln Glu Ile Phe Ser Glu Glu Met Gly Lys Val Asp Asp Ser
                85                  90                  95

Phe Phe His Arg Leu Glu Asp Ser Phe Leu Val Thr Glu Asp Lys Arg
            100                 105                 110

Gly Glu Arg His Pro Ile Phe Gly Asn Leu Glu Glu Glu Val Lys Tyr
        115                 120                 125

His Glu Asn Phe Pro Thr Ile Tyr His Leu Arg Gln Tyr Leu Ala Asp
    130                 135                 140

Asn Pro Glu Lys Val Asp Leu Arg Leu Val Tyr Leu Ala Leu Ala His
145                 150                 155                 160
```

-continued

```
Ile Ile Lys Phe Arg Gly His Phe Leu Ile Glu Gly Lys Phe Asp Thr
                165                 170                 175

Arg Asn Asn Asp Val Gln Arg Leu Phe Gln Glu Phe Leu Ala Val Tyr
            180                 185                 190

Asp Asn Thr Phe Glu Asn Ser Ser Leu Gln Glu Gln Asn Val Gln Val
        195                 200                 205

Glu Glu Ile Leu Thr Asp Lys Ile Ser Lys Ser Ala Lys Lys Asp Arg
    210                 215                 220

Val Leu Lys Leu Phe Pro Asn Glu Lys Ser Asn Gly Arg Phe Ala Glu
225                 230                 235                 240

Phe Leu Lys Leu Ile Val Gly Asn Gln Ala Asp Phe Lys Lys His Phe
                245                 250                 255

Glu Leu Glu Glu Lys Ala Pro Leu Gln Phe Ser Lys Asp Thr Tyr Glu
            260                 265                 270

Glu Glu Leu Glu Val Leu Leu Ala Gln Ile Gly Asp Asn Tyr Ala Glu
        275                 280                 285

Leu Phe Leu Ser Ala Lys Lys Leu Tyr Asp Ser Ile Leu Leu Ser Gly
    290                 295                 300

Ile Leu Thr Val Thr Asp Val Gly Thr Lys Ala Pro Leu Ser Ala Ser
305                 310                 315                 320

Met Ile Gln Arg Tyr Asn Glu His Gln Met Asp Leu Ala Gln Leu Lys
                325                 330                 335

Gln Phe Ile Arg Gln Lys Leu Ser Asp Lys Tyr Asn Glu Val Phe Ser
            340                 345                 350

Asp Val Ser Lys Asp Gly Tyr Ala Gly Tyr Ile Asp Gly Lys Thr Asn
        355                 360                 365

Gln Glu Ala Phe Tyr Lys Tyr Leu Lys Gly Leu Leu Asn Lys Ile Glu
    370                 375                 380

Gly Ser Gly Tyr Phe Leu Asp Lys Ile Glu Arg Glu Asp Phe Leu Arg
385                 390                 395                 400

Lys Gln Arg Thr Phe Asp Asn Gly Ser Ile Pro His Gln Ile His Leu
                405                 410                 415

Gln Glu Met Arg Ala Ile Ile Arg Arg Gln Ala Glu Phe Tyr Pro Phe
            420                 425                 430

Leu Ala Asp Asn Gln Asp Arg Ile Glu Lys Leu Leu Thr Phe Arg Ile
        435                 440                 445

Pro Tyr Tyr Val Gly Pro Leu Ala Arg Gly Lys Ser Asp Phe Ala Trp
    450                 455                 460

Leu Ser Arg Lys Ser Ala Asp Lys Ile Thr Pro Trp Asn Phe Asp Glu
465                 470                 475                 480

Ile Val Asp Lys Glu Ser Ser Ala Glu Ala Phe Ile Asn Arg Met Thr
                485                 490                 495

Asn Tyr Asp Leu Tyr Leu Pro Asn Gln Lys Val Leu Pro Lys His Ser
            500                 505                 510

Leu Leu Tyr Glu Lys Phe Thr Val Tyr Asn Glu Leu Thr Lys Val Lys
        515                 520                 525

Tyr Lys Thr Glu Gln Gly Lys Thr Ala Phe Phe Asp Ala Asn Met Lys
    530                 535                 540

Gln Glu Ile Phe Asp Gly Val Phe Lys Val Tyr Arg Lys Val Thr Lys
545                 550                 555                 560

Asp Lys Leu Met Asp Phe Leu Glu Lys Glu Phe Asp Glu Phe Arg Ile
                565                 570                 575

Val Asp Leu Thr Gly Leu Asp Lys Glu Asn Lys Val Phe Asn Ala Ser
```

```
        580                 585                 590

Tyr Gly Thr Tyr His Asp Leu Cys Lys Ile Leu Asp Lys Asp Phe Leu
            595                 600                 605

Asp Asn Ser Lys Asn Glu Lys Ile Leu Glu Asp Ile Val Leu Thr Leu
    610                 615                 620

Thr Leu Phe Glu Asp Arg Glu Met Ile Arg Lys Arg Leu Glu Asn Tyr
625                 630                 635                 640

Ser Asp Leu Leu Thr Lys Glu Gln Val Lys Lys Leu Glu Arg Arg His
                645                 650                 655

Tyr Thr Gly Trp Gly Arg Leu Ser Ala Glu Leu Ile His Gly Ile Arg
            660                 665                 670

Asn Lys Glu Ser Arg Lys Thr Ile Leu Asp Tyr Leu Ile Asp Asp Gly
        675                 680                 685

Asn Ser Asn Arg Asn Phe Met Gln Leu Ile Asn Asp Asp Ala Leu Ser
    690                 695                 700

Phe Lys Glu Glu Ile Ala Lys Ala Gln Val Ile Gly Glu Thr Asp Asn
705                 710                 715                 720

Leu Asn Gln Val Val Ser Asp Ile Ala Gly Ser Pro Ala Ile Lys Lys
                725                 730                 735

Gly Ile Leu Gln Ser Leu Lys Ile Val Asp Glu Leu Val Lys Ile Met
            740                 745                 750

Gly His Gln Pro Glu Asn Ile Val Val Glu Met Ala Arg Glu Asn Gln
        755                 760                 765

Phe Thr Asn Gln Gly Arg Arg Asn Ser Gln Gln Arg Leu Lys Gly Leu
    770                 775                 780

Thr Asp Ser Ile Lys Glu Phe Gly Ser Gln Ile Leu Lys Glu His Pro
785                 790                 795                 800

Val Glu Asn Ser Gln Leu Gln Asn Asp Arg Leu Phe Leu Tyr Tyr Leu
                805                 810                 815

Gln Asn Gly Arg Asp Met Tyr Thr Gly Glu Glu Leu Asp Ile Asp Tyr
            820                 825                 830

Leu Ser Gln Tyr Asp Ile Asp His Ile Ile Pro Gln Ala Phe Ile Lys
        835                 840                 845

Asp Asn Ser Ile Asp Asn Arg Val Leu Thr Ser Ser Lys Glu Asn Arg
    850                 855                 860

Gly Lys Ser Asp Asp Val Pro Ser Lys Asp Val Val Arg Lys Met Lys
865                 870                 875                 880

Ser Tyr Trp Ser Lys Leu Leu Ser Ala Lys Leu Ile Thr Gln Arg Lys
                885                 890                 895

Phe Asp Asn Leu Thr Lys Ala Glu Arg Gly Gly Leu Thr Asp Asp Asp
            900                 905                 910

Lys Ala Gly Phe Ile Lys Arg Gln Leu Val Glu Thr Arg Gln Ile Thr
        915                 920                 925

Lys His Val Ala Arg Ile Leu Asp Glu Arg Phe Asn Thr Glu Thr Asp
    930                 935                 940

Glu Asn Asn Lys Lys Ile Arg Gln Val Lys Ile Val Thr Leu Lys Ser
945                 950                 955                 960

Asn Leu Val Ser Asn Phe Arg Lys Glu Phe Glu Leu Tyr Lys Val Arg
                965                 970                 975

Glu Ile Asn Asp Tyr His His Ala His Asp Ala Tyr Leu Asn Ala Val
            980                 985                 990

Ile Gly Lys Ala Leu Leu Gly Val  Tyr Pro Gln Leu Glu  Pro Glu Phe
        995                 1000                1005
```

Val Tyr Gly Asp Tyr Pro His Phe His Gly His Lys Glu Asn Lys
    1010                1015                1020

Ala Thr Ala Lys Lys Phe Phe Tyr Ser Asn Ile Met Asn Phe Phe
    1025                1030                1035

Lys Lys Asp Asp Val Arg Thr Asp Lys Asn Gly Glu Ile Ile Trp
    1040                1045                1050

Lys Lys Asp Glu His Ile Ser Asn Ile Lys Lys Val Leu Ser Tyr
    1055                1060                1065

Pro Gln Val Asn Ile Val Lys Lys Val Glu Glu Gln Thr Gly Gly
    1070                1075                1080

Phe Ser Lys Glu Ser Ile Leu Pro Lys Gly Asn Ser Asp Lys Leu
    1085                1090                1095

Ile Pro Arg Lys Thr Lys Lys Phe Tyr Trp Asp Thr Lys Lys Tyr
    1100                1105                1110

Gly Gly Phe Asp Ser Pro Ile Val Ala Tyr Ser Ile Leu Val Ile
    1115                1120                1125

Ala Asp Ile Glu Lys Gly Lys Ser Lys Lys Leu Lys Thr Val Lys
    1130                1135                1140

Ala Leu Val Gly Val Thr Ile Met Glu Lys Met Thr Phe Glu Arg
    1145                1150                1155

Asp Pro Val Ala Phe Leu Glu Arg Lys Gly Tyr Arg Asn Val Gln
    1160                1165                1170

Glu Glu Asn Ile Ile Lys Leu Pro Lys Tyr Ser Leu Phe Lys Leu
    1175                1180                1185

Glu Asn Gly Arg Lys Arg Leu Leu Ala Ser Ala Arg Glu Leu Gln
    1190                1195                1200

Lys Gly Asn Glu Ile Val Leu Pro Asn His Leu Gly Thr Leu Leu
    1205                1210                1215

Tyr His Ala Lys Asn Ile His Lys Val Asp Glu Pro Lys His Leu
    1220                1225                1230

Asp Tyr Val Asp Lys His Lys Asp Glu Phe Lys Glu Leu Leu Asp
    1235                1240                1245

Val Val Ser Asn Phe Ser Lys Lys Tyr Thr Leu Ala Glu Gly Asn
    1250                1255                1260

Leu Glu Lys Ile Lys Glu Leu Tyr Ala Gln Asn Asn Gly Glu Asp
    1265                1270                1275

Leu Lys Glu Leu Ala Ser Ser Phe Ile Asn Leu Leu Thr Phe Thr
    1280                1285                1290

Ala Ile Gly Ala Pro Ala Thr Phe Lys Phe Phe Asp Lys Asn Ile
    1295                1300                1305

Asp Arg Lys Arg Tyr Thr Ser Thr Thr Glu Ile Leu Asn Ala Thr
    1310                1315                1320

Leu Ile His Gln Ser Ile Thr Gly Leu Tyr Glu Thr Arg Ile Asp
    1325                1330                1335

Leu Asn Lys Leu Gly Gly Asp
    1340                1345

<210> SEQ ID NO 2
<211> LENGTH: 1368
<212> TYPE: PRT
<213> ORGANISM: Streptococcus pyogenes
<220> FEATURE:
<221> NAME/KEY: misc_feature
<222> LOCATION: (10)..(21)
<223> OTHER INFORMATION: N-terminal RuvC-like domain
<220> FEATURE:
<221> NAME/KEY: misc_feature
<222> LOCATION: (759)..(766)
<223> OTHER INFORMATION: RuvC-like domain
<220> FEATURE:
<221> NAME/KEY: misc_feature
<222> LOCATION: (837)..(863)
<223> OTHER INFORMATION: HNH-like domain
<220> FEATURE:
<221> NAME/KEY: misc_feature
<222> LOCATION: (982)..(989)
<223> OTHER INFORMATION: RuvC-like domain

<400> SEQUENCE: 2

```
Met Asp Lys Lys Tyr Ser Ile Gly Leu Asp Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
        115                 120                 125

His Glu Lys Tyr Pro Thr Ile Tyr His Leu Arg Lys Lys Leu Val Asp
    130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
            180                 185                 190

Asn Gln Leu Phe Glu Glu Asn Pro Ile Asn Ala Ser Gly Val Asp Ala
        195                 200                 205

Lys Ala Ile Leu Ser Ala Arg Leu Ser Lys Ser Arg Arg Leu Glu Asn
    210                 215                 220

Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
            260                 265                 270

Asp Asp Leu Asp Asn Leu Leu Ala Gln Ile Gly Asp Gln Tyr Ala Asp
        275                 280                 285

Leu Phe Leu Ala Ala Lys Asn Leu Ser Asp Ala Ile Leu Leu Ser Asp
    290                 295                 300

Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
                325                 330                 335

Ala Leu Val Arg Gln Gln Leu Pro Glu Lys Tyr Lys Glu Ile Phe Phe
```

```
            340                 345                 350

Asp Gln Ser Lys Asn Gly Tyr Ala Gly Tyr Ile Asp Gly Gly Ala Ser
        355                 360                 365

Gln Glu Glu Phe Tyr Lys Phe Ile Lys Pro Ile Leu Glu Lys Met Asp
    370                 375                 380

Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
                405                 410                 415

Gly Glu Leu His Ala Ile Leu Arg Arg Gln Glu Asp Phe Tyr Pro Phe
            420                 425                 430

Leu Lys Asp Asn Arg Glu Lys Ile Glu Lys Ile Leu Thr Phe Arg Ile
        435                 440                 445

Pro Tyr Tyr Val Gly Pro Leu Ala Arg Gly Asn Ser Arg Phe Ala Trp
    450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
                485                 490                 495

Asn Phe Asp Lys Asn Leu Pro Asn Glu Lys Val Leu Pro Lys His Ser
            500                 505                 510

Leu Leu Tyr Glu Tyr Phe Thr Val Tyr Asn Glu Leu Thr Lys Val Lys
        515                 520                 525

Tyr Val Thr Glu Gly Met Arg Lys Pro Ala Phe Leu Ser Gly Glu Gln
    530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
                565                 570                 575

Ser Val Glu Ile Ser Gly Val Glu Asp Arg Phe Asn Ala Ser Leu Gly
            580                 585                 590

Thr Tyr His Asp Leu Leu Lys Ile Ile Lys Asp Lys Asp Phe Leu Asp
        595                 600                 605

Asn Glu Glu Asn Glu Asp Ile Leu Glu Asp Ile Val Leu Thr Leu Thr
    610                 615                 620

Leu Phe Glu Asp Arg Glu Met Ile Glu Glu Arg Leu Lys Thr Tyr Ala
625                 630                 635                 640

His Leu Phe Asp Asp Lys Val Met Lys Gln Leu Lys Arg Arg Arg Tyr
                645                 650                 655

Thr Gly Trp Gly Arg Leu Ser Arg Lys Leu Ile Asn Gly Ile Arg Asp
            660                 665                 670

Lys Gln Ser Gly Lys Thr Ile Leu Asp Phe Leu Lys Ser Asp Gly Phe
        675                 680                 685

Ala Asn Arg Asn Phe Met Gln Leu Ile His Asp Asp Ser Leu Thr Phe
    690                 695                 700

Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
                725                 730                 735

Ile Leu Gln Thr Val Lys Val Val Asp Glu Leu Val Lys Val Met Gly
            740                 745                 750

Arg His Lys Pro Glu Asn Ile Val Ile Glu Met Ala Arg Glu Asn Gln
        755                 760                 765
```

-continued

```
Thr Thr Gln Lys Gly Gln Lys Asn Ser Arg Glu Arg Met Lys Arg Ile
    770                 775                 780

Glu Glu Gly Ile Lys Glu Leu Gly Ser Gln Ile Leu Lys Glu His Pro
785                 790                 795                 800

Val Glu Asn Thr Gln Leu Gln Asn Glu Lys Leu Tyr Leu Tyr Tyr Leu
                805                 810                 815

Gln Asn Gly Arg Asp Met Tyr Val Asp Gln Glu Leu Asp Ile Asn Arg
            820                 825                 830

Leu Ser Asp Tyr Asp Val Asp His Ile Val Pro Gln Ser Phe Leu Lys
        835                 840                 845

Asp Asp Ser Ile Asp Asn Lys Val Leu Thr Arg Ser Asp Lys Asn Arg
    850                 855                 860

Gly Lys Ser Asp Asn Val Pro Ser Glu Glu Val Val Lys Lys Met Lys
865                 870                 875                 880

Asn Tyr Trp Arg Gln Leu Leu Asn Ala Lys Leu Ile Thr Gln Arg Lys
                885                 890                 895

Phe Asp Asn Leu Thr Lys Ala Glu Arg Gly Gly Leu Ser Glu Leu Asp
            900                 905                 910

Lys Ala Gly Phe Ile Lys Arg Gln Leu Val Glu Thr Arg Gln Ile Thr
        915                 920                 925

Lys His Val Ala Gln Ile Leu Asp Ser Arg Met Asn Thr Lys Tyr Asp
    930                 935                 940

Glu Asn Asp Lys Leu Ile Arg Glu Val Lys Val Ile Thr Leu Lys Ser
945                 950                 955                 960

Lys Leu Val Ser Asp Phe Arg Lys Asp Phe Gln Phe Tyr Lys Val Arg
                965                 970                 975

Glu Ile Asn Asn Tyr His His Ala His Asp Ala Tyr Leu Asn Ala Val
            980                 985                 990

Val Gly Thr Ala Leu Ile Lys Lys  Tyr Pro Lys Leu Glu  Ser Glu Phe
        995                 1000                1005

Val Tyr  Gly Asp Tyr Lys Val  Tyr Asp Val Arg Lys  Met Ile Ala
    1010                1015                1020

Lys Ser  Glu Gln Glu Ile Gly  Lys Ala Thr Ala Lys  Tyr Phe Phe
    1025                1030                1035

Tyr Ser  Asn Ile Met Asn Phe  Phe Lys Thr Glu Ile  Thr Leu Ala
    1040                1045                1050

Asn Gly  Glu Ile Arg Lys Arg  Pro Leu Ile Glu Thr  Asn Gly Glu
    1055                1060                1065

Thr Gly  Glu Ile Val Trp Asp  Lys Gly Arg Asp Phe  Ala Thr Val
    1070                1075                1080

Arg Lys  Val Leu Ser Met Pro  Gln Val Asn Ile Val  Lys Lys Thr
    1085                1090                1095

Glu Val  Gln Thr Gly Gly Phe  Ser Lys Glu Ser Ile  Leu Pro Lys
    1100                1105                1110

Arg Asn  Ser Asp Lys Leu Ile  Ala Arg Lys Lys Asp  Trp Asp Pro
    1115                1120                1125

Lys Lys  Tyr Gly Gly Phe Asp  Ser Pro Thr Val Ala  Tyr Ser Val
    1130                1135                1140

Leu Val  Val Ala Lys Val Glu  Lys Gly Lys Ser Lys  Lys Leu Lys
    1145                1150                1155

Ser Val  Lys Glu Leu Leu Gly  Ile Thr Ile Met Glu  Arg Ser Ser
    1160                1165                1170
```

-continued

Phe Glu Lys Asn Pro Ile Asp Phe Leu Glu Ala Lys Gly Tyr Lys
1175 1180 1185

Glu Val Lys Lys Asp Leu Ile Ile Lys Leu Pro Lys Tyr Ser Leu
1190 1195 1200

Phe Glu Leu Glu Asn Gly Arg Lys Arg Met Leu Ala Ser Ala Gly
1205 1210 1215

Glu Leu Gln Lys Gly Asn Glu Leu Ala Leu Pro Ser Lys Tyr Val
1220 1225 1230

Asn Phe Leu Tyr Leu Ala Ser His Tyr Glu Lys Leu Lys Gly Ser
1235 1240 1245

Pro Glu Asp Asn Glu Gln Lys Gln Leu Phe Val Glu Gln His Lys
1250 1255 1260

His Tyr Leu Asp Glu Ile Ile Glu Gln Ile Ser Glu Phe Ser Lys
1265 1270 1275

Arg Val Ile Leu Ala Asp Ala Asn Leu Asp Lys Val Leu Ser Ala
1280 1285 1290

Tyr Asn Lys His Arg Asp Lys Pro Ile Arg Glu Gln Ala Glu Asn
1295 1300 1305

Ile Ile His Leu Phe Thr Leu Thr Asn Leu Gly Ala Pro Ala Ala
1310 1315 1320

Phe Lys Tyr Phe Asp Thr Thr Ile Asp Arg Lys Arg Tyr Thr Ser
1325 1330 1335

Thr Lys Glu Val Leu Asp Ala Thr Leu Ile His Gln Ser Ile Thr
1340 1345 1350

Gly Leu Tyr Glu Thr Arg Ile Asp Leu Ser Gln Leu Gly Gly Asp
1355 1360 1365

<210> SEQ ID NO 3
<211> LENGTH: 4107
<212> TYPE: DNA
<213> ORGANISM: Streptococcus pyogenes

<400> SEQUENCE: 3
atggataaaa agtacagcat cgggctggac atcggtacaa actcagtggg gtgggccgtg 60
attacggacg agtacaaggt accctccaaa aaatttaaag tgctgggtaa cacggacaga 120
cactctataa agaaaaatct tattggagcc ttgctgttcg actcaggcga gacagccgaa 180
gccacaaggt tgaagcggac cgccaggagg cggtatacca ggagaaagaa ccgcatatgc 240
tacctgcaag aaatcttcag taacgagatg gcaaaggttg acgatagctt tttccatcgc 300
ctggaagaat cctttcttgt tgaggaagac aagaagcacg aacggcaccc catctttggc 360
aatattgtcg acgaagtggc atatcacgaa aagtacccga ctatctacca cctcaggaag 420
aagctggtgg actctaccga taaggcggac ctcagactta tttatttggc actcgcccac 480
atgattaaat ttagaggaca tttcttgatc gagggcgacc tgaacccgga caacagtgac 540
gtcgataagc tgttcatcca acttgtgcag acctacaatc aactgttcga agaaaaccct 600
ataaatgctt caggagtcga cgctaaagca atcctgtccg cgcgcctctc aaaatctaga 660
agacttgaga atctgattgc tcagttgccc ggggaaaaga aaaatggatt gtttggcaac 720
ctgatcgccc tcagtctcgg actgacccca aatttcaaaa gtaacttcga cctggccgaa 780
gacgctaagc tccagctgtc caaggacaca tacgatgacg acctcgacaa tctgctggcc 840
cagattgggg atcagtacgc cgatctcttt ttggcagcaa agaacctgtc cgacgccatc 900
ctgttgagcg atatcttgag agtgaacacc gaaattacta aagcacccct tagcgcatct 960

-continued atgatcaagc ggtacgacga gcatcatcag gatctgaccc tgctgaaggc tcttgtgagg 1020
caacagctcc ccgaaaaata caaggaaatc ttctttgacc agagcaaaaa cggctacgct 1080
ggctatatag atggtggggc cagtcaggag gaattctata aattcatcaa gcccattctc 1140
gagaaaatgg acggcacaga ggagttgctg gtcaaactta acagggagga cctgctgcgg 1200
aagcagcgga cctttgacaa cgggtctatc ccccaccaga ttcatctggg cgaactgcac 1260
gcaatcctga ggaggcagga ggatttttat ccttttctta aagataaccg cgagaaaata 1320
gaaaagattc ttacattcag gatcccgtac tacgtgggac ctctcgcccg gggcaattca 1380
cggtttgcct ggatgacaag gaagtcagag gagactatta caccttggaa cttcgaagaa 1440
gtggtggaca agggtgcatc tgcccagtct ttcatcgagc ggatgacaaa ttttgacaag 1500
aacctcccta atgagaaggt gctgcccaaa cattctctgc tctacgagta ctttaccgtc 1560
tacaatgaac tgactaaagt caagtacgtc accgagggaa tgaggaagcc ggcattcctt 1620
agtggagaac agaagaaggc gattgtagac ctgttgttca agaccaacag gaaggtgact 1680
gtgaagcaac ttaaagaaga ctactttaag aagatcgaat gttttgacag tgtggaaatt 1740
tcaggggttg aagaccgctt caatgcgtca ttggggactt accatgatct tctcaagatc 1800
ataaaggaca aagacttcct ggacaacgaa gaaaatgagg atattctcga agacatcgtc 1860
ctcaccctga ccctgttcga agacagggaa atgatagaag agcgcttgaa aacctatgcc 1920
cacctcttcg acgataaagt tatgaagcag ctgaagcgca ggagatacac aggatgggga 1980
agattgtcaa ggaagctgat caatggaatt agggataaac agagtggcaa gaccatactg 2040
gatttcctca aatctgatgg cttcgccaat aggaacttca tgcaactgat tcacgatgac 2100
tctcttacct tcaaggagga cattcaaaag gctcaggtga gcgggcaggg agactccctt 2160
catgaacaca tcgcgaattt ggcaggttcc cccgctatta aaaagggcat ccttcaaact 2220
gtcaaggtgg tggatgaatt ggtcaaggta atgggcagac ataagccaga aaatattgtg 2280
atcgagatgg cccgcgaaaa ccagaccaca cagaagggcc agaaaaatag tagagagcgg 2340
atgaagagga tcgaggaggg catcaaagag ctgggatctc agattctcaa agaacacccc 2400
gtagaaaaca cacagctgca gaacgaaaaa ttgtacttgt actatctgca gaacggcaga 2460
gacatgtacg tcgaccaaga acttgatatt aatagactgt ccgactatga cgtagaccat 2520
atcgtgcccc agtccttcct gaaggacgac tccattgata acaaagtctt gacaagaagc 2580
gacaagaaca ggggtaaaag tgataatgtg cctagcgagg aggtggtgaa aaaaatgaag 2640
aactactggc gacagctgct taatgcaaag ctcattacac aacggaagtt cgataatctg 2700
acgaaagcag agagaggtgg cttgtctgag ttggacaagg cagggtttat taagcggcag 2760
ctggtggaaa ctaggcagat cacaaagcac gtggcgcaga ttttggacag ccggatgaac 2820
acaaaatacg acgaaaatga taaactgata cgagaggtca aagttatcac gctgaaaagc 2880
aagctggtgt ccgattttcg gaaagacttc cagttctaca aagttcgcga gattaataac 2940
taccatcatg ctcacgatgc gtacctgaac gctgttgtcg ggaccgcctt gataaagaag 3000
tacccaaagc tggaatccga gttcgtatac ggggattaca aagtgtacga tgtgaggaaa 3060
atgatagcca agtccgagca ggagattgga aaggccacag ctaagtactt cttttattct 3120
aacatcatga atttttttaa gacggaaatt accctggcca acggagagat cagaaagcgg 3180
ccccttatag agacaaatgg tgaaacaggt gaaatcgtct gggataaggg cagggatttc 3240
gctactgtga ggaaggtgct gagtatgcca caggtaaata tcgtgaaaaa aaccgaagta 3300
cagaccggag gattttccaa ggaaagcatt ttgcctaaaa gaaactcaga caagctcatc 3360

```
gcccgcaaga aagattggga ccctaagaaa tacgggggat ttgactcacc caccgtagcc   3420

tattctgtgc tggtggtagc taaggtggaa aaaggaaagt ctaagaagct gaagtccgtg   3480

aaggaactct tgggaatcac tatcatggaa agatcatcct ttgaaaagaa ccctatcgat   3540

ttcctggagg ctaagggtta caaggaggtc aagaaagacc tcatcattaa actgccaaaa   3600

tactctctct tcgagctgga aaatggcagg aagagaatgt tggccagcgc cggagagctg   3660

caaaagggaa acgagcttgc tctgccctcc aaatatgtta attttctcta tctcgcttcc   3720

cactatgaaa agctgaaagg gtctcccgaa gataacgagc agaagcagct gttcgtcgaa   3780

cagcacaagc actatctgga tgaaataatc gaacaaataa gcgagttcag caaaagggtt   3840

atcctggcgg atgctaattt ggacaaagta ctgtctgctt ataacaagca ccgggataag   3900

cctattaggg aacaagccga gaatataatt cacctcttta cactcacgaa tctcggagcc   3960

cccgccgcct tcaaatactt tgatacgact atcgaccgga aacggtatac cagtaccaaa   4020

gaggtcctcg atgccaccct catccaccag tcaattactg gcctgtacga aacacggatc   4080

gacctctctc aactgggcgg cgactag                                      4107
```

```
<210> SEQ ID NO 4
<211> LENGTH: 1388
<212> TYPE: PRT
<213> ORGANISM: Streptococcus thermophilus
<220> FEATURE:
<221> NAME/KEY: misc_feature
<222> LOCATION: (10)..(21)
<223> OTHER INFORMATION: N-terminal RuvC-like domain
<220> FEATURE:
<221> NAME/KEY: misc_feature
<222> LOCATION: (760)..(767)
<223> OTHER INFORMATION: RuvC-like domain
<220> FEATURE:
<221> NAME/KEY: misc_feature
<222> LOCATION: (844)..(870)
<223> OTHER INFORMATION: HNH-like domain
<220> FEATURE:
<221> NAME/KEY: misc_feature
<222> LOCATION: (989)..(996)
<223> OTHER INFORMATION: RuvC-like domain

<400> SEQUENCE: 4

Met Thr Lys Pro Tyr Ser Ile Gly Leu Asp Ile Gly Thr Asn Ser Val
1               5                   10                  15

Gly Trp Ala Val Thr Thr Asp Asn Tyr Lys Val Pro Ser Lys Lys Met
            20                  25                  30

Lys Val Leu Gly Asn Thr Ser Lys Lys Tyr Ile Lys Lys Asn Leu Leu
        35                  40                  45

Gly Val Leu Leu Phe Asp Ser Gly Ile Thr Ala Glu Gly Arg Arg Leu
    50                  55                  60

Lys Arg Thr Ala Arg Arg Arg Tyr Thr Arg Arg Arg Asn Arg Ile Leu
65                  70                  75                  80

Tyr Leu Gln Glu Ile Phe Ser Thr Glu Met Ala Thr Leu Asp Asp Ala
                85                  90                  95

Phe Phe Gln Arg Leu Asp Asp Ser Phe Leu Val Pro Asp Asp Lys Arg
            100                 105                 110

Asp Ser Lys Tyr Pro Ile Phe Gly Asn Leu Val Glu Glu Lys Ala Tyr
        115                 120                 125

His Asp Glu Phe Pro Thr Ile Tyr His Leu Arg Lys Tyr Leu Ala Asp
    130                 135                 140

Ser Thr Lys Lys Ala Asp Leu Arg Leu Val Tyr Leu Ala Leu Ala His
```

-continued

```
145                 150                 155                 160

Met Ile Lys Tyr Arg Gly His Phe Leu Ile Glu Gly Glu Phe Asn Ser
                165                 170                 175

Lys Asn Asn Asp Ile Gln Lys Asn Phe Gln Asp Phe Leu Asp Thr Tyr
            180                 185                 190

Asn Ala Ile Phe Glu Ser Asp Leu Ser Leu Glu Asn Ser Lys Gln Leu
        195                 200                 205

Glu Glu Ile Val Lys Asp Lys Ile Ser Lys Leu Glu Lys Lys Asp Arg
    210                 215                 220

Ile Leu Lys Leu Phe Pro Gly Glu Lys Asn Ser Gly Ile Phe Ser Glu
225                 230                 235                 240

Phe Leu Lys Leu Ile Val Gly Asn Gln Ala Asp Phe Arg Lys Cys Phe
                245                 250                 255

Asn Leu Asp Glu Lys Ala Ser Leu His Phe Ser Lys Glu Ser Tyr Asp
            260                 265                 270

Glu Asp Leu Glu Thr Leu Leu Gly Tyr Ile Gly Asp Asp Tyr Ser Asp
        275                 280                 285

Val Phe Leu Lys Ala Lys Lys Leu Tyr Asp Ala Ile Leu Leu Ser Gly
    290                 295                 300

Phe Leu Thr Val Thr Asp Asn Glu Thr Glu Ala Pro Leu Ser Ser Ala
305                 310                 315                 320

Met Ile Lys Arg Tyr Asn Glu His Lys Glu Asp Leu Ala Leu Leu Lys
                325                 330                 335

Glu Tyr Ile Arg Asn Ile Ser Leu Lys Thr Tyr Asn Glu Val Phe Lys
            340                 345                 350

Asp Asp Thr Lys Asn Gly Tyr Ala Gly Tyr Ile Asp Gly Lys Thr Asn
        355                 360                 365

Gln Glu Asp Phe Tyr Val Tyr Leu Lys Lys Leu Leu Ala Glu Phe Glu
    370                 375                 380

Gly Ala Asp Tyr Phe Leu Glu Lys Ile Asp Arg Glu Asp Phe Leu Arg
385                 390                 395                 400

Lys Gln Arg Thr Phe Asp Asn Gly Ser Ile Pro Tyr Gln Ile His Leu
                405                 410                 415

Gln Glu Met Arg Ala Ile Leu Asp Lys Gln Ala Lys Phe Tyr Pro Phe
            420                 425                 430

Leu Ala Lys Asn Lys Glu Arg Ile Glu Lys Ile Leu Thr Phe Arg Ile
        435                 440                 445

Pro Tyr Tyr Val Gly Pro Leu Ala Arg Gly Asn Ser Asp Phe Ala Trp
    450                 455                 460

Ser Ile Arg Lys Arg Asn Glu Lys Ile Thr Pro Trp Asn Phe Glu Asp
465                 470                 475                 480

Val Ile Asp Lys Glu Ser Ser Ala Glu Ala Phe Ile Asn Arg Met Thr
                485                 490                 495

Ser Phe Asp Leu Tyr Leu Pro Glu Glu Lys Val Leu Pro Lys His Ser
            500                 505                 510

Leu Leu Tyr Glu Thr Phe Asn Val Tyr Asn Glu Leu Thr Lys Val Arg
        515                 520                 525

Phe Ile Ala Glu Ser Met Arg Asp Tyr Gln Phe Leu Asp Ser Lys Gln
    530                 535                 540

Lys Lys Asp Ile Val Arg Leu Tyr Phe Lys Asp Lys Arg Lys Val Thr
545                 550                 555                 560

Asp Lys Asp Ile Ile Glu Tyr Leu His Ala Ile Tyr Gly Tyr Asp Gly
                565                 570                 575
```

-continued

Ile Glu Leu Lys Gly Ile Glu Lys Gln Phe Asn Ser Ser Leu Ser Thr
580 585 590

Tyr His Asp Leu Leu Asn Ile Ile Asn Asp Lys Glu Phe Leu Asp Asp
595 600 605

Ser Ser Asn Glu Ala Ile Ile Glu Glu Ile Ile His Thr Leu Thr Ile
610 615 620

Phe Glu Asp Arg Glu Met Ile Lys Gln Arg Leu Ser Lys Phe Glu Asn
625 630 635 640

Ile Phe Asp Lys Ser Val Leu Lys Lys Leu Ser Arg Arg His Tyr Thr
645 650 655

Gly Trp Gly Lys Leu Ser Ala Lys Leu Ile Asn Gly Ile Arg Asp Glu
660 665 670

Lys Ser Gly Asn Thr Ile Leu Asp Tyr Leu Ile Asp Asp Gly Ile Ser
675 680 685

Asn Arg Asn Phe Met Gln Leu Ile His Asp Asp Ala Leu Ser Phe Lys
690 695 700

Lys Lys Ile Gln Lys Ala Gln Ile Ile Gly Asp Glu Asp Lys Gly Asn
705 710 715 720

Ile Lys Glu Val Val Lys Ser Leu Pro Gly Ser Pro Ala Ile Lys Lys
725 730 735

Gly Ile Leu Gln Ser Ile Lys Ile Val Asp Glu Leu Val Lys Val Met
740 745 750

Gly Gly Arg Lys Pro Glu Ser Ile Val Val Glu Met Ala Arg Glu Asn
755 760 765

Gln Tyr Thr Asn Gln Gly Lys Ser Asn Ser Gln Gln Arg Leu Lys Arg
770 775 780

Leu Glu Lys Ser Leu Lys Glu Leu Gly Ser Lys Ile Leu Lys Glu Asn
785 790 795 800

Ile Pro Ala Lys Leu Ser Lys Ile Asp Asn Asn Ala Leu Gln Asn Asp
805 810 815

Arg Leu Tyr Leu Tyr Tyr Leu Gln Asn Gly Lys Asp Met Tyr Thr Gly
820 825 830

Asp Asp Leu Asp Ile Asp Arg Leu Ser Asn Tyr Asp Ile Asp His Ile
835 840 845

Ile Pro Gln Ala Phe Leu Lys Asp Asn Ser Ile Asp Asn Lys Val Leu
850 855 860

Val Ser Ser Ala Ser Asn Arg Gly Lys Ser Asp Asp Val Pro Ser Leu
865 870 875 880

Glu Val Val Lys Lys Arg Lys Thr Phe Trp Tyr Gln Leu Leu Lys Ser
885 890 895

Lys Leu Ile Ser Gln Arg Lys Phe Asp Asn Leu Thr Lys Ala Glu Arg
900 905 910

Gly Gly Leu Ser Pro Glu Asp Lys Ala Gly Phe Ile Gln Arg Gln Leu
915 920 925

Val Glu Thr Arg Gln Ile Thr Lys His Val Ala Arg Leu Leu Asp Glu
930 935 940

Lys Phe Asn Asn Lys Lys Asp Glu Asn Asn Arg Ala Val Arg Thr Val
945 950 955 960

Lys Ile Ile Thr Leu Lys Ser Thr Leu Val Ser Gln Phe Arg Lys Asp
965 970 975

Phe Glu Leu Tyr Lys Val Arg Glu Ile Asn Asp Phe His His Ala His
980 985 990

-continued

```
Asp Ala Tyr Leu Asn Ala Val Val  Ala Ser Ala Leu Leu  Lys Lys Tyr
        995                 1000                 1005

Pro Lys  Leu Glu Pro Glu Phe  Val Tyr Gly Asp Tyr  Pro Lys Tyr
    1010                 1015                 1020

Asn Ser  Phe Arg Glu Arg Lys  Ser Ala Thr Glu Lys  Val Tyr Phe
    1025                 1030                 1035

Tyr Ser  Asn Ile Met Asn Ile  Phe Lys Lys Ser Ile  Ser Leu Ala
    1040                 1045                 1050

Asp Gly  Arg Val Ile Glu Arg  Pro Leu Ile Glu Val  Asn Glu Glu
    1055                 1060                 1065

Thr Gly  Glu Ser Val Trp Asn  Lys Glu Ser Asp Leu  Ala Thr Val
    1070                 1075                 1080

Arg Arg  Val Leu Ser Tyr Pro  Gln Val Asn Val Val  Lys Lys Val
    1085                 1090                 1095

Glu Glu  Gln Asn His Gly Leu  Asp Arg Gly Lys Pro  Lys Gly Leu
    1100                 1105                 1110

Phe Asn  Ala Asn Leu Ser Ser  Lys Pro Lys Pro Asn  Ser Asn Glu
    1115                 1120                 1125

Asn Leu  Val Gly Ala Lys Glu  Tyr Leu Asp Pro Lys  Lys Tyr Gly
    1130                 1135                 1140

Gly Tyr  Ala Gly Ile Ser Asn  Ser Phe Thr Val Leu  Val Lys Gly
    1145                 1150                 1155

Thr Ile  Glu Lys Gly Ala Lys  Lys Lys Ile Thr Asn  Val Leu Glu
    1160                 1165                 1170

Phe Gln  Gly Ile Ser Ile Leu  Asp Arg Ile Asn Tyr  Arg Lys Asp
    1175                 1180                 1185

Lys Leu  Asn Phe Leu Leu Glu  Lys Gly Tyr Lys Asp  Ile Glu Leu
    1190                 1195                 1200

Ile Ile  Glu Leu Pro Lys Tyr  Ser Leu Phe Glu Leu  Ser Asp Gly
    1205                 1210                 1215

Ser Arg  Arg Met Leu Ala Ser  Ile Leu Ser Thr Asn  Asn Lys Arg
    1220                 1225                 1230

Gly Glu  Ile His Lys Gly Asn  Gln Ile Phe Leu Ser  Gln Lys Phe
    1235                 1240                 1245

Val Lys  Leu Leu Tyr His Ala  Lys Arg Ile Ser Asn  Thr Ile Asn
    1250                 1255                 1260

Glu Asn  His Arg Lys Tyr Val  Glu Asn His Lys Lys  Glu Phe Glu
    1265                 1270                 1275

Glu Leu  Phe Tyr Tyr Ile Leu  Glu Phe Asn Glu Asn  Tyr Val Gly
    1280                 1285                 1290

Ala Lys  Lys Asn Gly Lys Leu  Leu Asn Ser Ala Phe  Gln Ser Trp
    1295                 1300                 1305

Gln Asn  His Ser Ile Asp Glu  Leu Cys Ser Ser Phe  Ile Gly Pro
    1310                 1315                 1320

Thr Gly  Ser Glu Arg Lys Gly  Leu Phe Glu Leu Thr  Ser Arg Gly
    1325                 1330                 1335

Ser Ala  Ala Asp Phe Glu Phe  Leu Gly Val Lys Ile  Pro Arg Tyr
    1340                 1345                 1350

Arg Asp  Tyr Thr Pro Ser Ser  Leu Leu Lys Asp Ala  Thr Leu Ile
    1355                 1360                 1365

His Gln  Ser Val Thr Gly Leu  Tyr Glu Thr Arg Ile  Asp Leu Ala
    1370                 1375                 1380

Lys Leu  Gly Glu Gly
```

1385

<210> SEQ ID NO 5
<211> LENGTH: 1334
<212> TYPE: PRT
<213> ORGANISM: Listeria innocua
<220> FEATURE:
<221> NAME/KEY: misc_feature
<222> LOCATION: (10)..(21)
<223> OTHER INFORMATION: N-terminal RuvC-like domain
<220> FEATURE:
<221> NAME/KEY: misc_feature
<222> LOCATION: (762)..(769)
<223> OTHER INFORMATION: RuvC-like domain
<220> FEATURE:
<221> NAME/KEY: misc_feature
<222> LOCATION: (840)..(866)
<223> OTHER INFORMATION: HNH-like domain
<220> FEATURE:
<221> NAME/KEY: misc_feature
<222> LOCATION: (985)..(992)
<223> OTHER INFORMATION: RuvC-like domain

<400> SEQUENCE: 5

```
Met Lys Lys Pro Tyr Thr Ile Gly Leu Asp Ile Gly Thr Asn Ser Val
1               5                   10                  15

Gly Trp Ala Val Leu Thr Asp Gln Tyr Asp Leu Val Lys Arg Lys Met
            20                  25                  30

Lys Ile Ala Gly Asp Ser Glu Lys Lys Gln Ile Lys Lys Asn Phe Trp
        35                  40                  45

Gly Val Arg Leu Phe Asp Glu Gly Gln Thr Ala Ala Asp Arg Arg Met
    50                  55                  60

Ala Arg Thr Ala Arg Arg Arg Ile Glu Arg Arg Arg Asn Arg Ile Ser
65                  70                  75                  80

Tyr Leu Gln Gly Ile Phe Ala Glu Glu Met Ser Lys Thr Asp Ala Asn
                85                  90                  95

Phe Phe Cys Arg Leu Ser Asp Ser Phe Tyr Val Asp Asn Glu Lys Arg
            100                 105                 110

Asn Ser Arg His Pro Phe Phe Ala Thr Ile Glu Glu Glu Val Glu Tyr
        115                 120                 125

His Lys Asn Tyr Pro Thr Ile Tyr His Leu Arg Glu Glu Leu Val Asn
    130                 135                 140

Ser Ser Glu Lys Ala Asp Leu Arg Leu Val Tyr Leu Ala Leu Ala His
145                 150                 155                 160

Ile Ile Lys Tyr Arg Gly Asn Phe Leu Ile Glu Gly Ala Leu Asp Thr
                165                 170                 175

Gln Asn Thr Ser Val Asp Gly Ile Tyr Lys Gln Phe Ile Gln Thr Tyr
            180                 185                 190

Asn Gln Val Phe Ala Ser Gly Ile Glu Asp Gly Ser Leu Lys Lys Leu
        195                 200                 205

Glu Asp Asn Lys Asp Val Ala Lys Ile Leu Val Glu Lys Val Thr Arg
    210                 215                 220

Lys Glu Lys Leu Glu Arg Ile Leu Lys Leu Tyr Pro Gly Glu Lys Ser
225                 230                 235                 240

Ala Gly Met Phe Ala Gln Phe Ile Ser Leu Ile Val Gly Ser Lys Gly
                245                 250                 255

Asn Phe Gln Lys Pro Phe Asp Leu Ile Glu Lys Ser Asp Ile Glu Cys
            260                 265                 270

Ala Lys Asp Ser Tyr Glu Glu Asp Leu Glu Ser Leu Leu Ala Leu Ile
        275                 280                 285
```

-continued

```
Gly Asp Glu Tyr Ala Glu Leu Phe Val Ala Ala Lys Asn Ala Tyr Ser
    290                 295                 300

Ala Val Val Leu Ser Ser Ile Ile Thr Val Ala Glu Thr Glu Thr Asn
305                 310                 315                 320

Ala Lys Leu Ser Ala Ser Met Ile Glu Arg Phe Asp Thr His Glu Glu
                325                 330                 335

Asp Leu Gly Glu Leu Lys Ala Phe Ile Lys Leu His Leu Pro Lys His
            340                 345                 350

Tyr Glu Glu Ile Phe Ser Asn Thr Glu Lys His Gly Tyr Ala Gly Tyr
        355                 360                 365

Ile Asp Gly Lys Thr Lys Gln Ala Asp Phe Tyr Lys Tyr Met Lys Met
    370                 375                 380

Thr Leu Glu Asn Ile Glu Gly Ala Asp Tyr Phe Ile Ala Lys Ile Glu
385                 390                 395                 400

Lys Glu Asn Phe Leu Arg Lys Gln Arg Thr Phe Asp Asn Gly Ala Ile
                405                 410                 415

Pro His Gln Leu His Leu Glu Glu Leu Glu Ala Ile Leu His Gln Gln
            420                 425                 430

Ala Lys Tyr Tyr Pro Phe Leu Lys Glu Asn Tyr Asp Lys Ile Lys Ser
        435                 440                 445

Leu Val Thr Phe Arg Ile Pro Tyr Phe Val Gly Pro Leu Ala Asn Gly
    450                 455                 460

Gln Ser Glu Phe Ala Trp Leu Thr Arg Lys Ala Asp Gly Glu Ile Arg
465                 470                 475                 480

Pro Trp Asn Ile Glu Glu Lys Val Asp Phe Gly Lys Ser Ala Val Asp
                485                 490                 495

Phe Ile Glu Lys Met Thr Asn Lys Asp Thr Tyr Leu Pro Lys Glu Asn
            500                 505                 510

Val Leu Pro Lys His Ser Leu Cys Tyr Gln Lys Tyr Leu Val Tyr Asn
        515                 520                 525

Glu Leu Thr Lys Val Arg Tyr Ile Asn Asp Gln Gly Lys Thr Ser Tyr
    530                 535                 540

Phe Ser Gly Gln Glu Lys Glu Gln Ile Phe Asn Asp Leu Phe Lys Gln
545                 550                 555                 560

Lys Arg Lys Val Lys Lys Lys Asp Leu Glu Leu Phe Leu Arg Asn Met
                565                 570                 575

Ser His Val Glu Ser Pro Thr Ile Glu Gly Leu Glu Asp Ser Phe Asn
            580                 585                 590

Ser Ser Tyr Ser Thr Tyr His Asp Leu Leu Lys Val Gly Ile Lys Gln
        595                 600                 605

Glu Ile Leu Asp Asn Pro Val Asn Thr Glu Met Leu Glu Asn Ile Val
    610                 615                 620

Lys Ile Leu Thr Val Phe Glu Asp Lys Arg Met Ile Lys Glu Gln Leu
625                 630                 635                 640

Gln Gln Phe Ser Asp Val Leu Asp Gly Val Val Leu Lys Lys Leu Glu
                645                 650                 655

Arg Arg His Tyr Thr Gly Trp Gly Arg Leu Ser Ala Lys Leu Leu Met
            660                 665                 670

Gly Ile Arg Asp Lys Gln Ser His Leu Thr Ile Leu Asp Tyr Leu Met
        675                 680                 685

Asn Asp Asp Gly Leu Asn Arg Asn Leu Met Gln Leu Ile Asn Asp Ser
    690                 695                 700
```

-continued

```
Asn Leu Ser Phe Lys Ser Ile Ile Glu Lys Glu Gln Val Thr Thr Ala
705                 710                 715                 720

Asp Lys Asp Ile Gln Ser Ile Val Ala Asp Leu Ala Gly Ser Pro Ala
                725                 730                 735

Ile Lys Lys Gly Ile Leu Gln Ser Leu Lys Ile Val Asp Glu Leu Val
            740                 745                 750

Ser Val Met Gly Tyr Pro Pro Gln Thr Ile Val Val Glu Met Ala Arg
        755                 760                 765

Glu Asn Gln Thr Thr Gly Lys Gly Lys Asn Asn Ser Arg Pro Arg Tyr
    770                 775                 780

Lys Ser Leu Glu Lys Ala Ile Lys Glu Phe Gly Ser Gln Ile Leu Lys
785                 790                 795                 800

Glu His Pro Thr Asp Asn Gln Glu Leu Arg Asn Asn Arg Leu Tyr Leu
                805                 810                 815

Tyr Tyr Leu Gln Asn Gly Lys Asp Met Tyr Thr Gly Gln Asp Leu Asp
            820                 825                 830

Ile His Asn Leu Ser Asn Tyr Asp Ile Asp His Ile Val Pro Gln Ser
        835                 840                 845

Phe Ile Thr Asp Asn Ser Ile Asp Asn Leu Val Leu Thr Ser Ser Ala
    850                 855                 860

Gly Asn Arg Glu Lys Gly Asp Asp Val Pro Pro Leu Glu Ile Val Arg
865                 870                 875                 880

Lys Arg Lys Val Phe Trp Glu Lys Leu Tyr Gln Gly Asn Leu Met Ser
                885                 890                 895

Lys Arg Lys Phe Asp Tyr Leu Thr Lys Ala Glu Arg Gly Gly Leu Thr
            900                 905                 910

Glu Ala Asp Lys Ala Arg Phe Ile His Arg Gln Leu Val Glu Thr Arg
        915                 920                 925

Gln Ile Thr Lys Asn Val Ala Asn Ile Leu His Gln Arg Phe Asn Tyr
    930                 935                 940

Glu Lys Asp Asp His Gly Asn Thr Met Lys Gln Val Arg Ile Val Thr
945                 950                 955                 960

Leu Lys Ser Ala Leu Val Ser Gln Phe Arg Lys Gln Phe Gln Leu Tyr
                965                 970                 975

Lys Val Arg Asp Val Asn Asp Tyr His His Ala His Asp Ala Tyr Leu
            980                 985                 990

Asn Gly Val Val Ala Asn Thr Leu  Leu Lys Val Tyr Pro  Gln Leu Glu
        995                 1000                1005

Pro Glu  Phe Val Tyr Gly Asp  Tyr His Gln Phe Asp  Trp Phe Lys
    1010                1015                1020

Ala Asn  Lys Ala Thr Ala Lys  Lys Gln Phe Tyr Thr  Asn Ile Met
    1025                1030                1035

Leu Phe  Phe Ala Gln Lys Asp  Arg Ile Ile Asp Glu  Asn Gly Glu
    1040                1045                1050

Ile Leu  Trp Asp Lys Lys Tyr  Leu Asp Thr Val Lys  Lys Val Met
    1055                1060                1065

Ser Tyr  Arg Gln Met Asn Ile  Val Lys Lys Thr Glu  Ile Gln Lys
    1070                1075                1080

Gly Glu  Phe Ser Lys Ala Thr  Ile Lys Pro Lys Gly  Asn Ser Ser
    1085                1090                1095

Lys Leu  Ile Pro Arg Lys Thr  Asn Trp Asp Pro Met  Lys Tyr Gly
    1100                1105                1110

Gly Leu  Asp Ser Pro Asn Met  Ala Tyr Ala Val Val  Ile Glu Tyr
```

```
    1115                1120                1125

Ala Lys  Gly Lys Asn Lys Leu  Val Phe Glu Lys Lys  Ile Ile Arg
    1130                1135                1140

Val Thr  Ile Met Glu Arg Lys  Ala Phe Glu Lys Asp  Glu Lys Ala
    1145                1150                1155

Phe Leu  Glu Glu Gln Gly Tyr  Arg Gln Pro Lys Val  Leu Ala Lys
    1160                1165                1170

Leu Pro  Lys Tyr Thr Leu Tyr  Glu Cys Glu Glu Gly  Arg Arg Arg
    1175                1180                1185

Met Leu  Ala Ser Ala Asn Glu  Ala Gln Lys Gly Asn  Gln Gln Val
    1190                1195                1200

Leu Pro  Asn His Leu Val Thr  Leu Leu His His Ala  Ala Asn Cys
    1205                1210                1215

Glu Val  Ser Asp Gly Lys Ser  Leu Asp Tyr Ile Glu  Ser Asn Arg
    1220                1225                1230

Glu Met  Phe Ala Glu Leu Leu  Ala His Val Ser Glu  Phe Ala Lys
    1235                1240                1245

Arg Tyr  Thr Leu Ala Glu Ala  Asn Leu Asn Lys Ile  Asn Gln Leu
    1250                1255                1260

Phe Glu  Gln Asn Lys Glu Gly  Asp Ile Lys Ala Ile  Ala Gln Ser
    1265                1270                1275

Phe Val  Asp Leu Met Ala Phe  Asn Ala Met Gly Ala  Pro Ala Ser
    1280                1285                1290

Phe Lys  Phe Phe Glu Thr Thr  Ile Glu Arg Lys Arg  Tyr Asn Asn
    1295                1300                1305

Leu Lys  Glu Leu Leu Asn Ser  Thr Ile Ile Tyr Gln  Ser Ile Thr
    1310                1315                1320

Gly Leu  Tyr Glu Ser Arg Lys  Arg Leu Asp Asp
    1325                1330


<210> SEQ ID NO 6
<211> LENGTH: 1053
<212> TYPE: PRT
<213> ORGANISM: Staphylococcus aureus

<400> SEQUENCE: 6

Met Lys Arg Asn Tyr Ile Leu Gly Leu Asp Ile Gly Ile Thr Ser Val
1               5                   10                  15

Gly Tyr Gly Ile Ile Asp Tyr Glu Thr Arg Asp Val Ile Asp Ala Gly
            20                  25                  30

Val Arg Leu Phe Lys Glu Ala Asn Val Glu Asn Asn Glu Gly Arg Arg
        35                  40                  45

Ser Lys Arg Gly Ala Arg Arg Leu Lys Arg Arg Arg Arg His Arg Ile
    50                  55                  60

Gln Arg Val Lys Lys Leu Leu Phe Asp Tyr Asn Leu Leu Thr Asp His
65                  70                  75                  80

Ser Glu Leu Ser Gly Ile Asn Pro Tyr Glu Ala Arg Val Lys Gly Leu
                85                  90                  95

Ser Gln Lys Leu Ser Glu Glu Glu Phe Ser Ala Ala Leu Leu His Leu
            100                 105                 110

Ala Lys Arg Arg Gly Val His Asn Val Asn Glu Val Glu Glu Asp Thr
        115                 120                 125

Gly Asn Glu Leu Ser Thr Lys Glu Gln Ile Ser Arg Asn Ser Lys Ala
    130                 135                 140
```

-continued

Leu Glu Glu Lys Tyr Val Ala Glu Leu Gln Leu Glu Arg Leu Lys Lys
145 150 155 160

Asp Gly Glu Val Arg Gly Ser Ile Asn Arg Phe Lys Thr Ser Asp Tyr
165 170 175

Val Lys Glu Ala Lys Gln Leu Leu Lys Val Gln Lys Ala Tyr His Gln
180 185 190

Leu Asp Gln Ser Phe Ile Asp Thr Tyr Ile Asp Leu Leu Glu Thr Arg
195 200 205

Arg Thr Tyr Tyr Glu Gly Pro Gly Glu Gly Ser Pro Phe Gly Trp Lys
210 215 220

Asp Ile Lys Glu Trp Tyr Glu Met Leu Met Gly His Cys Thr Tyr Phe
225 230 235 240

Pro Glu Glu Leu Arg Ser Val Lys Tyr Ala Tyr Asn Ala Asp Leu Tyr
245 250 255

Asn Ala Leu Asn Asp Leu Asn Asn Leu Val Ile Thr Arg Asp Glu Asn
260 265 270

Glu Lys Leu Glu Tyr Tyr Glu Lys Phe Gln Ile Ile Glu Asn Val Phe
275 280 285

Lys Gln Lys Lys Lys Pro Thr Leu Lys Gln Ile Ala Lys Glu Ile Leu
290 295 300

Val Asn Glu Glu Asp Ile Lys Gly Tyr Arg Val Thr Ser Thr Gly Lys
305 310 315 320

Pro Glu Phe Thr Asn Leu Lys Val Tyr His Asp Ile Lys Asp Ile Thr
325 330 335

Ala Arg Lys Glu Ile Ile Glu Asn Ala Glu Leu Leu Asp Gln Ile Ala
340 345 350

Lys Ile Leu Thr Ile Tyr Gln Ser Ser Glu Asp Ile Gln Glu Glu Leu
355 360 365

Thr Asn Leu Asn Ser Glu Leu Thr Gln Glu Glu Ile Glu Gln Ile Ser
370 375 380

Asn Leu Lys Gly Tyr Thr Gly Thr His Asn Leu Ser Leu Lys Ala Ile
385 390 395 400

Asn Leu Ile Leu Asp Glu Leu Trp His Thr Asn Asp Asn Gln Ile Ala
405 410 415

Ile Phe Asn Arg Leu Lys Leu Val Pro Lys Lys Val Asp Leu Ser Gln
420 425 430

Gln Lys Glu Ile Pro Thr Thr Leu Val Asp Asp Phe Ile Leu Ser Pro
435 440 445

Val Val Lys Arg Ser Phe Ile Gln Ser Ile Lys Val Ile Asn Ala Ile
450 455 460

Ile Lys Lys Tyr Gly Leu Pro Asn Asp Ile Ile Ile Glu Leu Ala Arg
465 470 475 480

Glu Lys Asn Ser Lys Asp Ala Gln Lys Met Ile Asn Glu Met Gln Lys
485 490 495

Arg Asn Arg Gln Thr Asn Glu Arg Ile Glu Glu Ile Ile Arg Thr Thr
500 505 510

Gly Lys Glu Asn Ala Lys Tyr Leu Ile Glu Lys Ile Lys Leu His Asp
515 520 525

Met Gln Glu Gly Lys Cys Leu Tyr Ser Leu Glu Ala Ile Pro Leu Glu
530 535 540

Asp Leu Leu Asn Asn Pro Phe Asn Tyr Glu Val Asp His Ile Ile Pro
545 550 555 560

Arg Ser Val Ser Phe Asp Asn Ser Phe Asn Asn Lys Val Leu Val Lys

-continued

```
                565                 570                 575

Gln Glu Glu Asn Ser Lys Lys Gly Asn Arg Thr Pro Phe Gln Tyr Leu
            580                 585                 590

Ser Ser Ser Asp Ser Lys Ile Ser Tyr Glu Thr Phe Lys Lys His Ile
        595                 600                 605

Leu Asn Leu Ala Lys Gly Lys Gly Arg Ile Ser Lys Thr Lys Lys Glu
    610                 615                 620

Tyr Leu Leu Glu Glu Arg Asp Ile Asn Arg Phe Ser Val Gln Lys Asp
625                 630                 635                 640

Phe Ile Asn Arg Asn Leu Val Asp Thr Arg Tyr Ala Thr Arg Gly Leu
                645                 650                 655

Met Asn Leu Leu Arg Ser Tyr Phe Arg Val Asn Asn Leu Asp Val Lys
            660                 665                 670

Val Lys Ser Ile Asn Gly Gly Phe Thr Ser Phe Leu Arg Arg Lys Trp
        675                 680                 685

Lys Phe Lys Lys Glu Arg Asn Lys Gly Tyr Lys His His Ala Glu Asp
    690                 695                 700

Ala Leu Ile Ile Ala Asn Ala Asp Phe Ile Phe Lys Glu Trp Lys Lys
705                 710                 715                 720

Leu Asp Lys Ala Lys Lys Val Met Glu Asn Gln Met Phe Glu Glu Lys
                725                 730                 735

Gln Ala Glu Ser Met Pro Glu Ile Glu Thr Glu Gln Glu Tyr Lys Glu
            740                 745                 750

Ile Phe Ile Thr Pro His Gln Ile Lys His Ile Lys Asp Phe Lys Asp
        755                 760                 765

Tyr Lys Tyr Ser His Arg Val Asp Lys Lys Pro Asn Arg Glu Leu Ile
    770                 775                 780

Asn Asp Thr Leu Tyr Ser Thr Arg Lys Asp Asp Lys Gly Asn Thr Leu
785                 790                 795                 800

Ile Val Asn Asn Leu Asn Gly Leu Tyr Asp Lys Asp Asn Asp Lys Leu
                805                 810                 815

Lys Lys Leu Ile Asn Lys Ser Pro Glu Lys Leu Leu Met Tyr His His
            820                 825                 830

Asp Pro Gln Thr Tyr Gln Lys Leu Lys Leu Ile Met Glu Gln Tyr Gly
        835                 840                 845

Asp Glu Lys Asn Pro Leu Tyr Lys Tyr Tyr Glu Glu Thr Gly Asn Tyr
    850                 855                 860

Leu Thr Lys Tyr Ser Lys Lys Asp Asn Gly Pro Val Ile Lys Lys Ile
865                 870                 875                 880

Lys Tyr Tyr Gly Asn Lys Leu Asn Ala His Leu Asp Ile Thr Asp Asp
                885                 890                 895

Tyr Pro Asn Ser Arg Asn Lys Val Val Lys Leu Ser Leu Lys Pro Tyr
            900                 905                 910

Arg Phe Asp Val Tyr Leu Asp Asn Gly Val Tyr Lys Phe Val Thr Val
        915                 920                 925

Lys Asn Leu Asp Val Ile Lys Lys Glu Asn Tyr Tyr Glu Val Asn Ser
    930                 935                 940

Lys Cys Tyr Glu Glu Ala Lys Lys Leu Lys Lys Ile Ser Asn Gln Ala
945                 950                 955                 960

Glu Phe Ile Ala Ser Phe Tyr Asn Asn Asp Leu Ile Lys Ile Asn Gly
                965                 970                 975

Glu Leu Tyr Arg Val Ile Gly Val Asn Asn Asp Leu Leu Asn Arg Ile
            980                 985                 990
```

```
Glu Val Asn Met Ile Asp Ile Thr  Tyr Arg Glu Tyr Leu  Glu Asn Met
        995                 1000                 1005

Asn Asp  Lys Arg Pro Pro Arg  Ile Ile Lys Thr Ile  Ala Ser Lys
    1010                 1015                 1020

Thr Gln  Ser Ile Lys Lys Tyr  Ser Thr Asp Ile Leu  Gly Asn Leu
    1025                 1030                 1035

Tyr Glu  Val Lys Ser Lys Lys  His Pro Gln Ile Ile  Lys Lys Gly
    1040                 1045                 1050
```

<210> SEQ ID NO 7
<211> LENGTH: 3159
<212> TYPE: DNA
<213> ORGANISM: Staphylococcus aureus

<400> SEQUENCE: 7

```
atgaaaagga actacattct ggggctggac atcgggatta caagcgtggg gtatgggatt     60
attgactatg aaacaaggga cgtgatcgac gcaggcgtca gactgttcaa ggaggccaac    120
gtggaaaaca atgagggacg gagaagcaag aggggagcca ggcgcctgaa acgacggaga    180
aggcacagaa tccagagggt gaagaaactg ctgttcgatt acaacctgct gaccgaccat    240
tctgagctga gtggaattaa tccttatgaa gccagggtga aaggcctgag tcagaagctg    300
tcagaggaag agttttccgc agctctgctg cacctggcta agcgccgagg agtgcataac    360
gtcaatgagg tggaagagga caccggcaac gagctgtcta caaaggaaca gatctcacgc    420
aatagcaaag ctctggaaga gaagtatgtc gcagagctgc agctggaacg gctgaagaaa    480
gatggcgagg tgagagggtc aattaatagg ttcaagacaa gcgactacgt caaagaagcc    540
aagcagctgc tgaaagtgca gaaggcttac caccagctgg atcagagctt catcgatact    600
tatatcgacc tgctggagac tcggagaacc tactatgagg gaccaggaga agggagcccc    660
ttcggatgga aagacatcaa ggaatggtac gagatgctga tgggacattg cacctatttt    720
ccagaagagc tgagaagcgt caagtacgct tataacgcag atctgtacaa cgccctgaat    780
gacctgaaca acctggtcat caccagggat gaaaacgaga aactggaata ctatgagaag    840
ttccagatca tcgaaaacgt gtttaagcag aagaaaaagc ctacactgaa acagattgct    900
aaggagatcc tggtcaacga agaggacatc aagggctacc gggtgacaag cactggaaaa    960
ccagagttca ccaatctgaa agtgtatcac gatattaagg acatcacagc acggaaagaa   1020
atcattgaga acgccgaact gctggatcag attgctaaga tcctgactat ctaccagagc   1080
tccgaggaca tccaggaaga gctgactaac ctgaacagcg agctgaccca ggaagagatc   1140
gaacagatta gtaatctgaa ggggtacacc ggaacacaca acctgtccct gaaagctatc   1200
aatctgattc tggatgagct gtggcataca aacgacaatc agattgcaat ctttaaccgg   1260
ctgaagctgg tcccaaaaaa ggtggacctg agtcagcaga aagagatccc aaccacactg   1320
gtggacgatt tcattctgtc acccgtggtc aagcggagct tcatccagag catcaaagtg   1380
atcaacgcca tcatcaagaa gtacggcctg cccaatgata tcattatcga gctggctagg   1440
gagaagaaca gcaaggacgc acagaagatg atcaatgaga tgcagaaacg aaaccggcag   1500
accaatgaac gcattgaaga gattatccga actaccggga aagagaacgc aaagtacctg   1560
attgaaaaaa tcaagctgca cgatatgcag gagggaaagt gtctgtattc tctggaggcc   1620
atcccccctgg aggacctgct gaacaatcca ttcaactacg aggtcgatca tattatcccc   1680
agaagcgtgt ccttcgacaa ttcctttaac aacaaggtgc tggtcaagca ggaagagaac   1740
```

tctaaaaagg gcaataggac tcctttccag tacctgtcta gttcagattc caagatctct 1800
tacgaaacct ttaaaaagca cattctgaat ctggccaaag gaaagggccg catcagcaag 1860
accaaaaagg agtacctgct ggaagagcgg gacatcaaca gattctccgt ccagaaggat 1920
tttattaacc ggaatctggt ggacacaaga tacgctactc gcggcctgat gaatctgctg 1980
cgatcctatt tccgggtgaa caatctggat gtgaaagtca agtccatcaa cggcgggttc 2040
acatcttttc tgaggcgcaa atggaagttt aaaaaggagc gcaacaaagg gtacaagcac 2100
catgccgaag atgctctgat tatcgcaaat gccgacttca tctttaagga gtggaaaaag 2160
ctggacaaag ccaagaaagt gatggagaac cagatgttcg aagagaagca ggccgaatct 2220
atgcccgaaa tcgagacaga acaggagtac aaggagattt tcatcactcc tcaccagatc 2280
aagcatatca aggatttcaa ggactacaag tactctcacc gggtggataa aaagcccaac 2340
agagagctga tcaatgacac cctgtatagt acaagaaaag acgataaggg gaataccctg 2400
attgtgaaca atctgaacgg actgtacgac aaagataatg acaagctgaa aaagctgatc 2460
aacaaaagtc ccgagaagct gctgatgtac caccatgatc ctcagacata tcagaaactg 2520
aagctgatta tggagcagta cggcgacgag aagaacccac tgtataagta ctatgaagag 2580
actgggaact acctgaccaa gtatagcaaa aaggataatg gccccgtgat caagaagatc 2640
aagtactatg ggaacaagct gaatgcccat ctggacatca cagacgatta ccctaacagt 2700
cgcaacaagg tggtcaagct gtcactgaag ccatacagat tcgatgtcta tctggacaac 2760
ggcgtgtata aatttgtgac tgtcaagaat ctggatgtca tcaaaaagga gaactactat 2820
gaagtgaata gcaagtgcta cgaagaggct aaaaagctga aaaagattag caaccaggca 2880
gagttcatcg cctcctttta caacaacgac ctgattaaga tcaatggcga actgtatagg 2940
gtcatcgggg tgaacaatga tctgctgaac cgcattgaag tgaatatgat tgacatcact 3000
taccgagagt atctggaaaa catgaatgat aagcgccccc ctcgaattat caaaacaatt 3060
gcctctaaga ctcagagtat caaaaagtac tcaaccgaca ttctgggaaa cctgtatgag 3120
gtgaagagca aaaagcaccc tcagattatc aaaaagggc 3159

<210> SEQ ID NO 8
<211> LENGTH: 3159
<212> TYPE: DNA
<213> ORGANISM: Staphylococcus aureus

<400> SEQUENCE: 8
atgaagcgga actacatcct gggcctggac atcggcatca ccagcgtggg ctacggcatc 60
atcgactacg agacacggga cgtgatcgat gccggcgtgc ggctgttcaa agaggccaac 120
gtggaaaaca acgagggcag gcggagcaag agaggcgcca gaaggctgaa gcggcggagg 180
cggcatagaa tccagagagt gaagaagctg ctgttcgact acaacctgct gaccgaccac 240
agcgagctga gcggcatcaa cccctacgag gccagagtga agggcctgag ccagaagctg 300
agcgaggaag agttctctgc cgccctgctg cacctggcca agagaagagg cgtgcacaac 360
gtgaacgagg tggaagagga caccggcaac gagctgtcca ccaaagagca gatcagccgg 420
aacagcaagg ccctggaaga gaaatacgtg gccgaactgc agctggaacg gctgaagaaa 480
gacggcgaag tgcggggcag catcaacaga ttcaagacca gcgactacgt gaaagaagcc 540
aaacagctgc tgaaggtgca gaaggcctac caccagctgg accagagctt catcgacacc 600
tacatcgacc tgctggaaac ccggcggacc tactatgagg gacctggcga gggcagcccc 660
ttcggctgga aggacatcaa agaatggtac gagatgctga tgggccactg cacctacttc 720

-continued

```
cccgaggaac tgcggagcgt gaagtacgcc tacaacgccg acctgtacaa cgccctgaac    780
gacctgaaca atctcgtgat caccagggac gagaacgaga agctggaata ttacgagaag    840
ttccagatca tcgagaacgt gttcaagcag aagaagaagc ccaccctgaa gcagatcgcc    900
aaagaaatcc tcgtgaacga agaggatatt aagggctaca gagtgaccag caccggcaag    960
cccgagttca ccaacctgaa ggtgtaccac gacatcaagg acattaccgc ccggaaagag   1020
attattgaga acgccgagct gctggatcag attgccaaga tcctgaccat ctaccagagc   1080
agcgaggaca tccaggaaga actgaccaat ctgaactccg agctgaccca ggaagagatc   1140
gagcagatct ctaatctgaa gggctatacc ggcacccaca acctgagcct gaaggccatc   1200
aacctgatcc tggacgagct gtggcacacc aacgacaacc agatcgctat cttcaaccgg   1260
ctgaagctgg tgcccaagaa ggtggacctg tcccagcaga aagagatccc caccaccctg   1320
gtggacgact tcatcctgag ccccgtcgtg aagagaagct tcatccagag catcaaagtg   1380
atcaacgcca tcatcaagaa gtacggcctg cccaacgaca tcattatcga gctggcccgc   1440
gagaagaact ccaaggacgc ccagaaaatg atcaacgaga tgcagaagcg gaaccggcag   1500
accaacgagc ggatcgagga aatcatccgg accaccggca aagagaacgc caagtacctg   1560
atcgagaaga tcaagctgca cgacatgcag gaaggcaagt gcctgtacag cctggaagcc   1620
atccctctgg aagatctgct gaacaacccc ttcaactatg aggtggacca catcatcccc   1680
agaagcgtgt ccttcgacaa cagcttcaac aacaaggtgc tcgtgaagca ggaagaaaac   1740
agcaagaagg gcaaccggac cccattccag tacctgagca gcagcgacag caagatcagc   1800
tacgaaacct tcaagaagca catcctgaat ctggccaagg gcaagggcag aatcagcaag   1860
accaagaaag agtatctgct ggaagaacgg gacatcaaca ggttctccgt gcagaaagac   1920
ttcatcaacc ggaacctggt ggataccaga tacgccacca gaggcctgat gaacctgctg   1980
cggagctact tcagagtgaa caacctggac gtgaaagtga agtccatcaa tggcggcttc   2040
accagctttc tgcggcggaa gtggaagttt aagaaagagc ggaacaaggg gtacaagcac   2100
cacgccgagg acgccctgat cattgccaac gccgatttca tcttcaaaga gtggaagaaa   2160
ctggacaagg ccaaaaaagt gatggaaaac cagatgttcg aggaaaagca ggccgagagc   2220
atgcccgaga tcgaaaccga gcaggagtac aaagagatct tcatcacccc ccaccagatc   2280
aagcacatta aggacttcaa ggactacaag tacagccacc gggtggacaa gaagcctaat   2340
agagagctga ttaacgacac cctgtactcc acccggaagg acgacaaggg caacaccctg   2400
atcgtgaaca atctgaacgg cctgtacgac aaggacaatg acaagctgaa aaagctgatc   2460
aacaagagcc ccgaaaagct gctgatgtac caccacgacc cccagaccta ccagaaactg   2520
aagctgatta tggaacagta cggcgacgag aagaatcccc tgtacaagta ctacgaggaa   2580
accgggaact acctgaccaa gtactccaaa aaggacaacg gccccgtgat caagaagatt   2640
aagtattacg gcaacaaact gaacgcccat ctggacatca ccgacgacta ccccaacagc   2700
agaaacaagg tcgtgaagct gtccctgaag ccctacagat tcgacgtgta cctggacaat   2760
ggcgtgtaca agttcgtgac cgtgaagaat ctggatgtga tcaaaaaaga aaactactac   2820
gaagtgaata gcaagtgcta tgaggaagct aagaagctga agaagatcag caaccaggcc   2880
gagtttatcg cctccttcta caacaacgat ctgatcaaga tcaacggcga gctgtataga   2940
gtgatcggcg tgaacaacga cctgctgaac cggatcgaag tgaacatgat cgacatcacc   3000
taccgcgagt acctggaaaa catgaacgac aagaggcccc ccaggatcat taagacaatc   3060
```

-continued

```
gcctccaaga cccagagcat taagaagtac agcacagaca ttctgggcaa cctgtatgaa   3120

gtgaaatcta agaagcaccc tcagatcatc aaaaagggc                          3159


<210> SEQ ID NO 9
<211> LENGTH: 3159
<212> TYPE: DNA
<213> ORGANISM: Staphylococcus aureus

<400> SEQUENCE: 9

atgaagcgca actacatcct cggactggac atcggcatta cctccgtggg atacggcatc     60

atcgattacg aaactaggga tgtgatcgac gctggagtca ggctgttcaa agaggcgaac    120

gtggagaaca acgaggggcg gcgctcaaag agggggcgcc gccggctgaa gcgccgccgc    180

agacatagaa tccagcgcgt gaagaagctg ctgttcgact acaaccttct gaccgaccac    240

tccgaacttt ccggcatcaa cccatatgag gctagagtga agggattgtc ccaaaagctg    300

tccgaggaag agttctccgc cgcgttgctc cacctcgcca agcgcagggg agtgcacaat    360

gtgaacgaag tggaagaaga taccggaaac gagctgtcca ccaaggagca gatcagccgg    420

aactccaagg ccctggaaga gaaatacgtg gcggaactgc aactggagcg gctgaagaaa    480

gacggagaag tgcgcggctc gatcaaccgc ttcaagacct cggactacgt gaaggaggcc    540

aagcagctcc tgaaagtgca aaaggcctat caccaacttg accagtcctt tatcgatacc    600

tacatcgatc tgctcgagac tcggcggact tactacgagg gtccagggga gggctcccca    660

tttggttgga aggatattaa ggagtggtac gaaatgctga tgggacactg cacatacttc    720

cctgaggagc tgcggagcgt gaaatacgca tacaacgcag acctgtacaa cgcgctgaac    780

gacctgaaca atctcgtgat cacccgggac gagaacgaaa agctcgagta ttacgaaaag    840

ttccagatta ttgagaacgt gttcaaacag aagaagaagc cgacactgaa gcagattgcc    900

aaggaaatcc tcgtgaacga agaggacatc aagggctatc gagtgacctc aacgggaaag    960

ccggagttca ccaatctgaa ggtctaccac gacatcaaag acattaccgc ccggaaggag   1020

atcattgaga acgcggagct gttggaccag attgcgaaga ttctgaccat ctaccaatcc   1080

tccgaggata ttcaggaaga actcaccaac ctcaacagcg aactgaccca ggaggagata   1140

gagcaaatct ccaacctgaa gggctacacc ggaactcata acctgagcct gaaggccatc   1200

aacttgatcc tggacgagct gtggcacacc aacgataacc agatcgctat tttcaatcgg   1260

ctgaagctgg tccccaagaa agtggacctc tcacaacaaa aggagatccc tactaccctt   1320

gtggacgatt tcattctgtc ccccgtggtc aagagaagct tcatacagtc aatcaaagtg   1380

atcaatgcca ttatcaagaa atacggtctg cccaacgaca ttatcattga gctcgcccgc   1440

gagaagaact cgaaggacgc ccagaagatg attaacgaaa tgcagaagag gaaccgacag   1500

actaacgaac ggatcgaaga aatcatccgg accaccggga aggaaaacgc gaagtacctg   1560

atcgaaaaga tcaagctcca tgacatgcag gaaggaaagt gtctgtactc gctggaggcc   1620

attccgctgg aggacttgct gaacaaccct tttaactacg aagtggatca tatcattccg   1680

aggagcgtgt cattcgacaa ttccttcaac aacaaggtcc tcgtgaagca ggaggaaaac   1740

tcgaagaagg gaaaccgcac gccgttccag tacctgagca gcagcgactc caagatttcc   1800

tacgaaacct tcaagaagca catcctcaac ctggcaaagg ggaagggtcg catctccaag   1860

accaagaagg aatatctgct ggaagaaaga gacatcaaca gattctccgt gcaaaaggac   1920

ttcatcaacc gcaacctcgt ggatactaga tacgctactc ggggtctgat gaacctcctg   1980

agaagctact ttagagtgaa caatctggac gtgaaggtca agtcgattaa cggaggtttc   2040
```

acctccttcc tgcggcgcaa gtggaagttc aagaaggaac ggaacaaggg ctacaagcac 2100
cacgccgagg acgccctgat cattgccaac gccgacttca tcttcaaaga atggaagaaa 2160
cttgacaagg ctaagaaggt catggaaaac cagatgttcg aagaaaagca ggccgagtct 2220
atgcctgaaa tcgagactga acaggagtac aaggaaatct ttattacgcc acaccagatc 2280
aaacacatca aggatttcaa ggattacaag tactcacatc gcgtggacaa aaagccgaac 2340
agggaactga tcaacgacac cctctactcc acccggaagg atgacaaagg gaataccctc 2400
atcgtcaaca accttaacgg cctgtacgac aaggacaacg ataagctgaa gaagctcatt 2460
aacaagtcgc ccgaaaagtt gctgatgtac caccacgacc ctcagactta ccagaagctc 2520
aagctgatca tggagcagta tggggacgag aaaaacccgt tgtacaagta ctacgaagaa 2580
actgggaatt atctgactaa gtactccaag aaagataacg gccccgtgat taagaagatt 2640
aagtactacg gcaacaagct gaacgcccat ctggacatca ccgatgacta ccctaattcc 2700
cgcaacaagg tcgtcaagct gagcctcaag ccctaccggt ttgatgtgta ccttgacaat 2760
ggagtgtaca agttcgtgac tgtgaagaac cttgacgtga tcaagaagga gaactactac 2820
gaagtcaact ccaagtgcta cgaggaagca aagaagttga agaagatctc gaaccaggcc 2880
gagttcattg cctccttcta taacaacgac ctgattaaga tcaacggcga actgtaccgc 2940
gtcattggcg tgaacaacga tctcctgaac cgcatcgaag tgaacatgat cgacatcact 3000
taccgggaat acctggagaa tatgaacgac aagcgcccgc cccggatcat taagactatc 3060
gcctcaaaga cccagtcgat caagaagtac agcaccgaca tcctgggcaa cctgtacgag 3120
gtcaaatcga agaagcaccc ccagatcatc aagaaggga 3159

<210> SEQ ID NO 10
<211> LENGTH: 3159
<212> TYPE: DNA
<213> ORGANISM: Staphylococcus aureus

<400> SEQUENCE: 10
atgaaaagga actacattct ggggctggcc atcgggatta caagcgtggg gtatgggatt 60
attgactatg aaacaaggga cgtgatcgac gcaggcgtca gactgttcaa ggaggccaac 120
gtggaaaaca atgagggacg gagaagcaag aggggagcca ggcgcctgaa acgacggaga 180
aggcacagaa tccagagggt gaagaaactg ctgttcgatt acaacctgct gaccgaccat 240
tctgagctga gtggaattaa tccttatgaa gccagggtga aaggcctgag tcagaagctg 300
tcagaggaag agttttccgc agctctgctg cacctggcta agcgccgagg agtgcataac 360
gtcaatgagg tggaagagga caccggcaac gagctgtcta caaaggaaca gatctcacgc 420
aatagcaaag ctctggaaga gaagtatgtc gcagagctgc agctggaacg gctgaagaaa 480
gatggcgagg tgagagggtc aattaatagg ttcaagacaa gcgactacgt caaagaagcc 540
aagcagctgc tgaaagtgca gaaggcttac caccagctgg atcagagctt catcgatact 600
tatatcgacc tgctggagac tcggagaacc tactatgagg gaccaggaga agggagcccc 660
ttcggatgga aagacatcaa ggaatggtac gagatgctga tgggacattg cacctatttt 720
ccagaagagc tgagaagcgt caagtacgct tataacgcag atctgtacaa cgccctgaat 780
gacctgaaca acctggtcat caccagggat gaaaacgaga aactggaata ctatgagaag 840
ttccagatca tcgaaaacgt gtttaagcag aagaaaaagc ctacactgaa acagattgct 900
aaggagatcc tggtcaacga agaggacatc aagggctacc gggtgacaag cactggaaaa 960

-continued ccagagttca ccaatctgaa agtgtatcac gatattaagg acatcacagc acggaaagaa 1020
atcattgaga acgccgaact gctggatcag attgctaaga tcctgactat ctaccagagc 1080
tccgaggaca tccaggaaga gctgactaac ctgaacagcg agctgaccca ggaagagatc 1140
gaacagatta gtaatctgaa ggggtacacc ggaacacaca acctgtccct gaaagctatc 1200
aatctgattc tggatgagct gtggcataca aacgacaatc agattgcaat ctttaaccgg 1260
ctgaagctgg tcccaaaaaa ggtggacctg agtcagcaga aagagatccc aaccacactg 1320
gtggacgatt tcattctgtc acccgtggtc aagcggagct tcatccagag catcaaagtg 1380
atcaacgcca tcatcaagaa gtacggcctg cccaatgata tcattatcga gctggctagg 1440
gagaagaaca gcaaggacgc acagaagatg atcaatgaga tgcagaaacg aaaccggcag 1500
accaatgaac gcattgaaga gattatccga actaccggga aagagaacgc aaagtacctg 1560
attgaaaaaa tcaagctgca cgatatgcag gagggaaagt gtctgtattc tctggaggcc 1620
atccccctgg aggacctgct gaacaatcca ttcaactacg aggtcgatca tattatcccc 1680
agaagcgtgt ccttcgacaa ttcctttaac aacaaggtgc tggtcaagca ggaagagaac 1740
tctaaaaagg gcaataggac tcctttccag tacctgtcta gttcagattc caagatctct 1800
tacgaaacct ttaaaaagca cattctgaat ctggccaaag gaaagggccg catcagcaag 1860
accaaaaagg agtacctgct ggaagagcgg gacatcaaca gattctccgt ccagaaggat 1920
tttattaacc ggaatctggt ggacacaaga tacgctactc gcggcctgat gaatctgctg 1980
cgatcctatt tccgggtgaa caatctggat gtgaaagtca agtccatcaa cggcgggttc 2040
acatcttttc tgaggcgcaa atggaagttt aaaaaggagc gcaacaaagg gtacaagcac 2100
catgccgaag atgctctgat tatcgcaaat gccgacttca tctttaagga gtggaaaaag 2160
ctggacaaag ccaagaaagt gatggagaac cagatgttcg aagagaagca ggccgaatct 2220
atgcccgaaa tcgagacaga acaggagtac aaggagattt tcatcactcc tcaccagatc 2280
aagcatatca aggatttcaa ggactacaag tactctcacc gggtggataa aaagcccaac 2340
agagagctga tcaatgacac cctgtatagt acaagaaaag acgataaggg gaataccctg 2400
attgtgaaca atctgaacgg actgtacgac aaagataatg acaagctgaa aaagctgatc 2460
aacaaaagtc ccgagaagct gctgatgtac caccatgatc ctcagacata tcagaaactg 2520
aagctgatta tggagcagta cggcgacgag aagaacccac tgtataagta ctatgaagag 2580
actgggaact acctgaccaa gtatagcaaa aaggataatg gccccgtgat caagaagatc 2640
aagtactatg ggaacaagct gaatgcccat ctggacatca cagacgatta ccctaacagt 2700
cgcaacaagg tggtcaagct gtcactgaag ccatacagat tcgatgtcta tctggacaac 2760
ggcgtgtata aatttgtgac tgtcaagaat ctggatgtca tcaaaaagga gaactactat 2820
gaagtgaata gcaagtgcta cgaagaggct aaaaagctga aaaagattag caaccaggca 2880
gagttcatcg cctcctttta caacaacgac ctgattaaga tcaatggcga actgtatagg 2940
gtcatcgggg tgaacaatga tctgctgaac cgcattgaag tgaatatgat tgacatcact 3000
taccgagagt atctggaaaa catgaatgat aagcgccccc ctcgaattat caaaacaatt 3060
gcctctaaga ctcagagtat caaaaagtac tcaaccgaca ttctgggaaa cctgtatgag 3120
gtgaagagca aaaagcaccc tcagattatc aaaaagggc 3159

<210> SEQ ID NO 11
<211> LENGTH: 3159
<212> TYPE: DNA
<213> ORGANISM: Staphylococcus aureus

<400> SEQUENCE: 11

```
atgaaaagga actacattct ggggctggac atcgggatta caagcgtggg gtatgggatt      60
attgactatg aaacaaggga cgtgatcgac gcaggcgtca gactgttcaa ggaggccaac     120
gtggaaaaca atgagggacg gagaagcaag aggggagcca ggcgcctgaa acgacggaga     180
aggcacagaa tccagagggt gaagaaactg ctgttcgatt acaacctgct gaccgaccat     240
tctgagctga gtggaattaa tccttatgaa gccagggtga aaggcctgag tcagaagctg     300
tcagaggaag agttttccgc agctctgctg cacctggcta agcgccgagg agtgcataac     360
gtcaatgagg tggaagagga caccggcaac gagctgtcta caaaggaaca gatctcacgc     420
aatagcaaag ctctggaaga gaagtatgtc gcagagctgc agctggaacg gctgaagaaa     480
gatggcgagg tgagagggtc aattaatagg ttcaagacaa gcgactacgt caaagaagcc     540
aagcagctgc tgaaagtgca gaaggcttac caccagctgg atcagagctt catcgatact     600
tatatcgacc tgctggagac tcggagaacc tactatgagg gaccaggaga agggagcccc     660
ttcggatgga aagacatcaa ggaatggtac gagatgctga tgggacattg cacctatttt     720
ccagaagagc tgagaagcgt caagtacgct tataacgcag atctgtacaa cgccctgaat     780
gacctgaaca acctggtcat caccagggat gaaaacgaga aactggaata ctatgagaag     840
ttccagatca tcgaaaacgt gtttaagcag aagaaaaagc ctacactgaa acagattgct     900
aaggagatcc tggtcaacga agaggacatc aagggctacc gggtgacaag cactggaaaa     960
ccagagttca ccaatctgaa agtgtatcac gatattaagg acatcacagc acggaaagaa    1020
atcattgaga acgccgaact gctggatcag attgctaaga tcctgactat ctaccagagc    1080
tccgaggaca tccaggaaga gctgactaac ctgaacagcg agctgaccca ggaagagatc    1140
gaacagatta gtaatctgaa ggggtacacc ggaacacaca acctgtccct gaaagctatc    1200
aatctgattc tggatgagct gtggcataca aacgacaatc agattgcaat ctttaaccgg    1260
ctgaagctgg tcccaaaaaa ggtggacctg agtcagcaga aagagatccc aaccacactg    1320
gtggacgatt tcattctgtc acccgtggtc aagcggagct tcatccagag catcaaagtg    1380
atcaacgcca tcatcaagaa gtacggcctg cccaatgata tcattatcga gctggctagg    1440
gagaagaaca gcaaggacgc acagaagatg atcaatgaga tgcagaaacg aaaccggcag    1500
accaatgaac gcattgaaga gattatccga actaccggga aagagaacgc aaagtacctg    1560
attgaaaaaa tcaagctgca cgatatgcag gagggaaagt gtctgtattc tctggaggcc    1620
atcccccctgg aggacctgct gaacaatcca ttcaactacg aggtcgatca tattatcccc    1680
agaagcgtgt ccttcgacaa ttcctttaac aacaaggtgc tggtcaagca ggaagaggcc    1740
tctaaaaagg gcaataggac tcctttccag tacctgtcta gttcagattc caagatctct    1800
tacgaaacct ttaaaaagca cattctgaat ctggccaaag gaaagggccg catcagcaag    1860
accaaaaagg agtacctgct ggaagagcgg gacatcaaca gattctccgt ccagaaggat    1920
tttattaacc ggaatctggt ggacacaaga tacgctactc gcggcctgat gaatctgctg    1980
cgatcctatt tccgggtgaa caatctggat gtgaaagtca agtccatcaa cggcgggttc    2040
acatcttttc tgaggcgcaa atggaagttt aaaaaggagc gcaacaaagg gtacaagcac    2100
catgccgaag atgctctgat tatcgcaaat gccgacttca tctttaagga gtggaaaaag    2160
ctggacaaag ccaagaaagt gatggagaac cagatgttcg aagagaagca ggccgaatct    2220
atgcccgaaa tcgagacaga acaggagtac aaggagattt tcatcactcc tcaccagatc    2280
```

-continued

```
aagcatatca aggatttcaa ggactacaag tactctcacc gggtggataa aaagcccaac   2340

agagagctga tcaatgacac cctgtatagt acaagaaaag acgataaggg gaatacoctg   2400

attgtgaaca atctgaacgg actgtacgac aaagataatg acaagctgaa aaagctgatc   2460

aacaaaagtc ccgagaagct gctgatgtac caccatgatc ctcagacata tcagaaactg   2520

aagctgatta tggagcagta cggcgacgag aagaacccac tgtataagta ctatgaagag   2580

actgggaact acctgaccaa gtatagcaaa aaggataatg gccccgtgat caagaagatc   2640

aagtactatg ggaacaagct gaatgcccat ctggacatca cagacgatta ccctaacagt   2700

cgcaacaagg tggtcaagct gtcactgaag ccatacagat tcgatgtcta tctggacaac   2760

ggcgtgtata aatttgtgac tgtcaagaat ctggatgtca tcaaaaagga gaactactat   2820

gaagtgaata gcaagtgcta cgaagaggct aaaaagctga aaaagattag caaccaggca   2880

gagttcatcg cctcctttta caacaacgac ctgattaaga tcaatggcga actgtatagg   2940

gtcatcgggg tgaacaatga tctgctgaac cgcattgaag tgaatatgat tgacatcact   3000

taccgagagt atctggaaaa catgaatgat aagcgccccc ctcgaattat caaaacaatt   3060

gcctctaaga ctcagagtat caaaaagtac tcaaccgaca ttctgggaaa cctgtatgag   3120

gtgaagagca aaaagcaccc tcagattatc aaaaagggc                          3159
```

<210> SEQ ID NO 12
<211> LENGTH: 1082
<212> TYPE: PRT
<213> ORGANISM: Neisseria meningitidis

<400> SEQUENCE: 12

```
Met Ala Ala Phe Lys Pro Asn Pro Ile Asn Tyr Ile Leu Gly Leu Asp
1               5                   10                  15

Ile Gly Ile Ala Ser Val Gly Trp Ala Met Val Glu Ile Asp Glu Asp
            20                  25                  30

Glu Asn Pro Ile Cys Leu Ile Asp Leu Gly Val Arg Val Phe Glu Arg
        35                  40                  45

Ala Glu Val Pro Lys Thr Gly Asp Ser Leu Ala Met Ala Arg Arg Leu
    50                  55                  60

Ala Arg Ser Val Arg Arg Leu Thr Arg Arg Arg Ala His Arg Leu Leu
65                  70                  75                  80

Arg Ala Arg Arg Leu Leu Lys Arg Glu Gly Val Leu Gln Ala Ala Asp
                85                  90                  95

Phe Asp Glu Asn Gly Leu Ile Lys Ser Leu Pro Asn Thr Pro Trp Gln
            100                 105                 110

Leu Arg Ala Ala Ala Leu Asp Arg Lys Leu Thr Pro Leu Glu Trp Ser
        115                 120                 125

Ala Val Leu Leu His Leu Ile Lys His Arg Gly Tyr Leu Ser Gln Arg
    130                 135                 140

Lys Asn Glu Gly Glu Thr Ala Asp Lys Glu Leu Gly Ala Leu Leu Lys
145                 150                 155                 160

Gly Val Ala Asp Asn Ala His Ala Leu Gln Thr Gly Asp Phe Arg Thr
                165                 170                 175

Pro Ala Glu Leu Ala Leu Asn Lys Phe Glu Lys Glu Ser Gly His Ile
            180                 185                 190

Arg Asn Gln Arg Gly Asp Tyr Ser His Thr Phe Ser Arg Lys Asp Leu
        195                 200                 205

Gln Ala Glu Leu Ile Leu Leu Phe Glu Lys Gln Lys Glu Phe Gly Asn
    210                 215                 220
```

-continued

Pro His Val Ser Gly Gly Leu Lys Glu Gly Ile Glu Thr Leu Leu Met
225 230 235 240

Thr Gln Arg Pro Ala Leu Ser Gly Asp Ala Val Gln Lys Met Leu Gly
245 250 255

His Cys Thr Phe Glu Pro Ala Glu Pro Lys Ala Ala Lys Asn Thr Tyr
260 265 270

Thr Ala Glu Arg Phe Ile Trp Leu Thr Lys Leu Asn Asn Leu Arg Ile
275 280 285

Leu Glu Gln Gly Ser Glu Arg Pro Leu Thr Asp Thr Glu Arg Ala Thr
290 295 300

Leu Met Asp Glu Pro Tyr Arg Lys Ser Lys Leu Thr Tyr Ala Gln Ala
305 310 315 320

Arg Lys Leu Leu Gly Leu Glu Asp Thr Ala Phe Phe Lys Gly Leu Arg
325 330 335

Tyr Gly Lys Asp Asn Ala Glu Ala Ser Thr Leu Met Glu Met Lys Ala
340 345 350

Tyr His Ala Ile Ser Arg Ala Leu Glu Lys Glu Gly Leu Lys Asp Lys
355 360 365

Lys Ser Pro Leu Asn Leu Ser Pro Glu Leu Gln Asp Glu Ile Gly Thr
370 375 380

Ala Phe Ser Leu Phe Lys Thr Asp Glu Asp Ile Thr Gly Arg Leu Lys
385 390 395 400

Asp Arg Ile Gln Pro Glu Ile Leu Glu Ala Leu Leu Lys His Ile Ser
405 410 415

Phe Asp Lys Phe Val Gln Ile Ser Leu Lys Ala Leu Arg Arg Ile Val
420 425 430

Pro Leu Met Glu Gln Gly Lys Arg Tyr Asp Glu Ala Cys Ala Glu Ile
435 440 445

Tyr Gly Asp His Tyr Gly Lys Lys Asn Thr Glu Glu Lys Ile Tyr Leu
450 455 460

Pro Pro Ile Pro Ala Asp Glu Ile Arg Asn Pro Val Val Leu Arg Ala
465 470 475 480

Leu Ser Gln Ala Arg Lys Val Ile Asn Gly Val Val Arg Arg Tyr Gly
485 490 495

Ser Pro Ala Arg Ile His Ile Glu Thr Ala Arg Glu Val Gly Lys Ser
500 505 510

Phe Lys Asp Arg Lys Glu Ile Glu Lys Arg Gln Glu Glu Asn Arg Lys
515 520 525

Asp Arg Glu Lys Ala Ala Ala Lys Phe Arg Glu Tyr Phe Pro Asn Phe
530 535 540

Val Gly Glu Pro Lys Ser Lys Asp Ile Leu Lys Leu Arg Leu Tyr Glu
545 550 555 560

Gln Gln His Gly Lys Cys Leu Tyr Ser Gly Lys Glu Ile Asn Leu Gly
565 570 575

Arg Leu Asn Glu Lys Gly Tyr Val Glu Ile Asp His Ala Leu Pro Phe
580 585 590

Ser Arg Thr Trp Asp Asp Ser Phe Asn Asn Lys Val Leu Val Leu Gly
595 600 605

Ser Glu Asn Gln Asn Lys Gly Asn Gln Thr Pro Tyr Glu Tyr Phe Asn
610 615 620

Gly Lys Asp Asn Ser Arg Glu Trp Gln Glu Phe Lys Ala Arg Val Glu
625 630 635 640

-continued

```
Thr Ser Arg Phe Pro Arg Ser Lys Lys Gln Arg Ile Leu Leu Gln Lys
                645                 650                 655

Phe Asp Glu Asp Gly Phe Lys Glu Arg Asn Leu Asn Asp Thr Arg Tyr
            660                 665                 670

Val Asn Arg Phe Leu Cys Gln Phe Val Ala Asp Arg Met Arg Leu Thr
        675                 680                 685

Gly Lys Gly Lys Lys Arg Val Phe Ala Ser Asn Gly Gln Ile Thr Asn
    690                 695                 700

Leu Leu Arg Gly Phe Trp Gly Leu Arg Lys Val Arg Ala Glu Asn Asp
705                 710                 715                 720

Arg His His Ala Leu Asp Ala Val Val Val Ala Cys Ser Thr Val Ala
                725                 730                 735

Met Gln Gln Lys Ile Thr Arg Phe Val Arg Tyr Lys Glu Met Asn Ala
            740                 745                 750

Phe Asp Gly Lys Thr Ile Asp Lys Glu Thr Gly Glu Val Leu His Gln
        755                 760                 765

Lys Thr His Phe Pro Gln Pro Trp Glu Phe Phe Ala Gln Glu Val Met
    770                 775                 780

Ile Arg Val Phe Gly Lys Pro Asp Gly Lys Pro Glu Phe Glu Glu Ala
785                 790                 795                 800

Asp Thr Pro Glu Lys Leu Arg Thr Leu Leu Ala Glu Lys Leu Ser Ser
                805                 810                 815

Arg Pro Glu Ala Val His Glu Tyr Val Thr Pro Leu Phe Val Ser Arg
            820                 825                 830

Ala Pro Asn Arg Lys Met Ser Gly Gln Gly His Met Glu Thr Val Lys
        835                 840                 845

Ser Ala Lys Arg Leu Asp Glu Gly Val Ser Val Leu Arg Val Pro Leu
    850                 855                 860

Thr Gln Leu Lys Leu Lys Asp Leu Glu Lys Met Val Asn Arg Glu Arg
865                 870                 875                 880

Glu Pro Lys Leu Tyr Glu Ala Leu Lys Ala Arg Leu Glu Ala His Lys
                885                 890                 895

Asp Asp Pro Ala Lys Ala Phe Ala Glu Pro Phe Tyr Lys Tyr Asp Lys
            900                 905                 910

Ala Gly Asn Arg Thr Gln Gln Val Lys Ala Val Arg Val Glu Gln Val
        915                 920                 925

Gln Lys Thr Gly Val Trp Val Arg Asn His Asn Gly Ile Ala Asp Asn
    930                 935                 940

Ala Thr Met Val Arg Val Asp Val Phe Glu Lys Gly Asp Lys Tyr Tyr
945                 950                 955                 960

Leu Val Pro Ile Tyr Ser Trp Gln Val Ala Lys Gly Ile Leu Pro Asp
                965                 970                 975

Arg Ala Val Val Gln Gly Lys Asp Glu Glu Asp Trp Gln Leu Ile Asp
            980                 985                 990

Asp Ser Phe Asn Phe Lys Phe Ser  Leu His Pro Asn Asp  Leu Val Glu
        995                 1000                 1005

Val Ile  Thr Lys Lys Ala Arg  Met Phe Gly Tyr Phe  Ala Ser Cys
    1010                 1015                 1020

His Arg  Gly Thr Gly Asn Ile  Asn Ile Arg Ile His  Asp Leu Asp
    1025                 1030                 1035

His Lys  Ile Gly Lys Asn Gly  Ile Leu Glu Gly Ile  Gly Val Lys
    1040                 1045                 1050

Thr Ala  Leu Ser Phe Gln Lys  Tyr Gln Ile Asp Glu  Leu Gly Lys
```

```
    1055                1060                1065

Glu Ile  Arg Pro Cys Arg Leu  Lys Lys Arg Pro Pro  Val Arg
    1070                1075                1080


<210> SEQ ID NO 13
<211> LENGTH: 3249
<212> TYPE: DNA
<213> ORGANISM: Neisseria meningitidis
<220> FEATURE:
<221> NAME/KEY: misc_feature
<222> LOCATION: (1)..(3249)
<223> OTHER INFORMATION: Exemplary codon optimized Cas9

<400> SEQUENCE: 13

atggccgcct tcaagcccaa ccccatcaac tacatcctgg gcctggacat cggcatcgcc     60

agcgtgggct gggccatggt ggagatcgac gaggacgaga accccatctg cctgatcgac    120

ctgggtgtgc gcgtgttcga gcgcgctgag gtgcccaaga ctggtgacag tctggctatg    180

gctcgccggc ttgctcgctc tgttcggcgc cttactcgcc ggcgcgctca ccgccttctg    240

cgcgctcgcc gcctgctgaa gcgcgagggt gtgctgcagg ctgccgactt cgacgagaac    300

ggcctgatca agagcctgcc caacactcct tggcagctgc gcgctgccgc tctggaccgc    360

aagctgactc ctctggagtg gagcgccgtg ctgctgcacc tgatcaagca ccgcggctac    420

ctgagccagc gcaagaacga gggcgagacc gccgacaagg agctgggtgc tctgctgaag    480

ggcgtggccg acaacgccca cgccctgcag actggtgact tccgcactcc tgctgagctg    540

gccctgaaca agttcgagaa ggagagcggc cacatccgca accagcgcgg cgactacagc    600

cacaccttca gccgcaagga cctgcaggcc gagctgatcc tgctgttcga gaagcagaag    660

gagttcggca acccccacgt gagcggcggc ctgaaggagg gcatcgagac cctgctgatg    720

acccagcgcc ccgccctgag cggcgacgcc gtgcagaaga tgctgggcca ctgcaccttc    780

gagccagccg agcccaaggc cgccaagaac acctacaccg ccgagcgctt catctggctg    840

accaagctga acaacctgcg catcctggag cagggcagcg agcgccccct gaccgacacc    900

gagcgcgcca ccctgatgga cgagccctac cgcaagagca agctgaccta cgcccaggcc    960

cgcaagctgc tgggtctgga ggacaccgcc ttcttcaagg gcctgcgcta cggcaaggac   1020

aacgccgagg ccagcaccct gatggagatg aaggcctacc acgccatcag ccgcgccctg   1080

gagaaggagg gcctgaagga caagaagagt cctctgaacc tgagccccga gctgcaggac   1140

gagatcggca ccgccttcag cctgttcaag accgacgagg acatcaccgg ccgcctgaag   1200

gaccgcatcc agcccgagat cctggaggcc ctgctgaagc acatcagctt cgacaagttc   1260

gtgcagatca gcctgaaggc cctgcgccgc atcgtgcccc tgatggagca gggcaagcgc   1320

tacgacgagg cctgcgccga gatctacggc gaccactacg gcaagaagaa caccgaggag   1380

aagatctacc tgcctcctat ccccgccgac gagatccgca accccgtggt gctgcgcgcc   1440

ctgagccagg cccgcaaggt gatcaacggc gtggtgcgcc gctacggcag ccccgcccgc   1500

atccacatcg agaccgcccg cgaggtgggc aagagcttca aggaccgcaa ggagatcgag   1560

aagcgccagg aggagaaccg caaggaccgc gagaaggccg ccgccaagtt ccgcgagtac   1620

ttccccaact tcgtgggcga gcccaagagc aaggacatcc tgaagctgcg cctgtacgag   1680

cagcagcacg gcaagtgcct gtacagcggc aaggagatca acctgggccg cctgaacgag   1740

aagggctacg tggagatcga ccacgccctg cccttcagcc gcacctggga cgacagcttc   1800

aacaacaagg tgctggtgct gggcagcgag aaccagaaca agggcaacca gaccccctac   1860
```

gagtacttca acggcaagga caacagccgc gagtggcagg agttcaaggc ccgcgtggag 1920
accagccgct tcccccgcag caagaagcag cgcatcctgc tgcagaagtt cgacgaggac 1980
ggcttcaagg agcgcaacct gaacgacacc cgctacgtga accgcttcct gtgccagttc 2040
gtggccgacc gcatgcgcct gaccggcaag ggcaagaagc gcgtgttcgc cagcaacggc 2100
cagatcacca acctgctgcg cggcttctgg ggcctgcgca aggtgcgcgc cgagaacgac 2160
cgccaccacg ccctggacgc cgtggtggtg gcctgcagca ccgtggccat gcagcagaag 2220
atcacccgct tcgtgcgcta caaggagatg aacgccttcg acggtaaaac catcgacaag 2280
gagaccggcg aggtgctgca ccagaagacc cacttccccc agccctggga gttcttcgcc 2340
caggaggtga tgatccgcgt gttcggcaag cccgacggca agcccgagtt cgaggaggcc 2400
gacacccccg agaagctgcg caccctgctg gccgagaagc tgagcagccg ccctgaggcc 2460
gtgcacgagt acgtgactcc tctgttcgtg agccgcgccc ccaaccgcaa gatgagcggt 2520
cagggtcaca tggagaccgt gaagagcgcc aagcgcctgg acgagggcgt gagcgtgctg 2580
cgcgtgcccc tgacccagct gaagctgaag gacctggaga agatggtgaa ccgcgagcgc 2640
gagcccaagc tgtacgaggc cctgaaggcc cgcctggagg cccacaagga cgacccccgcc 2700 aaggccttcg ccgagccctt ctacaagtac gacaaggccg gcaaccgcac ccagcaggtg 2760
aaggccgtgc gcgtggagca ggtgcagaag accggcgtgt gggtgcgcaa ccacaacggc 2820
atcgccgaca acgccaccat ggtgcgcgtg gacgtgttcg agaagggcga caagtactac 2880
ctggtgccca tctacagctg gcaggtggcc aagggcatcc tgcccgaccg cgccgtggtg 2940
cagggcaagg acgaggagga ctggcagctg atcgacgaca gcttcaactt caagttcagc 3000
ctgcacccca acgacctggt ggaggtgatc accaagaagg cccgcatgtt cggctacttc 3060
gccagctgcc accgcggcac cggcaacatc aacatccgca tccacgacct ggaccacaag 3120
atcggcaaga acggcatcct ggagggcatc ggcgtgaaga ccgccctgag cttccagaag 3180
taccagatcg acgagctggg caaggagatc cgcccctgcc gcctgaagaa gcgccctcct 3240
gtgcgctaa 3249

<210> SEQ ID NO 14
<211> LENGTH: 859
<212> TYPE: PRT
<213> ORGANISM: Artificial Sequence
<220> FEATURE:
<223> OTHER INFORMATION: Synthetic Cas9 consensus sequence derived from
Sm, Sp, St, and Li Cas9 sequences
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (8)..(18)
<223> OTHER INFORMATION: N-terminal RuvC-like domain
<220> FEATURE:
<221> NAME/KEY: misc_feature
<222> LOCATION: (21)..(21)
<223> OTHER INFORMATION: Xaa can be any naturally occurring amino acid
<220> FEATURE:
<221> NAME/KEY: misc_feature
<222> LOCATION: (23)..(23)
<223> OTHER INFORMATION: Xaa can be any naturally occurring amino acid
<220> FEATURE:
<221> NAME/KEY: misc_feature
<222> LOCATION: (24)..(24)
<223> OTHER INFORMATION: Xaa can be any naturally occurring amino acid
<220> FEATURE:
<221> NAME/KEY: misc_feature
<222> LOCATION: (26)..(26)

<223> OTHER INFORMATION: Xaa can be any naturally occurring amino acid
<220> FEATURE:
<221> NAME/KEY: misc_feature
<222> LOCATION: (29)..(31)
<223> OTHER INFORMATION: Each Xaa can independently be any naturally
occurring amino acid
<220> FEATURE:
<221> NAME/KEY: misc_feature
<222> LOCATION: (33)..(33)
<223> OTHER INFORMATION: Xaa can be any naturally occurring amino acid
<220> FEATURE:
<221> NAME/KEY: misc_feature
<222> LOCATION: (36)..(36)
<223> OTHER INFORMATION: Xaa can be any naturally occurring amino acid
<220> FEATURE:
<221> NAME/KEY: misc_feature
<222> LOCATION: (45)..(45)
<223> OTHER INFORMATION: Xaa can be any naturally occurring amino acid
<220> FEATURE:
<221> NAME/KEY: misc_feature
<222> LOCATION: (54)..(54)
<223> OTHER INFORMATION: Xaa can be any naturally occurring amino acid
<220> FEATURE:
<221> NAME/KEY: misc_feature
<222> LOCATION: (63)..(63)
<223> OTHER INFORMATION: Xaa can be any naturally occurring amino acid
<220> FEATURE:
<221> NAME/KEY: misc_feature
<222> LOCATION: (71)..(71)
<223> OTHER INFORMATION: Xaa can be any naturally occurring amino acid
<220> FEATURE:
<221> NAME/KEY: misc_feature
<222> LOCATION: (75)..(75)
<223> OTHER INFORMATION: Xaa can be any naturally occurring amino acid
<220> FEATURE:
<221> NAME/KEY: misc_feature
<222> LOCATION: (76)..(76)
<223> OTHER INFORMATION: Xaa can be any naturally occurring amino acid
<220> FEATURE:
<221> NAME/KEY: misc_feature
<222> LOCATION: (78)..(80)
<223> OTHER INFORMATION: Each Xaa can independently be any naturally
occurring amino acid
<220> FEATURE:
<221> NAME/KEY: misc_feature
<222> LOCATION: (82)..(82)
<223> OTHER INFORMATION: Xaa can be any naturally occurring amino acid
<220> FEATURE:
<221> NAME/KEY: misc_feature
<222> LOCATION: (84)..(84)
<223> OTHER INFORMATION: Xaa can be any naturally occurring amino acid
<220> FEATURE:
<221> NAME/KEY: misc_feature
<222> LOCATION: (85)..(85)
<223> OTHER INFORMATION: Xaa can be any naturally occurring amino acid
<220> FEATURE:
<221> NAME/KEY: misc_feature
<222> LOCATION: (89)..(89)
<223> OTHER INFORMATION: Xaa can be any naturally occurring amino acid
<220> FEATURE:
<221> NAME/KEY: misc_feature
<222> LOCATION: (90)..(90)
<223> OTHER INFORMATION: Xaa can be any naturally occurring amino acid
<220> FEATURE:
<221> NAME/KEY: misc_feature
<222> LOCATION: (98)..(98)
<223> OTHER INFORMATION: Xaa can be any naturally occurring amino acid
<220> FEATURE:
<221> NAME/KEY: misc_feature
<222> LOCATION: (100)..(100)
<223> OTHER INFORMATION: Xaa can be any naturally occurring amino acid
<220> FEATURE:
<221> NAME/KEY: misc_feature
<222> LOCATION: (106)..(106)
<223> OTHER INFORMATION: Xaa can be any naturally occurring amino acid
<220> FEATURE:
<221> NAME/KEY: misc_feature
<222> LOCATION: (113)..(113)
<223> OTHER INFORMATION: Xaa can be any naturally occurring amino acid
<220> FEATURE:
<221> NAME/KEY: misc_feature
<222> LOCATION: (116)..(116)
<223> OTHER INFORMATION: Xaa can be any naturally occurring amino acid
<220> FEATURE:
<221> NAME/KEY: misc_feature
<222> LOCATION: (125)..(125)
<223> OTHER INFORMATION: Xaa can be any naturally occurring amino acid
<220> FEATURE:
<221> NAME/KEY: misc_feature
<222> LOCATION: (126)..(126)
<223> OTHER INFORMATION: Xaa can be any naturally occurring amino acid
<220> FEATURE:
<221> NAME/KEY: misc_feature
<222> LOCATION: (128)..(133)
<223> OTHER INFORMATION: Each Xaa can independently be any naturally occurring amino acid
<220> FEATURE:
<221> NAME/KEY: misc_feature
<222> LOCATION: (135)..(135)
<223> OTHER INFORMATION: Xaa can be any naturally occurring amino acid
<220> FEATURE:
<221> NAME/KEY: misc_feature
<222> LOCATION: (137)..(137)
<223> OTHER INFORMATION: Xaa can be any naturally occurring amino acid
<220> FEATURE:
<221> NAME/KEY: misc_feature
<222> LOCATION: (139)..(147)
<223> OTHER INFORMATION: Each Xaa can independently be any naturally occurring amino acid
<220> FEATURE:
<221> NAME/KEY: misc_feature
<222> LOCATION: (153)..(155)
<223> OTHER INFORMATION: Each Xaa can independently be any naturally occurring amino acid
<220> FEATURE:
<221> NAME/KEY: misc_feature
<222> LOCATION: (157)..(157)
<223> OTHER INFORMATION: Xaa can be any naturally occurring amino acid
<220> FEATURE:
<221> NAME/KEY: misc_feature
<222> LOCATION: (159)..(159)
<223> OTHER INFORMATION: Xaa can be any naturally occurring amino acid
<220> FEATURE:
<221> NAME/KEY: misc_feature
<222> LOCATION: (161)..(161)
<223> OTHER INFORMATION: Xaa can be any naturally occurring amino acid
<220> FEATURE:
<221> NAME/KEY: misc_feature
<222> LOCATION: (163)..(163)
<223> OTHER INFORMATION: Xaa can be any naturally occurring amino acid
<220> FEATURE:
<221> NAME/KEY: misc_feature
<222> LOCATION: (166)..(168)
<223> OTHER INFORMATION: Each Xaa can independently be any naturally occurring amino acid
<220> FEATURE:
<221> NAME/KEY: misc_feature
<222> LOCATION: (170)..(170)
<223> OTHER INFORMATION: Xaa can be any naturally occurring amino acid
<220> FEATURE:
<221> NAME/KEY: misc_feature
<222> LOCATION: (171)..(171)
<223> OTHER INFORMATION: Xaa can be any naturally occurring amino acid
<220> FEATURE:
<221> NAME/KEY: misc_feature
<222> LOCATION: (173)..(175)
<223> OTHER INFORMATION: Each Xaa can independently be any naturally occurring amino acid
<220> FEATURE:
<221> NAME/KEY: misc_feature
<222> LOCATION: (177)..(177)
<223> OTHER INFORMATION: Xaa can be any naturally occurring amino acid
<220> FEATURE:
<221> NAME/KEY: misc_feature
<222> LOCATION: (183)..(183)
<223> OTHER INFORMATION: Xaa can be any naturally occurring amino acid
<220> FEATURE:
<221> NAME/KEY: misc_feature
<222> LOCATION: (185)..(187)
<223> OTHER INFORMATION: Each Xaa can independently be any naturally occurring amino acid
<220> FEATURE:
<221> NAME/KEY: misc_feature
<222> LOCATION: (189)..(189)
<223> OTHER INFORMATION: Xaa can be any naturally occurring amino acid
<220> FEATURE:
<221> NAME/KEY: misc_feature
<222> LOCATION: (192)..(195)
<223> OTHER INFORMATION: Each Xaa can independently be any naturally occurring amino acid
<220> FEATURE:
<221> NAME/KEY: misc_feature
<222> LOCATION: (198)..(198)
<223> OTHER INFORMATION: Xaa can be any naturally occurring amino acid
<220> FEATURE:
<221> NAME/KEY: misc_feature
<222> LOCATION: (199)..(199)
<223> OTHER INFORMATION: Xaa can be any naturally occurring amino acid
<220> FEATURE:
<221> NAME/KEY: misc_feature
<222> LOCATION: (202)..(202)
<223> OTHER INFORMATION: Xaa can be any naturally occurring amino acid
<220> FEATURE:
<221> NAME/KEY: misc_feature
<222> LOCATION: (206)..(206)
<223> OTHER INFORMATION: Xaa can be any naturally occurring amino acid
<220> FEATURE:
<221> NAME/KEY: misc_feature
<222> LOCATION: (207)..(207)
<223> OTHER INFORMATION: Xaa can be any naturally occurring amino acid
<220> FEATURE:
<221> NAME/KEY: misc_feature
<222> LOCATION: (210)..(210)
<223> OTHER INFORMATION: Xaa can be any naturally occurring amino acid
<220> FEATURE:
<221> NAME/KEY: misc_feature
<222> LOCATION: (212)..(212)
<223> OTHER INFORMATION: Xaa can be any naturally occurring amino acid
<220> FEATURE:
<221> NAME/KEY: misc_feature
<222> LOCATION: (213)..(213)
<223> OTHER INFORMATION: Xaa can be any naturally occurring amino acid
<220> FEATURE:
<221> NAME/KEY: misc_feature
<222> LOCATION: (219)..(219)
<223> OTHER INFORMATION: Xaa can be any naturally occurring amino acid
<220> FEATURE:
<221> NAME/KEY: misc_feature
<222> LOCATION: (220)..(220)
<223> OTHER INFORMATION: Xaa can be any naturally occurring amino acid
<220> FEATURE:
<221> NAME/KEY: misc_feature
<222> LOCATION: (222)..(222)
<223> OTHER INFORMATION: Xaa can be any naturally occurring amino acid
<220> FEATURE:
<221> NAME/KEY: misc_feature
<222> LOCATION: (224)..(224)
<223> OTHER INFORMATION: Xaa can be any naturally occurring amino acid
<220> FEATURE:
<221> NAME/KEY: misc_feature
<222> LOCATION: (226)..(226)
<223> OTHER INFORMATION: Xaa can be any naturally occurring amino acid
<220> FEATURE:
<221> NAME/KEY: misc_feature
<222> LOCATION: (236)..(236)
<223> OTHER INFORMATION: Xaa can be any naturally occurring amino acid
<220> FEATURE:
<221> NAME/KEY: misc_feature
<222> LOCATION: (240)..(240)
<223> OTHER INFORMATION: Xaa can be any naturally occurring amino acid
<220> FEATURE:
<221> NAME/KEY: misc_feature
<222> LOCATION: (241)..(241)
<223> OTHER INFORMATION: Xaa can be any naturally occurring amino acid
<220> FEATURE:
<221> NAME/KEY: misc_feature
<222> LOCATION: (244)..(246)

<223> OTHER INFORMATION: Each Xaa can independently be any naturally occurring amino acid
<220> FEATURE:
<221> NAME/KEY: misc_feature
<222> LOCATION: (248)..(248)
<223> OTHER INFORMATION: Xaa can be any naturally occurring amino acid
<220> FEATURE:
<221> NAME/KEY: misc_feature
<222> LOCATION: (249)..(249)
<223> OTHER INFORMATION: Xaa can be any naturally occurring amino acid
<220> FEATURE:
<221> NAME/KEY: misc_feature
<222> LOCATION: (250)..(250)
<223> OTHER INFORMATION: Xaa can be any naturally occurring amino acid
<220> FEATURE:
<221> NAME/KEY: misc_feature
<222> LOCATION: (252)..(254)
<223> OTHER INFORMATION: Each Xaa can independently be any naturally occurring amino acid
<220> FEATURE:
<221> NAME/KEY: misc_feature
<222> LOCATION: (256)..(256)
<223> OTHER INFORMATION: Xaa can be any naturally occurring amino acid
<220> FEATURE:
<221> NAME/KEY: misc_feature
<222> LOCATION: (257)..(257)
<223> OTHER INFORMATION: Xaa can be any naturally occurring amino acid
<220> FEATURE:
<221> NAME/KEY: misc_feature
<222> LOCATION: (268)..(268)
<223> OTHER INFORMATION: Xaa can be any naturally occurring amino acid
<220> FEATURE:
<221> NAME/KEY: misc_feature
<222> LOCATION: (271)..(271)
<223> OTHER INFORMATION: Xaa can be any naturally occurring amino acid
<220> FEATURE:
<221> NAME/KEY: misc_feature
<222> LOCATION: (273)..(273)
<223> OTHER INFORMATION: Xaa can be any naturally occurring amino acid
<220> FEATURE:
<221> NAME/KEY: misc_feature
<222> LOCATION: (277)..(277)
<223> OTHER INFORMATION: Xaa can be any naturally occurring amino acid
<220> FEATURE:
<221> NAME/KEY: misc_feature
<222> LOCATION: (280)..(280)
<223> OTHER INFORMATION: Xaa can be any naturally occurring amino acid
<220> FEATURE:
<221> NAME/KEY: misc_feature
<222> LOCATION: (281)..(281)
<223> OTHER INFORMATION: Xaa can be any naturally occurring amino acid
<220> FEATURE:
<221> NAME/KEY: misc_feature
<222> LOCATION: (283)..(283)
<223> OTHER INFORMATION: Xaa can be any naturally occurring amino acid
<220> FEATURE:
<221> NAME/KEY: misc_feature
<222> LOCATION: (289)..(289)
<223> OTHER INFORMATION: Xaa can be any naturally occurring amino acid
<220> FEATURE:
<221> NAME/KEY: misc_feature
<222> LOCATION: (290)..(290)
<223> OTHER INFORMATION: Xaa can be any naturally occurring amino acid
<220> FEATURE:
<221> NAME/KEY: misc_feature
<222> LOCATION: (292)..(294)
<223> OTHER INFORMATION: Each Xaa can independently be any naturally occurring amino acid
<220> FEATURE:
<221> NAME/KEY: misc_feature
<222> LOCATION: (301)..(301)
<223> OTHER INFORMATION: Xaa can be any naturally occurring amino acid
<220> FEATURE:
<221> NAME/KEY: misc_feature
<222> LOCATION: (308)..(308)
<223> OTHER INFORMATION: Xaa can be any naturally occurring amino acid
<220> FEATURE:
<221> NAME/KEY: misc_feature
<222> LOCATION: (319)..(322)

-continued

<223> OTHER INFORMATION: Each Xaa can independently be any naturally occurring amino acid
<220> FEATURE:
<221> NAME/KEY: misc_feature
<222> LOCATION: (328)..(328)
<223> OTHER INFORMATION: Xaa can be any naturally occurring amino acid
<220> FEATURE:
<221> NAME/KEY: misc_feature
<222> LOCATION: (329)..(329)
<223> OTHER INFORMATION: Xaa can be any naturally occurring amino acid
<220> FEATURE:
<221> NAME/KEY: misc_feature
<222> LOCATION: (335)..(337)
<223> OTHER INFORMATION: Each Xaa can independently be any naturally occurring amino acid
<220> FEATURE:
<221> NAME/KEY: misc_feature
<222> LOCATION: (346)..(346)
<223> OTHER INFORMATION: Xaa can be any naturally occurring amino acid
<220> FEATURE:
<221> NAME/KEY: misc_feature
<222> LOCATION: (347)..(347)
<223> OTHER INFORMATION: Xaa can be any naturally occurring amino acid
<220> FEATURE:
<221> NAME/KEY: misc_feature
<222> LOCATION: (356)..(361)
<223> OTHER INFORMATION: Each Xaa can independently be any naturally occurring amino acid
<220> FEATURE:
<221> NAME/KEY: misc_feature
<222> LOCATION: (363)..(363)
<223> OTHER INFORMATION: Xaa can be any naturally occurring amino acid
<220> FEATURE:
<221> NAME/KEY: misc_feature
<222> LOCATION: (370)..(373)
<223> OTHER INFORMATION: Each Xaa can independently be any naturally occurring amino acid
<220> FEATURE:
<221> NAME/KEY: misc_feature
<222> LOCATION: (375)..(375)
<223> OTHER INFORMATION: Xaa can be any naturally occurring amino acid
<220> FEATURE:
<221> NAME/KEY: misc_feature
<222> LOCATION: (376)..(376)
<223> OTHER INFORMATION: Xaa can be any naturally occurring amino acid
<220> FEATURE:
<221> NAME/KEY: misc_feature
<222> LOCATION: (379)..(379)
<223> OTHER INFORMATION: Xaa can be any naturally occurring amino acid
<220> FEATURE:
<221> NAME/KEY: misc_feature
<222> LOCATION: (386)..(390)
<223> OTHER INFORMATION: Each Xaa can independently be any naturally occurring amino acid
<220> FEATURE:
<221> NAME/KEY: misc_feature
<222> LOCATION: (393)..(393)
<223> OTHER INFORMATION: Xaa can be any naturally occurring amino acid
<220> FEATURE:
<221> NAME/KEY: misc_feature
<222> LOCATION: (395)..(395)
<223> OTHER INFORMATION: Xaa can be any naturally occurring amino acid
<220> FEATURE:
<221> NAME/KEY: misc_feature
<222> LOCATION: (396)..(396)
<223> OTHER INFORMATION: Xaa can be any naturally occurring amino acid
<220> FEATURE:
<221> NAME/KEY: misc_feature
<222> LOCATION: (398)..(398)
<223> OTHER INFORMATION: Xaa can be any naturally occurring amino acid
<220> FEATURE:
<221> NAME/KEY: misc_feature
<222> LOCATION: (400)..(400)
<223> OTHER INFORMATION: Xaa can be any naturally occurring amino acid
<220> FEATURE:
<221> NAME/KEY: misc_feature
<222> LOCATION: (403)..(403)
<223> OTHER INFORMATION: Xaa can be any naturally occurring amino acid
<220> FEATURE:

<221> NAME/KEY: misc_feature
<222> LOCATION: (407)..(407)
<223> OTHER INFORMATION: Xaa can be any naturally occurring amino acid
<220> FEATURE:
<221> NAME/KEY: misc_feature
<222> LOCATION: (410)..(410)
<223> OTHER INFORMATION: Xaa can be any naturally occurring amino acid
<220> FEATURE:
<221> NAME/KEY: misc_feature
<222> LOCATION: (411)..(411)
<223> OTHER INFORMATION: Xaa can be any naturally occurring amino acid
<220> FEATURE:
<221> NAME/KEY: misc_feature
<222> LOCATION: (413)..(416)
<223> OTHER INFORMATION: Each Xaa can independently be any naturally occurring amino acid
<220> FEATURE:
<221> NAME/KEY: misc_feature
<222> LOCATION: (418)..(418)
<223> OTHER INFORMATION: Xaa can be any naturally occurring amino acid
<220> FEATURE:
<221> NAME/KEY: misc_feature
<222> LOCATION: (422)..(422)
<223> OTHER INFORMATION: Xaa can be any naturally occurring amino acid
<220> FEATURE:
<221> NAME/KEY: misc_feature
<222> LOCATION: (428)..(428)
<223> OTHER INFORMATION: Xaa can be any naturally occurring amino acid
<220> FEATURE:
<221> NAME/KEY: misc_feature
<222> LOCATION: (431)..(431)
<223> OTHER INFORMATION: Xaa can be any naturally occurring amino acid
<220> FEATURE:
<221> NAME/KEY: misc_feature
<222> LOCATION: (433)..(433)
<223> OTHER INFORMATION: Xaa can be any naturally occurring amino acid
<220> FEATURE:
<221> NAME/KEY: misc_feature
<222> LOCATION: (437)..(439)
<223> OTHER INFORMATION: Each Xaa can independently be any naturally occurring amino acid
<220> FEATURE:
<221> NAME/KEY: misc_feature
<222> LOCATION: (445)..(445)
<223> OTHER INFORMATION: Xaa can be any naturally occurring amino acid
<220> FEATURE:
<221> NAME/KEY: misc_feature
<222> LOCATION: (451)..(451)
<223> OTHER INFORMATION: Xaa can be any naturally occurring amino acid
<220> FEATURE:
<221> NAME/KEY: misc_feature
<222> LOCATION: (456)..(456)
<223> OTHER INFORMATION: Xaa can be any naturally occurring amino acid
<220> FEATURE:
<221> NAME/KEY: misc_feature
<222> LOCATION: (459)..(459)
<223> OTHER INFORMATION: Xaa can be any naturally occurring amino acid
<220> FEATURE:
<221> NAME/KEY: misc_feature
<222> LOCATION: (465)..(469)
<223> OTHER INFORMATION: Each Xaa can independently be any naturally occurring amino acid
<220> FEATURE:
<221> NAME/KEY: misc_feature
<222> LOCATION: (481)..(481)
<223> OTHER INFORMATION: Xaa can be any naturally occurring amino acid
<220> FEATURE:
<221> NAME/KEY: misc_feature
<222> LOCATION: (482)..(482)
<223> OTHER INFORMATION: Xaa can be any naturally occurring amino acid
<220> FEATURE:
<221> NAME/KEY: misc_feature
<222> LOCATION: (484)..(484)
<223> OTHER INFORMATION: Xaa can be any naturally occurring amino acid
<220> FEATURE:
<221> NAME/KEY: misc_feature
<222> LOCATION: (490)..(490)
<223> OTHER INFORMATION: Xaa can be any naturally occurring amino acid
<220> FEATURE:

<221> NAME/KEY: misc_feature
<222> LOCATION: (494)..(494)
<223> OTHER INFORMATION: Xaa can be any naturally occurring amino acid
<220> FEATURE:
<221> NAME/KEY: misc_feature
<222> LOCATION: (495)..(502)
<223> OTHER INFORMATION: RuvC-like domain
<220> FEATURE:
<221> NAME/KEY: misc_feature
<222> LOCATION: (497)..(497)
<223> OTHER INFORMATION: Xaa can be any naturally occurring amino acid
<220> FEATURE:
<221> NAME/KEY: misc_feature
<222> LOCATION: (506)..(506)
<223> OTHER INFORMATION: Xaa can be any naturally occurring amino acid
<220> FEATURE:
<221> NAME/KEY: misc_feature
<222> LOCATION: (510)..(510)
<223> OTHER INFORMATION: Xaa can be any naturally occurring amino acid
<220> FEATURE:
<221> NAME/KEY: misc_feature
<222> LOCATION: (513)..(513)
<223> OTHER INFORMATION: Xaa can be any naturally occurring amino acid
<220> FEATURE:
<221> NAME/KEY: misc_feature
<222> LOCATION: (514)..(514)
<223> OTHER INFORMATION: Xaa can be any naturally occurring amino acid
<220> FEATURE:
<221> NAME/KEY: misc_feature
<222> LOCATION: (517)..(517)
<223> OTHER INFORMATION: Xaa can be any naturally occurring amino acid
<220> FEATURE:
<221> NAME/KEY: misc_feature
<222> LOCATION: (520)..(520)
<223> OTHER INFORMATION: Xaa can be any naturally occurring amino acid
<220> FEATURE:
<221> NAME/KEY: misc_feature
<222> LOCATION: (525)..(525)
<223> OTHER INFORMATION: Xaa can be any naturally occurring amino acid
<220> FEATURE:
<221> NAME/KEY: misc_feature
<222> LOCATION: (526)..(526)
<223> OTHER INFORMATION: Xaa can be any naturally occurring amino acid
<220> FEATURE:
<221> NAME/KEY: misc_feature
<222> LOCATION: (529)..(529)
<223> OTHER INFORMATION: Xaa can be any naturally occurring amino acid
<220> FEATURE:
<221> NAME/KEY: misc_feature
<222> LOCATION: (531)..(531)
<223> OTHER INFORMATION: Xaa can be any naturally occurring amino acid
<220> FEATURE:
<221> NAME/KEY: misc_feature
<222> LOCATION: (532)..(532)
<223> OTHER INFORMATION: Xaa can be any naturally occurring amino acid
<220> FEATURE:
<221> NAME/KEY: misc_feature
<222> LOCATION: (534)..(534)
<223> OTHER INFORMATION: Xaa can be any naturally occurring amino acid
<220> FEATURE:
<221> NAME/KEY: misc_feature
<222> LOCATION: (542)..(542)
<223> OTHER INFORMATION: Xaa can be any naturally occurring amino acid
<220> FEATURE:
<221> NAME/KEY: misc_feature
<222> LOCATION: (546)..(546)
<223> OTHER INFORMATION: Xaa can be any naturally occurring amino acid
<220> FEATURE:
<221> NAME/KEY: misc_feature
<222> LOCATION: (547)..(547)
<223> OTHER INFORMATION: Xaa can be any naturally occurring amino acid
<220> FEATURE:
<221> NAME/KEY: misc_feature
<222> LOCATION: (553)..(553)
<223> OTHER INFORMATION: Xaa can be any naturally occurring amino acid
<220> FEATURE:
<221> NAME/KEY: misc_feature
<222> LOCATION: (555)..(575)
<223> OTHER INFORMATION: HNH-like domain
<220> FEATURE:
<221> NAME/KEY: misc_feature
<222> LOCATION: (556)..(556)
<223> OTHER INFORMATION: Xaa can be any naturally occurring amino acid
<220> FEATURE:
<221> NAME/KEY: misc_feature
<222> LOCATION: (560)..(560)
<223> OTHER INFORMATION: Xaa can be any naturally occurring amino acid
<220> FEATURE:
<221> NAME/KEY: misc_feature
<222> LOCATION: (563)..(563)
<223> OTHER INFORMATION: Xaa can be any naturally occurring amino acid
<220> FEATURE:
<221> NAME/KEY: misc_feature
<222> LOCATION: (565)..(565)
<223> OTHER INFORMATION: Xaa can be any naturally occurring amino acid
<220> FEATURE:
<221> NAME/KEY: misc_feature
<222> LOCATION: (567)..(567)
<223> OTHER INFORMATION: Xaa can be any naturally occurring amino acid
<220> FEATURE:
<221> NAME/KEY: misc_feature
<222> LOCATION: (579)..(579)
<223> OTHER INFORMATION: Xaa can be any naturally occurring amino acid
<220> FEATURE:
<221> NAME/KEY: misc_feature
<222> LOCATION: (582)..(582)
<223> OTHER INFORMATION: Xaa can be any naturally occurring amino acid
<220> FEATURE:
<221> NAME/KEY: misc_feature
<222> LOCATION: (583)..(583)
<223> OTHER INFORMATION: Xaa can be any naturally occurring amino acid
<220> FEATURE:
<221> NAME/KEY: misc_feature
<222> LOCATION: (585)..(585)
<223> OTHER INFORMATION: Xaa can be any naturally occurring amino acid
<220> FEATURE:
<221> NAME/KEY: misc_feature
<222> LOCATION: (588)..(588)
<223> OTHER INFORMATION: Xaa can be any naturally occurring amino acid
<220> FEATURE:
<221> NAME/KEY: misc_feature
<222> LOCATION: (590)..(590)
<223> OTHER INFORMATION: Xaa can be any naturally occurring amino acid
<220> FEATURE:
<221> NAME/KEY: misc_feature
<222> LOCATION: (592)..(592)
<223> OTHER INFORMATION: Xaa can be any naturally occurring amino acid
<220> FEATURE:
<221> NAME/KEY: misc_feature
<222> LOCATION: (594)..(596)
<223> OTHER INFORMATION: Each Xaa can independently be any naturally
occurring amino acid
<220> FEATURE:
<221> NAME/KEY: misc_feature
<222> LOCATION: (610)..(610)
<223> OTHER INFORMATION: Xaa can be any naturally occurring amino acid
<220> FEATURE:
<221> NAME/KEY: misc_feature
<222> LOCATION: (616)..(616)
<223> OTHER INFORMATION: Xaa can be any naturally occurring amino acid
<220> FEATURE:
<221> NAME/KEY: misc_feature
<222> LOCATION: (628)..(628)
<223> OTHER INFORMATION: Xaa can be any naturally occurring amino acid
<220> FEATURE:
<221> NAME/KEY: misc_feature
<222> LOCATION: (631)..(631)
<223> OTHER INFORMATION: Xaa can be any naturally occurring amino acid
<220> FEATURE:
<221> NAME/KEY: misc_feature
<222> LOCATION: (633)..(633)
<223> OTHER INFORMATION: Xaa can be any naturally occurring amino acid
<220> FEATURE:
<221> NAME/KEY: misc_feature
<222> LOCATION: (634)..(634)
<223> OTHER INFORMATION: Xaa can be any naturally occurring amino acid
<220> FEATURE:
<221> NAME/KEY: misc_feature
<222> LOCATION: (636)..(636)
<223> OTHER INFORMATION: Xaa can be any naturally occurring amino acid
<220> FEATURE:
<221> NAME/KEY: misc_feature
<222> LOCATION: (638)..(641)
<223> OTHER INFORMATION: Each Xaa can independently be any naturally
occurring amino acid
<220> FEATURE:
<221> NAME/KEY: misc_feature
<222> LOCATION: (643)..(645)
<223> OTHER INFORMATION: Each Xaa can independently be any naturally
occurring amino acid
<220> FEATURE:
<221> NAME/KEY: misc_feature
<222> LOCATION: (653)..(653)
<223> OTHER INFORMATION: Xaa can be any naturally occurring amino acid
<220> FEATURE:
<221> NAME/KEY: misc_feature
<222> LOCATION: (657)..(657)
<223> OTHER INFORMATION: Xaa can be any naturally occurring amino acid
<220> FEATURE:
<221> NAME/KEY: misc_feature
<222> LOCATION: (659)..(659)
<223> OTHER INFORMATION: Xaa can be any naturally occurring amino acid
<220> FEATURE:
<221> NAME/KEY: misc_feature
<222> LOCATION: (660)..(660)
<223> OTHER INFORMATION: Xaa can be any naturally occurring amino acid
<220> FEATURE:
<221> NAME/KEY: misc_feature
<222> LOCATION: (665)..(665)
<223> OTHER INFORMATION: Xaa can be any naturally occurring amino acid
<220> FEATURE:
<221> NAME/KEY: misc_feature
<222> LOCATION: (666)..(666)
<223> OTHER INFORMATION: Xaa can be any naturally occurring amino acid
<220> FEATURE:
<221> NAME/KEY: misc_feature
<222> LOCATION: (668)..(668)
<223> OTHER INFORMATION: Xaa can be any naturally occurring amino acid
<220> FEATURE:
<221> NAME/KEY: misc_feature
<222> LOCATION: (669)..(669)
<223> OTHER INFORMATION: Xaa can be any naturally occurring amino acid
<220> FEATURE:
<221> NAME/KEY: misc_feature
<222> LOCATION: (670)..(677)
<223> OTHER INFORMATION: RuvC-like domain
<220> FEATURE:
<221> NAME/KEY: misc_feature
<222> LOCATION: (680)..(680)
<223> OTHER INFORMATION: Xaa can be any naturally occurring amino acid
<220> FEATURE:
<221> NAME/KEY: misc_feature
<222> LOCATION: (681)..(681)
<223> OTHER INFORMATION: Xaa can be any naturally occurring amino acid
<220> FEATURE:
<221> NAME/KEY: misc_feature
<222> LOCATION: (683)..(683)
<223> OTHER INFORMATION: Xaa can be any naturally occurring amino acid
<220> FEATURE:
<221> NAME/KEY: misc_feature
<222> LOCATION: (686)..(686)
<223> OTHER INFORMATION: Xaa can be any naturally occurring amino acid
<220> FEATURE:
<221> NAME/KEY: misc_feature
<222> LOCATION: (696)..(696)
<223> OTHER INFORMATION: Xaa can be any naturally occurring amino acid
<220> FEATURE:
<221> NAME/KEY: misc_feature
<222> LOCATION: (697)..(697)
<223> OTHER INFORMATION: Xaa can be any naturally occurring amino acid
<220> FEATURE:
<221> NAME/KEY: misc_feature
<222> LOCATION: (704)..(704)
<223> OTHER INFORMATION: Xaa can be any naturally occurring amino acid
<220> FEATURE:
<221> NAME/KEY: misc_feature
<222> LOCATION: (708)..(708)

<223> OTHER INFORMATION: Xaa can be any naturally occurring amino acid
<220> FEATURE:
<221> NAME/KEY: misc_feature
<222> LOCATION: (710)..(710)
<223> OTHER INFORMATION: Xaa can be any naturally occurring amino acid
<220> FEATURE:
<221> NAME/KEY: misc_feature
<222> LOCATION: (711)..(711)
<223> OTHER INFORMATION: Xaa can be any naturally occurring amino acid
<220> FEATURE:
<221> NAME/KEY: misc_feature
<222> LOCATION: (714)..(714)
<223> OTHER INFORMATION: Xaa can be any naturally occurring amino acid
<220> FEATURE:
<221> NAME/KEY: misc_feature
<222> LOCATION: (717)..(720)
<223> OTHER INFORMATION: Each Xaa can independently be any naturally
occurring amino acid
<220> FEATURE:
<221> NAME/KEY: misc_feature
<222> LOCATION: (722)..(722)
<223> OTHER INFORMATION: Xaa can be any naturally occurring amino acid
<220> FEATURE:
<221> NAME/KEY: misc_feature
<222> LOCATION: (725)..(725)
<223> OTHER INFORMATION: Xaa can be any naturally occurring amino acid
<220> FEATURE:
<221> NAME/KEY: misc_feature
<222> LOCATION: (727)..(727)
<223> OTHER INFORMATION: Xaa can be any naturally occurring amino acid
<220> FEATURE:
<221> NAME/KEY: misc_feature
<222> LOCATION: (733)..(735)
<223> OTHER INFORMATION: Each Xaa can independently be any naturally
occurring amino acid
<220> FEATURE:
<221> NAME/KEY: misc_feature
<222> LOCATION: (740)..(740)
<223> OTHER INFORMATION: Xaa can be any naturally occurring amino acid
<220> FEATURE:
<221> NAME/KEY: misc_feature
<222> LOCATION: (742)..(742)
<223> OTHER INFORMATION: Xaa can be any naturally occurring amino acid
<220> FEATURE:
<221> NAME/KEY: misc_feature
<222> LOCATION: (749)..(754)
<223> OTHER INFORMATION: Each Xaa can independently be any naturally
occurring amino acid
<220> FEATURE:
<221> NAME/KEY: misc_feature
<222> LOCATION: (758)..(761)
<223> OTHER INFORMATION: Each Xaa can independently be any naturally
occurring amino acid
<220> FEATURE:
<221> NAME/KEY: misc_feature
<222> LOCATION: (763)..(768)
<223> OTHER INFORMATION: Each Xaa can independently be any naturally
occurring amino acid
<220> FEATURE:
<221> NAME/KEY: misc_feature
<222> LOCATION: (771)..(771)
<223> OTHER INFORMATION: Xaa can be any naturally occurring amino acid
<220> FEATURE:
<221> NAME/KEY: misc_feature
<222> LOCATION: (774)..(777)
<223> OTHER INFORMATION: Each Xaa can independently be any naturally
occurring amino acid
<220> FEATURE:
<221> NAME/KEY: misc_feature
<222> LOCATION: (782)..(782)
<223> OTHER INFORMATION: Xaa can be any naturally occurring amino acid
<220> FEATURE:
<221> NAME/KEY: misc_feature
<222> LOCATION: (784)..(786)
<223> OTHER INFORMATION: Each Xaa can independently be any naturally
occurring amino acid
<220> FEATURE:
<221> NAME/KEY: misc_feature
<222> LOCATION: (788)..(788)

<223> OTHER INFORMATION: Xaa can be any naturally occurring amino acid
<220> FEATURE:
<221> NAME/KEY: misc_feature
<222> LOCATION: (790)..(790)
<223> OTHER INFORMATION: Xaa can be any naturally occurring amino acid
<220> FEATURE:
<221> NAME/KEY: misc_feature
<222> LOCATION: (795)..(795)
<223> OTHER INFORMATION: Xaa can be any naturally occurring amino acid
<220> FEATURE:
<221> NAME/KEY: misc_feature
<222> LOCATION: (799)..(799)
<223> OTHER INFORMATION: Xaa can be any naturally occurring amino acid
<220> FEATURE:
<221> NAME/KEY: misc_feature
<222> LOCATION: (801)..(801)
<223> OTHER INFORMATION: Xaa can be any naturally occurring amino acid
<220> FEATURE:
<221> NAME/KEY: misc_feature
<222> LOCATION: (802)..(802)
<223> OTHER INFORMATION: Xaa can be any naturally occurring amino acid
<220> FEATURE:
<221> NAME/KEY: misc_feature
<222> LOCATION: (804)..(804)
<223> OTHER INFORMATION: Xaa can be any naturally occurring amino acid
<220> FEATURE:
<221> NAME/KEY: misc_feature
<222> LOCATION: (806)..(813)
<223> OTHER INFORMATION: Each Xaa can independently be any naturally occurring amino acid
<220> FEATURE:
<221> NAME/KEY: misc_feature
<222> LOCATION: (815)..(818)
<223> OTHER INFORMATION: Each Xaa can independently be any naturally occurring amino acid
<220> FEATURE:
<221> NAME/KEY: misc_feature
<222> LOCATION: (820)..(820)
<223> OTHER INFORMATION: Xaa can be any naturally occurring amino acid
<220> FEATURE:
<221> NAME/KEY: misc_feature
<222> LOCATION: (823)..(827)
<223> OTHER INFORMATION: Each Xaa can independently be any naturally occurring amino acid
<220> FEATURE:
<221> NAME/KEY: misc_feature
<222> LOCATION: (829)..(829)
<223> OTHER INFORMATION: Xaa can be any naturally occurring amino acid
<220> FEATURE:
<221> NAME/KEY: misc_feature
<222> LOCATION: (830)..(830)
<223> OTHER INFORMATION: Xaa can be any naturally occurring amino acid
<220> FEATURE:
<221> NAME/KEY: misc_feature
<222> LOCATION: (832)..(832)
<223> OTHER INFORMATION: Xaa can be any naturally occurring amino acid
<220> FEATURE:
<221> NAME/KEY: misc_feature
<222> LOCATION: (835)..(837)
<223> OTHER INFORMATION: Each Xaa can independently be any naturally occurring amino acid
<220> FEATURE:
<221> NAME/KEY: misc_feature
<222> LOCATION: (842)..(844)
<223> OTHER INFORMATION: Each Xaa can independently be any naturally occurring amino acid
<220> FEATURE:
<221> NAME/KEY: misc_feature
<222> LOCATION: (846)..(846)
<223> OTHER INFORMATION: Xaa can be any naturally occurring amino acid
<220> FEATURE:
<221> NAME/KEY: misc_feature
<222> LOCATION: (848)..(848)
<223> OTHER INFORMATION: Xaa can be any naturally occurring amino acid
<220> FEATURE:
<221> NAME/KEY: misc_feature
<222> LOCATION: (851)..(851)
<223> OTHER INFORMATION: Xaa can be any naturally occurring amino acid
<220> FEATURE:

<221> NAME/KEY: misc_feature
<222> LOCATION: (857)..(857)
<223> OTHER INFORMATION: Xaa can be any naturally occurring amino acid
<220> FEATURE:
<221> NAME/KEY: misc_feature
<222> LOCATION: (857)..(857)
<223> OTHER INFORMATION: Xaa can be any naturally occurring amino acid

<400> SEQUENCE: 14

```
Met Lys Tyr Xaa Ile Gly Leu Asp Ile Gly Thr Asn Ser Val Gly Trp
1               5                   10                  15

Ala Val Thr Asp Xaa Tyr Xaa Xaa Lys Xaa Lys Gly Xaa Xaa Xaa Ile
            20                  25                  30

Xaa Lys Asn Xaa Gly Leu Phe Asp Gly Thr Ala Arg Xaa Arg Thr Ala
        35                  40                  45

Arg Arg Arg Arg Arg Xaa Asn Arg Ile Tyr Leu Gln Ile Phe Xaa Glu
    50                  55                  60

Met Asp Phe Phe Arg Leu Xaa Ser Phe Val Xaa Xaa Lys Xaa Xaa Xaa
65                  70                  75                  80

Pro Xaa Phe Xaa Xaa Glu Tyr His Xaa Xaa Pro Thr Ile Tyr His Leu
                85                  90                  95

Arg Xaa Leu Xaa Lys Asp Leu Arg Leu Xaa Tyr Leu Ala Leu Ala His
            100                 105                 110

Xaa Ile Lys Xaa Arg Gly Asn Phe Leu Ile Glu Gly Xaa Xaa Asn Xaa
        115                 120                 125

Xaa Xaa Xaa Xaa Xaa Tyr Xaa Phe Xaa Ile Xaa Xaa Xaa Xaa Xaa Xaa
    130                 135                 140

Xaa Xaa Xaa Pro Glu Lys Gly Phe Xaa Xaa Xaa Leu Xaa Gly Xaa Phe
145                 150                 155                 160

Xaa Phe Xaa Leu Glu Xaa Xaa Xaa Lys Xaa Xaa Tyr Xaa Xaa Xaa Leu
                165                 170                 175

Xaa Leu Leu Ile Gly Asp Xaa Tyr Xaa Xaa Xaa Phe Xaa Ala Lys Xaa
            180                 185                 190

Xaa Xaa Xaa Leu Ser Xaa Xaa Val Thr Xaa Ala Leu Ser Xaa Xaa Met
        195                 200                 205

Ile Xaa Arg Xaa Xaa His Asp Leu Leu Lys Xaa Xaa Tyr Xaa Glu Xaa
    210                 215                 220

Phe Xaa Lys Gly Tyr Ala Gly Tyr Ile Asp Gly Xaa Gln Phe Tyr Xaa
225                 230                 235                 240

Xaa Lys Leu Xaa Xaa Xaa Gly Xaa Xaa Xaa Lys Xaa Xaa Xaa Glu Xaa
                245                 250                 255

Xaa Leu Arg Lys Gln Arg Thr Phe Asp Asn Gly Xaa Ile Pro Xaa Gln
            260                 265                 270

Xaa His Leu Glu Xaa Ala Ile Xaa Xaa Gln Xaa Tyr Pro Phe Leu Asn
        275                 280                 285

Xaa Xaa Ile Xaa Xaa Xaa Thr Phe Arg Ile Pro Tyr Xaa Val Gly Pro
    290                 295                 300

Leu Ala Gly Xaa Ser Phe Ala Trp Arg Lys Ile Pro Trp Asn Xaa Xaa
305                 310                 315                 320

Xaa Xaa Asp Ser Ala Phe Ile Xaa Xaa Met Thr Asp Leu Pro Xaa Xaa
                325                 330                 335

Xaa Val Leu Pro Lys His Ser Leu Tyr Xaa Xaa Val Tyr Asn Glu Leu
            340                 345                 350

Thr Lys Val Xaa Xaa Xaa Xaa Xaa Xaa Lys Xaa Ile Phe Lys Arg Lys
        355                 360                 365
```

-continued

```
Val Xaa Xaa Xaa Xaa Gly Xaa Xaa Phe Asn Xaa Ser Thr Tyr His Asp
    370                 375                 380

Leu Xaa Xaa Xaa Xaa Xaa Leu Asp Xaa Asn Xaa Xaa Glu Xaa Ile Xaa
385                 390                 395                 400

Leu Thr Xaa Phe Glu Asp Xaa Met Ile Xaa Xaa Leu Xaa Xaa Xaa Xaa
                405                 410                 415

Lys Xaa Leu Arg Arg Xaa Tyr Thr Gly Trp Gly Xaa Leu Ser Xaa Leu
            420                 425                 430

Xaa Gly Ile Arg Xaa Xaa Xaa Ser Thr Ile Leu Asp Xaa Leu Asp Asn
        435                 440                 445

Arg Asn Xaa Met Gln Leu Ile Xaa Asp Leu Xaa Phe Lys Ile Lys Gln
    450                 455                 460

Xaa Xaa Xaa Xaa Xaa Gly Ser Pro Ala Ile Lys Lys Gly Ile Leu Gln
465                 470                 475                 480

Xaa Xaa Lys Xaa Val Asp Glu Leu Val Xaa Met Gly Pro Xaa Ile Val
                485                 490                 495

Xaa Glu Met Ala Arg Glu Asn Gln Thr Xaa Gly Asn Ser Xaa Arg Lys
            500                 505                 510

Xaa Xaa Lys Glu Xaa Gly Ser Xaa Ile Leu Lys Glu Xaa Xaa Asn Leu
        515                 520                 525

Xaa Asn Xaa Xaa Leu Xaa Leu Tyr Tyr Leu Gln Asn Gly Xaa Asp Met
    530                 535                 540

Tyr Xaa Xaa Leu Asp Ile Leu Ser Xaa Tyr Asp Xaa Asp His Ile Xaa
545                 550                 555                 560

Pro Gln Xaa Phe Xaa Asp Xaa Ser Ile Asp Asn Val Leu Ser Asn Arg
                565                 570                 575

Lys Asp Xaa Val Pro Xaa Xaa Val Xaa Lys Lys Xaa Trp Xaa Leu Xaa
            580                 585                 590

Leu Xaa Xaa Xaa Arg Lys Phe Asp Leu Thr Lys Ala Glu Arg Gly Gly
        595                 600                 605

Leu Xaa Asp Lys Ala Phe Ile Xaa Arg Gln Leu Val Glu Thr Arg Gln
    610                 615                 620

Ile Thr Lys Xaa Val Ala Xaa Leu Xaa Xaa Asn Xaa Asp Xaa Xaa Xaa
625                 630                 635                 640

Xaa Val Xaa Xaa Xaa Thr Leu Lys Ser Leu Val Ser Xaa Phe Arg Lys
                645                 650                 655

Xaa Phe Xaa Xaa Leu Tyr Lys Val Xaa Xaa Asn Xaa Xaa His His Ala
            660                 665                 670

His Asp Ala Tyr Leu Asn Val Xaa Xaa Leu Xaa Tyr Pro Xaa Leu Glu
        675                 680                 685

Glu Phe Val Tyr Gly Asp Tyr Xaa Xaa Lys Ala Thr Lys Phe Tyr Xaa
    690                 695                 700

Asn Ile Met Xaa Phe Xaa Xaa Gly Glu Xaa Trp Lys Xaa Xaa Xaa Xaa
705                 710                 715                 720

Val Xaa Met Gln Xaa Asn Xaa Val Lys Lys Glu Gln Xaa Xaa Xaa Pro
                725                 730                 735

Lys Asn Ser Xaa Leu Xaa Lys Asp Lys Tyr Gly Gly Xaa Xaa Xaa Xaa
            740                 745                 750

Xaa Xaa Lys Gly Lys Xaa Xaa Xaa Xaa Ile Xaa Xaa Xaa Xaa Xaa Xaa
        755                 760                 765

Phe Leu Xaa Gly Tyr Xaa Xaa Xaa Xaa Leu Pro Lys Tyr Xaa Leu Xaa
    770                 775                 780

Xaa Xaa Gly Xaa Arg Xaa Leu Ala Ser Glu Xaa Lys Gly Asn Xaa Leu
```

-continued

```
785                 790                 795                 800

Xaa Xaa Leu Xaa Ala Xaa Xaa Xaa Xaa Xaa Xaa Xaa Xaa Glu Xaa Xaa
                805                 810                 815

Xaa Xaa Phe Xaa Ala Asn Xaa Xaa Xaa Xaa Xaa Leu Xaa Xaa Gly Xaa
            820                 825                 830

Ala Phe Xaa Xaa Xaa Ile Arg Arg Tyr Xaa Xaa Xaa Thr Xaa Ile Xaa
        835                 840                 845

Gln Ser Xaa Thr Gly Leu Tyr Glu Xaa Arg Leu
    850                 855
```

<210> SEQ ID NO 15
<211> LENGTH: 8
<212> TYPE: PRT
<213> ORGANISM: Artificial Sequence
<220> FEATURE:
<223> OTHER INFORMATION: RuvC-like domain
<220> FEATURE:
<221> NAME/KEY: VARIANT
<222> LOCATION: (2)..(2)
<223> OTHER INFORMATION: Xaa is Val or His
<220> FEATURE:
<221> NAME/KEY: VARIANT
<222> LOCATION: (3)..(3)
<223> OTHER INFORMATION: Xaa is Ile, Leu, or Val
<220> FEATURE:
<221> NAME/KEY: VARIANT
<222> LOCATION: (5)..(5)
<223> OTHER INFORMATION: Xaa is Met or Thr

<400> SEQUENCE: 15

```
Ile Xaa Xaa Glu Xaa Ala Arg Glu
1               5
```

<210> SEQ ID NO 16
<211> LENGTH: 8
<212> TYPE: PRT
<213> ORGANISM: Artificial Sequence
<220> FEATURE:
<223> OTHER INFORMATION: RuvC-like domain
<220> FEATURE:
<221> NAME/KEY: VARIANT
<222> LOCATION: (3)..(3)
<223> OTHER INFORMATION: Xaa is Ile, Leu, or Val

<400> SEQUENCE: 16

```
Ile Val Xaa Glu Met Ala Arg Glu
1               5
```

<210> SEQ ID NO 17
<211> LENGTH: 8
<212> TYPE: PRT
<213> ORGANISM: Artificial Sequence
<220> FEATURE:
<223> OTHER INFORMATION: RuvC-like domain
<220> FEATURE:
<221> NAME/KEY: VARIANT
<222> LOCATION: (4)..(4)
<223> OTHER INFORMATION: Xaa is His or Leu
<220> FEATURE:
<221> NAME/KEY: VARIANT
<222> LOCATION: (7)..(7)
<223> OTHER INFORMATION: Xaa is Arg or Val
<220> FEATURE:
<221> NAME/KEY: VARIANT
<222> LOCATION: (8)..(8)
<223> OTHER INFORMATION: Xaa is Glu or Val

<400> SEQUENCE: 17

```
His His Ala Xaa Asp Ala Xaa Xaa
```

1 5

<210> SEQ ID NO 18
<211> LENGTH: 8
<212> TYPE: PRT
<213> ORGANISM: Artificial Sequence
<220> FEATURE:
<223> OTHER INFORMATION: RuvC-like domain

<400> SEQUENCE: 18

His His Ala His Asp Ala Tyr Leu
1 5

<210> SEQ ID NO 19
<211> LENGTH: 30
<212> TYPE: PRT
<213> ORGANISM: Artificial Sequence
<220> FEATURE:
<223> OTHER INFORMATION: N-terminal RuvC-like domain
<220> FEATURE:
<221> NAME/KEY: VARIANT
<222> LOCATION: (2)..(2)
<223> OTHER INFORMATION: Xaa is Lys or Pro
<220> FEATURE:
<221> NAME/KEY: VARIANT
<222> LOCATION: (4)..(4)
<223> OTHER INFORMATION: Xaa is Val, Leu, Ile, or Phe
<220> FEATURE:
<221> NAME/KEY: VARIANT
<222> LOCATION: (5)..(5)
<223> OTHER INFORMATION: Xaa is Gly, Ala, or Ser
<220> FEATURE:
<221> NAME/KEY: VARIANT
<222> LOCATION: (6)..(6)
<223> OTHER INFORMATION: Xaa is Leu, Ile, Val, or Phe
<220> FEATURE:
<221> NAME/KEY: MOD_RES
<222> LOCATION: (7)..(26)
<223> OTHER INFORMATION: N-terminal RuvC-like domain, each Xaa can be
any amino acid or absent, region may encompass 5-20 residues
<220> FEATURE:
<221> NAME/KEY: VARIANT
<222> LOCATION: (29)..(29)
<223> OTHER INFORMATION: Xaa is Asp, Glu, Asn, or Gln

<400> SEQUENCE: 19

Lys Xaa Tyr Xaa Xaa Xaa Xaa Xaa Xaa Xaa Xaa Xaa Xaa Xaa Xaa Xaa
1 5 10 15

Xaa Xaa Xaa Xaa Xaa Xaa Xaa Xaa Xaa Xaa Thr Asp Xaa Tyr
20 25 30

<210> SEQ ID NO 20
<211> LENGTH: 12
<212> TYPE: PRT
<213> ORGANISM: Artificial Sequence
<220> FEATURE:
<223> OTHER INFORMATION: N-terminal RuvC-like domain
<220> FEATURE:
<221> NAME/KEY: VARIANT
<222> LOCATION: (2)..(2)
<223> OTHER INFORMATION: Xaa is Ile, Val, Met, Leu, or Thr
<220> FEATURE:
<221> NAME/KEY: VARIANT
<222> LOCATION: (4)..(4)
<223> OTHER INFORMATION: Xaa is Thr, Ile, Val, Ser, Asn, Tyr, Glu, or
Leu
<220> FEATURE:
<221> NAME/KEY: VARIANT
<222> LOCATION: (5)..(5)
<223> OTHER INFORMATION: Xaa is Asn, Ser, Gly, Ala, Asp, Thr, Arg, Met,
or Phe
<220> FEATURE:
<221> NAME/KEY: VARIANT
<222> LOCATION: (6)..(6)
<223> OTHER INFORMATION: Xaa is Ser, Tyr, Asn, or Phe
<220> FEATURE:
<221> NAME/KEY: VARIANT
<222> LOCATION: (7)..(7)
<223> OTHER INFORMATION: Xaa is Val, Ile, Leu, Cys, Thr, or Phe
<220> FEATURE:
<221> NAME/KEY: VARIANT
<222> LOCATION: (9)..(9)
<223> OTHER INFORMATION: Xaa is Trp, Phe, Val, Tyr, Ser, or Leu
<220> FEATURE:
<221> NAME/KEY: VARIANT
<222> LOCATION: (10)..(10)
<223> OTHER INFORMATION: Xaa is Ala, Ser, Cys, Val, or Gly
<220> FEATURE:
<221> NAME/KEY: VARIANT
<222> LOCATION: (11)..(11)
<223> OTHER INFORMATION: Xaa is Val, Ile, Leu, Ala, Met, or His
<220> FEATURE:
<221> NAME/KEY: VARIANT
<222> LOCATION: (12)..(12)
<223> OTHER INFORMATION: Any amino acid or absent

<400> SEQUENCE: 20

```
Asp Xaa Gly Xaa Xaa Xaa Xaa Gly Xaa Xaa Xaa Xaa
1               5                   10
```

<210> SEQ ID NO 21
<211> LENGTH: 12
<212> TYPE: PRT
<213> ORGANISM: Artificial Sequence
<220> FEATURE:
<223> OTHER INFORMATION: N-terminal RuvC-like domain
<220> FEATURE:
<221> NAME/KEY: VARIANT
<222> LOCATION: (2)..(2)
<223> OTHER INFORMATION: Xaa is Ile, Val, Met, Leu, or Thr
<220> FEATURE:
<221> NAME/KEY: VARIANT
<222> LOCATION: (4)..(4)
<223> OTHER INFORMATION: Xaa is Thr, Ile, Val, Ser, Asn, Tyr, Glu, or Leu
<220> FEATURE:
<221> NAME/KEY: VARIANT
<222> LOCATION: (5)..(5)
<223> OTHER INFORMATION: Xaa is Asn, Ser, Gly, Ala, Asp, Thr, Arg, Met, or Phe
<220> FEATURE:
<221> NAME/KEY: VARIANT
<222> LOCATION: (7)..(7)
<223> OTHER INFORMATION: Xaa is Val, Ile, Leu, Cys, Thr, or Phe
<220> FEATURE:
<221> NAME/KEY: VARIANT
<222> LOCATION: (9)..(9)
<223> OTHER INFORMATION: Xaa is Trp, Phe, Val, Tyr, Ser, or Leu
<220> FEATURE:
<221> NAME/KEY: VARIANT
<222> LOCATION: (10)..(10)
<223> OTHER INFORMATION: Xaa is Ala, Ser, Cys, Val, or Gly
<220> FEATURE:
<221> NAME/KEY: VARIANT
<222> LOCATION: (11)..(11)
<223> OTHER INFORMATION: Xaa is Val, Ile, Leu, Ala, Met, or His
<220> FEATURE:
<221> NAME/KEY: VARIANT
<222> LOCATION: (12)..(12)
<223> OTHER INFORMATION: Any amino acid or absent

<400> SEQUENCE: 21

```
Asp Xaa Gly Xaa Xaa Ser Xaa Gly Xaa Xaa Xaa Xaa
1               5                   10
```

<210> SEQ ID NO 22
<211> LENGTH: 12
<212> TYPE: PRT

-continued

<213> ORGANISM: Artificial Sequence
<220> FEATURE:
<223> OTHER INFORMATION: N-terminal RuvC-like domain
<220> FEATURE:
<221> NAME/KEY: VARIANT
<222> LOCATION: (4)..(4)
<223> OTHER INFORMATION: Xaa is Thr, Ile, Val, Ser, Asn, Tyr, Glu, or Leu
<220> FEATURE:
<221> NAME/KEY: VARIANT
<222> LOCATION: (5)..(5)
<223> OTHER INFORMATION: Xaa is Asn, Ser, Gly, Ala, Asp, Thr, Arg, Met, or Phe
<220> FEATURE:
<221> NAME/KEY: VARIANT
<222> LOCATION: (11)..(11)
<223> OTHER INFORMATION: Xaa is Val, Ile, Leu, Ala, Met, or His
<220> FEATURE:
<221> NAME/KEY: VARIANT
<222> LOCATION: (12)..(12)
<223> OTHER INFORMATION: Any amino acid or absent

<400> SEQUENCE: 22

Asp Ile Gly Xaa Xaa Ser Val Gly Trp Ala Xaa Xaa
1               5                   10

<210> SEQ ID NO 23
<211> LENGTH: 12
<212> TYPE: PRT
<213> ORGANISM: Artificial Sequence
<220> FEATURE:
<223> OTHER INFORMATION: N-terminal RuvC-like domain
<220> FEATURE:
<221> NAME/KEY: MOD_RES
<222> LOCATION: (12)..(12)
<223> OTHER INFORMATION: Any non-polar alkyl amino acid or a hydroxyl amino acid

<400> SEQUENCE: 23

Asp Ile Gly Thr Asn Ser Val Gly Trp Ala Val Xaa
1               5                   10

<210> SEQ ID NO 24
<211> LENGTH: 73
<212> TYPE: PRT
<213> ORGANISM: Artificial Sequence
<220> FEATURE:
<223> OTHER INFORMATION: HNH-like domain
<220> FEATURE:
<221> NAME/KEY: VARIANT
<222> LOCATION: (8)..(8)
<223> OTHER INFORMATION: Xaa is Lys or Arg
<220> FEATURE:
<221> NAME/KEY: VARIANT
<222> LOCATION: (12)..(12)
<223> OTHER INFORMATION: Xaa is Val or Thr
<220> FEATURE:
<221> NAME/KEY: VARIANT
<222> LOCATION: (13)..(13)
<223> OTHER INFORMATION: Xaa is Gly or Asp
<220> FEATURE:
<221> NAME/KEY: VARIANT
<222> LOCATION: (14)..(14)
<223> OTHER INFORMATION: Xaa is Glu, Gln, or Asp
<220> FEATURE:
<221> NAME/KEY: VARIANT
<222> LOCATION: (15)..(15)
<223> OTHER INFORMATION: Xaa is Glu or Asp
<220> FEATURE:
<221> NAME/KEY: VARIANT
<222> LOCATION: (19)..(19)
<223> OTHER INFORMATION: Xaa is Asp, Asn, or His
<220> FEATURE:
<221> NAME/KEY: VARIANT
<222> LOCATION: (20)..(20)

```
<223> OTHER INFORMATION: Xaa is Tyr, Arg, or Asn
<220> FEATURE:
<221> NAME/KEY: VARIANT
<222> LOCATION: (23)..(23)
<223> OTHER INFORMATION: Xaa is Gln, Asp, or Asn
<220> FEATURE:
<221> NAME/KEY: MOD_RES
<222> LOCATION: (25)..(64)
<223> OTHER INFORMATION: HNH-like domain, each Xaa can be any amino
      acid or absent, region may encompass 15-40 residues
<220> FEATURE:
<221> NAME/KEY: VARIANT
<222> LOCATION: (67)..(67)
<223> OTHER INFORMATION: Xaa is Gly or Glu
<220> FEATURE:
<221> NAME/KEY: VARIANT
<222> LOCATION: (69)..(69)
<223> OTHER INFORMATION: Xaa is Ser or Gly
<220> FEATURE:
<221> NAME/KEY: VARIANT
<222> LOCATION: (71)..(71)
<223> OTHER INFORMATION: Xaa is Asp or Asn

<400> SEQUENCE: 24

Leu Tyr Tyr Leu Gln Asn Gly Xaa Asp Met Tyr Xaa Xaa Xaa Xaa Leu
1               5                   10                  15

Asp Ile Xaa Xaa Leu Ser Xaa Tyr Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa Xaa
    50                  55                  60

Asn Arg Xaa Lys Xaa Asp Xaa Val Pro
65                  70


<210> SEQ ID NO 25
<211> LENGTH: 27
<212> TYPE: PRT
<213> ORGANISM: Artificial Sequence
<220> FEATURE:
<223> OTHER INFORMATION: HNH-like domain
<220> FEATURE:
<221> NAME/KEY: VARIANT
<222> LOCATION: (1)..(1)
<223> OTHER INFORMATION: Xaa is Asp, Glu, Gln, or Asn
<220> FEATURE:
<221> NAME/KEY: VARIANT
<222> LOCATION: (2)..(2)
<223> OTHER INFORMATION: Xaa is Leu, Ile, Arg, Gln, Val, Met, or Lys
<220> FEATURE:
<221> NAME/KEY: VARIANT
<222> LOCATION: (3)..(3)
<223> OTHER INFORMATION: Xaa is Asp or Glu
<220> FEATURE:
<221> NAME/KEY: VARIANT
<222> LOCATION: (5)..(5)
<223> OTHER INFORMATION: Xaa is Ile, Val, Thr, Ala, or Leu
<220> FEATURE:
<221> NAME/KEY: VARIANT
<222> LOCATION: (6)..(6)
<223> OTHER INFORMATION: Xaa is Val, Tyr, Ile, Leu, Phe, or Trp
<220> FEATURE:
<221> NAME/KEY: VARIANT
<222> LOCATION: (8)..(8)
<223> OTHER INFORMATION: Xaa is Gln, His, Arg, Lys, Tyr, Ile, Leu, Phe,
      or Trp
<220> FEATURE:
<221> NAME/KEY: VARIANT
<222> LOCATION: (9)..(9)
<223> OTHER INFORMATION: Xaa is Ser, Ala, Asp, Thr, or Lys
<220> FEATURE:
<221> NAME/KEY: VARIANT
<222> LOCATION: (10)..(10)
```

<223> OTHER INFORMATION: Xaa is Phe, Leu, Val, Lys, Tyr, Met, Ile, Arg,
      Ala, Glu, Asp, or Gln
<220> FEATURE:
<221> NAME/KEY: VARIANT
<222> LOCATION: (11)..(11)
<223> OTHER INFORMATION: Xaa is Leu, Arg, Thr, Ile, Val, Ser, Cys, Tyr,
      Lys, Phe, or Gly
<220> FEATURE:
<221> NAME/KEY: VARIANT
<222> LOCATION: (12)..(12)
<223> OTHER INFORMATION: Xaa is Lys, Gln, Tyr, Thr, Phe, Leu, Trp, Met,
      Ala, Glu, Gly, or Ser
<220> FEATURE:
<221> NAME/KEY: VARIANT
<222> LOCATION: (13)..(13)
<223> OTHER INFORMATION: Xaa is Asp, Ser, Asn, Arg, Leu, or Thr
<220> FEATURE:
<221> NAME/KEY: VARIANT
<222> LOCATION: (14)..(14)
<223> OTHER INFORMATION: Xaa is Asp, Asn, or Ser
<220> FEATURE:
<221> NAME/KEY: VARIANT
<222> LOCATION: (15)..(15)
<223> OTHER INFORMATION: Xaa is Ser, Ala, Thr, Gly, or Arg
<220> FEATURE:
<221> NAME/KEY: VARIANT
<222> LOCATION: (16)..(16)
<223> OTHER INFORMATION: Xaa is Ile, Leu, Phe, Ser, Arg, Tyr, Gln, Trp,
      Asp, Lys, or His
<220> FEATURE:
<221> NAME/KEY: VARIANT
<222> LOCATION: (17)..(17)
<223> OTHER INFORMATION: Xaa is Asp, Ser, Ile, Asn, Glu, Ala, His, Phe,
      Leu, Gln, Met, Gly, Tyr, or Val
<220> FEATURE:
<221> NAME/KEY: VARIANT
<222> LOCATION: (19)..(19)
<223> OTHER INFORMATION: Xaa is Lys, Leu, Arg, Met, Thr, or Phe
<220> FEATURE:
<221> NAME/KEY: VARIANT
<222> LOCATION: (20)..(20)
<223> OTHER INFORMATION: Xaa is Val, Leu, Ile, Ala, or Thr
<220> FEATURE:
<221> NAME/KEY: VARIANT
<222> LOCATION: (21)..(21)
<223> OTHER INFORMATION: Xaa is Leu, Ile, Val, or Ala
<220> FEATURE:
<221> NAME/KEY: VARIANT
<222> LOCATION: (22)..(22)
<223> OTHER INFORMATION: Xaa is Thr, Val, Cys, Glu, Ser, or Ala
<220> FEATURE:
<221> NAME/KEY: VARIANT
<222> LOCATION: (23)..(23)
<223> OTHER INFORMATION: Xaa is Arg, Phe, Thr, Trp, Glu, Leu, Asn, Cys,
      Lys, Val, Ser, Gln, Ile, Tyr, His, or Ala
<220> FEATURE:
<221> NAME/KEY: VARIANT
<222> LOCATION: (24)..(24)
<223> OTHER INFORMATION: Xaa is Ser, Pro, Arg, Lys, Asn, Ala, His, Gln,
      Gly, or Leu
<220> FEATURE:
<221> NAME/KEY: VARIANT
<222> LOCATION: (25)..(25)
<223> OTHER INFORMATION: Xaa is Asp, Gly, Thr, Asn, Ser, Lys, Ala, Ile,
      Glu, Leu, Gln, Arg, or Tyr
<220> FEATURE:
<221> NAME/KEY: VARIANT
<222> LOCATION: (26)..(26)
<223> OTHER INFORMATION: Xaa is Lys, Val, Ala, Glu, Tyr, Ile, Cys, Leu,
      Ser, Thr, Gly, Lys, Met, Asp, or Phe

<400> SEQUENCE: 25

```
Xaa Xaa Xaa His Xaa Xaa Pro Xaa Xaa Xaa Xaa Xaa Xaa Xaa Xaa Xaa
1               5                   10                  15

Xaa Asn Xaa Xaa Xaa Xaa Xaa Xaa Xaa Xaa Asn
            20                  25
```

<210> SEQ ID NO 26
<211> LENGTH: 27
<212> TYPE: PRT
<213> ORGANISM: Artificial Sequence
<220> FEATURE:
<223> OTHER INFORMATION: HNH-like domain
<220> FEATURE:
<221> NAME/KEY: VARIANT
<222> LOCATION: (1)..(1)
<223> OTHER INFORMATION: Xaa is Asp or Glu
<220> FEATURE:
<221> NAME/KEY: VARIANT
<222> LOCATION: (2)..(2)
<223> OTHER INFORMATION: Xaa is Leu, Ile, Arg, Gln, Val, Met, or Lys
<220> FEATURE:
<221> NAME/KEY: VARIANT
<222> LOCATION: (3)..(3)
<223> OTHER INFORMATION: Xaa is Asp or Glu
<220> FEATURE:
<221> NAME/KEY: VARIANT
<222> LOCATION: (5)..(5)
<223> OTHER INFORMATION: Xaa is Ile, Val, Thr, Ala, or Leu
<220> FEATURE:
<221> NAME/KEY: VARIANT
<222> LOCATION: (6)..(6)
<223> OTHER INFORMATION: Xaa is Val, Tyr, Ile, Leu, Phe, or Trp
<220> FEATURE:
<221> NAME/KEY: VARIANT
<222> LOCATION: (8)..(8)
<223> OTHER INFORMATION: Xaa is Gln, His, Arg, Lys, Tyr, Ile, Leu, Phe,
or Trp
<220> FEATURE:
<221> NAME/KEY: VARIANT
<222> LOCATION: (10)..(10)
<223> OTHER INFORMATION: Xaa is Phe, Leu, Val, Lys, Tyr, Met, Ile, Arg,
Ala, Glu, Asp, or Gln
<220> FEATURE:
<221> NAME/KEY: VARIANT
<222> LOCATION: (11)..(11)
<223> OTHER INFORMATION: Xaa is Leu, Arg, Thr, Ile, Val, Ser, Cys, Tyr,
Lys, Phe, or Gly
<220> FEATURE:
<221> NAME/KEY: VARIANT
<222> LOCATION: (12)..(12)
<223> OTHER INFORMATION: Xaa is Lys, Gln, Tyr, Thr, Phe, Leu, Trp, Met,
Ala, Glu, Gly, or Ser
<220> FEATURE:
<221> NAME/KEY: VARIANT
<222> LOCATION: (16)..(16)
<223> OTHER INFORMATION: Xaa is Ile, Leu, Phe, Ser, Arg, Tyr, Gln, Trp,
Asp, Lys, or His
<220> FEATURE:
<221> NAME/KEY: VARIANT
<222> LOCATION: (17)..(17)
<223> OTHER INFORMATION: Xaa is Asp, Ser, Ile, Asn, Glu, Ala, His, Phe,
Leu, Gln, Met, Gly, Tyr, or Val
<220> FEATURE:
<221> NAME/KEY: VARIANT
<222> LOCATION: (22)..(22)
<223> OTHER INFORMATION: Xaa is Thr, Val, Cys, Glu, Ser, or Ala
<220> FEATURE:
<221> NAME/KEY: VARIANT
<222> LOCATION: (23)..(23)
<223> OTHER INFORMATION: Xaa is Arg, Phe, Thr, Trp, Glu, Leu, Asn, Cys,
Lys, Val, Ser, Gln, Ile, Tyr, His, or Ala
<220> FEATURE:
<221> NAME/KEY: VARIANT
<222> LOCATION: (24)..(24)
<223> OTHER INFORMATION: Xaa is Ser, Pro, Arg, Lys, Asn, Ala, His, Gln,
Gly, or Leu
<220> FEATURE:
<221> NAME/KEY: VARIANT
<222> LOCATION: (25)..(25)
<223> OTHER INFORMATION: Xaa is Asp, Gly, Thr, Asn, Ser, Lys, Ala, Ile,
Glu, Leu, Gln, Arg, or Tyr
<220> FEATURE:
<221> NAME/KEY: VARIANT
<222> LOCATION: (26)..(26)

<223> OTHER INFORMATION: Xaa is Lys, Val, Ala, Glu, Tyr, Ile, Cys, Leu,
      Ser, Thr, Gly, Lys, Met, Asp, or Phe

<400> SEQUENCE: 26

```
Xaa Xaa Xaa His Xaa Xaa Pro Xaa Ser Xaa Xaa Xaa Asp Asp Ser Xaa
1               5                   10                  15

Xaa Asn Lys Val Leu Xaa Xaa Xaa Xaa Xaa Asn
            20                  25
```

<210> SEQ ID NO 27
<211> LENGTH: 27
<212> TYPE: PRT
<213> ORGANISM: Artificial Sequence
<220> FEATURE:
<223> OTHER INFORMATION: HNH-like domain
<220> FEATURE:
<221> NAME/KEY: VARIANT
<222> LOCATION: (1)..(1)
<223> OTHER INFORMATION: Xaa is Asp or Glu
<220> FEATURE:
<221> NAME/KEY: VARIANT
<222> LOCATION: (3)..(3)
<223> OTHER INFORMATION: Xaa is Asp or Glu
<220> FEATURE:
<221> NAME/KEY: VARIANT
<222> LOCATION: (8)..(8)
<223> OTHER INFORMATION: Xaa is Gln, His, Arg, Lys, Tyr, Ile, Leu, or
      Trp
<220> FEATURE:
<221> NAME/KEY: VARIANT
<222> LOCATION: (10)..(10)
<223> OTHER INFORMATION: Xaa is Phe, Leu, Val, Lys, Tyr, Met, Ile, Arg,
      Ala, Glu, Asp, or Gln
<220> FEATURE:
<221> NAME/KEY: VARIANT
<222> LOCATION: (11)..(11)
<223> OTHER INFORMATION: Xaa is Leu, Arg, Thr, Ile, Val, Ser, Cys, Tyr,
      Lys, Phe, or Gly
<220> FEATURE:
<221> NAME/KEY: VARIANT
<222> LOCATION: (12)..(12)
<223> OTHER INFORMATION: Xaa is Lys, Gln, Tyr, Thr, Phe, Leu, Trp, Met,
      Ala, Glu, Gly, or Ser
<220> FEATURE:
<221> NAME/KEY: VARIANT
<222> LOCATION: (16)..(16)
<223> OTHER INFORMATION: Xaa is Ile, Leu, Phe, Ser, Arg, Tyr, Gln, Trp,
      Asp, Lys, or His
<220> FEATURE:
<221> NAME/KEY: VARIANT
<222> LOCATION: (17)..(17)
<223> OTHER INFORMATION: Xaa is Asp, Ser, Ile, Asn, Glu, Ala, His, Phe,
      Leu, Gln, Met, Gly, Tyr, or Val
<220> FEATURE:
<221> NAME/KEY: VARIANT
<222> LOCATION: (23)..(23)
<223> OTHER INFORMATION: Xaa is Arg, Phe, Thr, Trp, Glu, Leu, Asn, Cys,
      Lys, Val, Ser, Gln, Ile, Tyr, His, or Ala
<220> FEATURE:
<221> NAME/KEY: VARIANT
<222> LOCATION: (24)..(24)
<223> OTHER INFORMATION: Xaa is Ser, Pro, Arg, Lys, Asn, Ala, His, Gln,
      Gly, or Leu
<220> FEATURE:
<221> NAME/KEY: VARIANT
<222> LOCATION: (25)..(25)
<223> OTHER INFORMATION: Xaa is Asp, Gly, Thr, Asn, Ser, Lys, Ala, Ile,
      Glu, Leu, Gln, Arg, or Tyr
<220> FEATURE:
<221> NAME/KEY: VARIANT
<222> LOCATION: (26)..(26)
<223> OTHER INFORMATION: Xaa is Lys, Val, Ala, Glu, Tyr, Ile, Cys, Leu,
      Ser, Thr, Gly, Lys, Met, Asp, or Phe

<400> SEQUENCE: 27

-continued

```
Xaa Val Xaa His Ile Val Pro Xaa Ser Xaa Xaa Xaa Asp Asp Ser Xaa
1               5                   10                  15

Xaa Asn Lys Val Leu Thr Xaa Xaa Xaa Xaa Asn
            20                  25
```

<210> SEQ ID NO 28
<211> LENGTH: 27
<212> TYPE: PRT
<213> ORGANISM: Artificial Sequence
<220> FEATURE:
<223> OTHER INFORMATION: HNH-like domain
<220> FEATURE:
<221> NAME/KEY: VARIANT
<222> LOCATION: (2)..(2)
<223> OTHER INFORMATION: Xaa is Ile or Val
<220> FEATURE:
<221> NAME/KEY: VARIANT
<222> LOCATION: (6)..(6)
<223> OTHER INFORMATION: Xaa is Ile or Val
<220> FEATURE:
<221> NAME/KEY: VARIANT
<222> LOCATION: (9)..(9)
<223> OTHER INFORMATION: Xaa is Ala or Ser
<220> FEATURE:
<221> NAME/KEY: VARIANT
<222> LOCATION: (11)..(11)
<223> OTHER INFORMATION: Xaa is Ile or Leu
<220> FEATURE:
<221> NAME/KEY: VARIANT
<222> LOCATION: (12)..(12)
<223> OTHER INFORMATION: Xaa is Lys or Thr
<220> FEATURE:
<221> NAME/KEY: VARIANT
<222> LOCATION: (14)..(14)
<223> OTHER INFORMATION: Xaa is Asp or Asn
<220> FEATURE:
<221> NAME/KEY: VARIANT
<222> LOCATION: (19)..(19)
<223> OTHER INFORMATION: Xaa is Arg, Lys, or Leu
<220> FEATURE:
<221> NAME/KEY: VARIANT
<222> LOCATION: (22)..(22)
<223> OTHER INFORMATION: Xaa is Thr or Val
<220> FEATURE:
<221> NAME/KEY: VARIANT
<222> LOCATION: (23)..(23)
<223> OTHER INFORMATION: Xaa is Ser or Arg
<220> FEATURE:
<221> NAME/KEY: VARIANT
<222> LOCATION: (25)..(25)
<223> OTHER INFORMATION: Xaa is Lys, Asp, or Ala
<220> FEATURE:
<221> NAME/KEY: VARIANT
<222> LOCATION: (26)..(26)
<223> OTHER INFORMATION: Xaa is Glu, Lys, Gly, or Asn

<400> SEQUENCE: 28

```
Asp Xaa Asp His Ile Xaa Pro Gln Xaa Phe Xaa Xaa Asp Xaa Ser Ile
1               5                   10                  15

Asp Asn Xaa Val Leu Xaa Xaa Ser Xaa Xaa Asn
            20                  25
```

<210> SEQ ID NO 29
<211> LENGTH: 116
<212> TYPE: RNA
<213> ORGANISM: Artificial Sequence
<220> FEATURE:
<223> OTHER INFORMATION: gRNA
<220> FEATURE:
<221> NAME/KEY: misc_feature
<222> LOCATION: (1)..(20)
<223> OTHER INFORMATION: a, c, u, g, unknown or other
<220> FEATURE:
<221> NAME/KEY: misc_feature
<222> LOCATION: (1)..(20)
<223> OTHER INFORMATION: targeting region
<220> FEATURE:
<221> NAME/KEY: misc_feature
<222> LOCATION: (21)..(42)
<223> OTHER INFORMATION: first complementarity domain
<220> FEATURE:
<221> NAME/KEY: misc_feature
<222> LOCATION: (43)..(46)
<223> OTHER INFORMATION: linking domain
<220> FEATURE:
<221> NAME/KEY: misc_feature
<222> LOCATION: (47)..(70)
<223> OTHER INFORMATION: second complementarity domain

<400> SEQUENCE: 29
nnnnnnnnnn nnnnnnnnnn guuuuagagc uaugcuguuu uggaaacaaa acagcauagc 60
aaguuaaaau aaggcuaguc cguuaucaac uugaaaaagu ggcaccgagu cggugc 116

<210> SEQ ID NO 30
<211> LENGTH: 116
<212> TYPE: RNA
<213> ORGANISM: Artificial Sequence
<220> FEATURE:
<223> OTHER INFORMATION: gRNA
<220> FEATURE:
<221> NAME/KEY: misc_feature
<222> LOCATION: (1)..(20)
<223> OTHER INFORMATION: a, c, u, g, unknown or other
<220> FEATURE:
<221> NAME/KEY: misc_feature
<222> LOCATION: (1)..(20)
<223> OTHER INFORMATION: targeting region
<220> FEATURE:
<221> NAME/KEY: misc_feature
<222> LOCATION: (21)..(42)
<223> OTHER INFORMATION: first complementarity domain
<220> FEATURE:
<221> NAME/KEY: misc_feature
<222> LOCATION: (43)..(46)
<223> OTHER INFORMATION: linking domain
<220> FEATURE:
<221> NAME/KEY: misc_feature
<222> LOCATION: (47)..(70)
<223> OTHER INFORMATION: second complementarity domain

<400> SEQUENCE: 30
nnnnnnnnnn nnnnnnnnnn guauuagagc uaugcuguau uggaaacaau acagcauagc 60
aaguuaauau aaggcuaguc cguuaucaac uugaaaaagu ggcaccgagu cggugc 116

<210> SEQ ID NO 31
<211> LENGTH: 96
<212> TYPE: RNA
<213> ORGANISM: Artificial Sequence
<220> FEATURE:
<223> OTHER INFORMATION: gRNA
<220> FEATURE:
<221> NAME/KEY: misc_feature
<222> LOCATION: (1)..(20)
<223> OTHER INFORMATION: a, c, u, g, unknown or other
<220> FEATURE:
<221> NAME/KEY: misc_feature
<222> LOCATION: (1)..(20)
<223> OTHER INFORMATION: targeting domain
<220> FEATURE:
<221> NAME/KEY: misc_feature
<222> LOCATION: (21)..(32)
<223> OTHER INFORMATION: first complementarity domain
<220> FEATURE:
<221> NAME/KEY: misc_feature
<222> LOCATION: (33)..(36)
<223> OTHER INFORMATION: linking domain
<220> FEATURE:

<221> NAME/KEY: misc_feature
<222> LOCATION: (37)..(50)
<223> OTHER INFORMATION: second complementarity domain
<220> FEATURE:
<221> NAME/KEY: misc_feature
<222> LOCATION: (51)..(62)
<223> OTHER INFORMATION: proximal domain

<400> SEQUENCE: 31
nnnnnnnnnn nnnnnnnnnn guuuaagagc uagaaauagc aaguuuaaau aaggcuaguc 60
cguuaucaac uugaaaaagu ggcaccgagu cggugc 96

<210> SEQ ID NO 32
<211> LENGTH: 47
<212> TYPE: RNA
<213> ORGANISM: Artificial Sequence
<220> FEATURE:
<223> OTHER INFORMATION: gRNA proximal and tail domains derived from S.
pyogenes

<400> SEQUENCE: 32
aaggcuaguc cguuaucaac uugaaaaagu ggcaccgagu cggugcu 47

<210> SEQ ID NO 33
<211> LENGTH: 49
<212> TYPE: RNA
<213> ORGANISM: Artificial Sequence
<220> FEATURE:
<223> OTHER INFORMATION: gRNA proximal and tail domains

<400> SEQUENCE: 33
aaggcuaguc cguuaucaac uugaaaaagu ggcaccgagu cgguggugc 49

<210> SEQ ID NO 34
<211> LENGTH: 51
<212> TYPE: RNA
<213> ORGANISM: Artificial Sequence
<220> FEATURE:
<223> OTHER INFORMATION: gRNA proximal and tail domains

<400> SEQUENCE: 34
aaggcuaguc cguuaucaac uugaaaaagu ggcaccgagu cggugcggau c 51

<210> SEQ ID NO 35
<211> LENGTH: 31
<212> TYPE: RNA
<213> ORGANISM: Artificial Sequence
<220> FEATURE:
<223> OTHER INFORMATION: gRNA proximal and tail domains

<400> SEQUENCE: 35
aaggcuaguc cguuaucaac uugaaaaagu g 31

<210> SEQ ID NO 36
<211> LENGTH: 18
<212> TYPE: RNA
<213> ORGANISM: Artificial Sequence
<220> FEATURE:
<223> OTHER INFORMATION: gRNA proximal and tail domains

<400> SEQUENCE: 36
aaggcuaguc cguuauca 18

<210> SEQ ID NO 37
<211> LENGTH: 12
<212> TYPE: RNA

<213> ORGANISM: Artificial Sequence
<220> FEATURE:
<223> OTHER INFORMATION: gRNA proximal and tail domains

<400> SEQUENCE: 37
aaggcuaguc cg 12

<210> SEQ ID NO 38
<211> LENGTH: 102
<212> TYPE: RNA
<213> ORGANISM: Artificial Sequence
<220> FEATURE:
<223> OTHER INFORMATION: Unimolecular gRNA derived from S. aureus
<220> FEATURE:
<221> NAME/KEY: misc_feature
<222> LOCATION: (1)..(20)
<223> OTHER INFORMATION: n is a, c, g, or u
<220> FEATURE:
<221> NAME/KEY: misc_feature
<222> LOCATION: (1)..(20)
<223> OTHER INFORMATION: Targeting domain

<400> SEQUENCE: 38
nnnnnnnnnn nnnnnnnnnn guuuuaguac ucuggaaaca gaaucuacua aaacaaggca 60
aaaugccgug uuuaucucgu caacuuguug gcgagauuuu uu 102

<210> SEQ ID NO 39
<211> LENGTH: 42
<212> TYPE: RNA
<213> ORGANISM: Artificial
<220> FEATURE:
<223> OTHER INFORMATION: Modular gRNA derived from S. pyogenes
<220> FEATURE:
<221> NAME/KEY: misc_feature
<222> LOCATION: (1)..(20)
<223> OTHER INFORMATION: a, c, u, g, unknown or other
<220> FEATURE:
<221> NAME/KEY: misc_feature
<222> LOCATION: (1)..(20)
<223> OTHER INFORMATION: Targeting domain
<220> FEATURE:
<221> NAME/KEY: misc_feature
<222> LOCATION: (21)..(42)
<223> OTHER INFORMATION: First complementarity domain

<400> SEQUENCE: 39
nnnnnnnnnn nnnnnnnnnn guuuuagagc uaugcuguuu ug 42

<210> SEQ ID NO 40
<211> LENGTH: 85
<212> TYPE: RNA
<213> ORGANISM: Artificial Sequence
<220> FEATURE:
<223> OTHER INFORMATION: Modular gRNA derived from S. pyogenes
<220> FEATURE:
<221> NAME/KEY: misc_feature
<222> LOCATION: (1)..(9)
<223> OTHER INFORMATION: 5' extension domain
<220> FEATURE:
<221> NAME/KEY: misc_feature
<222> LOCATION: (10)..(33)
<223> OTHER INFORMATION: Second complementarity domain
<220> FEATURE:
<221> NAME/KEY: misc_feature
<222> LOCATION: (34)..(45)
<223> OTHER INFORMATION: Proximal domain
<220> FEATURE:
<221> NAME/KEY: misc_feature
<222> LOCATION: (46)..(85)
<223> OTHER INFORMATION: Tail domain

<400> SEQUENCE: 40

-continued ggaaccauuc aaaacagcau agcaaguuaa aauaaggcua guccguuauc aacuugaaaa 60
aguggcaccg agucggugcu uuuuu 85

<210> SEQ ID NO 41
<211> LENGTH: 62
<212> TYPE: RNA
<213> ORGANISM: Artificial Sequence
<220> FEATURE:
<223> OTHER INFORMATION: Unimolecular gRNA derived from S. pyogenes
<220> FEATURE:
<221> NAME/KEY: misc_feature
<222> LOCATION: (1)..(20)
<223> OTHER INFORMATION: a, c, u, g, unknown or other
<220> FEATURE:
<221> NAME/KEY: misc_feature
<222> LOCATION: (1)..(20)
<223> OTHER INFORMATION: Targeting domain
<220> FEATURE:
<221> NAME/KEY: misc_feature
<222> LOCATION: (21)..(32)
<223> OTHER INFORMATION: First complementarity domain
<220> FEATURE:
<221> NAME/KEY: misc_feature
<222> LOCATION: (33)..(36)
<223> OTHER INFORMATION: Linking domain
<220> FEATURE:
<221> NAME/KEY: misc_feature
<222> LOCATION: (37)..(50)
<223> OTHER INFORMATION: Second complementarity domain
<220> FEATURE:
<221> NAME/KEY: misc_feature
<222> LOCATION: (51)..(62)
<223> OTHER INFORMATION: Proximal domain

<400> SEQUENCE: 41
nnnnnnnnnn nnnnnnnnnn guuuuagagc uagaaauagc aaguuaaaau aaggcuaguc 60
cg 62

<210> SEQ ID NO 42
<211> LENGTH: 102
<212> TYPE: RNA
<213> ORGANISM: Artificial Sequence
<220> FEATURE:
<223> OTHER INFORMATION: Unimolecular gRNA derived from S. pyogenes
<220> FEATURE:
<221> NAME/KEY: misc_feature
<222> LOCATION: (1)..(20)
<223> OTHER INFORMATION: a, c, u, g, unknown or other
<220> FEATURE:
<221> NAME/KEY: misc_feature
<222> LOCATION: (1)..(20)
<223> OTHER INFORMATION: Targeting domain
<220> FEATURE:
<221> NAME/KEY: misc_feature
<222> LOCATION: (21)..(32)
<223> OTHER INFORMATION: First complementarity domain
<220> FEATURE:
<221> NAME/KEY: misc_feature
<222> LOCATION: (33)..(36)
<223> OTHER INFORMATION: Linking domain
<220> FEATURE:
<221> NAME/KEY: misc_feature
<222> LOCATION: (37)..(50)
<223> OTHER INFORMATION: Second complementarity domain
<220> FEATURE:
<221> NAME/KEY: misc_feature
<222> LOCATION: (51)..(62)
<223> OTHER INFORMATION: Proximal domain
<220> FEATURE:
<221> NAME/KEY: misc_feature
<222> LOCATION: (63)..(102)
<223> OTHER INFORMATION: Tail domain

<400> SEQUENCE: 42
nnnnnnnnnn nnnnnnnnnn guuuuagagc uagaaauagc aaguuaaaau aaggcuaguc 60
cguuaucaac uugaaaaagu ggcaccgagu cggugcuuuu uu 102

<210> SEQ ID NO 43
<211> LENGTH: 75
<212> TYPE: RNA
<213> ORGANISM: Artificial Sequence
<220> FEATURE:
<223> OTHER INFORMATION: Unimolecular gRNA derived from S. pyogenes
<220> FEATURE:
<221> NAME/KEY: misc_feature
<222> LOCATION: (1)..(20)
<223> OTHER INFORMATION: Targeting domain
<220> FEATURE:
<221> NAME/KEY: misc_feature
<222> LOCATION: (1)..(20)
<223> OTHER INFORMATION: a, c, u, g, unknown or other
<220> FEATURE:
<221> NAME/KEY: misc_feature
<222> LOCATION: (21)..(36)
<223> OTHER INFORMATION: First complementarity domain
<220> FEATURE:
<221> NAME/KEY: misc_feature
<222> LOCATION: (37)..(40)
<223> OTHER INFORMATION: Linking domain
<220> FEATURE:
<221> NAME/KEY: misc_feature
<222> LOCATION: (41)..(58)
<223> OTHER INFORMATION: Second complementarity domain
<220> FEATURE:
<221> NAME/KEY: misc_feature
<222> LOCATION: (59)..(70)
<223> OTHER INFORMATION: Proximal domain
<220> FEATURE:
<221> NAME/KEY: misc_feature
<222> LOCATION: (71)..(75)
<223> OTHER INFORMATION: Tail domain

<400> SEQUENCE: 43
nnnnnnnnnn nnnnnnnnnn guuuuagagc uaugcugaaa agcauagcaa guuaaaauaa 60
ggcuaguccg uuauc 75

<210> SEQ ID NO 44
<211> LENGTH: 87
<212> TYPE: RNA
<213> ORGANISM: Artificial Sequence
<220> FEATURE:
<223> OTHER INFORMATION: Unimolecular gRNA derived from S. pyogenes
<220> FEATURE:
<221> NAME/KEY: misc_feature
<222> LOCATION: (1)..(20)
<223> OTHER INFORMATION: a, c, u, g, unknown or other
<220> FEATURE:
<221> NAME/KEY: misc_feature
<222> LOCATION: (1)..(20)
<223> OTHER INFORMATION: Targeting domain
<220> FEATURE:
<221> NAME/KEY: misc_feature
<222> LOCATION: (21)..(32)
<223> OTHER INFORMATION: First complementarity domain
<220> FEATURE:
<221> NAME/KEY: misc_feature
<222> LOCATION: (43)..(46)
<223> OTHER INFORMATION: Linking domain
<220> FEATURE:
<221> NAME/KEY: misc_feature
<222> LOCATION: (57)..(70)
<223> OTHER INFORMATION: Second complementarity domain
<220> FEATURE:
<221> NAME/KEY: misc_feature
<222> LOCATION: (71)..(82)
<223> OTHER INFORMATION: Proximal domain -continued
<220> FEATURE:
<221> NAME/KEY: misc_feature
<222> LOCATION: (83)..(87)
<223> OTHER INFORMATION: Tail domain

<400> SEQUENCE: 44
nnnnnnnnnn nnnnnnnnnn guuuuagagc uaugcuguuu uggaaacaaa acagcauagc 60
aaguuaaaau aaggcuaguc cguuauc 87

<210> SEQ ID NO 45
<211> LENGTH: 42
<212> TYPE: RNA
<213> ORGANISM: Artificial Sequence
<220> FEATURE:
<223> OTHER INFORMATION: Modular gRNA derived from S. thermophilus
<220> FEATURE:
<221> NAME/KEY: misc_feature
<222> LOCATION: (1)..(20)
<223> OTHER INFORMATION: a, c, u, g, unknown or other
<220> FEATURE:
<221> NAME/KEY: misc_feature
<222> LOCATION: (1)..(20)
<223> OTHER INFORMATION: Targeting domain
<220> FEATURE:
<221> NAME/KEY: misc_feature
<222> LOCATION: (21)..(42)
<223> OTHER INFORMATION: First complementarity domain

<400> SEQUENCE: 45
nnnnnnnnnn nnnnnnnnnn guuuuagagc uguguuguuu cg 42

<210> SEQ ID NO 46
<211> LENGTH: 78
<212> TYPE: RNA
<213> ORGANISM: Artificial Sequence
<220> FEATURE:
<223> OTHER INFORMATION: Modular gRNA derived from S. thermophilus
<220> FEATURE:
<221> NAME/KEY: misc_feature
<222> LOCATION: (1)..(3)
<223> OTHER INFORMATION: 5' extension domain
<220> FEATURE:
<221> NAME/KEY: misc_feature
<222> LOCATION: (4)..(27)
<223> OTHER INFORMATION: Second complementarity domain
<220> FEATURE:
<221> NAME/KEY: misc_feature
<222> LOCATION: (28)..(40)
<223> OTHER INFORMATION: Proximal domain
<220> FEATURE:
<221> NAME/KEY: misc_feature
<222> LOCATION: (41)..(78)
<223> OTHER INFORMATION: Tail domain

<400> SEQUENCE: 46
gggcgaaaca acacagcgag uuaaaauaag gcuuaguccg uacucaacuu gaaaaggugg 60
caccgauucg guguuuuu 78

<210> SEQ ID NO 47
<211> LENGTH: 85
<212> TYPE: RNA
<213> ORGANISM: Artificial Sequence
<220> FEATURE:
<223> OTHER INFORMATION: Modular gRNA derived from S. pyogenes

<400> SEQUENCE: 47
gaaccauuca aaacagcaua gcaaguuaaa auaaggcuag uccguuauca acuugaaaaa 60
guggcaccga gucggugcuu uuuuu 85

<210> SEQ ID NO 48
<211> LENGTH: 96
<212> TYPE: RNA
<213> ORGANISM: Artificial Sequence
<220> FEATURE:
<223> OTHER INFORMATION: gRNA from S. pyogenes
<220> FEATURE:
<221> NAME/KEY: misc_feature
<222> LOCATION: (1)..(20)
<223> OTHER INFORMATION: n is a, c, g, or u
<220> FEATURE:
<221> NAME/KEY: misc_feature
<222> LOCATION: (1)..(20)
<223> OTHER INFORMATION: Targeting domain

<400> SEQUENCE: 48
nnnnnnnnnn nnnnnnnnnn guuuuagagc uagaaauagc aaguuaaaau aaggcuaguc 60
cguuaucaac uugaaaaagu ggcaccgagu cggugc 96

<210> SEQ ID NO 49
<211> LENGTH: 96
<212> TYPE: RNA
<213> ORGANISM: Artificial Sequence
<220> FEATURE:
<223> OTHER INFORMATION: gRNA
<220> FEATURE:
<221> NAME/KEY: misc_feature
<222> LOCATION: (1)..(20)
<223> OTHER INFORMATION: n is a, c, g, or u
<220> FEATURE:
<221> NAME/KEY: misc_feature
<222> LOCATION: (1)..(20)
<223> OTHER INFORMATION: Targeting domain
<220> FEATURE:
<221> NAME/KEY: misc_feature
<222> LOCATION: (21)..(32)
<223> OTHER INFORMATION: First complementarity domain
<220> FEATURE:
<221> NAME/KEY: misc_feature
<222> LOCATION: (33)..(36)
<223> OTHER INFORMATION: Linking domain
<220> FEATURE:
<221> NAME/KEY: misc_feature
<222> LOCATION: (37)..(50)
<223> OTHER INFORMATION: Second complementarity domain
<220> FEATURE:
<221> NAME/KEY: misc_feature
<222> LOCATION: (51)..(62)
<223> OTHER INFORMATION: Proximal domain

<400> SEQUENCE: 49
nnnnnnnnnn nnnnnnnnnn guauuagagc uagaaauagc aaguuaauau aaggcuaguc 60
cguuaucaac uugaaaaagu ggcaccgagu cggugc 96

<210> SEQ ID NO 50
<211> LENGTH: 104
<212> TYPE: RNA
<213> ORGANISM: Artificial Sequence
<220> FEATURE:
<223> OTHER INFORMATION: gRNA
<220> FEATURE:
<221> NAME/KEY: misc_feature
<222> LOCATION: (1)..(20)
<223> OTHER INFORMATION: n is a, c, g, or u
<220> FEATURE:
<221> NAME/KEY: misc_feature
<222> LOCATION: (1)..(20)
<223> OTHER INFORMATION: Targeting domain
<220> FEATURE:
<221> NAME/KEY: misc_feature
<222> LOCATION: (21)..(36)
<223> OTHER INFORMATION: First complementarity domain
<220> FEATURE:
<221> NAME/KEY: misc_feature
<222> LOCATION: (37)..(40)
<223> OTHER INFORMATION: Linking domain
<220> FEATURE:
<221> NAME/KEY: misc_feature
<222> LOCATION: (41)..(58)
<223> OTHER INFORMATION: Second complementarity domain

<400> SEQUENCE: 50
nnnnnnnnnn nnnnnnnnnn guuuuagagc uaugcugaaa agcauagcaa guuaaaauaa 60
ggcuaguccg uuaucaacuu gaaaaagugg caccgagucg gugc 104

<210> SEQ ID NO 51
<211> LENGTH: 106
<212> TYPE: RNA
<213> ORGANISM: Artificial Sequence
<220> FEATURE:
<223> OTHER INFORMATION: gRNA
<220> FEATURE:
<221> NAME/KEY: misc_feature
<222> LOCATION: (1)..(20)
<223> OTHER INFORMATION: n is a, c, g, or u
<220> FEATURE:
<221> NAME/KEY: misc_feature
<222> LOCATION: (1)..(20)
<223> OTHER INFORMATION: Targeting domain
<220> FEATURE:
<221> NAME/KEY: misc_feature
<222> LOCATION: (21)..(37)
<223> OTHER INFORMATION: First complementarity domain
<220> FEATURE:
<221> NAME/KEY: misc_feature
<222> LOCATION: (38)..(41)
<223> OTHER INFORMATION: Linking domain
<220> FEATURE:
<221> NAME/KEY: misc_feature
<222> LOCATION: (42)..(60)
<223> OTHER INFORMATION: Second complementarity domain

<400> SEQUENCE: 51
nnnnnnnnnn nnnnnnnnnn guuuuagagc uaugcuggaa acagcauagc aaguuaaaau 60
aaggcuaguc cguuaucaac uugaaaaagu ggcaccgagu cggugc 106

<210> SEQ ID NO 52
<211> LENGTH: 12
<212> TYPE: PRT
<213> ORGANISM: Peptoniphilus duerdenii

<400> SEQUENCE: 52

Asp Ile Gly Thr Ala Ser Val Gly Trp Ala Val Thr
1 5 10

<210> SEQ ID NO 53
<211> LENGTH: 12
<212> TYPE: PRT
<213> ORGANISM: Treponema denticola

<400> SEQUENCE: 53

Asp Val Gly Thr Gly Ser Val Gly Trp Ala Val Thr
1 5 10

<210> SEQ ID NO 54
<211> LENGTH: 12
<212> TYPE: PRT
<213> ORGANISM: S. mutans

<400> SEQUENCE: 54

```
Asp Ile Gly Thr Asn Ser Val Gly Trp Ala Val Val
1               5                   10


<210> SEQ ID NO 55
<211> LENGTH: 12
<212> TYPE: PRT
<213> ORGANISM: S. pyogenes

<400> SEQUENCE: 55

Asp Ile Gly Thr Asn Ser Val Gly Trp Ala Val Ile
1               5                   10


<210> SEQ ID NO 56
<211> LENGTH: 12
<212> TYPE: PRT
<213> ORGANISM: L. innocua

<400> SEQUENCE: 56

Asp Ile Gly Thr Asn Ser Val Gly Trp Ala Val Leu
1               5                   10


<210> SEQ ID NO 57
<211> LENGTH: 12
<212> TYPE: PRT
<213> ORGANISM: Flavobacterium branchiophilum FL-15

<400> SEQUENCE: 57

Asp Leu Gly Thr Asn Ser Ile Gly Trp Ala Val Val
1               5                   10


<210> SEQ ID NO 58
<211> LENGTH: 11
<212> TYPE: PRT
<213> ORGANISM: Pedobacter glucosidilyticus

<400> SEQUENCE: 58

Asp Leu Gly Thr Asn Ser Ile Gly Trp Ala Ile
1               5                   10


<210> SEQ ID NO 59
<211> LENGTH: 12
<212> TYPE: PRT
<213> ORGANISM: Bacteroides fragilis, NCTC 9343

<400> SEQUENCE: 59

Asp Leu Gly Thr Asn Ser Ile Gly Trp Ala Leu Val
1               5                   10


<210> SEQ ID NO 60
<211> LENGTH: 12
<212> TYPE: PRT
<213> ORGANISM: Fusobacterium nucleatum

<400> SEQUENCE: 60

Asp Ile Gly Thr Asn Ser Val Gly Trp Cys Val Thr
1               5                   10


<210> SEQ ID NO 61
<211> LENGTH: 12
<212> TYPE: PRT
<213> ORGANISM: Acidaminococcus sp. D21

<400> SEQUENCE: 61

Asp Ile Gly Thr Asn Ser Val Gly Tyr Ala Val Thr
1               5                   10
```

<210> SEQ ID NO 62
<211> LENGTH: 12
<212> TYPE: PRT
<213> ORGANISM: Coprococcus catus GD-7

<400> SEQUENCE: 62

Asp Met Gly Thr Gly Ser Leu Gly Trp Ala Val Thr
1 5 10

<210> SEQ ID NO 63
<211> LENGTH: 12
<212> TYPE: PRT
<213> ORGANISM: Oenococcus kitaharae DSM 17330

<400> SEQUENCE: 63

Asp Ile Gly Thr Ser Ser Val Gly Trp Ala Ala Ile
1 5 10

<210> SEQ ID NO 64
<211> LENGTH: 12
<212> TYPE: PRT
<213> ORGANISM: Catenibacterium mitsuokai DSM 15897

<400> SEQUENCE: 64

Asp Leu Gly Thr Gly Ser Val Gly Trp Ala Val Val
1 5 10

<210> SEQ ID NO 65
<211> LENGTH: 12
<212> TYPE: PRT
<213> ORGANISM: Mycoplasma gallisepticum str. F

<400> SEQUENCE: 65

Asp Leu Gly Val Gly Ser Val Gly Trp Ala Ile Val
1 5 10

<210> SEQ ID NO 66
<211> LENGTH: 12
<212> TYPE: PRT
<213> ORGANISM: Mycoplasma ovipneumoniae SC01

<400> SEQUENCE: 66

Asp Leu Gly Ile Ala Ser Ile Gly Trp Ala Ile Ile
1 5 10

<210> SEQ ID NO 67
<211> LENGTH: 12
<212> TYPE: PRT
<213> ORGANISM: Mycoplasma canis PG 14

<400> SEQUENCE: 67

Asp Leu Gly Ile Ala Ser Val Gly Trp Ala Ile Val
1 5 10

<210> SEQ ID NO 68
<211> LENGTH: 12
<212> TYPE: PRT
<213> ORGANISM: Mycoplasma synoviae 53

<400> SEQUENCE: 68

Asp Leu Gly Val Ala Ser Val Gly Trp Ser Ile Val
1 5 10

-continued

<210> SEQ ID NO 69
<211> LENGTH: 12
<212> TYPE: PRT
<213> ORGANISM: Eubacterium rectale

<400> SEQUENCE: 69

Asp Ile Gly Ile Ala Ser Val Gly Trp Ala Ile Leu
1 5 10

<210> SEQ ID NO 70
<211> LENGTH: 12
<212> TYPE: PRT
<213> ORGANISM: Enterococcus faecalis TX0012

<400> SEQUENCE: 70

Asp Leu Gly Ile Ser Ser Val Gly Trp Ser Val Ile
1 5 10

<210> SEQ ID NO 71
<211> LENGTH: 12
<212> TYPE: PRT
<213> ORGANISM: Ilyobacter polytropus DSM 2926

<400> SEQUENCE: 71

Asp Ile Gly Ile Ala Ser Val Gly Trp Ser Val Ile
1 5 10

<210> SEQ ID NO 72
<211> LENGTH: 12
<212> TYPE: PRT
<213> ORGANISM: Ruminococcus albus 8

<400> SEQUENCE: 72

Asp Val Gly Ile Gly Ser Ile Gly Trp Ala Val Ile
1 5 10

<210> SEQ ID NO 73
<211> LENGTH: 12
<212> TYPE: PRT
<213> ORGANISM: Elusimicrobium minutum Pei191

<400> SEQUENCE: 73

Asp Leu Gly Val Gly Ser Ile Gly Phe Ala Ile Val
1 5 10

<210> SEQ ID NO 74
<211> LENGTH: 12
<212> TYPE: PRT
<213> ORGANISM: Akkermansia muciniphila

<400> SEQUENCE: 74

Asp Ile Gly Tyr Ala Ser Ile Gly Trp Ala Val Ile
1 5 10

<210> SEQ ID NO 75
<211> LENGTH: 12
<212> TYPE: PRT
<213> ORGANISM: Prevotella ruminicola

<400> SEQUENCE: 75

Asp Thr Gly Thr Asn Ser Leu Gly Trp Ala Ile Val
1 5 10

<210> SEQ ID NO 76
<211> LENGTH: 12

<212> TYPE: PRT
<213> ORGANISM: Cand. Puniceispirillum marinum

<400> SEQUENCE: 76

Asp Leu Gly Thr Asn Ser Ile Gly Trp Cys Leu Leu
1 5 10

<210> SEQ ID NO 77
<211> LENGTH: 12
<212> TYPE: PRT
<213> ORGANISM: Rhodospirillum rubrum

<400> SEQUENCE: 77

Asp Ile Gly Thr Asp Ser Leu Gly Trp Ala Val Phe
1 5 10

<210> SEQ ID NO 78
<211> LENGTH: 12
<212> TYPE: PRT
<213> ORGANISM: Lactobacillus rhamnosus GG

<400> SEQUENCE: 78

Asp Ile Gly Ser Asn Ser Ile Gly Phe Ala Val Val
1 5 10

<210> SEQ ID NO 79
<211> LENGTH: 12
<212> TYPE: PRT
<213> ORGANISM: Sphaerochaeta globus str. Buddy

<400> SEQUENCE: 79

Asp Leu Gly Val Gly Ser Ile Gly Val Ala Val Ala
1 5 10

<210> SEQ ID NO 80
<211> LENGTH: 12
<212> TYPE: PRT
<213> ORGANISM: Rhodopseudomonas palustris

<400> SEQUENCE: 80

Asp Leu Gly Ile Ala Ser Cys Gly Trp Gly Val Val
1 5 10

<210> SEQ ID NO 81
<211> LENGTH: 12
<212> TYPE: PRT
<213> ORGANISM: Mycoplasma mobile 163K

<400> SEQUENCE: 81

Asp Leu Gly Ile Ala Ser Val Gly Trp Cys Leu Thr
1 5 10

<210> SEQ ID NO 82
<211> LENGTH: 12
<212> TYPE: PRT
<213> ORGANISM: Streptococcus thermophilus LMD-9

<400> SEQUENCE: 82

Asp Ile Gly Ile Gly Ser Val Gly Val Gly Ile Leu
1 5 10

<210> SEQ ID NO 83
<211> LENGTH: 12
<212> TYPE: PRT
<213> ORGANISM: Staphylococcus lugdunensis M23590

<400> SEQUENCE: 83

Asp Ile Gly Ile Thr Ser Val Gly Tyr Gly Leu Ile
1 5 10

<210> SEQ ID NO 84
<211> LENGTH: 12
<212> TYPE: PRT
<213> ORGANISM: Eubacterium dolichum DSM 3991

<400> SEQUENCE: 84

Asp Ile Gly Ile Thr Ser Val Gly Phe Gly Ile Ile
1 5 10

<210> SEQ ID NO 85
<211> LENGTH: 12
<212> TYPE: PRT
<213> ORGANISM: Lactobacillus coryniformis KCTC 3535

<400> SEQUENCE: 85

Asp Val Gly Ile Thr Ser Thr Gly Tyr Ala Val Leu
1 5 10

<210> SEQ ID NO 86
<211> LENGTH: 12
<212> TYPE: PRT
<213> ORGANISM: Nitratifractor salsuginis DSM 16511

<400> SEQUENCE: 86

Asp Leu Gly Ile Thr Ser Phe Gly Tyr Ala Ile Leu
1 5 10

<210> SEQ ID NO 87
<211> LENGTH: 12
<212> TYPE: PRT
<213> ORGANISM: Bifidobacterium bifidum S17

<400> SEQUENCE: 87

Asp Ile Gly Asn Ala Ser Val Gly Trp Ser Ala Phe
1 5 10

<210> SEQ ID NO 88
<211> LENGTH: 12
<212> TYPE: PRT
<213> ORGANISM: Lactobacillus gasseri

<400> SEQUENCE: 88

Asp Val Gly Thr Asn Ser Cys Gly Trp Val Ala Met
1 5 10

<210> SEQ ID NO 89
<211> LENGTH: 12
<212> TYPE: PRT
<213> ORGANISM: Acidothermus cellulolyticus 11B

<400> SEQUENCE: 89

Asp Val Gly Glu Arg Ser Ile Gly Leu Ala Ala Val
1 5 10

<210> SEQ ID NO 90
<211> LENGTH: 12
<212> TYPE: PRT
<213> ORGANISM: Bifidobacterium longum DJO10A

<400> SEQUENCE: 90

Asp Val Gly Leu Asn Ser Val Gly Leu Ala Ala Val
1 5 10

<210> SEQ ID NO 91
<211> LENGTH: 12
<212> TYPE: PRT
<213> ORGANISM: Bifidobacterium dentium

<400> SEQUENCE: 91

Asp Val Gly Leu Met Ser Val Gly Leu Ala Ala Ile
1 5 10

<210> SEQ ID NO 92
<211> LENGTH: 12
<212> TYPE: PRT
<213> ORGANISM: Corynebacterium diphtheriae

<400> SEQUENCE: 92

Asp Val Gly Thr Phe Ser Val Gly Leu Ala Ala Ile
1 5 10

<210> SEQ ID NO 93
<211> LENGTH: 12
<212> TYPE: PRT
<213> ORGANISM: Staphylococcus pseudintermedius ED99

<400> SEQUENCE: 93

Asp Ile Gly Thr Gly Ser Val Gly Tyr Ala Cys Met
1 5 10

<210> SEQ ID NO 94
<211> LENGTH: 12
<212> TYPE: PRT
<213> ORGANISM: Capnocytophaga ochracea

<400> SEQUENCE: 94

Asp Leu Gly Thr Thr Ser Ile Gly Phe Ala His Ile
1 5 10

<210> SEQ ID NO 95
<211> LENGTH: 12
<212> TYPE: PRT
<213> ORGANISM: Prevotella denticola

<400> SEQUENCE: 95

Asp Leu Gly Thr Asn Ser Ile Gly Ser Ser Val Arg
1 5 10

<210> SEQ ID NO 96
<211> LENGTH: 12
<212> TYPE: PRT
<213> ORGANISM: Ralstonia solanacearum

<400> SEQUENCE: 96

Asp Ile Gly Thr Asn Ser Ile Gly Trp Ala Val Ile
1 5 10

<210> SEQ ID NO 97
<211> LENGTH: 12
<212> TYPE: PRT
<213> ORGANISM: Pasteurella multocida str. Pm70

<400> SEQUENCE: 97

Asp Leu Gly Ile Ala Ser Val Gly Trp Ala Val Val 1 5 10

<210> SEQ ID NO 98
<211> LENGTH: 12
<212> TYPE: PRT
<213> ORGANISM: Comamonas granuli

<400> SEQUENCE: 98

Asp Ile Gly Ile Ala Ser Val Gly Trp Ala Val Leu
1 5 10

<210> SEQ ID NO 99
<211> LENGTH: 12
<212> TYPE: PRT
<213> ORGANISM: Helicobacter mustelae 12198

<400> SEQUENCE: 99

Asp Ile Gly Ile Ala Ser Ile Gly Trp Ala Val Ile
1 5 10

<210> SEQ ID NO 100
<211> LENGTH: 12
<212> TYPE: PRT
<213> ORGANISM: Agathobacter rectalis

<400> SEQUENCE: 100

Asp Ile Gly Ile Ala Ser Val Gly Trp Ala Ile Ile
1 5 10

<210> SEQ ID NO 101
<211> LENGTH: 12
<212> TYPE: PRT
<213> ORGANISM: Clostridium cellulolyticum H10

<400> SEQUENCE: 101

Asp Val Gly Ile Ala Ser Val Gly Trp Ala Val Ile
1 5 10

<210> SEQ ID NO 102
<211> LENGTH: 11
<212> TYPE: PRT
<213> ORGANISM: Methylophilus sp. OH31

<400> SEQUENCE: 102

Asp Ile Gly Ile Ala Ser Val Gly Trp Ala Leu
1 5 10

<210> SEQ ID NO 103
<211> LENGTH: 12
<212> TYPE: PRT
<213> ORGANISM: Neisseria meningitidis

<400> SEQUENCE: 103

Asp Ile Gly Ile Ala Ser Val Gly Trp Ala Met Val
1 5 10

<210> SEQ ID NO 104
<211> LENGTH: 12
<212> TYPE: PRT
<213> ORGANISM: Clostridium perfringens

<400> SEQUENCE: 104

Asp Ile Gly Ile Thr Ser Val Gly Trp Ala Val Ile
1 5 10

<210> SEQ ID NO 105
<211> LENGTH: 12
<212> TYPE: PRT
<213> ORGANISM: Wolinella succinogenes DSM 1740

<400> SEQUENCE: 105

Asp Leu Gly Ile Ser Ser Leu Gly Trp Ala Ile Val
1 5 10

<210> SEQ ID NO 106
<211> LENGTH: 12
<212> TYPE: PRT
<213> ORGANISM: Azospirillum sp. B510

<400> SEQUENCE: 106

Asp Leu Gly Thr Asn Ser Ile Gly Trp Gly Leu Leu
1 5 10

<210> SEQ ID NO 107
<211> LENGTH: 12
<212> TYPE: PRT
<213> ORGANISM: Verminephrobacter eiseniae

<400> SEQUENCE: 107

Asp Leu Gly Ser Thr Ser Leu Gly Trp Ala Ile Phe
1 5 10

<210> SEQ ID NO 108
<211> LENGTH: 12
<212> TYPE: PRT
<213> ORGANISM: Campylobacter jejuni, NCTC 11168

<400> SEQUENCE: 108

Asp Ile Gly Ile Ser Ser Ile Gly Trp Ala Phe Ser
1 5 10

<210> SEQ ID NO 109
<211> LENGTH: 12
<212> TYPE: PRT
<213> ORGANISM: Parvibaculum lavamentivorans DS-1

<400> SEQUENCE: 109

Asp Ile Gly Thr Thr Ser Ile Gly Phe Ser Val Ile
1 5 10

<210> SEQ ID NO 110
<211> LENGTH: 12
<212> TYPE: PRT
<213> ORGANISM: Dinoroseobacter shibae DFL 12

<400> SEQUENCE: 110

Asp Ile Gly Thr Ser Ser Ile Gly Trp Trp Leu Tyr
1 5 10

<210> SEQ ID NO 111
<211> LENGTH: 12
<212> TYPE: PRT
<213> ORGANISM: Nitrobacter hamburgensis X14

<400> SEQUENCE: 111

Asp Leu Gly Ser Asn Ser Leu Gly Trp Phe Val Thr
1 5 10

<210> SEQ ID NO 112

<211> LENGTH: 12
<212> TYPE: PRT
<213> ORGANISM: Bradyrhizobium sp. BTAi1

<400> SEQUENCE: 112

Asp Leu Gly Ala Asn Ser Leu Gly Trp Phe Val Val
1 5 10

<210> SEQ ID NO 113
<211> LENGTH: 15
<212> TYPE: PRT
<213> ORGANISM: Bacillus cereus

<400> SEQUENCE: 113

Asp Ile Gly Leu Arg Ile Gly Ile Thr Ser Cys Gly Trp Ser Ile
1 5 10 15

<210> SEQ ID NO 114
<211> LENGTH: 12
<212> TYPE: PRT
<213> ORGANISM: Sutterella wadsworthensis

<400> SEQUENCE: 114

Asp Met Gly Ala Lys Tyr Thr Gly Val Phe Tyr Ala
1 5 10

<210> SEQ ID NO 115
<211> LENGTH: 12
<212> TYPE: PRT
<213> ORGANISM: Wolinella succinogenes DSM 1740

<400> SEQUENCE: 115

Asp Leu Gly Gly Lys Asn Thr Gly Phe Phe Ser Phe
1 5 10

<210> SEQ ID NO 116
<211> LENGTH: 12
<212> TYPE: PRT
<213> ORGANISM: Francisella tularensis

<400> SEQUENCE: 116

Asp Leu Gly Val Lys Asn Thr Gly Val Phe Ser Ala
1 5 10

<210> SEQ ID NO 117
<211> LENGTH: 12
<212> TYPE: PRT
<213> ORGANISM: Gamma proteobacterium HTCC5015

<400> SEQUENCE: 117

Asp Leu Gly Ala Lys Phe Thr Gly Val Ala Leu Tyr
1 5 10

<210> SEQ ID NO 118
<211> LENGTH: 12
<212> TYPE: PRT
<213> ORGANISM: Legionella pneumophila str. Paris

<400> SEQUENCE: 118

Asp Leu Gly Gly Lys Phe Thr Gly Val Cys Leu Ser
1 5 10

<210> SEQ ID NO 119
<211> LENGTH: 12
<212> TYPE: PRT

<213> ORGANISM: Parasutterella excrementihominis

<400> SEQUENCE: 119

Asp Leu Gly Gly Thr Tyr Thr Gly Thr Phe Ile Thr
1 5 10

<210> SEQ ID NO 120
<211> LENGTH: 12
<212> TYPE: PRT
<213> ORGANISM: S. thermophilus

<400> SEQUENCE: 120

Asp Ile Gly Thr Asn Ser Val Gly Trp Ala Val Thr
1 5 10

<210> SEQ ID NO 121
<211> LENGTH: 12
<212> TYPE: PRT
<213> ORGANISM: Eubacterium yurii

<400> SEQUENCE: 121

Asp Val Gly Thr Asn Ser Val Gly Trp Ala Val Thr
1 5 10

<210> SEQ ID NO 122
<211> LENGTH: 12
<212> TYPE: PRT
<213> ORGANISM: Butyrivibrio hungatei

<400> SEQUENCE: 122

Asp Met Gly Thr Asn Ser Val Gly Trp Ala Val Thr
1 5 10

<210> SEQ ID NO 123
<211> LENGTH: 12
<212> TYPE: PRT
<213> ORGANISM: Solobacterium moorei F0204

<400> SEQUENCE: 123

Asp Val Gly Thr Ser Ser Val Gly Trp Ala Val Thr
1 5 10

<210> SEQ ID NO 124
<211> LENGTH: 27
<212> TYPE: PRT
<213> ORGANISM: Treponema denticola

<400> SEQUENCE: 124

Asp Ile Asp His Ile Tyr Pro Gln Ser Lys Ile Lys Asp Asp Ser Ile
1 5 10 15

Ser Asn Arg Val Leu Val Cys Ser Ser Cys Asn
20 25

<210> SEQ ID NO 125
<211> LENGTH: 27
<212> TYPE: PRT
<213> ORGANISM: Coprococcus catus GD-7

<400> SEQUENCE: 125

Asp Ile Asp His Ile Tyr Pro Gln Ser Lys Thr Met Asp Asp Ser Leu
1 5 10 15

Asn Asn Arg Val Leu Val Lys Lys Asn Tyr Asn
20 25

<210> SEQ ID NO 126
<211> LENGTH: 27
<212> TYPE: PRT
<213> ORGANISM: Peptoniphilus duerdenii

<400> SEQUENCE: 126

Asp Gln Asp His Ile Tyr Pro Lys Ser Lys Ile Tyr Asp Asp Ser Leu
1 5 10 15

Glu Asn Arg Val Leu Val Lys Lys Asn Leu Asn
20 25

<210> SEQ ID NO 127
<211> LENGTH: 27
<212> TYPE: PRT
<213> ORGANISM: Catenibacterium mitsuokai DSM 15897

<400> SEQUENCE: 127

Gln Ile Asp His Ile Val Pro Gln Ser Leu Val Lys Asp Asp Ser Phe
1 5 10 15

Asp Asn Arg Val Leu Val Val Pro Ser Glu Asn
20 25

<210> SEQ ID NO 128
<211> LENGTH: 27
<212> TYPE: PRT
<213> ORGANISM: S. mutans

<400> SEQUENCE: 128

Asp Ile Asp His Ile Ile Pro Gln Ala Phe Ile Lys Asp Asn Ser Ile
1 5 10 15

Asp Asn Arg Val Leu Thr Ser Ser Lys Glu Asn
20 25

<210> SEQ ID NO 129
<211> LENGTH: 27
<212> TYPE: PRT
<213> ORGANISM: S. thermophilus

<400> SEQUENCE: 129

Asp Ile Asp His Ile Ile Pro Gln Ala Phe Leu Lys Asp Asn Ser Ile
1 5 10 15

Asp Asn Lys Val Leu Val Ser Ser Ala Ser Asn
20 25

<210> SEQ ID NO 130
<211> LENGTH: 27
<212> TYPE: PRT
<213> ORGANISM: Oenococcus kitaharae DSM 17330

<400> SEQUENCE: 130

Asp Ile Asp His Ile Ile Pro Gln Ala Tyr Thr Lys Asp Asn Ser Leu
1 5 10 15

Asp Asn Arg Val Leu Val Ser Asn Ile Thr Asn
20 25

<210> SEQ ID NO 131
<211> LENGTH: 27
<212> TYPE: PRT
<213> ORGANISM: L. inocua

<400> SEQUENCE: 131

Asp Ile Asp His Ile Val Pro Gln Ser Phe Ile Thr Asp Asn Ser Ile 1 5 10 15

Asp Asn Leu Val Leu Thr Ser Ser Ala Gly Asn
20 25

<210> SEQ ID NO 132
<211> LENGTH: 27
<212> TYPE: PRT
<213> ORGANISM: S. pyogenes

<400> SEQUENCE: 132

Asp Val Asp His Ile Val Pro Gln Ser Phe Leu Lys Asp Asp Ser Ile
1 5 10 15

Asp Asn Lys Val Leu Thr Arg Ser Asp Lys Asn
20 25

<210> SEQ ID NO 133
<211> LENGTH: 27
<212> TYPE: PRT
<213> ORGANISM: Acidaminococcus sp. D21

<400> SEQUENCE: 133

Asn Ile Asp His Ile Tyr Pro Gln Ser Met Val Lys Asp Asp Ser Leu
1 5 10 15

Asp Asn Lys Val Leu Val Gln Ser Glu Ile Asn
20 25

<210> SEQ ID NO 134
<211> LENGTH: 27
<212> TYPE: PRT
<213> ORGANISM: Lactobacillus rhamnosus GG

<400> SEQUENCE: 134

Asp Ile Asp His Ile Leu Pro Gln Ser Leu Ile Lys Asp Asp Ser Leu
1 5 10 15

Asp Asn Arg Val Leu Val Asn Ala Thr Ile Asn
20 25

<210> SEQ ID NO 135
<211> LENGTH: 27
<212> TYPE: PRT
<213> ORGANISM: Lactobacillus gasseri

<400> SEQUENCE: 135

Asp Ile Asp His Ile Leu Pro Gln Ser Phe Ile Lys Asp Asp Ser Leu
1 5 10 15

Glu Asn Arg Val Leu Val Lys Lys Ala Val Asn
20 25

<210> SEQ ID NO 136
<211> LENGTH: 27
<212> TYPE: PRT
<213> ORGANISM: Staphylococcus pseudintermedius ED99

<400> SEQUENCE: 136

Glu Val Asp His Ile Phe Pro Arg Ser Phe Ile Lys Asp Asp Ser Ile
1 5 10 15

Asp Asn Lys Val Leu Val Ile Lys Lys Met Asn
20 25

<210> SEQ ID NO 137
<211> LENGTH: 27
<212> TYPE: PRT

<213> ORGANISM: Olsenella uli

<400> SEQUENCE: 137

Glu Val Asp His Ile Ile Pro Arg Ser Tyr Ile Lys Asp Asp Ser Phe
1 5 10 15

Glu Asn Lys Val Leu Val Tyr Arg Glu Glu Asn
20 25

<210> SEQ ID NO 138
<211> LENGTH: 27
<212> TYPE: PRT
<213> ORGANISM: Bifidobacterium bifidum S17

<400> SEQUENCE: 138

Asp Ile Asp His Ile Ile Pro Gln Ala Val Thr Gln Asn Asp Ser Ile
1 5 10 15

Asp Asn Arg Val Leu Val Ala Arg Ala Glu Asn
20 25

<210> SEQ ID NO 139
<211> LENGTH: 27
<212> TYPE: PRT
<213> ORGANISM: Mycoplasma gallisepticum str. F

<400> SEQUENCE: 139

Glu Ile Asp His Ile Ile Pro Tyr Ser Ile Ser Phe Asp Asp Ser Ser
1 5 10 15

Ser Asn Lys Leu Leu Val Leu Ala Glu Ser Asn
20 25

<210> SEQ ID NO 140
<211> LENGTH: 27
<212> TYPE: PRT
<213> ORGANISM: Mycoplasma canis PG 14

<400> SEQUENCE: 140

Glu Ile Asp His Ile Ile Pro Tyr Ser Leu Cys Phe Asp Asp Ser Ser
1 5 10 15

Ala Asn Lys Val Leu Val His Lys Gln Ser Asn
20 25

<210> SEQ ID NO 141
<211> LENGTH: 27
<212> TYPE: PRT
<213> ORGANISM: Ilyobacter polytropus DSM 2926

<400> SEQUENCE: 141

Asp Ile Asp His Ile Ile Pro Tyr Ser Arg Ser Met Asp Asp Ser Tyr
1 5 10 15

Ser Asn Lys Val Leu Val Leu Ser Gly Glu Asn
20 25

<210> SEQ ID NO 142
<211> LENGTH: 27
<212> TYPE: PRT
<213> ORGANISM: Uncultured Termite group 1 bacterium

<400> SEQUENCE: 142

Asp Ile Asp His Ile Ile Pro Tyr Ser Lys Ser Met Asp Asp Ser Phe
1 5 10 15

Asn Asn Lys Val Leu Cys Leu Ala Glu Glu Asn
20 25

<210> SEQ ID NO 143
<211> LENGTH: 27
<212> TYPE: PRT
<213> ORGANISM: Campylobacter jejuni

<400> SEQUENCE: 143

```
Glu Ile Asp His Ile Tyr Pro Tyr Ser Arg Ser Phe Asp Asp Ser Tyr
1               5                   10                  15

Met Asn Lys Val Leu Val Phe Thr Lys Gln Asn
            20                  25
```

<210> SEQ ID NO 144
<211> LENGTH: 27
<212> TYPE: PRT
<213> ORGANISM: Clostridium cellulolyticum H10

<400> SEQUENCE: 144

```
Gln Ile Asp His Ile Tyr Pro Tyr Ser Arg Ser Met Asp Asp Ser Tyr
1               5                   10                  15

Met Asn Lys Val Leu Val Leu Thr Asp Glu Asn
            20                  25
```

<210> SEQ ID NO 145
<211> LENGTH: 27
<212> TYPE: PRT
<213> ORGANISM: Clostridium perfringens

<400> SEQUENCE: 145

```
Glu Ile Asp His Ile Ile Pro Phe Ser Arg Ser Phe Asp Asp Ser Leu
1               5                   10                  15

Ser Asn Lys Ile Leu Val Leu Gly Ser Glu Asn
            20                  25
```

<210> SEQ ID NO 146
<211> LENGTH: 27
<212> TYPE: PRT
<213> ORGANISM: N. meningitides

<400> SEQUENCE: 146

```
Glu Ile Asp His Ala Leu Pro Phe Ser Arg Thr Trp Asp Asp Ser Phe
1               5                   10                  15

Asn Asn Lys Val Leu Val Leu Gly Ser Glu Asn
            20                  25
```

<210> SEQ ID NO 147
<211> LENGTH: 27
<212> TYPE: PRT
<213> ORGANISM: Pasteurella multocida str. Pm70

<400> SEQUENCE: 147

```
Glu Ile Asp His Ala Leu Pro Phe Ser Arg Thr Trp Asp Asp Ser Phe
1               5                   10                  15

Asn Asn Lys Val Leu Val Leu Ala Ser Glu Asn
            20                  25
```

<210> SEQ ID NO 148
<211> LENGTH: 27
<212> TYPE: PRT
<213> ORGANISM: Enterococcus faecalis TX0012

<400> SEQUENCE: 148

-continued

```
Glu Ile Asp His Ile Ile Pro Ile Ser Ile Ser Leu Asp Asp Ser Ile
1               5                   10                  15

Asn Asn Lys Val Leu Val Leu Ser Lys Ala Asn
            20                  25
```

```
<210> SEQ ID NO 149
<211> LENGTH: 27
<212> TYPE: PRT
<213> ORGANISM: Eubacterium dolichum DSM 3991

<400> SEQUENCE: 149

Glu Val Asp His Ile Ile Pro Ile Ser Ile Ser Leu Asp Asp Ser Ile
1               5                   10                  15

Thr Asn Lys Val Leu Val Thr His Arg Glu Asn
            20                  25
```

```
<210> SEQ ID NO 150
<211> LENGTH: 27
<212> TYPE: PRT
<213> ORGANISM: Acidovorax ebreus

<400> SEQUENCE: 150

Gln Val Asp His Ala Leu Pro Tyr Ser Arg Ser Tyr Asp Asp Ser Lys
1               5                   10                  15

Asn Asn Lys Val Leu Val Leu Thr His Glu Asn
            20                  25
```

```
<210> SEQ ID NO 151
<211> LENGTH: 27
<212> TYPE: PRT
<213> ORGANISM: Streptococcus thermophilus LMD-9

<400> SEQUENCE: 151

Glu Val Asp His Ile Leu Pro Leu Ser Ile Thr Phe Asp Asp Ser Leu
1               5                   10                  15

Ala Asn Lys Val Leu Val Tyr Ala Thr Ala Asn
            20                  25
```

```
<210> SEQ ID NO 152
<211> LENGTH: 27
<212> TYPE: PRT
<213> ORGANISM: Eubacterium rectale

<400> SEQUENCE: 152

Glu Ile Asp His Ile Ile Pro Arg Ser Ile Ser Phe Asp Asp Ala Arg
1               5                   10                  15

Ser Asn Lys Val Leu Val Tyr Arg Ser Glu Asn
            20                  25
```

```
<210> SEQ ID NO 153
<211> LENGTH: 27
<212> TYPE: PRT
<213> ORGANISM: Staphylococcus lugdunensis M23590

<400> SEQUENCE: 153

Glu Val Asp His Ile Ile Pro Arg Ser Val Ser Phe Asp Asn Ser Tyr
1               5                   10                  15

His Asn Lys Val Leu Val Lys Gln Ser Glu Asn
            20                  25
```

```
<210> SEQ ID NO 154
<211> LENGTH: 27
```

<212> TYPE: PRT
<213> ORGANISM: Roseburia intestinalis

<400> SEQUENCE: 154

Asp Ile Asp His Ile Leu Pro Tyr Ser Ile Thr Phe Asp Asp Ser Phe
1 5 10 15

Arg Asn Lys Val Leu Val Thr Ser Gln Glu Asn
20 25

<210> SEQ ID NO 155
<211> LENGTH: 27
<212> TYPE: PRT
<213> ORGANISM: Wolinella succinogenes DSM 1740

<400> SEQUENCE: 155

Glu Ile Asp His Ile Leu Pro Arg Ser Arg Ser Ala Asp Asp Ser Phe
1 5 10 15

Ala Asn Lys Val Leu Cys Leu Ala Arg Ala Asn
20 25

<210> SEQ ID NO 156
<211> LENGTH: 27
<212> TYPE: PRT
<213> ORGANISM: Cand. Puniceispirillum marinum

<400> SEQUENCE: 156

Glu Ile Glu His Leu Leu Pro Phe Ser Leu Thr Leu Asp Asp Ser Met
1 5 10 15

Ala Asn Lys Thr Val Cys Phe Arg Gln Ala Asn
20 25

<210> SEQ ID NO 157
<211> LENGTH: 27
<212> TYPE: PRT
<213> ORGANISM: Azospirillum sp. B510

<400> SEQUENCE: 157

Asp Ile Asp His Ile Leu Pro Phe Ser Val Ser Leu Asp Asp Ser Ala
1 5 10 15

Ala Asn Lys Val Val Cys Leu Arg Glu Ala Asn
20 25

<210> SEQ ID NO 158
<211> LENGTH: 27
<212> TYPE: PRT
<213> ORGANISM: Bradyrhizobium sp. BTAi1

<400> SEQUENCE: 158

Asp Ile Asp His Leu Ile Pro Phe Ser Ile Ser Trp Asp Asp Ser Ala
1 5 10 15

Ala Asn Lys Val Val Cys Met Arg Tyr Ala Asn
20 25

<210> SEQ ID NO 159
<211> LENGTH: 27
<212> TYPE: PRT
<213> ORGANISM: Nitrobacter hamburgensis X14

<400> SEQUENCE: 159

Asp Ile Asp His Ile Leu Pro Val Ala Met Thr Leu Asp Asp Ser Pro
1 5 10 15

Ala Asn Lys Ile Ile Cys Met Arg Tyr Ala Asn 20 25

<210> SEQ ID NO 160
<211> LENGTH: 27
<212> TYPE: PRT
<213> ORGANISM: Dinoroseobacter shibae

<400> SEQUENCE: 160

Asp Val Asp His Ile Leu Pro Tyr Ser Arg Thr Leu Asp Asp Ser Phe
1 5 10 15

Pro Asn Arg Thr Leu Cys Leu Arg Glu Ala Asn
20 25

<210> SEQ ID NO 161
<211> LENGTH: 27
<212> TYPE: PRT
<213> ORGANISM: Verminephrobacter eiseniae

<400> SEQUENCE: 161

Glu Ile Glu His Ile Leu Pro Phe Ser Arg Thr Leu Asp Asp Ser Leu
1 5 10 15

Asn Asn Arg Thr Val Ala Met Arg Arg Ala Asn
20 25

<210> SEQ ID NO 162
<211> LENGTH: 27
<212> TYPE: PRT
<213> ORGANISM: Lactobacillus coryniformis KCTC 3535

<400> SEQUENCE: 162

Glu Val Asp His Ile Ile Pro Tyr Ser Ile Ser Trp Asp Asp Ser Tyr
1 5 10 15

Thr Asn Lys Val Leu Thr Ser Ala Lys Cys Asn
20 25

<210> SEQ ID NO 163
<211> LENGTH: 27
<212> TYPE: PRT
<213> ORGANISM: Rhodopseudomonas palustris

<400> SEQUENCE: 163

Gln Val Asp His Ile Leu Pro Trp Ser Arg Phe Gly Asp Asp Ser Tyr
1 5 10 15

Leu Asn Lys Thr Leu Cys Thr Ala Arg Ser Asn
20 25

<210> SEQ ID NO 164
<211> LENGTH: 27
<212> TYPE: PRT
<213> ORGANISM: Ralstonia syzygii R24

<400> SEQUENCE: 164

Gln Val Asp His Ile Leu Pro Phe Ser Lys Thr Leu Asp Asp Ser Phe
1 5 10 15

Ala Asn Lys Val Leu Ala Gln His Asp Ala Asn
20 25

<210> SEQ ID NO 165
<211> LENGTH: 27
<212> TYPE: PRT
<213> ORGANISM: Helicobacter mustelae 12198

<400> SEQUENCE: 165

Gln Ile Asp His Ala Phe Pro Leu Ser Arg Ser Leu Asp Asp Ser Gln
1 5 10 15

Ser Asn Lys Val Leu Cys Leu Thr Ser Ser Asn
20 25

<210> SEQ ID NO 166
<211> LENGTH: 27
<212> TYPE: PRT
<213> ORGANISM: Mycoplasma mobile 163K

<400> SEQUENCE: 166

Asp Ile Asp His Ile Val Pro Arg Ser Ile Ser Phe Asp Asp Ser Phe
1 5 10 15

Ser Asn Leu Val Ile Val Asn Lys Leu Asp Asn
20 25

<210> SEQ ID NO 167
<211> LENGTH: 27
<212> TYPE: PRT
<213> ORGANISM: Mycoplasma ovipneumoniae SC01

<400> SEQUENCE: 167

Glu Ile Glu His Ile Ile Pro Tyr Ser Met Ser Tyr Asp Asn Ser Gln
1 5 10 15

Ala Asn Lys Ile Leu Thr Glu Lys Ala Glu Asn
20 25

<210> SEQ ID NO 168
<211> LENGTH: 27
<212> TYPE: PRT
<213> ORGANISM: Mycoplasma synoviae 53

<400> SEQUENCE: 168

Glu Ile Asp His Val Ile Pro Tyr Ser Lys Ser Ala Asp Asp Ser Trp
1 5 10 15

Phe Asn Lys Leu Leu Val Lys Lys Ser Thr Asn
20 25

<210> SEQ ID NO 169
<211> LENGTH: 27
<212> TYPE: PRT
<213> ORGANISM: Aminomonas paucivorans DSM 12260

<400> SEQUENCE: 169

Glu Met Asp His Ile Leu Pro Tyr Ser Arg Ser Leu Asp Asn Gly Trp
1 5 10 15

His Asn Arg Val Leu Val His Gly Lys Asp Asn
20 25

<210> SEQ ID NO 170
<211> LENGTH: 27
<212> TYPE: PRT
<213> ORGANISM: Ruminococcus albus 8

<400> SEQUENCE: 170

Glu Val Asp His Ile Val Pro Tyr Ser Leu Ile Leu Asp Asn Thr Ile
1 5 10 15

Asn Asn Lys Ala Leu Val Tyr Ala Glu Glu Asn
20 25

<210> SEQ ID NO 171

<211> LENGTH: 27
<212> TYPE: PRT
<213> ORGANISM: Fibrobacter succinogenes

<400> SEQUENCE: 171

Glu Ile Glu His Val Ile Pro Gln Ser Leu Tyr Phe Asp Asp Ser Phe
1 5 10 15

Ser Asn Lys Val Ile Cys Glu Ala Glu Val Asn
20 25

<210> SEQ ID NO 172
<211> LENGTH: 27
<212> TYPE: PRT
<213> ORGANISM: Bacteroides fragilis, NCTC 9343

<400> SEQUENCE: 172

Asp Ile Glu His Ile Ile Pro Gln Ala Arg Leu Phe Asp Asp Ser Phe
1 5 10 15

Ser Asn Lys Thr Leu Glu Ala Arg Ser Val Asn
20 25

<210> SEQ ID NO 173
<211> LENGTH: 27
<212> TYPE: PRT
<213> ORGANISM: Capnocytophaga sputigena

<400> SEQUENCE: 173

Glu Ile Glu His Ile Val Pro Lys Ala Arg Val Phe Asp Asp Ser Phe
1 5 10 15

Ser Asn Lys Thr Leu Thr Phe His Arg Ile Asn
20 25

<210> SEQ ID NO 174
<211> LENGTH: 28
<212> TYPE: PRT
<213> ORGANISM: Finegoldia magna

<400> SEQUENCE: 174

Asp Lys Asp His Ile Ile Pro Gln Ser Met Lys Lys Asp Asp Ser Ile
1 5 10 15

Ile Asn Asn Leu Val Leu Val Asn Lys Asn Ala Asn
20 25

<210> SEQ ID NO 175
<211> LENGTH: 27
<212> TYPE: PRT
<213> ORGANISM: Parvibaculum lavamentivorans DS-1

<400> SEQUENCE: 175

Glu Val Glu His Ile Trp Pro Arg Ser Arg Ser Phe Asp Asn Ser Pro
1 5 10 15

Arg Asn Lys Thr Leu Cys Arg Lys Asp Val Asn
20 25

<210> SEQ ID NO 176
<211> LENGTH: 27
<212> TYPE: PRT
<213> ORGANISM: Bacillus cereus

<400> SEQUENCE: 176

Ile Val Asn His Ile Ile Pro Tyr Asn Arg Ser Phe Asp Asp Thr Tyr
1 5 10 15

His Asn Arg Val Leu Thr Leu Thr Glu Thr Lys
20 25

<210> SEQ ID NO 177
<211> LENGTH: 27
<212> TYPE: PRT
<213> ORGANISM: Prevotella micans

<400> SEQUENCE: 177

Asp Met Glu His Thr Ile Pro Lys Ser Ile Ser Phe Asp Asn Ser Asp
1 5 10 15

Gln Asn Leu Thr Leu Cys Glu Ser Tyr Tyr Asn
20 25

<210> SEQ ID NO 178
<211> LENGTH: 27
<212> TYPE: PRT
<213> ORGANISM: Prevotella ruminicola

<400> SEQUENCE: 178

Asp Ile Glu His Thr Ile Pro Arg Ser Ala Gly Gly Asp Ser Thr Lys
1 5 10 15

Met Asn Leu Thr Leu Cys Ser Ser Arg Phe Asn
20 25

<210> SEQ ID NO 179
<211> LENGTH: 27
<212> TYPE: PRT
<213> ORGANISM: Flavobacterium columnare

<400> SEQUENCE: 179

Asp Ile Glu His Thr Ile Pro Arg Ser Ile Ser Gln Asp Asn Ser Gln
1 5 10 15

Met Asn Lys Thr Leu Cys Ser Leu Lys Phe Asn
20 25

<210> SEQ ID NO 180
<211> LENGTH: 27
<212> TYPE: PRT
<213> ORGANISM: Rhodospirillum rubrum

<400> SEQUENCE: 180

Asp Ile Asp His Val Ile Pro Leu Ala Arg Gly Gly Arg Asp Ser Leu
1 5 10 15

Asp Asn Met Val Leu Cys Gln Ser Asp Ala Asn
20 25

<210> SEQ ID NO 181
<211> LENGTH: 27
<212> TYPE: PRT
<213> ORGANISM: Elusimicrobium minutum Pei191

<400> SEQUENCE: 181

Asp Ile Glu His Leu Phe Pro Ile Ala Glu Ser Glu Asp Asn Gly Arg
1 5 10 15

Asn Asn Leu Val Ile Ser His Ser Ala Cys Asn
20 25

<210> SEQ ID NO 182
<211> LENGTH: 27
<212> TYPE: PRT
<213> ORGANISM: Sphaerochaeta globus str. Buddy

<400> SEQUENCE: 182

Asp Val Asp His Ile Phe Pro Arg Asp Asp Thr Ala Asp Asn Ser Tyr
1 5 10 15

Gly Asn Lys Val Val Ala His Arg Gln Cys Asn
20 25

<210> SEQ ID NO 183
<211> LENGTH: 27
<212> TYPE: PRT
<213> ORGANISM: Nitratifractor salsuginis DSM 16511

<400> SEQUENCE: 183

Asp Ile Glu His Ile Val Pro Gln Ser Leu Gly Gly Leu Ser Thr Asp
1 5 10 15

Tyr Asn Thr Ile Val Thr Leu Lys Ser Val Asn
20 25

<210> SEQ ID NO 184
<211> LENGTH: 27
<212> TYPE: PRT
<213> ORGANISM: Acidothermus cellulolyticus 11B

<400> SEQUENCE: 184

Glu Leu Asp His Ile Val Pro Arg Thr Asp Gly Gly Ser Asn Arg His
1 5 10 15

Glu Asn Leu Ala Ile Thr Cys Gly Ala Cys Asn
20 25

<210> SEQ ID NO 185
<211> LENGTH: 28
<212> TYPE: PRT
<213> ORGANISM: Bifidobacterium longum DJO10A

<400> SEQUENCE: 185

Glu Met Asp His Ile Val Pro Arg Lys Gly Val Gly Ser Thr Asn Thr
1 5 10 15

Arg Thr Asn Phe Ala Ala Val Cys Ala Glu Cys Asn
20 25

<210> SEQ ID NO 186
<211> LENGTH: 28
<212> TYPE: PRT
<213> ORGANISM: Bifidobacterium dentium

<400> SEQUENCE: 186

Glu Met Asp His Ile Val Pro Arg Lys Gly Val Gly Ser Thr Asn Thr
1 5 10 15

Arg Val Asn Leu Ala Ala Ala Cys Ala Ala Cys Asn
20 25

<210> SEQ ID NO 187
<211> LENGTH: 28
<212> TYPE: PRT
<213> ORGANISM: Corynebacterium diphtheriae

<400> SEQUENCE: 187

Glu Met Asp His Ile Val Pro Arg Ala Gly Gln Gly Ser Thr Asn Thr
1 5 10 15

Arg Glu Asn Leu Val Ala Val Cys His Arg Cys Asn
20 25

<210> SEQ ID NO 188
<211> LENGTH: 33
<212> TYPE: PRT
<213> ORGANISM: Sutterella wadsworthensis

<400> SEQUENCE: 188

```
Glu Ile Asp His Ile Leu Pro Arg Ser Leu Ile Lys Asp Ala Arg Gly
1               5                   10                  15

Ile Val Phe Asn Ala Glu Pro Asn Leu Ile Tyr Ala Ser Ser Arg Gly
            20                  25                  30

Asn
```

<210> SEQ ID NO 189
<211> LENGTH: 33
<212> TYPE: PRT
<213> ORGANISM: Gamma proteobacterium HTCC5015

<400> SEQUENCE: 189

```
Glu Ile Asp His Ile Ile Pro Arg Ser Leu Thr Gly Arg Thr Lys Lys
1               5                   10                  15

Thr Val Phe Asn Ser Glu Ala Asn Leu Ile Tyr Cys Ser Ser Lys Gly
            20                  25                  30

Asn
```

<210> SEQ ID NO 190
<211> LENGTH: 33
<212> TYPE: PRT
<213> ORGANISM: Parasutterella excrementihominis

<400> SEQUENCE: 190

```
Glu Ile Asp His Ile Ile Pro Arg Ser Leu Thr Leu Lys Lys Ser Glu
1               5                   10                  15

Ser Ile Tyr Asn Ser Glu Val Asn Leu Ile Phe Val Ser Ala Gln Gly
            20                  25                  30

Asn
```

<210> SEQ ID NO 191
<211> LENGTH: 33
<212> TYPE: PRT
<213> ORGANISM: Legionella pneumophila str. Paris

<400> SEQUENCE: 191

```
Glu Ile Asp His Ile Tyr Pro Arg Ser Leu Ser Lys Lys His Phe Gly
1               5                   10                  15

Val Ile Phe Asn Ser Glu Val Asn Leu Ile Tyr Cys Ser Ser Gln Gly
            20                  25                  30

Asn
```

<210> SEQ ID NO 192
<211> LENGTH: 33
<212> TYPE: PRT
<213> ORGANISM: Wolinella succinogenes DSM 1740

<400> SEQUENCE: 192

```
Glu Ile Asp His Ile Leu Pro Arg Ser His Thr Leu Lys Ile Tyr Gly
1               5                   10                  15

Thr Val Phe Asn Pro Glu Gly Asn Leu Ile Tyr Val His Gln Lys Cys
            20                  25                  30

Asn
```

<210> SEQ ID NO 193
<211> LENGTH: 30
<212> TYPE: PRT
<213> ORGANISM: Francisella tularensis

<400> SEQUENCE: 193

Glu Leu Asp His Ile Ile Pro Arg Ser His Lys Lys Tyr Gly Thr Leu
1               5                   10                  15

Asn Asp Glu Ala Asn Leu Ile Cys Val Thr Arg Gly Asp Asn
            20                  25                  30

<210> SEQ ID NO 194
<211> LENGTH: 27
<212> TYPE: PRT
<213> ORGANISM: Akkermansia muciniphila

<400> SEQUENCE: 194

Glu Leu Glu His Ile Val Pro His Ser Phe Arg Gln Ser Asn Ala Leu
1               5                   10                  15

Ser Ser Leu Val Leu Thr Trp Pro Gly Val Asn
            20                  25

<210> SEQ ID NO 195
<211> LENGTH: 27
<212> TYPE: PRT
<213> ORGANISM: Solobacterium moorei F0204

<400> SEQUENCE: 195

Asp Ile Asp His Ile Tyr Pro Arg Ser Lys Ile Lys Asp Asp Ser Ile
1               5                   10                  15

Thr Asn Arg Val Leu Val Glu Lys Asp Ile Asn
            20                  25

<210> SEQ ID NO 196
<211> LENGTH: 28
<212> TYPE: PRT
<213> ORGANISM: Veillonella atypica ACS-134-V-Col7a

<400> SEQUENCE: 196

Tyr Asp Ile Asp His Ile Tyr Pro Arg Ser Leu Thr Lys Asp Asp Ser
1               5                   10                  15

Phe Asp Asn Leu Val Leu Cys Glu Arg Thr Ala Asn
            20                  25

<210> SEQ ID NO 197
<211> LENGTH: 28
<212> TYPE: PRT
<213> ORGANISM: Fusobacterium nucleatum

<400> SEQUENCE: 197

Asp Ile Asp His Ile Tyr Pro Arg Ser Lys Val Ile Lys Asp Asp Ser
1               5                   10                  15

Phe Asp Asn Leu Val Leu Val Leu Lys Asn Glu Asn
            20                  25

<210> SEQ ID NO 198
<211> LENGTH: 27
<212> TYPE: PRT
<213> ORGANISM: Filifactor alocis

<400> SEQUENCE: 198

Asp Arg Asp His Ile Tyr Pro Gln Ser Lys Ile Lys Asp Asp Ser Ile

-continued

```
1               5                   10                  15

Asp Asn Leu Val Leu Val Asn Lys Thr Tyr Asn
            20                  25
```

<210> SEQ ID NO 199
<211> LENGTH: 5
<212> TYPE: DNA
<213> ORGANISM: Streptococcus thermophilus
<220> FEATURE:
<221> NAME/KEY: misc_feature
<222> LOCATION: (1)..(1)
<223> OTHER INFORMATION: Any nucleotide (e.g., A, G, C, or T)
<220> FEATURE:
<221> NAME/KEY: misc_feature
<222> LOCATION: (4)..(4)
<223> OTHER INFORMATION: Any nucleotide (e.g., A, G, C, or T)

<400> SEQUENCE: 199 nggng 5

<210> SEQ ID NO 200
<211> LENGTH: 7
<212> TYPE: DNA
<213> ORGANISM: Streptococcus thermophilus
<220> FEATURE:
<221> NAME/KEY: misc_feature
<222> LOCATION: (1)..(1)
<223> OTHER INFORMATION: Any nucleotide (e.g., A, G, C, or T)
<220> FEATURE:
<221> NAME/KEY: misc_feature
<222> LOCATION: (2)..(2)
<223> OTHER INFORMATION: Any nucleotide (e.g., A, G, C, or T)
<220> FEATURE:
<221> NAME/KEY: misc_feature
<222> LOCATION: (7)..(7)
<223> OTHER INFORMATION: A or T

<400> SEQUENCE: 200 nnagaaw 7

<210> SEQ ID NO 201
<211> LENGTH: 4
<212> TYPE: DNA
<213> ORGANISM: Streptococcus mutans
<220> FEATURE:
<221> NAME/KEY: misc_feature
<222> LOCATION: (1)..(1)
<223> OTHER INFORMATION: Any nucleotide (e.g., A, G, C, or T)
<220> FEATURE:
<221> NAME/KEY: misc_feature
<222> LOCATION: (4)..(4)
<223> OTHER INFORMATION: A or G

<400> SEQUENCE: 201 naar 4

<210> SEQ ID NO 202
<211> LENGTH: 5
<212> TYPE: DNA
<213> ORGANISM: Staphylococcus aureus
<220> FEATURE:
<221> NAME/KEY: misc_feature
<222> LOCATION: (1)..(1)
<223> OTHER INFORMATION: Any nucleotide (e.g., A, G, C, or T)
<220> FEATURE:
<221> NAME/KEY: misc_feature
<222> LOCATION: (2)..(2)
<223> OTHER INFORMATION: Any nucleotide (e.g., A, G, C, or T)
<220> FEATURE:
<221> NAME/KEY: misc_feature
<222> LOCATION: (4)..(4)

<223> OTHER INFORMATION: A or G
<220> FEATURE:
<221> NAME/KEY: misc_feature
<222> LOCATION: (5)..(5)
<223> OTHER INFORMATION: A or G

<400> SEQUENCE: 202 nngrr 5

<210> SEQ ID NO 203
<211> LENGTH: 6
<212> TYPE: DNA
<213> ORGANISM: Staphylococcus aureus
<220> FEATURE:
<221> NAME/KEY: misc_feature
<222> LOCATION: (1)..(1)
<223> OTHER INFORMATION: Any nucleotide (e.g., A, G, C, or T)
<220> FEATURE:
<221> NAME/KEY: misc_feature
<222> LOCATION: (2)..(2)
<223> OTHER INFORMATION: Any nucleotide (e.g., A, G, C, or T)
<220> FEATURE:
<221> NAME/KEY: misc_feature
<222> LOCATION: (4)..(4)
<223> OTHER INFORMATION: A or G
<220> FEATURE:
<221> NAME/KEY: misc_feature
<222> LOCATION: (5)..(5)
<223> OTHER INFORMATION: A or G
<220> FEATURE:
<221> NAME/KEY: misc_feature
<222> LOCATION: (6)..(6)
<223> OTHER INFORMATION: Any nucleotide (e.g., A, G, C, or T)

<400> SEQUENCE: 203 nngrrn 6

<210> SEQ ID NO 204
<211> LENGTH: 6
<212> TYPE: DNA
<213> ORGANISM: Staphylococcus aureus
<220> FEATURE:
<221> NAME/KEY: misc_feature
<222> LOCATION: (1)..(1)
<223> OTHER INFORMATION: Any nucleotide (e.g., A, G, C, or T)
<220> FEATURE:
<221> NAME/KEY: misc_feature
<222> LOCATION: (2)..(2)
<223> OTHER INFORMATION: Any nucleotide (e.g., A, G, C, or T)
<220> FEATURE:
<221> NAME/KEY: misc_feature
<222> LOCATION: (4)..(4)
<223> OTHER INFORMATION: A or G
<220> FEATURE:
<221> NAME/KEY: misc_feature
<222> LOCATION: (5)..(5)
<223> OTHER INFORMATION: A or G

<400> SEQUENCE: 204 nngrrt 6

<210> SEQ ID NO 205
<211> LENGTH: 6
<212> TYPE: DNA
<213> ORGANISM: Staphylococcus aureus
<220> FEATURE:
<221> NAME/KEY: misc_feature
<222> LOCATION: (1)..(1)
<223> OTHER INFORMATION: Any nucleotide (e.g., A, G, C, or T)
<220> FEATURE:
<221> NAME/KEY: misc_feature
<222> LOCATION: (2)..(2)
<223> OTHER INFORMATION: Any nucleotide (e.g., A, G, C, or T)

<220> FEATURE:
<221> NAME/KEY: misc_feature
<222> LOCATION: (4)..(4)
<223> OTHER INFORMATION: A or G
<220> FEATURE:
<221> NAME/KEY: misc_feature
<222> LOCATION: (5)..(5)
<223> OTHER INFORMATION: A or G
<220> FEATURE:
<221> NAME/KEY: misc_feature
<222> LOCATION: (6)..(6)
<223> OTHER INFORMATION: A, G, or C

<400> SEQUENCE: 205 nngrrv 6

<210> SEQ ID NO 206

<400> SEQUENCE: 206

000

<210> SEQ ID NO 207

<400> SEQUENCE: 207

000

<210> SEQ ID NO 208

<400> SEQUENCE: 208

000

<210> SEQ ID NO 209

<400> SEQUENCE: 209

000

<210> SEQ ID NO 210

<400> SEQUENCE: 210

000

<210> SEQ ID NO 211

<400> SEQUENCE: 211

000

<210> SEQ ID NO 212

<400> SEQUENCE: 212

000

<210> SEQ ID NO 213

<400> SEQUENCE: 213

000

<210> SEQ ID NO 214

<400> SEQUENCE: 214

000

<210> SEQ ID NO 215

<400> SEQUENCE: 215

000

<210> SEQ ID NO 216

<400> SEQUENCE: 216

000

<210> SEQ ID NO 217

<400> SEQUENCE: 217

000

<210> SEQ ID NO 218

<400> SEQUENCE: 218

000

<210> SEQ ID NO 219

<400> SEQUENCE: 219

000

<210> SEQ ID NO 220

<400> SEQUENCE: 220

000

<210> SEQ ID NO 221

<400> SEQUENCE: 221

000

<210> SEQ ID NO 222

<400> SEQUENCE: 222

000

<210> SEQ ID NO 223

<400> SEQUENCE: 223

000

<210> SEQ ID NO 224

<400> SEQUENCE: 224

000

<210> SEQ ID NO 225

<400> SEQUENCE: 225

000

<210> SEQ ID NO 226

<400> SEQUENCE: 226

000

<210> SEQ ID NO 227

<400> SEQUENCE: 227

000

<210> SEQ ID NO 228

<400> SEQUENCE: 228

000

<210> SEQ ID NO 229

<400> SEQUENCE: 229

000

<210> SEQ ID NO 230

<400> SEQUENCE: 230

000

<210> SEQ ID NO 231

<400> SEQUENCE: 231

000

<210> SEQ ID NO 232

<400> SEQUENCE: 232

000

<210> SEQ ID NO 233

<400> SEQUENCE: 233

000

<210> SEQ ID NO 234

<400> SEQUENCE: 234

000

<210> SEQ ID NO 235

<400> SEQUENCE: 235

000

<210> SEQ ID NO 236

<400> SEQUENCE: 236

000

<210> SEQ ID NO 237

<400> SEQUENCE: 237

000

<210> SEQ ID NO 238

<400> SEQUENCE: 238

000

<210> SEQ ID NO 239

<400> SEQUENCE: 239

000

<210> SEQ ID NO 240

<400> SEQUENCE: 240

000

<210> SEQ ID NO 241

<400> SEQUENCE: 241

000

<210> SEQ ID NO 242

<400> SEQUENCE: 242

000

<210> SEQ ID NO 243

<400> SEQUENCE: 243

000

<210> SEQ ID NO 244

<400> SEQUENCE: 244

000

<210> SEQ ID NO 245

<400> SEQUENCE: 245

000

<210> SEQ ID NO 246

<400> SEQUENCE: 246

000

<210> SEQ ID NO 247

<400> SEQUENCE: 247

000

<210> SEQ ID NO 248

<400> SEQUENCE: 248

000

<210> SEQ ID NO 249

<400> SEQUENCE: 249

000

<210> SEQ ID NO 250

<400> SEQUENCE: 250

000

<210> SEQ ID NO 251
<211> LENGTH: 17
<212> TYPE: RNA
<213> ORGANISM: Artificial Sequence
<220> FEATURE:
<223> OTHER INFORMATION: Targeting domain

<400> SEQUENCE: 251
gaaggaaacu agcuaaa 17

<210> SEQ ID NO 252
<211> LENGTH: 20
<212> TYPE: RNA
<213> ORGANISM: Artificial Sequence
<220> FEATURE:
<223> OTHER INFORMATION: Targeting domain

<400> SEQUENCE: 252
ggagaaggaa acuagcuaaa 20

<210> SEQ ID NO 253
<211> LENGTH: 20
<212> TYPE: RNA
<213> ORGANISM: Artificial Sequence
<220> FEATURE:
<223> OTHER INFORMATION: Targeting domain

<400> SEQUENCE: 253
gggagaagga aacuagcuaa 20

<210> SEQ ID NO 254
<211> LENGTH: 20
<212> TYPE: RNA
<213> ORGANISM: Artificial Sequence
<220> FEATURE:
<223> OTHER INFORMATION: Targeting domain

<400> SEQUENCE: 254
guauccucua ugaugggaga 20

<210> SEQ ID NO 255
<211> LENGTH: 20
<212> TYPE: RNA
<213> ORGANISM: Artificial Sequence
<220> FEATURE:
<223> OTHER INFORMATION: Targeting domain

<400> SEQUENCE: 255
guuuccuucu cccaucauag 20

<210> SEQ ID NO 256
<211> LENGTH: 20

<212> TYPE: RNA
<213> ORGANISM: Artificial Sequence
<220> FEATURE:
<223> OTHER INFORMATION: Targeting domain

<400> SEQUENCE: 256
guccugguau ccucuaugau 20

<210> SEQ ID NO 257
<211> LENGTH: 17
<212> TYPE: RNA
<213> ORGANISM: Artificial Sequence
<220> FEATURE:
<223> OTHER INFORMATION: Targeting domain

<400> SEQUENCE: 257
agaaggaaac uagcuaa 17

<210> SEQ ID NO 258
<211> LENGTH: 17
<212> TYPE: RNA
<213> ORGANISM: Artificial Sequence
<220> FEATURE:
<223> OTHER INFORMATION: Targeting domain

<400> SEQUENCE: 258
uccucuauga ugggaga 17

<210> SEQ ID NO 259
<211> LENGTH: 17
<212> TYPE: RNA
<213> ORGANISM: Artificial Sequence
<220> FEATURE:
<223> OTHER INFORMATION: Targeting domain

<400> SEQUENCE: 259
ccugguaucc ucuauga 17

<210> SEQ ID NO 260
<211> LENGTH: 17
<212> TYPE: RNA
<213> ORGANISM: Artificial Sequence
<220> FEATURE:
<223> OTHER INFORMATION: Targeting domain

<400> SEQUENCE: 260
ccaucauaga ggauacc 17

<210> SEQ ID NO 261
<211> LENGTH: 17
<212> TYPE: RNA
<213> ORGANISM: Artificial Sequence
<220> FEATURE:
<223> OTHER INFORMATION: Targeting domain

<400> SEQUENCE: 261
uccuucuccc aucauag 17

<210> SEQ ID NO 262
<211> LENGTH: 17
<212> TYPE: RNA
<213> ORGANISM: Artificial Sequence
<220> FEATURE:
<223> OTHER INFORMATION: Targeting domain

<400> SEQUENCE: 262
uagcaguauc cucuugg 17

<210> SEQ ID NO 263
<211> LENGTH: 17
<212> TYPE: RNA
<213> ORGANISM: Artificial Sequence
<220> FEATURE:
<223> OTHER INFORMATION: Targeting domain

<400> SEQUENCE: 263
uuagcaguau ccucuug 17

<210> SEQ ID NO 264
<211> LENGTH: 17
<212> TYPE: RNA
<213> ORGANISM: Artificial Sequence
<220> FEATURE:
<223> OTHER INFORMATION: Targeting domain

<400> SEQUENCE: 264
aacuggaaug acugaau 17

<210> SEQ ID NO 265
<211> LENGTH: 17
<212> TYPE: RNA
<213> ORGANISM: Artificial Sequence
<220> FEATURE:
<223> OTHER INFORMATION: Targeting domain

<400> SEQUENCE: 265
cugguauccu cuaugau 17

<210> SEQ ID NO 266
<211> LENGTH: 17
<212> TYPE: RNA
<213> ORGANISM: Artificial Sequence
<220> FEATURE:
<223> OTHER INFORMATION: Targeting domain

<400> SEQUENCE: 266
aauuagcagu auccucu 17

<210> SEQ ID NO 267
<211> LENGTH: 17
<212> TYPE: RNA
<213> ORGANISM: Artificial Sequence
<220> FEATURE:
<223> OTHER INFORMATION: Targeting domain

<400> SEQUENCE: 267
auuagcagua uccucuu 17

<210> SEQ ID NO 268
<211> LENGTH: 20
<212> TYPE: RNA
<213> ORGANISM: Artificial Sequence
<220> FEATURE:
<223> OTHER INFORMATION: Targeting domain

<400> SEQUENCE: 268
aguccuggua uccucuauga 20

<210> SEQ ID NO 269
<211> LENGTH: 20
<212> TYPE: RNA
<213> ORGANISM: Artificial Sequence
<220> FEATURE:
<223> OTHER INFORMATION: Targeting domain

<400> SEQUENCE: 269
cucccaucau agaggauacc 20

<210> SEQ ID NO 270
<211> LENGTH: 20
<212> TYPE: RNA
<213> ORGANISM: Artificial Sequence
<220> FEATURE:
<223> OTHER INFORMATION: Targeting domain

<400> SEQUENCE: 270
aauuagcagu auccucuugg 20

<210> SEQ ID NO 271
<211> LENGTH: 20
<212> TYPE: RNA
<213> ORGANISM: Artificial Sequence
<220> FEATURE:
<223> OTHER INFORMATION: Targeting domain

<400> SEQUENCE: 271
aaauuagcag uauccucuug 20

<210> SEQ ID NO 272
<211> LENGTH: 20
<212> TYPE: RNA
<213> ORGANISM: Artificial Sequence
<220> FEATURE:
<223> OTHER INFORMATION: Targeting domain

<400> SEQUENCE: 272
aaaaacugga augacugaau 20

<210> SEQ ID NO 273
<211> LENGTH: 20
<212> TYPE: RNA
<213> ORGANISM: Artificial Sequence
<220> FEATURE:
<223> OTHER INFORMATION: Targeting domain

<400> SEQUENCE: 273
aaaaauuagc aguauccucu 20

<210> SEQ ID NO 274
<211> LENGTH: 20
<212> TYPE: RNA
<213> ORGANISM: Artificial Sequence
<220> FEATURE:
<223> OTHER INFORMATION: Targeting domain

<400> SEQUENCE: 274
aaaauuagca guauccucuu 20

<210> SEQ ID NO 275
<211> LENGTH: 17
<212> TYPE: RNA
<213> ORGANISM: Artificial Sequence
<220> FEATURE:
<223> OTHER INFORMATION: Targeting domain

<400> SEQUENCE: 275
gaaucggaac aaggcaa 17

<210> SEQ ID NO 276
<211> LENGTH: 17
<212> TYPE: RNA
<213> ORGANISM: Artificial Sequence
<220> FEATURE:
<223> OTHER INFORMATION: Targeting domain

<400> SEQUENCE: 276
gaccaauagc cuugaca 17

<210> SEQ ID NO 277
<211> LENGTH: 17
<212> TYPE: RNA
<213> ORGANISM: Artificial Sequence
<220> FEATURE:
<223> OTHER INFORMATION: Targeting domain

<400> SEQUENCE: 277
ggcuauuggu caaggca 17

<210> SEQ ID NO 278
<211> LENGTH: 17
<212> TYPE: RNA
<213> ORGANISM: Artificial Sequence
<220> FEATURE:
<223> OTHER INFORMATION: Targeting domain

<400> SEQUENCE: 278
gucaaggcua uugguca 17

<210> SEQ ID NO 279
<211> LENGTH: 17
<212> TYPE: RNA
<213> ORGANISM: Artificial Sequence
<220> FEATURE:
<223> OTHER INFORMATION: Targeting domain

<400> SEQUENCE: 279
guguguggaa cugcuga 17

<210> SEQ ID NO 280
<211> LENGTH: 17
<212> TYPE: RNA
<213> ORGANISM: Artificial Sequence
<220> FEATURE:
<223> OTHER INFORMATION: Targeting domain

<400> SEQUENCE: 280
gggccggcgg cuggcua 17

<210> SEQ ID NO 281
<211> LENGTH: 17
<212> TYPE: RNA
<213> ORGANISM: Artificial Sequence
<220> FEATURE:
<223> OTHER INFORMATION: Targeting domain

<400> SEQUENCE: 281
gaguauccag ugaggcc 17

<210> SEQ ID NO 282
<211> LENGTH: 17
<212> TYPE: RNA
<213> ORGANISM: Artificial Sequence
<220> FEATURE:
<223> OTHER INFORMATION: Targeting domain

<400> SEQUENCE: 282
gcugacaaaa gaagucc 17

<210> SEQ ID NO 283
<211> LENGTH: 17
<212> TYPE: RNA
<213> ORGANISM: Artificial Sequence
<220> FEATURE:
<223> OTHER INFORMATION: Targeting domain

<400> SEQUENCE: 283
ggccaggggc cggcggc 17

<210> SEQ ID NO 284
<211> LENGTH: 17
<212> TYPE: RNA
<213> ORGANISM: Artificial Sequence
<220> FEATURE:
<223> OTHER INFORMATION: Targeting domain

<400> SEQUENCE: 284
gggaaggggc ccccaag 17

<210> SEQ ID NO 285
<211> LENGTH: 17
<212> TYPE: RNA
<213> ORGANISM: Artificial Sequence
<220> FEATURE:
<223> OTHER INFORMATION: Targeting domain

<400> SEQUENCE: 285
gagauagugu ggggaag 17

<210> SEQ ID NO 286
<211> LENGTH: 17
<212> TYPE: RNA
<213> ORGANISM: Artificial Sequence
<220> FEATURE:
<223> OTHER INFORMATION: Targeting domain

<400> SEQUENCE: 286
guauccagug aggccag 17

<210> SEQ ID NO 287
<211> LENGTH: 17
<212> TYPE: RNA
<213> ORGANISM: Artificial Sequence
<220> FEATURE:
<223> OTHER INFORMATION: Targeting domain

<400> SEQUENCE: 287
gugaggccag gggccgg 17

<210> SEQ ID NO 288
<211> LENGTH: 17
<212> TYPE: RNA
<213> ORGANISM: Artificial Sequence
<220> FEATURE:
<223> OTHER INFORMATION: Targeting domain

<400> SEQUENCE: 288
gcuggccaac ccauggg 17

<210> SEQ ID NO 289

<211> LENGTH: 17
<212> TYPE: RNA
<213> ORGANISM: Artificial Sequence
<220> FEATURE:
<223> OTHER INFORMATION: Targeting domain

<400> SEQUENCE: 289
ggcuaaacuc cacccau 17

<210> SEQ ID NO 290
<211> LENGTH: 17
<212> TYPE: RNA
<213> ORGANISM: Artificial Sequence
<220> FEATURE:
<223> OTHER INFORMATION: Targeting domain

<400> SEQUENCE: 290
ggauacucua agacuau 17

<210> SEQ ID NO 291
<211> LENGTH: 17
<212> TYPE: RNA
<213> ORGANISM: Artificial Sequence
<220> FEATURE:
<223> OTHER INFORMATION: Targeting domain

<400> SEQUENCE: 291
ggggccggcg gcuggcu 17

<210> SEQ ID NO 292
<211> LENGTH: 20
<212> TYPE: RNA
<213> ORGANISM: Artificial Sequence
<220> FEATURE:
<223> OTHER INFORMATION: Targeting domain

<400> SEQUENCE: 292
ggcuagggau gaagaauaaa 20

<210> SEQ ID NO 293
<211> LENGTH: 20
<212> TYPE: RNA
<213> ORGANISM: Artificial Sequence
<220> FEATURE:
<223> OTHER INFORMATION: Targeting domain

<400> SEQUENCE: 293
gagugugugg aacugcugaa 20

<210> SEQ ID NO 294
<211> LENGTH: 20
<212> TYPE: RNA
<213> ORGANISM: Artificial Sequence
<220> FEATURE:
<223> OTHER INFORMATION: Targeting domain

<400> SEQUENCE: 294
ggaaugacug aaucggaaca 20

<210> SEQ ID NO 295
<211> LENGTH: 20
<212> TYPE: RNA
<213> ORGANISM: Artificial Sequence
<220> FEATURE:
<223> OTHER INFORMATION: Targeting domain

<400> SEQUENCE: 295
gcauugagau agugugggga 20

<210> SEQ ID NO 296
<211> LENGTH: 20
<212> TYPE: RNA
<213> ORGANISM: Artificial Sequence
<220> FEATURE:
<223> OTHER INFORMATION: Targeting domain

<400> SEQUENCE: 296
gcuauugguc aaggcaaggc 20

<210> SEQ ID NO 297
<211> LENGTH: 20
<212> TYPE: RNA
<213> ORGANISM: Artificial Sequence
<220> FEATURE:
<223> OTHER INFORMATION: Targeting domain

<400> SEQUENCE: 297
guggggaagg ggcccccaag 20

<210> SEQ ID NO 298
<211> LENGTH: 20
<212> TYPE: RNA
<213> ORGANISM: Artificial Sequence
<220> FEATURE:
<223> OTHER INFORMATION: Targeting domain

<400> SEQUENCE: 298
ggcaaggcug gccaacccau 20

<210> SEQ ID NO 299
<211> LENGTH: 20
<212> TYPE: RNA
<213> ORGANISM: Artificial Sequence
<220> FEATURE:
<223> OTHER INFORMATION: Targeting domain

<400> SEQUENCE: 299
guuugccuug ucaaggcuau 20

<210> SEQ ID NO 300
<211> LENGTH: 20
<212> TYPE: RNA
<213> ORGANISM: Artificial Sequence
<220> FEATURE:
<223> OTHER INFORMATION: Targeting domain

<400> SEQUENCE: 300
gcuaaacucc acccaugggu 20

<210> SEQ ID NO 301
<211> LENGTH: 17
<212> TYPE: RNA
<213> ORGANISM: Artificial Sequence
<220> FEATURE:
<223> OTHER INFORMATION: Targeting domain

<400> SEQUENCE: 301
caaauaucug ucugaaa 17

<210> SEQ ID NO 302
<211> LENGTH: 17
<212> TYPE: RNA

<213> ORGANISM: Artificial Sequence
<220> FEATURE:
<223> OTHER INFORMATION: Targeting domain

<400> SEQUENCE: 302
uagggaugaa gaauaaa 17

<210> SEQ ID NO 303
<211> LENGTH: 17
<212> TYPE: RNA
<213> ORGANISM: Artificial Sequence
<220> FEATURE:
<223> OTHER INFORMATION: Targeting domain

<400> SEQUENCE: 303
ugagauagug uggggaa 17

<210> SEQ ID NO 304
<211> LENGTH: 17
<212> TYPE: RNA
<213> ORGANISM: Artificial Sequence
<220> FEATURE:
<223> OTHER INFORMATION: Targeting domain

<400> SEQUENCE: 304
uguguggaac ugcugaa 17

<210> SEQ ID NO 305
<211> LENGTH: 17
<212> TYPE: RNA
<213> ORGANISM: Artificial Sequence
<220> FEATURE:
<223> OTHER INFORMATION: Targeting domain

<400> SEQUENCE: 305
augacugaau cggaaca 17

<210> SEQ ID NO 306
<211> LENGTH: 17
<212> TYPE: RNA
<213> ORGANISM: Artificial Sequence
<220> FEATURE:
<223> OTHER INFORMATION: Targeting domain

<400> SEQUENCE: 306
caaggcuggc caaccca 17

<210> SEQ ID NO 307
<211> LENGTH: 17
<212> TYPE: RNA
<213> ORGANISM: Artificial Sequence
<220> FEATURE:
<223> OTHER INFORMATION: Targeting domain

<400> SEQUENCE: 307
uggcuaaacu ccaccca 17

<210> SEQ ID NO 308
<211> LENGTH: 17
<212> TYPE: RNA
<213> ORGANISM: Artificial Sequence
<220> FEATURE:
<223> OTHER INFORMATION: Targeting domain

<400> SEQUENCE: 308
uggguggagu uuagcca 17

<210> SEQ ID NO 309
<211> LENGTH: 17
<212> TYPE: RNA
<213> ORGANISM: Artificial Sequence
<220> FEATURE:
<223> OTHER INFORMATION: Targeting domain

<400> SEQUENCE: 309
aguauccagu gaggcca 17

<210> SEQ ID NO 310
<211> LENGTH: 17
<212> TYPE: RNA
<213> ORGANISM: Artificial Sequence
<220> FEATURE:
<223> OTHER INFORMATION: Targeting domain

<400> SEQUENCE: 310
ucaaguuugc cuuguca 17

<210> SEQ ID NO 311
<211> LENGTH: 17
<212> TYPE: RNA
<213> ORGANISM: Artificial Sequence
<220> FEATURE:
<223> OTHER INFORMATION: Targeting domain

<400> SEQUENCE: 311
uugagauagu gugggga 17

<210> SEQ ID NO 312
<211> LENGTH: 17
<212> TYPE: RNA
<213> ORGANISM: Artificial Sequence
<220> FEATURE:
<223> OTHER INFORMATION: Targeting domain

<400> SEQUENCE: 312
auaaauuaga gaaaaac 17

<210> SEQ ID NO 313
<211> LENGTH: 17
<212> TYPE: RNA
<213> ORGANISM: Artificial Sequence
<220> FEATURE:
<223> OTHER INFORMATION: Targeting domain

<400> SEQUENCE: 313
ccggccccug gccucac 17

<210> SEQ ID NO 314
<211> LENGTH: 17
<212> TYPE: RNA
<213> ORGANISM: Artificial Sequence
<220> FEATURE:
<223> OTHER INFORMATION: Targeting domain

<400> SEQUENCE: 314
agccagccgc cggcccc 17

<210> SEQ ID NO 315
<211> LENGTH: 17
<212> TYPE: RNA
<213> ORGANISM: Artificial Sequence
<220> FEATURE:

<223> OTHER INFORMATION: Targeting domain

<400> SEQUENCE: 315
cugucugaaa cgguccc                                                      17

<210> SEQ ID NO 316
<211> LENGTH: 17
<212> TYPE: RNA
<213> ORGANISM: Artificial Sequence
<220> FEATURE:
<223> OTHER INFORMATION: Targeting domain

<400> SEQUENCE: 316 augggguggag uuuagcc                                                     17

<210> SEQ ID NO 317
<211> LENGTH: 17
<212> TYPE: RNA
<213> ORGANISM: Artificial Sequence
<220> FEATURE:
<223> OTHER INFORMATION: Targeting domain

<400> SEQUENCE: 317
caucccuagc cagccgc                                                      17

<210> SEQ ID NO 318
<211> LENGTH: 17
<212> TYPE: RNA
<213> ORGANISM: Artificial Sequence
<220> FEATURE:
<223> OTHER INFORMATION: Targeting domain

<400> SEQUENCE: 318
auuggucaag gcaaggc                                                      17

<210> SEQ ID NO 319
<211> LENGTH: 17
<212> TYPE: RNA
<213> ORGANISM: Artificial Sequence
<220> FEATURE:
<223> OTHER INFORMATION: Targeting domain

<400> SEQUENCE: 319
ccagugaggc caggggc                                                      17

<210> SEQ ID NO 320
<211> LENGTH: 17
<212> TYPE: RNA
<213> ORGANISM: Artificial Sequence
<220> FEATURE:
<223> OTHER INFORMATION: Targeting domain

<400> SEQUENCE: 320
uuccacacac ucgcuuc                                                      17

<210> SEQ ID NO 321
<211> LENGTH: 17
<212> TYPE: RNA
<213> ORGANISM: Artificial Sequence
<220> FEATURE:
<223> OTHER INFORMATION: Targeting domain

<400> SEQUENCE: 321
cgcuucugga acgucug                                                      17

<210> SEQ ID NO 322
<211> LENGTH: 17
<212> TYPE: RNA
<213> ORGANISM: Artificial Sequence
<220> FEATURE:
<223> OTHER INFORMATION: Targeting domain

<400> SEQUENCE: 322
ucuuagagua uccagug 17

<210> SEQ ID NO 323
<211> LENGTH: 17
<212> TYPE: RNA
<213> ORGANISM: Artificial Sequence
<220> FEATURE:
<223> OTHER INFORMATION: Targeting domain

<400> SEQUENCE: 323
uuugcauuga gauagug 17

<210> SEQ ID NO 324
<211> LENGTH: 17
<212> TYPE: RNA
<213> ORGANISM: Artificial Sequence
<220> FEATURE:
<223> OTHER INFORMATION: Targeting domain

<400> SEQUENCE: 324
uuccagaagc gagugug 17

<210> SEQ ID NO 325
<211> LENGTH: 17
<212> TYPE: RNA
<213> ORGANISM: Artificial Sequence
<220> FEATURE:
<223> OTHER INFORMATION: Targeting domain

<400> SEQUENCE: 325
ugcauugaga uagugug 17

<210> SEQ ID NO 326
<211> LENGTH: 17
<212> TYPE: RNA
<213> ORGANISM: Artificial Sequence
<220> FEATURE:
<223> OTHER INFORMATION: Targeting domain

<400> SEQUENCE: 326
aaggcuggcc aacccau 17

<210> SEQ ID NO 327
<211> LENGTH: 17
<212> TYPE: RNA
<213> ORGANISM: Artificial Sequence
<220> FEATURE:
<223> OTHER INFORMATION: Targeting domain

<400> SEQUENCE: 327
ugccuuguca aggcuau 17

<210> SEQ ID NO 328
<211> LENGTH: 17
<212> TYPE: RNA
<213> ORGANISM: Artificial Sequence
<220> FEATURE:
<223> OTHER INFORMATION: Targeting domain

<400> SEQUENCE: 328
aaacuccacc caugggu 17

<210> SEQ ID NO 329
<211> LENGTH: 17
<212> TYPE: RNA
<213> ORGANISM: Artificial Sequence
<220> FEATURE:
<223> OTHER INFORMATION: Targeting domain

<400> SEQUENCE: 329
uugcauugag auagugu 17

<210> SEQ ID NO 330
<211> LENGTH: 20
<212> TYPE: RNA
<213> ORGANISM: Artificial Sequence
<220> FEATURE:
<223> OTHER INFORMATION: Targeting domain

<400> SEQUENCE: 330
augcaaauau cugucugaaa 20

<210> SEQ ID NO 331
<211> LENGTH: 20
<212> TYPE: RNA
<213> ORGANISM: Artificial Sequence
<220> FEATURE:
<223> OTHER INFORMATION: Targeting domain

<400> SEQUENCE: 331
acugaaucgg aacaaggcaa 20

<210> SEQ ID NO 332
<211> LENGTH: 20
<212> TYPE: RNA
<213> ORGANISM: Artificial Sequence
<220> FEATURE:
<223> OTHER INFORMATION: Targeting domain

<400> SEQUENCE: 332
cauugagaua guguggggaa 20

<210> SEQ ID NO 333
<211> LENGTH: 20
<212> TYPE: RNA
<213> ORGANISM: Artificial Sequence
<220> FEATURE:
<223> OTHER INFORMATION: Targeting domain

<400> SEQUENCE: 333
cuugaccaau agccuugaca 20

<210> SEQ ID NO 334
<211> LENGTH: 20
<212> TYPE: RNA
<213> ORGANISM: Artificial Sequence
<220> FEATURE:
<223> OTHER INFORMATION: Targeting domain

<400> SEQUENCE: 334
aggcaaggcu ggccaaccca 20

<210> SEQ ID NO 335
<211> LENGTH: 20

-continued

<212> TYPE: RNA
<213> ORGANISM: Artificial Sequence
<220> FEATURE:
<223> OTHER INFORMATION: Targeting domain

<400> SEQUENCE: 335
cccuggcuaa acuccaccca 20

<210> SEQ ID NO 336
<211> LENGTH: 20
<212> TYPE: RNA
<213> ORGANISM: Artificial Sequence
<220> FEATURE:
<223> OTHER INFORMATION: Targeting domain

<400> SEQUENCE: 336
ccaugggugg aguuuagcca 20

<210> SEQ ID NO 337
<211> LENGTH: 20
<212> TYPE: RNA
<213> ORGANISM: Artificial Sequence
<220> FEATURE:
<223> OTHER INFORMATION: Targeting domain

<400> SEQUENCE: 337
uagaguaucc agugaggcca 20

<210> SEQ ID NO 338
<211> LENGTH: 20
<212> TYPE: RNA
<213> ORGANISM: Artificial Sequence
<220> FEATURE:
<223> OTHER INFORMATION: Targeting domain

<400> SEQUENCE: 338
caaggcuauu ggucaaggca 20

<210> SEQ ID NO 339
<211> LENGTH: 20
<212> TYPE: RNA
<213> ORGANISM: Artificial Sequence
<220> FEATURE:
<223> OTHER INFORMATION: Targeting domain

<400> SEQUENCE: 339
cuugucaagg cuauugguca 20

<210> SEQ ID NO 340
<211> LENGTH: 20
<212> TYPE: RNA
<213> ORGANISM: Artificial Sequence
<220> FEATURE:
<223> OTHER INFORMATION: Targeting domain

<400> SEQUENCE: 340
uggucaaguu ugccuuguca 20

<210> SEQ ID NO 341
<211> LENGTH: 20
<212> TYPE: RNA
<213> ORGANISM: Artificial Sequence
<220> FEATURE:
<223> OTHER INFORMATION: Targeting domain

<400> SEQUENCE: 341
cgagugugug gaacugcuga 20

<210> SEQ ID NO 342
<211> LENGTH: 20
<212> TYPE: RNA
<213> ORGANISM: Artificial Sequence
<220> FEATURE:
<223> OTHER INFORMATION: Targeting domain

<400> SEQUENCE: 342
caggggccgg cggcuggcua 20

<210> SEQ ID NO 343
<211> LENGTH: 20
<212> TYPE: RNA
<213> ORGANISM: Artificial Sequence
<220> FEATURE:
<223> OTHER INFORMATION: Targeting domain

<400> SEQUENCE: 343
agaauaaauu agagaaaaac 20

<210> SEQ ID NO 344
<211> LENGTH: 20
<212> TYPE: RNA
<213> ORGANISM: Artificial Sequence
<220> FEATURE:
<223> OTHER INFORMATION: Targeting domain

<400> SEQUENCE: 344
ccgccggccc cuggccucac 20

<210> SEQ ID NO 345
<211> LENGTH: 20
<212> TYPE: RNA
<213> ORGANISM: Artificial Sequence
<220> FEATURE:
<223> OTHER INFORMATION: Targeting domain

<400> SEQUENCE: 345
ccuagccagc cgccggcccc 20

<210> SEQ ID NO 346
<211> LENGTH: 20
<212> TYPE: RNA
<213> ORGANISM: Artificial Sequence
<220> FEATURE:
<223> OTHER INFORMATION: Targeting domain

<400> SEQUENCE: 346
uaucugucug aaacgguccc 20

<210> SEQ ID NO 347
<211> LENGTH: 20
<212> TYPE: RNA
<213> ORGANISM: Artificial Sequence
<220> FEATURE:
<223> OTHER INFORMATION: Targeting domain

<400> SEQUENCE: 347
cccaugggug gaguuuagcc 20

<210> SEQ ID NO 348
<211> LENGTH: 20
<212> TYPE: RNA
<213> ORGANISM: Artificial Sequence
<220> FEATURE:
<223> OTHER INFORMATION: Targeting domain

<400> SEQUENCE: 348
uuagaguauc cagugaggcc 20

<210> SEQ ID NO 349
<211> LENGTH: 20
<212> TYPE: RNA
<213> ORGANISM: Artificial Sequence
<220> FEATURE:
<223> OTHER INFORMATION: Targeting domain

<400> SEQUENCE: 349
acggcugaca aaagaagucc 20

<210> SEQ ID NO 350
<211> LENGTH: 20
<212> TYPE: RNA
<213> ORGANISM: Artificial Sequence
<220> FEATURE:
<223> OTHER INFORMATION: Targeting domain

<400> SEQUENCE: 350
cuucaucccu agccagccgc 20

<210> SEQ ID NO 351
<211> LENGTH: 20
<212> TYPE: RNA
<213> ORGANISM: Artificial Sequence
<220> FEATURE:
<223> OTHER INFORMATION: Targeting domain

<400> SEQUENCE: 351
ugaggccagg ggccggcggc 20

<210> SEQ ID NO 352
<211> LENGTH: 20
<212> TYPE: RNA
<213> ORGANISM: Artificial Sequence
<220> FEATURE:
<223> OTHER INFORMATION: Targeting domain

<400> SEQUENCE: 352
uauccaguga ggccaggggc 20

<210> SEQ ID NO 353
<211> LENGTH: 20
<212> TYPE: RNA
<213> ORGANISM: Artificial Sequence
<220> FEATURE:
<223> OTHER INFORMATION: Targeting domain

<400> SEQUENCE: 353
caguuccaca cacucgcuuc 20

<210> SEQ ID NO 354
<211> LENGTH: 20
<212> TYPE: RNA
<213> ORGANISM: Artificial Sequence
<220> FEATURE:
<223> OTHER INFORMATION: Targeting domain

<400> SEQUENCE: 354
auugagauag uguggggaag 20

<210> SEQ ID NO 355
<211> LENGTH: 20
<212> TYPE: RNA
<213> ORGANISM: Artificial Sequence
<220> FEATURE:
<223> OTHER INFORMATION: Targeting domain

<400> SEQUENCE: 355
agaguaucca gugaggccag 20

<210> SEQ ID NO 356
<211> LENGTH: 20
<212> TYPE: RNA
<213> ORGANISM: Artificial Sequence
<220> FEATURE:
<223> OTHER INFORMATION: Targeting domain

<400> SEQUENCE: 356
ccagugaggc caggggccgg 20

<210> SEQ ID NO 357
<211> LENGTH: 20
<212> TYPE: RNA
<213> ORGANISM: Artificial Sequence
<220> FEATURE:
<223> OTHER INFORMATION: Targeting domain

<400> SEQUENCE: 357
aaggcuggcc aacccauggg 20

<210> SEQ ID NO 358
<211> LENGTH: 20
<212> TYPE: RNA
<213> ORGANISM: Artificial Sequence
<220> FEATURE:
<223> OTHER INFORMATION: Targeting domain

<400> SEQUENCE: 358
acucgcuucu ggaacgucug 20

<210> SEQ ID NO 359
<211> LENGTH: 20
<212> TYPE: RNA
<213> ORGANISM: Artificial Sequence
<220> FEATURE:
<223> OTHER INFORMATION: Targeting domain

<400> SEQUENCE: 359
uagucuuaga guauccagug 20

<210> SEQ ID NO 360
<211> LENGTH: 20
<212> TYPE: RNA
<213> ORGANISM: Artificial Sequence
<220> FEATURE:
<223> OTHER INFORMATION: Targeting domain

<400> SEQUENCE: 360
auauuugcau ugagauagug 20

<210> SEQ ID NO 361
<211> LENGTH: 20
<212> TYPE: RNA
<213> ORGANISM: Artificial Sequence
<220> FEATURE:
<223> OTHER INFORMATION: Targeting domain

<400> SEQUENCE: 361
acguuccaga agcgagugug 20

<210> SEQ ID NO 362
<211> LENGTH: 20
<212> TYPE: RNA
<213> ORGANISM: Artificial Sequence
<220> FEATURE:
<223> OTHER INFORMATION: Targeting domain

<400> SEQUENCE: 362
auuugcauug agauagugug 20

<210> SEQ ID NO 363
<211> LENGTH: 20
<212> TYPE: RNA
<213> ORGANISM: Artificial Sequence
<220> FEATURE:
<223> OTHER INFORMATION: Targeting domain

<400> SEQUENCE: 363
ccuggcuaaa cuccacccau 20

<210> SEQ ID NO 364
<211> LENGTH: 20
<212> TYPE: RNA
<213> ORGANISM: Artificial Sequence
<220> FEATURE:
<223> OTHER INFORMATION: Targeting domain

<400> SEQUENCE: 364
acuggauacu cuaagacuau 20

<210> SEQ ID NO 365
<211> LENGTH: 20
<212> TYPE: RNA
<213> ORGANISM: Artificial Sequence
<220> FEATURE:
<223> OTHER INFORMATION: Targeting domain

<400> SEQUENCE: 365
ccaggggccg gcggcuggcu 20

<210> SEQ ID NO 366
<211> LENGTH: 20
<212> TYPE: RNA
<213> ORGANISM: Artificial Sequence
<220> FEATURE:
<223> OTHER INFORMATION: Targeting domain

<400> SEQUENCE: 366
uauuugcauu gagauagugu 20

<210> SEQ ID NO 367
<211> LENGTH: 19
<212> TYPE: RNA
<213> ORGANISM: Artificial Sequence
<220> FEATURE:
<223> OTHER INFORMATION: Targeting domain

<400> SEQUENCE: 367
guuuccuucu cccaucaua 19

<210> SEQ ID NO 368

<211> LENGTH: 23
<212> TYPE: RNA
<213> ORGANISM: Artificial Sequence
<220> FEATURE:
<223> OTHER INFORMATION: Targeting domain

<400> SEQUENCE: 368
gcuaguuucc uucucccauc aua 23

<210> SEQ ID NO 369
<211> LENGTH: 19
<212> TYPE: RNA
<213> ORGANISM: Artificial Sequence
<220> FEATURE:
<223> OTHER INFORMATION: Targeting domain

<400> SEQUENCE: 369
gaauaaauua gagaaaaac 19

<210> SEQ ID NO 370
<211> LENGTH: 22
<212> TYPE: RNA
<213> ORGANISM: Artificial Sequence
<220> FEATURE:
<223> OTHER INFORMATION: Targeting domain

<400> SEQUENCE: 370
gaagaauaaa uuagagaaaa ac 22

<210> SEQ ID NO 371
<211> LENGTH: 23
<212> TYPE: RNA
<213> ORGANISM: Artificial Sequence
<220> FEATURE:
<223> OTHER INFORMATION: Targeting domain

<400> SEQUENCE: 371
ggaagaauaa auuagagaaa aac 23

<210> SEQ ID NO 372
<211> LENGTH: 24
<212> TYPE: RNA
<213> ORGANISM: Artificial Sequence
<220> FEATURE:
<223> OTHER INFORMATION: Targeting domain

<400> SEQUENCE: 372
gggaagaaua aauuagagaa aaac 24

<210> SEQ ID NO 373
<211> LENGTH: 20
<212> TYPE: RNA
<213> ORGANISM: Artificial Sequence
<220> FEATURE:
<223> OTHER INFORMATION: Targeting domain

<400> SEQUENCE: 373
gaaggaaacu agcuaaaggg 20

<210> SEQ ID NO 374
<211> LENGTH: 22
<212> TYPE: RNA
<213> ORGANISM: Artificial Sequence
<220> FEATURE:
<223> OTHER INFORMATION: Targeting domain

<400> SEQUENCE: 374

-continued gagaaggaaa cuagcuaaag gg 22

<210> SEQ ID NO 375
<211> LENGTH: 23
<212> TYPE: RNA
<213> ORGANISM: Artificial Sequence
<220> FEATURE:
<223> OTHER INFORMATION: Targeting domain

<400> SEQUENCE: 375
ggagaaggaa acuagcuaaa ggg 23

<210> SEQ ID NO 376
<211> LENGTH: 24
<212> TYPE: RNA
<213> ORGANISM: Artificial Sequence
<220> FEATURE:
<223> OTHER INFORMATION: Targeting domain

<400> SEQUENCE: 376
gggagaagga aacuagcuaa aggg 24

<210> SEQ ID NO 377
<211> LENGTH: 18
<212> TYPE: RNA
<213> ORGANISM: Artificial Sequence
<220> FEATURE:
<223> OTHER INFORMATION: Targeting domain

<400> SEQUENCE: 377
uuuccuucuc ccaucaua 18

<210> SEQ ID NO 378
<211> LENGTH: 20
<212> TYPE: RNA
<213> ORGANISM: Artificial Sequence
<220> FEATURE:
<223> OTHER INFORMATION: Targeting domain

<400> SEQUENCE: 378
aguuuccuuc ucccaucaua 20

<210> SEQ ID NO 379
<211> LENGTH: 21
<212> TYPE: RNA
<213> ORGANISM: Artificial Sequence
<220> FEATURE:
<223> OTHER INFORMATION: Targeting domain

<400> SEQUENCE: 379
uaguuuccuu cucccaucau a 21

<210> SEQ ID NO 380
<211> LENGTH: 22
<212> TYPE: RNA
<213> ORGANISM: Artificial Sequence
<220> FEATURE:
<223> OTHER INFORMATION: Targeting domain

<400> SEQUENCE: 380
cuaguuuccu ucucccauca ua 22

<210> SEQ ID NO 381
<211> LENGTH: 24
<212> TYPE: RNA

<213> ORGANISM: Artificial Sequence
<220> FEATURE:
<223> OTHER INFORMATION: Targeting domain

<400> SEQUENCE: 381
agcuaguuuc cuucucccau caua 24

<210> SEQ ID NO 382
<211> LENGTH: 18
<212> TYPE: RNA
<213> ORGANISM: Artificial Sequence
<220> FEATURE:
<223> OTHER INFORMATION: Targeting domain

<400> SEQUENCE: 382
agagaaaaac uggaauga 18

<210> SEQ ID NO 383
<211> LENGTH: 19
<212> TYPE: RNA
<213> ORGANISM: Artificial Sequence
<220> FEATURE:
<223> OTHER INFORMATION: Targeting domain

<400> SEQUENCE: 383
uagagaaaaa cuggaauga 19

<210> SEQ ID NO 384
<211> LENGTH: 20
<212> TYPE: RNA
<213> ORGANISM: Artificial Sequence
<220> FEATURE:
<223> OTHER INFORMATION: Targeting domain

<400> SEQUENCE: 384
uuagagaaaa acuggaauga 20

<210> SEQ ID NO 385
<211> LENGTH: 21
<212> TYPE: RNA
<213> ORGANISM: Artificial Sequence
<220> FEATURE:
<223> OTHER INFORMATION: Targeting domain

<400> SEQUENCE: 385
auuagagaaa aacuggaaug a 21

<210> SEQ ID NO 386
<211> LENGTH: 22
<212> TYPE: RNA
<213> ORGANISM: Artificial Sequence
<220> FEATURE:
<223> OTHER INFORMATION: Targeting domain

<400> SEQUENCE: 386
aauuagagaa aaacuggaau ga 22

<210> SEQ ID NO 387
<211> LENGTH: 23
<212> TYPE: RNA
<213> ORGANISM: Artificial Sequence
<220> FEATURE:
<223> OTHER INFORMATION: Targeting domain

<400> SEQUENCE: 387
aaauuagaga aaaacuggaa uga 23

<210> SEQ ID NO 388
<211> LENGTH: 24
<212> TYPE: RNA
<213> ORGANISM: Artificial Sequence
<220> FEATURE:
<223> OTHER INFORMATION: Targeting domain

<400> SEQUENCE: 388
uaaauuagag aaaaacugga auga 24

<210> SEQ ID NO 389
<211> LENGTH: 18
<212> TYPE: RNA
<213> ORGANISM: Artificial Sequence
<220> FEATURE:
<223> OTHER INFORMATION: Targeting domain

<400> SEQUENCE: 389
aauaaauuag agaaaaac 18

<210> SEQ ID NO 390
<211> LENGTH: 21
<212> TYPE: RNA
<213> ORGANISM: Artificial Sequence
<220> FEATURE:
<223> OTHER INFORMATION: Targeting domain

<400> SEQUENCE: 390
aagaauaaau uagagaaaaa c 21

<210> SEQ ID NO 391
<211> LENGTH: 18
<212> TYPE: RNA
<213> ORGANISM: Artificial Sequence
<220> FEATURE:
<223> OTHER INFORMATION: Targeting domain

<400> SEQUENCE: 391
aggaaacuag cuaaaggg 18

<210> SEQ ID NO 392
<211> LENGTH: 19
<212> TYPE: RNA
<213> ORGANISM: Artificial Sequence
<220> FEATURE:
<223> OTHER INFORMATION: Targeting domain

<400> SEQUENCE: 392
aaggaaacua gcuaaaggg 19

<210> SEQ ID NO 393
<211> LENGTH: 21
<212> TYPE: RNA
<213> ORGANISM: Artificial Sequence
<220> FEATURE:
<223> OTHER INFORMATION: Targeting domain

<400> SEQUENCE: 393
agaaggaaac uagcuaaagg g 21

<210> SEQ ID NO 394
<211> LENGTH: 18
<212> TYPE: RNA
<213> ORGANISM: Artificial Sequence
<220> FEATURE:

-continued

<223> OTHER INFORMATION: Targeting domain

<400> SEQUENCE: 394
uggggaaggg gcccccaa 18

<210> SEQ ID NO 395
<211> LENGTH: 19
<212> TYPE: RNA
<213> ORGANISM: Artificial Sequence
<220> FEATURE:
<223> OTHER INFORMATION: Targeting domain

<400> SEQUENCE: 395
guggggaagg ggcccccaa 19

<210> SEQ ID NO 396
<211> LENGTH: 20
<212> TYPE: RNA
<213> ORGANISM: Artificial Sequence
<220> FEATURE:
<223> OTHER INFORMATION: Targeting domain

<400> SEQUENCE: 396
uguggggaag gggcccccaa 20

<210> SEQ ID NO 397
<211> LENGTH: 21
<212> TYPE: RNA
<213> ORGANISM: Artificial Sequence
<220> FEATURE:
<223> OTHER INFORMATION: Targeting domain

<400> SEQUENCE: 397
guguggggaa ggggccccca a 21

<210> SEQ ID NO 398
<211> LENGTH: 22
<212> TYPE: RNA
<213> ORGANISM: Artificial Sequence
<220> FEATURE:
<223> OTHER INFORMATION: Targeting domain

<400> SEQUENCE: 398
agugugggga aggggccccc aa 22

<210> SEQ ID NO 399
<211> LENGTH: 23
<212> TYPE: RNA
<213> ORGANISM: Artificial Sequence
<220> FEATURE:
<223> OTHER INFORMATION: Targeting domain

<400> SEQUENCE: 399
uagugugggg aaggggcccc caa 23

<210> SEQ ID NO 400
<211> LENGTH: 24
<212> TYPE: RNA
<213> ORGANISM: Artificial Sequence
<220> FEATURE:
<223> OTHER INFORMATION: Targeting domain

<400> SEQUENCE: 400 auagugugg gaaggggccc ccaa 24

<210> SEQ ID NO 401
<211> LENGTH: 18
<212> TYPE: RNA
<213> ORGANISM: Artificial Sequence
<220> FEATURE:
<223> OTHER INFORMATION: Targeting domain

<400> SEQUENCE: 401
accucagacg uuccagaa 18

<210> SEQ ID NO 402
<211> LENGTH: 19
<212> TYPE: RNA
<213> ORGANISM: Artificial Sequence
<220> FEATURE:
<223> OTHER INFORMATION: Targeting domain

<400> SEQUENCE: 402
aaccucagac guuccagaa 19

<210> SEQ ID NO 403
<211> LENGTH: 20
<212> TYPE: RNA
<213> ORGANISM: Artificial Sequence
<220> FEATURE:
<223> OTHER INFORMATION: Targeting domain

<400> SEQUENCE: 403
uaaccucaga cguuccagaa 20

<210> SEQ ID NO 404
<211> LENGTH: 21
<212> TYPE: RNA
<213> ORGANISM: Artificial Sequence
<220> FEATURE:
<223> OTHER INFORMATION: Targeting domain

<400> SEQUENCE: 404
auaaccucag acguuccaga a 21

<210> SEQ ID NO 405
<211> LENGTH: 22
<212> TYPE: RNA
<213> ORGANISM: Artificial Sequence
<220> FEATURE:
<223> OTHER INFORMATION: Targeting domain

<400> SEQUENCE: 405
gauaaccuca gacguuccag aa 22

<210> SEQ ID NO 406
<211> LENGTH: 23
<212> TYPE: RNA
<213> ORGANISM: Artificial Sequence
<220> FEATURE:
<223> OTHER INFORMATION: Targeting domain

<400> SEQUENCE: 406
ugauaaccuc agacguucca gaa 23

<210> SEQ ID NO 407
<211> LENGTH: 24
<212> TYPE: RNA
<213> ORGANISM: Artificial Sequence
<220> FEATURE:
<223> OTHER INFORMATION: Targeting domain

<400> SEQUENCE: 407
uugauaaccu cagacguucc agaa 24

<210> SEQ ID NO 408
<211> LENGTH: 18
<212> TYPE: RNA
<213> ORGANISM: Artificial Sequence
<220> FEATURE:
<223> OTHER INFORMATION: Targeting domain

<400> SEQUENCE: 408
cgccggcccc uggccuca 18

<210> SEQ ID NO 409
<211> LENGTH: 19
<212> TYPE: RNA
<213> ORGANISM: Artificial Sequence
<220> FEATURE:
<223> OTHER INFORMATION: Targeting domain

<400> SEQUENCE: 409
ccgccggccc cuggccuca 19

<210> SEQ ID NO 410
<211> LENGTH: 20
<212> TYPE: RNA
<213> ORGANISM: Artificial Sequence
<220> FEATURE:
<223> OTHER INFORMATION: Targeting domain

<400> SEQUENCE: 410
gccgccggcc ccuggccuca 20

<210> SEQ ID NO 411
<211> LENGTH: 21
<212> TYPE: RNA
<213> ORGANISM: Artificial Sequence
<220> FEATURE:
<223> OTHER INFORMATION: Targeting domain

<400> SEQUENCE: 411
agccgccggc cccuggccuc a 21

<210> SEQ ID NO 412
<211> LENGTH: 22
<212> TYPE: RNA
<213> ORGANISM: Artificial Sequence
<220> FEATURE:
<223> OTHER INFORMATION: Targeting domain

<400> SEQUENCE: 412
cagccgccgg ccccuggccu ca 22

<210> SEQ ID NO 413
<211> LENGTH: 23
<212> TYPE: RNA
<213> ORGANISM: Artificial Sequence
<220> FEATURE:
<223> OTHER INFORMATION: Targeting domain

<400> SEQUENCE: 413
ccagccgccg gccccuggcc uca 23

<210> SEQ ID NO 414
<211> LENGTH: 24

<212> TYPE: RNA
<213> ORGANISM: Artificial Sequence
<220> FEATURE:
<223> OTHER INFORMATION: Targeting domain

<400> SEQUENCE: 414
gccagccgcc ggccccuggc cuca 24

<210> SEQ ID NO 415
<211> LENGTH: 18
<212> TYPE: RNA
<213> ORGANISM: Artificial Sequence
<220> FEATURE:
<223> OTHER INFORMATION: Targeting domain

<400> SEQUENCE: 415
ggcaaggcug gccaaccc 18

<210> SEQ ID NO 416
<211> LENGTH: 19
<212> TYPE: RNA
<213> ORGANISM: Artificial Sequence
<220> FEATURE:
<223> OTHER INFORMATION: Targeting domain

<400> SEQUENCE: 416
aggcaaggcu ggccaaccc 19

<210> SEQ ID NO 417
<211> LENGTH: 20
<212> TYPE: RNA
<213> ORGANISM: Artificial Sequence
<220> FEATURE:
<223> OTHER INFORMATION: Targeting domain

<400> SEQUENCE: 417
aaggcaaggc uggccaaccc 20

<210> SEQ ID NO 418
<211> LENGTH: 21
<212> TYPE: RNA
<213> ORGANISM: Artificial Sequence
<220> FEATURE:
<223> OTHER INFORMATION: Targeting domain

<400> SEQUENCE: 418
caaggcaagg cuggccaacc c 21

<210> SEQ ID NO 419
<211> LENGTH: 22
<212> TYPE: RNA
<213> ORGANISM: Artificial Sequence
<220> FEATURE:
<223> OTHER INFORMATION: Targeting domain

<400> SEQUENCE: 419
ucaaggcaag gcuggccaac cc 22

<210> SEQ ID NO 420
<211> LENGTH: 23
<212> TYPE: RNA
<213> ORGANISM: Artificial Sequence
<220> FEATURE:
<223> OTHER INFORMATION: Targeting domain

<400> SEQUENCE: 420
gucaaggcaa ggcuggccaa ccc 23

<210> SEQ ID NO 421
<211> LENGTH: 24
<212> TYPE: RNA
<213> ORGANISM: Artificial Sequence
<220> FEATURE:
<223> OTHER INFORMATION: Targeting domain

<400> SEQUENCE: 421
ggucaaggca aggcuggcca accc 24

<210> SEQ ID NO 422
<211> LENGTH: 18
<212> TYPE: RNA
<213> ORGANISM: Artificial Sequence
<220> FEATURE:
<223> OTHER INFORMATION: Targeting domain

<400> SEQUENCE: 422
ggcuggccaa cccauggg 18

<210> SEQ ID NO 423
<211> LENGTH: 19
<212> TYPE: RNA
<213> ORGANISM: Artificial Sequence
<220> FEATURE:
<223> OTHER INFORMATION: Targeting domain

<400> SEQUENCE: 423
aggcuggcca acccauggg 19

<210> SEQ ID NO 424
<211> LENGTH: 21
<212> TYPE: RNA
<213> ORGANISM: Artificial Sequence
<220> FEATURE:
<223> OTHER INFORMATION: Targeting domain

<400> SEQUENCE: 424
caaggcuggc caacccaugg g 21

<210> SEQ ID NO 425
<211> LENGTH: 22
<212> TYPE: RNA
<213> ORGANISM: Artificial Sequence
<220> FEATURE:
<223> OTHER INFORMATION: Targeting domain

<400> SEQUENCE: 425
gcaaggcugg ccaacccaug gg 22

<210> SEQ ID NO 426
<211> LENGTH: 23
<212> TYPE: RNA
<213> ORGANISM: Artificial Sequence
<220> FEATURE:
<223> OTHER INFORMATION: Targeting domain

<400> SEQUENCE: 426
ggcaaggcug gccaacccau ggg 23

<210> SEQ ID NO 427
<211> LENGTH: 24
<212> TYPE: RNA
<213> ORGANISM: Artificial Sequence
<220> FEATURE:
<223> OTHER INFORMATION: Targeting domain

<400> SEQUENCE: 427
aggcaaggcu ggccaaccca uggg 24

<210> SEQ ID NO 428
<211> LENGTH: 18
<212> TYPE: RNA
<213> ORGANISM: Artificial Sequence
<220> FEATURE:
<223> OTHER INFORMATION: Targeting domain

<400> SEQUENCE: 428
gagugugugg aacugcug 18

<210> SEQ ID NO 429
<211> LENGTH: 19
<212> TYPE: RNA
<213> ORGANISM: Artificial Sequence
<220> FEATURE:
<223> OTHER INFORMATION: Targeting domain

<400> SEQUENCE: 429
cgagugugug gaacugcug 19

<210> SEQ ID NO 430
<211> LENGTH: 20
<212> TYPE: RNA
<213> ORGANISM: Artificial Sequence
<220> FEATURE:
<223> OTHER INFORMATION: Targeting domain

<400> SEQUENCE: 430
gcgagugugu ggaacugcug 20

<210> SEQ ID NO 431
<211> LENGTH: 21
<212> TYPE: RNA
<213> ORGANISM: Artificial Sequence
<220> FEATURE:
<223> OTHER INFORMATION: Targeting domain

<400> SEQUENCE: 431
agcgagugug uggaacugcu g 21

<210> SEQ ID NO 432
<211> LENGTH: 22
<212> TYPE: RNA
<213> ORGANISM: Artificial Sequence
<220> FEATURE:
<223> OTHER INFORMATION: Targeting domain

<400> SEQUENCE: 432
aagcgagugu guggaacugc ug 22

<210> SEQ ID NO 433
<211> LENGTH: 23
<212> TYPE: RNA
<213> ORGANISM: Artificial Sequence
<220> FEATURE:
<223> OTHER INFORMATION: Targeting domain

<400> SEQUENCE: 433
gaagcgagug uguggaacug cug 23

<210> SEQ ID NO 434
<211> LENGTH: 24
<212> TYPE: RNA
<213> ORGANISM: Artificial Sequence
<220> FEATURE:
<223> OTHER INFORMATION: Targeting domain

<400> SEQUENCE: 434
agaagcgagu guguggaacu gcug 24

<210> SEQ ID NO 435
<211> LENGTH: 18
<212> TYPE: RNA
<213> ORGANISM: Artificial Sequence
<220> FEATURE:
<223> OTHER INFORMATION: Targeting domain

<400> SEQUENCE: 435
ccuggcuaaa cuccaccc 18

<210> SEQ ID NO 436
<211> LENGTH: 19
<212> TYPE: RNA
<213> ORGANISM: Artificial Sequence
<220> FEATURE:
<223> OTHER INFORMATION: Targeting domain

<400> SEQUENCE: 436
cccuggcuaa acuccaccc 19

<210> SEQ ID NO 437
<211> LENGTH: 20
<212> TYPE: RNA
<213> ORGANISM: Artificial Sequence
<220> FEATURE:
<223> OTHER INFORMATION: Targeting domain

<400> SEQUENCE: 437
ucccuggcua aacuccaccc 20

<210> SEQ ID NO 438
<211> LENGTH: 21
<212> TYPE: RNA
<213> ORGANISM: Artificial Sequence
<220> FEATURE:
<223> OTHER INFORMATION: Targeting domain

<400> SEQUENCE: 438
gucccuggcu aaacuccacc c 21

<210> SEQ ID NO 439
<211> LENGTH: 22
<212> TYPE: RNA
<213> ORGANISM: Artificial Sequence
<220> FEATURE:
<223> OTHER INFORMATION: Targeting domain

<400> SEQUENCE: 439
ggucccuggc uaaacuccac cc 22

<210> SEQ ID NO 440
<211> LENGTH: 23
<212> TYPE: RNA
<213> ORGANISM: Artificial Sequence
<220> FEATURE:
<223> OTHER INFORMATION: Targeting domain

<400> SEQUENCE: 440
cggucccugg cuaaacucca ccc 23

<210> SEQ ID NO 441
<211> LENGTH: 24
<212> TYPE: RNA
<213> ORGANISM: Artificial Sequence
<220> FEATURE:
<223> OTHER INFORMATION: Targeting domain

<400> SEQUENCE: 441
acggucccug gcuaaacucc accc 24

<210> SEQ ID NO 442
<211> LENGTH: 18
<212> TYPE: RNA
<213> ORGANISM: Artificial Sequence
<220> FEATURE:
<223> OTHER INFORMATION: Targeting domain

<400> SEQUENCE: 442
ggcggcuggc uagggaug 18

<210> SEQ ID NO 443
<211> LENGTH: 19
<212> TYPE: RNA
<213> ORGANISM: Artificial Sequence
<220> FEATURE:
<223> OTHER INFORMATION: Targeting domain

<400> SEQUENCE: 443
cggcggcugg cuagggaug 19

<210> SEQ ID NO 444
<211> LENGTH: 20
<212> TYPE: RNA
<213> ORGANISM: Artificial Sequence
<220> FEATURE:
<223> OTHER INFORMATION: Targeting domain

<400> SEQUENCE: 444
ccggcggcug gcuagggaug 20

<210> SEQ ID NO 445
<211> LENGTH: 21
<212> TYPE: RNA
<213> ORGANISM: Artificial Sequence
<220> FEATURE:
<223> OTHER INFORMATION: Targeting domain

<400> SEQUENCE: 445
gccggcggcu ggcuagggau g 21

<210> SEQ ID NO 446
<211> LENGTH: 22
<212> TYPE: RNA
<213> ORGANISM: Artificial Sequence
<220> FEATURE:
<223> OTHER INFORMATION: Targeting domain

<400> SEQUENCE: 446
ggccggcggc uggcuaggga ug 22

<210> SEQ ID NO 447

-continued

<211> LENGTH: 23
<212> TYPE: RNA
<213> ORGANISM: Artificial Sequence
<220> FEATURE:
<223> OTHER INFORMATION: Targeting domain

<400> SEQUENCE: 447
gggccggcgg cuggcuaggg aug 23

<210> SEQ ID NO 448
<211> LENGTH: 24
<212> TYPE: RNA
<213> ORGANISM: Artificial Sequence
<220> FEATURE:
<223> OTHER INFORMATION: Targeting domain

<400> SEQUENCE: 448
ggggccggcg gcuggcuagg gaug 24

<210> SEQ ID NO 449
<211> LENGTH: 18
<212> TYPE: RNA
<213> ORGANISM: Artificial Sequence
<220> FEATURE:
<223> OTHER INFORMATION: Targeting domain

<400> SEQUENCE: 449
aggggccggc ggcuggcu 18

<210> SEQ ID NO 450
<211> LENGTH: 19
<212> TYPE: RNA
<213> ORGANISM: Artificial Sequence
<220> FEATURE:
<223> OTHER INFORMATION: Targeting domain

<400> SEQUENCE: 450
caggggccgg cggcuggcu 19

<210> SEQ ID NO 451
<211> LENGTH: 21
<212> TYPE: RNA
<213> ORGANISM: Artificial Sequence
<220> FEATURE:
<223> OTHER INFORMATION: Targeting domain

<400> SEQUENCE: 451
gccaggggcc ggcggcuggc u 21

<210> SEQ ID NO 452
<211> LENGTH: 22
<212> TYPE: RNA
<213> ORGANISM: Artificial Sequence
<220> FEATURE:
<223> OTHER INFORMATION: Targeting domain

<400> SEQUENCE: 452
ggccaggggc cggcggcugg cu 22

<210> SEQ ID NO 453
<211> LENGTH: 23
<212> TYPE: RNA
<213> ORGANISM: Artificial Sequence
<220> FEATURE:
<223> OTHER INFORMATION: Targeting domain

<400> SEQUENCE: 453
aggccagggg ccggcggcug gcu 23

<210> SEQ ID NO 454
<211> LENGTH: 24
<212> TYPE: RNA
<213> ORGANISM: Artificial Sequence
<220> FEATURE:
<223> OTHER INFORMATION: Targeting domain

<400> SEQUENCE: 454
gaggccaggg gccggcggcu ggcu 24

<210> SEQ ID NO 455
<211> LENGTH: 18
<212> TYPE: RNA
<213> ORGANISM: Artificial Sequence
<220> FEATURE:
<223> OTHER INFORMATION: Targeting domain

<400> SEQUENCE: 455
aaacuugacc aauagucu 18

<210> SEQ ID NO 456
<211> LENGTH: 19
<212> TYPE: RNA
<213> ORGANISM: Artificial Sequence
<220> FEATURE:
<223> OTHER INFORMATION: Targeting domain

<400> SEQUENCE: 456
caaacuugac caauagucu 19

<210> SEQ ID NO 457
<211> LENGTH: 20
<212> TYPE: RNA
<213> ORGANISM: Artificial Sequence
<220> FEATURE:
<223> OTHER INFORMATION: Targeting domain

<400> SEQUENCE: 457
gcaaacuuga ccaauagucu 20

<210> SEQ ID NO 458
<211> LENGTH: 21
<212> TYPE: RNA
<213> ORGANISM: Artificial Sequence
<220> FEATURE:
<223> OTHER INFORMATION: Targeting domain

<400> SEQUENCE: 458
ggcaaacuug accaauaguc u 21

<210> SEQ ID NO 459
<211> LENGTH: 22
<212> TYPE: RNA
<213> ORGANISM: Artificial Sequence
<220> FEATURE:
<223> OTHER INFORMATION: Targeting domain

<400> SEQUENCE: 459
aggcaaacuu gaccaauagu cu 22

<210> SEQ ID NO 460
<211> LENGTH: 23
<212> TYPE: RNA

<213> ORGANISM: Artificial Sequence
<220> FEATURE:
<223> OTHER INFORMATION: Targeting domain

<400> SEQUENCE: 460
aaggcaaacu ugaccaauag ucu 23

<210> SEQ ID NO 461
<211> LENGTH: 24
<212> TYPE: RNA
<213> ORGANISM: Artificial Sequence
<220> FEATURE:
<223> OTHER INFORMATION: Targeting domain

<400> SEQUENCE: 461
caaggcaaac uugaccaaua gucu 24

<210> SEQ ID NO 462
<211> LENGTH: 18
<212> TYPE: RNA
<213> ORGANISM: Artificial Sequence
<220> FEATURE:
<223> OTHER INFORMATION: Targeting domain

<400> SEQUENCE: 462
uucagacaga uauuugca 18

<210> SEQ ID NO 463
<211> LENGTH: 19
<212> TYPE: RNA
<213> ORGANISM: Artificial Sequence
<220> FEATURE:
<223> OTHER INFORMATION: Targeting domain

<400> SEQUENCE: 463
uuucagacag auauuugca 19

<210> SEQ ID NO 464
<211> LENGTH: 20
<212> TYPE: RNA
<213> ORGANISM: Artificial Sequence
<220> FEATURE:
<223> OTHER INFORMATION: Targeting domain

<400> SEQUENCE: 464
guuucagaca gauauuugca 20

<210> SEQ ID NO 465
<211> LENGTH: 21
<212> TYPE: RNA
<213> ORGANISM: Artificial Sequence
<220> FEATURE:
<223> OTHER INFORMATION: Targeting domain

<400> SEQUENCE: 465
cguuucagac agauauuugc a 21

<210> SEQ ID NO 466
<211> LENGTH: 22
<212> TYPE: RNA
<213> ORGANISM: Artificial Sequence
<220> FEATURE:
<223> OTHER INFORMATION: Targeting domain

<400> SEQUENCE: 466
ccguuucaga cagauauuug ca 22

<210> SEQ ID NO 467
<211> LENGTH: 23
<212> TYPE: RNA
<213> ORGANISM: Artificial Sequence
<220> FEATURE:
<223> OTHER INFORMATION: Targeting domain

<400> SEQUENCE: 467
accguuucag acagauauuu gca 23

<210> SEQ ID NO 468
<211> LENGTH: 24
<212> TYPE: RNA
<213> ORGANISM: Artificial Sequence
<220> FEATURE:
<223> OTHER INFORMATION: Targeting domain

<400> SEQUENCE: 468
gaccguuuca gacagauauu ugca 24

<210> SEQ ID NO 469
<211> LENGTH: 18
<212> TYPE: RNA
<213> ORGANISM: Artificial Sequence
<220> FEATURE:
<223> OTHER INFORMATION: Targeting domain

<400> SEQUENCE: 469
aguuuccuuc ucccauca 18

<210> SEQ ID NO 470
<211> LENGTH: 19
<212> TYPE: RNA
<213> ORGANISM: Artificial Sequence
<220> FEATURE:
<223> OTHER INFORMATION: Targeting domain

<400> SEQUENCE: 470
uaguuuccuu cucccauca 19

<210> SEQ ID NO 471
<211> LENGTH: 20
<212> TYPE: RNA
<213> ORGANISM: Artificial Sequence
<220> FEATURE:
<223> OTHER INFORMATION: Targeting domain

<400> SEQUENCE: 471
cuaguuuccu ucucccauca 20

<210> SEQ ID NO 472
<211> LENGTH: 21
<212> TYPE: RNA
<213> ORGANISM: Artificial Sequence
<220> FEATURE:
<223> OTHER INFORMATION: Targeting domain

<400> SEQUENCE: 472
gcuaguuucc uucucccauc a 21

<210> SEQ ID NO 473
<211> LENGTH: 22
<212> TYPE: RNA
<213> ORGANISM: Artificial Sequence
<220> FEATURE:

-continued

<223> OTHER INFORMATION: Targeting domain

<400> SEQUENCE: 473
agcuaguuuc cuucucccau ca 22

<210> SEQ ID NO 474
<211> LENGTH: 23
<212> TYPE: RNA
<213> ORGANISM: Artificial Sequence
<220> FEATURE:
<223> OTHER INFORMATION: Targeting domain

<400> SEQUENCE: 474
uagcuaguuu ccuucuccca uca 23

<210> SEQ ID NO 475
<211> LENGTH: 24
<212> TYPE: RNA
<213> ORGANISM: Artificial Sequence
<220> FEATURE:
<223> OTHER INFORMATION: Targeting domain

<400> SEQUENCE: 475
uuagcuaguu uccuucuccc auca 24

<210> SEQ ID NO 476
<211> LENGTH: 18
<212> TYPE: RNA
<213> ORGANISM: Artificial Sequence
<220> FEATURE:
<223> OTHER INFORMATION: Targeting domain

<400> SEQUENCE: 476
auugagauag ugugggga 18

<210> SEQ ID NO 477
<211> LENGTH: 19
<212> TYPE: RNA
<213> ORGANISM: Artificial Sequence
<220> FEATURE:
<223> OTHER INFORMATION: Targeting domain

<400> SEQUENCE: 477
cauugagaua gugugggga 19

<210> SEQ ID NO 478
<211> LENGTH: 21
<212> TYPE: RNA
<213> ORGANISM: Artificial Sequence
<220> FEATURE:
<223> OTHER INFORMATION: Targeting domain

<400> SEQUENCE: 478
ugcauugaga uagugugggg a 21

<210> SEQ ID NO 479
<211> LENGTH: 22
<212> TYPE: RNA
<213> ORGANISM: Artificial Sequence
<220> FEATURE:
<223> OTHER INFORMATION: Targeting domain

<400> SEQUENCE: 479
uugcauugag auagugugggg ga 22

<210> SEQ ID NO 480
<211> LENGTH: 23
<212> TYPE: RNA
<213> ORGANISM: Artificial Sequence
<220> FEATURE:
<223> OTHER INFORMATION: Targeting domain

<400> SEQUENCE: 480
uuugcauuga gauagugugg gga 23

<210> SEQ ID NO 481
<211> LENGTH: 24
<212> TYPE: RNA
<213> ORGANISM: Artificial Sequence
<220> FEATURE:
<223> OTHER INFORMATION: Targeting domain

<400> SEQUENCE: 481
auuugcauug agauagugug ggga 24

<210> SEQ ID NO 482
<211> LENGTH: 18
<212> TYPE: RNA
<213> ORGANISM: Artificial Sequence
<220> FEATURE:
<223> OTHER INFORMATION: Targeting domain

<400> SEQUENCE: 482
ucccaucaua gaggauac 18

<210> SEQ ID NO 483
<211> LENGTH: 19
<212> TYPE: RNA
<213> ORGANISM: Artificial Sequence
<220> FEATURE:
<223> OTHER INFORMATION: Targeting domain

<400> SEQUENCE: 483
cucccaucau agaggauac 19

<210> SEQ ID NO 484
<211> LENGTH: 20
<212> TYPE: RNA
<213> ORGANISM: Artificial Sequence
<220> FEATURE:
<223> OTHER INFORMATION: Targeting domain

<400> SEQUENCE: 484
ucucccauca uagaggauac 20

<210> SEQ ID NO 485
<211> LENGTH: 21
<212> TYPE: RNA
<213> ORGANISM: Artificial Sequence
<220> FEATURE:
<223> OTHER INFORMATION: Targeting domain

<400> SEQUENCE: 485
uucucccauc auagaggaua c 21

<210> SEQ ID NO 486
<211> LENGTH: 22
<212> TYPE: RNA
<213> ORGANISM: Artificial Sequence
<220> FEATURE:
<223> OTHER INFORMATION: Targeting domain

```
<400> SEQUENCE: 486

cuucucccau cauagaggau ac                                          22

<210> SEQ ID NO 487
<211> LENGTH: 23
<212> TYPE: RNA
<213> ORGANISM: Artificial Sequence
<220> FEATURE:
<223> OTHER INFORMATION: Targeting domain

<400> SEQUENCE: 487

ccuucuccca ucauagagga uac                                         23

<210> SEQ ID NO 488
<211> LENGTH: 24
<212> TYPE: RNA
<213> ORGANISM: Artificial Sequence
<220> FEATURE:
<223> OTHER INFORMATION: Targeting domain

<400> SEQUENCE: 488

uccuucuccc aucauagagg auac                                        24

<210> SEQ ID NO 489
<211> LENGTH: 18
<212> TYPE: RNA
<213> ORGANISM: Artificial Sequence
<220> FEATURE:
<223> OTHER INFORMATION: Targeting domain

<400> SEQUENCE: 489

uguggggaag gggccccc                                               18

<210> SEQ ID NO 490
<211> LENGTH: 19
<212> TYPE: RNA
<213> ORGANISM: Artificial Sequence
<220> FEATURE:
<223> OTHER INFORMATION: Targeting domain

<400> SEQUENCE: 490

guguggggaa ggggccccc                                              19

<210> SEQ ID NO 491
<211> LENGTH: 20
<212> TYPE: RNA
<213> ORGANISM: Artificial Sequence
<220> FEATURE:
<223> OTHER INFORMATION: Targeting domain

<400> SEQUENCE: 491

agugugggga aggggccccc                                             20

<210> SEQ ID NO 492
<211> LENGTH: 21
<212> TYPE: RNA
<213> ORGANISM: Artificial Sequence
<220> FEATURE:
<223> OTHER INFORMATION: Targeting domain

<400> SEQUENCE: 492

uagugugggg aaggggcccc c                                           21

<210> SEQ ID NO 493
<211> LENGTH: 22
```

<212> TYPE: RNA
<213> ORGANISM: Artificial Sequence
<220> FEATURE:
<223> OTHER INFORMATION: Targeting domain

<400> SEQUENCE: 493
auaguguggg gaaggggccc cc 22

<210> SEQ ID NO 494
<211> LENGTH: 23
<212> TYPE: RNA
<213> ORGANISM: Artificial Sequence
<220> FEATURE:
<223> OTHER INFORMATION: Targeting domain

<400> SEQUENCE: 494
gauagugugg ggaaggggcc ccc 23

<210> SEQ ID NO 495
<211> LENGTH: 24
<212> TYPE: RNA
<213> ORGANISM: Artificial Sequence
<220> FEATURE:
<223> OTHER INFORMATION: Targeting domain

<400> SEQUENCE: 495
agauagugug gggaaggggc cccc 24

<210> SEQ ID NO 496
<211> LENGTH: 18
<212> TYPE: RNA
<213> ORGANISM: Artificial Sequence
<220> FEATURE:
<223> OTHER INFORMATION: Targeting domain

<400> SEQUENCE: 496
caugggugga guuuagcc 18

<210> SEQ ID NO 497
<211> LENGTH: 19
<212> TYPE: RNA
<213> ORGANISM: Artificial Sequence
<220> FEATURE:
<223> OTHER INFORMATION: Targeting domain

<400> SEQUENCE: 497 ccauggguggg aguuuagcc 19

<210> SEQ ID NO 498
<211> LENGTH: 21
<212> TYPE: RNA
<213> ORGANISM: Artificial Sequence
<220> FEATURE:
<223> OTHER INFORMATION: Targeting domain

<400> SEQUENCE: 498
acccaugggu ggaguuuagc c 21

<210> SEQ ID NO 499
<211> LENGTH: 22
<212> TYPE: RNA
<213> ORGANISM: Artificial Sequence
<220> FEATURE:
<223> OTHER INFORMATION: Targeting domain

<400> SEQUENCE: 499
aacccauggg uggaguuuag cc 22

<210> SEQ ID NO 500
<211> LENGTH: 23
<212> TYPE: RNA
<213> ORGANISM: Artificial Sequence
<220> FEATURE:
<223> OTHER INFORMATION: Targeting domain

<400> SEQUENCE: 500
caacccaugg guggaguuua gcc 23

<210> SEQ ID NO 501
<211> LENGTH: 24
<212> TYPE: RNA
<213> ORGANISM: Artificial Sequence
<220> FEATURE:
<223> OTHER INFORMATION: Targeting domain

<400> SEQUENCE: 501
ccaacccaug gguggaguuu agcc 24

<210> SEQ ID NO 502
<211> LENGTH: 18
<212> TYPE: RNA
<213> ORGANISM: Artificial Sequence
<220> FEATURE:
<223> OTHER INFORMATION: Targeting domain

<400> SEQUENCE: 502
ccaugggugg aguuuagc 18

<210> SEQ ID NO 503
<211> LENGTH: 19
<212> TYPE: RNA
<213> ORGANISM: Artificial Sequence
<220> FEATURE:
<223> OTHER INFORMATION: Targeting domain

<400> SEQUENCE: 503
cccaugggug gaguuuagc 19

<210> SEQ ID NO 504
<211> LENGTH: 20
<212> TYPE: RNA
<213> ORGANISM: Artificial Sequence
<220> FEATURE:
<223> OTHER INFORMATION: Targeting domain

<400> SEQUENCE: 504
acccaugggu ggaguuuagc 20

<210> SEQ ID NO 505
<211> LENGTH: 21
<212> TYPE: RNA
<213> ORGANISM: Artificial Sequence
<220> FEATURE:
<223> OTHER INFORMATION: Targeting domain

<400> SEQUENCE: 505
aacccauggg uggaguuuag c 21

<210> SEQ ID NO 506
<211> LENGTH: 22
<212> TYPE: RNA
<213> ORGANISM: Artificial Sequence
<220> FEATURE:
<223> OTHER INFORMATION: Targeting domain

<400> SEQUENCE: 506
caacccaugg guggaguuua gc 22

<210> SEQ ID NO 507
<211> LENGTH: 23
<212> TYPE: RNA
<213> ORGANISM: Artificial Sequence
<220> FEATURE:
<223> OTHER INFORMATION: Targeting domain

<400> SEQUENCE: 507
ccaacccaug gguggaguuu agc 23

<210> SEQ ID NO 508
<211> LENGTH: 24
<212> TYPE: RNA
<213> ORGANISM: Artificial Sequence
<220> FEATURE:
<223> OTHER INFORMATION: Targeting domain

<400> SEQUENCE: 508
gccaacccau ggguggaguu uagc 24

<210> SEQ ID NO 509
<211> LENGTH: 18
<212> TYPE: RNA
<213> ORGANISM: Artificial Sequence
<220> FEATURE:
<223> OTHER INFORMATION: Targeting domain

<400> SEQUENCE: 509
ugauaaccuc agacguuc 18

<210> SEQ ID NO 510
<211> LENGTH: 19
<212> TYPE: RNA
<213> ORGANISM: Artificial Sequence
<220> FEATURE:
<223> OTHER INFORMATION: Targeting domain

<400> SEQUENCE: 510
uugauaaccu cagacguuc 19

<210> SEQ ID NO 511
<211> LENGTH: 20
<212> TYPE: RNA
<213> ORGANISM: Artificial Sequence
<220> FEATURE:
<223> OTHER INFORMATION: Targeting domain

<400> SEQUENCE: 511
auugauaacc ucagacguuc 20

<210> SEQ ID NO 512
<211> LENGTH: 21
<212> TYPE: RNA
<213> ORGANISM: Artificial Sequence
<220> FEATURE:
<223> OTHER INFORMATION: Targeting domain

<400> SEQUENCE: 512
uauugauaac cucagacguu c 21

<210> SEQ ID NO 513
<211> LENGTH: 22
<212> TYPE: RNA
<213> ORGANISM: Artificial Sequence
<220> FEATURE:
<223> OTHER INFORMATION: Targeting domain

<400> SEQUENCE: 513
uuauugauaa ccucagacgu uc 22

<210> SEQ ID NO 514
<211> LENGTH: 23
<212> TYPE: RNA
<213> ORGANISM: Artificial Sequence
<220> FEATURE:
<223> OTHER INFORMATION: Targeting domain

<400> SEQUENCE: 514
cuuauugaua accucagacg uuc 23

<210> SEQ ID NO 515
<211> LENGTH: 24
<212> TYPE: RNA
<213> ORGANISM: Artificial Sequence
<220> FEATURE:
<223> OTHER INFORMATION: Targeting domain

<400> SEQUENCE: 515
gcuuauugau aaccucagac guuc 24

<210> SEQ ID NO 516
<211> LENGTH: 18
<212> TYPE: RNA
<213> ORGANISM: Artificial Sequence
<220> FEATURE:
<223> OTHER INFORMATION: Targeting domain

<400> SEQUENCE: 516
cauugagaua gugugggg 18

<210> SEQ ID NO 517
<211> LENGTH: 19
<212> TYPE: RNA
<213> ORGANISM: Artificial Sequence
<220> FEATURE:
<223> OTHER INFORMATION: Targeting domain

<400> SEQUENCE: 517
gcauugagau agugugggg 19

<210> SEQ ID NO 518
<211> LENGTH: 20
<212> TYPE: RNA
<213> ORGANISM: Artificial Sequence
<220> FEATURE:
<223> OTHER INFORMATION: Targeting domain

<400> SEQUENCE: 518
ugcauugaga uagugugggg 20

<210> SEQ ID NO 519
<211> LENGTH: 21
<212> TYPE: RNA
<213> ORGANISM: Artificial Sequence
<220> FEATURE:
<223> OTHER INFORMATION: Targeting domain

<400> SEQUENCE: 519
uugcauugag auagugug gg g 21

<210> SEQ ID NO 520
<211> LENGTH: 22
<212> TYPE: RNA
<213> ORGANISM: Artificial Sequence
<220> FEATURE:
<223> OTHER INFORMATION: Targeting domain

<400> SEQUENCE: 520
uuugcauuga gauagugugg gg 22

<210> SEQ ID NO 521
<211> LENGTH: 23
<212> TYPE: RNA
<213> ORGANISM: Artificial Sequence
<220> FEATURE:
<223> OTHER INFORMATION: Targeting domain

<400> SEQUENCE: 521
auuugcauug agauagugug ggg 23

<210> SEQ ID NO 522
<211> LENGTH: 24
<212> TYPE: RNA
<213> ORGANISM: Artificial Sequence
<220> FEATURE:
<223> OTHER INFORMATION: Targeting domain

<400> SEQUENCE: 522
uauuugcauu gagauagugu gggg 24

<210> SEQ ID NO 523
<211> LENGTH: 18
<212> TYPE: RNA
<213> ORGANISM: Artificial Sequence
<220> FEATURE:
<223> OTHER INFORMATION: Targeting domain

<400> SEQUENCE: 523
aggcuggcca acccaugg 18

<210> SEQ ID NO 524
<211> LENGTH: 19
<212> TYPE: RNA
<213> ORGANISM: Artificial Sequence
<220> FEATURE:
<223> OTHER INFORMATION: Targeting domain

<400> SEQUENCE: 524
aaggcuggcc aacccaugg 19

<210> SEQ ID NO 525
<211> LENGTH: 20
<212> TYPE: RNA
<213> ORGANISM: Artificial Sequence
<220> FEATURE:
<223> OTHER INFORMATION: Targeting domain

<400> SEQUENCE: 525
caaggcuggc caacccaugg 20

<210> SEQ ID NO 526

<211> LENGTH: 21
<212> TYPE: RNA
<213> ORGANISM: Artificial Sequence
<220> FEATURE:
<223> OTHER INFORMATION: Targeting domain

<400> SEQUENCE: 526
gcaaggcugg ccaacccaug g 21

<210> SEQ ID NO 527
<211> LENGTH: 22
<212> TYPE: RNA
<213> ORGANISM: Artificial Sequence
<220> FEATURE:
<223> OTHER INFORMATION: Targeting domain

<400> SEQUENCE: 527
ggcaaggcug gccaacccau gg 22

<210> SEQ ID NO 528
<211> LENGTH: 23
<212> TYPE: RNA
<213> ORGANISM: Artificial Sequence
<220> FEATURE:
<223> OTHER INFORMATION: Targeting domain

<400> SEQUENCE: 528
aggcaaggcu ggccaaccca ugg 23

<210> SEQ ID NO 529
<211> LENGTH: 24
<212> TYPE: RNA
<213> ORGANISM: Artificial Sequence
<220> FEATURE:
<223> OTHER INFORMATION: Targeting domain

<400> SEQUENCE: 529
aaggcaaggc uggccaaccc augg 24

<210> SEQ ID NO 530
<211> LENGTH: 18
<212> TYPE: RNA
<213> ORGANISM: Artificial Sequence
<220> FEATURE:
<223> OTHER INFORMATION: Targeting domain

<400> SEQUENCE: 530
agcgagugug uggaacug 18

<210> SEQ ID NO 531
<211> LENGTH: 19
<212> TYPE: RNA
<213> ORGANISM: Artificial Sequence
<220> FEATURE:
<223> OTHER INFORMATION: Targeting domain

<400> SEQUENCE: 531
aagcgagugu guggaacug 19

<210> SEQ ID NO 532
<211> LENGTH: 20
<212> TYPE: RNA
<213> ORGANISM: Artificial Sequence
<220> FEATURE:
<223> OTHER INFORMATION: Targeting domain

<400> SEQUENCE: 532
gaagcgagug uguggaacug                                              20

<210> SEQ ID NO 533
<211> LENGTH: 21
<212> TYPE: RNA
<213> ORGANISM: Artificial Sequence
<220> FEATURE:
<223> OTHER INFORMATION: Targeting domain

<400> SEQUENCE: 533
agaagcgagu guguggaacu g                                            21

<210> SEQ ID NO 534
<211> LENGTH: 22
<212> TYPE: RNA
<213> ORGANISM: Artificial Sequence
<220> FEATURE:
<223> OTHER INFORMATION: Targeting domain

<400> SEQUENCE: 534
cagaagcgag uguguggaac ug                                           22

<210> SEQ ID NO 535
<211> LENGTH: 23
<212> TYPE: RNA
<213> ORGANISM: Artificial Sequence
<220> FEATURE:
<223> OTHER INFORMATION: Targeting domain

<400> SEQUENCE: 535
ccagaagcga guguguggaa cug                                          23

<210> SEQ ID NO 536
<211> LENGTH: 24
<212> TYPE: RNA
<213> ORGANISM: Artificial Sequence
<220> FEATURE:
<223> OTHER INFORMATION: Targeting domain

<400> SEQUENCE: 536
uccagaagcg agugugugga acug                                         24

<210> SEQ ID NO 537
<211> LENGTH: 18
<212> TYPE: RNA
<213> ORGANISM: Artificial Sequence
<220> FEATURE:
<223> OTHER INFORMATION: Targeting domain

<400> SEQUENCE: 537
auuugcauug agauagug                                                18

<210> SEQ ID NO 538
<211> LENGTH: 19
<212> TYPE: RNA
<213> ORGANISM: Artificial Sequence
<220> FEATURE:
<223> OTHER INFORMATION: Targeting domain

<400> SEQUENCE: 538
uauuugcauu gagauagug                                               19

<210> SEQ ID NO 539
<211> LENGTH: 21
<212> TYPE: RNA

<213> ORGANISM: Artificial Sequence
<220> FEATURE:
<223> OTHER INFORMATION: Targeting domain

<400> SEQUENCE: 539
gauauuugca uugagauagu g 21

<210> SEQ ID NO 540
<211> LENGTH: 22
<212> TYPE: RNA
<213> ORGANISM: Artificial Sequence
<220> FEATURE:
<223> OTHER INFORMATION: Targeting domain

<400> SEQUENCE: 540
agauauuugc auugagauag ug 22

<210> SEQ ID NO 541
<211> LENGTH: 23
<212> TYPE: RNA
<213> ORGANISM: Artificial Sequence
<220> FEATURE:
<223> OTHER INFORMATION: Targeting domain

<400> SEQUENCE: 541
cagauauuug cauugagaua gug 23

<210> SEQ ID NO 542
<211> LENGTH: 24
<212> TYPE: RNA
<213> ORGANISM: Artificial Sequence
<220> FEATURE:
<223> OTHER INFORMATION: Targeting domain

<400> SEQUENCE: 542
acagauauuu gcauugagau agug 24

<210> SEQ ID NO 543
<211> LENGTH: 18
<212> TYPE: RNA
<213> ORGANISM: Artificial Sequence
<220> FEATURE:
<223> OTHER INFORMATION: Targeting domain

<400> SEQUENCE: 543
guuccagaag cgagugug 18

<210> SEQ ID NO 544
<211> LENGTH: 19
<212> TYPE: RNA
<213> ORGANISM: Artificial Sequence
<220> FEATURE:
<223> OTHER INFORMATION: Targeting domain

<400> SEQUENCE: 544
cguuccagaa gcgagugug 19

<210> SEQ ID NO 545
<211> LENGTH: 21
<212> TYPE: RNA
<213> ORGANISM: Artificial Sequence
<220> FEATURE:
<223> OTHER INFORMATION: Targeting domain

<400> SEQUENCE: 545
gacguuccag aagcgagugu g 21

<210> SEQ ID NO 546
<211> LENGTH: 22
<212> TYPE: RNA
<213> ORGANISM: Artificial Sequence
<220> FEATURE:
<223> OTHER INFORMATION: Targeting domain

<400> SEQUENCE: 546
agacguucca gaagcgagug ug 22

<210> SEQ ID NO 547
<211> LENGTH: 23
<212> TYPE: RNA
<213> ORGANISM: Artificial Sequence
<220> FEATURE:
<223> OTHER INFORMATION: Targeting domain

<400> SEQUENCE: 547
cagacguucc agaagcgagu gug 23

<210> SEQ ID NO 548
<211> LENGTH: 24
<212> TYPE: RNA
<213> ORGANISM: Artificial Sequence
<220> FEATURE:
<223> OTHER INFORMATION: Targeting domain

<400> SEQUENCE: 548
ucagacguuc cagaagcgag ugug 24

<210> SEQ ID NO 549
<211> LENGTH: 18
<212> TYPE: RNA
<213> ORGANISM: Artificial Sequence
<220> FEATURE:
<223> OTHER INFORMATION: Targeting domain

<400> SEQUENCE: 549
uugcauugag auagugug 18

<210> SEQ ID NO 550
<211> LENGTH: 19
<212> TYPE: RNA
<213> ORGANISM: Artificial Sequence
<220> FEATURE:
<223> OTHER INFORMATION: Targeting domain

<400> SEQUENCE: 550
uuugcauuga gauagugug 19

<210> SEQ ID NO 551
<211> LENGTH: 21
<212> TYPE: RNA
<213> ORGANISM: Artificial Sequence
<220> FEATURE:
<223> OTHER INFORMATION: Targeting domain

<400> SEQUENCE: 551
uauuugcauu gagauagugu g 21

<210> SEQ ID NO 552
<211> LENGTH: 22
<212> TYPE: RNA
<213> ORGANISM: Artificial Sequence
<220> FEATURE:

<223> OTHER INFORMATION: Targeting domain

<400> SEQUENCE: 552
auauuugcau ugagauagug ug 22

<210> SEQ ID NO 553
<211> LENGTH: 23
<212> TYPE: RNA
<213> ORGANISM: Artificial Sequence
<220> FEATURE:
<223> OTHER INFORMATION: Targeting domain

<400> SEQUENCE: 553
gauauuugca uugagauagu gug 23

<210> SEQ ID NO 554
<211> LENGTH: 24
<212> TYPE: RNA
<213> ORGANISM: Artificial Sequence
<220> FEATURE:
<223> OTHER INFORMATION: Targeting domain

<400> SEQUENCE: 554
agauauuugc auugagauag ugug 24

<210> SEQ ID NO 555
<211> LENGTH: 18
<212> TYPE: RNA
<213> ORGANISM: Artificial Sequence
<220> FEATURE:
<223> OTHER INFORMATION: Targeting domain

<400> SEQUENCE: 555
uauuugcauu gagauagu 18

<210> SEQ ID NO 556
<211> LENGTH: 19
<212> TYPE: RNA
<213> ORGANISM: Artificial Sequence
<220> FEATURE:
<223> OTHER INFORMATION: Targeting domain

<400> SEQUENCE: 556
auauuugcau ugagauagu 19

<210> SEQ ID NO 557
<211> LENGTH: 20
<212> TYPE: RNA
<213> ORGANISM: Artificial Sequence
<220> FEATURE:
<223> OTHER INFORMATION: Targeting domain

<400> SEQUENCE: 557
gauauuugca uugagauagu 20

<210> SEQ ID NO 558
<211> LENGTH: 21
<212> TYPE: RNA
<213> ORGANISM: Artificial Sequence
<220> FEATURE:
<223> OTHER INFORMATION: Targeting domain

<400> SEQUENCE: 558
agauauuugc auugagauag u 21

<210> SEQ ID NO 559
<211> LENGTH: 22
<212> TYPE: RNA
<213> ORGANISM: Artificial Sequence
<220> FEATURE:
<223> OTHER INFORMATION: Targeting domain

<400> SEQUENCE: 559
cagauauuug cauugagaua gu 22

<210> SEQ ID NO 560
<211> LENGTH: 23
<212> TYPE: RNA
<213> ORGANISM: Artificial Sequence
<220> FEATURE:
<223> OTHER INFORMATION: Targeting domain

<400> SEQUENCE: 560
acagauauuu gcauugagau agu 23

<210> SEQ ID NO 561
<211> LENGTH: 24
<212> TYPE: RNA
<213> ORGANISM: Artificial Sequence
<220> FEATURE:
<223> OTHER INFORMATION: Targeting domain

<400> SEQUENCE: 561
gacagauauu ugcauugaga uagu 24

<210> SEQ ID NO 562
<211> LENGTH: 18
<212> TYPE: RNA
<213> ORGANISM: Artificial Sequence
<220> FEATURE:
<223> OTHER INFORMATION: Targeting domain

<400> SEQUENCE: 562
cguuccagaa gcgagugu 18

<210> SEQ ID NO 563
<211> LENGTH: 19
<212> TYPE: RNA
<213> ORGANISM: Artificial Sequence
<220> FEATURE:
<223> OTHER INFORMATION: Targeting domain

<400> SEQUENCE: 563
acguuccaga agcgagugu 19

<210> SEQ ID NO 564
<211> LENGTH: 20
<212> TYPE: RNA
<213> ORGANISM: Artificial Sequence
<220> FEATURE:
<223> OTHER INFORMATION: Targeting domain

<400> SEQUENCE: 564
gacguuccag aagcgagugu 20

<210> SEQ ID NO 565
<211> LENGTH: 21
<212> TYPE: RNA
<213> ORGANISM: Artificial Sequence
<220> FEATURE:
<223> OTHER INFORMATION: Targeting domain -continued

<400> SEQUENCE: 565
agacguucca gaagcgagug u 21

<210> SEQ ID NO 566
<211> LENGTH: 22
<212> TYPE: RNA
<213> ORGANISM: Artificial Sequence
<220> FEATURE:
<223> OTHER INFORMATION: Targeting domain

<400> SEQUENCE: 566
cagacguucc agaagcgagu gu 22

<210> SEQ ID NO 567
<211> LENGTH: 23
<212> TYPE: RNA
<213> ORGANISM: Artificial Sequence
<220> FEATURE:
<223> OTHER INFORMATION: Targeting domain

<400> SEQUENCE: 567
ucagacguuc cagaagcgag ugu 23

<210> SEQ ID NO 568
<211> LENGTH: 24
<212> TYPE: RNA
<213> ORGANISM: Artificial Sequence
<220> FEATURE:
<223> OTHER INFORMATION: Targeting domain

<400> SEQUENCE: 568
cucagacguu ccagaagcga gugu 24

<210> SEQ ID NO 569
<211> LENGTH: 18
<212> TYPE: RNA
<213> ORGANISM: Artificial Sequence
<220> FEATURE:
<223> OTHER INFORMATION: Targeting domain

<400> SEQUENCE: 569
uuugcauuga gauagugu 18

<210> SEQ ID NO 570
<211> LENGTH: 19
<212> TYPE: RNA
<213> ORGANISM: Artificial Sequence
<220> FEATURE:
<223> OTHER INFORMATION: Targeting domain

<400> SEQUENCE: 570
auuugcauug agauagugu 19

<210> SEQ ID NO 571
<211> LENGTH: 21
<212> TYPE: RNA
<213> ORGANISM: Artificial Sequence
<220> FEATURE:
<223> OTHER INFORMATION: Targeting domain

<400> SEQUENCE: 571
auauuugcau ugagauagug u 21

<210> SEQ ID NO 572
<211> LENGTH: 22

<212> TYPE: RNA
<213> ORGANISM: Artificial Sequence
<220> FEATURE:
<223> OTHER INFORMATION: Targeting domain

<400> SEQUENCE: 572
gauauuugca uugagauagu gu 22

<210> SEQ ID NO 573
<211> LENGTH: 23
<212> TYPE: RNA
<213> ORGANISM: Artificial Sequence
<220> FEATURE:
<223> OTHER INFORMATION: Targeting domain

<400> SEQUENCE: 573
agauauuugc auugagauag ugu 23

<210> SEQ ID NO 574
<211> LENGTH: 24
<212> TYPE: RNA
<213> ORGANISM: Artificial Sequence
<220> FEATURE:
<223> OTHER INFORMATION: Targeting domain

<400> SEQUENCE: 574
cagauauuug cauugagaua gugu 24

<210> SEQ ID NO 575
<211> LENGTH: 18
<212> TYPE: RNA
<213> ORGANISM: Artificial Sequence
<220> FEATURE:
<223> OTHER INFORMATION: Targeting domain

<400> SEQUENCE: 575
gaauaaauua gagaaaaa 18

<210> SEQ ID NO 576
<211> LENGTH: 19
<212> TYPE: RNA
<213> ORGANISM: Artificial Sequence
<220> FEATURE:
<223> OTHER INFORMATION: Targeting domain

<400> SEQUENCE: 576
agaauaaauu agagaaaaa 19

<210> SEQ ID NO 577
<211> LENGTH: 20
<212> TYPE: RNA
<213> ORGANISM: Artificial Sequence
<220> FEATURE:
<223> OTHER INFORMATION: Targeting domain

<400> SEQUENCE: 577
aagaauaaau uagagaaaaa 20

<210> SEQ ID NO 578
<211> LENGTH: 21
<212> TYPE: RNA
<213> ORGANISM: Artificial Sequence
<220> FEATURE:
<223> OTHER INFORMATION: Targeting domain

<400> SEQUENCE: 578

-continued gaagaauaaa uuagagaaaa a 21

<210> SEQ ID NO 579
<211> LENGTH: 22
<212> TYPE: RNA
<213> ORGANISM: Artificial Sequence
<220> FEATURE:
<223> OTHER INFORMATION: Targeting domain

<400> SEQUENCE: 579
ggaagaauaa auuagagaaa aa 22

<210> SEQ ID NO 580
<211> LENGTH: 23
<212> TYPE: RNA
<213> ORGANISM: Artificial Sequence
<220> FEATURE:
<223> OTHER INFORMATION: Targeting domain

<400> SEQUENCE: 580
gggaagaaua aauuagagaa aaa 23

<210> SEQ ID NO 581
<211> LENGTH: 24
<212> TYPE: RNA
<213> ORGANISM: Artificial Sequence
<220> FEATURE:
<223> OTHER INFORMATION: Targeting domain

<400> SEQUENCE: 581
agggaagaau aaauuagaga aaaa 24

<210> SEQ ID NO 582
<211> LENGTH: 18
<212> TYPE: RNA
<213> ORGANISM: Artificial Sequence
<220> FEATURE:
<223> OTHER INFORMATION: Targeting domain

<400> SEQUENCE: 582
cuagggauga agaauaaa 18

<210> SEQ ID NO 583
<211> LENGTH: 19
<212> TYPE: RNA
<213> ORGANISM: Artificial Sequence
<220> FEATURE:
<223> OTHER INFORMATION: Targeting domain

<400> SEQUENCE: 583
gcuagggaug aagaauaaa 19

<210> SEQ ID NO 584
<211> LENGTH: 21
<212> TYPE: RNA
<213> ORGANISM: Artificial Sequence
<220> FEATURE:
<223> OTHER INFORMATION: Targeting domain

<400> SEQUENCE: 584
uggcuaggga ugaagaauaa a 21

<210> SEQ ID NO 585
<211> LENGTH: 22
<212> TYPE: RNA
<213> ORGANISM: Artificial Sequence
<220> FEATURE:
<223> OTHER INFORMATION: Targeting domain

<400> SEQUENCE: 585
cuggcuaggg augaagaaua aa 22

<210> SEQ ID NO 586
<211> LENGTH: 23
<212> TYPE: RNA
<213> ORGANISM: Artificial Sequence
<220> FEATURE:
<223> OTHER INFORMATION: Targeting domain

<400> SEQUENCE: 586
gcuggcuagg gaugaagaau aaa 23

<210> SEQ ID NO 587
<211> LENGTH: 24
<212> TYPE: RNA
<213> ORGANISM: Artificial Sequence
<220> FEATURE:
<223> OTHER INFORMATION: Targeting domain

<400> SEQUENCE: 587
ggcuggcuag ggaugaagaa uaaa 24

<210> SEQ ID NO 588
<211> LENGTH: 18
<212> TYPE: RNA
<213> ORGANISM: Artificial Sequence
<220> FEATURE:
<223> OTHER INFORMATION: Targeting domain

<400> SEQUENCE: 588
agaaggaaac uagcuaaa 18

<210> SEQ ID NO 589
<211> LENGTH: 19
<212> TYPE: RNA
<213> ORGANISM: Artificial Sequence
<220> FEATURE:
<223> OTHER INFORMATION: Targeting domain

<400> SEQUENCE: 589
gagaaggaaa cuagcuaaa 19

<210> SEQ ID NO 590
<211> LENGTH: 21
<212> TYPE: RNA
<213> ORGANISM: Artificial Sequence
<220> FEATURE:
<223> OTHER INFORMATION: Targeting domain

<400> SEQUENCE: 590
gggagaagga aacuagcuaa a 21

<210> SEQ ID NO 591
<211> LENGTH: 22
<212> TYPE: RNA
<213> ORGANISM: Artificial Sequence
<220> FEATURE:
<223> OTHER INFORMATION: Targeting domain

<400> SEQUENCE: 591
ugggagaagg aaacuagcua aa 22

<210> SEQ ID NO 592
<211> LENGTH: 23
<212> TYPE: RNA
<213> ORGANISM: Artificial Sequence
<220> FEATURE:
<223> OTHER INFORMATION: Targeting domain

<400> SEQUENCE: 592
augggagaag gaaacuagcu aaa 23

<210> SEQ ID NO 593
<211> LENGTH: 24
<212> TYPE: RNA
<213> ORGANISM: Artificial Sequence
<220> FEATURE:
<223> OTHER INFORMATION: Targeting domain

<400> SEQUENCE: 593
gaugggagaa ggaaacuagc uaaa 24

<210> SEQ ID NO 594
<211> LENGTH: 18
<212> TYPE: RNA
<213> ORGANISM: Artificial Sequence
<220> FEATURE:
<223> OTHER INFORMATION: Targeting domain

<400> SEQUENCE: 594
aaaacuggaa ugacugaa 18

<210> SEQ ID NO 595
<211> LENGTH: 19
<212> TYPE: RNA
<213> ORGANISM: Artificial Sequence
<220> FEATURE:
<223> OTHER INFORMATION: Targeting domain

<400> SEQUENCE: 595
aaaaacugga augacugaa 19

<210> SEQ ID NO 596
<211> LENGTH: 20
<212> TYPE: RNA
<213> ORGANISM: Artificial Sequence
<220> FEATURE:
<223> OTHER INFORMATION: Targeting domain

<400> SEQUENCE: 596
gaaaaacugg aaugacugaa 20

<210> SEQ ID NO 597
<211> LENGTH: 21
<212> TYPE: RNA
<213> ORGANISM: Artificial Sequence
<220> FEATURE:
<223> OTHER INFORMATION: Targeting domain

<400> SEQUENCE: 597
agaaaaacug gaaugacuga a 21

<210> SEQ ID NO 598
<211> LENGTH: 22
<212> TYPE: RNA
<213> ORGANISM: Artificial Sequence
<220> FEATURE:
<223> OTHER INFORMATION: Targeting domain

<400> SEQUENCE: 598
gagaaaaacu ggaaugacug aa 22

<210> SEQ ID NO 599
<211> LENGTH: 23
<212> TYPE: RNA
<213> ORGANISM: Artificial Sequence
<220> FEATURE:
<223> OTHER INFORMATION: Targeting domain

<400> SEQUENCE: 599
agagaaaaac uggaaugacu gaa 23

<210> SEQ ID NO 600
<211> LENGTH: 24
<212> TYPE: RNA
<213> ORGANISM: Artificial Sequence
<220> FEATURE:
<223> OTHER INFORMATION: Targeting domain

<400> SEQUENCE: 600
uagagaaaaa cuggaaugac ugaa 24

<210> SEQ ID NO 601
<211> LENGTH: 18
<212> TYPE: RNA
<213> ORGANISM: Artificial Sequence
<220> FEATURE:
<223> OTHER INFORMATION: Targeting domain

<400> SEQUENCE: 601
gcuagggaug aagaauaa 18

<210> SEQ ID NO 602
<211> LENGTH: 19
<212> TYPE: RNA
<213> ORGANISM: Artificial Sequence
<220> FEATURE:
<223> OTHER INFORMATION: Targeting domain

<400> SEQUENCE: 602
ggcuagggau gaagaauaa 19

<210> SEQ ID NO 603
<211> LENGTH: 20
<212> TYPE: RNA
<213> ORGANISM: Artificial Sequence
<220> FEATURE:
<223> OTHER INFORMATION: Targeting domain

<400> SEQUENCE: 603
uggcuaggga ugaagaauaa 20

<210> SEQ ID NO 604
<211> LENGTH: 21
<212> TYPE: RNA
<213> ORGANISM: Artificial Sequence
<220> FEATURE:
<223> OTHER INFORMATION: Targeting domain

<400> SEQUENCE: 604
cuggcuaggg augaagaaua a 21

<210> SEQ ID NO 605

<211> LENGTH: 22
<212> TYPE: RNA
<213> ORGANISM: Artificial Sequence
<220> FEATURE:
<223> OTHER INFORMATION: Targeting domain

<400> SEQUENCE: 605
gcuggcuagg gaugaagaau aa 22

<210> SEQ ID NO 606
<211> LENGTH: 23
<212> TYPE: RNA
<213> ORGANISM: Artificial Sequence
<220> FEATURE:
<223> OTHER INFORMATION: Targeting domain

<400> SEQUENCE: 606
ggcuggcuag ggaugaagaa uaa 23

<210> SEQ ID NO 607
<211> LENGTH: 24
<212> TYPE: RNA
<213> ORGANISM: Artificial Sequence
<220> FEATURE:
<223> OTHER INFORMATION: Targeting domain

<400> SEQUENCE: 607
cggcuggcua gggaugaaga auaa 24

<210> SEQ ID NO 608
<211> LENGTH: 18
<212> TYPE: RNA
<213> ORGANISM: Artificial Sequence
<220> FEATURE:
<223> OTHER INFORMATION: Targeting domain

<400> SEQUENCE: 608
gagaaggaaa cuagcuaa 18

<210> SEQ ID NO 609
<211> LENGTH: 19
<212> TYPE: RNA
<213> ORGANISM: Artificial Sequence
<220> FEATURE:
<223> OTHER INFORMATION: Targeting domain

<400> SEQUENCE: 609
ggagaaggaa acuagcuaa 19

<210> SEQ ID NO 610
<211> LENGTH: 21
<212> TYPE: RNA
<213> ORGANISM: Artificial Sequence
<220> FEATURE:
<223> OTHER INFORMATION: Targeting domain

<400> SEQUENCE: 610
ugggagaagg aaacuagcua a 21

<210> SEQ ID NO 611
<211> LENGTH: 22
<212> TYPE: RNA
<213> ORGANISM: Artificial Sequence
<220> FEATURE:
<223> OTHER INFORMATION: Targeting domain

<400> SEQUENCE: 611
augggagaag gaaacuagcu aa 22

<210> SEQ ID NO 612
<211> LENGTH: 23
<212> TYPE: RNA
<213> ORGANISM: Artificial Sequence
<220> FEATURE:
<223> OTHER INFORMATION: Targeting domain

<400> SEQUENCE: 612
gaugggagaa ggaaacuagc uaa 23

<210> SEQ ID NO 613
<211> LENGTH: 24
<212> TYPE: RNA
<213> ORGANISM: Artificial Sequence
<220> FEATURE:
<223> OTHER INFORMATION: Targeting domain

<400> SEQUENCE: 613
ugaugggaga aggaaacuag cuaa 24

<210> SEQ ID NO 614
<211> LENGTH: 18
<212> TYPE: RNA
<213> ORGANISM: Artificial Sequence
<220> FEATURE:
<223> OTHER INFORMATION: Targeting domain

<400> SEQUENCE: 614
auagucuuag aguaucca 18

<210> SEQ ID NO 615
<211> LENGTH: 19
<212> TYPE: RNA
<213> ORGANISM: Artificial Sequence
<220> FEATURE:
<223> OTHER INFORMATION: Targeting domain

<400> SEQUENCE: 615
aauagucuua gaguaucca 19

<210> SEQ ID NO 616
<211> LENGTH: 20
<212> TYPE: RNA
<213> ORGANISM: Artificial Sequence
<220> FEATURE:
<223> OTHER INFORMATION: Targeting domain

<400> SEQUENCE: 616
caauagucuu agaguaucca 20

<210> SEQ ID NO 617
<211> LENGTH: 21
<212> TYPE: RNA
<213> ORGANISM: Artificial Sequence
<220> FEATURE:
<223> OTHER INFORMATION: Targeting domain

<400> SEQUENCE: 617
ccaauagucu uagaguaucc a 21

<210> SEQ ID NO 618
<211> LENGTH: 22
<212> TYPE: RNA

<213> ORGANISM: Artificial Sequence
<220> FEATURE:
<223> OTHER INFORMATION: Targeting domain

<400> SEQUENCE: 618
accaauaguc uuagaguauc ca 22

<210> SEQ ID NO 619
<211> LENGTH: 23
<212> TYPE: RNA
<213> ORGANISM: Artificial Sequence
<220> FEATURE:
<223> OTHER INFORMATION: Targeting domain

<400> SEQUENCE: 619
gaccaauagu cuuagaguau cca 23

<210> SEQ ID NO 620
<211> LENGTH: 24
<212> TYPE: RNA
<213> ORGANISM: Artificial Sequence
<220> FEATURE:
<223> OTHER INFORMATION: Targeting domain

<400> SEQUENCE: 620
ugaccaauag ucuuagagua ucca 24

<210> SEQ ID NO 621
<211> LENGTH: 18
<212> TYPE: RNA
<213> ORGANISM: Artificial Sequence
<220> FEATURE:
<223> OTHER INFORMATION: Targeting domain

<400> SEQUENCE: 621
auccucuaug augggaga 18

<210> SEQ ID NO 622
<211> LENGTH: 19
<212> TYPE: RNA
<213> ORGANISM: Artificial Sequence
<220> FEATURE:
<223> OTHER INFORMATION: Targeting domain

<400> SEQUENCE: 622
uauccucuau gaugggaga 19

<210> SEQ ID NO 623
<211> LENGTH: 21
<212> TYPE: RNA
<213> ORGANISM: Artificial Sequence
<220> FEATURE:
<223> OTHER INFORMATION: Targeting domain

<400> SEQUENCE: 623
gguauccucu augaugggag a 21

<210> SEQ ID NO 624
<211> LENGTH: 22
<212> TYPE: RNA
<213> ORGANISM: Artificial Sequence
<220> FEATURE:
<223> OTHER INFORMATION: Targeting domain

<400> SEQUENCE: 624
ugguauccuc uaugauggga ga 22

<210> SEQ ID NO 625
<211> LENGTH: 23
<212> TYPE: RNA
<213> ORGANISM: Artificial Sequence
<220> FEATURE:
<223> OTHER INFORMATION: Targeting domain

<400> SEQUENCE: 625
cugguauccu cuaugauggg aga 23

<210> SEQ ID NO 626
<211> LENGTH: 24
<212> TYPE: RNA
<213> ORGANISM: Artificial Sequence
<220> FEATURE:
<223> OTHER INFORMATION: Targeting domain

<400> SEQUENCE: 626
ccugguaucc ucuaugaugg gaga 24

<210> SEQ ID NO 627
<211> LENGTH: 18
<212> TYPE: RNA
<213> ORGANISM: Artificial Sequence
<220> FEATURE:
<223> OTHER INFORMATION: Targeting domain

<400> SEQUENCE: 627
uccugguauc cucuauga 18

<210> SEQ ID NO 628
<211> LENGTH: 19
<212> TYPE: RNA
<213> ORGANISM: Artificial Sequence
<220> FEATURE:
<223> OTHER INFORMATION: Targeting domain

<400> SEQUENCE: 628
guccugguau ccucuauga 19

<210> SEQ ID NO 629
<211> LENGTH: 21
<212> TYPE: RNA
<213> ORGANISM: Artificial Sequence
<220> FEATURE:
<223> OTHER INFORMATION: Targeting domain

<400> SEQUENCE: 629
aaguccuggu auccucuaug a 21

<210> SEQ ID NO 630
<211> LENGTH: 22
<212> TYPE: RNA
<213> ORGANISM: Artificial Sequence
<220> FEATURE:
<223> OTHER INFORMATION: Targeting domain

<400> SEQUENCE: 630
gaaguccugg uauccucuau ga 22

<210> SEQ ID NO 631
<211> LENGTH: 23
<212> TYPE: RNA
<213> ORGANISM: Artificial Sequence
<220> FEATURE:

-continued

<223> OTHER INFORMATION: Targeting domain

<400> SEQUENCE: 631
agaaguccug guauccucua uga 23

<210> SEQ ID NO 632
<211> LENGTH: 24
<212> TYPE: RNA
<213> ORGANISM: Artificial Sequence
<220> FEATURE:
<223> OTHER INFORMATION: Targeting domain

<400> SEQUENCE: 632
aagaaguccu gguauccucu auga 24

<210> SEQ ID NO 633
<211> LENGTH: 18
<212> TYPE: RNA
<213> ORGANISM: Artificial Sequence
<220> FEATURE:
<223> OTHER INFORMATION: Targeting domain

<400> SEQUENCE: 633
ggagaaggaa acuagcua 18

<210> SEQ ID NO 634
<211> LENGTH: 19
<212> TYPE: RNA
<213> ORGANISM: Artificial Sequence
<220> FEATURE:
<223> OTHER INFORMATION: Targeting domain

<400> SEQUENCE: 634
gggagaagga aacuagcua 19

<210> SEQ ID NO 635
<211> LENGTH: 20
<212> TYPE: RNA
<213> ORGANISM: Artificial Sequence
<220> FEATURE:
<223> OTHER INFORMATION: Targeting domain

<400> SEQUENCE: 635
ugggagaagg aaacuagcua 20

<210> SEQ ID NO 636
<211> LENGTH: 21
<212> TYPE: RNA
<213> ORGANISM: Artificial Sequence
<220> FEATURE:
<223> OTHER INFORMATION: Targeting domain

<400> SEQUENCE: 636
augggagaag gaaacuagcu a 21

<210> SEQ ID NO 637
<211> LENGTH: 22
<212> TYPE: RNA
<213> ORGANISM: Artificial Sequence
<220> FEATURE:
<223> OTHER INFORMATION: Targeting domain

<400> SEQUENCE: 637
gaugggagaa ggaaacuagc ua 22

-continued

<210> SEQ ID NO 638
<211> LENGTH: 23
<212> TYPE: RNA
<213> ORGANISM: Artificial Sequence
<220> FEATURE:
<223> OTHER INFORMATION: Targeting domain

<400> SEQUENCE: 638
ugaugggaga aggaaacuag cua 23

<210> SEQ ID NO 639
<211> LENGTH: 24
<212> TYPE: RNA
<213> ORGANISM: Artificial Sequence
<220> FEATURE:
<223> OTHER INFORMATION: Targeting domain

<400> SEQUENCE: 639
augaugggag aaggaaacua gcua 24

<210> SEQ ID NO 640
<211> LENGTH: 18
<212> TYPE: RNA
<213> ORGANISM: Artificial Sequence
<220> FEATURE:
<223> OTHER INFORMATION: Targeting domain

<400> SEQUENCE: 640
aaagggaaga auaaauua 18

<210> SEQ ID NO 641
<211> LENGTH: 19
<212> TYPE: RNA
<213> ORGANISM: Artificial Sequence
<220> FEATURE:
<223> OTHER INFORMATION: Targeting domain

<400> SEQUENCE: 641
uaaagggaag aauaaauua 19

<210> SEQ ID NO 642
<211> LENGTH: 20
<212> TYPE: RNA
<213> ORGANISM: Artificial Sequence
<220> FEATURE:
<223> OTHER INFORMATION: Targeting domain

<400> SEQUENCE: 642
cuaaagggaa gaauaaauua 20

<210> SEQ ID NO 643
<211> LENGTH: 21
<212> TYPE: RNA
<213> ORGANISM: Artificial Sequence
<220> FEATURE:
<223> OTHER INFORMATION: Targeting domain

<400> SEQUENCE: 643
gcuaaaggga agaauaaauu a 21

<210> SEQ ID NO 644
<211> LENGTH: 22
<212> TYPE: RNA
<213> ORGANISM: Artificial Sequence
<220> FEATURE:
<223> OTHER INFORMATION: Targeting domain

<400> SEQUENCE: 644
agcuaaaggg aagaauaaau ua 22

<210> SEQ ID NO 645
<211> LENGTH: 23
<212> TYPE: RNA
<213> ORGANISM: Artificial Sequence
<220> FEATURE:
<223> OTHER INFORMATION: Targeting domain

<400> SEQUENCE: 645
uagcuaaagg gaagaauaaa uua 23

<210> SEQ ID NO 646
<211> LENGTH: 24
<212> TYPE: RNA
<213> ORGANISM: Artificial Sequence
<220> FEATURE:
<223> OTHER INFORMATION: Targeting domain

<400> SEQUENCE: 646
cuagcuaaag ggaagaauaa auua 24

<210> SEQ ID NO 647
<211> LENGTH: 18
<212> TYPE: RNA
<213> ORGANISM: Artificial Sequence
<220> FEATURE:
<223> OTHER INFORMATION: Targeting domain

<400> SEQUENCE: 647
agaguaucca gugaggcc 18

<210> SEQ ID NO 648
<211> LENGTH: 19
<212> TYPE: RNA
<213> ORGANISM: Artificial Sequence
<220> FEATURE:
<223> OTHER INFORMATION: Targeting domain

<400> SEQUENCE: 648
uagaguaucc agugaggcc 19

<210> SEQ ID NO 649
<211> LENGTH: 21
<212> TYPE: RNA
<213> ORGANISM: Artificial Sequence
<220> FEATURE:
<223> OTHER INFORMATION: Targeting domain

<400> SEQUENCE: 649
cuuagaguau ccagugaggc c 21

<210> SEQ ID NO 650
<211> LENGTH: 22
<212> TYPE: RNA
<213> ORGANISM: Artificial Sequence
<220> FEATURE:
<223> OTHER INFORMATION: Targeting domain

<400> SEQUENCE: 650
ucuuagagua uccagugagg cc 22

<210> SEQ ID NO 651
<211> LENGTH: 23

<212> TYPE: RNA
<213> ORGANISM: Artificial Sequence
<220> FEATURE:
<223> OTHER INFORMATION: Targeting domain

<400> SEQUENCE: 651
gucuuagagu auccagugag gcc 23

<210> SEQ ID NO 652
<211> LENGTH: 24
<212> TYPE: RNA
<213> ORGANISM: Artificial Sequence
<220> FEATURE:
<223> OTHER INFORMATION: Targeting domain

<400> SEQUENCE: 652
agucuuagag uauccaguga ggcc 24

<210> SEQ ID NO 653
<211> LENGTH: 18
<212> TYPE: RNA
<213> ORGANISM: Artificial Sequence
<220> FEATURE:
<223> OTHER INFORMATION: Targeting domain

<400> SEQUENCE: 653
uagaguaucc agugaggc 18

<210> SEQ ID NO 654
<211> LENGTH: 19
<212> TYPE: RNA
<213> ORGANISM: Artificial Sequence
<220> FEATURE:
<223> OTHER INFORMATION: Targeting domain

<400> SEQUENCE: 654
uuagaguauc cagugaggc 19

<210> SEQ ID NO 655
<211> LENGTH: 20
<212> TYPE: RNA
<213> ORGANISM: Artificial Sequence
<220> FEATURE:
<223> OTHER INFORMATION: Targeting domain

<400> SEQUENCE: 655
cuuagaguau ccagugaggc 20

<210> SEQ ID NO 656
<211> LENGTH: 21
<212> TYPE: RNA
<213> ORGANISM: Artificial Sequence
<220> FEATURE:
<223> OTHER INFORMATION: Targeting domain

<400> SEQUENCE: 656
ucuuagagua uccagugagg c 21

<210> SEQ ID NO 657
<211> LENGTH: 22
<212> TYPE: RNA
<213> ORGANISM: Artificial Sequence
<220> FEATURE:
<223> OTHER INFORMATION: Targeting domain

<400> SEQUENCE: 657
gucuuagagu auccagugag gc 22

<210> SEQ ID NO 658
<211> LENGTH: 23
<212> TYPE: RNA
<213> ORGANISM: Artificial Sequence
<220> FEATURE:
<223> OTHER INFORMATION: Targeting domain

<400> SEQUENCE: 658
agucuuagag uauccaguga ggc 23

<210> SEQ ID NO 659
<211> LENGTH: 24
<212> TYPE: RNA
<213> ORGANISM: Artificial Sequence
<220> FEATURE:
<223> OTHER INFORMATION: Targeting domain

<400> SEQUENCE: 659
uagucuuaga guauccagug aggc 24

<210> SEQ ID NO 660
<211> LENGTH: 18
<212> TYPE: RNA
<213> ORGANISM: Artificial Sequence
<220> FEATURE:
<223> OTHER INFORMATION: Targeting domain

<400> SEQUENCE: 660
caggggccgg cggcuggc 18

<210> SEQ ID NO 661
<211> LENGTH: 19
<212> TYPE: RNA
<213> ORGANISM: Artificial Sequence
<220> FEATURE:
<223> OTHER INFORMATION: Targeting domain

<400> SEQUENCE: 661
ccaggggccg gcggcuggc 19

<210> SEQ ID NO 662
<211> LENGTH: 20
<212> TYPE: RNA
<213> ORGANISM: Artificial Sequence
<220> FEATURE:
<223> OTHER INFORMATION: Targeting domain

<400> SEQUENCE: 662
gccaggggcc ggcggcuggc 20

<210> SEQ ID NO 663
<211> LENGTH: 21
<212> TYPE: RNA
<213> ORGANISM: Artificial Sequence
<220> FEATURE:
<223> OTHER INFORMATION: Targeting domain

<400> SEQUENCE: 663
ggccaggggc cggcggcugg c 21

<210> SEQ ID NO 664
<211> LENGTH: 22
<212> TYPE: RNA
<213> ORGANISM: Artificial Sequence
<220> FEATURE:
<223> OTHER INFORMATION: Targeting domain

<400> SEQUENCE: 664
aggccagggg ccggcggcug gc 22

<210> SEQ ID NO 665
<211> LENGTH: 23
<212> TYPE: RNA
<213> ORGANISM: Artificial Sequence
<220> FEATURE:
<223> OTHER INFORMATION: Targeting domain

<400> SEQUENCE: 665
gaggccaggg gccggcggcu ggc 23

<210> SEQ ID NO 666
<211> LENGTH: 24
<212> TYPE: RNA
<213> ORGANISM: Artificial Sequence
<220> FEATURE:
<223> OTHER INFORMATION: Targeting domain

<400> SEQUENCE: 666
ugaggccagg ggccggcggc uggc 24

<210> SEQ ID NO 667
<211> LENGTH: 18
<212> TYPE: RNA
<213> ORGANISM: Artificial Sequence
<220> FEATURE:
<223> OTHER INFORMATION: Targeting domain

<400> SEQUENCE: 667
aaaauuagca guauccuc 18

<210> SEQ ID NO 668
<211> LENGTH: 19
<212> TYPE: RNA
<213> ORGANISM: Artificial Sequence
<220> FEATURE:
<223> OTHER INFORMATION: Targeting domain

<400> SEQUENCE: 668
aaaaauuagc aguauccuc 19

<210> SEQ ID NO 669
<211> LENGTH: 20
<212> TYPE: RNA
<213> ORGANISM: Artificial Sequence
<220> FEATURE:
<223> OTHER INFORMATION: Targeting domain

<400> SEQUENCE: 669
aaaaaauuag caguauccuc 20

<210> SEQ ID NO 670
<211> LENGTH: 21
<212> TYPE: RNA
<213> ORGANISM: Artificial Sequence
<220> FEATURE:
<223> OTHER INFORMATION: Targeting domain

<400> SEQUENCE: 670
aaaaaaauua gcaguauccu c 21

-continued

<210> SEQ ID NO 671
<211> LENGTH: 22
<212> TYPE: RNA
<213> ORGANISM: Artificial Sequence
<220> FEATURE:
<223> OTHER INFORMATION: Targeting domain

<400> SEQUENCE: 671
aaaaaaaauu agcaguaucc uc 22

<210> SEQ ID NO 672
<211> LENGTH: 23
<212> TYPE: RNA
<213> ORGANISM: Artificial Sequence
<220> FEATURE:
<223> OTHER INFORMATION: Targeting domain

<400> SEQUENCE: 672
uaaaaaaaau uagcaguauc cuc 23

<210> SEQ ID NO 673
<211> LENGTH: 24
<212> TYPE: RNA
<213> ORGANISM: Artificial Sequence
<220> FEATURE:
<223> OTHER INFORMATION: Targeting domain

<400> SEQUENCE: 673
auaaaaaaaa uuagcaguau ccuc 24

<210> SEQ ID NO 674
<211> LENGTH: 18
<212> TYPE: RNA
<213> ORGANISM: Artificial Sequence
<220> FEATURE:
<223> OTHER INFORMATION: Targeting domain

<400> SEQUENCE: 674
guuccacaca cucgcuuc 18

<210> SEQ ID NO 675
<211> LENGTH: 19
<212> TYPE: RNA
<213> ORGANISM: Artificial Sequence
<220> FEATURE:
<223> OTHER INFORMATION: Targeting domain

<400> SEQUENCE: 675
aguuccacac acucgcuuc 19

<210> SEQ ID NO 676
<211> LENGTH: 21
<212> TYPE: RNA
<213> ORGANISM: Artificial Sequence
<220> FEATURE:
<223> OTHER INFORMATION: Targeting domain

<400> SEQUENCE: 676
gcaguuccac acacucgcuu c 21

<210> SEQ ID NO 677
<211> LENGTH: 22
<212> TYPE: RNA
<213> ORGANISM: Artificial Sequence
<220> FEATURE:
<223> OTHER INFORMATION: Targeting domain

<400> SEQUENCE: 677
agcaguucca cacacucgcu uc 22

<210> SEQ ID NO 678
<211> LENGTH: 23
<212> TYPE: RNA
<213> ORGANISM: Artificial Sequence
<220> FEATURE:
<223> OTHER INFORMATION: Targeting domain

<400> SEQUENCE: 678
cagcaguucc acacacucgc uuc 23

<210> SEQ ID NO 679
<211> LENGTH: 24
<212> TYPE: RNA
<213> ORGANISM: Artificial Sequence
<220> FEATURE:
<223> OTHER INFORMATION: Targeting domain

<400> SEQUENCE: 679
ucagcaguuc cacacacucg cuuc 24

<210> SEQ ID NO 680
<211> LENGTH: 18
<212> TYPE: RNA
<213> ORGANISM: Artificial Sequence
<220> FEATURE:
<223> OTHER INFORMATION: Targeting domain

<400> SEQUENCE: 680
uauccucuau gaugggag 18

<210> SEQ ID NO 681
<211> LENGTH: 19
<212> TYPE: RNA
<213> ORGANISM: Artificial Sequence
<220> FEATURE:
<223> OTHER INFORMATION: Targeting domain

<400> SEQUENCE: 681
guauccucua ugaugggag 19

<210> SEQ ID NO 682
<211> LENGTH: 20
<212> TYPE: RNA
<213> ORGANISM: Artificial Sequence
<220> FEATURE:
<223> OTHER INFORMATION: Targeting domain

<400> SEQUENCE: 682
gguauccucu augaugggag 20

<210> SEQ ID NO 683
<211> LENGTH: 21
<212> TYPE: RNA
<213> ORGANISM: Artificial Sequence
<220> FEATURE:
<223> OTHER INFORMATION: Targeting domain

<400> SEQUENCE: 683
ugguauccuc uaugauggga g 21

<210> SEQ ID NO 684

<211> LENGTH: 22
<212> TYPE: RNA
<213> ORGANISM: Artificial Sequence
<220> FEATURE:
<223> OTHER INFORMATION: Targeting domain

<400> SEQUENCE: 684
cugguauccu cuaugauggg ag 22

<210> SEQ ID NO 685
<211> LENGTH: 23
<212> TYPE: RNA
<213> ORGANISM: Artificial Sequence
<220> FEATURE:
<223> OTHER INFORMATION: Targeting domain

<400> SEQUENCE: 685
ccugguaucc ucuaugaugg gag 23

<210> SEQ ID NO 686
<211> LENGTH: 24
<212> TYPE: RNA
<213> ORGANISM: Artificial Sequence
<220> FEATURE:
<223> OTHER INFORMATION: Targeting domain

<400> SEQUENCE: 686
uccugguauc cucuaugaug ggag 24

<210> SEQ ID NO 687
<211> LENGTH: 18
<212> TYPE: RNA
<213> ORGANISM: Artificial Sequence
<220> FEATURE:
<223> OTHER INFORMATION: Targeting domain

<400> SEQUENCE: 687
gccggcggcu ggcuaggg 18

<210> SEQ ID NO 688
<211> LENGTH: 19
<212> TYPE: RNA
<213> ORGANISM: Artificial Sequence
<220> FEATURE:
<223> OTHER INFORMATION: Targeting domain

<400> SEQUENCE: 688
ggccggcggc uggcuaggg 19

<210> SEQ ID NO 689
<211> LENGTH: 20
<212> TYPE: RNA
<213> ORGANISM: Artificial Sequence
<220> FEATURE:
<223> OTHER INFORMATION: Targeting domain

<400> SEQUENCE: 689
gggccggcgg cuggcuaggg 20

<210> SEQ ID NO 690
<211> LENGTH: 21
<212> TYPE: RNA
<213> ORGANISM: Artificial Sequence
<220> FEATURE:
<223> OTHER INFORMATION: Targeting domain

<400> SEQUENCE: 690

```
ggggccggcg gcuggcuagg g                                          21

<210> SEQ ID NO 691
<211> LENGTH: 22
<212> TYPE: RNA
<213> ORGANISM: Artificial Sequence
<220> FEATURE:
<223> OTHER INFORMATION: Targeting domain

<400> SEQUENCE: 691

aggggccggc ggcuggcuag gg                                         22

<210> SEQ ID NO 692
<211> LENGTH: 23
<212> TYPE: RNA
<213> ORGANISM: Artificial Sequence
<220> FEATURE:
<223> OTHER INFORMATION: Targeting domain

<400> SEQUENCE: 692

caggggccgg cggcuggcua ggg                                        23

<210> SEQ ID NO 693
<211> LENGTH: 24
<212> TYPE: RNA
<213> ORGANISM: Artificial Sequence
<220> FEATURE:
<223> OTHER INFORMATION: Targeting domain

<400> SEQUENCE: 693

ccaggggccg gcggcuggcu aggg                                       24

<210> SEQ ID NO 694
<211> LENGTH: 18
<212> TYPE: RNA
<213> ORGANISM: Artificial Sequence
<220> FEATURE:
<223> OTHER INFORMATION: Targeting domain

<400> SEQUENCE: 694

ugguauccuc uaugaugg                                              18

<210> SEQ ID NO 695
<211> LENGTH: 19
<212> TYPE: RNA
<213> ORGANISM: Artificial Sequence
<220> FEATURE:
<223> OTHER INFORMATION: Targeting domain

<400> SEQUENCE: 695

cugguauccu cuaugaugg                                             19

<210> SEQ ID NO 696
<211> LENGTH: 20
<212> TYPE: RNA
<213> ORGANISM: Artificial Sequence
<220> FEATURE:
<223> OTHER INFORMATION: Targeting domain

<400> SEQUENCE: 696

ccugguaucc ucuaugaugg                                            20

<210> SEQ ID NO 697
<211> LENGTH: 21
<212> TYPE: RNA
```

<213> ORGANISM: Artificial Sequence
<220> FEATURE:
<223> OTHER INFORMATION: Targeting domain

<400> SEQUENCE: 697
uccugguauc cucuaugaug g 21

<210> SEQ ID NO 698
<211> LENGTH: 22
<212> TYPE: RNA
<213> ORGANISM: Artificial Sequence
<220> FEATURE:
<223> OTHER INFORMATION: Targeting domain

<400> SEQUENCE: 698
guccugguau ccucuaugau gg 22

<210> SEQ ID NO 699
<211> LENGTH: 23
<212> TYPE: RNA
<213> ORGANISM: Artificial Sequence
<220> FEATURE:
<223> OTHER INFORMATION: Targeting domain

<400> SEQUENCE: 699
aguccuggua uccucuauga ugg 23

<210> SEQ ID NO 700
<211> LENGTH: 24
<212> TYPE: RNA
<213> ORGANISM: Artificial Sequence
<220> FEATURE:
<223> OTHER INFORMATION: Targeting domain

<400> SEQUENCE: 700
aaguccuggu auccucuaug augg 24

<210> SEQ ID NO 701
<211> LENGTH: 18
<212> TYPE: RNA
<213> ORGANISM: Artificial Sequence
<220> FEATURE:
<223> OTHER INFORMATION: Targeting domain

<400> SEQUENCE: 701
guccugguau ccucuaug 18

<210> SEQ ID NO 702
<211> LENGTH: 19
<212> TYPE: RNA
<213> ORGANISM: Artificial Sequence
<220> FEATURE:
<223> OTHER INFORMATION: Targeting domain

<400> SEQUENCE: 702
aguccuggua uccucuaug 19

<210> SEQ ID NO 703
<211> LENGTH: 20
<212> TYPE: RNA
<213> ORGANISM: Artificial Sequence
<220> FEATURE:
<223> OTHER INFORMATION: Targeting domain

<400> SEQUENCE: 703
aaguccuggu auccucuaug 20

<210> SEQ ID NO 704
<211> LENGTH: 21
<212> TYPE: RNA
<213> ORGANISM: Artificial Sequence
<220> FEATURE:
<223> OTHER INFORMATION: Targeting domain

<400> SEQUENCE: 704
gaaguccugg uauccucuau g 21

<210> SEQ ID NO 705
<211> LENGTH: 22
<212> TYPE: RNA
<213> ORGANISM: Artificial Sequence
<220> FEATURE:
<223> OTHER INFORMATION: Targeting domain

<400> SEQUENCE: 705
agaaguccug guauccucua ug 22

<210> SEQ ID NO 706
<211> LENGTH: 23
<212> TYPE: RNA
<213> ORGANISM: Artificial Sequence
<220> FEATURE:
<223> OTHER INFORMATION: Targeting domain

<400> SEQUENCE: 706
aagaaguccu gguauccucu aug 23

<210> SEQ ID NO 707
<211> LENGTH: 24
<212> TYPE: RNA
<213> ORGANISM: Artificial Sequence
<220> FEATURE:
<223> OTHER INFORMATION: Targeting domain

<400> SEQUENCE: 707
aaagaagucc ugguauccuc uaug 24

<210> SEQ ID NO 708
<211> LENGTH: 18
<212> TYPE: RNA
<213> ORGANISM: Artificial Sequence
<220> FEATURE:
<223> OTHER INFORMATION: Targeting domain

<400> SEQUENCE: 708
cuaaagggaa gaauaaau 18

<210> SEQ ID NO 709
<211> LENGTH: 19
<212> TYPE: RNA
<213> ORGANISM: Artificial Sequence
<220> FEATURE:
<223> OTHER INFORMATION: Targeting domain

<400> SEQUENCE: 709
gcuaaaggga agaauaaau 19

<210> SEQ ID NO 710
<211> LENGTH: 20
<212> TYPE: RNA
<213> ORGANISM: Artificial Sequence
<220> FEATURE:

<223> OTHER INFORMATION: Targeting domain

<400> SEQUENCE: 710
agcuaaaggg aagaauaaau 20

<210> SEQ ID NO 711
<211> LENGTH: 21
<212> TYPE: RNA
<213> ORGANISM: Artificial Sequence
<220> FEATURE:
<223> OTHER INFORMATION: Targeting domain

<400> SEQUENCE: 711
uagcuaaagg gaagaauaaa u 21

<210> SEQ ID NO 712
<211> LENGTH: 22
<212> TYPE: RNA
<213> ORGANISM: Artificial Sequence
<220> FEATURE:
<223> OTHER INFORMATION: Targeting domain

<400> SEQUENCE: 712
cuagcuaaag ggaagaauaa au 22

<210> SEQ ID NO 713
<211> LENGTH: 23
<212> TYPE: RNA
<213> ORGANISM: Artificial Sequence
<220> FEATURE:
<223> OTHER INFORMATION: Targeting domain

<400> SEQUENCE: 713
acuagcuaaa gggaagaaua aau 23

<210> SEQ ID NO 714
<211> LENGTH: 24
<212> TYPE: RNA
<213> ORGANISM: Artificial Sequence
<220> FEATURE:
<223> OTHER INFORMATION: Targeting domain

<400> SEQUENCE: 714
aacuagcuaa agggaagaau aaau 24

<210> SEQ ID NO 715
<211> LENGTH: 18
<212> TYPE: RNA
<213> ORGANISM: Artificial Sequence
<220> FEATURE:
<223> OTHER INFORMATION: Targeting domain

<400> SEQUENCE: 715
aaacuggaau gacugaau 18

<210> SEQ ID NO 716
<211> LENGTH: 19
<212> TYPE: RNA
<213> ORGANISM: Artificial Sequence
<220> FEATURE:
<223> OTHER INFORMATION: Targeting domain

<400> SEQUENCE: 716
aaaacuggaa ugacugaau 19

<210> SEQ ID NO 717
<211> LENGTH: 21
<212> TYPE: RNA
<213> ORGANISM: Artificial Sequence
<220> FEATURE:
<223> OTHER INFORMATION: Targeting domain

<400> SEQUENCE: 717
gaaaaacugg aaugacugaa u 21

<210> SEQ ID NO 718
<211> LENGTH: 22
<212> TYPE: RNA
<213> ORGANISM: Artificial Sequence
<220> FEATURE:
<223> OTHER INFORMATION: Targeting domain

<400> SEQUENCE: 718
agaaaaacug gaaugacuga au 22

<210> SEQ ID NO 719
<211> LENGTH: 23
<212> TYPE: RNA
<213> ORGANISM: Artificial Sequence
<220> FEATURE:
<223> OTHER INFORMATION: Targeting domain

<400> SEQUENCE: 719
gagaaaaacu ggaaugacug aau 23

<210> SEQ ID NO 720
<211> LENGTH: 24
<212> TYPE: RNA
<213> ORGANISM: Artificial Sequence
<220> FEATURE:
<223> OTHER INFORMATION: Targeting domain

<400> SEQUENCE: 720
agagaaaaac uggaaugacu gaau 24

<210> SEQ ID NO 721
<211> LENGTH: 18
<212> TYPE: RNA
<213> ORGANISM: Artificial Sequence
<220> FEATURE:
<223> OTHER INFORMATION: Targeting domain

<400> SEQUENCE: 721
ccugguaucc ucuaugau 18

<210> SEQ ID NO 722
<211> LENGTH: 19
<212> TYPE: RNA
<213> ORGANISM: Artificial Sequence
<220> FEATURE:
<223> OTHER INFORMATION: Targeting domain

<400> SEQUENCE: 722
uccugguauc cucuaugau 19

<210> SEQ ID NO 723
<211> LENGTH: 21
<212> TYPE: RNA
<213> ORGANISM: Artificial Sequence
<220> FEATURE:
<223> OTHER INFORMATION: Targeting domain

<400> SEQUENCE: 723
aguccuggua uccucuauga u 21

<210> SEQ ID NO 724
<211> LENGTH: 22
<212> TYPE: RNA
<213> ORGANISM: Artificial Sequence
<220> FEATURE:
<223> OTHER INFORMATION: Targeting domain

<400> SEQUENCE: 724
aaguccuggu auccucuaug au 22

<210> SEQ ID NO 725
<211> LENGTH: 23
<212> TYPE: RNA
<213> ORGANISM: Artificial Sequence
<220> FEATURE:
<223> OTHER INFORMATION: Targeting domain

<400> SEQUENCE: 725
gaaguccugg uauccucuau gau 23

<210> SEQ ID NO 726
<211> LENGTH: 24
<212> TYPE: RNA
<213> ORGANISM: Artificial Sequence
<220> FEATURE:
<223> OTHER INFORMATION: Targeting domain

<400> SEQUENCE: 726
agaaguccug guauccucua ugau 24

<210> SEQ ID NO 727
<211> LENGTH: 18
<212> TYPE: RNA
<213> ORGANISM: Artificial Sequence
<220> FEATURE:
<223> OTHER INFORMATION: Targeting domain

<400> SEQUENCE: 727
aaauuagcag uauccucu 18

<210> SEQ ID NO 728
<211> LENGTH: 19
<212> TYPE: RNA
<213> ORGANISM: Artificial Sequence
<220> FEATURE:
<223> OTHER INFORMATION: Targeting domain

<400> SEQUENCE: 728
aaaauuagca guauccucu 19

<210> SEQ ID NO 729
<211> LENGTH: 21
<212> TYPE: RNA
<213> ORGANISM: Artificial Sequence
<220> FEATURE:
<223> OTHER INFORMATION: Targeting domain

<400> SEQUENCE: 729
aaaaaauuag caguauccuc u 21

<210> SEQ ID NO 730
<211> LENGTH: 22

<212> TYPE: RNA
<213> ORGANISM: Artificial Sequence
<220> FEATURE:
<223> OTHER INFORMATION: Targeting domain

<400> SEQUENCE: 730
aaaaaaauua gcaguauccu cu 22

<210> SEQ ID NO 731
<211> LENGTH: 23
<212> TYPE: RNA
<213> ORGANISM: Artificial Sequence
<220> FEATURE:
<223> OTHER INFORMATION: Targeting domain

<400> SEQUENCE: 731
aaaaaaaauu agcaguaucc ucu 23

<210> SEQ ID NO 732
<211> LENGTH: 24
<212> TYPE: RNA
<213> ORGANISM: Artificial Sequence
<220> FEATURE:
<223> OTHER INFORMATION: Targeting domain

<400> SEQUENCE: 732
uaaaaaaaau uagcaguauc cucu 24

<210> SEQ ID NO 733
<211> LENGTH: 18
<212> TYPE: RNA
<213> ORGANISM: Artificial Sequence
<220> FEATURE:
<223> OTHER INFORMATION: Targeting domain

<400> SEQUENCE: 733
cacucgcuuc uggaacgu 18

<210> SEQ ID NO 734
<211> LENGTH: 19
<212> TYPE: RNA
<213> ORGANISM: Artificial Sequence
<220> FEATURE:
<223> OTHER INFORMATION: Targeting domain

<400> SEQUENCE: 734
acacucgcuu cuggaacgu 19

<210> SEQ ID NO 735
<211> LENGTH: 20
<212> TYPE: RNA
<213> ORGANISM: Artificial Sequence
<220> FEATURE:
<223> OTHER INFORMATION: Targeting domain

<400> SEQUENCE: 735
cacacucgcu ucuggaacgu 20

<210> SEQ ID NO 736
<211> LENGTH: 21
<212> TYPE: RNA
<213> ORGANISM: Artificial Sequence
<220> FEATURE:
<223> OTHER INFORMATION: Targeting domain

<400> SEQUENCE: 736
acacacucgc uucuggaacg u 21

<210> SEQ ID NO 737
<211> LENGTH: 22
<212> TYPE: RNA
<213> ORGANISM: Artificial Sequence
<220> FEATURE:
<223> OTHER INFORMATION: Targeting domain

<400> SEQUENCE: 737
cacacacucg cuucuggaac gu 22

<210> SEQ ID NO 738
<211> LENGTH: 23
<212> TYPE: RNA
<213> ORGANISM: Artificial Sequence
<220> FEATURE:
<223> OTHER INFORMATION: Targeting domain

<400> SEQUENCE: 738
ccacacacuc gcuucuggaa cgu 23

<210> SEQ ID NO 739
<211> LENGTH: 24
<212> TYPE: RNA
<213> ORGANISM: Artificial Sequence
<220> FEATURE:
<223> OTHER INFORMATION: Targeting domain

<400> SEQUENCE: 739
uccacacacu cgcuucugga acgu 24

<210> SEQ ID NO 740
<211> LENGTH: 18
<212> TYPE: RNA
<213> ORGANISM: Artificial Sequence
<220> FEATURE:
<223> OTHER INFORMATION: Targeting domain

<400> SEQUENCE: 740
cucaaugcaa auaucugu 18

<210> SEQ ID NO 741
<211> LENGTH: 19
<212> TYPE: RNA
<213> ORGANISM: Artificial Sequence
<220> FEATURE:
<223> OTHER INFORMATION: Targeting domain

<400> SEQUENCE: 741
ucucaaugca aauaucugu 19

<210> SEQ ID NO 742
<211> LENGTH: 20
<212> TYPE: RNA
<213> ORGANISM: Artificial Sequence
<220> FEATURE:
<223> OTHER INFORMATION: Targeting domain

<400> SEQUENCE: 742
aucucaaugc aaauaucugu 20

<210> SEQ ID NO 743
<211> LENGTH: 21
<212> TYPE: RNA
<213> ORGANISM: Artificial Sequence
<220> FEATURE:
<223> OTHER INFORMATION: Targeting domain

<400> SEQUENCE: 743
uaucucaaug caaauaucug u 21

<210> SEQ ID NO 744
<211> LENGTH: 22
<212> TYPE: RNA
<213> ORGANISM: Artificial Sequence
<220> FEATURE:
<223> OTHER INFORMATION: Targeting domain

<400> SEQUENCE: 744
cuaucucaau gcaaauaucu gu 22

<210> SEQ ID NO 745
<211> LENGTH: 23
<212> TYPE: RNA
<213> ORGANISM: Artificial Sequence
<220> FEATURE:
<223> OTHER INFORMATION: Targeting domain

<400> SEQUENCE: 745
acuaucucaa ugcaaauauc ugu 23

<210> SEQ ID NO 746
<211> LENGTH: 24
<212> TYPE: RNA
<213> ORGANISM: Artificial Sequence
<220> FEATURE:
<223> OTHER INFORMATION: Targeting domain

<400> SEQUENCE: 746
cacuaucuca augcaaauau cugu 24

<210> SEQ ID NO 747
<211> LENGTH: 18
<212> TYPE: RNA
<213> ORGANISM: Artificial Sequence
<220> FEATURE:
<223> OTHER INFORMATION: Targeting domain

<400> SEQUENCE: 747
aguuccacac acucgcuu 18

<210> SEQ ID NO 748
<211> LENGTH: 19
<212> TYPE: RNA
<213> ORGANISM: Artificial Sequence
<220> FEATURE:
<223> OTHER INFORMATION: Targeting domain

<400> SEQUENCE: 748
caguuccaca cacucgcuu 19

<210> SEQ ID NO 749
<211> LENGTH: 20
<212> TYPE: RNA
<213> ORGANISM: Artificial Sequence
<220> FEATURE:
<223> OTHER INFORMATION: Targeting domain

<400> SEQUENCE: 749
gcaguuccac acacucgcuu 20

<210> SEQ ID NO 750
<211> LENGTH: 21
<212> TYPE: RNA
<213> ORGANISM: Artificial Sequence
<220> FEATURE:
<223> OTHER INFORMATION: Targeting domain

<400> SEQUENCE: 750
agcaguucca cacacucgcu u 21

<210> SEQ ID NO 751
<211> LENGTH: 22
<212> TYPE: RNA
<213> ORGANISM: Artificial Sequence
<220> FEATURE:
<223> OTHER INFORMATION: Targeting domain

<400> SEQUENCE: 751
cagcaguucc acacacucgc uu 22

<210> SEQ ID NO 752
<211> LENGTH: 23
<212> TYPE: RNA
<213> ORGANISM: Artificial Sequence
<220> FEATURE:
<223> OTHER INFORMATION: Targeting domain

<400> SEQUENCE: 752
ucagcaguuc cacacacucg cuu 23

<210> SEQ ID NO 753
<211> LENGTH: 24
<212> TYPE: RNA
<213> ORGANISM: Artificial Sequence
<220> FEATURE:
<223> OTHER INFORMATION: Targeting domain

<400> SEQUENCE: 753
uucagcaguu ccacacacuc gcuu 24

<210> SEQ ID NO 754
<211> LENGTH: 18
<212> TYPE: RNA
<213> ORGANISM: Artificial Sequence
<220> FEATURE:
<223> OTHER INFORMATION: Targeting domain

<400> SEQUENCE: 754
aauuagcagu auccucuu 18

<210> SEQ ID NO 755
<211> LENGTH: 19
<212> TYPE: RNA
<213> ORGANISM: Artificial Sequence
<220> FEATURE:
<223> OTHER INFORMATION: Targeting domain

<400> SEQUENCE: 755
aaauuagcag uauccucuu 19

<210> SEQ ID NO 756
<211> LENGTH: 21
<212> TYPE: RNA
<213> ORGANISM: Artificial Sequence
<220> FEATURE:
<223> OTHER INFORMATION: Targeting domain

<400> SEQUENCE: 756
aaaaauuagc aguauccucu u 21

<210> SEQ ID NO 757
<211> LENGTH: 22
<212> TYPE: RNA
<213> ORGANISM: Artificial Sequence
<220> FEATURE:
<223> OTHER INFORMATION: Targeting domain

<400> SEQUENCE: 757
aaaaaauuag caguauccuc uu 22

<210> SEQ ID NO 758
<211> LENGTH: 23
<212> TYPE: RNA
<213> ORGANISM: Artificial Sequence
<220> FEATURE:
<223> OTHER INFORMATION: Targeting domain

<400> SEQUENCE: 758
aaaaaaauua gcaguauccu cuu 23

<210> SEQ ID NO 759
<211> LENGTH: 24
<212> TYPE: RNA
<213> ORGANISM: Artificial Sequence
<220> FEATURE:
<223> OTHER INFORMATION: Targeting domain

<400> SEQUENCE: 759
aaaaaaaauu agcaguaucc ucuu 24

<210> SEQ ID NO 760
<211> LENGTH: 17
<212> TYPE: RNA
<213> ORGANISM: Artificial Sequence
<220> FEATURE:
<223> OTHER INFORMATION: Targeting domain

<400> SEQUENCE: 760
gaagaaaacu agcuaaa 17

<210> SEQ ID NO 761
<211> LENGTH: 17
<212> TYPE: RNA
<213> ORGANISM: Artificial Sequence
<220> FEATURE:
<223> OTHER INFORMATION: Targeting domain

<400> SEQUENCE: 761
gcagcaguau ccucuug 17

<210> SEQ ID NO 762
<211> LENGTH: 20
<212> TYPE: RNA
<213> ORGANISM: Artificial Sequence
<220> FEATURE:
<223> OTHER INFORMATION: Targeting domain

<400> SEQUENCE: 762
ggagaagaaa acuagcuaaa 20

<210> SEQ ID NO 763

<211> LENGTH: 20
<212> TYPE: RNA
<213> ORGANISM: Artificial Sequence
<220> FEATURE:
<223> OTHER INFORMATION: Targeting domain

<400> SEQUENCE: 763
gggagaagaa aacuagcuaa 20

<210> SEQ ID NO 764
<211> LENGTH: 20
<212> TYPE: RNA
<213> ORGANISM: Artificial Sequence
<220> FEATURE:
<223> OTHER INFORMATION: Targeting domain

<400> SEQUENCE: 764
guccugguau cuucuauggu 20

<210> SEQ ID NO 765
<211> LENGTH: 17
<212> TYPE: RNA
<213> ORGANISM: Artificial Sequence
<220> FEATURE:
<223> OTHER INFORMATION: Targeting domain

<400> SEQUENCE: 765
agaagaaaac uagcuaa 17

<210> SEQ ID NO 766
<211> LENGTH: 17
<212> TYPE: RNA
<213> ORGANISM: Artificial Sequence
<220> FEATURE:
<223> OTHER INFORMATION: Targeting domain

<400> SEQUENCE: 766
aguccuggua ucuucua 17

<210> SEQ ID NO 767
<211> LENGTH: 17
<212> TYPE: RNA
<213> ORGANISM: Artificial Sequence
<220> FEATURE:
<223> OTHER INFORMATION: Targeting domain

<400> SEQUENCE: 767
ccaccauaga agauacc 17

<210> SEQ ID NO 768
<211> LENGTH: 17
<212> TYPE: RNA
<213> ORGANISM: Artificial Sequence
<220> FEATURE:
<223> OTHER INFORMATION: Targeting domain

<400> SEQUENCE: 768
ccugguaucu ucuaugg 17

<210> SEQ ID NO 769
<211> LENGTH: 17
<212> TYPE: RNA
<213> ORGANISM: Artificial Sequence
<220> FEATURE:
<223> OTHER INFORMATION: Targeting domain

<400> SEQUENCE: 769
cagcaguauc cucuugg 17

<210> SEQ ID NO 770
<211> LENGTH: 17
<212> TYPE: RNA
<213> ORGANISM: Artificial Sequence
<220> FEATURE:
<223> OTHER INFORMATION: Targeting domain

<400> SEQUENCE: 770
aauuggaaug acugaau 17

<210> SEQ ID NO 771
<211> LENGTH: 17
<212> TYPE: RNA
<213> ORGANISM: Artificial Sequence
<220> FEATURE:
<223> OTHER INFORMATION: Targeting domain

<400> SEQUENCE: 771
cugguaucuu cuauggu 17

<210> SEQ ID NO 772
<211> LENGTH: 17
<212> TYPE: RNA
<213> ORGANISM: Artificial Sequence
<220> FEATURE:
<223> OTHER INFORMATION: Targeting domain

<400> SEQUENCE: 772
agcagcagua uccucuu 17

<210> SEQ ID NO 773
<211> LENGTH: 20
<212> TYPE: RNA
<213> ORGANISM: Artificial Sequence
<220> FEATURE:
<223> OTHER INFORMATION: Targeting domain

<400> SEQUENCE: 773
agaaguccug guaucuucua 20

<210> SEQ ID NO 774
<211> LENGTH: 20
<212> TYPE: RNA
<213> ORGANISM: Artificial Sequence
<220> FEATURE:
<223> OTHER INFORMATION: Targeting domain

<400> SEQUENCE: 774
cucccaccau agaagauacc 20

<210> SEQ ID NO 775
<211> LENGTH: 20
<212> TYPE: RNA
<213> ORGANISM: Artificial Sequence
<220> FEATURE:
<223> OTHER INFORMATION: Targeting domain

<400> SEQUENCE: 775
aguccuggua ucuucuaugg 20

<210> SEQ ID NO 776
<211> LENGTH: 20
<212> TYPE: RNA

<213> ORGANISM: Artificial Sequence
<220> FEATURE:
<223> OTHER INFORMATION: Targeting domain

<400> SEQUENCE: 776
aagcagcagu auccucuugg 20

<210> SEQ ID NO 777
<211> LENGTH: 20
<212> TYPE: RNA
<213> ORGANISM: Artificial Sequence
<220> FEATURE:
<223> OTHER INFORMATION: Targeting domain

<400> SEQUENCE: 777
uaagcagcag uauccucuug 20

<210> SEQ ID NO 778
<211> LENGTH: 20
<212> TYPE: RNA
<213> ORGANISM: Artificial Sequence
<220> FEATURE:
<223> OTHER INFORMATION: Targeting domain

<400> SEQUENCE: 778
agaauaaauu agagaaaaau 20

<210> SEQ ID NO 779
<211> LENGTH: 20
<212> TYPE: RNA
<213> ORGANISM: Artificial Sequence
<220> FEATURE:
<223> OTHER INFORMATION: Targeting domain

<400> SEQUENCE: 779
aaaaauugga augacugaau 20

<210> SEQ ID NO 780
<211> LENGTH: 20
<212> TYPE: RNA
<213> ORGANISM: Artificial Sequence
<220> FEATURE:
<223> OTHER INFORMATION: Targeting domain

<400> SEQUENCE: 780
auuaagcagc aguauccucu 20

<210> SEQ ID NO 781
<211> LENGTH: 20
<212> TYPE: RNA
<213> ORGANISM: Artificial Sequence
<220> FEATURE:
<223> OTHER INFORMATION: Targeting domain

<400> SEQUENCE: 781
uuaagcagca guauccucuu 20

<210> SEQ ID NO 782
<211> LENGTH: 17
<212> TYPE: RNA
<213> ORGANISM: Artificial Sequence
<220> FEATURE:
<223> OTHER INFORMATION: Targeting domain

<400> SEQUENCE: 782
auaaauuaga gaaaaau 17

<210> SEQ ID NO 783
<211> LENGTH: 17
<212> TYPE: RNA
<213> ORGANISM: Artificial Sequence
<220> FEATURE:
<223> OTHER INFORMATION: Targeting domain

<400> SEQUENCE: 783
aagcagcagu auccucu 17

<210> SEQ ID NO 784
<211> LENGTH: 20
<212> TYPE: RNA
<213> ORGANISM: Artificial Sequence
<220> FEATURE:
<223> OTHER INFORMATION: Targeting domain

<400> SEQUENCE: 784
gaagaaaacu agcuaaaggg 20

<210> SEQ ID NO 785
<211> LENGTH: 22
<212> TYPE: RNA
<213> ORGANISM: Artificial Sequence
<220> FEATURE:
<223> OTHER INFORMATION: Targeting domain

<400> SEQUENCE: 785
gagaagaaaa cuagcuaaag gg 22

<210> SEQ ID NO 786
<211> LENGTH: 23
<212> TYPE: RNA
<213> ORGANISM: Artificial Sequence
<220> FEATURE:
<223> OTHER INFORMATION: Targeting domain

<400> SEQUENCE: 786
ggagaagaaa acuagcuaaa ggg 23

<210> SEQ ID NO 787
<211> LENGTH: 24
<212> TYPE: RNA
<213> ORGANISM: Artificial Sequence
<220> FEATURE:
<223> OTHER INFORMATION: Targeting domain

<400> SEQUENCE: 787
gggagaagaa aacuagcuaa aggg 24

<210> SEQ ID NO 788
<211> LENGTH: 19
<212> TYPE: RNA
<213> ORGANISM: Artificial Sequence
<220> FEATURE:
<223> OTHER INFORMATION: Targeting domain

<400> SEQUENCE: 788
gaauaaauua gagaaaaau 19

<210> SEQ ID NO 789
<211> LENGTH: 22
<212> TYPE: RNA
<213> ORGANISM: Artificial Sequence
<220> FEATURE:

<223> OTHER INFORMATION: Targeting domain

<400> SEQUENCE: 789
gaagaauaaa uuagagaaaa au 22

<210> SEQ ID NO 790
<211> LENGTH: 23
<212> TYPE: RNA
<213> ORGANISM: Artificial Sequence
<220> FEATURE:
<223> OTHER INFORMATION: Targeting domain

<400> SEQUENCE: 790
ggaagaauaa auuagagaaa aau 23

<210> SEQ ID NO 791
<211> LENGTH: 24
<212> TYPE: RNA
<213> ORGANISM: Artificial Sequence
<220> FEATURE:
<223> OTHER INFORMATION: Targeting domain

<400> SEQUENCE: 791
gggaagaaua aauuagagaa aaau 24

<210> SEQ ID NO 792
<211> LENGTH: 18
<212> TYPE: RNA
<213> ORGANISM: Artificial Sequence
<220> FEATURE:
<223> OTHER INFORMATION: Targeting domain

<400> SEQUENCE: 792
agagaaaaau uggaauga 18

<210> SEQ ID NO 793
<211> LENGTH: 19
<212> TYPE: RNA
<213> ORGANISM: Artificial Sequence
<220> FEATURE:
<223> OTHER INFORMATION: Targeting domain

<400> SEQUENCE: 793
uagagaaaaa uuggaauga 19

<210> SEQ ID NO 794
<211> LENGTH: 20
<212> TYPE: RNA
<213> ORGANISM: Artificial Sequence
<220> FEATURE:
<223> OTHER INFORMATION: Targeting domain

<400> SEQUENCE: 794
uuagagaaaa auuggaauga 20

<210> SEQ ID NO 795
<211> LENGTH: 21
<212> TYPE: RNA
<213> ORGANISM: Artificial Sequence
<220> FEATURE:
<223> OTHER INFORMATION: Targeting domain

<400> SEQUENCE: 795
auuagagaaa aauuggaaug a 21

<210> SEQ ID NO 796
<211> LENGTH: 22
<212> TYPE: RNA
<213> ORGANISM: Artificial Sequence
<220> FEATURE:
<223> OTHER INFORMATION: Targeting domain

<400> SEQUENCE: 796
aauuagagaa aaauuggaau ga 22

<210> SEQ ID NO 797
<211> LENGTH: 23
<212> TYPE: RNA
<213> ORGANISM: Artificial Sequence
<220> FEATURE:
<223> OTHER INFORMATION: Targeting domain

<400> SEQUENCE: 797
aaauuagaga aaaauuggaa uga 23

<210> SEQ ID NO 798
<211> LENGTH: 24
<212> TYPE: RNA
<213> ORGANISM: Artificial Sequence
<220> FEATURE:
<223> OTHER INFORMATION: Targeting domain

<400> SEQUENCE: 798
uaaauuagag aaaaauugga auga 24

<210> SEQ ID NO 799
<211> LENGTH: 18
<212> TYPE: RNA
<213> ORGANISM: Artificial Sequence
<220> FEATURE:
<223> OTHER INFORMATION: Targeting domain

<400> SEQUENCE: 799
agaaaacuag cuaaaggg 18

<210> SEQ ID NO 800
<211> LENGTH: 19
<212> TYPE: RNA
<213> ORGANISM: Artificial Sequence
<220> FEATURE:
<223> OTHER INFORMATION: Targeting domain

<400> SEQUENCE: 800
aagaaaacua gcuaaaggg 19

<210> SEQ ID NO 801
<211> LENGTH: 21
<212> TYPE: RNA
<213> ORGANISM: Artificial Sequence
<220> FEATURE:
<223> OTHER INFORMATION: Targeting domain

<400> SEQUENCE: 801
agaagaaaac uagcuaaagg g 21

<210> SEQ ID NO 802
<211> LENGTH: 18
<212> TYPE: RNA
<213> ORGANISM: Artificial Sequence
<220> FEATURE:
<223> OTHER INFORMATION: Targeting domain

<400> SEQUENCE: 802 aauaaaauuag agaaaaau 18

<210> SEQ ID NO 803
<211> LENGTH: 21
<212> TYPE: RNA
<213> ORGANISM: Artificial Sequence
<220> FEATURE:
<223> OTHER INFORMATION: Targeting domain

<400> SEQUENCE: 803
aagaauaaau uagagaaaaa u 21

<210> SEQ ID NO 804
<211> LENGTH: 18
<212> TYPE: RNA
<213> ORGANISM: Artificial Sequence
<220> FEATURE:
<223> OTHER INFORMATION: Targeting domain

<400> SEQUENCE: 804
aguuuucuuc ucccacca 18

<210> SEQ ID NO 805
<211> LENGTH: 19
<212> TYPE: RNA
<213> ORGANISM: Artificial Sequence
<220> FEATURE:
<223> OTHER INFORMATION: Targeting domain

<400> SEQUENCE: 805
uaguuuucuu cucccacca 19

<210> SEQ ID NO 806
<211> LENGTH: 20
<212> TYPE: RNA
<213> ORGANISM: Artificial Sequence
<220> FEATURE:
<223> OTHER INFORMATION: Targeting domain

<400> SEQUENCE: 806
cuaguuuucu ucucccacca 20

<210> SEQ ID NO 807
<211> LENGTH: 21
<212> TYPE: RNA
<213> ORGANISM: Artificial Sequence
<220> FEATURE:
<223> OTHER INFORMATION: Targeting domain

<400> SEQUENCE: 807
gcuaguuuuc uucucccacc a 21

<210> SEQ ID NO 808
<211> LENGTH: 22
<212> TYPE: RNA
<213> ORGANISM: Artificial Sequence
<220> FEATURE:
<223> OTHER INFORMATION: Targeting domain

<400> SEQUENCE: 808
agcuaguuuu cuucucccac ca 22

<210> SEQ ID NO 809
<211> LENGTH: 23

<212> TYPE: RNA
<213> ORGANISM: Artificial Sequence
<220> FEATURE:
<223> OTHER INFORMATION: Targeting domain

<400> SEQUENCE: 809
uagcuaguuu ucuucuccca cca 23

<210> SEQ ID NO 810
<211> LENGTH: 24
<212> TYPE: RNA
<213> ORGANISM: Artificial Sequence
<220> FEATURE:
<223> OTHER INFORMATION: Targeting domain

<400> SEQUENCE: 810
uuagcuaguu uucuucuccc acca 24

<210> SEQ ID NO 811
<211> LENGTH: 18
<212> TYPE: RNA
<213> ORGANISM: Artificial Sequence
<220> FEATURE:
<223> OTHER INFORMATION: Targeting domain

<400> SEQUENCE: 811
ucccaccaua gaagauac 18

<210> SEQ ID NO 812
<211> LENGTH: 19
<212> TYPE: RNA
<213> ORGANISM: Artificial Sequence
<220> FEATURE:
<223> OTHER INFORMATION: Targeting domain

<400> SEQUENCE: 812
cucccaccau agaagauac 19

<210> SEQ ID NO 813
<211> LENGTH: 20
<212> TYPE: RNA
<213> ORGANISM: Artificial Sequence
<220> FEATURE:
<223> OTHER INFORMATION: Targeting domain

<400> SEQUENCE: 813
ucucccacca uagaagauac 20

<210> SEQ ID NO 814
<211> LENGTH: 21
<212> TYPE: RNA
<213> ORGANISM: Artificial Sequence
<220> FEATURE:
<223> OTHER INFORMATION: Targeting domain

<400> SEQUENCE: 814
uucucccacc auagaagaua c 21

<210> SEQ ID NO 815
<211> LENGTH: 22
<212> TYPE: RNA
<213> ORGANISM: Artificial Sequence
<220> FEATURE:
<223> OTHER INFORMATION: Targeting domain

<400> SEQUENCE: 815
cuucucccac cauagaagau ac 22

<210> SEQ ID NO 816
<211> LENGTH: 23
<212> TYPE: RNA
<213> ORGANISM: Artificial Sequence
<220> FEATURE:
<223> OTHER INFORMATION: Targeting domain

<400> SEQUENCE: 816
ucuucuccca ccauagaaga uac 23

<210> SEQ ID NO 817
<211> LENGTH: 24
<212> TYPE: RNA
<213> ORGANISM: Artificial Sequence
<220> FEATURE:
<223> OTHER INFORMATION: Targeting domain

<400> SEQUENCE: 817
uucuucuccc accauagaag auac 24

<210> SEQ ID NO 818
<211> LENGTH: 18
<212> TYPE: RNA
<213> ORGANISM: Artificial Sequence
<220> FEATURE:
<223> OTHER INFORMATION: Targeting domain

<400> SEQUENCE: 818
agaagaaaac uagcuaaa 18

<210> SEQ ID NO 819
<211> LENGTH: 19
<212> TYPE: RNA
<213> ORGANISM: Artificial Sequence
<220> FEATURE:
<223> OTHER INFORMATION: Targeting domain

<400> SEQUENCE: 819
gagaagaaaa cuagcuaaa 19

<210> SEQ ID NO 820
<211> LENGTH: 21
<212> TYPE: RNA
<213> ORGANISM: Artificial Sequence
<220> FEATURE:
<223> OTHER INFORMATION: Targeting domain

<400> SEQUENCE: 820
gggagaagaa aacuagcuaa a 21

<210> SEQ ID NO 821
<211> LENGTH: 22
<212> TYPE: RNA
<213> ORGANISM: Artificial Sequence
<220> FEATURE:
<223> OTHER INFORMATION: Targeting domain

<400> SEQUENCE: 821
ugggagaaga aaacuagcua aa 22

<210> SEQ ID NO 822
<211> LENGTH: 23
<212> TYPE: RNA
<213> ORGANISM: Artificial Sequence
<220> FEATURE:
<223> OTHER INFORMATION: Targeting domain

<400> SEQUENCE: 822
gugggagaag aaaacuagcu aaa 23

<210> SEQ ID NO 823
<211> LENGTH: 24
<212> TYPE: RNA
<213> ORGANISM: Artificial Sequence
<220> FEATURE:
<223> OTHER INFORMATION: Targeting domain

<400> SEQUENCE: 823
ggugggagaa gaaaacuagc uaaa 24

<210> SEQ ID NO 824
<211> LENGTH: 18
<212> TYPE: RNA
<213> ORGANISM: Artificial Sequence
<220> FEATURE:
<223> OTHER INFORMATION: Targeting domain

<400> SEQUENCE: 824
aaaauuggaa ugacugaa 18

<210> SEQ ID NO 825
<211> LENGTH: 19
<212> TYPE: RNA
<213> ORGANISM: Artificial Sequence
<220> FEATURE:
<223> OTHER INFORMATION: Targeting domain

<400> SEQUENCE: 825
aaaaauugga augacugaa 19

<210> SEQ ID NO 826
<211> LENGTH: 20
<212> TYPE: RNA
<213> ORGANISM: Artificial Sequence
<220> FEATURE:
<223> OTHER INFORMATION: Targeting domain

<400> SEQUENCE: 826
gaaaaauugg aaugacugaa 20

<210> SEQ ID NO 827
<211> LENGTH: 21
<212> TYPE: RNA
<213> ORGANISM: Artificial Sequence
<220> FEATURE:
<223> OTHER INFORMATION: Targeting domain

<400> SEQUENCE: 827
agaaaaauug gaaugacuga a 21

<210> SEQ ID NO 828
<211> LENGTH: 22
<212> TYPE: RNA
<213> ORGANISM: Artificial Sequence
<220> FEATURE:
<223> OTHER INFORMATION: Targeting domain

<400> SEQUENCE: 828
gagaaaaauu ggaaugacug aa 22

<210> SEQ ID NO 829
<211> LENGTH: 23
<212> TYPE: RNA
<213> ORGANISM: Artificial Sequence
<220> FEATURE:
<223> OTHER INFORMATION: Targeting domain

<400> SEQUENCE: 829
agagaaaaau uggaaugacu gaa 23

<210> SEQ ID NO 830
<211> LENGTH: 24
<212> TYPE: RNA
<213> ORGANISM: Artificial Sequence
<220> FEATURE:
<223> OTHER INFORMATION: Targeting domain

<400> SEQUENCE: 830
uagagaaaaa uuggaaugac ugaa 24

<210> SEQ ID NO 831
<211> LENGTH: 18
<212> TYPE: RNA
<213> ORGANISM: Artificial Sequence
<220> FEATURE:
<223> OTHER INFORMATION: Targeting domain

<400> SEQUENCE: 831
gagaagaaaa cuagcuaa 18

<210> SEQ ID NO 832
<211> LENGTH: 19
<212> TYPE: RNA
<213> ORGANISM: Artificial Sequence
<220> FEATURE:
<223> OTHER INFORMATION: Targeting domain

<400> SEQUENCE: 832
ggagaagaaa acuagcuaa 19

<210> SEQ ID NO 833
<211> LENGTH: 21
<212> TYPE: RNA
<213> ORGANISM: Artificial Sequence
<220> FEATURE:
<223> OTHER INFORMATION: Targeting domain

<400> SEQUENCE: 833
ugggagaaga aaacuagcua a 21

<210> SEQ ID NO 834
<211> LENGTH: 22
<212> TYPE: RNA
<213> ORGANISM: Artificial Sequence
<220> FEATURE:
<223> OTHER INFORMATION: Targeting domain

<400> SEQUENCE: 834
gugggagaag aaaacuagcu aa 22

<210> SEQ ID NO 835
<211> LENGTH: 23
<212> TYPE: RNA
<213> ORGANISM: Artificial Sequence
<220> FEATURE:
<223> OTHER INFORMATION: Targeting domain

<400> SEQUENCE: 835
ggugggagaa gaaaacuagc uaa 23

<210> SEQ ID NO 836
<211> LENGTH: 24
<212> TYPE: RNA
<213> ORGANISM: Artificial Sequence
<220> FEATURE:
<223> OTHER INFORMATION: Targeting domain

<400> SEQUENCE: 836
uggugggaga agaaaacuag cuaa 24

<210> SEQ ID NO 837
<211> LENGTH: 18
<212> TYPE: RNA
<213> ORGANISM: Artificial Sequence
<220> FEATURE:
<223> OTHER INFORMATION: Targeting domain

<400> SEQUENCE: 837
ggagaagaaa acuagcua 18

<210> SEQ ID NO 838
<211> LENGTH: 19
<212> TYPE: RNA
<213> ORGANISM: Artificial Sequence
<220> FEATURE:
<223> OTHER INFORMATION: Targeting domain

<400> SEQUENCE: 838
gggagaagaa aacuagcua 19

<210> SEQ ID NO 839
<211> LENGTH: 20
<212> TYPE: RNA
<213> ORGANISM: Artificial Sequence
<220> FEATURE:
<223> OTHER INFORMATION: Targeting domain

<400> SEQUENCE: 839
ugggagaaga aaacuagcua 20

<210> SEQ ID NO 840
<211> LENGTH: 21
<212> TYPE: RNA
<213> ORGANISM: Artificial Sequence
<220> FEATURE:
<223> OTHER INFORMATION: Targeting domain

<400> SEQUENCE: 840
gugggagaag aaaacuagcu a 21

<210> SEQ ID NO 841
<211> LENGTH: 22
<212> TYPE: RNA
<213> ORGANISM: Artificial Sequence
<220> FEATURE:
<223> OTHER INFORMATION: Targeting domain

<400> SEQUENCE: 841
ggugggagaa gaaaacuagc ua 22

<210> SEQ ID NO 842

-continued

<211> LENGTH: 23
<212> TYPE: RNA
<213> ORGANISM: Artificial Sequence
<220> FEATURE:
<223> OTHER INFORMATION: Targeting domain

<400> SEQUENCE: 842
uggugggaga agaaaacuag cua 23

<210> SEQ ID NO 843
<211> LENGTH: 24
<212> TYPE: RNA
<213> ORGANISM: Artificial Sequence
<220> FEATURE:
<223> OTHER INFORMATION: Targeting domain

<400> SEQUENCE: 843 augguggggag aagaaaacua gcua 24

<210> SEQ ID NO 844
<211> LENGTH: 18
<212> TYPE: RNA
<213> ORGANISM: Artificial Sequence
<220> FEATURE:
<223> OTHER INFORMATION: Targeting domain

<400> SEQUENCE: 844
uuaagcagca guauccuc 18

<210> SEQ ID NO 845
<211> LENGTH: 19
<212> TYPE: RNA
<213> ORGANISM: Artificial Sequence
<220> FEATURE:
<223> OTHER INFORMATION: Targeting domain

<400> SEQUENCE: 845
auuaagcagc aguauccuc 19

<210> SEQ ID NO 846
<211> LENGTH: 20
<212> TYPE: RNA
<213> ORGANISM: Artificial Sequence
<220> FEATURE:
<223> OTHER INFORMATION: Targeting domain

<400> SEQUENCE: 846
aauuaagcag caguauccuc 20

<210> SEQ ID NO 847
<211> LENGTH: 21
<212> TYPE: RNA
<213> ORGANISM: Artificial Sequence
<220> FEATURE:
<223> OTHER INFORMATION: Targeting domain

<400> SEQUENCE: 847
aaauuaagca gcaguauccu c 21

<210> SEQ ID NO 848
<211> LENGTH: 22
<212> TYPE: RNA
<213> ORGANISM: Artificial Sequence
<220> FEATURE:
<223> OTHER INFORMATION: Targeting domain

<400> SEQUENCE: 848
aaaauuaagc agcaguaucc uc 22

<210> SEQ ID NO 849
<211> LENGTH: 23
<212> TYPE: RNA
<213> ORGANISM: Artificial Sequence
<220> FEATURE:
<223> OTHER INFORMATION: Targeting domain

<400> SEQUENCE: 849
aaaaauuaag cagcaguauc cuc 23

<210> SEQ ID NO 850
<211> LENGTH: 24
<212> TYPE: RNA
<213> ORGANISM: Artificial Sequence
<220> FEATURE:
<223> OTHER INFORMATION: Targeting domain

<400> SEQUENCE: 850
aaaaaauuaa gcagcaguau ccuc 24

<210> SEQ ID NO 851
<211> LENGTH: 18
<212> TYPE: RNA
<213> ORGANISM: Artificial Sequence
<220> FEATURE:
<223> OTHER INFORMATION: Targeting domain

<400> SEQUENCE: 851
uaucuucuau ggugggag 18

<210> SEQ ID NO 852
<211> LENGTH: 19
<212> TYPE: RNA
<213> ORGANISM: Artificial Sequence
<220> FEATURE:
<223> OTHER INFORMATION: Targeting domain

<400> SEQUENCE: 852
guaucuucua uggugggag 19

<210> SEQ ID NO 853
<211> LENGTH: 20
<212> TYPE: RNA
<213> ORGANISM: Artificial Sequence
<220> FEATURE:
<223> OTHER INFORMATION: Targeting domain

<400> SEQUENCE: 853
gguaucuucu augguggggag 20

<210> SEQ ID NO 854
<211> LENGTH: 21
<212> TYPE: RNA
<213> ORGANISM: Artificial Sequence
<220> FEATURE:
<223> OTHER INFORMATION: Targeting domain

<400> SEQUENCE: 854
ugguaucuuc uaugguggga g 21

<210> SEQ ID NO 855
<211> LENGTH: 22
<212> TYPE: RNA

<213> ORGANISM: Artificial Sequence
<220> FEATURE:
<223> OTHER INFORMATION: Targeting domain

<400> SEQUENCE: 855
cugguaucuu cuaugguggg ag 22

<210> SEQ ID NO 856
<211> LENGTH: 23
<212> TYPE: RNA
<213> ORGANISM: Artificial Sequence
<220> FEATURE:
<223> OTHER INFORMATION: Targeting domain

<400> SEQUENCE: 856
ccugguaucu ucuauggugg gag 23

<210> SEQ ID NO 857
<211> LENGTH: 24
<212> TYPE: RNA
<213> ORGANISM: Artificial Sequence
<220> FEATURE:
<223> OTHER INFORMATION: Targeting domain

<400> SEQUENCE: 857
uccugguauc uucuauggug ggag 24

<210> SEQ ID NO 858
<211> LENGTH: 18
<212> TYPE: RNA
<213> ORGANISM: Artificial Sequence
<220> FEATURE:
<223> OTHER INFORMATION: Targeting domain

<400> SEQUENCE: 858
uccugguauc uucuaugg 18

<210> SEQ ID NO 859
<211> LENGTH: 19
<212> TYPE: RNA
<213> ORGANISM: Artificial Sequence
<220> FEATURE:
<223> OTHER INFORMATION: Targeting domain

<400> SEQUENCE: 859
guccugguau cuucuaugg 19

<210> SEQ ID NO 860
<211> LENGTH: 21
<212> TYPE: RNA
<213> ORGANISM: Artificial Sequence
<220> FEATURE:
<223> OTHER INFORMATION: Targeting domain

<400> SEQUENCE: 860
aaguccuggu aucuucuaug g 21

<210> SEQ ID NO 861
<211> LENGTH: 22
<212> TYPE: RNA
<213> ORGANISM: Artificial Sequence
<220> FEATURE:
<223> OTHER INFORMATION: Targeting domain

<400> SEQUENCE: 861
gaaguccugg uaucuucuau gg 22

<210> SEQ ID NO 862
<211> LENGTH: 23
<212> TYPE: RNA
<213> ORGANISM: Artificial Sequence
<220> FEATURE:
<223> OTHER INFORMATION: Targeting domain

<400> SEQUENCE: 862
agaaguccug guaucuucua ugg 23

<210> SEQ ID NO 863
<211> LENGTH: 24
<212> TYPE: RNA
<213> ORGANISM: Artificial Sequence
<220> FEATURE:
<223> OTHER INFORMATION: Targeting domain

<400> SEQUENCE: 863
aagaaguccu gguaucuucu augg 24

<210> SEQ ID NO 864
<211> LENGTH: 18
<212> TYPE: RNA
<213> ORGANISM: Artificial Sequence
<220> FEATURE:
<223> OTHER INFORMATION: Targeting domain

<400> SEQUENCE: 864
ugguaucuuc uauggugg 18

<210> SEQ ID NO 865
<211> LENGTH: 19
<212> TYPE: RNA
<213> ORGANISM: Artificial Sequence
<220> FEATURE:
<223> OTHER INFORMATION: Targeting domain

<400> SEQUENCE: 865
cugguaucuu cuauggugg 19

<210> SEQ ID NO 866
<211> LENGTH: 20
<212> TYPE: RNA
<213> ORGANISM: Artificial Sequence
<220> FEATURE:
<223> OTHER INFORMATION: Targeting domain

<400> SEQUENCE: 866
ccugguaucu ucuauggugg 20

<210> SEQ ID NO 867
<211> LENGTH: 21
<212> TYPE: RNA
<213> ORGANISM: Artificial Sequence
<220> FEATURE:
<223> OTHER INFORMATION: Targeting domain

<400> SEQUENCE: 867
uccugguauc uucuauggug g 21

<210> SEQ ID NO 868
<211> LENGTH: 22
<212> TYPE: RNA
<213> ORGANISM: Artificial Sequence
<220> FEATURE:

<223> OTHER INFORMATION: Targeting domain

<400> SEQUENCE: 868
guccugguau cuucuauggu gg 22

<210> SEQ ID NO 869
<211> LENGTH: 23
<212> TYPE: RNA
<213> ORGANISM: Artificial Sequence
<220> FEATURE:
<223> OTHER INFORMATION: Targeting domain

<400> SEQUENCE: 869
aguccuggua ucuucuaugg ugg 23

<210> SEQ ID NO 870
<211> LENGTH: 24
<212> TYPE: RNA
<213> ORGANISM: Artificial Sequence
<220> FEATURE:
<223> OTHER INFORMATION: Targeting domain

<400> SEQUENCE: 870
aaguccuggu aucuucuaug gugg 24

<210> SEQ ID NO 871
<211> LENGTH: 18
<212> TYPE: RNA
<213> ORGANISM: Artificial Sequence
<220> FEATURE:
<223> OTHER INFORMATION: Targeting domain

<400> SEQUENCE: 871
guccugguau cuucuaug 18

<210> SEQ ID NO 872
<211> LENGTH: 19
<212> TYPE: RNA
<213> ORGANISM: Artificial Sequence
<220> FEATURE:
<223> OTHER INFORMATION: Targeting domain

<400> SEQUENCE: 872
aguccuggua ucuucuaug 19

<210> SEQ ID NO 873
<211> LENGTH: 20
<212> TYPE: RNA
<213> ORGANISM: Artificial Sequence
<220> FEATURE:
<223> OTHER INFORMATION: Targeting domain

<400> SEQUENCE: 873
aaguccuggu aucuucuaug 20

<210> SEQ ID NO 874
<211> LENGTH: 21
<212> TYPE: RNA
<213> ORGANISM: Artificial Sequence
<220> FEATURE:
<223> OTHER INFORMATION: Targeting domain

<400> SEQUENCE: 874
gaaguccugg uaucuucuau g 21

-continued

<210> SEQ ID NO 875
<211> LENGTH: 22
<212> TYPE: RNA
<213> ORGANISM: Artificial Sequence
<220> FEATURE:
<223> OTHER INFORMATION: Targeting domain

<400> SEQUENCE: 875
agaaguccug guaucuucua ug 22

<210> SEQ ID NO 876
<211> LENGTH: 23
<212> TYPE: RNA
<213> ORGANISM: Artificial Sequence
<220> FEATURE:
<223> OTHER INFORMATION: Targeting domain

<400> SEQUENCE: 876
aagaaguccu gguaucuucu aug 23

<210> SEQ ID NO 877
<211> LENGTH: 24
<212> TYPE: RNA
<213> ORGANISM: Artificial Sequence
<220> FEATURE:
<223> OTHER INFORMATION: Targeting domain

<400> SEQUENCE: 877
aaagaagucc ugguaucuuc uaug 24

<210> SEQ ID NO 878
<211> LENGTH: 18
<212> TYPE: RNA
<213> ORGANISM: Artificial Sequence
<220> FEATURE:
<223> OTHER INFORMATION: Targeting domain

<400> SEQUENCE: 878
aaauuggaau gacugaau 18

<210> SEQ ID NO 879
<211> LENGTH: 19
<212> TYPE: RNA
<213> ORGANISM: Artificial Sequence
<220> FEATURE:
<223> OTHER INFORMATION: Targeting domain

<400> SEQUENCE: 879
aaaauuggaa ugacugaau 19

<210> SEQ ID NO 880
<211> LENGTH: 21
<212> TYPE: RNA
<213> ORGANISM: Artificial Sequence
<220> FEATURE:
<223> OTHER INFORMATION: Targeting domain

<400> SEQUENCE: 880
gaaaaauugg aaugacugaa u 21

<210> SEQ ID NO 881
<211> LENGTH: 22
<212> TYPE: RNA
<213> ORGANISM: Artificial Sequence
<220> FEATURE:
<223> OTHER INFORMATION: Targeting domain

<400> SEQUENCE: 881
agaaaaauug gaaugacuga au 22

<210> SEQ ID NO 882
<211> LENGTH: 23
<212> TYPE: RNA
<213> ORGANISM: Artificial Sequence
<220> FEATURE:
<223> OTHER INFORMATION: Targeting domain

<400> SEQUENCE: 882
gagaaaaauu ggaaugacug aau 23

<210> SEQ ID NO 883
<211> LENGTH: 24
<212> TYPE: RNA
<213> ORGANISM: Artificial Sequence
<220> FEATURE:
<223> OTHER INFORMATION: Targeting domain

<400> SEQUENCE: 883
agagaaaaau uggaaugacu gaau 24

<210> SEQ ID NO 884
<211> LENGTH: 18
<212> TYPE: RNA
<213> ORGANISM: Artificial Sequence
<220> FEATURE:
<223> OTHER INFORMATION: Targeting domain

<400> SEQUENCE: 884
uaagcagcag uauccucu 18

<210> SEQ ID NO 885
<211> LENGTH: 19
<212> TYPE: RNA
<213> ORGANISM: Artificial Sequence
<220> FEATURE:
<223> OTHER INFORMATION: Targeting domain

<400> SEQUENCE: 885
uuaagcagca guauccucu 19

<210> SEQ ID NO 886
<211> LENGTH: 21
<212> TYPE: RNA
<213> ORGANISM: Artificial Sequence
<220> FEATURE:
<223> OTHER INFORMATION: Targeting domain

<400> SEQUENCE: 886
aauuaagcag caguauccuc u 21

<210> SEQ ID NO 887
<211> LENGTH: 22
<212> TYPE: RNA
<213> ORGANISM: Artificial Sequence
<220> FEATURE:
<223> OTHER INFORMATION: Targeting domain

<400> SEQUENCE: 887
aaauuaagca gcaguauccu cu 22

<210> SEQ ID NO 888
<211> LENGTH: 23

<212> TYPE: RNA
<213> ORGANISM: Artificial Sequence
<220> FEATURE:
<223> OTHER INFORMATION: Targeting domain

<400> SEQUENCE: 888
aaaauuaagc agcaguaucc ucu 23

<210> SEQ ID NO 889
<211> LENGTH: 24
<212> TYPE: RNA
<213> ORGANISM: Artificial Sequence
<220> FEATURE:
<223> OTHER INFORMATION: Targeting domain

<400> SEQUENCE: 889
aaaaauuaag cagcaguauc cucu 24

<210> SEQ ID NO 890
<211> LENGTH: 18
<212> TYPE: RNA
<213> ORGANISM: Artificial Sequence
<220> FEATURE:
<223> OTHER INFORMATION: Targeting domain

<400> SEQUENCE: 890
ccugguaucu ucuauggu 18

<210> SEQ ID NO 891
<211> LENGTH: 19
<212> TYPE: RNA
<213> ORGANISM: Artificial Sequence
<220> FEATURE:
<223> OTHER INFORMATION: Targeting domain

<400> SEQUENCE: 891
uccugguauc uucuauggu 19

<210> SEQ ID NO 892
<211> LENGTH: 21
<212> TYPE: RNA
<213> ORGANISM: Artificial Sequence
<220> FEATURE:
<223> OTHER INFORMATION: Targeting domain

<400> SEQUENCE: 892
aguccuggua ucuucuaugg u 21

<210> SEQ ID NO 893
<211> LENGTH: 22
<212> TYPE: RNA
<213> ORGANISM: Artificial Sequence
<220> FEATURE:
<223> OTHER INFORMATION: Targeting domain

<400> SEQUENCE: 893
aaguccuggu aucuucuaug gu 22

<210> SEQ ID NO 894
<211> LENGTH: 23
<212> TYPE: RNA
<213> ORGANISM: Artificial Sequence
<220> FEATURE:
<223> OTHER INFORMATION: Targeting domain

<400> SEQUENCE: 894

-continued gaaguccugg uaucuucuau ggu 23

<210> SEQ ID NO 895
<211> LENGTH: 24
<212> TYPE: RNA
<213> ORGANISM: Artificial Sequence
<220> FEATURE:
<223> OTHER INFORMATION: Targeting domain

<400> SEQUENCE: 895
agaaguccug guaucuucua uggu 24

<210> SEQ ID NO 896
<211> LENGTH: 18
<212> TYPE: RNA
<213> ORGANISM: Artificial Sequence
<220> FEATURE:
<223> OTHER INFORMATION: Targeting domain

<400> SEQUENCE: 896
aagcagcagu auccucuu 18

<210> SEQ ID NO 897
<211> LENGTH: 19
<212> TYPE: RNA
<213> ORGANISM: Artificial Sequence
<220> FEATURE:
<223> OTHER INFORMATION: Targeting domain

<400> SEQUENCE: 897
uaagcagcag uauccucuu 19

<210> SEQ ID NO 898
<211> LENGTH: 21
<212> TYPE: RNA
<213> ORGANISM: Artificial Sequence
<220> FEATURE:
<223> OTHER INFORMATION: Targeting domain

<400> SEQUENCE: 898
auuaagcagc aguauccucu u 21

<210> SEQ ID NO 899
<211> LENGTH: 22
<212> TYPE: RNA
<213> ORGANISM: Artificial Sequence
<220> FEATURE:
<223> OTHER INFORMATION: Targeting domain

<400> SEQUENCE: 899
aauuaagcag caguauccuc uu 22

<210> SEQ ID NO 900
<211> LENGTH: 23
<212> TYPE: RNA
<213> ORGANISM: Artificial Sequence
<220> FEATURE:
<223> OTHER INFORMATION: Targeting domain

<400> SEQUENCE: 900
aaauuaagca gcaguauccu cuu 23

<210> SEQ ID NO 901
<211> LENGTH: 24
<212> TYPE: RNA
<213> ORGANISM: Artificial Sequence
<220> FEATURE:
<223> OTHER INFORMATION: Targeting domain

<400> SEQUENCE: 901
aaaauuaagc agcaguaucc ucuu 24

<210> SEQ ID NO 902
<211> LENGTH: 4758
<212> TYPE: DNA
<213> ORGANISM: Homo sapiens
<220> FEATURE:
<221> NAME/KEY: misc_feature
<222> LOCATION: (2716)..(2719)
<223> OTHER INFORMATION: HPFH deletion site (4 bp del -225 to -222)
<220> FEATURE:
<221> NAME/KEY: misc_feature
<222> LOCATION: (2748)..(2753)
<223> OTHER INFORMATION: GATA1 binding motif
<220> FEATURE:
<221> NAME/KEY: misc_feature
<222> LOCATION: (2762)..(2767)
<223> OTHER INFORMATION: GATA1 binding motif
<220> FEATURE:
<221> NAME/KEY: misc_feature
<222> LOCATION: (2791)..(2799)
<223> OTHER INFORMATION: FKLF transcription factor binding motif
<220> FEATURE:
<221> NAME/KEY: misc_feature
<222> LOCATION: (2823)..(2830)
<223> OTHER INFORMATION: CP1/Coup TFII binding motif
<220> FEATURE:
<221> NAME/KEY: misc_feature
<222> LOCATION: (2824)..(2836)
<223> OTHER INFORMATION: HPFH deletion site (13 bp del -114 to -102)
<220> FEATURE:
<221> NAME/KEY: misc_feature
<222> LOCATION: (2991)..(2993)
<223> OTHER INFORMATION: Start codon

<400> SEQUENCE: 902
tttaggaagt caaggtttag gcagggatag ccattctatt ttattagggg caatactatt 60
tccaacggca tctggctttt ctcagccctt gtgaggctct acagggaggt tgaggtgtta 120
gagatcagag caggaaacag gtttttcttt ccacggtaac tacaatgaag tgatccttac 180
tttactaagg aacttttcat tttaagtgtt gacgcatgcc taaagaggtg aaattaatcc 240
cataccctta agtctacaga ctggtcacag catttcaagg aggagacctc attgtaagct 300
tctagggagg tggggactta ggtgaaggaa atgagccagc agaagctcac aagtcagcat 360
cagcgtgtca tgtctcagca gcagaacagc acggtcagat gaaaatatag tgtgaagaat 420
ttgtataaca ttaattgaga aggcagattc actggagttc ttatataatt gaaagttaat 480
gcacgttaat aagcaagagt ttagtttaat gtgatggtgt tatgaactta acgcttgtgt 540
ctccagaaaa ttcacatgct gaatccccaa ctcccaattg gctccatttg tgggggaggc 600
tttggaaaag taatcaggtt tagaggagct catgagagca gatccccatc atagaattat 660
tttcctcatc agaagcagag agattagcca tttctcttcc ttctggtgag gacacagtgg 720
gaagtcagcc acctgcaacc caggaagaga gccctgacca ggaaccagca gaaaagtgag 780
aaaaaatcct gttgttgaag tcacccagtc tatgctattt tgttatagca ccttgcacta 840
agtaaggcag atgaagaaag agaaaaaaat aagcttcggt gttcagtgga ttagaaacca 900
tgtttatctc aggtttacaa atctccactt gtcctctgtg tttcagaata aaataccaac 960
tctactactc tcatctgtaa gatgcaaata gtaagcctga gcccttctgt ctaactttga 1020
attctatttt ttcttcaacg tactttaggc ttgtaatgtg tttatataca gtgaaatgtc 1080

-continued

```
aagttctttc tttatatttc tttctttctt ttttttcctc agcctcagag ttttccacat   1140
gcccttccta ctttcaggaa cttctttctc caaacgtctt ctgcctggct ccatcaaatc   1200
ataaaggacc cacttcaaat gccatcactc actaccattt cacaattcgc actttctttc   1260
tttgtccttt tttttttag taaaacaagt ttataaaaaa ttgaaggaat aaatgaatgg   1320
ctacttcata ggcagagtag acgcaagggc tactggttgc cgatttttat tgttattttt   1380
caatagtatg ctaaacaagg ggtagattat ttatgctgcc catttttaga ccataaaaga   1440
taacttcctg atgttgccat ggcatttttt tccttttaat tttatttcat ttcattttaa   1500
tttcgaaggt acatgtgcag gatgtgcagg cttgttacat gggtaaatgt gtgtctttct   1560
ggccttttag ccatctgtat caatgagcag atataagctt tacacaggat catgaaggat   1620
gaaagaattt caccaatatt ataataattt caatcaacct gatagcttag ggataaact   1680
aatttgaaga tacagcttgc ctccgataag ccagaattcc agagcttctg gcattataat   1740
ctagcaaggt tagagatcat ggatcacttt cagagaaaaa caaaaacaaa ctaaccaaaa   1800
gcaaaacaga accaaaaaac caccataaat acttcctacc ctgttaatgg tccaatatgt   1860
cagaaacagc actgtgttag aaataaagct gtctaaagta cactaatatt cgagttataa   1920
tagtgtgtgg actattagtc aataaaaaca acccttgcct ctttagagtt gttttccatg   1980
tacacgcaca tcttatgtct tagagtaaga ttccctgaga agtgaaccta gcatttatac   2040
aagataatta attctaatcc acagtacctg ccaaagaaca ttctaccatc atctttactg   2100
agcatagaag agctacgcca aaaccctggg tcatcagcca gcacacacac ttatccagtg   2160
gtaaatacac atcatctggt gtatacatac atacctgaat atggaatcaa atatttttct   2220
aagatgaaac agtcatgatt tatttcaaat aggtacggat aagtagatat tgaggtaagc   2280
attaggtctt atattatgta acactaatct attactgcgc tgaaactgtg gctttataga   2340
aattgttttc actgcactat tgagaaatta agagataatg gcaaaagtca caaagagtat   2400
attcaaaaag aagtatagca ctttttcctt agaaaccact gctaactgaa agagactaag   2460
atttgtcccg tcaaaaatcc tggacctatg cctaaaacac atttcacaat ccctgaactt   2520
ttcaaaaatt ggtacatgct ttagctttaa actacaggcc tcactggagc tagagacaag   2580
aaggtaaaaa acggctgaca aaagaagtcc tggtatcctc tatgatggga gaaggaaact   2640
agctaaaggg aagaataaat tagagaaaaa ctggaatgac tgaatcggaa caaggcaaag   2700
gctataaaaa aaattagcag tatcctcttg ggggcccctt ccccacacta tctcaatgca   2760
aatatctgtc tgaaacggtc cctggctaaa ctccacccat gggttggcca gccttgcctt   2820
gaccaatagc cttgacaagg caaacttgac caatagtctt agagtatcca gtgaggccag   2880
gggccggcgg ctggctaggg atgaagaata aaaggaagca cccttcagca gttccacaca   2940
ctcgcttctg gaacgtctga ggttatcaat aagctcctag tccagacgcc atgggtcatt   3000
tcacagagga ggacaaggct actatcacaa gcctgtgggg caaggtgaat gtggaagatg   3060
ctggaggaga aaccctggga aggtaggctc tggtgaccag gacaagggag ggaaggaagg   3120
accctgtgcc tggcaaaagt ccaggtcgct tctcaggatt tgtggcacct tctgactgtc   3180
aaactgttct tgtcaatctc acaggctcct ggttgtctac ccatggaccc agaggttctt   3240
tgacagcttt ggcaacctgt cctctgcctc tgccatcatg ggcaacccca aagtcaaggc   3300
acatggcaag aaggtgctga cttccttggg agatgccaca aagcacctgg atgatctcaa   3360
gggcaccttt gcccagctga gtgaactgca ctgtgacaag ctgcatgtgg atcctgagaa   3420
cttcaaggtg agtccaggag atgtttcagc cctgttgcct ttagtctcga ggcaacttag   3480
```

```
acaacggagt attgatctga gcacagcagg gtgtgagctg tttgaagata ctggggttgg   3540

gggtgaagaa actgcagagg actaactggg ctgagaccca gtggtaatgt tttagggcct   3600

aaggagtgcc tctaaaaatc tagatggaca attttgactt tgagaaaaga gaggtggaaa   3660

tgaggaaaat gacttttctt tattagattc cagtagaaag aactttcatc tttccctcat   3720

ttttgttgtt ttaaaacatc tatctggagg caggacaagt atggtcgtta aaaagatgca   3780

ggcagaaggc atatattggc tcagtcaaag tggggaactt tggtggccaa acatacattg   3840

ctaaggctat tcctatatca gctggacaca tataaaatgc tgctaatgct tcattacaaa   3900

cttatatcct ttaattccag atgggggcaa agtatgtcca ggggtgagga acaattgaaa   3960

catttgggct ggagtagatt ttgaaagtca gctctgtgtg tgtgtgtgtg tgtgcgcgcg   4020

cgcgtgtgtg tgtgtgtgtc agcgtgtgtt tcttttaacg tcttcagcct acaacataca   4080

gggttcatgg tggcaagaag atagcaagat ttaaattatg gccagtgact agtgcttgaa   4140

ggggaacaac tacctgcatt taatgggaag gcaaaatctc aggctttgag ggaagttaac   4200

ataggcttga ttctgggtgg aagcttggtg tgtagttatc tggaggccag gctggagctc   4260

tcagctcact atgggttcat ctttattgtc tcctttcatc tcaacagctc ctgggaaatg   4320

tgctggtgac cgttttggca atccatttcg gcaaagaatt cacccctgag gtgcaggctt   4380

cctggcagaa gatggtgact gcagtggcca gtgccctgtc ctccagatac cactgagctc   4440

actgcccatg attcagagct ttcaaggata ggctttattc tgcaagcaat acaaataata   4500

aatctattct gctgagagat cacacatgat ttcttcagc tcttttttt acatcttttt   4560

aaatatatga gccacaaagg gtttatattg agggaagtgt gtatgtgtat ttctgcatgc   4620

ctgtttgtgt ttgtggtgtg tgcatgctcc tcatttattt ttatatgaga tgtgcatttt   4680

gatgagcaaa taaaagcagt aaagacactt gtacacggga gttctgcaag tgggagtaaa   4740

tggtgtagga gaaatccg                                                 4758
```

<210> SEQ ID NO 903
<211> LENGTH: 4773
<212> TYPE: DNA
<213> ORGANISM: Homo sapiens
<220> FEATURE:
<221> NAME/KEY: misc_feature
<222> LOCATION: (1233)..(1238)
<223> OTHER INFORMATION: GATA1 binding site
<220> FEATURE:
<221> NAME/KEY: misc_feature
<222> LOCATION: (2672)..(2677)
<223> OTHER INFORMATION: GATA1 binding site
<220> FEATURE:
<221> NAME/KEY: misc_feature
<222> LOCATION: (2686)..(2691)
<223> OTHER INFORMATION: GATA1 binding site
<220> FEATURE:
<221> NAME/KEY: misc_feature
<222> LOCATION: (2715)..(2723)
<223> OTHER INFORMATION: FKLF transcription factor binding motif
<220> FEATURE:
<221> NAME/KEY: misc_feature
<222> LOCATION: (2747)..(2754)
<223> OTHER INFORMATION: CP1/Coup TFII binding motif
<220> FEATURE:
<221> NAME/KEY: misc_feature
<222> LOCATION: (2748)..(2760)
<223> OTHER INFORMATION: HPFH deletion site (13 bp del -114 to -102)
<220> FEATURE:
<221> NAME/KEY: misc_feature
<222> LOCATION: (2915)..(2917)
<223> OTHER INFORMATION: Start codon

<400> SEQUENCE: 903

```
ttatgtcatt accagagtta aaattctata atggcttctc actccctacc actgaggaca     60
agtttatgtc cttaggttta tgcttccctg aaacaatacc acctgctatt ctccacttta    120
catatcaacg gcactggttc tttatctaac tctctggcac agcaggagtt tgttttcttc    180
tgcttcagag ctttgaattt actatttcag cttctaaact ttatttggca atgccttccc    240
atggcagatt ccttctgtca ttttgcctct gttcgaatac tttctcctta atttcattct    300
tagttaataa tatctgaaat tattttgttg tttaacttaa ttattaattt tatgtatgtt    360
ctacctagat tataatcttc agaggaaagt tttattctct gacttattta acttaaatgc    420
ccactacttt aaaaattatg acatttattt aacagatatt tgctgaacaa atgtttgaaa    480
atacatggga aagaatgctt gaaaacactt gaaattgctt gtgtaaagaa acagttttat    540
cagttaggat ttaatcaatg tcagaagcaa tgatatagga aaaatcgagg aataagacag    600
ttatggataa ggagaaatca acaaactctt aaaagatatt gcctcaaaag cataagagga    660
aataagggtt tatacatgac ttttagaaca ctgccttggt ttttggataa atggggaagt    720
tgtttgaaaa caggagggat cctagatatt ccttagtctg aggaggagca attaagattc    780
acttgtttag aggctgggag tggtggctca cgcctgtaat cccagaattt tgggaggcca    840
aggcaggcag atcacctgag gtcaagagtt caagaccaac ctggccaaca tggtgaaatc    900
ccatctctac aaaaatacaa aaattagaca ggcatgatgg caagtgcctg taatcccagc    960
tacttgggag gctgaggaag gagaattgct tgaacctgga aggcaggagt tgcagtgagc   1020
cgagatcata ccactgcact ccagcctggg tgacagaaca agactctgtc tcaaaaaaaa   1080
aaaagagaga ttcaaaagat tcacttgttt aggccttagc gggcttagac accagtctct   1140
gacacattct taaaggtcag gctctacaaa tggaacccaa ccagactctc agatatggcc   1200
aaagatctat acacacccat ctcacagatc ccctatctta aagagaccct aatttgggtt   1260
cacctcagtc tctataatct gtaccagcat accaataaaa atctttctca cccatcctta   1320
gattgagaga agtcacttat tattatgtga gtaactggaa gatactgata agttgacaaa   1380
tctttttctt tcctttctta ttcaactttt attttaactt ccaaagaaca agtgcaatat   1440
gtgcagcttt gttgcgcagg tcaacatgta tctttctggt cttttagccg cctaacactt   1500
tgagcagata taagccttac acaggattat gaagtctgaa aggattccac caatattatt   1560
ataattccta tcaacctgat aggttagggg aaggtagagc tctcctccaa taagccagat   1620
ttccagagtt tctgacgtca taatctacca aggtcatgga tcgagttcag agaaaaaaca   1680
aaagcaaaac caaacctacc aaaaaataaa aatcccaaag aaaaaataaa gaaaaaaaca   1740
gcatgaatac ttcctgccat gttaagtggc caatatgtca gaaacagcac tgagttacag   1800
ataaagatgt ctaaactaca gtgacatccc agctgtcaca gtgtgtggac tattagtcaa   1860
taaaacagtc cctgcctctt aagagttgtt ttccatgcaa atacatgtct tatgtcttag   1920
aataagattc cctaagaagt gaacctagca tttatacaag ataattaatt ctaatccata   1980
gtatctggta aagagcattc taccatcatc tttaccgagc atagaagagc tacaccaaaa   2040
ccctgggtca tcagccagca catacactta tccagtgata aatacacatc atcgggtgcc   2100
tacatacata cctgaatata aaaaaaatac ttttgctgag atgaaacagg cgtgatttat   2160
ttcaaatagg tacggataag tagatattga agtaaggatt cagtcttata ttatattaca   2220
taacattaat ctattcctgc actgaaactg ttgctttata ggatttttca ctacactaat   2280
gagaacttaa gagataatgg cctaaaacca cagagagtat attcaaagat aagtatagca   2340
```

```
cttcttattt ggaaaccaat gcttactaaa tgagactaag acgtgtccca tcaaaaatcc   2400
tggacctatg cctaaaacac atttcacaat ccctgaactt ttcaaaaatt ggtacatgct   2460
ttaactttaa actacaggcc tcactggagc tacagacaag aaggtgaaaa acggctgaca   2520
aaagaagtcc tggtatcttc tatggtggga gaagaaaact agctaaaggg aagaataaat   2580
tagagaaaaa ttggaatgac tgaatcggaa caaggcaaag gctataaaaa aaattaagca   2640
gcagtatcct cttgggggcc ccttccccac actatctcaa tgcaaatatc tgtctgaaac   2700
ggtccctggc taaactccac ccatgggttg gccagccttg ccttgaccaa tagccttgac   2760
aaggcaaact tgaccaatag tcttagagta tccagtgagg ccaggggccg gcggctggct   2820
agggatgaag aataaaagga agcacccttc agcagttcca cacactcgct tctggaacgt   2880
ctgaggttat caataagctc ctagtccaga cgccatgggt catttcacag aggaggacaa   2940
ggctactatc acaagcctgt ggggcaaggt gaatgtggaa gatgctggag gagaaaccct   3000
gggaaggtag gctctggtga ccaggacaag ggagggaagg aaggaccctg tgcctggcaa   3060
aagtccaggt cgcttctcag gatttgtggc accttctgac tgtcaaactg ttcttgtcaa   3120
tctcacaggc tcctggttgt ctacccatgg acccagaggt tctttgacag ctttggcaac   3180
ctgtcctctg cctctgccat catgggcaac cccaaagtca aggcacatgg caagaaggtg   3240
ctgacttcct tgggagatgc cataaagcac ctggatgatc tcaagggcac ctttgcccag   3300
ctgagtgaac tgcactgtga caagctgcat gtggatcctg agaacttcaa ggtgagtcca   3360
ggagatgttt cagcactgtt gcctttagtc tcgaggcaac ttagacaact gagtattgat   3420
ctgagcacag cagggtgtga gctgtttgaa gatactgggg ttgggagtga agaaactgca   3480
gaggactaac tgggctgaga cccagtggca atgttttagg gcctaaggag tgcctctgaa   3540
aatctagatg gacaactttg actttgagaa aagagaggtg gaaatgagga aaatgacttt   3600
tctttattag atttcggtag aaagaacttt cacctttccc ctatttttgt tattcgtttt   3660
aaaacatcta tctggaggca ggacaagtat ggtcattaaa aagatgcagg cagaaggcat   3720
atattggctc agtcaaagtg gggaactttg gtggccaaac atacattgct aaggctattc   3780
ctatatcagc tggacacata taaaatgctg ctaatgcttc attacaaact tatatccttt   3840
aattccagat gggggcaaag tatgtccagg ggtgaggaac aattgaaaca tttgggctgg   3900
agtagatttt gaaagtcagc tctgtgtgtg tgtgtgtgtg tgtgcgcgcg tgtgtttgtg   3960
tgtgtgtgag agcgtgtgtt tcttttaacg ttttcagcct acagcataca gggttcatgg   4020
tggcaagaag ataacaagat ttaaattatg gccagtgact agtgctgcaa gaagaacaac   4080
tacctgcatt taatgggaaa gcaaaatctc aggctttgag ggaagttaac ataggcttga   4140
ttctgggtgg aagcttggtg tgtagttatc tggaggccag gctggagctc tcagctcact   4200
atgggttcat ctttattgtc tcctttcatc tcaacagctc ctgggaaatg tgctggtgac   4260
cgttttggca atccatttcg gcaaagaatt cacccctgag gtgcaggctt cctggcagaa   4320
gatggtgact ggagtggcca gtgccctgtc ctccagatac cactgagctc actgcccatg   4380
atgcagagct ttcaaggata ggctttattc tgcaagcaat caaataataa atctattctg   4440
ctaagagatc acacatggtt gtcttcagtt cttttttat gtctttttaa atatatgagc   4500
cacaaagggt tttatgttga gggatgtgtt tatgtgtatt tatacatggc tatgtgtgtt   4560
tgtgtcatgt gcacactcca cactttttg tttacgttag atgtgggttt tgatgagcaa   4620
ataaaagaac taggcaataa agaaacttgt acatgggagt tctgcaagtg ggagtaaaag   4680
```

-continued

```
gtgcaggaga aatctggttg gaagaaagac ctctatagga caggactcct cagaaacaga   4740

tgttttggaa gagatgggga aaggttcagt gaa                                4773


<210> SEQ ID NO 904
<211> LENGTH: 87
<212> TYPE: DNA
<213> ORGANISM: Artificial Sequence
<220> FEATURE:
<223> OTHER INFORMATION: ssODN1 5' homology arm

<400> SEQUENCE: 904

gggtgcttcc ttttattctt catccctagc cagccgccgg cccctggcct cactggatac     60

tctaagacta ttggtcaagt ttgcctt                                         87


<210> SEQ ID NO 905
<211> LENGTH: 89
<212> TYPE: DNA
<213> ORGANISM: Artificial Sequence
<220> FEATURE:
<223> OTHER INFORMATION: ssODN1 3' homology arm

<400> SEQUENCE: 905

gtcaaggcaa ggctggccaa cccatgggtg gagtttagcc agggaccgtt tcagacagat     60

atttgcattg agatagtgtg gggaagggg                                       89


<210> SEQ ID NO 906
<211> LENGTH: 176
<212> TYPE: DNA
<213> ORGANISM: Artificial Sequence
<220> FEATURE:
<223> OTHER INFORMATION: ssODN1

<400> SEQUENCE: 906

gggtgcttcc ttttattctt catccctagc cagccgccgg cccctggcct cactggatac     60

tctaagacta ttggtcaagt ttgccttgtc aaggcaaggc tggccaaccc atgggtggag    120

tttagccagg gaccgtttca gacagatatt tgcattgaga tagtgtgggg aagggg        176


<210> SEQ ID NO 907
<211> LENGTH: 87
<212> TYPE: DNA
<213> ORGANISM: Artificial Sequence
<220> FEATURE:
<223> OTHER INFORMATION: PhTx ssODN1 5' homology arm
<220> FEATURE:
<221> NAME/KEY: misc_feature
<222> LOCATION: (1)..(1)
<223> OTHER INFORMATION: Modified to contain phosphorothioate

<400> SEQUENCE: 907

gggtgcttcc ttttattctt catccctagc cagccgccgg cccctggcct cactggatac     60

tctaagacta ttggtcaagt ttgcctt                                         87


<210> SEQ ID NO 908
<211> LENGTH: 89
<212> TYPE: DNA
<213> ORGANISM: Artificial Sequence
<220> FEATURE:
<223> OTHER INFORMATION: PhTx ssODN1 3' homology arm
<220> FEATURE:
<221> NAME/KEY: misc_feature
<222> LOCATION: (89)..(89)
<223> OTHER INFORMATION: Modified to contain phosphorothioate

<400> SEQUENCE: 908
```

gtcaaggcaa ggctggccaa cccatgggtg gagtttagcc agggaccgtt tcagacagat 60
atttgcattg agatagtgtg gggaagggg 89

<210> SEQ ID NO 909
<211> LENGTH: 176
<212> TYPE: DNA
<213> ORGANISM: Artificial Sequence
<220> FEATURE:
<223> OTHER INFORMATION: PhTx ssODN1
<220> FEATURE:
<221> NAME/KEY: misc_feature
<222> LOCATION: (1)..(1)
<223> OTHER INFORMATION: Modified to contain phosphorothioate
<220> FEATURE:
<221> NAME/KEY: misc_feature
<222> LOCATION: (176)..(176)
<223> OTHER INFORMATION: Modified to contain phosphorothioate

<400> SEQUENCE: 909
gggtgcttcc ttttattctt catccctagc cagccgccgg cccctggcct cactggatac 60
tctaagacta ttggtcaagt ttgccttgtc aaggcaaggc tggccaaccc atgggtggag 120
tttagccagg gaccgtttca gacagatatt tgcattgaga tagtgtgggg aagggg 176

<210> SEQ ID NO 910
<211> LENGTH: 17
<212> TYPE: DNA
<213> ORGANISM: Artificial Sequence
<220> FEATURE:
<223> OTHER INFORMATION: targeting domain

<400> SEQUENCE: 910
ggctattggt caaggca 17

<210> SEQ ID NO 911
<211> LENGTH: 20
<212> TYPE: DNA
<213> ORGANISM: Artificial Sequence
<220> FEATURE:
<223> OTHER INFORMATION: targeting domain

<400> SEQUENCE: 911
caaggctatt ggtcaaggca 20

<210> SEQ ID NO 912
<211> LENGTH: 17
<212> TYPE: DNA
<213> ORGANISM: Artificial Sequence
<220> FEATURE:
<223> OTHER INFORMATION: targeting domain

<400> SEQUENCE: 912
tgccttgtca aggctat 17

<210> SEQ ID NO 913
<211> LENGTH: 20
<212> TYPE: DNA
<213> ORGANISM: Artificial Sequence
<220> FEATURE:
<223> OTHER INFORMATION: targeting domain

<400> SEQUENCE: 913
gtttgccttg tcaaggctat 20

<210> SEQ ID NO 914

<211> LENGTH: 17
<212> TYPE: DNA
<213> ORGANISM: Artificial Sequence
<220> FEATURE:
<223> OTHER INFORMATION: targeting domain

<400> SEQUENCE: 914
gaccaatagc cttgaca 17

<210> SEQ ID NO 915
<211> LENGTH: 20
<212> TYPE: DNA
<213> ORGANISM: Artificial Sequence
<220> FEATURE:
<223> OTHER INFORMATION: targeting domain

<400> SEQUENCE: 915
cttgaccaat agccttgaca 20

<210> SEQ ID NO 916
<211> LENGTH: 17
<212> TYPE: DNA
<213> ORGANISM: Artificial Sequence
<220> FEATURE:
<223> OTHER INFORMATION: targeting domain

<400> SEQUENCE: 916
gtcaaggcta ttggtca 17

<210> SEQ ID NO 917
<211> LENGTH: 20
<212> TYPE: DNA
<213> ORGANISM: Artificial Sequence
<220> FEATURE:
<223> OTHER INFORMATION: targeting domain

<400> SEQUENCE: 917
cttgtcaagg ctattggtca 20

<210> SEQ ID NO 918
<211> LENGTH: 17
<212> TYPE: DNA
<213> ORGANISM: Artificial Sequence
<220> FEATURE:
<223> OTHER INFORMATION: targeting domain

<400> SEQUENCE: 918
tcaagtttgc cttgtca 17

<210> SEQ ID NO 919
<211> LENGTH: 20
<212> TYPE: DNA
<213> ORGANISM: Artificial Sequence
<220> FEATURE:
<223> OTHER INFORMATION: targeting domain

<400> SEQUENCE: 919
tggtcaagtt tgccttgtca 20

<210> SEQ ID NO 920
<211> LENGTH: 20
<212> TYPE: RNA
<213> ORGANISM: Artificial Sequence
<220> FEATURE:
<223> OTHER INFORMATION: targeting domain plus PAM (NGG)

<400> SEQUENCE: 920
ggcuauuggu caaggcaagg 20

<210> SEQ ID NO 921
<211> LENGTH: 23
<212> TYPE: RNA
<213> ORGANISM: Artificial Sequence
<220> FEATURE:
<223> OTHER INFORMATION: targeting domain plus PAM (NGG)

<400> SEQUENCE: 921
caaggcuauu ggucaaggca agg 23

<210> SEQ ID NO 922
<211> LENGTH: 20
<212> TYPE: RNA
<213> ORGANISM: Artificial Sequence
<220> FEATURE:
<223> OTHER INFORMATION: targeting domain plus PAM (NGG)

<400> SEQUENCE: 922
ugccuuguca aggcuauugg 20

<210> SEQ ID NO 923
<211> LENGTH: 23
<212> TYPE: RNA
<213> ORGANISM: Artificial Sequence
<220> FEATURE:
<223> OTHER INFORMATION: targeting domain plus PAM (NGG)

<400> SEQUENCE: 923
guuugccuug ucaaggcuau ugg 23

<210> SEQ ID NO 924
<211> LENGTH: 20
<212> TYPE: RNA
<213> ORGANISM: Artificial Sequence
<220> FEATURE:
<223> OTHER INFORMATION: targeting domain plus PAM (NGG)

<400> SEQUENCE: 924
gaccaauagc cuugacaagg 20

<210> SEQ ID NO 925
<211> LENGTH: 23
<212> TYPE: RNA
<213> ORGANISM: Artificial Sequence
<220> FEATURE:
<223> OTHER INFORMATION: targeting domain plus PAM (NGG)

<400> SEQUENCE: 925
cuugaccaau agccuugaca agg 23

<210> SEQ ID NO 926
<211> LENGTH: 20
<212> TYPE: RNA
<213> ORGANISM: Artificial Sequence
<220> FEATURE:
<223> OTHER INFORMATION: targeting domain plus PAM (NGG)

<400> SEQUENCE: 926
gucaaggcua uuggucaagg 20

<210> SEQ ID NO 927
<211> LENGTH: 23
<212> TYPE: RNA

<213> ORGANISM: Artificial Sequence
<220> FEATURE:
<223> OTHER INFORMATION: targeting domain plus PAM (NGG)

<400> SEQUENCE: 927
cuugucaagg cuauugguca agg 23

<210> SEQ ID NO 928
<211> LENGTH: 20
<212> TYPE: RNA
<213> ORGANISM: Artificial Sequence
<220> FEATURE:
<223> OTHER INFORMATION: targeting domain plus PAM (NGG)

<400> SEQUENCE: 928
ucaaguuugc cuugucaagg 20

<210> SEQ ID NO 929
<211> LENGTH: 23
<212> TYPE: RNA
<213> ORGANISM: Artificial Sequence
<220> FEATURE:
<223> OTHER INFORMATION: targeting domain plus PAM (NGG)

<400> SEQUENCE: 929
uggucaaguu ugccuuguca agg 23

<210> SEQ ID NO 930
<211> LENGTH: 20
<212> TYPE: DNA
<213> ORGANISM: Artificial Sequence
<220> FEATURE:
<223> OTHER INFORMATION: targeting domain plus PAM (NGG)

<400> SEQUENCE: 930
ggctattggt caaggcaagg 20

<210> SEQ ID NO 931
<211> LENGTH: 23
<212> TYPE: DNA
<213> ORGANISM: Artificial Sequence
<220> FEATURE:
<223> OTHER INFORMATION: targeting domain plus PAM (NGG)

<400> SEQUENCE: 931
caaggctatt ggtcaaggca agg 23

<210> SEQ ID NO 932
<211> LENGTH: 20
<212> TYPE: DNA
<213> ORGANISM: Artificial Sequence
<220> FEATURE:
<223> OTHER INFORMATION: targeting domain plus PAM (NGG)

<400> SEQUENCE: 932
tgccttgtca aggctattgg 20

<210> SEQ ID NO 933
<211> LENGTH: 23
<212> TYPE: DNA
<213> ORGANISM: Artificial Sequence
<220> FEATURE:
<223> OTHER INFORMATION: targeting domain plus PAM (NGG)

<400> SEQUENCE: 933
gtttgccttg tcaaggctat tgg 23

<210> SEQ ID NO 934
<211> LENGTH: 20
<212> TYPE: DNA
<213> ORGANISM: Artificial Sequence
<220> FEATURE:
<223> OTHER INFORMATION: targeting domain plus PAM (NGG)

<400> SEQUENCE: 934
gaccaatagc cttgacaagg 20

<210> SEQ ID NO 935
<211> LENGTH: 23
<212> TYPE: DNA
<213> ORGANISM: Artificial Sequence
<220> FEATURE:
<223> OTHER INFORMATION: targeting domain plus PAM (NGG)

<400> SEQUENCE: 935
cttgaccaat agccttgaca agg 23

<210> SEQ ID NO 936
<211> LENGTH: 20
<212> TYPE: DNA
<213> ORGANISM: Artificial Sequence
<220> FEATURE:
<223> OTHER INFORMATION: targeting domain plus PAM (NGG)

<400> SEQUENCE: 936
gtcaaggcta ttggtcaagg 20

<210> SEQ ID NO 937
<211> LENGTH: 23
<212> TYPE: DNA
<213> ORGANISM: Artificial Sequence
<220> FEATURE:
<223> OTHER INFORMATION: targeting domain plus PAM (NGG)

<400> SEQUENCE: 937
cttgtcaagg ctattggtca agg 23

<210> SEQ ID NO 938
<211> LENGTH: 20
<212> TYPE: DNA
<213> ORGANISM: Artificial Sequence
<220> FEATURE:
<223> OTHER INFORMATION: targeting domain plus PAM (NGG)

<400> SEQUENCE: 938
tcaagtttgc cttgtcaagg 20

<210> SEQ ID NO 939
<211> LENGTH: 23
<212> TYPE: DNA
<213> ORGANISM: Artificial Sequence
<220> FEATURE:
<223> OTHER INFORMATION: targeting domain plus PAM (NGG)

<400> SEQUENCE: 939
tggtcaagtt tgccttgtca agg 23

<210> SEQ ID NO 940
<211> LENGTH: 17
<212> TYPE: RNA
<213> ORGANISM: Artificial Sequence
<220> FEATURE:

<223> OTHER INFORMATION: targeting domain

<400> SEQUENCE: 940
aguauccagu gaggcca 17

<210> SEQ ID NO 941
<211> LENGTH: 20
<212> TYPE: RNA
<213> ORGANISM: Artificial Sequence
<220> FEATURE:
<223> OTHER INFORMATION: targeting domain

<400> SEQUENCE: 941
ggcaaggcug gccaacccau 20

<210> SEQ ID NO 942
<211> LENGTH: 20
<212> TYPE: RNA
<213> ORGANISM: Artificial Sequence
<220> FEATURE:
<223> OTHER INFORMATION: targeting domain

<400> SEQUENCE: 942
uauuugcauu gagauagugu 20

<210> SEQ ID NO 943
<211> LENGTH: 17
<212> TYPE: DNA
<213> ORGANISM: Artificial Sequence
<220> FEATURE:
<223> OTHER INFORMATION: targeting domain

<400> SEQUENCE: 943
agtatccagt gaggcca 17

<210> SEQ ID NO 944
<211> LENGTH: 20
<212> TYPE: DNA
<213> ORGANISM: Artificial Sequence
<220> FEATURE:
<223> OTHER INFORMATION: targeting domain

<400> SEQUENCE: 944
ggcaaggctg gccaacccat 20

<210> SEQ ID NO 945
<211> LENGTH: 20
<212> TYPE: DNA
<213> ORGANISM: Artificial Sequence
<220> FEATURE:
<223> OTHER INFORMATION: targeting domain

<400> SEQUENCE: 945
tatttgcatt gagatagtgt 20

<210> SEQ ID NO 946
<211> LENGTH: 20
<212> TYPE: RNA
<213> ORGANISM: Artificial Sequence
<220> FEATURE:
<223> OTHER INFORMATION: targeting domain plus PAM (NGG)

<400> SEQUENCE: 946
aguauccagu gaggccaggg 20

<210> SEQ ID NO 947
<211> LENGTH: 23
<212> TYPE: RNA
<213> ORGANISM: Artificial Sequence
<220> FEATURE:
<223> OTHER INFORMATION: targeting domain plus PAM (NGG)

<400> SEQUENCE: 947
ggcaaggcug gccaacccau ggg 23

<210> SEQ ID NO 948
<211> LENGTH: 23
<212> TYPE: RNA
<213> ORGANISM: Artificial Sequence
<220> FEATURE:
<223> OTHER INFORMATION: targeting domain plus PAM (NGG)

<400> SEQUENCE: 948
uauuugcauu gagauagugu ggg 23

<210> SEQ ID NO 949
<211> LENGTH: 20
<212> TYPE: DNA
<213> ORGANISM: Artificial Sequence
<220> FEATURE:
<223> OTHER INFORMATION: targeting domain plus PAM (NGG)

<400> SEQUENCE: 949
agtatccagt gaggccaggg 20

<210> SEQ ID NO 950
<211> LENGTH: 23
<212> TYPE: DNA
<213> ORGANISM: Artificial Sequence
<220> FEATURE:
<223> OTHER INFORMATION: targeting domain plus PAM (NGG)

<400> SEQUENCE: 950
ggcaaggctg gccaacccat ggg 23

<210> SEQ ID NO 951
<211> LENGTH: 23
<212> TYPE: DNA
<213> ORGANISM: Artificial Sequence
<220> FEATURE:
<223> OTHER INFORMATION: targeting domain plus PAM (NGG)

<400> SEQUENCE: 951
tatttgcatt gagatagtgt ggg 23

<210> SEQ ID NO 952
<211> LENGTH: 20
<212> TYPE: RNA
<213> ORGANISM: Artificial Sequence
<220> FEATURE:
<223> OTHER INFORMATION: targeting domain

<400> SEQUENCE: 952
cuaacaguug cuuuuaucac 20

<210> SEQ ID NO 953
<211> LENGTH: 20
<212> TYPE: RNA
<213> ORGANISM: Artificial Sequence
<220> FEATURE:
<223> OTHER INFORMATION: targeting domain

<400> SEQUENCE: 953
gggcgugggu gggguagaag 20

<210> SEQ ID NO 954
<211> LENGTH: 20
<212> TYPE: RNA
<213> ORGANISM: Artificial Sequence
<220> FEATURE:
<223> OTHER INFORMATION: targeting domain

<400> SEQUENCE: 954
cucuuagaca uaacacacca 20

<210> SEQ ID NO 955
<211> LENGTH: 20
<212> TYPE: RNA
<213> ORGANISM: Artificial Sequence
<220> FEATURE:
<223> OTHER INFORMATION: targeting domain

<400> SEQUENCE: 955
aucagaggcc aaacccuucc 20

<210> SEQ ID NO 956
<211> LENGTH: 20
<212> TYPE: DNA
<213> ORGANISM: Artificial Sequence
<220> FEATURE:
<223> OTHER INFORMATION: targeting domain

<400> SEQUENCE: 956
ctaacagttg cttttatcac 20

<210> SEQ ID NO 957
<211> LENGTH: 20
<212> TYPE: DNA
<213> ORGANISM: Artificial Sequence
<220> FEATURE:
<223> OTHER INFORMATION: targeting domain

<400> SEQUENCE: 957
gggcgtgggt ggggtagaag 20

<210> SEQ ID NO 958
<211> LENGTH: 20
<212> TYPE: DNA
<213> ORGANISM: Artificial Sequence
<220> FEATURE:
<223> OTHER INFORMATION: targeting domain

<400> SEQUENCE: 958
ctcttagaca taacacacca 20

<210> SEQ ID NO 959
<211> LENGTH: 20
<212> TYPE: DNA
<213> ORGANISM: Artificial Sequence
<220> FEATURE:
<223> OTHER INFORMATION: targeting domain

<400> SEQUENCE: 959
atcagaggcc aaacccttcc 20

<210> SEQ ID NO 960
<211> LENGTH: 23

-continued

<212> TYPE: RNA
<213> ORGANISM: Artificial Sequence
<220> FEATURE:
<223> OTHER INFORMATION: targeting domain plus PAM (NGG)

<400> SEQUENCE: 960
cuaacaguug cuuuuaucac agg 23

<210> SEQ ID NO 961
<211> LENGTH: 23
<212> TYPE: RNA
<213> ORGANISM: Artificial Sequence
<220> FEATURE:
<223> OTHER INFORMATION: targeting domain plus PAM (NGG)

<400> SEQUENCE: 961
gggcgugggu gggguagaag agg 23

<210> SEQ ID NO 962
<211> LENGTH: 23
<212> TYPE: RNA
<213> ORGANISM: Artificial Sequence
<220> FEATURE:
<223> OTHER INFORMATION: targeting domain plus PAM (NGG)

<400> SEQUENCE: 962
cucuuagaca uaacacacca ggg 23

<210> SEQ ID NO 963
<211> LENGTH: 23
<212> TYPE: RNA
<213> ORGANISM: Artificial Sequence
<220> FEATURE:
<223> OTHER INFORMATION: targeting domain plus PAM (NGG)

<400> SEQUENCE: 963
aucagaggcc aaacccuucc ugg 23

<210> SEQ ID NO 964
<211> LENGTH: 23
<212> TYPE: DNA
<213> ORGANISM: Artificial Sequence
<220> FEATURE:
<223> OTHER INFORMATION: targeting domain plus PAM (NGG)

<400> SEQUENCE: 964
ctaacagttg cttttatcac agg 23

<210> SEQ ID NO 965
<211> LENGTH: 23
<212> TYPE: DNA
<213> ORGANISM: Artificial Sequence
<220> FEATURE:
<223> OTHER INFORMATION: targeting domain plus PAM (NGG)

<400> SEQUENCE: 965
gggcgtgggt ggggtagaag agg 23

<210> SEQ ID NO 966
<211> LENGTH: 23
<212> TYPE: DNA
<213> ORGANISM: Artificial Sequence
<220> FEATURE:
<223> OTHER INFORMATION: targeting domain plus PAM (NGG)

<400> SEQUENCE: 966
ctcttagaca taacacacca ggg 23

<210> SEQ ID NO 967
<211> LENGTH: 23
<212> TYPE: DNA
<213> ORGANISM: Artificial Sequence
<220> FEATURE:
<223> OTHER INFORMATION: targeting domain plus PAM (NGG)

<400> SEQUENCE: 967
atcagaggcc aaacccttcc tgg 23

<210> SEQ ID NO 968
<211> LENGTH: 115
<212> TYPE: DNA
<213> ORGANISM: Artificial Sequence
<220> FEATURE:
<223> OTHER INFORMATION: +58 DHS enhancer

<400> SEQUENCE: 968
caactttgaa gctagtctag tgcaagctaa cagttgcttt tatcacaggc tccaggaagg 60
gtttggcctc tgattagggt gggggcgtgg gtggggtaga agaggactgg cagac 115

<210> SEQ ID NO 969
<211> LENGTH: 801
<212> TYPE: DNA
<213> ORGANISM: Artificial Sequence
<220> FEATURE:
<223> OTHER INFORMATION: +58 DHS enhancer region including ~500 bp
upstream and ~200 bp downstream

<400> SEQUENCE: 969
aggtaccttt tgtgtgtatg tgctgattga gggcccattg agaatatttt gacttttagg 60
gaagctccaa actctcaaac cacagggatc acaacacata cgtgtgtctg ttatgacgtt 120
atatgtaagc atcacaacag gcagagaatg tctgcacccc accctggaaa acagcctgac 180
tgtgccccat gggcaaacca gactagttta taggggggttc tactctgagg tactgatgga 240
ccttgggtgc tattcctgtg ataaggaagg cagctagaca ggacttggga gttatctgta 300
gtgagatggc tgaaaagcga tacagggctg gctctatgcc ccaggtgtgc ataagtaaga 360
gcagatagct gattccagtg caaagtccat acaggtaata acataggcca gaaaagagat 420
atggcatcta ctcttagaca taacacacca gggtcaatac aactttgaag ctagtctagt 480
gcaagctaac agttgctttt atcacaggct ccaggaaggg tttggcctct gattagggtg 540
ggggcgtggg tggggtagaa gaggactggc agacctctcc atcggtggcc gtttgcccag 600
gggggcctct ttcggaaggc tctcttggtg atggagaatt ggattttatt tctcaatggg 660
aatgaaataa tttgtatgcc atgccgtgtg gactcccaaa attgtaaagg aggtgaagct 720
tcccctgtct gcactctccc ctcctcataa ttgtccattt ttcatctgtc gggctgtcca 780
cccatccatc acatataggc a 801

<210> SEQ ID NO 970
<211> LENGTH: 100
<212> TYPE: RNA
<213> ORGANISM: Artificial Sequence
<220> FEATURE:
<223> OTHER INFORMATION: Unmodified Sp35 gRNA (OLI7066)

<400> SEQUENCE: 970
cuugucaagg cuauugguca guuuuagagc uagaaauagc aaguuaaaau aaggcuaguc 60

```
cguuaucaac uugaaaaagu ggcaccgagu cggugcuuuu                     100
```

```
<210> SEQ ID NO 971
<211> LENGTH: 100
<212> TYPE: RNA
<213> ORGANISM: Artificial Sequence
<220> FEATURE:
<223> OTHER INFORMATION: Sp35 gRNA w/ 5' PS (OLI8568)
<220> FEATURE:
<221> NAME/KEY: misc_feature
<222> LOCATION: (1)..(1)
<223> OTHER INFORMATION: Modified to contain phosphorothioate
<220> FEATURE:
<221> NAME/KEY: misc_feature
<222> LOCATION: (2)..(2)
<223> OTHER INFORMATION: Modified to contain phosphorothioate
<220> FEATURE:
<221> NAME/KEY: misc_feature
<222> LOCATION: (3)..(3)
<223> OTHER INFORMATION: Modified to contain phosphorothioate

<400> SEQUENCE: 971

cuugucaagg cuauugguca guuuuagagc uagaaauagc aaguuaaaau aaggcuaguc   60

cguuaucaac uugaaaaagu ggcaccgagu cggugcuuuu                       100
```

```
<210> SEQ ID NO 972
<211> LENGTH: 100
<212> TYPE: RNA
<213> ORGANISM: Artificial Sequence
<220> FEATURE:
<223> OTHER INFORMATION: Sp35 gRNA w/ 5' OMe (OLI8569)
<220> FEATURE:
<221> NAME/KEY: misc_feature
<222> LOCATION: (1)..(1)
<223> OTHER INFORMATION: Modified to contain 2-o-methyl
<220> FEATURE:
<221> NAME/KEY: misc_feature
<222> LOCATION: (2)..(2)
<223> OTHER INFORMATION: Modified to contain 2-o-methyl
<220> FEATURE:
<221> NAME/KEY: misc_feature
<222> LOCATION: (3)..(3)
<223> OTHER INFORMATION: Modified to contain 2-o-methyl

<400> SEQUENCE: 972

cuugucaagg cuauugguca guuuuagagc uagaaauagc aaguuaaaau aaggcuaguc   60

cguuaucaac uugaaaaagu ggcaccgagu cggugcuuuu                       100
```

```
<210> SEQ ID NO 973
<211> LENGTH: 100
<212> TYPE: RNA
<213> ORGANISM: Artificial Sequence
<220> FEATURE:
<223> OTHER INFORMATION: Sp35 gRNA w/ 3' PS/OMe (OLI8396)
<220> FEATURE:
<221> NAME/KEY: misc_feature
<222> LOCATION: (97)..(97)
<223> OTHER INFORMATION: Modified to contain phosphorothioate, 2-o-
      methyl
<220> FEATURE:
<221> NAME/KEY: misc_feature
<222> LOCATION: (98)..(98)
<223> OTHER INFORMATION: Modified to contain phosphorothioate, 2-o-
      methyl
<220> FEATURE:
<221> NAME/KEY: misc_feature
<222> LOCATION: (99)..(99)
<223> OTHER INFORMATION: Modified to contain phosphorothioate, 2-o-
      methyl

<400> SEQUENCE: 973
```

cuugucaagg cuauugguca guuuuagagc uagaaauagc aaguuaaaau aaggcuaguc 60
cguuaucaac uugaaaaagu ggcaccgagu cggugcuuuu 100

<210> SEQ ID NO 974
<211> LENGTH: 100
<212> TYPE: RNA
<213> ORGANISM: Artificial Sequence
<220> FEATURE:
<223> OTHER INFORMATION: Sp35 gRNA w/ 3' PS/OMe (OLI8395)
<220> FEATURE:
<221> NAME/KEY: misc_feature
<222> LOCATION: (1)..(1)
<223> OTHER INFORMATION: Modified to contain phosphorothioate, 2-o-methyl
<220> FEATURE:
<221> NAME/KEY: misc_feature
<222> LOCATION: (2)..(2)
<223> OTHER INFORMATION: Modified to contain phosphorothioate, 2-o-methyl
<220> FEATURE:
<221> NAME/KEY: misc_feature
<222> LOCATION: (3)..(3)
<223> OTHER INFORMATION: Modified to contain phosphorothioate, 2-o-methyl

<400> SEQUENCE: 974
cuugucaagg cuauugguca guuuuagagc uagaaauagc aaguuaaaau aaggcuaguc 60
cguuaucaac uugaaaaagu ggcaccgagu cggugcuuuu 100

<210> SEQ ID NO 975
<211> LENGTH: 100
<212> TYPE: RNA
<213> ORGANISM: Artificial Sequence
<220> FEATURE:
<223> OTHER INFORMATION: Sp35 gRNA w/ 5' and 3' PS/OMe (OLI8394)
<220> FEATURE:
<221> NAME/KEY: misc_feature
<222> LOCATION: (1)..(1)
<223> OTHER INFORMATION: Modified to contain phosphorothioate, 2-o-methyl
<220> FEATURE:
<221> NAME/KEY: misc_feature
<222> LOCATION: (2)..(2)
<223> OTHER INFORMATION: Modified to contain phosphorothioate, 2-o-methyl
<220> FEATURE:
<221> NAME/KEY: misc_feature
<222> LOCATION: (3)..(3)
<223> OTHER INFORMATION: Modified to contain phosphorothioate, 2-o-methyl
<220> FEATURE:
<221> NAME/KEY: misc_feature
<222> LOCATION: (97)..(97)
<223> OTHER INFORMATION: Modified to contain phosphorothioate, 2-o-methyl
<220> FEATURE:
<221> NAME/KEY: misc_feature
<222> LOCATION: (98)..(98)
<223> OTHER INFORMATION: Modified to contain phosphorothioate, 2-o-methyl
<220> FEATURE:
<221> NAME/KEY: misc_feature
<222> LOCATION: (99)..(99)
<223> OTHER INFORMATION: Modified to contain phosphorothioate, 2-o-methyl

<400> SEQUENCE: 975
cuugucaagg cuauugguca guuuuagagc uagaaauagc aaguuaaaau aaggcuaguc 60
cguuaucaac uugaaaaagu ggcaccgagu cggugcuuuu 100

<210> SEQ ID NO 976

<211> LENGTH: 97
<212> TYPE: RNA
<213> ORGANISM: Artificial Sequence
<220> FEATURE:
<223> OTHER INFORMATION: Sp35 gRNA 97mer (OLI8018)

<400> SEQUENCE: 976
gucaaggcua uuggucaguu uuagagcuag aaauagcaag uuaaaauaag gcuaguccgu 60
uaucaacuug aaaaaguggc accgagucgg ugcuuuu 97

<210> SEQ ID NO 977
<211> LENGTH: 98
<212> TYPE: RNA
<213> ORGANISM: Artificial Sequence
<220> FEATURE:
<223> OTHER INFORMATION: Sp35 gRNA 98mer (OLI8019)

<400> SEQUENCE: 977
ugucaaggcu auuggucagu uuuagagcua gaaauagcaa guuaaaauaa ggcuaguccg 60
uuaucaacuu gaaaaagugg caccgagucg gugcuuuu 98

<210> SEQ ID NO 978
<211> LENGTH: 99
<212> TYPE: RNA
<213> ORGANISM: Artificial Sequence
<220> FEATURE:
<223> OTHER INFORMATION: Sp35 gRNA 99mer (OLI8020)

<400> SEQUENCE: 978
uugucaaggc uauuggucag uuuuagagcu agaaauagca aguuaaaaua aggcuagucc 60
guuaucaacu ugaaaaagug gcaccgaguc ggugcuuuu 99

<210> SEQ ID NO 979
<211> LENGTH: 100
<212> TYPE: RNA
<213> ORGANISM: Artificial Sequence
<220> FEATURE:
<223> OTHER INFORMATION: Sp35 gRNA w/ 5' C->A (OLI8397)

<400> SEQUENCE: 979
auugucaagg cuauugguca guuuuagagc uagaaauagc aaguuaaaau aaggcuaguc 60
cguuaucaac uugaaaaagu ggcaccgagu cggugcuuuu 100

<210> SEQ ID NO 980
<211> LENGTH: 100
<212> TYPE: DNA
<213> ORGANISM: Artificial Sequence
<220> FEATURE:
<223> OTHER INFORMATION: Unmodified Sp35 gRNA (OLI7066)

<400> SEQUENCE: 980
cttgtcaagg ctattggtca gttttagagc tagaaatagc aagttaaaat aaggctagtc 60
cgttatcaac ttgaaaaagt ggcaccgagt cggtgctttt 100

<210> SEQ ID NO 981
<211> LENGTH: 100
<212> TYPE: DNA
<213> ORGANISM: Artificial Sequence
<220> FEATURE:
<223> OTHER INFORMATION: Sp35 gRNA w/ 5' PS (OLI8568)
<220> FEATURE:
<221> NAME/KEY: misc_feature
<222> LOCATION: (1)..(1)
<223> OTHER INFORMATION: Modified to contain phosphorothioate
<220> FEATURE:
<221> NAME/KEY: misc_feature
<222> LOCATION: (2)..(2)
<223> OTHER INFORMATION: Modified to contain phosphorothioate
<220> FEATURE:
<221> NAME/KEY: misc_feature
<222> LOCATION: (3)..(3)
<223> OTHER INFORMATION: Modified to contain phosphorothioate

<400> SEQUENCE: 981
cttgtcaagg ctattggtca gttttagagc tagaaatagc aagttaaaat aaggctagtc 60
cgttatcaac ttgaaaaagt ggcaccgagt cggtgctttt 100

<210> SEQ ID NO 982
<211> LENGTH: 100
<212> TYPE: DNA
<213> ORGANISM: Artificial Sequence
<220> FEATURE:
<223> OTHER INFORMATION: Sp35 gRNA w/ 5' OMe (OLI8569)
<220> FEATURE:
<221> NAME/KEY: misc_feature
<222> LOCATION: (1)..(1)
<223> OTHER INFORMATION: Modified to contain 2-o-methyl
<220> FEATURE:
<221> NAME/KEY: misc_feature
<222> LOCATION: (2)..(2)
<223> OTHER INFORMATION: Modified to contain 2-o-methyl
<220> FEATURE:
<221> NAME/KEY: misc_feature
<222> LOCATION: (3)..(3)
<223> OTHER INFORMATION: Modified to contain 2-o-methyl

<400> SEQUENCE: 982
cttgtcaagg ctattggtca gttttagagc tagaaatagc aagttaaaat aaggctagtc 60
cgttatcaac ttgaaaaagt ggcaccgagt cggtgctttt 100

<210> SEQ ID NO 983
<211> LENGTH: 100
<212> TYPE: DNA
<213> ORGANISM: Artificial Sequence
<220> FEATURE:
<223> OTHER INFORMATION: Sp35 gRNA w/ 3' PS/OMe (OLI8396)
<220> FEATURE:
<221> NAME/KEY: misc_feature
<222> LOCATION: (97)..(97)
<223> OTHER INFORMATION: Modified to contain phosphorothioate, 2-o-methyl
<220> FEATURE:
<221> NAME/KEY: misc_feature
<222> LOCATION: (98)..(98)
<223> OTHER INFORMATION: Modified to contain phosphorothioate, 2-o-methyl
<220> FEATURE:
<221> NAME/KEY: misc_feature
<222> LOCATION: (99)..(99)
<223> OTHER INFORMATION: Modified to contain phosphorothioate, 2-o-methyl

<400> SEQUENCE: 983
cttgtcaagg ctattggtca gttttagagc tagaaatagc aagttaaaat aaggctagtc 60
cgttatcaac ttgaaaaagt ggcaccgagt cggtgctttt 100

<210> SEQ ID NO 984
<211> LENGTH: 100
<212> TYPE: DNA
<213> ORGANISM: Artificial Sequence
<220> FEATURE:
<223> OTHER INFORMATION: Sp35 gRNA w/ 3' PS/OMe (OLI8395)
<220> FEATURE:
<221> NAME/KEY: misc_feature
<222> LOCATION: (97)..(97)
<223> OTHER INFORMATION: Modified to contain phosphorothioate, 2-o-methyl
<220> FEATURE:
<221> NAME/KEY: misc_feature
<222> LOCATION: (98)..(98)
<223> OTHER INFORMATION: Modified to contain phosphorothioate, 2-o-methyl
<220> FEATURE:
<221> NAME/KEY: misc_feature
<222> LOCATION: (99)..(99)
<223> OTHER INFORMATION: Modified to contain phosphorothioate, 2-o-methyl

<400> SEQUENCE: 984
cttgtcaagg ctattggtca gttttagagc tagaaatagc aagttaaaat aaggctagtc 60
cgttatcaac ttgaaaaagt ggcaccgagt cggtgctttt 100

<210> SEQ ID NO 985
<211> LENGTH: 100
<212> TYPE: DNA
<213> ORGANISM: Artificial Sequence
<220> FEATURE:
<223> OTHER INFORMATION: Sp35 gRNA w/ 5' and 3' PS/OMe (OLI8394)
<220> FEATURE:
<221> NAME/KEY: misc_feature
<222> LOCATION: (1)..(1)
<223> OTHER INFORMATION: Modified to contain phosphorothioate, 2-o-methyl
<220> FEATURE:
<221> NAME/KEY: misc_feature
<222> LOCATION: (2)..(2)
<223> OTHER INFORMATION: Modified to contain phosphorothioate, 2-o-methyl
<220> FEATURE:
<221> NAME/KEY: misc_feature
<222> LOCATION: (3)..(3)
<223> OTHER INFORMATION: Modified to contain phosphorothioate, 2-o-methyl
<220> FEATURE:
<221> NAME/KEY: misc_feature
<222> LOCATION: (97)..(97)
<223> OTHER INFORMATION: Modified to contain phosphorothioate, 2-o-methyl
<220> FEATURE:
<221> NAME/KEY: misc_feature
<222> LOCATION: (98)..(98)
<223> OTHER INFORMATION: Modified to contain phosphorothioate, 2-o-methyl
<220> FEATURE:
<221> NAME/KEY: misc_feature
<222> LOCATION: (99)..(99)
<223> OTHER INFORMATION: Modified to contain phosphorothioate, 2-o-methyl

<400> SEQUENCE: 985
cttgtcaagg ctattggtca gttttagagc tagaaatagc aagttaaaat aaggctagtc 60
cgttatcaac ttgaaaaagt ggcaccgagt cggtgctttt 100

<210> SEQ ID NO 986
<211> LENGTH: 97
<212> TYPE: DNA
<213> ORGANISM: Artificial Sequence
<220> FEATURE:
<223> OTHER INFORMATION: Sp35 gRNA 97mer (OLI8018)

<400> SEQUENCE: 986
gtcaaggcta ttggtcagtt ttagagctag aaatagcaag ttaaaataag gctagtccgt 60
tatcaacttg aaaaagtggc accgagtcgg tgctttt 97

<210> SEQ ID NO 987
<211> LENGTH: 98
<212> TYPE: DNA
<213> ORGANISM: Artificial Sequence
<220> FEATURE:
<223> OTHER INFORMATION: Sp35 gRNA 98mer (OLI8019)

<400> SEQUENCE: 987
tgtcaaggct attggtcagt tttagagcta gaaatagcaa gttaaaataa ggctagtccg 60
ttatcaactt gaaaaagtgg caccgagtcg gtgctttt 98

<210> SEQ ID NO 988
<211> LENGTH: 99
<212> TYPE: DNA
<213> ORGANISM: Artificial Sequence
<220> FEATURE:
<223> OTHER INFORMATION: Sp35 gRNA 99mer (OLI8020)

<400> SEQUENCE: 988
ttgtcaaggc tattggtcag ttttagagct agaaatagca agttaaaata aggctagtcc 60
gttatcaact tgaaaaagtg gcaccgagtc ggtgcttttt 99

<210> SEQ ID NO 989
<211> LENGTH: 100
<212> TYPE: DNA
<213> ORGANISM: Artificial Sequence
<220> FEATURE:
<223> OTHER INFORMATION: Sp35 gRNA w/ 5' C->A (OLI8397))

<400> SEQUENCE: 989
attgtcaagg ctattggtca gttttagagc tagaaatagc aagttaaaat aaggctagtc 60
cgttatcaac ttgaaaaagt ggcaccgagt cggtgctttt 100

<210> SEQ ID NO 990
<211> LENGTH: 180
<212> TYPE: DNA
<213> ORGANISM: Artificial Sequence
<220> FEATURE:
<223> OTHER INFORMATION: PhTx ssODN 13nt - positive strand (OLI16414)
<220> FEATURE:
<221> NAME/KEY: misc_feature
<222> LOCATION: (1)..(1)
<223> OTHER INFORMATION: Modified to contain phosphorothioate
<220> FEATURE:
<221> NAME/KEY: misc_feature
<222> LOCATION: (179)..(179)
<223> OTHER INFORMATION: Modified to contain phosphorothioate

<400> SEQUENCE: 990
aagggtgctt ccttttattc ttcatcccta gccagccgcc ggcccctggc ctcactggat 60
actctaagac tattggtcaa gtttgccttg tcaaggcaag gctggccaac ccatgggtgg 120
agtttagcca gggaccgttt cagacagata tttgcattga gatagtgtgg ggaaggggcc 180

<210> SEQ ID NO 991
<211> LENGTH: 90
<212> TYPE: DNA
<213> ORGANISM: Artificial Sequence
<220> FEATURE:
<223> OTHER INFORMATION: 5' homology arm: PhTx ssODN 13nt - positive
strand (OLI16414)
<220> FEATURE:
<221> NAME/KEY: misc_feature
<222> LOCATION: (1)..(1)
<223> OTHER INFORMATION: Modified to contain phosphorothioate

<400> SEQUENCE: 991

```
aagggtgctt ccttttattc ttcatcccta gccagccgcc ggcccctggc ctcactggat     60

actctaagac tattggtcaa gtttgccttg                                      90


<210> SEQ ID NO 992
<211> LENGTH: 90
<212> TYPE: DNA
<213> ORGANISM: Artificial Sequence
<220> FEATURE:
<223> OTHER INFORMATION: 3' homology arm: PhTx ssODN 13nt - positive
      strand (OLI16414)
<220> FEATURE:
<221> NAME/KEY: misc_feature
<222> LOCATION: (89)..(89)
<223> OTHER INFORMATION: Modified to contain phosphorothioate

<400> SEQUENCE: 992

tcaaggcaag gctggccaac ccatgggtgg agtttagcca gggaccgttt cagacagata     60

tttgcattga gatagtgtgg ggaaggggcc                                      90


<210> SEQ ID NO 993
<211> LENGTH: 180
<212> TYPE: DNA
<213> ORGANISM: Artificial Sequence
<220> FEATURE:
<223> OTHER INFORMATION: PhTx ssODN 13nt - negative strand (OLI16412)
<220> FEATURE:
<221> NAME/KEY: misc_feature
<222> LOCATION: (1)..(1)
<223> OTHER INFORMATION: Modified to contain phosphorothioate
<220> FEATURE:
<221> NAME/KEY: misc_feature
<222> LOCATION: (179)..(179)
<223> OTHER INFORMATION: Modified to contain phosphorothioate

<400> SEQUENCE: 993

ggccccttcc ccacactatc tcaatgcaaa tatctgtctg aaacggtccc tggctaaact     60

ccacccatgg gttggccagc cttgccttga caaggcaaac ttgaccaata gtcttagagt    120

atccagtgag gccaggggcc ggcggctggc tagggatgaa gaataaaagg aagcaccctt    180


<210> SEQ ID NO 994
<211> LENGTH: 90
<212> TYPE: DNA
<213> ORGANISM: Artificial Sequence
<220> FEATURE:
<223> OTHER INFORMATION: 5' homology arm: PhTx ssODN 13nt - negative
      strand (OLI16412)
<220> FEATURE:
<221> NAME/KEY: misc_feature
<222> LOCATION: (1)..(1)
<223> OTHER INFORMATION: Modified to contain phosphorothioate

<400> SEQUENCE: 994

ggccccttcc ccacactatc tcaatgcaaa tatctgtctg aaacggtccc tggctaaact     60

ccacccatgg gttggccagc cttgccttga                                      90


<210> SEQ ID NO 995
<211> LENGTH: 90
<212> TYPE: DNA
<213> ORGANISM: Artificial Sequence
<220> FEATURE:
<223> OTHER INFORMATION: 3' homology arm: PhTx ssODN 13nt - negative
      strand (OLI16412)
<220> FEATURE:
<221> NAME/KEY: misc_feature
<222> LOCATION: (89)..(89)
<223> OTHER INFORMATION: Modified to contain phosphorothioate
```

-continued

```
<400> SEQUENCE: 995

caaggcaaac ttgaccaata gtcttagagt atccagtgag gccaggggcc ggcggctggc     60

tagggatgaa gaataaaagg aagcaccctt                                      90


<210> SEQ ID NO 996
<211> LENGTH: 125
<212> TYPE: DNA
<213> ORGANISM: Artificial Sequence
<220> FEATURE:
<223> OTHER INFORMATION: synthetic

<400> SEQUENCE: 996

gaggtctgcc agtcctcttc taccccaccc acgcccccac cctaatcaga ggccaaaccc     60

ttcctggagc ctgtgataaa agcaactgtt agcttgcact agactagctt caaagttgta    120

ttgac                                                                125
```

SYSTEMS AND METHODS FOR THE TREATMENT OF HEMOGLOBINOPATHIES

REFERENCE TO RELATED APPLICATIONS

The present application is a continuation of International Application No. PCT/US2018/022516, filed Mar. 14, 2018, which claims the benefit of U.S. Provisional Application No. 62/471,342, filed Mar. 14, 2017, the contents of which are hereby incorporated by reference in their entirety.

SEQUENCE LISTING

This application contains a Sequence Listing, which was submitted in ASCII format via EFS-Web, and is hereby incorporated by reference in its entirety. The ASCII copy, created on Sep. 12, 2019, is named 8013US07_SequenceListing.txt and is 355 KB in size.

FIELD

This application contains a Sequence Listing, which was submitted in ASCII format via EFSWeb, and is hereby incorporated by reference in its entirety. The ASCII copy, created on May 30, 2023, is named SubstituteSequenceListing.txt and is 355 KB in size.

BACKGROUND

Hemoglobin (Hb) carries oxygen in erythrocytes or red blood cells (RBCs) from the lungs to tissues. During prenatal development and until shortly after birth, hemoglobin is present in the form of fetal hemoglobin (HbF), a tetrameric protein composed of two alpha (α)-globin chains and two gamma (γ)-globin chains. HbF is largely replaced by adult hemoglobin (HbA), a tetrameric protein in which the γ-globin chains of HbF are replaced with beta (β)-globin chains, through a process known as globin switching. The average adult makes less than 1% HbF out of total hemoglobin (Thein 2009). The α-hemoglobin gene is located on chromosome 16, while the β-hemoglobin gene (HBB), A gamma (Aγ)-globin chain (HBG1, also known as gamma globin A), and G gamma (Gγ)-globin chain (HBG2, also known as gamma globin G) are located on chromosome 11 within the globin gene cluster (also referred to as the globin locus).

Mutations in HBB can cause hemoglobin disorders (i.e., hemoglobinopathies) including sickle cell disease (SCD) and beta-thalassemia (β-Thal). Approximately 93,000 people in the United States are diagnosed with a hemoglobinopathy. Worldwide, 300,000 children are born with hemoglobinopathies every year (Angastiniotis 1998). Because these conditions are associated with HBB mutations, their symptoms typically do not manifest until after globin switching from HbF to HbA.

SCD is the most common inherited hematologic disease in the United States, affecting approximately 80,000 people (Brousseau 2010). SCD is most common in people of African ancestry, for whom the prevalence of SCD is 1 in 500. In Africa, the prevalence of SCD is 15 million (Aliyu 2008). SCD is also more common in people of Indian, Saudi Arabian and Mediterranean descent. In those of Hispanic-American descent, the prevalence of sickle cell disease is 1 in 1,000 (Lewis 2014).

SCD is caused by a single homozygous mutation in the HBB gene, c. 17A>T (HbS mutation). The sickle mutation is a point mutation (GAG>GTG) on HBB that results in substitution of valine for glutamic acid at amino acid position 6 in exon 1. The valine at position 6 of the β-hemoglobin chain is hydrophobic and causes a change in conformation of the β-globin protein when it is not bound to oxygen. This change of conformation causes HbS proteins to polymerize in the absence of oxygen, leading to deformation (i.e., sickling) of RBCs. SCD is inherited in an autosomal recessive manner, so that only patients with two HbS alleles have the disease. Heterozygous subjects have sickle cell trait, and may suffer from anemia and/or painful crises if they are severely dehydrated or oxygen deprived.

Sickle shaped RBCs cause multiple symptoms, including anemia, sickle cell crises, vaso-occlusive crises, aplastic crises, and acute chest syndrome. Sickle shaped RBCs are less elastic than wild-type RBCs and therefore cannot pass as easily through capillary beds and cause occlusion and ischemia (i.e., vaso-occlusion). Vaso-occlusive crisis occurs when sickle cells obstruct blood flow in the capillary bed of an organ leading to pain, ischemia, and necrosis. These episodes typically last 5-7 days. The spleen plays a role in clearing dysfunctional RBCs, and is therefore typically enlarged during early childhood and subject to frequent vaso-occlusive crises. By the end of childhood, the spleen in SCD patients is often infarcted, which leads to autosplenectomy. Hemolysis is a constant feature of SCD and causes anemia. Sickle cells survive for 10-20 days in circulation, while healthy RBCs survive for 90-120 days. SCD subjects are transfused as necessary to maintain adequate hemoglobin levels. Frequent transfusions place subjects at risk for infection with HIV, Hepatitis B, and Hepatitis C. Subjects may also suffer from acute chest crises and infarcts of extremities, end organs, and the central nervous system.

Subjects with SCD have decreased life expectancies. The prognosis for patients with SCD is steadily improving with careful, life-long management of crises and anemia. As of 2001, the average life expectancy of subjects with sickle cell disease was the mid-to-late 50's. Current treatments for SCD involve hydration and pain management during crises, and transfusions as needed to correct anemia.

Thalassemias (e.g., β-Thal, δ-Thal, and β/δ-Thal) cause chronic anemia. β-Thal is estimated to affect approximately 1 in 100,000 people worldwide. Its prevalence is higher in certain populations, including those of European descent, where its prevalence is approximately 1 in 10,000. β-Thal major, the more severe form of the disease, is life-threatening unless treated with lifelong blood transfusions and chelation therapy. In the United States, there are approximately 3,000 subjects with β-Thal major. β-Thal intermedia does not require blood transfusions, but it may cause growth delay and significant systemic abnormalities, and it frequently requires lifelong chelation therapy. Although HbA makes up the majority of hemoglobin in adult RBCs, approximately 3% of adult hemoglobin is in the form of HbA2, an HbA variant in which the two γ-globin chains are replaced with two delta (Δ)-globin chains. δ-Thal is associated with mutations in the A hemoglobin gene (HBD) that cause a loss of HBD expression. Co-inheritance of the HBD mutation can mask a diagnosis of β-Thal (i.e., β/δ-Thal) by decreasing the level of HbA2 to the normal range (Bouva 2006). β/δ-Thal is usually caused by deletion of the HBB and HBD sequences in both alleles. In homozygous (δo/δo βo/βo) patients, HBG is expressed, leading to production of HbF alone.

Like SCD, β-Thal is caused by mutations in the HBB gene. The most common HBB mutations leading to β-Thal are: c.-136C>G, c.92+1G>A, c.92+6T>C, c.93-21G>A, c.118C>T, c.316-106C>G, c.25_26delAA, c.27_28insG, c.92+5G>C, c.118C>T, c.135delC, c.315+1G>A, c.-78A>G, c.52A>T, c.59A>G, c.92+5G>C, c.124_127delTTCT, c.316-197C>T, c.-78A>G, c.52A>T, c.124_127delTTCT, c.316-197C>T, c.-138C>T, c.-79A>G, c.92+5G>C, c.75T>A, c.316-2A>G, and c.316-2A>C. These and other mutations associated with β-Thal cause mutated or absent β-globin chains, which causes a disruption of the normal Hb α-hemoglobin to β-hemoglobin ratio. Excess α-globin chains precipitate in erythroid precursors in the bone marrow.

In β-Thal major, both alleles of HBB contain nonsense, frameshift, or splicing mutations that leads to complete absence of β-globin production (denoted $\beta^0/\beta^0$). β-Thal major results in severe reduction in β-globin chains, leading to significant precipitation of α-globin chains in RBCs and more severe anemia.

β-Thal intermedia results from mutations in the 5' or 3' untranslated region of HBB, mutations in the promoter region or polyadenylation signal of HBB, or splicing mutations within the HBB gene. Patient genotypes are denoted βo/β+ or β+/β+. βo represents absent expression of a β-globin chain; β+ represents a dysfunctional but present β-globin chain. Phenotypic expression varies among patients. Since there is some production of β-globin, β-Thal intermedia results in less precipitation of α-globin chains in the erythroid precursors and less severe anemia than β-Thal major. However, there are more significant consequences of erythroid lineage expansion secondary to chronic anemia.

Subjects with β-Thal major present between the ages of 6 months and 2 years, and suffer from failure to thrive, fevers, hepatosplenomegaly, and diarrhea. Adequate treatment includes regular transfusions. Therapy for β-Thal major also includes splenectomy and treatment with hydroxyurea. If patients are regularly transfused, they will develop normally until the beginning of the second decade. At that time, they require chelation therapy (in addition to continued transfusions) to prevent complications of iron overload. Iron overload may manifest as growth delay or delay of sexual maturation. In adulthood, inadequate chelation therapy may lead to cardiomyopathy, cardiac arrhythmias, hepatic fibrosis and/or cirrhosis, diabetes, thyroid and parathyroid abnormalities, thrombosis, and osteoporosis. Frequent transfusions also put subjects at risk for infection with HIV, hepatitis B and hepatitis C.

β-Thal intermedia subjects generally present between the ages of 2-6 years. They do not generally require blood transfusions. However, bone abnormalities occur due to chronic hypertrophy of the erythroid lineage to compensate for chronic anemia. Subjects may have fractures of the long bones due to osteoporosis. Extramedullary erythropoiesis is common and leads to enlargement of the spleen, liver, and lymph nodes. It may also cause spinal cord compression and neurologic problems. Subjects also suffer from lower extremity ulcers and are at increased risk for thrombotic events, including stroke, pulmonary embolism, and deep vein thrombosis. Treatment of β-Thal intermedia includes splenectomy, folic acid supplementation, hydroxyurea therapy, and radiotherapy for extramedullary masses. Chelation therapy is used in subjects who develop iron overload.

Life expectancy is often diminished in β-Thal patients. Subjects with β-Thal major who do not receive transfusion therapy generally die in their second or third decade. Subjects with β-Thal major who receive regular transfusions and adequate chelation therapy can live into their fifth decade and beyond. Cardiac failure secondary to iron toxicity is the leading cause of death in β-Thal major subjects due to iron toxicity.

A variety of new treatments are currently in development for SCD and β-Thal. Delivery of an anti-sickling HBB gene via gene therapy is currently being investigated in clinical trials. However, the long-term efficacy and safety of this approach is unknown. Transplantation with hematopoietic stem cells (HSCs) from an HLA-matched allogeneic stem cell donor has been demonstrated to cure SCD and β-Thal, but this procedure involves risks including those associated with ablation therapy, which is required to prepare the subject for transplant, increases risk of life-threatening opportunistic infections, and risk of graft vs. host disease after transplantation. In addition, matched allogeneic donors often cannot be identified. Thus, there is a need for improved methods of managing these and other hemoglobinopathies.

SUMMARY

Provided herein are genome editing systems, guide RNAs, and CRISPR-mediated methods for altering one or more γ-globin genes (e.g., HBG1, HBG2, or HBG1 and HBG2), the erythroid specific enhancer of the BCL11A gene (BCL11Ae), or a combination thereof, and increasing expression of fetal hemoglobin (HbF). In certain embodiments, genome editing systems, guide RNAs, and CRISPR-mediated methods may alter a 13 nucleotide (nt) target region that is 5' of the transcription site of the HBG1, HBG2, or HBG1 and HBG2 gene ("13 nt target region"). In certain embodiments, one or more gRNAs comprising a targeting domain set forth in SEQ ID NOs:251-901 or 940-942 may be used to introduce alterations in the 13 nt target region. In certain embodiments, one or more gRNAs comprising a sequence set forth in SEQ ID NOs:970-979 may be used to introduce alterations in the 13 nt target region. In certain embodiments, genome editing systems, guide RNAs, and CRISPR-mediated methods may alter a GATA1 binding motif in BCL11Ae that is in the +58 DNase I hypersensitive site (DHS) region of intron 2 of the BCL11A gene ("GATA1 binding motif in BCL11Ae"). In certain embodiments, one or more gRNAs comprising a targeting domain set forth in SEQ ID NOs:952-955 may be used to introduce alterations in the GATA1 binding motif in BCL11Ae. In certain embodiments, one or more gRNAs may be used to introduce alterations in the GATA1 binding motif in BCL11Ae and one or more gRNAs may be used to introduce alterations in the 13 nt target region of HBG1 and/or HBG2.

Provided herein in certain embodiments are gRNAs for use in CRISPR/Cas-mediated methods of increasing expression (i.e., transcriptional activity) of one or more γ-globin genes (e.g., HBG1, HBG2, or HBG1 and HBG2). In certain embodiments, the gRNAs may be generated via in vitro transcription or chemical synthesis. In certain embodiments, the gRNA may comprise one or more modifications. In certain embodiments, the one or more modifications may be selected from the group consisting of phosphorothioate and 2'-O-methyl groups. In certain embodiments, the one or more modifications may be at or near the 5' end, 3' end, or both of the gRNA. In certain embodiments, the gRNA may comprise a truncated form of a full-length gRNA (e.g., SEQ ID NO:970). In certain embodiments, the gRNA may comprise, consist essentially of, or consist of a sequence selected from the group consisting of SEQ ID NOs: 339 and 970-979. In certain embodiments, the gRNA may differ by no more than 3 nucleotides from a sequence selected from the group consisting of SEQ ID NOs: 339 and 970-979.

Provided herein in certain embodiments are the use of optional genome editing system components such as oligonucleotide donor templates. In certain embodiments, donor templates for use in targeting the 13 nt target region may include, without limitation, donor templates encoding alterations (e.g., deletions) of HBG1 c.-114 to -102, HBG1 c.-225 to -222, and/or HBG2 c.-114 to -102. In certain embodiments, 5' and 3' homology arms and exemplary full-length donor templates encoding deletions such as c. -114 to -102 are also presented below (e.g., SEQ ID NOS: 904-909, 990-995). In certain embodiments, the template nucleic acid may be a single stranded oligodeoxynucleotide (ssODN). In certain embodiments, the template nucleic acid may be a positive strand or a negative strand. In certain embodiments, the ssODN may comprise a 5' homology arm, a replacement sequence, and a 3' homology arm. In certain embodiments, the 5' homology arm may be about 25 to about 200 nucleotides or more in length, e.g., at least about 25, 50, 75, 100, 125, 150, 175, or 200 nucleotides in length; the replacement sequence may comprise 0 nucleotides in length; and the 3' homology arm may be about 25 to about 200 nucleotides or more in length, e.g., at least about 25, 50, 75, 100, 125, 150, 175, or 200 nucleotides in length. In certain embodiments, the 5' homology arm may comprise about 50 to 100 bp, e.g., 55 to 95, 60 to 90, 70 to 90, or 80 to 90 bp, homology 5' to the 13 nt target region and the 3' homology arm may comprise about 50 to 100 bp, e.g., 55 to 95, 60 to 90, 70 to 90, or 80 to 90 bp, homology 3' to the 13 nt target region. In certain embodiments, the 13 nt target region may be HBG1 c.-114 to -102 (e.g., nucleotides 2824-2836 of SEQ ID NO:902 (HBG1)), HBG2 c.-114 to -102 (e.g., nucleotides 2748-2760 of SEQ ID NO:903 (HBG2)), or a combination thereof. In certain embodiments, the ssODN may comprise one or more phosphorothioates.

BRIEF DESCRIPTION OF THE DRAWINGS

The accompanying drawings are intended to provide illustrative, and schematic rather than comprehensive, examples of certain aspects and embodiments of the present disclosure. The drawings are not intended to be limiting or binding to any particular theory or model, and are not necessarily to scale. Without limiting the foregoing, nucleic acids and polypeptides may be depicted as linear sequences, or as schematic two- or three-dimensional structures; these depictions are intended to be illustrative rather than limiting or binding to any particular model or theory regarding their structure.

FIG. 1. Each gene in the β-globin gene cluster is transcriptionally regulated by a proximal promoter. While not wishing to be bound by any particular theory, it is generally thought that $A_\gamma$ and/or $G_\gamma$ expression is activated by engagement between the proximal promoter with the distal strong erythroid-specific enhancer, the locus control region (LCR). Long-range transactivation by the LCR is thought to be mediated by alteration of chromatin configuration/confirmation. The LCR is marked by 4 erythroid specific Dnase I hypersensitive sites (HS1-4) and 2 distal enhancer elements (5' HS and 3' HS1). β-like gene globin gene expression is regulated in a developmental stage-specific manner, and expression of globin genes changes coincide with changes in the main site of blood production.

FIG. 3A Gene editing as determined by T7E1 endonuclease assay analysis (referred to interchangeably as a “T7E1 analysis”) of HBG1 and HBG2 locus-specific PCR products amplified from genomic DNA extracted from K562 cells after electroporation with DNA encoding *S. pyogenes*-specific gRNAs and plasmid DNA encoding *S. pyogenes* Cas9. FIG. 3B Gene editing as determined by DNA sequence analysis of PCR products amplified from the HBG1 locus in genomic DNA extracted from K562 cells after electroporation with DNA encoding the indicated gRNA and Cas9 plasmid. FIG. 3C Gene editing as determined by DNA sequence analysis of PCR products amplified from the HBG2 locus in genomic DNA extracted from K562 cells after electroporation with DNA encoding the indicated gRNA and Cas9 plasmid. For FIG. 3B-C, the types of editing events (insertions, deletions) and subtypes of deletions (13 nt target partially [12 nt HPFH] or fully [13-26 nt HPFH] deleted, other sequences deleted [other deletions]) are indicated by the differently shaded/patterned bars.

FIG. 4A depicts the percentage of indels detected by T7E1 analysis of HBG1 and HBG2 specific PCR products amplified from gDNA extracted from CB $CD34^+$ cells treated with the indicated RNPs or donor matched untreated control cells (n=3 CB $CD34^+$ cells, 3 separate experiments). Data shown represent the mean and error bars correspond to standard deviation across the 3 separate donors/experiments. FIG. 4B depicts the percentage of indels detected by T7E1 analysis of HBG2 specific PCR product amplified from gDNA extracted from CB $CD34^+$ cells or adult $CD34^+$ cells treated with the indicated RNPs or donor matched untreated control cells (n=3 CB $CD34^+$ cells, n=3 mobilized peripheral blood (mPB) $CD34^+$ cells, 3 separate experiments). Data shown represent the mean and error bars correspond to standard deviation across the 3 separate donors/experiments. FIG. 4C (Top panel) depicts indels as detected by T7E1 analysis of HBG2 PCR products amplified from gDNA extracted from human CB $CD34^+$ cells electroporated with HBG Sp35 RNP or HBG Sp37 RNP+/−ssODN (unmodified or with PhTx modified 5' and 3' ends). The lower left panel shows the level of gene editing as determined by Sanger DNA sequence analysis of gDNA from cells edited with HBG Sp37 RNP and ssODN. The lower right panel shows the specific types of deletions detected within total deletions.

FIG. 5A depicts the percentage of indels detected by T7E1 analysis of HBG2 PCR product amplified from gDNA extracted from mPB $CD34^+$ cells treated with the RNP or donor matched untreated control cells. FIG. 5B depicts the fold change in HBG mRNA expression in day 7 erythroblasts that were differentiated from RNP treated and untreated donor matched control mPB $CD34^+$ cells. mRNA levels are normalized to GAPDH and calibrated to the levels detected in untreated controls on the corresponding days of differentiation.

FIG. 6A shows hematopoietic myeloid/erythroid colony forming cell (CFC) potential, where the number and subtype of colonies are indicated (GEMM: granulocyte-erythroid-monocyte-macrophage colony, E: erythroid colony, GM: granulocyte-macrophage colony, M: macrophage colony, G: granulocyte colony). FIG. 6B depicts the percentage of Glycophorin A expressed over the time course of erythroid differentiation as determined by flow cytometry analysis at the indicated time points and for the indicated samples.

FIG. 10C depicts the % of HbF protein detected by HPLC analysis (% HbF=100%×HbF/(HbF+HbA). FIG. 10D depicts the hematopoietic activity of the RNP treated and donor matched untreated control $CD34^+$ cells in colony forming cell (CFC) assays. CFCs shown are per thousand $CD34^+$ cells plated. FIG. 10E depicts human blood $CD45^+$ cell reconstitution of the peripheral blood in immunodeficient mice (NSG) 1 month after transplantation with donor matched human mPB $CD34^+$ that were either untreated (0 μM), or treated with one of two doses (2.5 and 3.75 μM) of D10A RNP and paired gRNAs. FIG. 10F depicts human blood $CD45^+$ cell reconstitution of the peripheral blood in immunodeficient mice (NSG) 2 months after transplantation. FIGS. 10G and 10H depict the lineage distributions following human $CD45^+$ blood cell reconstitution of NSG mice at 1 month (FIG. 10G) and 2 months (FIG. 10H).

FIG. 15A depicts the percentage of indels detected by T7E1 analysis of HBG2 PCR product amplified from gDNA extracted from mPB $CD34^+$ cells treated with the BCL11Ae RNP and nonspecific ssODN or donor matched untreated control cells. FIG. 15B depicts the fold change in HBG mRNA expression in day 10 erythroblasts that were differentiated from BCL11Ae RNP treated and untreated donor matched control mPB $CD34^+$ cells (mRNA levels are normalized to GAPDH and calibrated to the levels detected in untreated controls on the corresponding days of differentiation). FIG. 15C depicts the percentage of Glycophorin A expressed over the time course of erythroid differentiation of mPB $CD34^+$ cells +/−treatment with BCL11Ae RNP and nonspecific ssODN, as determined by flow cytometry analysis at the indicated time points and for the indicated samples.

FIG. 16A depicts the percentage of indels detected by sequencing the HBG PCR product amplified from adult human $CD34^+$ cells from mPB electroporated with Cas9 complexed with Sp37 IVT or Sp37 Synthetic gRNAs. Next generation sequencing (NGS) (co-amplification and sequencing of HBG1 and HBG2 PCR product) was used to detect the indels. FIG. 16B depicts the percentage viability of the adult human mPB $CD34^+$ cells 48 hours after electroporation with Cas9 complexed with Sp37 IVT or Sp37 Synthetic gRNAs.

FIG. 18A depicts the percentage of indels detected by sequencing the HBG PCR product from genomic DNA extracted at 72 hours post-electroporation. The grey portion of the bar represents the 13 nt indel deletion, whereas the white portion of the bar represents other indels. FIG. 18B depicts the percent viability of cells 48 hours post-electroporation. FIG. 18C depicts the percentage of relative expression levels of gamma-globin chains over total beta-like globin chains (gamma chains/[gamma chains+beta chain]) detected by ultra-performance liquid chromatography (UPLC).

DETAILED DESCRIPTION

Definitions and Abbreviations

Figure 1:
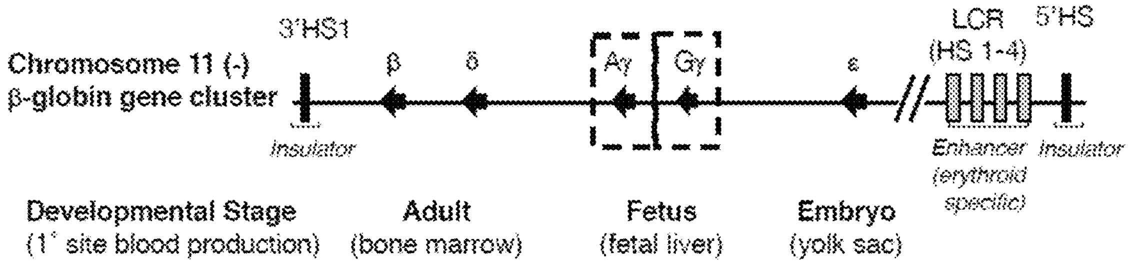
FIG. 1 depicts, in schematic form, HBG1 and HBG2 gene(s) in the context of the β-globin gene cluster on human chromosome 11.
Figure 2A:
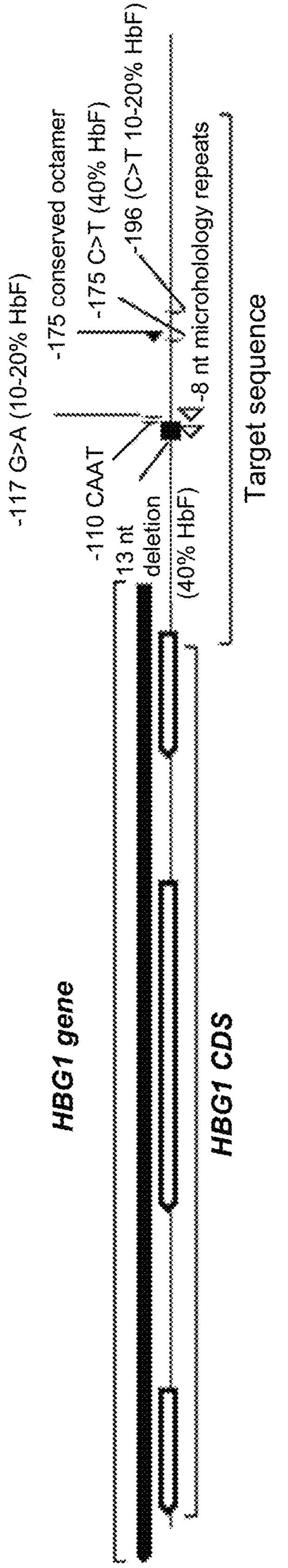
FIGS. 2A-2B depict HBG1 and HBG2 genes, coding sequences (CDS) and small deletions and point mutations in and upstream of the HBG1 and HBG2 proximal promoters that have been identified in patients and associated with elevation of fetal hemoglobin (HbF). Core elements within the proximal promoters (CAAT box, 13 nt sequence) that have been deleted in some patients with hereditary persistence of fetal hemoglobin (HPFH). The ‘target sequence’ region of each locus, which has been screened for gRNA binding target sites, is also identified.
Figure 2B:
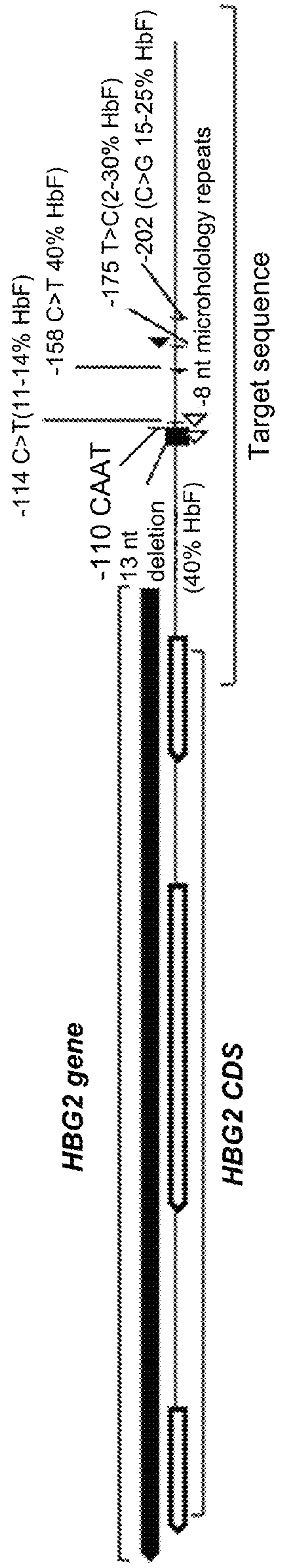

Unless otherwise specified, each of the following terms has the meaning associated with it in this section.

The indefinite articles "a" and "an" refer to at least one of the associated noun, and are used interchangeably with the terms "at least one" and "one or more." For example, "a module" means at least one module, or one or more modules.

The conjunctions "or" and "and/or" are used interchangeably as non-exclusive disjunctions.

"Domain" is used to describe a segment of a protein or nucleic acid. Unless otherwise indicated, a domain is not required to have any specific functional property.

An "indel" is an insertion and/or deletion in a nucleic acid sequence. An indel may be the product of the repair of a DNA double strand break, such as a double strand break formed by a genome editing system of the present disclosure. An indel is most commonly formed when a break is repaired by an "error prone" repair pathway such as the NHEJ pathway described below.

"Gene conversion" refers to the alteration of a DNA sequence by incorporation of an endogenous homologous sequence (e.g. a homologous sequence within a gene array). "Gene correction" refers to the alteration of a DNA sequence by incorporation of an exogenous homologous sequence, such as an exogenous single- or double stranded donor template DNA. Gene conversion and gene correction are products of the repair of DNA double-strand breaks by HDR pathways such as those described below.

Indels, gene conversion, gene correction, and other genome editing outcomes are typically assessed by sequencing (most commonly by "next-gen" or "sequencing-by-synthesis" methods, though Sanger sequencing may still be used) and are quantified by the relative frequency of numerical changes (e.g., ±1, ±2 or more bases) at a site of interest among all sequencing reads. DNA samples for sequencing may be prepared by a variety of methods known in the art, and may involve the amplification of sites of interest by polymerase chain reaction (PCR), the capture of DNA ends generated by double strand breaks, as in the GUIDEseq process described in Tsai 2016 (incorporated by reference herein) or by other means well known in the art. Genome editing outcomes may also be assessed by in situ hybridization methods such as the FiberComb™ system commercialized by Genomic Vision (Bagneux, France), and by any other suitable methods known in the art.

"Alt-HDR," "alternative homology-directed repair," or "alternative HDR" are used interchangeably to refer to the process of repairing DNA damage using a homologous nucleic acid (e.g., an endogenous homologous sequence, e.g., a sister chromatid, or an exogenous nucleic acid, e.g., a template nucleic acid). Alt-HDR is distinct from canonical HDR in that the process utilizes different pathways from canonical HDR, and can be inhibited by the canonical HDR mediators, RAD51 and BRCA2. Alt-HDR is also distinguished by the involvement of a single-stranded or nicked homologous nucleic acid template, whereas canonical HDR generally involves a double-stranded homologous template.

"Canonical HDR," "canonical homology-directed repair" or "cHDR" refer to the process of repairing DNA damage using a homologous nucleic acid (e.g., an endogenous homologous sequence, e.g., a sister chromatid, or an exogenous nucleic acid, e.g., a template nucleic acid). Canonical HDR typically acts when there has been significant resection at the double strand break, forming at least one single stranded portion of DNA. In a normal cell, cHDR typically involves a series of steps such as recognition of the break, stabilization of the break, resection, stabilization of single stranded DNA, formation of a DNA crossover intermediate, resolution of the crossover intermediate, and ligation. The process requires RAD51 and BRCA2, and the homologous nucleic acid is typically double-stranded.

Unless indicated otherwise, the term "HDR" as used herein encompasses both canonical HDR and alt-HDR.

"Non-homologous end joining" or "NHEJ" refers to ligation mediated repair and/or non-template mediated repair including canonical NHEJ (cNHEJ) and alternative NHEJ (altNHEJ), which in turn includes microhomology-mediated end joining (MMEJ), single-strand annealing (SSA), and synthesis-dependent microhomology-mediated end joining (SD-MMEJ).

“Replacement” or “replaced,” when used with reference to a modification of a molecule (e.g. a nucleic acid or protein), does not require a process limitation but merely indicates that the replacement entity is present.

“Subject” means a human, mouse, or non-human primate. A human subject can be any age (e.g., an infant, child, young adult, or adult), and may suffer from a disease, or may be in need of alteration of a gene.

“Treat,” “treating,” and “treatment” mean the treatment of a disease in a subject (e.g., a human subject), including one or more of inhibiting the disease, i.e., arresting or preventing its development or progression; relieving the disease, i.e., causing regression of the disease state; relieving one or more symptoms of the disease; and curing the disease.

“Prevent,” “preventing,” and “prevention” refer to the prevention of a disease in a subject, including (a) avoiding or precluding the disease; (b) affecting the predisposition toward the disease; or (c) preventing or delaying the onset of at least one symptom of the disease.

A “kit” refers to any collection of two or more components that together constitute a functional unit that can be employed for a specific purpose. By way of illustration (and not limitation), one kit according to this disclosure can include a guide RNA complexed or able to complex with an RNA-guided nuclease, and accompanied by (e.g. suspended in, or suspendable in) a pharmaceutically acceptable carrier. The kit can be used to introduce the complex into, for example, a cell or a subject, for the purpose of causing a desired genomic alteration in such cell or subject. The components of a kit can be packaged together, or they may be separately packaged. Kits according to this disclosure also optionally include directions for use (DFU) that describe the use of the kit e.g., according to a method of this disclosure. The DFU can be physically packaged with the kit, or it can be made available to a user of the kit, for instance by electronic means.

The terms “polynucleotide”, “nucleotide sequence”, “nucleic acid”, “nucleic acid molecule”, “nucleic acid sequence”, and “oligonucleotide” refer to a series of nucleotide bases (also called “nucleotides”) in DNA and RNA, and mean any chain of two or more nucleotides. The polynucleotides, nucleotide sequences, nucleic acids etc. can be chimeric mixtures or derivatives or modified versions thereof, single-stranded or double-stranded. They can be modified at the base moiety, sugar moiety, or phosphate backbone, for example, to improve stability of the molecule, its hybridization parameters, etc. A nucleotide sequence typically carries genetic information, including, but not limited to, the information used by cellular machinery to make proteins and enzymes. These terms include double- or single-stranded genomic DNA, RNA, any synthetic and genetically manipulated polynucleotide, and both sense and antisense polynucleotides. These terms also include nucleic acids containing modified bases.

Conventional IUPAC notation is used in nucleotide sequences presented herein, as shown in Table 1, below (see also Cornish-Bowden A, Nucleic Acids Res. 1985 May 10; 13(9):3021-30, incorporated by reference herein). It should be noted, however, that “T” denotes “Thymine or Uracil” in those instances where a sequence may be encoded by either DNA or RNA, for example in gRNA targeting domains.

TABLE 1

IUPAC nucleic acid notation

| Character | Base |
|---|---|
| A | Adenine |
| T | Thymine or Uracil |
| G | Guanine |
| C | Cytosine |
| U | Uracil |
| K | G or T/U |
| M | A or C |
| R | A or G |
| Y | C or T/U |
| S | C or G |
| W | A or T/U |
| B | C, G or T/U |
| V | A, C or G |
| H | A, C or T/U |
| D | A, G or T/U |
| N | A, C, G or T/U |

The terms “protein,” “peptide” and “polypeptide” are used interchangeably to refer to a sequential chain of amino acids linked together via peptide bonds. The terms include individual proteins, groups or complexes of proteins that associate together, as well as fragments or portions, variants, derivatives and analogs of such proteins. Peptide sequences are presented herein using conventional notation, beginning with the amino or N-terminus on the left, and proceeding to the carboxyl or C-terminus on the right. Standard one-letter or three-letter abbreviations can be used.

The notations “c.-114 to -102 region,” “13 nt target region” and the like refer to a sequence that is 5' of the transcription start site (TSS) of the HBG1 and/or HBG2 gene. The HBG1 c.-114 to -102 region is exemplified in SEQ ID NO:902 (HBG1) at positions 2824-2836 and the HBG2 c.-114 to -102 region is exemplified in SEQ ID NO:903 (HBG2) at positions 2748-2760. The term “13 nt deletion” and the like refer to deletions of the 13 nt target region.

The term “proximal HBG1/2 promoter target sequence” denotes the region within 50, 100, 200, 300, 400, or 500 bp of a proximal HBG1/2 promoter sequence including the 13 nt target region. Alterations by genome editing systems according to this disclosure facilitate (e.g. cause, promote or tend to increase the likelihood of) upregulation of HbF production in erythroid progeny.

The term “GATA1 binding motif in BCL11Ae” refers to the sequence that is the GATA1 binding motif in the erythroid specific enhancer of BC11A (BC11Ae) that is in the +58 DNase I hypersensitive site (DHS) region of intron 2 of the BC11A gene. The genomic coordinates for the GATA1 binding motif in BC11Ae are chr2: 60,495,265 to 60,495,270. The +58 DHS site comprises a 115 base pair (bp) sequence as set forth in SEQ ID NO:968. The +58 DHS site sequence, including ~500 bp upstream and ~200 bp downstream is set forth in SEQ ID NO:969.

Overview

The various embodiments of this disclosure generally relate to genome editing systems configured to introduce alterations (e.g., a deletion or insertion, or other mutation) into chromosomal DNA that enhance transcription of the HBG1 and/or HBG2 genes, which encode the Aγ and Gγ subunits of hemoglobin, respectively. Exemplary mutations are made in or around the 13 nt target region of HBG1 and/or HBG2.

Fetal hemoglobin (HbF) expression can also be induced through targeted disruption of the erythroid cell specific expression of a transcriptional repressor, BCL11A, which encodes a repressor that silences HBG1 and HBG2 (Canvers 2015). Another gene editing strategy disclosed herein is to increase HbF expression by targeting disruption the of the erythroid specific enhancer of BC11A (BC11Ae) (also discussed in commonly-assigned International Patent Publication No. WO 2015/148860 by Friedland et al. ("Friedland," incorporated by reference herein in its entirety). In certain embodiments, the region of BC11Ae targeted for disruption may be the GATA1 binding motif in BC11Ae. In certain embodiments, genome editing systems disclosed herein may be used to introduce alterations into the GATA1 binding motif in BCL11Ae and the 13 nt target region of HBG1 and/or HBG2.

The genome editing systems of this disclosure can include an RNA-guided nuclease such as Cas9 or Cpf1 and one or more gRNAs having a targeting domain that is complementary to a sequence in or near the target region, and optionally one or more of a DNA donor template that encodes a specific mutation (such as a deletion or insertion) in or near the target region, and/or an agent that enhances the efficiency with which such mutations are generated including, without limitation, a random oligonucleotide, a small molecule agonist or antagonist of a gene product involved in DNA repair or a DNA damage response, or a peptide agent.

A variety of approaches to the introduction of mutations into the 13 nt target region, proximal HBG1/2 promoter target sequence, and/or the GATA1 binding motif in BC11Ae may be employed in the embodiments of the present disclosure. In one approach, a single alteration, such as a double-strand break, is made within the 13 nt target region, proximal HBG1/2 promoter target sequence, and/or the GATA1 binding motif in BCL11Ae, and is repaired in a way that disrupts the function of the region, for example by the formation of an indel or by the incorporation of a donor template sequence that encodes the deletion of the region. In a second approach, two or more alterations are made on either side of the region, resulting in the deletion of the intervening sequence, including the 13 nt target region and/or the GATA1 binding motif in BCL11Ae.

The treatment of hemogolobinopathies by gene therapy and/or genome editing is complicated by the fact that the cells that are phenotypically affected by the disease, erythrocytes or RBCs, are enucleated, and do not contain genetic material encoding either the aberrant hemoglobin protein (Hb) subunits nor the Aγ or Gγ subunits targeted in the exemplary genome editing approaches described above. This complication is addressed, in certain embodiments of this disclosure, by the alteration of cells that are competent to differentiate into, or otherwise give rise to, erythrocytes. Cells within the erythroid lineage that are altered according to various embodiments of this disclosure include, without limitation, hematopoietic stem and progenitor cells (HSCs), erythroblasts (including basophilic, polychromatic and/or orthochromatic erythroblasts), proerythroblasts, polychromatic erythrocytes or reticulocytes, embryonic stem (ES) cells, and/or induced pluripotent stem (iPSC) cells. These cells may be altered in situ (e.g. within a tissue of a subject) or ex vivo. Implementations of genome editing systems for in situ and ex vivo alteration of cells is described under the heading "Implementation of genome editing systems: delivery, formulations, and routes of administration" below.

In certain embodiments, alterations that result in induction of Aγ and/or Gγ expression are obtained through the use of a genome editing system comprising an RNA-guided nuclease and at least one gRNA having a targeting domain complementary to a sequence within the 13 nt target region of HBG1 and/or HBG2 or proximate thereto (e.g., within 10, 20, 30, 40, or 50, 100, 200, 300, 400 or 500 bases of the 13 nt target region). As is discussed in greater detail below, the RNA-guided nuclease and gRNA form a complex that is capable of associating with and altering the 13 nt target region or a region proximate thereto. Examples of suitable targeting domains directed to the 13 nt target region of HBG1 and/or HBG2 or proximate thereto for use in the embodiments disclosed herein include, without limitation, those set forth in SEQ ID NOs:251-901, 940-942. In certain embodiments, gRNAs targeting the 13 nt target region of HBG1 and/or HBG2 or proximate thereto may include modifications including, without limitation, addition of one or more PhTx or 2'-O-methyl groups. The modifications may be at or near the 5' end or 3' end of the gRNA or at or near the 5' and 3' ends of the gRNA. In certain embodiments, the gRNAs may be in vitro transcribed gRNAs or chemically synthesized gRNAs. Examples of suitable gRNAs directed to the 13 nt target region of HBG1 and/or HBG2 for use in the embodiments disclosed herein include, without limitation, those set forth in SEQ ID NOs:970-979.

In certain embodiments, alterations that result in induction of HbF expression are obtained through the use of a genome editing system comprising an RNA-guided nuclease and at least one gRNA having a targeting domain complementary to a sequence within the GATA1 binding motif in BCL11Ae or proximate thereto (e.g., within 10, 20, 30, 40, or 50, 100, 200, 300, 400 or 500 bases of the GATA1 binding motif in BCL11Ae). In certain embodiments, the RNA-guided nuclease and gRNA form a complex that is capable of associating with and altering the GATA1 binding motif in BCL11Ae. Examples of suitable targeting domains directed to the GATA1 binding motif in BCL11Ae for use in the embodiments disclosed herein include, without limitation, those set forth in SEQ ID NOs:952-955.

The genome editing system can be implemented in a variety of ways, as is discussed below in detail. As an example, a genome editing system of this disclosure can be implemented as a ribonucleoprotein complex or a plurality of complexes in which multiple gRNAs are used. This ribonucleoprotein complex can be introduced into a target cell using art-known methods, including electroporation, as described in commonly-assigned International Patent Publication No. WO 2016/182959 by Jennifer Gori ("Gori," incorporated by reference herein in its entirety).

The ribonucleoprotein complexes within these compositions are introduced into target cells by art-known methods, including without limitation electroporation (e.g. using the Nucleofection™ technology commercialized by Lonza, Basel, Switzerland or similar technologies commercialized by, for example, Maxcyte Inc. Gaithersburg, Maryland) and lipofection (e.g. using Lipofectamine™ reagent commercialized by Thermo Fisher Scientific, Waltham Massachusetts). Alternatively, or additionally, ribonucleoprotein complexes are formed within the target cells themselves following introduction of nucleic acids encoding the RNA-guided nuclease and/or gRNA. These and other delivery modalities are described in general terms below and in Gori.

Cells that have been altered ex vivo according to this disclosure can be manipulated (e.g. expanded, passaged, frozen, differentiated, de-differentiated, transduced with a transgene, etc.) prior to their delivery to a subject. The cells are, variously, delivered to a subject from which they are obtained (in an "autologous" transplant), or to a recipient who is immunologically distinct from a donor of the cells (in an "allogeneic" transplant).

In some cases, an autologous transplant includes the steps of obtaining, from the subject, a plurality of cells, either circulating in peripheral blood, or within the marrow or other tissue (e.g. spleen, skin, etc.), and manipulating those cells to enrich for cells in the erythroid lineage (e.g. by induction to generate iPSCs, purification of cells expressing certain cell surface markers such as CD34, CD90, CD49f and/or not expressing surface markers characteristic of non-erythroid lineages such as CD10, CD14, CD38, etc.). The cells are, optionally or additionally, expanded, transduced with a transgene, exposed to a cytokine or other peptide or small molecule agent, and/or frozen/thawed prior to transduction with a genome editing system targeting the 13 nt target region, proximal HBG1/2 promoter target sequence, and/or the GATA1 binding motif in BCL11Ae. The genome editing system can be implemented or delivered to the cells in any suitable format, including as a ribonucleoprotein complex, as separated protein and nucleic acid components, and/or as nucleic acids encoding the components of the genome editing system.

However it is implemented, a genome editing system may include, or may be co-delivered with, one or more factors that improve the viability of the cells during and after editing, including without limitation an aryl hydrocarbon receptor antagonist such as StemRegenin-1 (SRI), UM171, LGC0006, alpha-napthoflavone, and CH-223191, and/or an innate immune response antagonist such as cyclosporin A, dexamethasone, reservatrol, a MyD88 inhibitory peptide, an RNAi agent targeting Myd88, a B 18R recombinant protein, a glucocorticoid, OxPAPC, a TLR antagonist, rapamycin, BX795, and a RLR shRNA. These and other factors that improve the viability of the cells during and after editing are described in Gori, under the heading "I. Optimization of Stem Cells" from page 36 through page 61, which is incorporated by reference herein.

The cells, following delivery of the genome editing system, are optionally manipulated e.g. to enrich for HSCs and/or cells in the erythroid lineage and/or for edited cells, to expand them, freeze/thaw, or otherwise prepare the cells for return to the subject. The edited cells are then returned to the subject, for instance in the circulatory system by means of intravenous delivery or delivery or into a solid tissue such as bone marrow.

Functionally, alteration of the 13 nt target region, proximal HBG1/2 promoter target sequence, and/or the GATA1 binding motif in BCL11Ae using the compositions, methods and genome editing systems of this disclosure results in significant induction, among hemoglobin-expressing cells, of Aγ and/or Gγ subunits (referred to interchangeably as HbF expression), e.g. at least 5%, 10%, 15%, 20%, 25%, 30%, 35%, 40%, 45%, 50% or greater induction of Aγ and/or Gγ subunit expression relative to unmodified controls. This induction of protein expression is generally the result of alteration of the 13 nt target region, proximal HBG1/2 promoter target sequence, and/or the GATA1 binding motif in BCL11Ae (expressed, e.g. in terms of the percentage of total genomes comprising indel mutations within the plurality of cells) in some or all of the plurality of cells that are treated, e.g. at least 5%, 10%, 15%, 20%, 25%, 30%, 35%, 40%, 45%, 50% of the plurality of cells comprise at least one allele comprising a sequence alteration, including, without limitation, an indel, insertion, or deletion in or near the 13 nt target region, proximal HBG1/2 promoter target sequence, and/or the GATA1 binding motif in BCL11Ae.

The functional effects of alterations caused or facilitated by the genome editing systems and methods of the present disclosure can be assessed in any number of suitable ways. For example, the effects of alterations on expression of fetal hemoglobin can be assessed at the protein or mRNA level. Expression of HBG1 and HBG2 mRNA can be assessed by digital droplet PCR (ddPCR), which is performed on cDNA samples obtained by reverse transcription of mRNA harvested from treated or untreated samples. Primers for HBG1, HBG2, HBB, and/or HBA may be used individually or multiplexed using methods known in the art. For example, ddPCR analysis of samples may be conducted using the QX200™ ddPCR system commercialized by Bio Rad (Hercules, CA), and associated protocols published by BioRad. Fetal hemoglobin protein may be assessed by high pressure liquid chromatography (HPLC), for example, according to the methods discussed on pp. 143-44 in Chang 2017, incorporated by reference herein, or fast protein liquid chromatography (FPLC), using ion-exchange and/or reverse phase columns to resolve HbF, HbB and HbA and/or Aγ and Gγ globin chains as is known in the art.

It should be noted that the rate at which the 13 nt target region, proximal HBG1/2 promoter target sequence, and/or the GATA1 binding motif in BCL11Ae is altered in the target cells can be modified by the use of optional genome editing system components such as oligonucleotide donor templates. Donor template design is described in general terms below under the heading "Donor template design." Donor templates for use in targeting the 13 nt target region may include, without limitation, donor templates encoding alterations (e.g., deletions) of HBG1 c.-114 to -102 (corresponding to nucleotides 2824-2836 of SEQ ID NO: 902), HBG1 c.-225 to -222 (corresponding to nucleotides 2716-2719 of SEQ ID NO:902)), and/or HBG2 c.-114 to -102 (corresponding to nucleotides 2748-2760 of SEQ ID NO:903). Exemplary 5' and 3' homology arms, and exemplary full-length donor templates encoding deletions such as c. -114 to -102 are also presented below (SEQ ID NOS: 904-909, 990-995). Donor templates used herein may be non-specific templates that are non-homologous to regions of DNA within or near the target sequence. In certain embodiments, donor templates for use in targeting the 13 nt target region may include, without limitation, non-target specific templates that are nonhomologous to regions of DNA within or near the 13 nt target region. For example, a non-specific donor template for use in targeting the 13 nt target region may be non-homologous to the regions of DNA within or near the 13 nt target region and may comprise a donor template encoding the deletion of HBG1 c.-225 to -222 (corresponding to nucleotides 2716-2719 of SEQ ID NO:902). In certain embodiments, donor templates for use in targeting the GATA1 binding motif in BC11Ae may include, without limitation, non-target specific templates that are nonhomologous to regions of DNA within or near GATA1 binding motif in BC11Ae target sequence. Other donor templates for use in targeting BC11Ae may include, without limitation, donor templates including alterations (e.g., deletions) of BC11Ae, including, without limitation, the GATA1 motif in BC11Ae.

The embodiments described herein may be used in all classes of vertebrate including, but not limited to, primates, mice, rats, rabbits, pigs, dogs, and cats.

This overview has focused on a handful of exemplary embodiments that illustrate the principles of genome editing systems and CRISPR-mediated methods of altering cells. For clarity, however, this disclosure encompasses modifications and variations that have not been expressly addressed above, but will be evident to those of skill in the art. With that in mind, the following disclosure is intended to illustrate the operating principles of genome editing systems more generally. What follows should not be understood as limiting, but rather illustrative of certain principles of genome editing systems and CRISPR-mediated methods utilizing these systems, which, in combination with the instant disclosure, will inform those of skill in the art about additional implementations and modifications that are within its scope.

Genome Editing Systems

The term "genome editing system" refers to any system having RNA-guided DNA editing activity. Genome editing systems of the present disclosure include at least two components adapted from naturally occurring CRISPR systems: a guide RNA (gRNA) and an RNA-guided nuclease. These two components form a complex that is capable of associating with a specific nucleic acid sequence and editing the DNA in or around that nucleic acid sequence, for instance by making one or more of a single-strand break (an SSB or nick), a double-strand break (a DSB) and/or a point mutation.

Naturally occurring CRISPR systems are organized evolutionarily into two classes and five types (Makarova 2011, incorporated by reference herein), and while genome editing systems of the present disclosure may adapt components of any type or class of naturally occurring CRISPR system, the embodiments presented herein are generally adapted from Class 2, and type II or V CRISPR systems. Class 2 systems, which encompass types II and V, are characterized by relatively large, multidomain RNA-guided nuclease proteins (e.g., Cas9 or Cpf1) and one or more guide RNAs (e.g., a crRNA and, optionally, a tracrRNA) that form ribonucleoprotein (RNP) complexes that associate with (i.e. target) and cleave specific loci complementary to a targeting (or spacer) sequence of the crRNA. Genome editing systems according to the present disclosure similarly target and edit cellular DNA sequences, but differ significantly from CRISPR systems occurring in nature. For example, the unimolecular guide RNAs described herein do not occur in nature, and both guide RNAs and RNA-guided nucleases according to this disclosure may incorporate any number of non-naturally occurring modifications.

Genome editing systems can be implemented (e.g. administered or delivered to a cell or a subject) in a variety of ways, and different implementations may be suitable for distinct applications. For instance, a genome editing system is implemented, in certain embodiments, as a protein/RNA complex (a ribonucleoprotein, or RNP), which can be included in a pharmaceutical composition that optionally includes a pharmaceutically acceptable carrier and/or an encapsulating agent, such as, without limitation, a lipid or polymer micro- or nano-particle, micelle, or liposome. In certain embodiments, a genome editing system is implemented as one or more nucleic acids encoding the RNA-guided nuclease and guide RNA components described above (optionally with one or more additional components); in certain embodiments, the genome editing system is implemented as one or more vectors comprising such nucleic acids, for instance a viral vector such as an adeno-associated virus (see section below under the heading "Implementation of genome editing systems: delivery, formulations, and routes of administration"); and in certain embodiments, the genome editing system is implemented as a combination of any of the foregoing. Additional or modified implementations that operate according to the principles set forth herein will be apparent to the skilled artisan and are within the scope of this disclosure.

It should be noted that the genome editing systems of the present disclosure can be targeted to a single specific nucleotide sequence, or may be targeted to—and capable of editing in parallel—two or more specific nucleotide sequences through the use of two or more guide RNAs. The use of multiple gRNAs is referred to as "multiplexing" throughout this disclosure, and can be employed to target multiple, unrelated target sequences of interest, or to form multiple SSBs or DSBs within a single target domain and, in some cases, to generate specific edits within such target domain. For example, International Patent Publication No. WO 2015/138510 by Maeder et al. ("Maeder," incorporated by reference herein), describes a genome editing system for correcting a point mutation (C.2991+1655A to G) in the human CEP290 gene that results in the creation of a cryptic splice site, which in turn reduces or eliminates the function of the gene. The genome editing system of Maeder utilizes two guide RNAs targeted to sequences on either side of (i.e. flanking) the point mutation, and forms DSBs that flank the mutation. This, in turn, promotes deletion of the intervening sequence, including the mutation, thereby eliminating the cryptic splice site and restoring normal gene function.

As another example, International Patent Publication No. WO 2016/073990 by Cotta-Ramusino et al. ("Cotta-Ramusino," incorporated by reference herein), describes a genome editing system that utilizes two gRNAs in combination with a Cas9 nickase (a Cas9 that makes a single strand nick such as *S. pyogenes* D10A), an arrangement termed a "dual-nickase system." The dual-nickase system of Cotta-Ramusino is configured to make two nicks on opposite strands of a sequence of interest that are offset by one or more nucleotides, which nicks combine to create a double strand break having an overhang (5' in the case of Cotta-Ramusino, though 3' overhangs are also possible). The overhang, in turn, can facilitate homology directed repair events in some circumstances. And, as another example, International Patent Publication No. WO 2015/070083 by Palestrant et al. (incorporated by reference herein) describes a gRNA targeted to a nucleotide sequence encoding Cas9 (referred to as a "governing RNA"), which can be included in a genome editing system comprising one or more additional gRNAs to permit transient expression of a Cas9 that might otherwise be constitutively expressed, for example in some virally transduced cells. These multiplexing applications are intended to be exemplary, rather than limiting, and the skilled artisan will appreciate that other applications of multiplexing are generally compatible with the genome editing systems described here.

As disclosed herein, in certain embodiments, genome editing systems may comprise multiple gRNAs that may be used to introduce mutations into the GATA1 binding motif in BCL11Ae or the 13 nt target region of HBG1 and/or HBG2. In certain embodiments, genome editing systems disclosed herein may comprise multiple gRNAs used to introduce mutations into the GATA1 binding motif in BCL11Ae and the 13 nt target region of HBG1 and/or HBG2.

Genome editing systems can, in some instances, form double strand breaks that are repaired by cellular DNA double-strand break mechanisms such as NHEJ or HDR. These mechanisms are described throughout the literature (see, e.g., Davis & Maizels 2014 (describing Alt-HDR); Frit 2014 (describing Alt-NHEJ); Iyama & Wilson 2013 (describing canonical HDR and NHEJ pathways generally)).

Where genome editing systems operate by forming DSBs, such systems optionally include one or more components that promote or facilitate a particular mode of double-strand break repair or a particular repair outcome. For instance, Cotta-Ramusino also describes genome editing systems in which a single stranded oligonucleotide "donor template" is added; the donor template is incorporated into a target region of cellular DNA that is cleaved by the genome editing system, and can result in a change in the target sequence.

In certain embodiments, genome editing systems modify a target sequence, or modify expression of a gene in or near the target sequence, without causing single- or double-strand breaks. For example, a genome editing system may include an RNA-guided nuclease fused to a functional domain that acts on DNA, thereby modifying the target sequence or its expression. As one example, an RNA-guided nuclease can be connected to (e.g. fused to) a cytidine deaminase functional domain, and may operate by generating targeted C-to-A substitutions. Exemplary nuclease/deaminase fusions are described in Komor 2016, which is incorporated by reference. Alternatively, a genome editing system may utilize a cleavage-inactivated (i.e. a "dead") nuclease, such as a dead Cas9 (dCas9), and may operate by forming stable complexes on one or more targeted regions of cellular DNA, thereby interfering with functions involving the targeted region(s) including, without limitation, mRNA transcription, chromatin remodeling, etc.

Guide RNA (gRNA) Molecules

The terms "guide RNA" and "gRNA" refer to any nucleic acid that promotes the specific association (or "targeting") of an RNA-guided nuclease such as a Cas9 or a Cpf1 to a target sequence such as a genomic or episomal sequence in a cell. gRNAs can be unimolecular (comprising a single RNA molecule, and referred to alternatively as chimeric), or modular (comprising more than one, and typically two, separate RNA molecules, such as a crRNA and a tracrRNA, which are usually associated with one another, for instance by duplexing). gRNAs and their component parts are described throughout the literature, for instance in Briner 2014 (incorporated herein by reference) and Cotta-Ramusino. Examples of modular and unimolecular gRNAs that may be used according to the embodiments herein include, without limitation, the sequences set forth in SEQ ID NOs:29-31 and 38-51. Examples of gRNA proximal and tail domains that may be used according to the embodiments herein include, without limitation, the sequences set forth in SEQ ID NOs:32-37.

In bacteria and archea, type II CRISPR systems generally comprise an RNA-guided nuclease protein such as Cas9, a CRISPR RNA (crRNA) that includes a 5' region that is complementary to a foreign sequence, and a trans-activating crRNA (tracrRNA) that includes a 5' region that is complementary to, and forms a duplex with, a 3' region of the crRNA. While not intending to be bound by any theory, it is thought that this duplex facilitates the formation of—and is necessary for the activity of—the Cas9/gRNA complex. As type II CRISPR systems were adapted for use in gene editing, it was discovered that the crRNA and tracrRNA could be joined into a single unimolecular or chimeric guide RNA, in one non-limiting example, by means of a four nucleotide (e.g. GAAA) "tetraloop" or "linker" sequence bridging complementary regions of the crRNA (at its 3' end) and the tracrRNA (at its 5' end) (Mali 2013; Jiang 2013; Jinek 2012; all incorporated by reference herein).

Guide RNAs, whether unimolecular or modular, include a "targeting domain" that is fully or partially complementary to a target domain within a target sequence, such as a DNA sequence in the genome of a cell where editing is desired. Targeting domains are referred to by various names in the literature, including without limitation "guide sequences" (Hsu 2013, incorporated by reference herein), "complementarity regions" (Cotta-Ramusino), "spacers" (Briner 2014) and generically as "crRNAs" (Jiang 2013). Irrespective of the names they are given, targeting domains are typically 10-30 nucleotides in length, and in certain embodiments are 16-24 nucleotides in length (for instance, 16, 17, 18, 19, 20, 21, 22, 23 or 24 nucleotides in length), and are at or near the 5' terminus of in the case of a Cas9 gRNA, and at or near the 3' terminus in the case of a Cpf1 gRNA.

In addition to the targeting domains, gRNAs typically (but not necessarily, as discussed below) include a plurality of domains that may influence the formation or activity of gRNA/Cas9 complexes. For instance, as mentioned above, the duplexed structure formed by first and secondary complementarity domains of a gRNA (also referred to as a repeat:anti-repeat duplex) interacts with the recognition (REC) lobe of Cas9 and can mediate the formation of Cas9/gRNA complexes (Nishimasu 2014; Nishimasu 2015; both incorporated by reference herein). It should be noted that the first and/or second complementarity domains may contain one or more poly-A tracts, which can be recognized by RNA polymerases as a termination signal. The sequence of the first and second complementarity domains are, therefore, optionally modified to eliminate these tracts and promote the complete in vitro transcription of gRNAs, for instance through the use of A-G swaps as described in Briner 2014, or A-U swaps. These and other similar modifications to the first and second complementarity domains are within the scope of the present disclosure.

Along with the first and second complementarity domains, Cas9 gRNAs typically include two or more additional duplexed regions that are involved in nuclease activity in vivo but not necessarily in vitro. (Nishimasu 2015). A first stem-loop one near the 3' portion of the second complementarity domain is referred to variously as the "proximal domain," (Cotta-Ramusino) "stem loop 1" (Nishimasu 2014 and 2015) and the "nexus" (Briner 2014). One or more additional stem loop structures are generally present near the 3' end of the gRNA, with the number varying by species: *S. pyogenes* gRNAs typically include two 3' stem loops (for a total of four stem loop structures including the repeat:anti-repeat duplex), while *S. aureus* and other species have only one (for a total of three stem loop structures). A description of conserved stem loop structures (and gRNA structures more generally) organized by species is provided in Briner 2014.

While the foregoing description has focused on gRNAs for use with Cas9, it should be appreciated that other RNA-guided nucleases exist which utilize gRNAs that differ in some ways from those described to this point. For instance, Cpf1 ("CRISPR from Prevotella and Franciscella 1") is a recently discovered RNA-guided nuclease that does not require a tracrRNA to function. (Zetsche 2015a, incorporated by reference herein). A gRNA for use in a Cpf1 genome editing system generally includes a targeting domain and a complementarity domain (alternately referred to as a "handle"). It should also be noted that, in gRNAs for use with Cpf1, the targeting domain is usually present at or near the 3' end, rather than the 5' end as described above in connection with Cas9 gRNAs (the handle is at or near the 5' end of a Cpf1 gRNA).

Those of skill in the art will appreciate, however, that although structural differences may exist between gRNAs from different prokaryotic species, or between Cpf1 and Cas9 gRNAs, the principles by which gRNAs operate are generally consistent. Because of this consistency of operation, gRNAs can be defined, in broad terms, by their targeting domain sequences, and skilled artisans will appreciate that a given targeting domain sequence can be incorporated in any suitable gRNA, including a unimolecular or chimeric gRNA, or a gRNA that includes one or more chemical modifications and/or sequential modifications (substitutions, additional nucleotides, truncations, etc.). Thus, for economy of presentation in this disclosure, gRNAs may be described solely in terms of their targeting domain sequences.

More generally, skilled artisans will appreciate that some aspects of the present disclosure relate to systems, methods and compositions that can be implemented using multiple RNA-guided nucleases. For this reason, unless otherwise specified, the term gRNA should be understood to encompass any suitable gRNA that can be used with any RNA-guided nuclease, and not only those gRNAs that are compatible with a particular species of Cas9 or Cpf1. By way of illustration, the term gRNA can, in certain embodiments, include a gRNA for use with any RNA-guided nuclease occurring in a Class 2 CRISPR system, such as a type II or type V or CRISPR system, or an RNA-guided nuclease derived or adapted therefrom.

gRNA Design

Methods for selection and validation of target sequences as well as off-target analyses have been described previously (see, e.g., Mali 2013; Hsu 2013; Fu 2014; Heigwer 2014; Bae 2014; Xiao 2014; all incorporated by reference herein). As a non-limiting example, gRNA design may involve the use of a software tool to optimize the choice of potential target sequences corresponding to a user's target sequence, e.g., to minimize total off-target activity across the genome. While off-target activity is not limited to cleavage, the cleavage efficiency at each off-target sequence can be predicted, e.g., using an experimentally-derived weighting scheme. These and other guide selection methods are described in detail in Maeder and Cotta-Ramusino.

With respect to selection of gRNA targeting domain sequences directed to HBG1/2 target sites (e.g. the 13 nt target region), an in-silico gRNA target domain identification tool was utilized, and the hits were stratified into four tiers. For *S. pyogenes*, tier 1 targeting domains were selected based on (1) distance upstream or downstream from either end of the target site (i.e., HBG1/2 13 nt target region), specifically within 400 bp of either end of the target site, (2) a high level of orthogonality, and (3) the presence of 5' G. Tier 2 targeting domains were selected based on (1) distance upstream or downstream from either end of the target site (i.e., HBG1/2 13 nt target region), specifically within 400 bp of either end of the target site, and (2) a high level of orthogonality. Tier 3 targeting domains were selected based on (1) distance upstream or downstream from either end of the target site (i.e., HBG1/2 13 nt target region), specifically within 400 bp of either end of the target site and (2) the presence of 5' G. Tier 4 targeting domains were selected based on distance upstream or downstream from either end of the target site (i.e., HBG1/2 13 nt target region), specifically within 400 bp of either end of the target site.

For *S. aureus*, tier 1 targeting domains were selected based on (1) distance upstream or downstream from either end of the target site (i.e., HBG1/2 13 nt target region), specifically within 400 bp of either end of the target site, (2) a high level of orthogonality, (3) the presence of 5' G, and (4) PAM having the sequence NNGRRT (SEQ ID NO:204). Tier 2 targeting domains were selected based on (1) distance upstream or downstream from either end of the target site (i.e., HBG1/2 13 nt target), specifically within 400 bp of either end of the target site, (2) a high level of orthogonality, and (3) PAM having the sequence NNGRRT (SEQ ID NO:204). Tier 3 targeting domains were selected based on (1) distance upstream or downstream from either end of the target site (i.e., HBG1/2 13 nt target region), specifically within 400 bp of either end of the target site, and (2) PAM having the sequence NNGRRT (SEQ ID NO:204). Tier 4 targeting domains were selected based on (1) distance upstream or downstream from either end of the target site (i.e., HBG1/2 13 nt target), specifically within 400 bp of either end of the target site, and (2) PAM having the sequence NNGRRV (SEQ ID NO:205).

Table 2, below, presents targeting domains for *S. pyogenes* and *S. aureus* gRNAs, broken out by (a) tier (1, 2, 3 or 4) and (b) HBG1 or HBG2.

TABLE 2 gRNA targeting domain sequences for HBG1/2 target sites

| | HBG1 | HBG2 |
|---|---|---|
| | *S. pyogenes* | |
| Tier 1 | 251-256 | 760-764 |
| Tier 2 | 257-274 | 765-781 |
| Tier 3 | 275-300 | 275-281, 283-300 |
| Tier 4 | 301-366 | 301-311, 313-342, 344-348, 350-366, 782, 783 |
| | *S. aureus* | |
| Tier 1 | 367-376 | 784-791 |
| Tier 2 | 343, 377-393 | 778, 792-803 |
| Tier 3 | 357, 365, 394-461 | 357, 365, 394-461 |
| Tier 4 | 252-254, 256, 268, 272-274, 292, 295, 347, 348, 353, 360-362, 366, 598-759 | 292, 295. 347, 348, 353, 360-362, 366, 462-468 476-481, 489-587, 601-607, 614-620, 640-666, 674-679, 687-693, 708-714, 733-753, 762-764, 775, 779-781, 804-901 |

In certain embodiments, the gRNAs described herein may be chemically synthesized. As shown in Example 8 below, chemically synthesized Sp37 gRNA (targeting domain set forth in SEQ ID NO:933), which targets the 13 nt deletion associated with HPFH, produced an increased amount of indels compared to in vitro transcribed Sp37 gRNA. Additional exemplary gRNAs that may be chemically synthesized are set forth in SEQ ID NO:970-979 (Table 10).

gRNAs may be designed to target the erythroid specific enhancer of BC11A (BC11Ae) to disrupt expression of a transcriptional repressor, BCL11A (described in Friedland). gRNAs were designed to target the GATA1 binding motif that is in the erythroid specific enhancer of BCL11A that is in the +58 DHS region of intron 2 (i.e., the GATA1 binding motif in BCL11Ae), where the +58 DHS enhancer region comprises the sequence set forth in SEQ ID NO:968. Targeting domain sequences of gRNAs that were designed to target disruption of the GATA1 binding motif in BCL11Ae, include, but are not limited to, the sequences set forth in SEQ ID NOs:952-955. Targeting domain sequences plus PAM (NGG) of gRNAs that were designed to target disruption of the GATA1 binding motif in BCL11Ae, include, but are not limited to, the sequences set forth in SEQ ID NOs:960-963.

gRNA Modifications

The activity, stability, or other characteristics of gRNAs can be altered through the incorporation of certain modifications. As one example, transiently expressed or delivered nucleic acids can be prone to degradation by, e.g., cellular nucleases. Accordingly, the gRNAs described herein can contain one or more modified nucleosides or nucleotides which introduce stability toward nucleases. While not wishing to be bound by theory it is also believed that certain modified gRNAs described herein can exhibit a reduced innate immune response when introduced into cells. Those of skill in the art will be aware of certain cellular responses commonly observed in cells, e.g., mammalian cells, in response to exogenous nucleic acids, particularly those of viral or bacterial origin. Such responses, which can include induction of cytokine expression and release and cell death, may be reduced or eliminated altogether by the modifications presented herein.

Certain exemplary modifications discussed in this section can be included at any position within a gRNA sequence including, without limitation at or near the 5' end (e.g., within 1-10, 1-5, or 1-2 nucleotides of the 5' end) and/or at or near the 3' end (e.g., within 1-10, 1-5, or 1-2 nucleotides of the 3' end). In some cases, modifications are positioned within functional motifs, such as the repeat-anti-repeat duplex of a Cas9 gRNA, a stem loop structure of a Cas9 or Cpf1 gRNA, and/or a targeting domain of a gRNA.

As one example, the 5' end of a gRNA can include a eukaryotic mRNA cap structure or cap analog (e.g., a G(5')ppp(5')G cap analog, a m7G(5')ppp(5')G cap analog, or a 3'-O-Me-m7G(5')ppp(5')G anti reverse cap analog (ARCA)), as shown below:

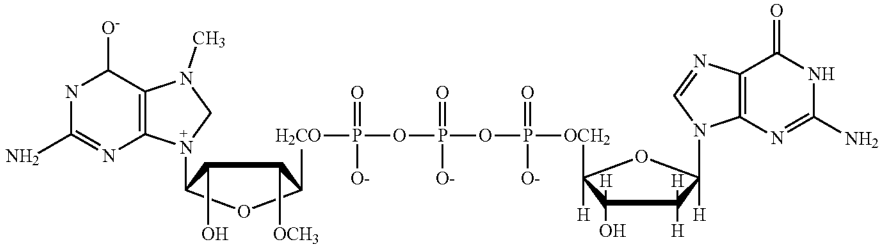

The cap or cap analog can be included during either chemical synthesis or in vitro transcription of the gRNA.

Along similar lines, the 5' end of the gRNA can lack a 5' triphosphate group. For instance, in vitro transcribed gRNAs can be phosphatase-treated (e.g., using calf intestinal alkaline phosphatase) to remove a 5' triphosphate group.

Another common modification involves the addition, at the 3' end of a gRNA, of a plurality (e.g., 1-10, 10-20, or 25-200) of adenine (A) residues referred to as a polyA tract. The polyA tract can be added to a gRNA during chemical synthesis, following in vitro transcription using a polyadenosine polymerase (e.g., *E. coli* Poly(A)Polymerase), or in vivo by means of a polyadenylation sequence, as described in Maeder.

It should be noted that the modifications described herein can be combined in any suitable manner, e.g. a gRNA, whether transcribed in vivo from a DNA vector, or in vitro transcribed gRNA, can include either or both of a 5' cap structure or cap analog and a 3' polyA tract.

Guide RNAs can be modified at a 3' terminal U ribose. For example, the two terminal hydroxyl groups of the U ribose can be oxidized to aldehyde groups and a concomitant opening of the ribose ring to afford a modified nucleoside as shown below:

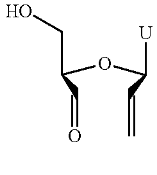

wherein "U" can be an unmodified or modified uridine.

The 3' terminal U ribose can be modified with a 2'3' cyclic phosphate as shown below:

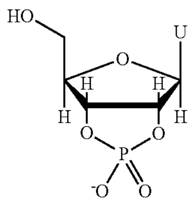

wherein "U" can be an unmodified or modified uridine.

Guide RNAs can contain 3' nucleotides which can be stabilized against degradation, e.g., by incorporating one or more of the modified nucleotides described herein. In certain embodiments, uridines can be replaced with modified uridines, e.g., 5-(2-amino)propyl uridine, and 5-bromo uridine, or with any of the modified uridines described herein; adenosines and guanosines can be replaced with modified adenosines and guanosines, e.g., with modifications at the 8-position, e.g., 8-bromo guanosine, or with any of the modified adenosines or guanosines described herein.

In certain embodiments, sugar-modified ribonucleotides can be incorporated into the gRNA, e.g., wherein the 2' OH-group is replaced by a group selected from H, —OR, —R (wherein R can be, e.g., alkyl, cycloalkyl, aryl, aralkyl, heteroaryl or sugar), halo, —SH, —SR (wherein R can be, e.g., alkyl, cycloalkyl, aryl, aralkyl, heteroaryl or sugar), amino (wherein amino can be, e.g., $NH_2$; alkylamino, dialkylamino, heterocyclyl, arylamino, diarylamino, heteroarylamino, diheteroarylamino, or amino acid); or cyano (—CN). In certain embodiments, the phosphate backbone can be modified as described herein, e.g., with a phosphorothioate (PhTx) group. In certain embodiments, one or more of the nucleotides of the gRNA can each independently be a modified or unmodified nucleotide including, but not limited to 2'-sugar modified, such as, 2'-O-methyl, 2'-O-methoxyethyl, or 2'-Fluoro modified including, e.g., 2'-F or 2'-O-methyl, adenosine (A), 2'-F or 2'-O-methyl, cytidine (C), 2'-F or 2'-O-methyl, uridine (U), 2'-F or 2'-O-methyl, thymidine (T), 2'-F or 2'-O-methyl, guanosine (G), 2'-O-methoxyethyl-5-methyluridine (Teo), 2'-O-methoxyethyladenosine (Aeo), 2'-O-methoxyethyl-5-methylcytidine (m5Ceo), and any combinations thereof.

Guide RNAs can also include "locked" nucleic acids (LNA) in which the 2' OH-group can be connected, e.g., by a C1-6 alkylene or C1-6 heteroalkylene bridge, to the 4' carbon of the same ribose sugar. Any suitable moiety can be used to provide such bridges, include without limitation methylene, propylene, ether, or amino bridges; O-amino (wherein amino can be, e.g., $NH_2$; alkylamino, dialkylamino, heterocyclyl, arylamino, diarylamino, heteroarylamino, or diheteroarylamino, ethylenediamine, or polyamino) and aminoalkoxy or $O(CH_2)_n$-amino (wherein amino can be, e.g., $NH_2$; alkylamino, dialkylamino, heterocyclyl, arylamino, diarylamino, heteroarylamino, or diheteroarylamino, ethylenediamine, or polyamino).

In certain embodiments, a gRNA can include a modified nucleotide which is multicyclic (e.g., tricyclo; and "unlocked" forms, such as glycol nucleic acid (GNA) (e.g., R-GNA or S-GNA, where ribose is replaced by glycol units attached to phosphodiester bonds), or threose nucleic acid (TNA, where ribose is replaced with α-L-threofuranosyl-(3'-2')).

Generally, gRNAs include the sugar group ribose, which is a 5-membered ring having an oxygen. Exemplary modified gRNAs can include, without limitation, replacement of the oxygen in ribose (e.g., with sulfur (S), selenium (Se), or alkylene, such as, e.g., methylene or ethylene); addition of a double bond (e.g., to replace ribose with cyclopentenyl or cyclohexenyl); ring contraction of ribose (e.g., to form a 4-membered ring of cyclobutane or oxetane); ring expansion of ribose (e.g., to form a 6- or 7-membered ring having an additional carbon or heteroatom, such as for example, anhydrohexitol, altritol, mannitol, cyclohexanyl, cyclohexenyl, and morpholino that also has a phosphoramidate backbone). Although the majority of sugar analog alterations are localized to the 2' position, other sites are amenable to modification, including the 4' position. In certain embodiments, a gRNA comprises a 4'-S, 4'-Se or a 4'-C-aminomethyl-2'-O-Me modification.

In certain embodiments, deaza nucleotides, e.g., 7-deaza-adenosine, can be incorporated into the gRNA. In certain embodiments, O- and N-alkylated nucleotides, e.g., N6-methyl adenosine, can be incorporated into the gRNA. In certain embodiments, one or more or all of the nucleotides in a gRNA are deoxynucleotides.

Examples of gRNAs that include modifications and that may be used according to the embodiments herein include, without limitation, gRNAs that target the 13 nt target region. In certain embodiments, gRNAs may contain one or more modifications. In certain embodiments, the modifications may be at or near the 5'end, 3' end or both the 5' and 3' ends of the gRNA. In certain embodiments, modifications may include, without limitation, addition of one or more PhTx groups or one or more 2'-O-methyl groups. In certain embodiments, the Sp35 gRNA (SEQ ID NO:970) may contain modifications at or near the 5'end and/or 3' ends. Exemplary gRNAs that include modifications of Sp35 gRNA, such as additions of one or more of PhTx groups and/or 2'-O-methyl groups are set forth in Table 10.

In certain embodiments, gRNAs used according to the embodiments herein may include truncated forms of a full length gRNA. In certain embodiments, truncated gRNAs may have one or more nucleotides removed from the 5' or 3' end of the gRNA compared with a full-length gRNA. In certain embodiments, truncated gRNAs have one or more nucleotides removed from the protospacer region of the gRNA. Examples of gRNAs that are truncated that may be used according to the embodiments herein include, without limitation, the truncated forms of the gRNA Sp35 (SEQ ID NO:970), such as the sequences set forth in SEQ ID NOs: 976-978 (Table 10).

RNA-Guided Nucleases

RNA-guided nucleases according to the present disclosure include, but are not limited to, naturally-occurring Class 2 CRISPR nucleases such as Cas9, and Cpf1, as well as other nucleases derived or obtained therefrom. In functional terms, RNA-guided nucleases are defined as those nucleases that: (a) interact with (e.g. complex with) a gRNA; and (b) together with the gRNA, associate with, and optionally cleave or modify, a target region of a DNA that includes (i) a sequence complementary to the targeting domain of the gRNA and, optionally, (ii) an additional sequence referred to as a "protospacer adjacent motif," or "PAM," which is described in greater detail below. As the following examples will illustrate, RNA-guided nucleases can be defined, in broad terms, by their PAM specificity and cleavage activity, even though variations may exist between individual RNA-guided nucleases that share the same PAM specificity or cleavage activity. Skilled artisans will appreciate that some aspects of the present disclosure relate to systems, methods and compositions that can be implemented using any suitable RNA-guided nuclease having a certain PAM specificity and/or cleavage activity. For this reason, unless otherwise specified, the term RNA-guided nuclease should be understood as a generic term, and not limited to any particular type (e.g. Cas9 vs. Cpf1), species (e.g. *S. pyogenes* vs. *S. aureus*) or variation (e.g. full-length vs. truncated or split; naturally-occurring PAM specificity vs. engineered PAM specificity, etc.) of RNA-guided nuclease.

The PAM sequence takes its name from its sequential relationship to the "protospacer" sequence that is complementary to gRNA targeting domains (or "spacers"). Together with protospacer sequences, PAM sequences define target regions or sequences for specific RNA-guided nuclease/gRNA combinations.

Various RNA-guided nucleases may require different sequential relationships between PAMs and protospacers. In general, Cas9s recognize PAM sequences that are 3' of the protospacer. Cpf1, on the other hand, generally recognizes PAM sequences that are 5' of the protospacer.

In addition to recognizing specific sequential orientations of PAMs and protospacers, RNA-guided nucleases can also recognize specific PAM sequences. *S. aureus* Cas9, for instance, recognizes a PAM sequence of NNGRRT or NNGRRV, wherein the N residues are immediately 3' of the region recognized by the gRNA targeting domain. *S. pyogenes* Cas9 recognizes NGG PAM sequences. And *F. novicida* Cpf1 recognizes a TIN PAM sequence. PAM sequences have been identified for a variety of RNA-guided nucleases, and a strategy for identifying novel PAM sequences has been described by Shmakov 2015. It should also be noted that engineered RNA-guided nucleases can have PAM specificities that differ from the PAM specificities of reference molecules (for instance, in the case of an engineered RNA-guided nuclease, the reference molecule may be the naturally occurring variant from which the RNA-guided nuclease is derived, or the naturally occurring variant having the greatest amino acid sequence homology to the engineered RNA-guided nuclease). Examples of PAMs that may be used according to the embodiments herein include, without limitation, the sequences set forth in SEQ ID NOs: 199-205.

In addition to their PAM specificity, RNA-guided nucleases can be characterized by their DNA cleavage activity: naturally-occurring RNA-guided nucleases typically form DSBs in target nucleic acids, but engineered variants have been produced that generate only SSBs (discussed above and in Ran & Hsu 2013, incorporated by reference herein), or that do not cut at all.

Cas9

Crystal structures have been determined for *S. pyogenes* Cas9 (Jinek 2014), and for *S. aureus* Cas9 in complex with a unimolecular guide RNA and a target DNA (Nishimasu 2014; Anders 2014; and Nishimasu 2015).

A naturally occurring Cas9 protein comprises two lobes: a recognition (REC) lobe and a nuclease (NUC) lobe; each of which comprise particular structural and/or functional domains. The REC lobe comprises an arginine-rich bridge helix (BH) domain, and at least one REC domain (e.g. a REC1 domain and, optionally, a REC2 domain). The REC lobe does not share structural similarity with other known proteins, indicating that it is a unique functional domain. While not wishing to be bound by any theory, mutational analyses suggest specific functional roles for the BH and REC domains: the BH domain appears to play a role in gRNA:DNA recognition, while the REC domain is thought to interact with the repeat:anti-repeat duplex of the gRNA and to mediate the formation of the Cas9/gRNA complex.

The NUC lobe comprises a RuvC domain, an HNH domain, and a PAM-interacting (PI) domain. The RuvC domain shares structural similarity to retroviral integrase superfamily members and cleaves the non-complementary (i.e. bottom) strand of the target nucleic acid. It may be formed from two or more split RuvC motifs (such as RuvC I, RuvCII, and RuvCIII in *S. pyogenes* and *S. aureus*). The HNH domain, meanwhile, is structurally similar to HNN endonuclease motifs, and cleaves the complementary (i.e. top) strand of the target nucleic acid. The PI domain, as its name suggests, contributes to PAM specificity. Examples of polypeptide sequences encoding Cas9 RuvC-like and Cas9 HNH-like domains that may be used according to the embodiments herein are set forth in SEQ ID NOs: 15-23, 52-123 (RuvC-like domains) and SEQ ID NOs:24-28, 124-198 (HNH-like domains).

While certain functions of Cas9 are linked to (but not necessarily fully determined by) the specific domains set forth above, these and other functions may be mediated or influenced by other Cas9 domains, or by multiple domains on either lobe. For instance, in *S. pyogenes* Cas9, as described in Nishimasu 2014, the repeat:antirepeat duplex of the gRNA falls into a groove between the REC and NUC lobes, and nucleotides in the duplex interact with amino acids in the BH, PI, and REC domains. Some nucleotides in the first stem loop structure also interact with amino acids in multiple domains (PI, BH and REC1), as do some nucleotides in the second and third stem loops (RuvC and PI domains). Examples of polypeptide sequences encoding Cas9 molecules that may be used according to the embodiments herein are set forth in SEQ ID NOs: 1-2, 4-6, 12, 14.

Cpf1

The crystal structure of Acidaminococcus sp. Cpf1 in complex with crRNA and a double-stranded (ds) DNA target including a TTTN PAM sequence has been solved by Yamano 2016 (incorporated by reference herein). Cpf1, like Cas9, has two lobes: a REC (recognition) lobe, and a NUC (nuclease) lobe. The REC lobe includes REC1 and REC2 domains, which lack similarity to any known protein structures. The NUC lobe, meanwhile, includes three RuvC domains (RuvC-I, -II and -III) and a BH domain. However, in contrast to Cas9, the Cpf1 REC lobe lacks an HNH domain, and includes other domains that also lack similarity to known protein structures: a structurally unique PI domain, three Wedge (WED) domains (WED-I, -II and -III), and a nuclease (Nuc) domain.

While Cas9 and Cpf1 share similarities in structure and function, it should be appreciated that certain Cpf1 activities are mediated by structural domains that are not analogous to any Cas9 domains. For instance, cleavage of the complementary strand of the target DNA appears to be mediated by the Nuc domain, which differs sequentially and spatially from the HNH domain of Cas9. Additionally, the non-targeting portion of Cpf1 gRNA (the handle) adopts a pseudoknot structure, rather than a stem loop structure formed by the repeat:antirepeat duplex in Cas9 gRNAs.

Modifications of RNA-guided Nucleases

The RNA-guided nucleases described above have activities and properties that can be useful in a variety of applications, but the skilled artisan will appreciate that RNA-guided nucleases can also be modified in certain instances, to alter cleavage activity, PAM specificity, or other structural or functional features.

Turning first to modifications that alter cleavage activity, mutations that reduce or eliminate the activity of domains within the NUC lobe have been described above. Exemplary mutations that may be made in the RuvC domains, in the Cas9 HNH domain, or in the Cpf1 Nuc domain are described in Ran & Hsu 2013 and Yamano 2016, as well as in Cotta-Ramusino. In general, mutations that reduce or eliminate activity in one of the two nuclease domains result in RNA-guided nucleases with nickase activity, but it should be noted that the type of nickase activity varies depending on which domain is inactivated. As one example, inactivation of a RuvC domain of a Cas9 will result in a nickase that cleaves the complementary or top strand. On the other hand, inactivation of a Cas9 HNH domain results in a nickase that cleaves the bottom or non-complementary strand.

Modifications of PAM specificity relative to naturally occurring Cas9 reference molecules has been described by Kleinstiver et al. for both *S. pyogenes* (Kleinstiver 2015a) and *S. aureus* (Kleinstiver 2015b. Kleinstiver et al. have also described modifications that improve the targeting fidelity of Cas9 (Kleinstiver 2016). Each of these references is incorporated by reference herein.

RNA-guided nucleases have been split into two or more parts, as described by Zetsche 2015b and by Fine 2015, both incorporated by reference herein.

RNA-guided nucleases can be, in certain embodiments, size-optimized or truncated, for instance via one or more deletions that reduce the size of the nuclease while still retaining gRNA association, target and PAM recognition, and cleavage activities. In certain embodiments, RNA guided nucleases are bound, covalently or non-covalently, to another polypeptide, nucleotide, or other structure, optionally by means of a linker. Exemplary bound nucleases and linkers are described by Guilinger 2014, which is incorporated by reference for all purposes herein.

RNA-guided nucleases also optionally include a tag, such as, but not limited to, a nuclear localization signal to facilitate movement of RNA-guided nuclease protein into the nucleus. In certain embodiments, the RNA-guided nuclease can incorporate C- and/or N-terminal nuclear localization signals. Nuclear localization sequences are known in the art and are described in Maeder and elsewhere.

The foregoing list of modifications is intended to be exemplary in nature, and the skilled artisan will appreciate, in view of the instant disclosure, that other modifications may be possible or desirable in certain applications. For brevity, therefore, exemplary systems, methods and compositions of the present disclosure are presented with reference to particular RNA-guided nucleases, but it should be understood that the RNA-guided nucleases used may be modified in ways that do not alter their operating principles. Such modifications are within the scope of the present disclosure.

Nucleic Acids Encoding RNA-Guided Nucleases

Nucleic acids encoding RNA-guided nucleases, e.g., Cas9, Cpf1 or functional fragments thereof, are provided herein. Examples of nucleic acid sequences encoding Cas9 molecules that may be used according to the embodiments herein are set forth in SEQ ID NOs:3, 7-11, 13. Exemplary nucleic acids encoding RNA-guided nucleases have been described previously (see, e.g., Cong 2013; Wang 2013; Mali 2013; Jinek 2012).

In some cases, a nucleic acid encoding an RNA-guided nuclease can be a synthetic nucleic acid sequence. For example, the synthetic nucleic acid molecule can be chemically modified. In certain embodiments, an mRNA encoding an RNA-guided nuclease will have one or more (e.g., all) of the following properties: it can be capped; polyadenylated; and substituted with κ-methylcytidine and/or pseudouridine.

Synthetic nucleic acid sequences can also be codon optimized, e.g., at least one non-common codon or less-common codon has been replaced by a common codon. For example, the synthetic nucleic acid can direct the synthesis of an optimized messenger mRNA, e.g., optimized for expression in a mammalian expression system, e.g., described herein. Examples of codon optimized Cas9 coding sequences are presented in Cotta-Ramusino.

In addition, or alternatively, a nucleic acid encoding an RNA-guided nuclease may comprise a nuclear localization sequence (NLS). Nuclear localization sequences are known in the art.

Functional Analysis of Candidate Molecules

Candidate RNA-guided nucleases, gRNAs, and complexes thereof, can be evaluated by standard methods known in the art. See, e.g. Cotta-Ramusino. The stability of RNP complexes may be evaluated by differential scanning fluorimetry, as described below.

Differential Scanning Fluorimetry (DSF)

The thermostability of ribonucleoprotein (RNP) complexes comprising gRNAs and RNA-guided nucleases can be measured via DSF. The DSF technique measures the thermostability of a protein, which can increase under favorable conditions such as the addition of a binding RNA molecule, e.g., a gRNA.

A DSF assay can be performed according to any suitable protocol, and can be employed in any suitable setting, including without limitation (a) testing different conditions (e.g. different stoichiometric ratios of gRNA: RNA-guided nuclease protein, different buffer solutions, etc.) to identify optimal conditions for RNP formation; and (b) testing modifications (e.g. chemical modifications, alterations of sequence, etc.) of an RNA-guided nuclease and/or a gRNA to identify those modifications that improve RNP formation or stability. One readout of a DSF assay is a shift in melting temperature of the RNP complex; a relatively high shift suggests that the RNP complex is more stable (and may thus have greater activity or more favorable kinetics of formation, kinetics of degradation, or another functional characteristic) relative to a reference RNP complex characterized by a lower shift. When the DSF assay is deployed as a screening tool, a threshold melting temperature shift may be specified, so that the output is one or more RNPs having a melting temperature shift at or above the threshold. For instance, the threshold can be 5-10° C. (e.g. 5°, 6°, 7°, 8°, 9°, 10°) or more, and the output may be one or more RNPs characterized by a melting temperature shift greater than or equal to the threshold.

Two non-limiting examples of DSF assay conditions are set forth below:

To determine the best solution to form RNP complexes, a fixed concentration (e.g. 2 μM) of Cas9 in water+10× SYPRO Orange® (Life Technologies cat # S-6650) is dispensed into a 384 well plate. An equimolar amount ofgRNA diluted in solutions with varied pH and salt is then added. After incubating at room temperature for 10' and brief centrifugation to remove any bubbles, a Bio-Rad CFX384™ Real-Time System C, 1000 Touch™ Thermal Cycler with the Bio-Rad CFX Manager software is used to run a gradient from 20° C. to 90° C. with a 1° C. increase in temperature every 10 seconds.

The second assay consists of mixing various concentrations of gRNA with fixed concentration (e.g. 2 μM) Cas9 in optimal buffer from assay 1 above and incubating (e.g. at RT for 10') in a 384 well plate. An equal volume of optimal buffer+10×SYPRO Orange® (Life Technologies cat # S-6650) is added and the plate sealed with Microseal® B adhesive (MSB-1001). Following brief centrifugation to remove any bubbles, a Bio-Rad CFX384™ Real-Time System C1000 Touch™ Thermal Cycler with the Bio-Rad CFX Manager software is used to run a gradient from 20° C. to 90° C. with a 1° C. increase in temperature every 10 seconds.

Genome Editing Strategies

The genome editing systems described above are used, in various embodiments of the present disclosure, to generate edits in (i.e. to alter) targeted regions of DNA within or obtained from a cell. Various strategies are described herein to generate particular edits, and these strategies are generally described in terms of the desired repair outcome, the number and positioning of individual edits (e.g. SSBs or DSBs), and the target sites of such edits.

Genome editing strategies that involve the formation of SSBs or DSBs are characterized by repair outcomes including: (a) deletion of all or part of a targeted region; (b) insertion into or replacement of all or part of a targeted region; or (c) interruption of all or part of a targeted region. This grouping is not intended to be limiting, or to be binding to any particular theory or model, and is offered solely for economy of presentation. Skilled artisans will appreciate that the listed outcomes are not mutually exclusive and that some repairs may result in other outcomes. The description of a particular editing strategy or method should not be understood to require a particular repair outcome unless otherwise specified.

Replacement of a targeted region generally involves the replacement of all or part of the existing sequence within the targeted region with a homologous sequence, for instance through gene correction or gene conversion, two repair outcomes that are mediated by HDR pathways. HDR is promoted by the use of a donor template, which can be single-stranded or double stranded, as described in greater detail below. Single or double stranded templates can be exogenous, in which case they will promote gene correction, or they can be endogenous (e.g. a homologous sequence within the cellular genome), to promote gene conversion. Exogenous templates can have asymmetric overhangs (i.e. the portion of the template that is complementary to the site of the DSB may be offset in a 3' or 5' direction, rather than being centered within the donor template), for instance as described by Richardson 2016 (incorporated by reference herein). In instances where the template is single stranded, it can correspond to either the complementary (top) or non-complementary (bottom) strand of the targeted region.

Gene conversion and gene correction are facilitated, in some cases, by the formation of one or more nicks in or around the targeted region, as described in Ran and Cotta-Ramusino. In some cases, a dual-nickase strategy is used to form two offset SSBs that, in turn, form a single DSB having an overhang (e.g. a 5' overhang).

Interruption and/or deletion of all or part of a targeted sequence can be achieved by a variety of repair outcomes. As one example, a sequence can be deleted by simultaneously generating two or more DSBs that flank a targeted region, which is then excised when the DSBs are repaired, as is described in Maeder for the LCA10 mutation. As another example, a sequence can be interrupted by a deletion generated by formation of a double strand break with single-stranded overhangs, followed by exonucleolytic processing of the overhangs prior to repair.

One specific subset of target sequence interruptions is mediated by the formation of an indel within the targeted sequence, where the repair outcome is typically mediated by NHEJ pathways (including Alt-NHEJ). NHEJ is referred to as an "error prone" repair pathway because of its association with indel mutations. In some cases, however, a DSB is repaired by NHEJ without alteration of the sequence around it (a so-called "perfect" or "scarless" repair); this generally requires the two ends of the DSB to be perfectly ligated. Indels, meanwhile, are thought to arise from enzymatic processing of free DNA ends before they are ligated that adds and/or removes nucleotides from either or both strands of either or both free ends.

Because the enzymatic processing of free DSB ends may be stochastic in nature, indel mutations tend to be variable, occurring along a distribution, and can be influenced by a variety of factors, including the specific target site, the cell type used, the genome editing strategy used, etc. Even so, it is possible to draw limited generalizations about indel formation: deletions formed by repair of a single DSB are most commonly in the 1-50 bp range, but can reach greater than 100-200 bp. Insertions formed by repair of a single DSB tend to be shorter and often include short duplications of the sequence immediately surrounding the break site. However, it is possible to obtain large insertions, and in these cases, the inserted sequence has often been traced to other regions of the genome or to plasmid DNA present in the cells.

Indel mutations—and genome editing systems configured to produce indels—are useful for interrupting target sequences, for example, when the generation of a specific final sequence is not required and/or where a frameshift mutation would be tolerated. They can also be useful in settings where particular sequences are preferred, insofar as the certain sequences desired tend to occur preferentially from the repair of an SSB or DSB at a given site. Indel mutations are also a useful tool for evaluating or screening the activity of particular genome editing systems and their components. In these and other settings, indels can be characterized by (a) their relative and absolute frequencies in the genomes of cells contacted with genome editing systems and (b) the distribution of numerical differences relative to the unedited sequence, e.g. ±1, ±2, ±3, etc. As one example, in a lead-finding setting, multiple gRNAs can be screened to identify those gRNAs that most efficiently drive cutting at a target site based on an indel readout under controlled conditions. Guides that produce indels at or above a threshold frequency, or that produce a particular distribution of indels, can be selected for further study and development. Indel frequency and distribution can also be useful as a readout for evaluating different genome editing system implementations or formulations and delivery methods, for instance by keeping the gRNA constant and varying certain other reaction conditions or delivery methods.

Multiplex Strategies

Genome editing systems according to this disclosure may also be employed for multiplex gene editing to generate two or more DSBs, either in the same locus or in different loci. Any of the RNA-guided nucleases and gRNAs disclosed herein may be used in genome editing systems for multiplex gene editing. Strategies for editing that involve the formation of multiple DSBs, or SSBs, are described in, for instance, Cotta-Ramusino.

As disclosed herein, multiple gRNAs may be used in genome editing systems to introduce alterations (e.g., deletions, insertions) into the 13 nt target region of HBG1 and/or HBG2. In certain embodiments, one or more gRNAs comprising a targeting domain set forth in SEQ ID NOs:251-901, 940-942 may be used to introduce alterations in the 13 nt target region of HBG1 and/or HBG2. In certain embodiments, one or more gRNAs comprising a sequence set forth in SEQ ID NOs:970-979 may be used to introduce alterations in the 13 nt target region of HBG1 and/or HBG2. In other embodiments, multiple gRNAs may be used in genome editing systems to introduce alterations into the GATA1 binding motif in BCL11Ae. In certain embodiments, one or more gRNAs comprising a targeting domain set forth in SEQ ID NOs:952-955 may be used to introduce alterations in the GATA1 binding motif in BCL11Ae. Multiple gRNAs may also be used in genome editing systems to introduce alterations into the GATA binding motif in BCL11Ae and the 13 nt target region of HBG1 and/or HBG2. In certain embodiments, one or more gRNAs comprising a targeting domain set forth in SEQ ID NOs:952-955 may be used to introduce alterations in the GATA1 binding motif in BCL11Ae and one or more gRNAs comprising a targeting domain set forth in SEQ ID NOs:251-901, 940-942 and/or one or more gRNAs comprising a sequence set forth in SEQ ID NOs:970-979 may be used to introduce alterations in the 13 nt target region of HBG1 and/or HBG2.

Donor Template Design

Donor template design is described in detail in the literature, for instance in Cotta-Ramusino. DNA oligomer donor templates (oligodeoxynucleotides, ODNs, or template nucleic acids), which can be single stranded (ssODNs) or double-stranded (dsODNs), can be used to facilitate HDR-based repair of DSBs or to boost overall editing rate, and are particularly useful for introducing alterations into a target DNA sequence, inserting a new sequence into the target sequence, or replacing the target sequence altogether.

Whether single-stranded or double stranded, donor templates generally include regions that are homologous to regions of DNA within or near (e.g. flanking or adjoining) a target sequence to be cleaved. These homologous regions are referred to here as "homology arms," and are illustrated schematically below:

[5' homology arm]-[replacement sequence]--[3' homology arm].

The homology arms can have any suitable length (including 0 nucleotides if only one homology arm is used), and 3' and 5' homology arms can have the same length, or can differ in length. The selection of appropriate homology arm lengths can be influenced by a variety of factors, such as the desire to avoid homologies or microhomologies with certain sequences such as Alu repeats or other very common elements. For example, a 5' homology arm can be shortened to avoid a sequence repeat element. In other embodiments, a 3' homology arm can be shortened to avoid a sequence repeat element. In some embodiments, both the 5' and the 3' homology arms can be shortened to avoid including certain sequence repeat elements. In addition, some homology arm designs can improve the efficiency of editing or increase the frequency of a desired repair outcome. For example, Richardson 2016, which is incorporated by reference, found that the relative asymmetry of 3' and 5' homology arms of single stranded donor templates influenced repair rates and/or outcomes.

Replacement sequences in donor templates have been described elsewhere, including in Cotta-Ramusino et al. A replacement sequence can be any suitable length (including zero nucleotides, where the desired repair outcome is a deletion), and typically includes one, two, three or more sequence modifications relative to the naturally-occurring sequence within a cell in which editing is desired. One common sequence modification involves the alteration of the naturally-occurring sequence to repair a mutation that is related to a disease or condition of which treatment is desired. Another common sequence modification involves the alteration of one or more sequences that are complementary to, or then, the PAM sequence of the RNA-guided nuclease or the targeting domain of the gRNA(s) being used to generate an SSB or DSB, to reduce or eliminate repeated cleavage of the target site after the replacement sequence has been incorporated into the target site.

Where a linear ssODN is used, it can be configured to (i) anneal to the nicked strand of the target nucleic acid, (ii) anneal to the intact strand of the target nucleic acid, (iii) anneal to the plus strand of the target nucleic acid, and/or (iv) anneal to the minus strand of the target nucleic acid. An ssODN may have any suitable length, e.g., about, at least, or no more than 150-200 nucleotides (e.g., 150, 160, 170, 180, 190, or 200 nucleotides).

It should be noted that a template nucleic acid can also be a nucleic acid vector, such as a viral genome or circular double stranded DNA, e.g., a plasmid. Nucleic acid vectors comprising donor templates can include other coding or non-coding elements. For example, a template nucleic acid can be delivered as part of a viral genome (e.g. in an AAV or lentiviral genome) that includes certain genomic backbone elements (e.g. inverted terminal repeats, in the case of an AAV genome) and optionally includes additional sequences coding for a gRNA and/or an RNA-guided nuclease. In certain embodiments, the donor template can be adjacent to, or flanked by, target sites recognized by one or more gRNAs, to facilitate the formation of free DSBs on one or both ends of the donor template that can participate in repair of corresponding SSBs or DSBs formed in cellular DNA using the same gRNAs. Exemplary nucleic acid vectors suitable for use as donor templates are described in Cotta-Ramusino, which is incorporated by reference.

Whatever format is used, a template nucleic acid can be designed to avoid undesirable sequences. In certain embodiments, one or both homology arms can be shortened to avoid overlap with certain sequence repeat elements, e.g., Alu repeats, LINE elements, etc.

In certain embodiments, silent, non-pathogenic SNPs may be included in the ssODN donor template to allow for identification of a gene editing event.

In certain embodiments, a donor template may be a non-specific template that is non-homologous to regions of DNA within or near a target sequence to be cleaved. In certain embodiments, donor templates for use in targeting the GATA1 binding motif in BCL11Ae may include, without limitation, non-target specific templates that are nonhomologous to regions of DNA within or near the GATA1 binding motif in BCL11Ae. In certain embodiments, donor templates for use in targeting the 13 nt target region may include, without limitation, non-target specific templates that are nonhomologous to regions of DNA within or near the 13 nt target region.

A donor template or template nucleic acid, as that term is used herein, refers to a nucleic acid sequence which can be used in conjunction with an RNA nuclease molecule and one or more gRNA molecules to alter (e.g., delete, disrupt, or modify) a target DNA sequence. In certain embodiments, the template nucleic acid results in a 13 nt deletion at the 13 nt target region of HBG1 and/or HBG2. In certain embodiments, the alteration (e.g., deletion) may be selected from HBG1 13 del c.-114 to -102, HBG2 13 del c.-114 to -102, or a combination thereof. In certain embodiments, the 13 nt target region may be selected from HBG1 c.-114 to -102 (e.g., nucleotides 2824-2836 of SEQ ID NO:902 (HBG1)), and HBG2 c.-114 to -102 (e.g., nucleotides 2748-2760 of SEQ ID NO:903 (HBG2)), or a combination thereof. In certain embodiments, the template nucleic acid may be a positive strand or a negative strand.

For example, a template nucleic acid for introducing the 13 nt deletion at the 13 nt target region (HBG1 c.-114 to -102 (e.g., nucleotides 2824-2836 of SEQ ID NO:902 (HBG1)), HBG2 c.-114 to -102 (e.g., nucleotides 2748-2760 of SEQ ID NO:903 (HBG2)), or a combination thereof may comprise a 5' homology arm, a replacement sequence, and a 3' homology arm, where the replacement sequence is 0 nucleotides or 0 bp. In certain embodiments, the 5' homology arm comprises about 200 nucleotides in length, e.g., at least 25, 50, 75, 100, 125, 150, 175, or 200 nucleotides in length. In certain embodiments, the 5' homology arm comprises about 50 to 100 bp, e.g., 55 to 95, 60 to 90, 70 to 90, or 80 to 90 bp, homology 5' of the 13 nt target region (e.g., HBG1 c.-114 to -102 (e.g., nucleotides 2824-2836 of SEQ ID NO:902 (HBG1)) or HBG2 c.-114 to -102 (e.g., nucleotides 2748-2760 of SEQ ID NO:903 (HBG2)). In certain embodiments, the 5' homology arm comprises, consists essentially of, or consists of SEQ ID NO:904 (ssODN1 5' homology arm), SEQ ID NO:907 (PhTx ssODN1 5'homology arm), SEQ ID NO:991 (OLI16414 5' homology arm), or SEQ ID NO:994 (OLI16412 5' homology arm). In certain embodiments, the 3' homology arm comprises about 200 nucleotides in length, e.g., at least 25, 50, 75, 100, 125, 150, 175, or 200 nucleotides in length. In certain embodiments, the 3' homology arm comprises about 50 to 100 bp, e.g., 55 to 95, 60 to 90, 70 to 90, or 80 to 90 bp, homology 3' of the 13 nt target region (e.g., HBG1 c.-114 to -102 (e.g., nucleotides 2824-2836 of SEQ ID NO:902 (HBG1)) or HBG2 c.-114 to -102 (e.g., nucleotides 2748-2760 of SEQ ID NO:903 (HBG2)). In certain embodiments, the 3' homology arm comprises, consists essentially of, or consists of SEQ ID NO:905 (ssODN1 3' homology arm), SEQ ID NO:908 (PhTx ssODN1 3'homology arm), SEQ ID NO:992 (OLI16414 3' homology arm), or SEQ ID NO:995 (OLI16412 3' homology arm). In certain embodiments, the template nucleic acid comprises, consists essentially of, or consists of SEQ ID NO:906 (ssODN1), SEQ ID NO:909 (PhTx ssODN1), SEQ ID NO:990 (OLI16414), or SEQ ID NO:995 (OLI16412).

In certain embodiments, the template nucleic acid comprises one or more phosphorothioate (PhTx) modifications. In certain embodiments, the 5' homology arm comprises one or more PhTx modifications. In certain embodiments, the 3' homology arm comprises one or more PhTx modifications. In certain embodiments, the template nucleic acid comprises one or more PhTx modifications at or near the 5' end and/or 3' end.

In certain embodiments, the ssODNs for introducing the 13 nt deletion at the 13 nt target region described herein may be used in conjunction with an RNA nuclease and one or more gRNAs that target the 13 nt target region, for example, the gRNAs disclosed in Table 10. In certain embodiments, the gRNAs may be chemically synthesized gRNAs.

Target Cells

Genome editing systems according to this disclosure can be used to manipulate or alter a cell, e.g., to edit or alter a target nucleic acid. The manipulating can occur, in various embodiments, in vivo or ex vivo.

A variety of cell types can be manipulated or altered according to the embodiments of this disclosure, and in some cases, such as in vivo applications, a plurality of cell types are altered or manipulated, for example by delivering genome editing systems according to this disclosure to a plurality of cell types. In other cases, however, it may be desirable to limit manipulation or alteration to a particular cell type or types. For instance, it can be desirable in some instances to edit a cell with limited differentiation potential or a terminally differentiated cell, such as a photoreceptor cell in the case of Maeder, in which modification of a genotype is expected to result in a change in cell phenotype. In other cases, however, it may be desirable to edit a less differentiated, multipotent or pluripotent, stem or progenitor cell. By way of example, the cell may be an embryonic stem cell, induced pluripotent stem cell (iPSC), hematopoietic stem/progenitor cell (HSPC), or other stem or progenitor cell type that differentiates into a cell type of relevance to a given application or indication.

As a corollary, the cell being altered or manipulated is, variously, a dividing cell or a non-dividing cell, depending on the cell type(s) being targeted and/or the desired editing outcome.

When cells are manipulated or altered ex vivo, the cells can be used (e.g. administered to a subject) immediately, or they can be maintained or stored for later use. Those of skill in the art will appreciate that cells can be maintained in culture or stored (e.g. frozen in liquid nitrogen) using any suitable method known in the art.

Implementation of Genome Editing Systems: Delivery. Formulations. And Routes of Administration As discussed above, the genome editing systems of this disclosure can be implemented in any suitable manner, meaning that the components of such systems, including without limitation the RNA-guided nuclease, gRNA, and optional donor template nucleic acid, can be delivered, formulated, or administered in any suitable form or combination of forms that results in the transduction, expression or introduction of a genome editing system and/or causes a desired repair outcome in a cell, tissue or subject. Tables 3 and 4 set forth several, non-limiting examples of genome editing system implementations. Those of skill in the art will appreciate, however, that these listings are not comprehensive, and that other implementations are possible. With reference to Table 3 in particular, the table lists several exemplary implementations of a genome editing system comprising a single gRNA and an optional donor template. However, genome editing systems according to this disclosure can incorporate multiple gRNAs, multiple RNA-guided nucleases, and other components such as proteins, and a variety of implementations will be evident to the skilled artisan based on the principles illustrated in the table. In the table, [N/A] indicates that the genome editing system does not include the indicated component.

TABLE 3

<table>
<tr><th colspan="4">Genome Editing System Components</th></tr>
<tr><th>RNA-guided Nuclease</th><th>gRNA</th><th>Donor Template</th><th>Comments</th></tr>
<tr><td>Protein</td><td>RNA</td><td>[N/A]</td><td>An RNA-guided nuclease protein complexed with a gRNA molecule (an RNP complex)</td></tr>
<tr><td>Protein</td><td>RNA</td><td>DNA</td><td>An RNP complex as described above plus a single-stranded or double stranded donor template.</td></tr>
<tr><td>Protein</td><td>DNA</td><td>[N/A]</td><td>An RNA-guided nuclease protein plus gRNA transcribed from DNA.</td></tr>
<tr><td>Protein</td><td>DNA</td><td>DNA</td><td>An RNA-guided nuclease protein plus gRNA-encoding DNA and a separate DNA donor template.</td></tr>
<tr><td>Protein</td><td colspan="2">DNA</td><td>An RNA-guided nuclease protein and a single DNA encoding both a gRNA and a donor template.</td></tr>
<tr><td colspan="3">DNA</td><td>A DNA or DNA vector encoding an RNA-guided nuclease, a gRNA and a donor template.</td></tr>
<tr><td>DNA</td><td>DNA</td><td>[N/A]</td><td>Two separate DNAs, or two separate DNA vectors, encoding the RNA-guided nuclease and the gRNA, respectively.</td></tr>
<tr><td>DNA</td><td>DNA</td><td>DNA</td><td>Three separate DNAs, or three separate DNA vectors, encoding the RNA-guided nuclease, the gRNA and the donor template, respectively.</td></tr>
<tr><td colspan="2">DNA</td><td>[N/A]</td><td>A DNA or DNA vector encoding an RNA-guided nuclease and a gRNA</td></tr>
<tr><td colspan="2">DNA</td><td>DNA</td><td>A first DNA or DNA vector encoding an RNA-guided nuclease and a gRNA, and a second DNA or DNA vector encoding a donor template.</td></tr>
<tr><td>DNA</td><td colspan="2">DNA</td><td>A first DNA or DNA vector encoding an RNA-guided nuclease and second DNA or DNA vector encoding a gRNA and a donor template.</td></tr>
<tr><td colspan="3">DNA<br>DNA</td><td>A first DNA or DNA vector encoding an RNA-guided nuclease and a donor template, and a second DNA or DNA vector encoding a gRNA</td></tr>
<tr><td colspan="3">DNA<br>RNA</td><td>A DNA or DNA vector encoding an RNA-guided nuclease and a donor template, and a gRNA</td></tr>
<tr><td>RNA</td><td></td><td>[N/A]</td><td>An RNA or RNA vector encoding an RNA-guided nuclease and comprising a gRNA</td></tr>
<tr><td>RNA</td><td></td><td>DNA</td><td>An RNA or RNA vector encoding an RNA-guided nuclease and comprising a gRNA, and a DNA or DNA vector encoding a donor template.</td></tr>
</table>

Table 4 summarizes various delivery methods for the components of genome editing systems, as described herein. Again, the listing is intended to be exemplary rather than limiting.

TABLE 4

| Delivery Vector/Mode | | Delivery into Non-Dividing Cells | Duration of Expression | Genome Integration | Type of Molecule Delivered |
|---|---|---|---|---|---|
| Physical (e.g., electroporation, particle gun, Calcium Phosphate transfection, cell compression or squeezing) | | YES | Transient | NO | Nucleic Acids and Proteins |
| Viral | Retrovirus | NO | Stable | YES | RNA |
| | Lentivirus | YES | Stable | YES/NO with modifications | RNA |
| | Adenovirus | YES | Transient | NO | DNA |
| | Adeno-Associated Virus (AAV) | YES | Stable | NO | DNA |
| | Vaccinia Virus | YES | Very Transient | NO | DNA |
| | Herpes Simplex Virus | YES | Stable | NO | DNA |
| Non-Viral | Cationic Liposomes | YES | Transient | Depends on what is delivered | Nucleic Acids and Proteins |
| | Polymeric Nanoparticles | YES | Transient | Depends on what is delivered | Nucleic Acids and Proteins |
| Biological Non-Viral Delivery Vehicles | Attenuated Bacteria | YES | Transient | NO | Nucleic Acids |
| | Engineered Bacteriophages | YES | Transient | NO | Nucleic Acids |
| | Mammalian Virus-like Particles | YES | Transient | NO | Nucleic Acids |
| | Biological liposomes: Erythrocyte Ghosts and Exosomes | YES | Transient | NO | Nucleic Acids |

Nucleic Acid-Based Delivery of Genome Editing Systems

Nucleic acids encoding the various elements of a genome editing system according to the present disclosure can be administered to subjects or delivered into cells by art-known methods or as described herein. For example, RNA-guided nuclease-encoding and/or gRNA-encoding DNA, as well as donor template nucleic acids can be delivered by, e.g., vectors (e.g., viral or non-viral vectors), non-vector based methods (e.g., using naked DNA or DNA complexes), or a combination thereof.

Nucleic acids encoding genome editing systems or components thereof can be delivered directly to cells as naked DNA or RNA, for instance by means of transfection or electroporation, or can be conjugated to molecules (e.g., N-acetylgalactosamine) promoting uptake by the target cells (e.g., erythrocytes, HSCs). Nucleic acid vectors, such as the vectors summarized in Table 4, can also be used.

Nucleic acid vectors can comprise one or more sequences encoding genome editing system components, such as an RNA-guided nuclease, a gRNA and/or a donor template. A vector can also comprise a sequence encoding a signal peptide (e.g., for nuclear localization, nucleolar localization, or mitochondrial localization), associated with (e.g., inserted into or fused to) a sequence coding for a protein. As one example, a nucleic acid vectors can include a Cas9 coding sequence that includes one or more nuclear localization sequences (e.g., a nuclear localization sequence from SV40).

The nucleic acid vector can also include any suitable number of regulatory/control elements, e.g., promoters, enhancers, introns, polyadenylation signals, Kozak consensus sequences, or internal ribosome entry sites (IRES). These elements are well known in the art, and are described in Cotta-Ramusino.

Nucleic acid vectors according to this disclosure include recombinant viral vectors. Exemplary viral vectors are set forth in Table 4, and additional suitable viral vectors and their use and production are described in Cotta-Ramusino. Other viral vectors known in the art can also be used. In addition, viral particles can be used to deliver genome editing system components in nucleic acid and/or peptide form. For example, "empty" viral particles can be assembled to contain any suitable cargo. Viral vectors and viral particles can also be engineered to incorporate targeting ligands to alter target tissue specificity.

In addition to viral vectors, non-viral vectors can be used to deliver nucleic acids encoding genome editing systems according to the present disclosure. One important category of non-viral nucleic acid vectors are nanoparticles, which can be organic or inorganic. Nanoparticles are well known in the art, and are summarized in Cotta-Ramusino. Any suitable nanoparticle design can be used to deliver genome editing system components or nucleic acids encoding such components. For instance, organic (e.g. lipid and/or polymer) nonparticles can be suitable for use as delivery vehicles in certain embodiments of this disclosure. Exemplary lipids for use in nanoparticle formulations, and/or gene transfer are shown in Table 5, and Table 6 lists exemplary polymers for use in gene transfer and/or nanoparticle formulations.

TABLE 5

| Lipids Used for Gene Transfer | | |
|---|---|---|
| Lipid | Abbreviation | Feature |
| 1,2-Dioleoyl-sn-glycero-3-phosphatidylcholine | DOPC | Helper |
| 1,2-Dioleoyl-sn-glycero-3-phosphatidylethanolamine | DOPE | Helper |
| Cholesterol | | Helper |
| N-[1-(2,3-Dioleyloxy)propyl]N,N,N-trimethylammonium chloride | DOTMA | Cationic |
| 1,2-Dioleoyloxy-3-trimethylammonium-propane | DOTAP | Cationic |
| Dioctadecylamidoglycylspermine | DOGS | Cationic |
| N-(3-Aminopropyl)-N,N-dimethyl-2,3-bis(dodecyloxy)-1-propanaminium bromide | GAP-DLRIE | Cationic |
| Cetyltrimethylammonium bromide | CTAB | Cationic |
| 6-Lauroxyhexyl ornithinate | LHON | Cationic |
| 1-(2,3-Dioleoyloxypropyl)-2,4,6-trimethylpyridinium | 20c | Cationic |
| 2,3-Diolcyloxy-N-[2(sperminecarboxamido-ethyl]-N,N-dimethyl-1-propanaminium trifluoroacetate | DOSPA | Cationic |
| 1,2-Dioleyl-3-trimethylammonium-propane | DOPA | Cationic |
| N-(2-Hydroxyethyl)-N,N-dimethyl-2,3-bis(tetradecyloxy)-1-propanaminium bromide | MDRIE | Cationic |
| Dimyristooxypropyl dimethyl hydroxyethyl ammonium bromide | DMRI | Cationic |
| 3β-[N-(N',N'-Dimethylaminoethane)-carbamoyl]cholesterol | DC-Chol | Cationic |
| Bis-guanidium-tren-cholesterol | BGTC | Cationic |
| 1,3-Diodeoxy-2-(6-carboxy-spermyl)-propylamide | DOSPER | Cationic |
| Dimethyloctadecylammonium bromide | DDAB | Cationic |
| Dioctadecylamidoglicylspermidin | DSL | Cationic |
| rac-[(2,3-Dioctadecyloxypropyl)(2-hydroxyethyl)]-dimethylammonium chloride | CLIP-1 | Cationic |
| rac-[2(2,3-Dihexadecyloxypropyl-oxymethyloxy)ethyl]trimethylammonium bromide | CLIP-6 | Cationic |
| Ethyldimyristoylphosphatidylcholine | EDMPC | Cationic |
| 1,2-Distcaryloxy-N,N-dimethyl-3-aminopropane | DSDMA | Cationic |
| 1,2-Dimyristoyl-trimethylammonium propane | DMTAP | Cationic |
| O,O'-Dimyristyl-N-lysyl aspartate | DMKE | Cationic |
| 1,2-Distearoyl-sn-glycero-3-ethylphosphocholine | DSEPC | Cationic |
| N-Palmitoyl D-erythro-sphingosyl carbamoyl-spermine | CCS | Cationic |
| N-t-Butyl-N0-tetradecyl-3-tetradecylaminopropionamidine | diC14-amidine | Cationic |
| Octadecenolyoxy[ethyl-2-heptadecenyl-3 hydroxyethyl] imidazolinium chloride | DOTIM | Cationic |
| N1-Cholesteryloxycarbonyl-3,7-diazanonane-1,9-diamine | CDAN | Cationic |
| 2-(3-[Bis(3-amino-propyl)-amino]propylamino)-N-ditetradecylcarbamoylme-ethyl-acetamide | RPR209120 | Cationic |
| 1,2-dilinoleyloxy-3- dimethylaminopropane | DLinDMA | Cationic |
| 2,2-dilinoleyl-4-dimethylaminoethyl-[1,3]- dioxolane | DLin-KC2-DMA | Cationic |
| dilinoleyl- methyl-4-dimethylaminobutyrate | DLin-MC3-DMA | Cationic |

TABLE 6

| Polymers Used for Gene Transfer | |
|---|---|
| Polymer | Abbreviation |
| Poly(ethylene)glycol | PEG |
| Polyethylenimine | PEI |
| Dithiobis(succinimidylpropionate) | DSP |
| Dimethyl-3,3'-dithiobispropionimidate | DTBP |
| Poly(ethylene imine) biscarbamate | PEIC |
| Poly(L-lysine) | PLL |
| Histidine modified PLL | |
| Poly(N-vinylpyrrolidonc) | PVP |
| Poly(propylenimine) | PPI |
| Poly(amidoamine) | PAMAM |
| Poly(amido ethylenimine) | SS-PAEI |
| Triethylenetetramine | TETA |
| Poly(β-aminoester) | |
| Poly(4-hydroxy-L-proline ester) | PHP |
| Poly(allylamine) | |
| Poly(α-[4-aminobutyl]-L-glycolic acid) | PAGA |
| Poly(D,L-lactic-co-glycolic acid) | PLGA |
| Poly(N-ethyl-4-vinylpyridinium bromide) | |
| Poly(phosphazene)s | PPZ |
| Poly(phosphoester)s | PPE |
| Poly(phosphoramidate)s | PPA |
| Poly(N-2-hydroxypropylmethacrylamide) | pHPMA |
| Poly(2-(dimethylamino)ethyl methacrylate) | pDMAEMA |
| Poly(2-aminoethyl propylene phosphate) | PPE-EA |

TABLE 6-continued

| Polymers Used for Gene Transfer | |
|---|---|
| Polymer | Abbreviation |
| Chitosan | |
| Galactosylated chitosan | |
| N-Dodacylated chitosan | |
| Histone | |
| Collagen | |
| Dextran-spermine | D-SPM |

Non-viral vectors optionally include targeting modifications to improve uptake and/or selectively target certain cell types. These targeting modifications can include e.g., cell specific antigens, monoclonal antibodies, single chain antibodies, aptamers, polymers, sugars (e.g., N-acetylgalactosamine (GalNAc)), and cell penetrating peptides. Such vectors also optionally use fusogenic and endosome-destabilizing peptides/polymers, undergo acid-triggered conformational changes (e.g., to accelerate endosomal escape of the cargo), and/or incorporate a stimuli-cleavable polymer, e.g., for release in a cellular compartment. For example, disulfide-based cationic polymers that are cleaved in the reducing cellular environment can be used.

In certain embodiments, one or more nucleic acid molecules (e.g., DNA molecules) other than the components of a genome editing system, e.g., the RNA-guided nuclease component and/or the gRNA component described herein, are delivered. In certain embodiments, the nucleic acid molecule is delivered at the same time as one or more of the components of the Genome editing system. In certain embodiments, the nucleic acid molecule is delivered before or after (e.g., less than about 30 minutes, 1 hour, 2 hours, 3 hours, 6 hours, 9 hours, 12 hours, 1 day, 2 days, 3 days, 1 week, 2 weeks, or 4 weeks) one or more of the components of the Genome editing system are delivered. In certain embodiments, the nucleic acid molecule is delivered by a different means than one or more of the components of the genome editing system, e.g., the RNA-guided nuclease component and/or the gRNA component, are delivered. The nucleic acid molecule can be delivered by any of the delivery methods described herein. For example, the nucleic acid molecule can be delivered by a viral vector, e.g., an integration-deficient lentivirus, and the RNA-guided nuclease molecule component and/or the gRNA component can be delivered by electroporation, e.g., such that the toxicity caused by nucleic acids (e.g., DNAs) can be reduced. In certain embodiments, the nucleic acid molecule encodes a therapeutic protein, e.g., a protein described herein. In certain embodiments, the nucleic acid molecule encodes an RNA molecule, e.g., an RNA molecule described herein.

Delivery of RNPs and/or RNA Encoding Genome Editing System Components

RNPs (complexes of gRNAs and RNA-guided nucleases) and/or RNAs encoding RNA-guided nucleases and/or gRNAs, can be delivered into cells or administered to subjects by art-known methods, some of which are described in Cotta-Ramusino. In vitro, RNA-guided nuclease-encoding and/or gRNA-encoding RNA can be delivered, e.g., by microinjection, electroporation, transient cell compression or squeezing (see, e.g., Lee 2012). Lipid-mediated transfection, peptide-mediated delivery, GalNAc- or other conjugate-mediated delivery, and combinations thereof, can also be used for delivery in vitro and in vivo. A protective, interactive, non-condensing (PINC) system may be used for delivery.

In vitro delivery via electroporation comprises mixing the cells with the RNA encoding RNA-guided nucleases and/or gRNAs, with or without donor template nucleic acid molecules, in a cartridge, chamber or cuvette and applying one or more electrical impulses of defined duration and amplitude. Systems and protocols for electroporation are known in the art, and any suitable electroporation tool and/or protocol can be used in connection with the various embodiments of this disclosure.

Route of Administration

Genome editing systems, or cells altered or manipulated using such systems, can be administered to subjects by any suitable mode or route, whether local or systemic. Systemic modes of administration include oral and parenteral routes. Parenteral routes include, by way of example, intravenous, intramarrow, intrarterial, intramuscular, intradermal, subcutaneous, intranasal, and intraperitoneal routes. Components administered systemically can be modified or formulated to target, e.g., HSCs, hematopoietic stem/progenitor cells, or erythroid progenitors or precursor cells.

Local modes of administration include, by way of example, intramarrow injection into the trabecular bone or intrafemoral injection into the marrow space, and infusion into the portal vein. In certain embodiments, significantly smaller amounts of the components (compared with systemic approaches) can exert an effect when administered locally (for example, directly into the bone marrow) compared to when administered systemically (for example, intravenously). Local modes of administration can reduce or eliminate the incidence of potentially toxic side effects that may occur when therapeutically effective amounts of a component are administered systemically.

Administration can be provided as a periodic bolus (for example, intravenously) or as continuous infusion from an internal reservoir or from an external reservoir (for example, from an intravenous bag or implantable pump). Components can be administered locally, for example, by continuous release from a sustained release drug delivery device.

In addition, components can be formulated to permit release over a prolonged period of time. A release system can include a matrix of a biodegradable material or a material which releases the incorporated components by diffusion. The components can be homogeneously or heterogeneously distributed within the release system. A variety of release systems can be useful, however, the choice of the appropriate system will depend upon rate of release required by a particular application. Both non-degradable and degradable release systems can be used. Suitable release systems include polymers and polymeric matrices, non-polymeric matrices, or inorganic and organic excipients and diluents such as, but not limited to, calcium carbonate and sugar (for example, trehalose). Release systems may be natural or synthetic. However, synthetic release systems are preferred because generally they are more reliable, more reproducible and produce more defined release profiles. The release system material can be selected so that components having different molecular weights are released by diffusion through or degradation of the material.

Representative synthetic, biodegradable polymers include, for example: polyamides such as poly(amino acids) and poly(peptides); polyesters such as poly(lactic acid), poly(glycolic acid), poly(lactic-co-glycolic acid), and poly (caprolactone); poly(anhydrides); polyorthoesters; polycarbonates; and chemical derivatives thereof (substitutions, additions of chemical groups, for example, alkyl, alkylene, hydroxylations, oxidations, and other modifications routinely made by those skilled in the art), copolymers and mixtures thereof. Representative synthetic, non-degradable polymers include, for example: polyethers such as poly (ethylene oxide), poly(ethylene glycol), and poly(tetramethylene oxide); vinyl polymers-polyacrylates and polymethacrylates such as methyl, ethyl, other alkyl, hydroxyethyl methacrylate, acrylic and methacrylic acids, and others such as poly(vinyl alcohol), poly(vinyl pyrolidone), and poly (vinyl acetate); poly(urethanes); cellulose and its derivatives such as alkyl, hydroxyalkyl, ethers, esters, nitrocellulose, and various cellulose acetates; polysiloxanes; and any chemical derivatives thereof (substitutions, additions of chemical groups, for example, alkyl, alkylene, hydroxylations, oxidations, and other modifications routinely made by those skilled in the art), copolymers and mixtures thereof.

Poly(lactide-co-glycolide) microsphere can also be used. Typically the microspheres are composed of a polymer of lactic acid and glycolic acid, which are structured to form hollow spheres. The spheres can be approximately 15-30 microns in diameter and can be loaded with components described herein. In some embodiments, genome editing systems, system components and/or nucleic acids encoding system components, are delivered with a block copolymer such as a poloxamer or a poloxamine.

Multi-Modal or Differential Delivery of Components

Skilled artisans will appreciate, in view of the instant disclosure, that different components of genome editing systems disclosed herein can be delivered together or separately and simultaneously or nonsimultaneously. Separate and/or asynchronous delivery of genome editing system components can be particularly desirable to provide temporal or spatial control over the function of genome editing systems and to limit certain effects caused by their activity.

Different or differential modes as used herein refer to modes of delivery that confer different pharmacodynamic or pharmacokinetic properties on the subject component molecule, e.g., a RNA-guided nuclease molecule, gRNA, template nucleic acid, or payload. For example, the modes of delivery can result in different tissue distribution, different half-life, or different temporal distribution, e.g., in a selected compartment, tissue, or organ.

Some modes of delivery, e.g., delivery by a nucleic acid vector that persists in a cell, or in progeny of a cell, e.g., by autonomous replication or insertion into cellular nucleic acid, result in more persistent expression of and presence of a component. Examples include viral, e.g., AAV or lentivirus, delivery.

By way of example, the components of a genome editing system, e.g., a RNA-guided nuclease and a gRNA, can be delivered by modes that differ in terms of resulting half-life or persistent of the delivered component the body, or in a particular compartment, tissue or organ. In certain embodiments, a gRNA can be delivered by such modes. The RNA-guided nuclease molecule component can be delivered by a mode which results in less persistence or less exposure to the body or a particular compartment or tissue or organ.

More generally, in certain embodiments, a first mode of delivery is used to deliver a first component and a second mode of delivery is used to deliver a second component. The first mode of delivery confers a first pharmacodynamic or pharmacokinetic property. The first pharmacodynamic property can be, e.g., distribution, persistence, or exposure, of the component, or of a nucleic acid that encodes the component, in the body, a compartment, tissue or organ. The second mode of delivery confers a second pharmacodynamic or pharmacokinetic property. The second pharmacodynamic property can be, e.g., distribution, persistence, or exposure, of the component, or of a nucleic acid that encodes the component, in the body, a compartment, tissue or organ.

In certain embodiments, the first pharmacodynamic or pharmacokinetic property, e.g., distribution, persistence or exposure, is more limited than the second pharmacodynamic or pharmacokinetic property.

In certain embodiments, the first mode of delivery is selected to optimize, e.g., minimize, a pharmacodynamic or pharmacokinetic property, e.g., distribution, persistence or exposure.

In certain embodiments, the second mode of delivery is selected to optimize, e.g., maximize, a pharmacodynamic or pharmacokinetic property, e.g., distribution, persistence or exposure.

In certain embodiments, the first mode of delivery comprises the use of a relatively persistent element, e.g., a nucleic acid, e.g., a plasmid or viral vector, e.g., an AAV or lentivirus. As such vectors are relatively persistent product transcribed from them would be relatively persistent.

In certain embodiments, the second mode of delivery comprises a relatively transient element, e.g., an RNA or protein.

In certain embodiments, the first component comprises gRNA, and the delivery mode is relatively persistent, e.g., the gRNA is transcribed from a plasmid or viral vector, e.g., an AAV or lentivirus.

Transcription of these genes would be of little physiological consequence because the genes do not encode for a protein product, and the gRNAs are incapable of acting in isolation. The second component, a RNA-guided nuclease molecule, is delivered in a transient manner, for example as mRNA or as protein, ensuring that the full RNA-guided nuclease molecule/gRNA complex is only present and active for a short period of time.

Furthermore, the components can be delivered in different molecular form or with different delivery vectors that complement one another to enhance safety and tissue specificity.

Use of differential delivery modes can enhance performance, safety, and/or efficacy, e.g., the likelihood of an eventual off-target modification can be reduced. Delivery of immunogenic components, e.g., Cas9 molecules, by less persistent modes can reduce immunogenicity, as peptides from the bacterially-derived Cas enzyme are displayed on the surface of the cell by MHC molecules. A two-part delivery system can alleviate these drawbacks.

Differential delivery modes can be used to deliver components to different, but overlapping target regions. The formation active complex is minimized outside the overlap of the target regions. Thus, in certain embodiments, a first component, e.g., a gRNA is delivered by a first delivery mode that results in a first spatial, e.g., tissue, distribution. A second component, e.g., a RNA-guided nuclease molecule is delivered by a second delivery mode that results in a second spatial, e.g., tissue, distribution. In certain embodiments, the first mode comprises a first element selected from a liposome, nanoparticle, e.g., polymeric nanoparticle, and a nucleic acid, e.g., viral vector. The second mode comprises a second element selected from the group. In certain embodiments, the first mode of delivery comprises a first targeting element, e.g., a cell specific receptor or an antibody, and the second mode of delivery does not include that element. In certain embodiments, the second mode of delivery comprises a second targeting element, e.g., a second cell specific receptor or second antibody.

When the RNA-guided nuclease molecule is delivered in a virus delivery vector, a liposome, or polymeric nanoparticle, there is the potential for delivery to and therapeutic activity in multiple tissues, when it may be desirable to only target a single tissue. A two-part delivery system can resolve this challenge and enhance tissue specificity. If the gRNA and the RNA-guided nuclease molecule are packaged in separated delivery vehicles with distinct but overlapping tissue tropism, the fully functional complex is only be formed in the tissue that is targeted by both vectors.

EXAMPLES

The principles and embodiments described above are further illustrated by the non-limiting examples that follow:

Example 1: Screening of *S. Pyoenes* gRNAs Delivered to K562 Cells as Ribonucleoprotein Complexes for Use in Causing 13 nt Deletions in HBG1 and HBG2 Regulatory Regions gRNAs targeting a 26 nt fragment spanning and including the 13 nucleotides at the 13 nt target region of HBG1 and HBG2 were designed by standard methods. After gRNAs were designed in silico and tiered, a subset of the gRNAs were selected and screened for activity and specificity in human K562 cells. The gRNAs selected for screening are set forth in Table 7. Briefly, gRNAs were in vitro transcribed and then complexed with *S. pyogenes* wildtype (Wt) Cas9 protein to form ribonucleoprotein complexes (RNPs). The gRNAs complexed to *S. pyogenes* Cas9 protein were modified sgRNAs ((e.g., 5' ARCA capped and 3' polyA (20A) tail; Table 7) and target the HBG1 and HBG2 regulatory regions. To allow for direct comparison of the activity of these RNPs in K562 cells and human CD34+ cells, RNPs were first delivered to K562 cells by electroporation (Amaxa Nucleofector).

Figure 3A:
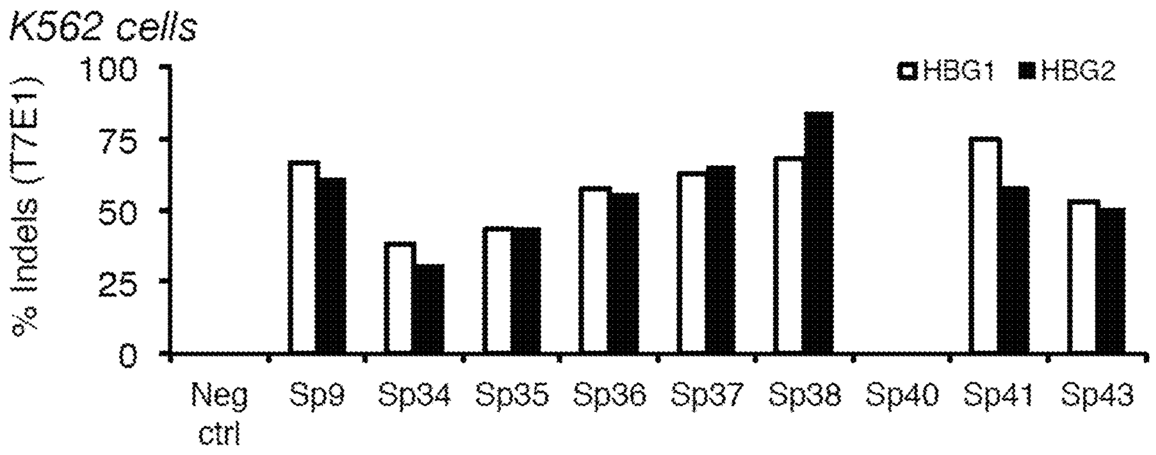
FIGS. 3A-C show data from gRNA screening for incorporation of the 13 nt deletion in human K562 erythroleukemia cells.

Three days after RNP electroporation, gDNA was extracted from K562 cells and then the HBG1 and HBG2 loci were PCR amplified from the gDNA. Gene editing was evaluated in the PCR products by T7E1 endonuclease assay analysis. Eight out of nine RNPs supported a high percentage of NHEJ. Sp37 RNP, the only gRNA shown to be active in human CD34+ cells (<10% editing in CD34+ cells) was highly active in K562 cells, with >60% indels detected at both HBG1 and HBG2 and eight cut in both the HBG1 and HBG2 targeted regions in the promoter sequences (FIG. 3A).

TABLE 7

Selected gRNAs for screening in K562 cells or CD34+ cells

| gRNA ID | Targeting domain sequence (RNA) | Targeting domain sequence (DNA) | Targeting domain sequence plus PAM (NGG) (RNA) | Targeting domain sequence plus PAM (NGG) (DNA) | Sense |
|---|---|---|---|---|---|
| Sp9 | GGCUAUUG GUCAAGGC A (SEQ ID NO: 277) | GGCTATTG GTCAAGGC A (SEQ ID NO: 910) | GGCUAUUGG UCAAGGCAA GG (SEQ ID NO: 920) | GGCTATT GGTCAAGG CAAGG (SEQ ID NO: 930) | Anti-sense |
| Sp36 | CAAGGCUA UUGGUCAA GGCA (SEQ ID NO: 338) | CAAGGCTAT TGGTCAAGG CA (SEQ ID NO: 911) | CAAGGCUAU UGGUCAAGG CAAGG (SEQ ID NO: 921) | CAAGGCTA TTGGTCAA GGCAAGG (SEQ ID NO: 931) | Anti-sense |
| Sp40 | UGCCUUGU CAAGGCUA U (SEQ ID NO: 327) | TGCCTTGTC AAGGCTAT (SEQ ID NO: 912) | UGCCUUGUC AAGGCUAUU GG (SEQ ID NO: 922) | TGCCTTGT CAAGGCTA TTGG (SEQ ID NO: 932) | Anti-sense |
| Sp42 | GUUUGCCU UGUCAAGG CUAU (SEQ ID NO: 299) | GTTTGCCTT GTCAAGGCT AT (SEQ ID NO: 913) | GUUUGCCUU GUCAAGGCU AUUGG (SEQ ID NO: 923) | GTTTGCCT TGTCAAGG CTATTGG (SEQ ID NO: 933) | Anti-sense |
| Sp38 | GACCAAUA GCCUUGAC A (SEQ ID NO: 276) | GACCAATAG CCTTGACA (SEQ ID NO: 914) | GACCAAUAG CCUUGACA GG (SEQ ID NO: 924) | GACCAATA GCCTTGAC AAGG (SEQ ID NO: 934) | Sense |
| Sp37 | CUUGACCA AUAGCCUU GACA (SEQ ID NO: 333) | CTTGACCAA TAGCCTTGA CA (SEQ ID NO: 915) | CUUGACCAA UAGCCUUGA CAAGG (SEQ ID NO: 925) | CTTGACCA ATAGCCTT GACAAGG (SEQ ID NO: 935) | Sense |
| Sp43 | GUCAAGGC UAUUGGUC A (SEQ ID NO: 278) | GTCAAGGCT ATTGGTCA (SEQ ID NO: 916) | GUCAAGGCU AUUGGUCAA GG (SEQ ID NO: 926) | GTCAAGGC TATTGGTC AAGG (SEQ ID NO: 936) | Anti-sense |
| Sp35 | CUUGUCAA GGCUAUUG GUCA (SEQ ID NO: 339) | CTTGTCAAG GCTATTGGT CA (SEQ ID NO: 917) | CUUGUCAAG GCUAUUGGU CAAGG (SEQ ID NO: 927) | CTTGTCAA GGCTATTG GTCAAGG (SEQ ID NO: 937) | Anti-sense |
| Sp41 | UCAAGUUU GCCUUGUC A (SEQ ID NO: 310) | TCAAGTTTG CCTTGTCA (SEQ ID NO: 918) | UCAAGUUUG CCUUGUCAA GG (SEQ ID NO: 928) | TCAAGTTT GCCTTGTC AAGG (SEQ ID NO: 938) | Anti-sense |
| Sp34 | UGGUCAAG UUUGCCUU GUCA (SEQ ID NO: 340) | TGGTCAAGT TTGCCTTGT CA (SEQ ID NO: 919) | UGGUCAAGU UUGCCUUGU CAAGG (SEQ ID NO: 929) | TGGTCAAG TTTGCCTT GTCAAGG (SEQ ID NO: 939) | Anti-sense |
| Sp85 | AGUAUCCA GUGAGGCC A (SEQ ID NO: 940) | AGTATCCAG TGAGGCCA (SEQ ID NO: 943) | AGUAUCCAG UGAGGCCAG GG (SEQ ID NO: 946) | AGTATCCA GTGAGGCC AGGG (SEQ ID NO: 949) | Anti-sense |
| SpA | GGCAAGGC UGGCCAAC CCAU (SEQ ID NO: 941) | GGCAAGGCT GGCCAACCC AT (SEQ ID NO: 944) | GGCAAGGCU GGCCAACCC AUGGG (SEQ ID NO: 947) | GGCAAGGC TGGCCAAC CCATGGG (SEQ ID NO: 950) | Sense |
| SpB | UAUUUGCA UUGAGAUA GUGU (SEQ ID NO: 942) | TATTTGCAT TGAGATAGT GT (SEQ ID NO: 945) | UAUUUGCAU UGAGAUAGU GUGGG (SEQ ID NO: 948) | TATTTGCA TTGAGATA GTGTGGG (SEQ ID NO: 951) | Sense |

Figure 3B:
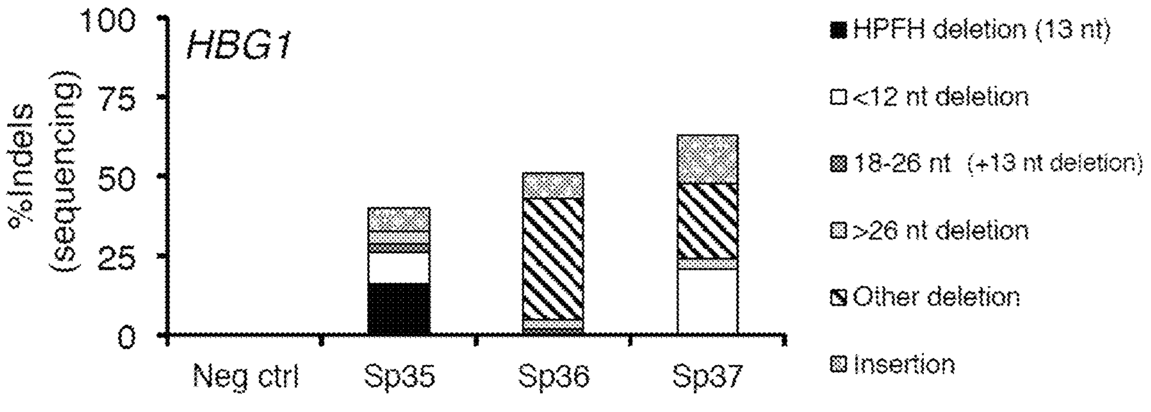
Figure 3C:
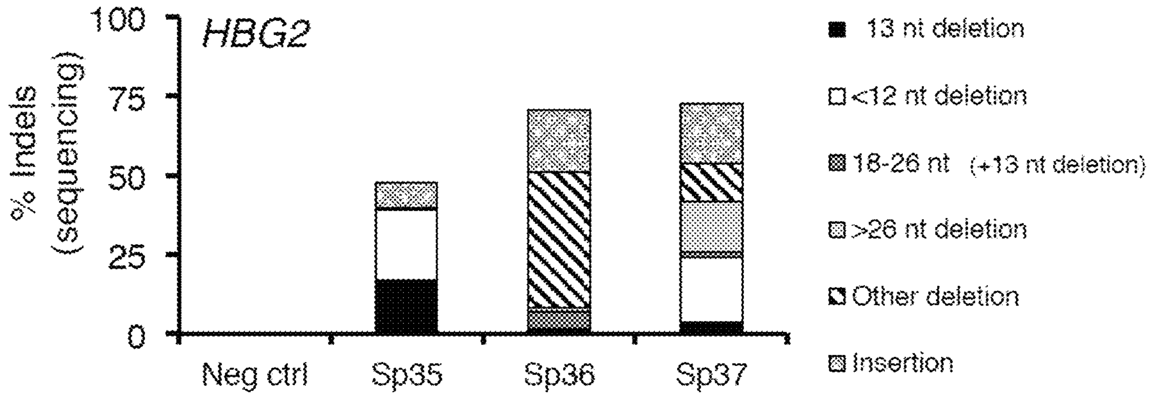

The HBG1 and HBG2 PCR products for the K562 cells that were targeted with the eight active sgRNAs were then analyzed by DNA sequencing analysis and scored for insertions and deletions detected. The deletions were subdivided into precise 13 nt deletions at the target site, 13 nt target site inclusive and proximal small deletions (18-26 nt), 12 nt deletions (i.e., partial deletion) of the 13 nt target site, >26 nt deletions that span a portion of the HPFH target site, and other deletions, e.g., deletions proximal to but outside the HPFH target site. Seven of the eight sgRNAs targeted deletion of the 13 nt (HPFH mutation induction) (FIG. 3B) for HBG1. At least five of the eight sgRNAs also supported targeted deletion of the 13 nt in HBG2 promoter region (FIG. 3C). Note that DNA sequence results for HBG2 in cells treated with HBG Sp34 sgRNA were not available. These data indicate that Cas9 and sgRNA support precise induction of the 13 nt deletions. FIGS. 3B-3C depict examples of the types of deletions observed in target sequences in HBG1.

Figure 4A:
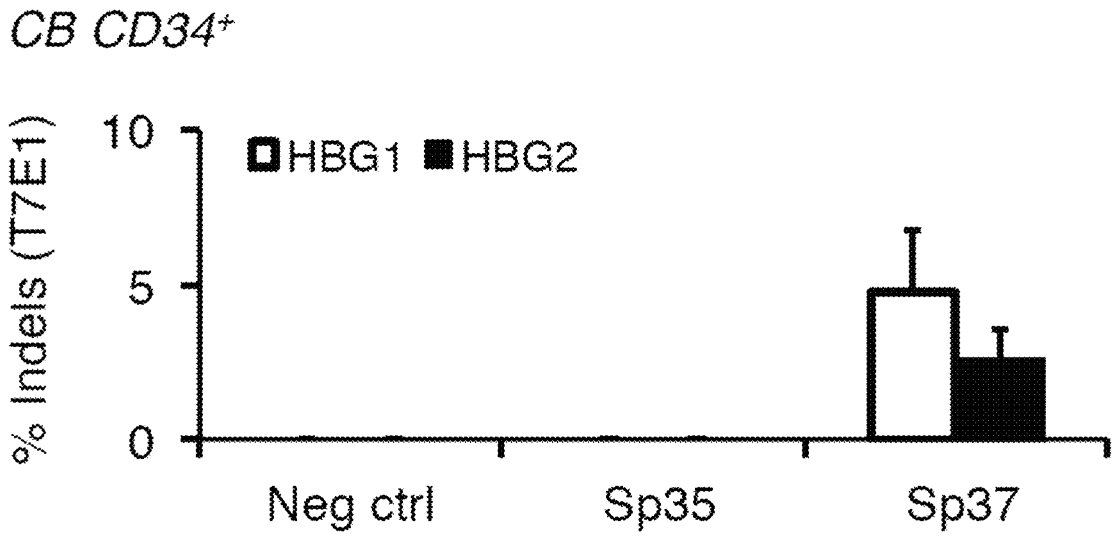
FIGS. 4A-C depict results of gene editing in human cord blood (CB) and human adult $CD34^+$ cells after electroporation with RNPs complexed to in vitro transcribed *S. pyogenes* gRNAs that target a specific 13 nt sequence for deletion (HBG sgRNAs Sp35 and Sp37).

Example 2: Cas9 RNP Containing gRNA Targeting the 13 nt Deletion Mutation Supports Gene Editing in Human Hematopoietic Stem/Progenitor Cells Of the RNPs containing different gRNAs tested in human cord blood (CB) CD34+ cells, only Sp37 resulted in detectable editing at the target site in the HBG1 and HBG2 promoters as determined by T7E1 analysis of indels in HBG1 and HBG2 specific PCR products amplified from gDNA extracted from electroporated CB CD34$^+$ cells from a three cord blood donors (FIG. 4A). The average level of editing detected in cells electroporated with Cas9 protein complexed to Sp37 was 5±2% indels at HBG1 and 3+1% indels detected at HBG2 (3 separate experiments, and CB donors).

Figure 4B:
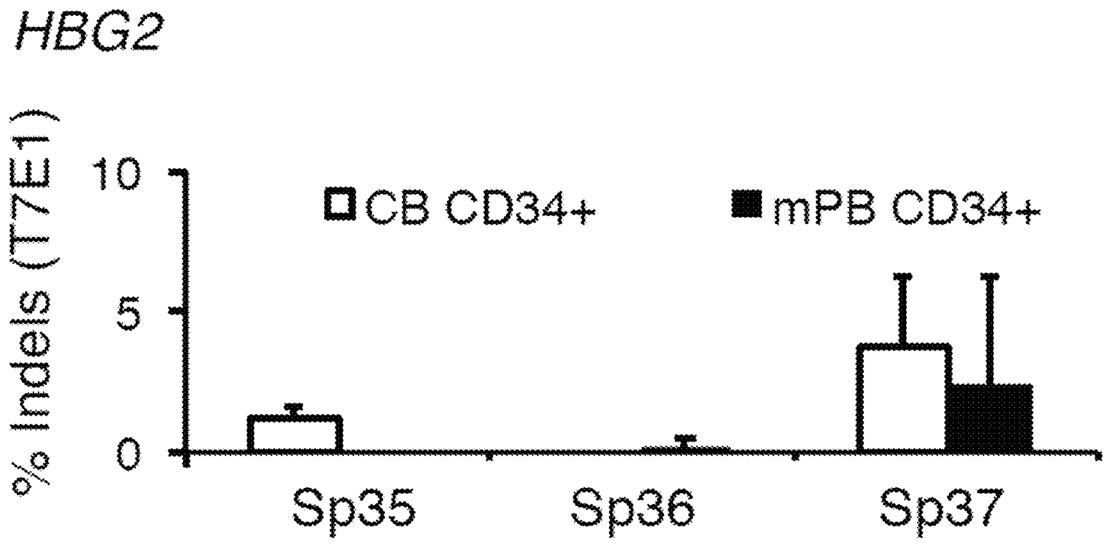

Next, three *S. pyogenes* gRNAs whose target sites are within the HBG promoter (Sp35, Sp36, Sp37) were complexed to wild-type *S. pyogenes* Cas9 protein to form ribonucleoprotein complexes. These HBG targeted RNPS were electroporated into CB CD34$^+$ cells (n=3 donors) and adult mobilized peripheral blood (mPB) CD34$^+$ cell donors (n=3 donors). Then the level of editing at the target site was analyzed by T7E1 endonuclease analysis of the HBG2 PCR products amplified from genomic DNA extracted from the samples approximately 3 days after Cas9 RNP delivery. Each of these RNPs supported only low level gene editing in both the CB and adult CD34$^+$ cells across 3 donors and 3 separate experiments (FIG. 4B).

To increase gene editing and the occurrence of the 13 nt deletion at the target site, single strand deoxynucleotide donor repair templates (ssODNs) that encoded 87 nt and 89 nt of homology on each side of the targeted deletion site was generated. The ssODNs, either unmodified at the ends (i.e., ssODN1, SEQ ID NO:906, Table 8) or modified to contain phosphorothioates (PhTx) at the 5' and 3' ends (i.e., PhTx ssODN1, SEQ ID NO:909, Table 8). The ssODN was designed to 'encode' the 13 nt deletion with sequence homology arms engineered flanking this absent sequence to create a perfect deletion.

TABLE 8

Single strand deoxynucleotide donor repair templates (ssODN)

| ssODN ID | SEQ ID NO | Sequence |
|---|---|---|
| ssODN1 5' homology arm | 904 | **GGGTGCTTCCTTTTATTCTTCATCCCTAGCCAGCCGCCGGCCCCTGGCCTCACTGGATACTCTAAGACTATTGGTCAAGTTTGCCTT** |
| ssODN1 3' homology arm | 905 | GTCAAGGCAAGGCTGGCCAACCCATGGGTGGAGTTTAGCCAGGGACCGTTTCAGACAGATATTTGCATTGAGATAGTGTGGGGAAGGGG |
| ssODN1 | 906 | **GGGTGCTTCCTTTTATTCTTCATCCCTAGCCAGCCGCCGGCCCCTGGCCTCACTGGATACTCTAAGACTATTGGTCAAGTTTGCCTT**GTCAAGGCAAGGCTGGCCAACCCATGGGTGGAGTTTAGCCAGGGACCGTTTCAGACAGATATTTGCATTGAGATAGTGTGGGGAAGGGG |
| PhTx ssODN1 5' homology arm | 907 | **G*GGTGCTTCCTTTTATTCTTCATCCCTAGCCAGCCGCCGGCCCCTGGCCTCACTGGATACTCTAAGACTATTGGTCAAGTTTGCCTT** |
| PhTx ssODN1 3' homology arm | 908 | GTCAAGGCAAGGCTGGCCAACCCATGGGTGGAGTTTAGCCAGGGACCGTTTCAGACAGATATTTGCATTGAGATAGTGTGGGGAAGGG*G |

TABLE 8-continued

Single strand deoxynucleotide donor repair templates (ssODN)

| ssODN ID | SEQ ID NO | Sequence |
|---|---|---|
| PhTx ssODN1 | 909 | **G*GGTGCTTCCTTTTATTCTTCATCCCTAGCCAGCCGCCGGCCCCTGGCCTCACTGGATACTCTAAGACTATTGGTCAAGTTTGCCTT**GTCAAGGCAAGGCTGGCCAACCCATGGGTGGAGTTTAGCCAGGGACCGTTTCAGACAGATATTTGCATTGAGATAGTGTGGGGAAGGG*G |

Figure 4C:
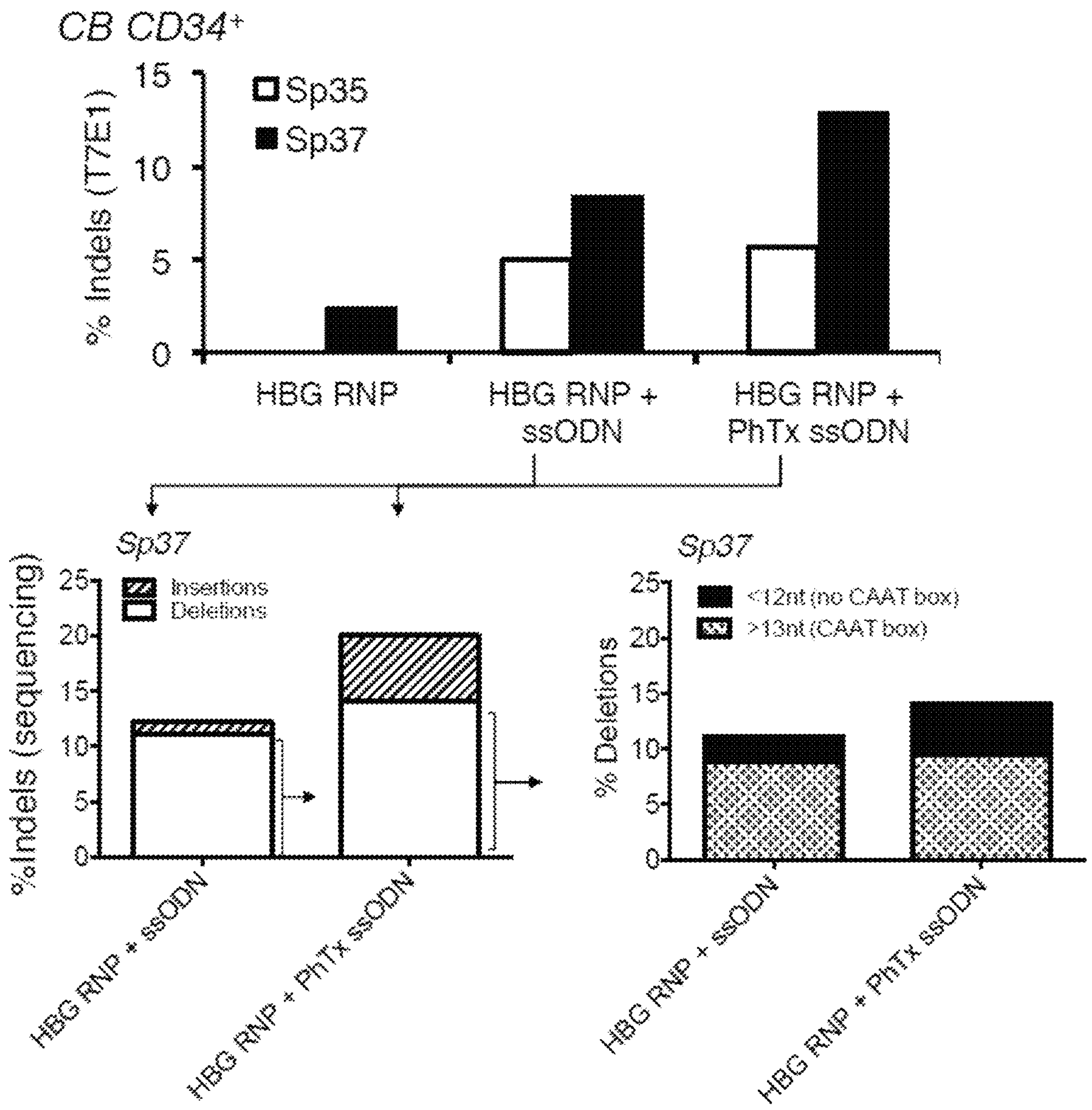

The homology arms flanking the deletion are indicated by bold [5' homology arm] and underline [3' homology arm]).
Note
the absence of the 13 bp sequence in ssODN1 and PhTx ssODN1.
*Represents modification by phosphorothioate.

ssODN1 and PhTx ssODN1 were co-delivered with RNP targeting HBG containing the Sp37 gRNA (HBG Sp37 RNP) or HBG Sp35 (HBG Sp35 RNP) to CB CD34$^+$ cells. Co-delivery of the ssODN donor encoding the 13 nt deletion with HBG Sp35 RNP or HBG Sp37 RNP led to a 6-fold and 5-fold increase in gene editing of the target site, respectively, as determined by T7E1 analysis of the HBG2 PCR product (FIG. 4C). DNA sequencing analysis (Sanger sequencing) of the HBG2 PCR product indicated that 20% gene editing in cells that were treated with HBG Sp37 RNP and the PhTx modified ssODN1, with 15% deletions and 5% insertions (FIG. 4C, lower left panel). Further analysis of the specific type and size of deletions at the target site revealed that 75% of the total deletions detected contained the 13 nt deletion (which included deletion at c. −110 of the CAAT box in the proximal promoter), the absence of which is associated with elevation of HbF expression (FIG. 4C, lower right panel). The remaining ¼ of deletions were partial deletions that did not span the full 13 nt deletion. These data indicate that co-delivery of a homologous ssODN that is engineered to have a deletion supported precise gene editing (deletion) at HBG in human CD34$^+$ cells.

Figure 5A:
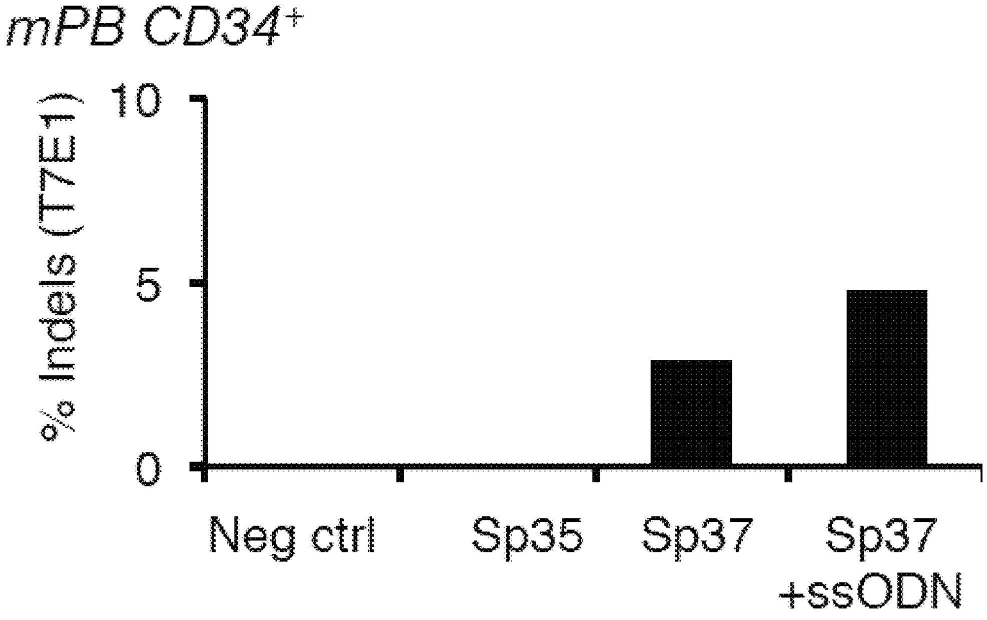
FIGS. 5A-B depict gene editing of HBG in adult human mobilized peripheral blood (mPB) $CD34^+$ cells and induction of fetal hemoglobin in erythroid progeny of RNP treated cells after electroporation of mPB $CD34^+$ cells with HBG Sp37 RNP+/−ssODN encoding the 13 nt deletion.

Example 3: Cas9 RNP Targeting the 13 nt Deletion Mutation Supports Gene Editing in Human Adult Mobilized Peripheral Blood Hematopoietic Stem/Progenitor Cells with Increased HBG Expression in Erythroblast Progeny To determine whether editing HBG with Cas9 RNP complexed to Sp37 gRNA or Sp35 gRNA (i.e., the gRNAs that target the 13 nt deletion that is associated with HPFH) in the HBG promoter supports an increase in HBG expression in erythroid progeny of edited CD34$^+$ cells, human adult CD34$^+$ cells from mobilized peripheral blood (mPB) were electroporated with the RNPs. Briefly, mPB CD34$^+$ cells were prestimulated for 2 days with human cytokines and PGE2 in StemSpan SFEM and then electroporated with Cas9 protein precomplexed to Sp35 and Sp37, respectively. T7E1 analysis of HBG PCR product indicated ~3% indels detected for mPB CD34$^+$ cells treated with RNP complexed to Sp37 while no editing was detected for cells that were treated with RNP complexed to Sp35 (FIG. 5A).

Figure 5B:
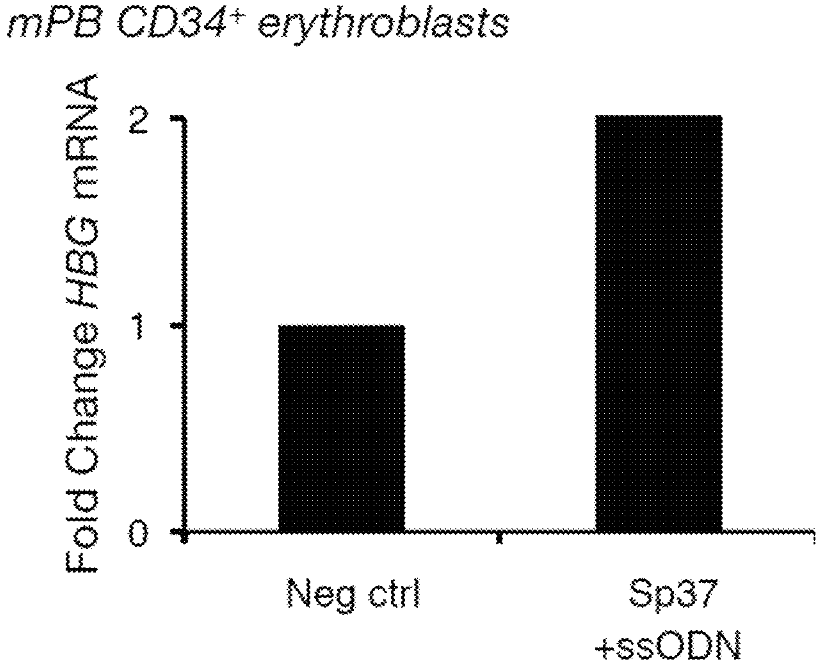
Figure 6A:
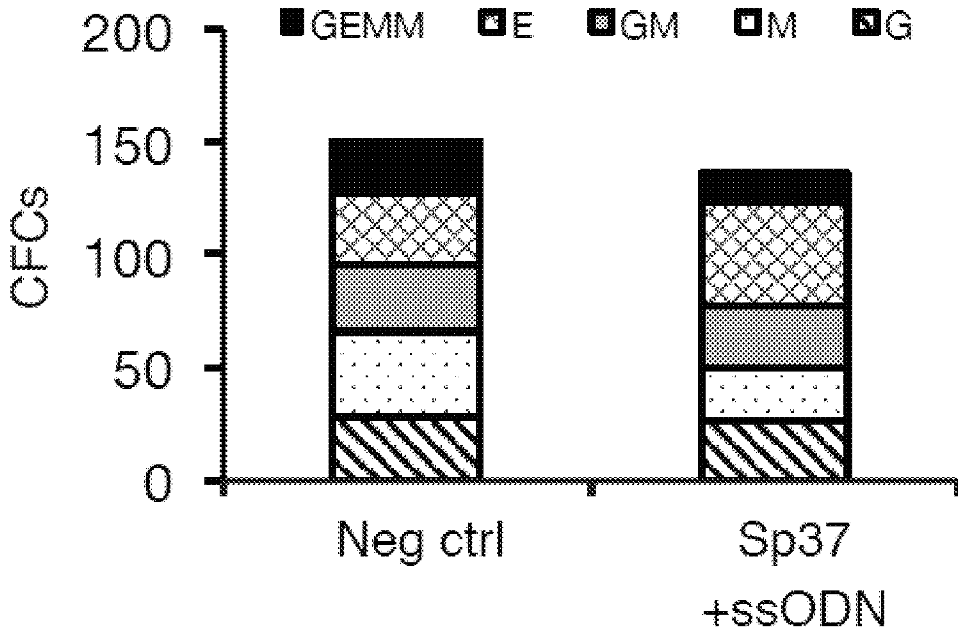
FIGS. 6A-B depict the ex vivo differentiation potential of RNP treated and untreated mPB $CD34^+$ cells from the same donor.
Figure 6B:
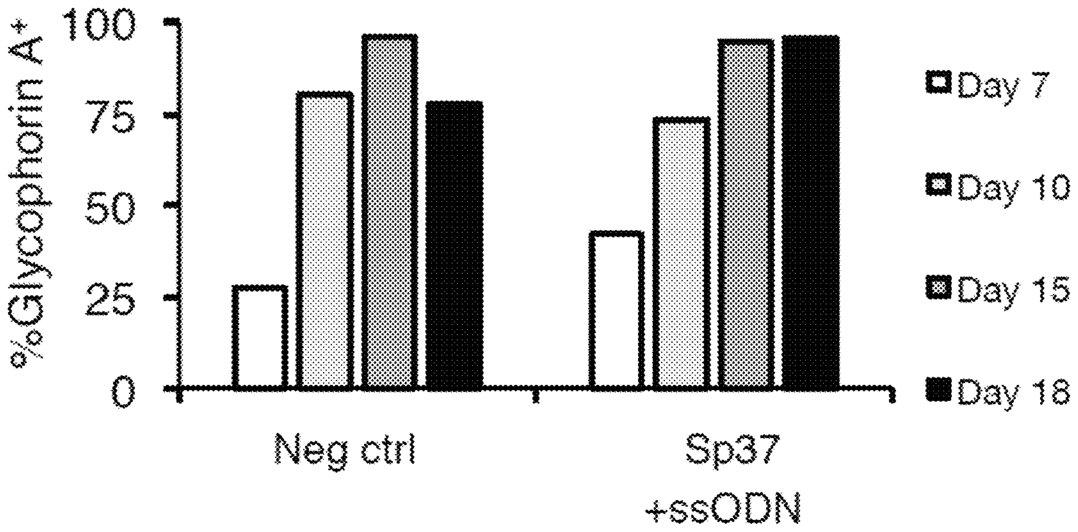

In order to increase gene editing at the target site and to increase the occurrence of the 13 nt deletion at the target site, PhTx ssODN1 (SEQ ID NO:909) was co-delivered with the precomplexed RNP targeting HBG containing the Sp37 gRNA. Co-delivery of the ssODN donor encoding the 13 nt deletion led to a nearly 2-fold increase in gene editing of the target site (FIG. 5A). To determine whether editing HBG increases production of fetal hemoglobin in erythroid progeny of edited adult CD34$^+$ cells, the cells were differentiated into erythroblasts by culture for up to 18 days in the presence of human cytokines (erythropoietin, SCF, IL3), human plasma (Octoplas), and other supplements (hydrocortisone, heparin, transferrin). Over the time course of differentiation, mRNA was collected to evaluate HBG gene expression in the erythroid progeny of RNP treated mPB CD34$^+$ cells and donor matched negative (untreated) controls. By day 7 of differentiation, erythroblast progeny of human CD34$^+$ cells that were treated with HBG Sp37 RNP and 13 nt deletion encoding ssODN (~5% indels detected in gDNA from the bulk cell population by T7E1 analysis) exhibited a 2-fold increase in HBG mRNA production (FIG. 5B). Importantly, CD34$^+$ cells that were electroporated with HBG RNP maintained their ex vivo hematopoietic activity (i.e., no difference in the quantity or diversity of erythroid and myeloid colonies compared to untreated donor matched CD34$^+$ cell negative control), as determined in hematopoietic colony forming cell (CFC) assays (FIG. 6A). Furthermore, the erythroblasts differentiated from RNP treated CD34$^+$ cells maintained the kinetics of differentiation observed for donor matched untreated control cells as determined by flow analysis for acquisition of erythroid phenotype (% Glycophorin A$^+$ cells) (FIG. 6B). These data indicate that targeted disruption of HBG1/HBG2 proximal promoter region supported an increase in HBG expression in erythroid progeny of RNP treated adult hematopoietic stem/progenitor cells without altering differentiation potential.

Figure 7A:
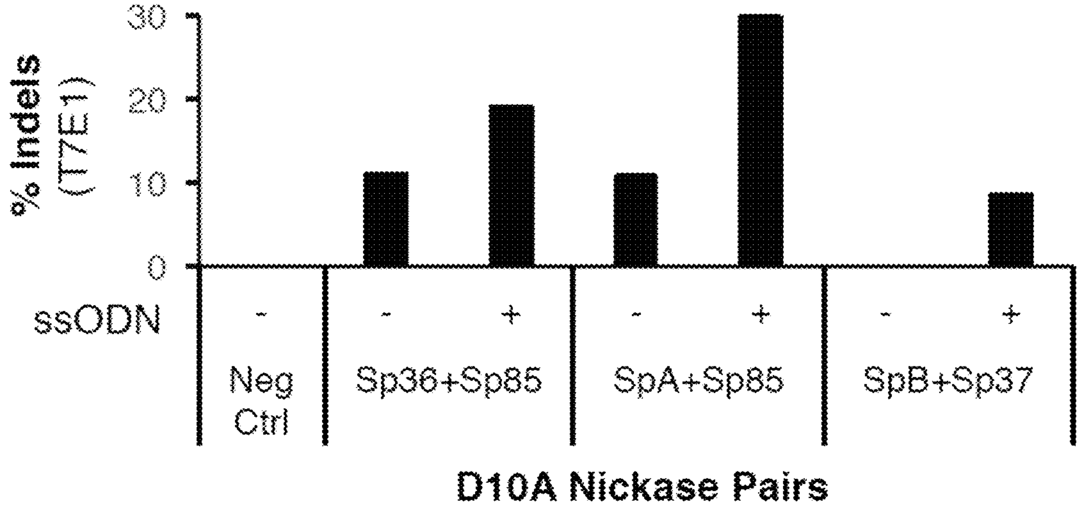
FIG. 7A depicts indels detected by T7E1 analysis of HBG PCR product amplified from gDNA extracted from human mPB $CD34^+$ cells treated with HBG RNPs (D10A paired nickases). For a subset of samples, cells also received ssODN encoding the 13 nt deletion plus silent SNPs to monitor for HDR (ssODN).
Figure 7B:
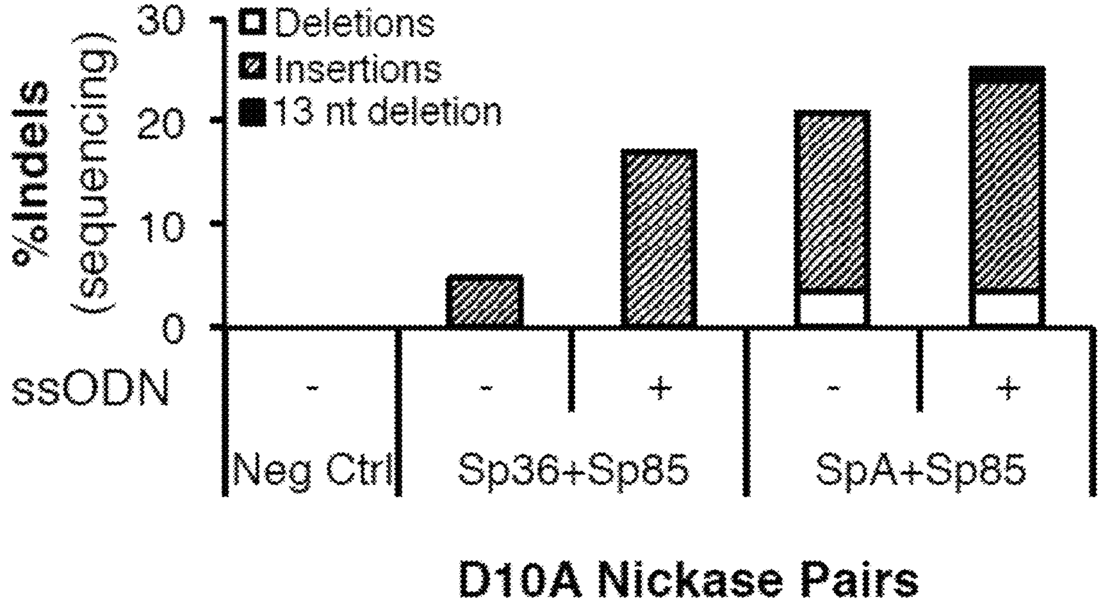
FIG. 7B depicts DNA sequencing analysis for select subset of samples shown in FIG. 7A. The indels were subdivided according to the type of indel (insertion, 13 nt deletion, or other deletion).

Example 4: Cas9 RNP Targeting the HPFH Mutation Supports Gene Editing in Human Adult Mobilized Peripheral Blood Hematopoietic Stem/Progenitor Cells with Increased HBG Expression in Erythroblast Progeny To determine whether co-delivery of paired nickase RNPs targeting HBG would increase targeted disruption of the proximal HBG promoter, mPB CD34$^+$ cells were cultured for 2 days with human cytokines and PGE2 in StemSpan SFEM and then electroporated with *S. pyogenes* D10A Cas9 protein precomplexed to two gRNAs that target sites flanking the site of the 13 nt deletion. The targeting domain sequences for gRNAs used in nickase pairs in this example (including, without limitation, SpA, Sp85 and SpB) are presented in Table 7. D10A nickase pairs were selected such that the PAMs for the targets were oriented outward and the distance between the cut sites were <100 nt. gRNAs were complexed with D10A Cas9 protein to form RNP complexes and then human CD34$^+$ cells and paired nickase were subject to electroporation. To determine whether co-delivery of an ssODN that encoded the 13 nt deletion would increase editing and introduction of the mutation into the cells, in some experiments, ssODN1 was added to the cell RNP mixture prior to electroporation. Approximately 3 days after electroporation, gDNA was extracted from the RNP treated cells and analyzed by T7E1 endonuclease assay and/or Sanger DNA sequencing of HBG2 PCR products amplified from the extracted gDNA. Of the three D10A nickase pairs tested, indels detected by T7E1 endonuclease analysis were increased for one nickase pair (gRNAs SpA+Sp85) samples for which ssODN1 was included (FIG. 7A). DNA sequencing analysis was performed on limited samples shown in FIG. 7A. DNA sequencing analysis showed up to -27% indels at the target site, with insertions as the dominant indel detected, followed by deletions of the targeted region (area between the cut sites of the paired nickases), and the 13 nt deletion mutation was also detected at a frequency of 2-3% when ssODN1 encoding the deletion was co-delivered (FIG. 7B). Silent, non-pathogenic SNPs were included in the ssODN1 donor template, and were detected in the sequences that contained the 13 nt deletion, indicating that creation of the HFPH mutation occurred through an HDR event.

Figure 8A:
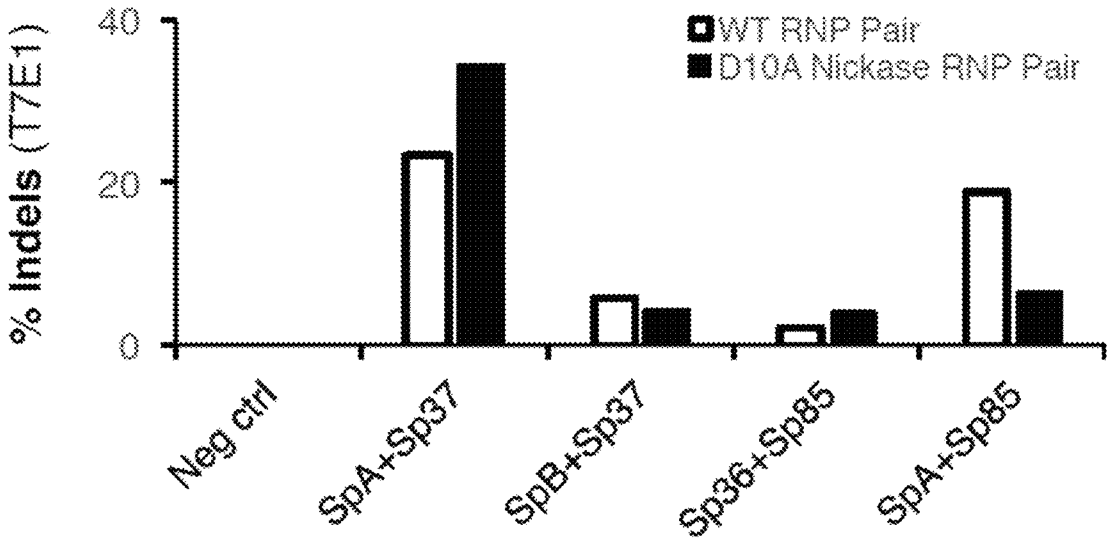
FIG. 8A depicts the indels at the HBG target site after electroporation of mPB $CD34^+$ cells with the indicated pairs of gRNAs complexed in D10A nickase and WT RNP pairs.
Figure 8B:
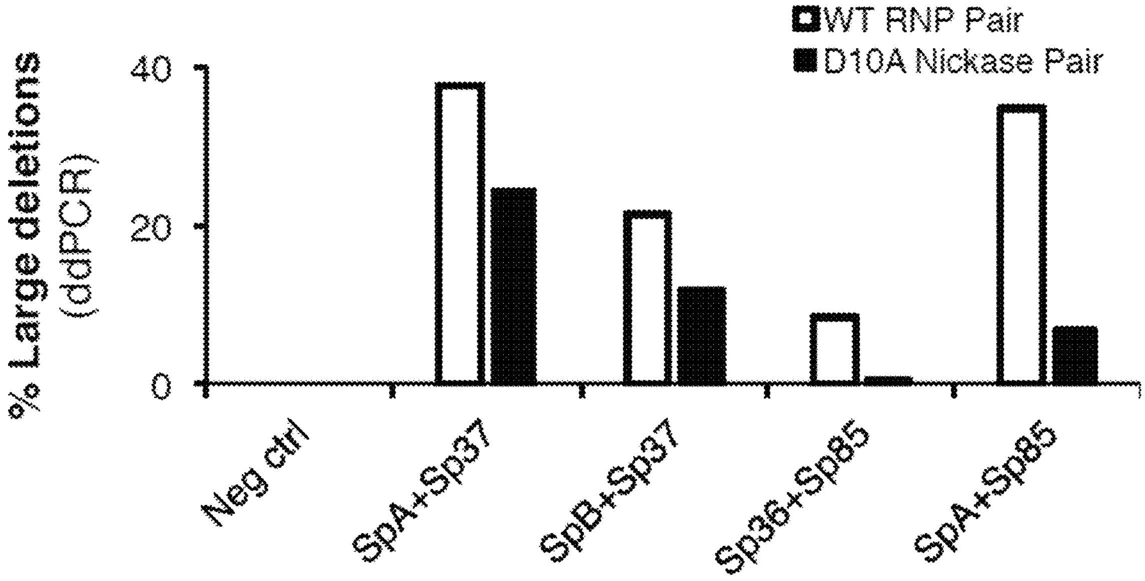
FIG. 8B depicts the large deletion events (e.g. deletion of HBG2) after electroporation of mPB $CD34^+$ cells with the indicated pairs of gRNAs complexed in D10A nickase and WT RNPs.
Figure 8C:
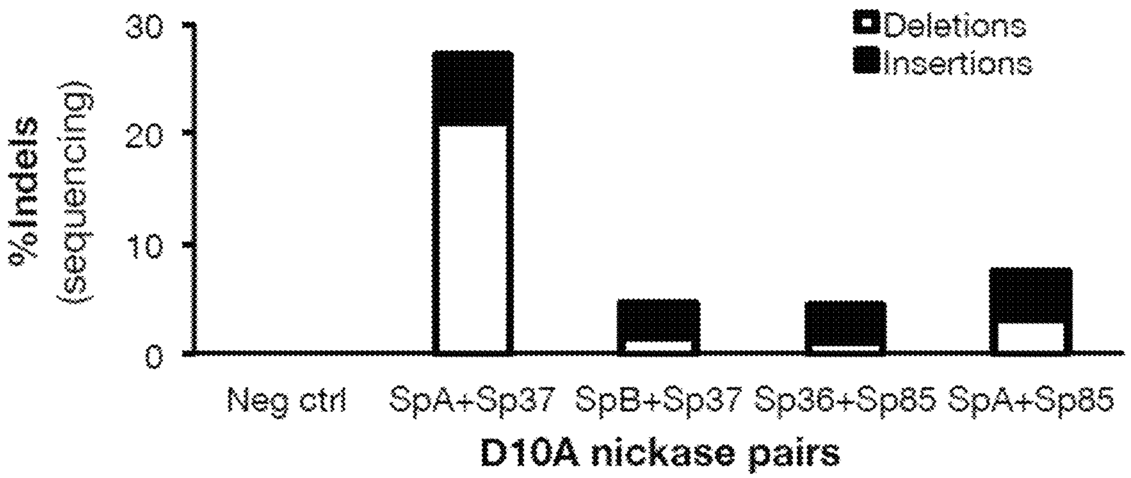
FIG. 8C depicts DNA sequencing analysis and the subtypes of events (insertions, deletions) detected in gDNA from mPB $CD34^+$ cells treated with paired D10A nickase pairs.
Figure 8D:
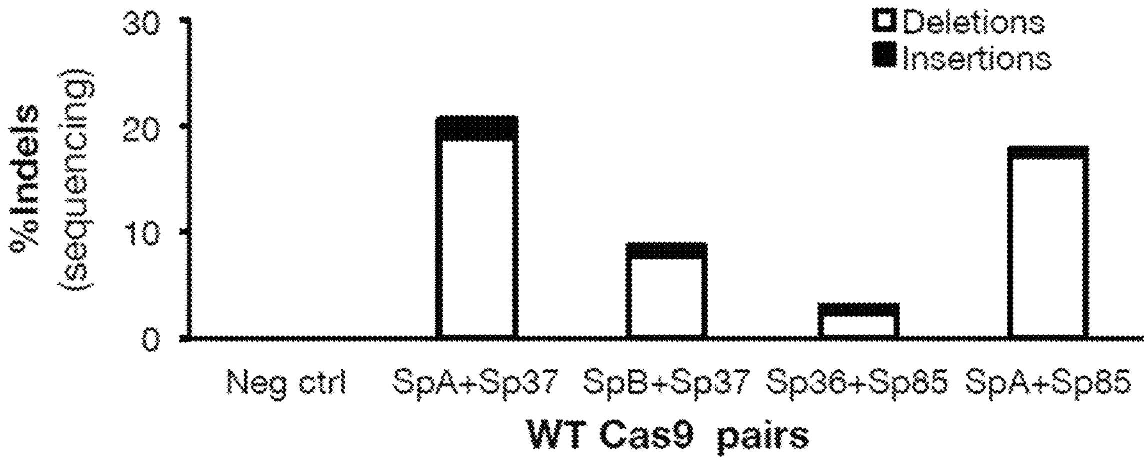
FIG. 8D depicts DNA sequencing analysis and the subtypes of events (insertions, deletions) detected in gDNA from mPB $CD34^+$ cells treated with paired WT RNP pairs.

Example 5: D10A Paired RNPs Electroporated into Adult CD34$^+$ Cells Supports Induction of HbF Protein in Erythroid Progeny To further optimize editing conditions in mPB CD34$^+$ cells at the target site and to evaluate editing in additional human cell donors, human mPB CD34$^+$ cells were electroporated with D10A Cas9 and WT Cas9 paired RNPs targeting HBG. The most efficient guide pair for both D10A Cas9 and WT Cas9 RNPs was Sp37+SpA, which supported >30% indels as determined by T7E1 endonuclease analysis of HBG2 PCR products (FIG. 8A). Given that editing at both HBG1 and HBG2 could result in large deletions of HBG2 and the intergenic region between HBG2 and HBG1, indels were further characterized in order to capture local indels by T7E1 endonuclease assay and sequencing and large deletion by ddPCR analysis. Large deletions were detected in all samples at variable frequencies for both D10A Cas9 and WT Cas9 RNP nickase pairs (FIG. 8B). Illumina sequencing analysis of indels correlated with indels determined by T7E1 analysis (FIG. 8C-8D).

To determine whether CD34$^+$ cells edited with dual nickases at the HBG promoter gave rise to erythroid progeny with elevated HbF expression, donor matched RNP treated and untreated controls were induced toward erythroid differentiation and then evaluated for maintenance of indels during differentiation and for expression of HbF mRNA and protein. The level of editing (as determined by T7E1 endonuclease assay) was evaluated over the first 2 weeks of erythroid differentiation in the progeny of RNP treated cells prior to enucleation. Indels were detected in the erythroid progeny at every time point assayed suggesting that the editing that occurred in the CD34$^+$ cells was maintained during erythroid differentiation and that edited CD34$^+$ cells maintain erythroid differentiation potential.

Figure 9:
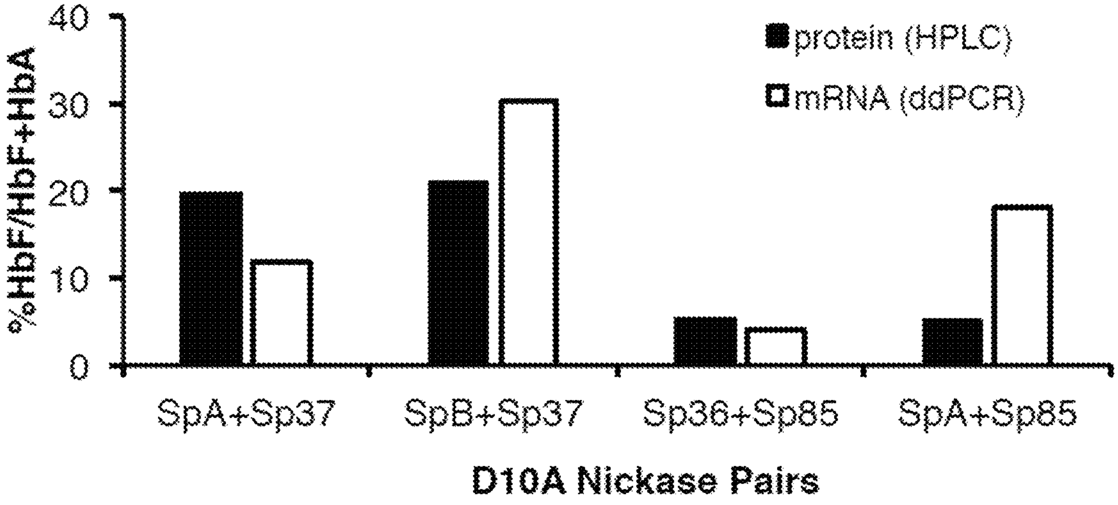
FIG. 9 depicts the summary of HbF protein and mRNA expression in the progeny of mPB $CD34^+$ cells treated with paired RNPs targeting HBG, for the experiments shown in FIGS. 7 and 8. HbF protein (by HPLC analysis) and HbF mRNA expression (ddPCR analysis) were evaluated in erythroid progeny of RNP treated human mPB CD34 cells (background levels of HbF detected in donor matched untreated controls were subtracted from the levels detected in progeny of RNP treated $CD34^+$ cells).

The levels of HBG mRNA (day 10 of differentiation) and HbF protein (day 20-23 of differentiation) were quantified by ddPCR and HPLC analysis (according to the HPLC method described in Chang 2017 at pp. 143-44, incorporated by reference herein), respectively (FIG. 9). A ~2-fold increase (+40% in in HBG transcripts vs. unedited donor matched control) was observed for HBG:HBA ratio (data not shown) and the ratio of HbF/HbF+HbA (i.e. HBG mRNA/HGB+HBB mRNA) increased to 30% above the level detected in donor matched untreated control samples.

For the D10A Cas9 nickase pairs, upregulation of HbF mRNA and protein was detected in erythroid progeny (FIG. 9). With respect to HbF protein analysis, two pairs supported 20% HbF induction for two D10A nickase pairs. No HbF upregulation was detected in erythroid progeny of WT Cas9 RNP treated CD34$^+$ cells (data not shown).

Figure 10A:
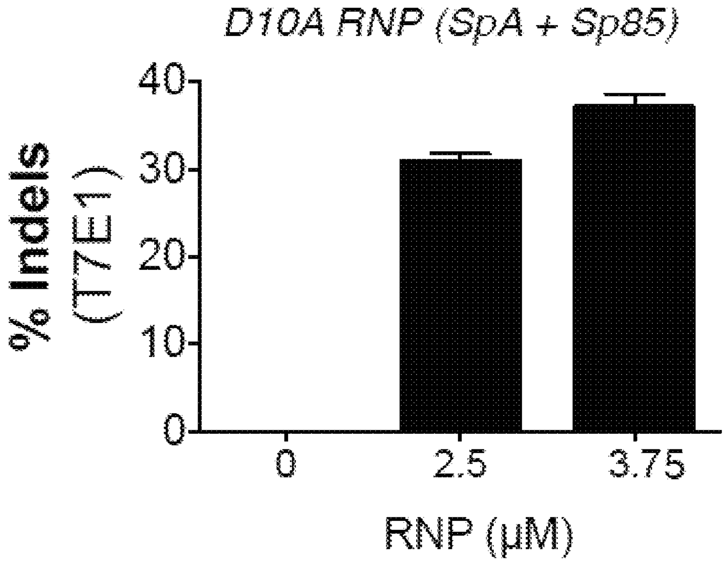
FIGS. 10A-H depict the indel frequencies and ex vivo and in vivo short-term hematopoietic potential of $CD34^+$ cells after treatment with different concentrations (0, 2.5, 3.7 μM) of paired D10A nickase RNPs (SpA+Sp85). Indels were evaluated by T7E1 analysis (FIG. 10A) and by Illumina sequencing analysis (insertions and deletions, FIG. 10B).
Figure 10B:
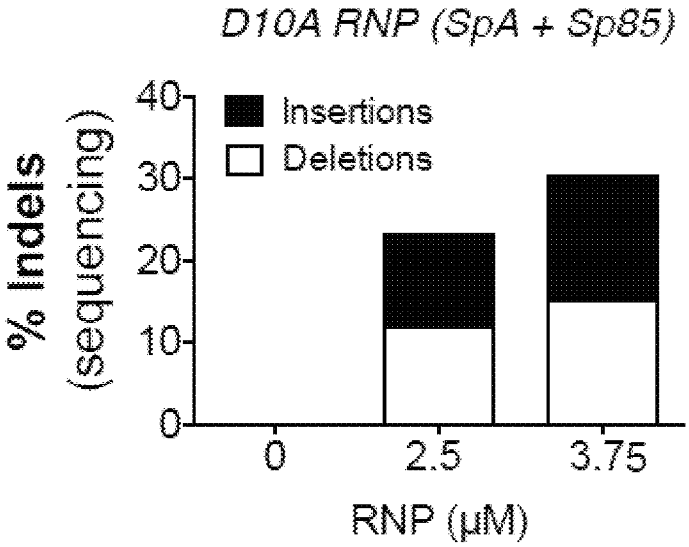
Figure 10C:
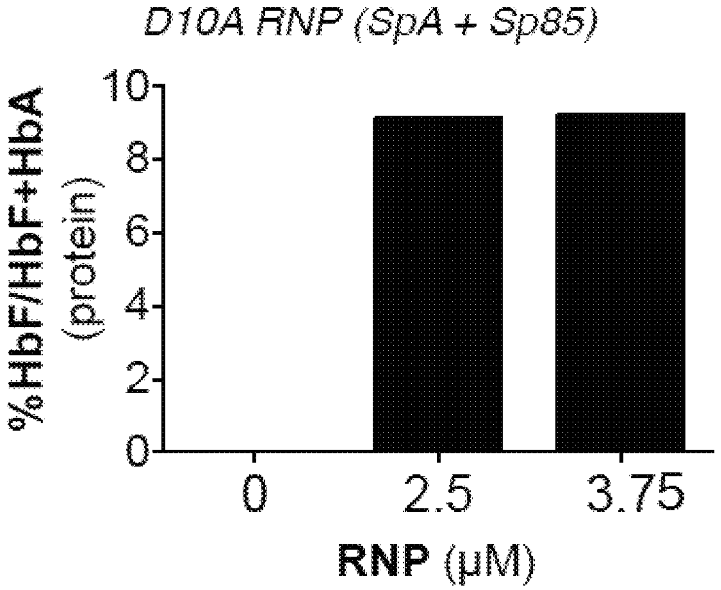
Figure 10D:
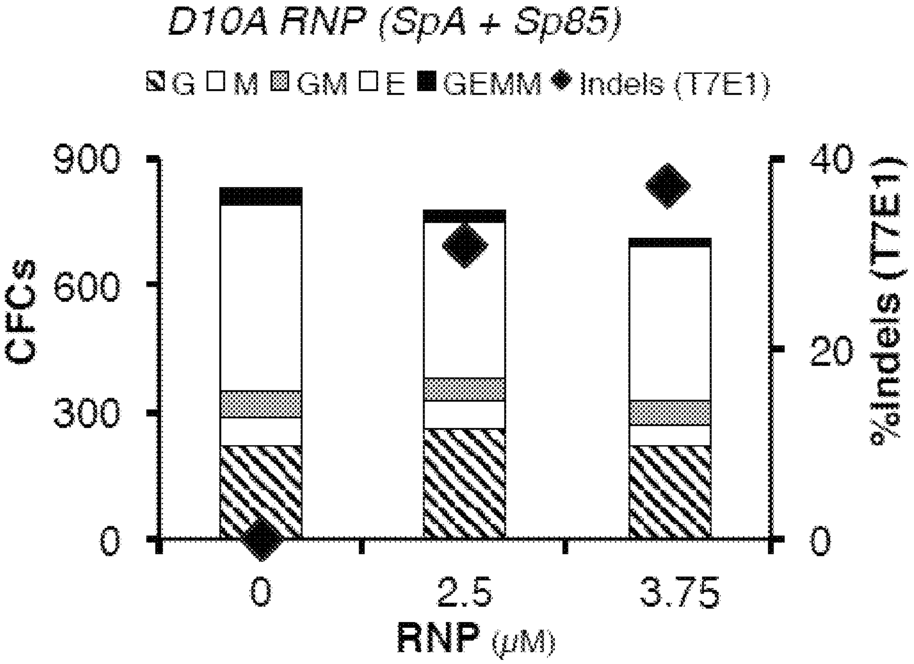
Figure 10E:
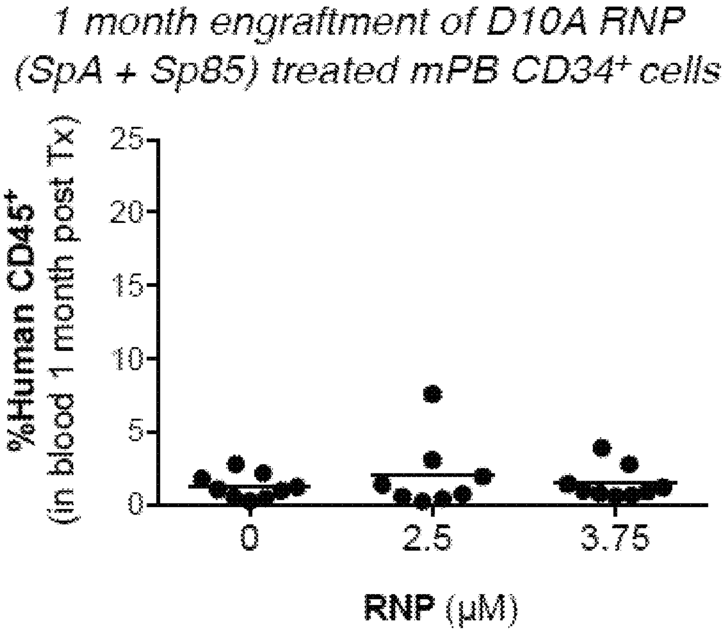
Figure 10F:
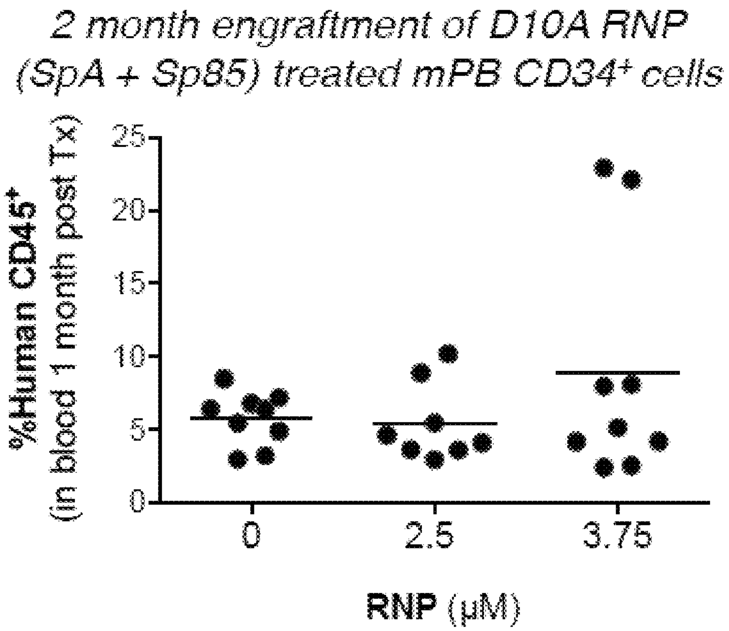
Figure 10G:
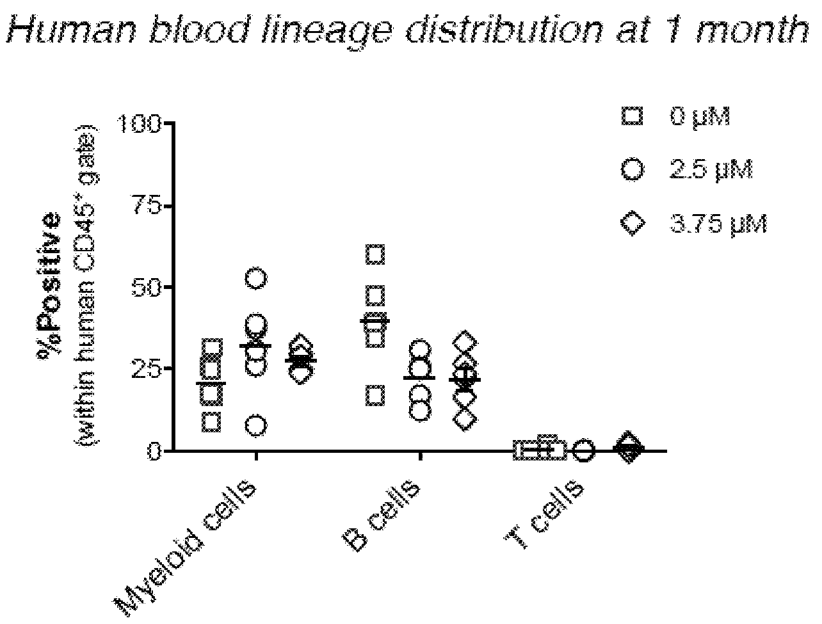
Figure 10H:
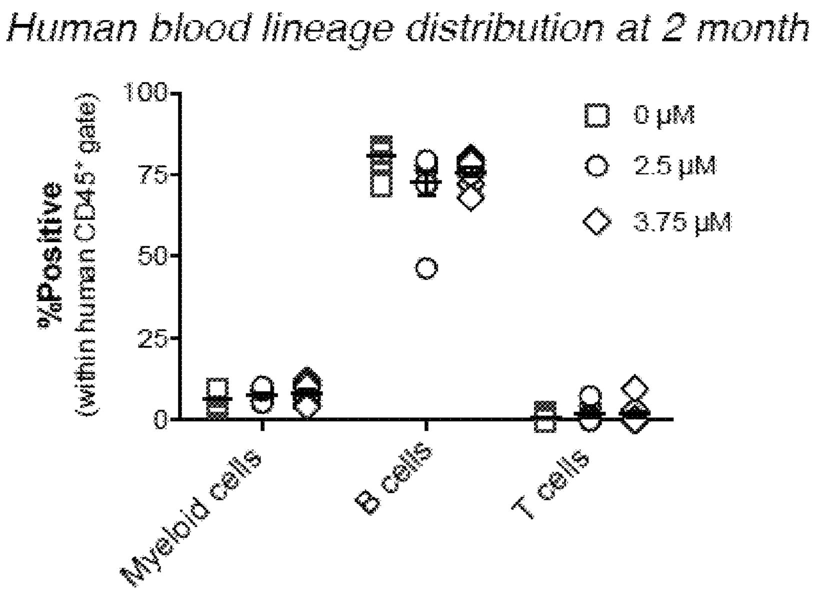

Example 6: Increasing the Dose of RNP Increases Total Editing Efficiency in Human Adult CD34$^+$ Cells at the HBG Locus The concentration of D10A Cas9 RNP for the nickase pair SpA+Sp85 was increased (2.5 μM standard concentration and 3.7 μM) and delivered to mPB $CD34^+$ cells by electroporation. The increased RNP concentration supported an increase in indels at the HBG target site to >30% (FIG. 10A) as determined by T7E1 endonuclease analysis of the HBG PCR product amplified for gDNA extracted 3 days after electroporation of $CD34^+$ cells. Sequencing analysis indicated that increasing the RNP concentration increased insertions (FIG. 10B). Erythroid progeny of RNP treated $CD34^+$ cells also had an increase in HbF protein production (FIG. 10C). Importantly, the hematopoietic colony forming potential was maintained after editing (FIG. 10D). These cells were then transplanted into immunodeficient mice and their engraftment 1 month (FIG. 10E) and 2 months (FIG. 10F) after transplantation was evaluated by sampling the peripheral blood and measuring the percentage of human $CD45^+$ cells. Early engraftment data showed no difference in engraftment between recipient cohorts of donor matched untreated controls (0 μM RNP) and mice transplanted with RNP treated cells. Furthermore, there was no difference in human blood lineage distribution (myeloid, B cell, T cell) within the human $CD45^+$ fraction among cohorts at indicated time points (FIG. 10G-H).

Figure 11A:
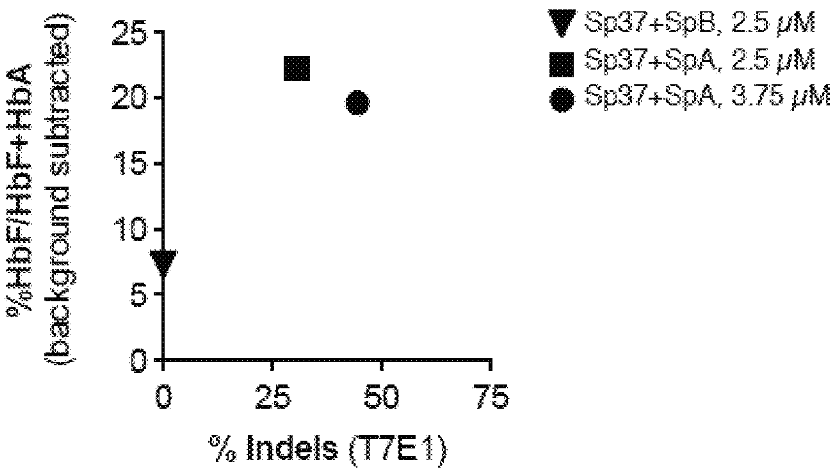
FIG. 11A correlates HbF levels as assayed by HPLC and indel frequency as assessed by T7E1 analysis for two D10A nickase RNP pairs (SP37+SPB and SP37+SPA) delivered at the indicated concentrations to mPB $CD34^+$ cells. HbF levels were analyzed in erythroid progeny (day 18) of edited $CD34^+$ cells. HbF protein detected in donor-matched untreated controls were subtracted from edited samples.
Figure 11B:
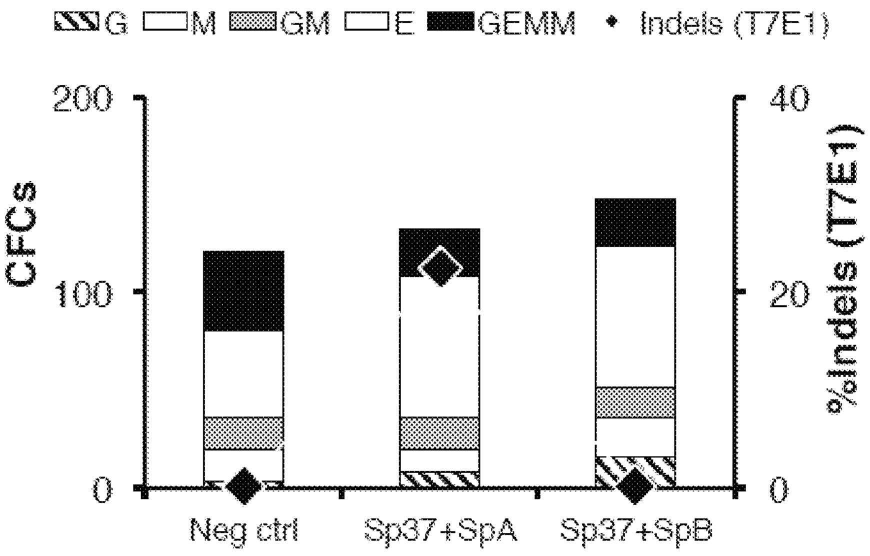
FIG. 11B depicts indel rates overlaid on hematopoietic colony forming cell (CFC) activity associated with $CD34^+$ cells treated with the indicated D10A nickase pairs or untreated controls.
Figure 11C:
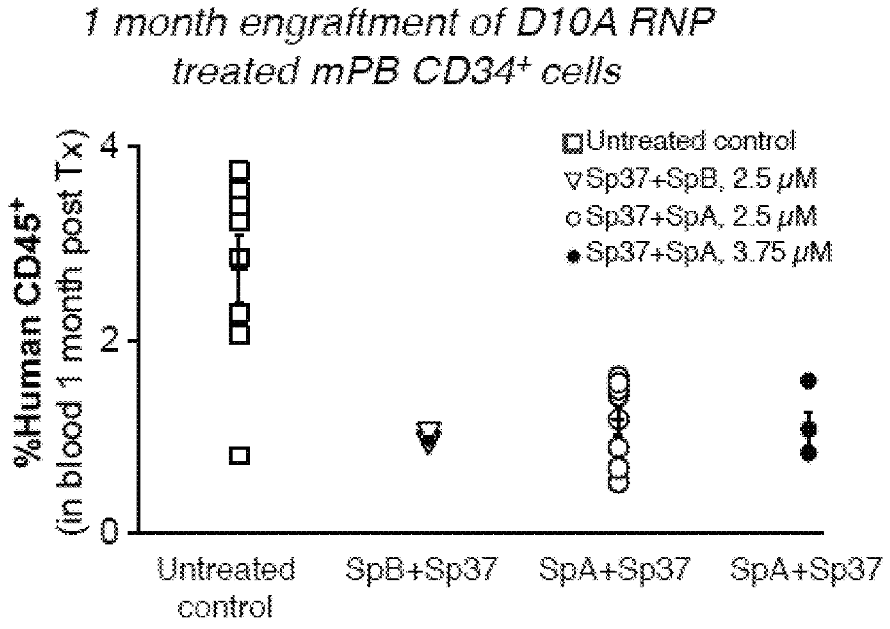
FIG. 11C depicts human $CD45^+$ blood cell reconstitution of immunodeficient NSG mice one month after transplantation of mPB $CD34^+$ cells treated with indicated D10 RNP nickase pairs at the concentrations given or donor matched untreated controls.
Figure 11D:
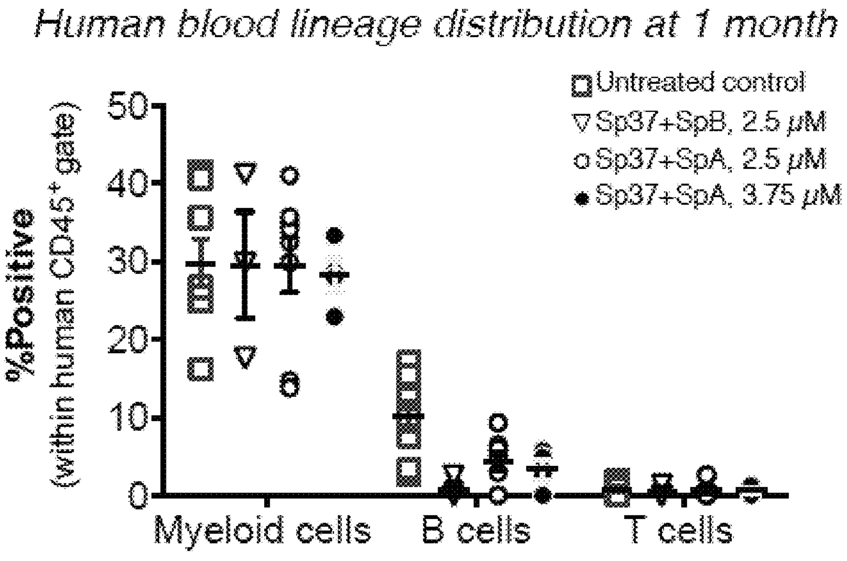
FIG. 11D depicts the human blood lineage distribution detected in the human $CD45^+$ fraction in mouse peripheral blood one month post-transplant.

Two additional D10A nickase pairs were also tested in RNP dose response studies in adult mPB $CD34^+$ cells (Sp37+SpA, Sp37+SpB). Here, mPB $CD34^+$ cells were electroporated with D10A paired nickases delivered at 0, 2.5, and 3.75 μM of total RNP. RNP treated cells were differentiated into erythroid progeny and the HbF protein levels (% HbF/HbF+HbA) were analyzed by HPLC analysis. The indel frequency detected in $CD34^+$ cells was plotted with the HbF levels detected in erythroid progeny in order to correlate editing and HbF induction (FIG. 11A). RNP treated and untreated control mPB $CD34^+$ cells were also differentiated into colonies to evaluate ex vivo hematopoietic activity. Colony forming cell (CFC) activity was maintained for the progeny of RNP treated and donor matched untreated control $CD34^+$ cells (FIG. 11B). There was no difference in the percentage of human $CD45^+$ cells in the mouse peripheral blood 1 month after transplantation and no difference in blood lineage distribution (FIG. 11C-D) for cells exposed to different D10A RNP pairs at different doses compared to untreated donor matched control $CD34^+$ cells.

Figure 12:
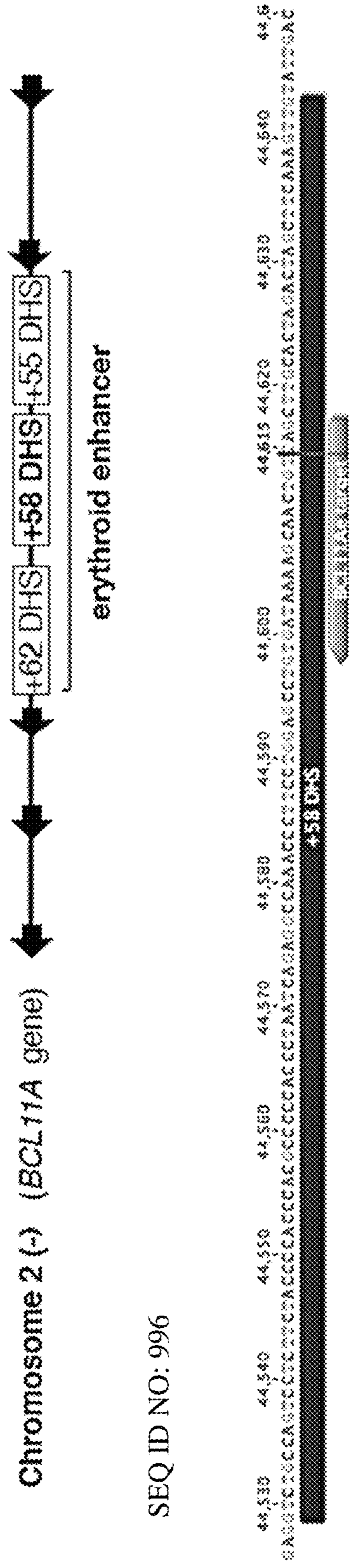
FIG. 12 depicts a target site for derepression of HbF, the GATA1 motif of the +58 DNase I hypersensitive site (DHS) erythroid specific enhancer of BCL11A (BCL11Ae) (genomic coordinates: chr2: 60,495,265 to 60,495,270).

Example 7: Co-Delivery of RNP Targeting the Erythroid Specific Enhancer of BCL11A and a Non-Specific (N) Single Strand Deoxynucleotide Sequence or Paired RNPs Increases Gene Editing in Human $CD34^+$ Cells and Supports Induction of Fetal Hemoglobin Expression in Erythroid Progeny Fetal hemoglobin expression can be induced through targeted disruption of the erythroid cell specific expression of a transcriptional repressor, BCL11A (Canvers 2015). One potential strategy to increase HbF expression through a gene editing strategy is to multiplex gene editing for introduction of 13 nt deletion associated in the HBG proximal promoter and also for targeted disruption of the GATA1 binding motif in the erythroid specific enhancer of BCL11A that is in the +58 DHS region of intron 2 of the BCL11A gene (FIG. 12). In order to accomplish this multiplex strategy to increase HbF expression through multiplex gene editing, the effect of disruption of BCL11A erythroid enhancer (BCL11Ae) must first be determined as a single editing event.

Figure 13A:
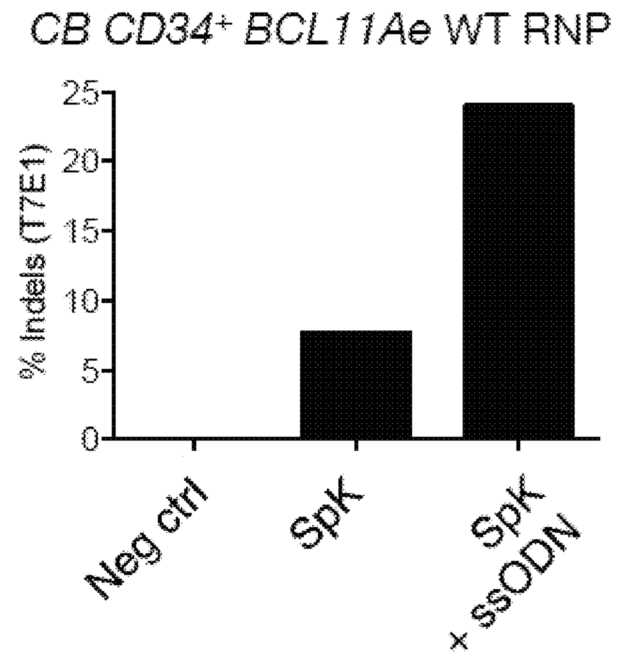
FIG. 13A depicts the percentage of indels detected by T7E1 endonuclease analysis of BCL11A PCR products amplified from gDNA extracted from CB $CD34^+$ cells treated with the indicated RNP+/−ssODN or donor matched untreated control cells. Data shown represent the mean of three 3 separate donors/experiments.
Figure 13B:
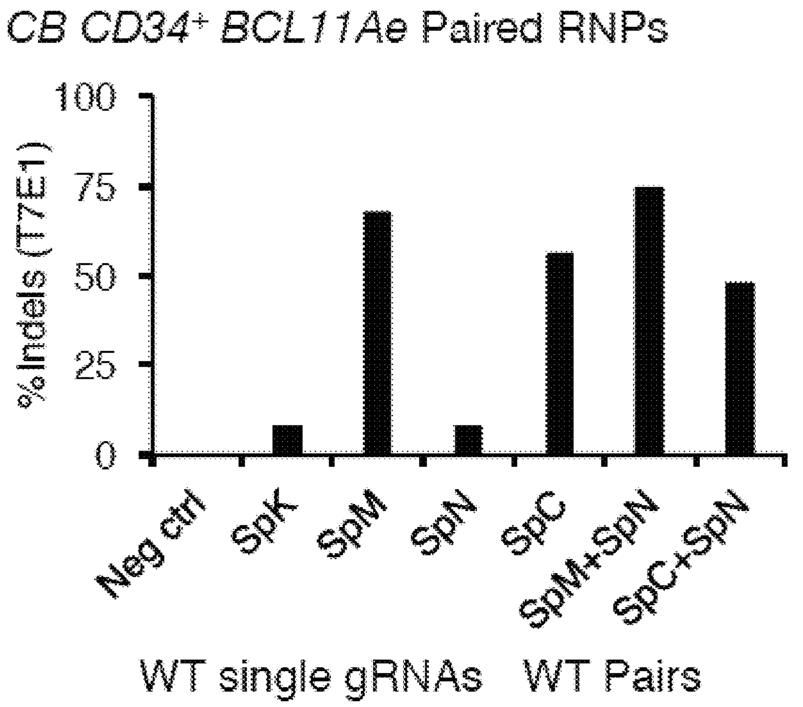
FIG. 13B depicts indels detected by T7E1 endonuclease analysis of BCL11A PCR products amplified from gDNA extracted from CB $CD34^+$ cells treated with the indicated WT RNP (single gRNA targeting the BCL11A erythroid enhancer complexed to WT *S. pyogenes* Cas9 having both RuvC and HNH activity) or paired nickase RNP (paired gRNAs targeting the BCL11A erythroid enhancer complexed to *S. pyogenes* Cas9 nickases sharing the same HNH single stranded cutting activity (e.g. D10A), as well as the hematopoietic activity of cells in each condition.

In this experiment, CB $CD34^+$ cells were electroporated with *S. pyogenes* WT Cas9 complexed to in vitro transcribed sgRNA targeting the GATA1 motif in the +58 DHS region of intron 2 of BCL11A gene (gRNA SpK, Table 9) (FIG. 13A). To determine whether co-delivery of a non-target specific ssODN would increase editing of the target sequence, BCL11Ae RNP was co-delivered with ssODN (which is nonhomologous to the BCL11Ae target sequence) in CB $CD34^+$ cells. T7E1 analysis of BCL11A erythroid enhancer PCR product from gDNA extracted from CB $CD34^+$ cells treated with BCL11Ae RNP indicated that ~5% indels was achieved (FIG. 13A). Co-delivery of BCL11Ae RNP with a non-target specific ssODN increase in indels by 5-fold to 20% as detected by T7E1 endonuclease analysis. Illumina sequencing analysis indicated that >90% of edits had disruption of the GATA1 motif in the +DHS 58 region enhancer in intron 2 of the BCL11A gene (data not shown). To increase editing, human CB $CD34^+$ cells were electroporated with WT Cas9 RNP (single gRNAs complexed to WT Cas9) or with WT Cas9 paired RNPs (paired gRNAs complexed to WT Cas9), so that the cut sites in each pair flank the target site for excision of the GATA1 motif (gRNAs SpC, SpK, SpM, SpN) (Table 9). Two of the single gRNAs and two pairs had >50% indels as determined by T7E1 endonuclease analysis (FIG. 13B).

TABLE 9

Select gRNA sequences targeting BCL11A erythroid enhancer for screening in $CD34^+$ cells

| gRNA ID | Targeting domain sequence (RNA) | Targeting domain sequence (DNA) | Targeting domain sequence plus PAM (NGG) (RNA) | Targeting domain sequence plus PAM (NGG) (DNA) | Sense |
|---|---|---|---|---|---|
| SpK | CUAACA GUUGCU UUUAUC AC (SEQ ID NO: 952) | CTAACAG TTGCTTT TATCAC (SEQ ID NO: 956) | CUAACAG UUGCUUU UAUCACA GG (SEQ ID NO: 960) | CTAACAG TTGCTTT TATCACA GG (SEQ ID NO: 964) | Anti-sense |
| SpM | GGGCGU GGGUGG GGUAGA AG (SEQ ID NO: 953) | GGGCGTG GGTGGGG TAGAAG (SEQ ID NO: 957) | GGGCGUG GGUGGGG UAGAAGA GG (SEQ ID NO: 961) | GGGCGTG GGTGGGG TAGAAGA GG (SEQ ID NO: 965) | Anti-sense |
| SpN | CUCUUA GACAUAA CACACCA (SEQ ID NO: 954) | CTCTTAG ACATAAC ACACCA (SEQ ID NO: 958) | CUCUUAG ACAUAAC ACACCAG GG (SEQ ID NO: 962) | CTCTTAG ACATAAC ACACCAG GG (SEQ ID NO: 966) | Anti-sense |
| SpC | AUCAGAG GCCAAAC CCUUCC (SEQ ID NO: 955) | ATCAGAG GCCAAAC CCTTCC (SEQ ID NO: 959) | AUCAGAG GCCAAAC CCUUCCU GG (SEQ ID NO: 963) | ATCAGAG GCCAAAC CCTTCCT GG (SEQ ID NO: 967) | Sense |

Figure 14A:
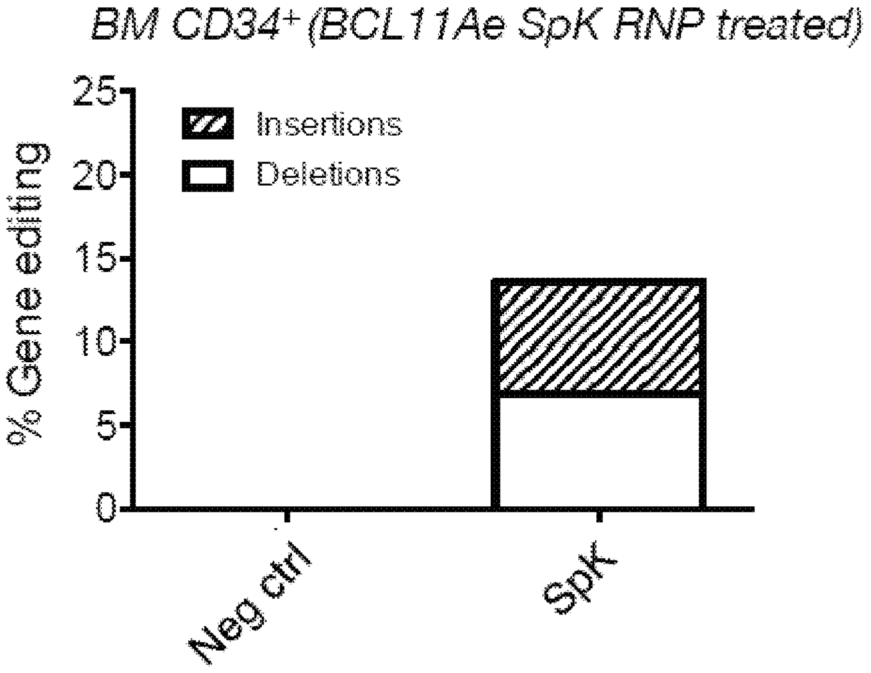
FIG. 14A depicts the editing frequency of BCL11Ae (using single gRNA approach targeting the GATA1 motif) in adult human BM $CD34^+$ cells.
Figure 14B:
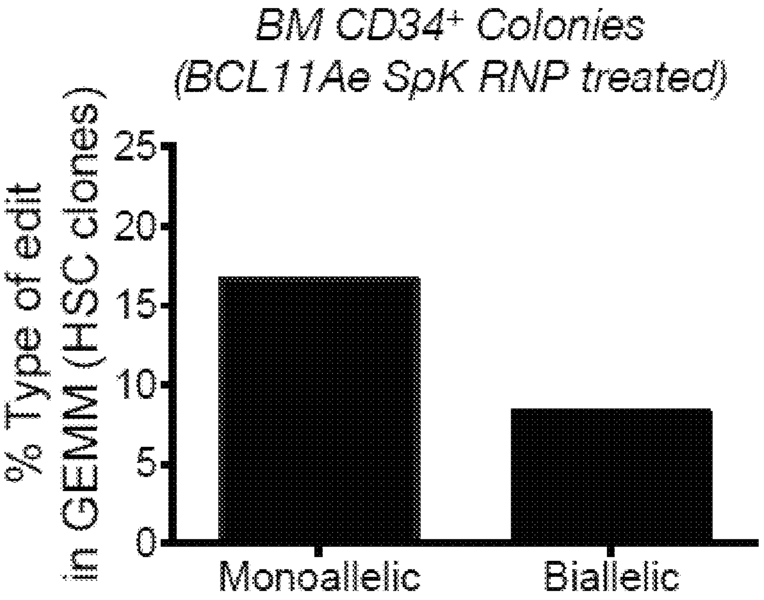
FIG. 14B depicts the monoallelic and bialleleic editing detected in hematopoietic colonies (GEMMs, clonal progeny of BCL11Ae RNP treated $CD34^+$ cells) as determined by DNA sequencing analysis.
Figure 14C:
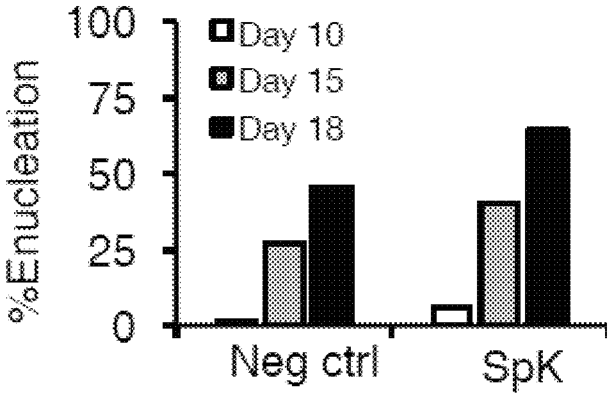
FIG. 14C depicts the kinetics of erythroblast maturation (enucleation as determined by $DRAQ5^-$ cells detected by flow cytometry analysis).
Figure 14D:
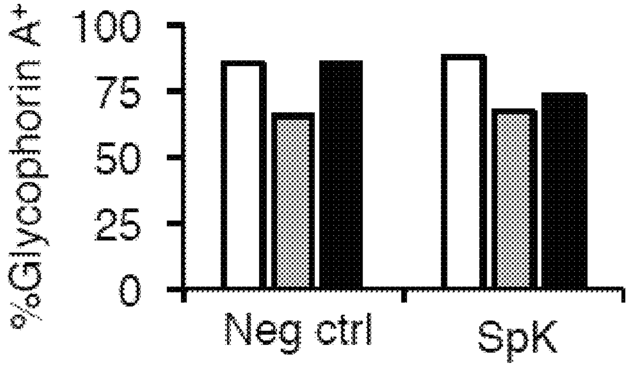
FIG. 14D depicts the acquisition of erythroid phenotype (Glycophorin $A^+$ cells) in differentiated control and RNP-treated BM $CD34^+$ cells.
Figure 14E:
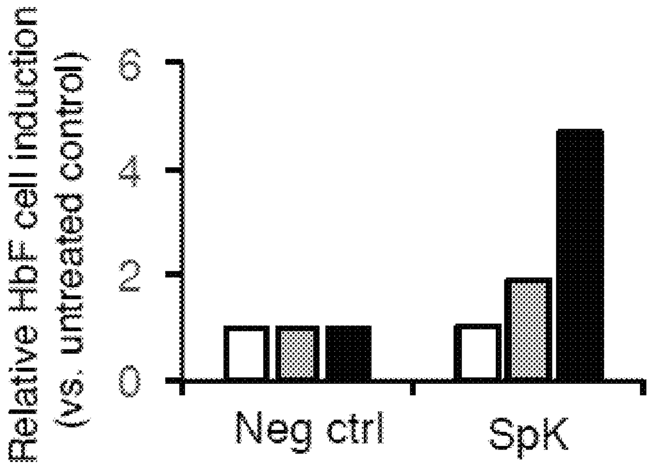
FIG. 14E shows the fold increase in $HbF^+$ cells as determined by flow cytometry analysis relative to HbF+ cells in untreated donor matched control samples.

Next, human adult bone marrow $CD34^+$ cells were electroporated with the BC11Ae RNP. DNA sequencing analysis of the BCL11A PCR product amplified from gDNA extracted from marrow $CD34^+$ cells indicated 15% gene editing comprised of insertions and deletions (FIG. 14A). Importantly, all deletions resulted in deletion of the GATA1 motif and all insertions disrupted GATA1 motif through addition of a small number of bp in the motif. $CD34^+$ cells were plated into colony forming assays and the mixed hematopoietic colonies (GEMMs), which correspond to $CD34^+$ cell clones, were picked. gDNA was isolated and analyzed by Illumina sequencing to quantify monoallelic and biallelic disruption of the target site. Most GEMMs differentiated from the CD34$^+$ cell clones had monoallelic disruption and biallelic disruption was also detected, with the overall indel rate ~⅔ higher compared to what was detected in the bulk CD34+ cell population (FIG. 14B). This was likely a reflection of the percentage of common myeloid progenitors (CMPs) that give rise to GEMMs that make up a larger fraction of the heterogenous CD34$^+$ cells versus the other lineages present, but not captured/differentiated in the short-term CFC assays. The RNP treated marrow CD34$^+$ cells also maintained similar kinetics of erythroid maturation (enucleation, FIG. 14C) and differentiation (phenotype acquisition, FIG. 14D) compared to donor matched untreated control cells. Erythroid progeny of edited marrow CD34$^+$ cells exhibited ~5-fold increase in HbF induction as determined by flow cytometry analysis (FIG. 14E).

Figure 15A:
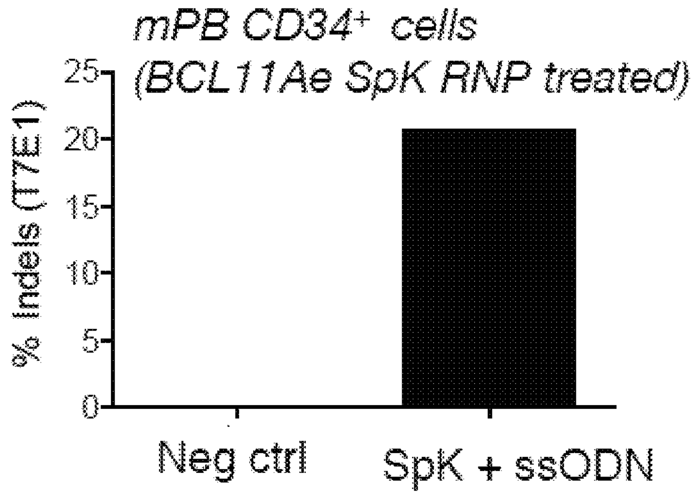
FIGS. 15A-C depict gene editing of BCL11Ae in adult human mPB $CD34^+$ cells and induction of fetal hemoglobin in erythroid progeny of RNP and ssODN treated cells after electroporation of mPB $CD34^+$ cells with BCL11Ae RNP+ nonspecific ssODN.
Figure 15B:
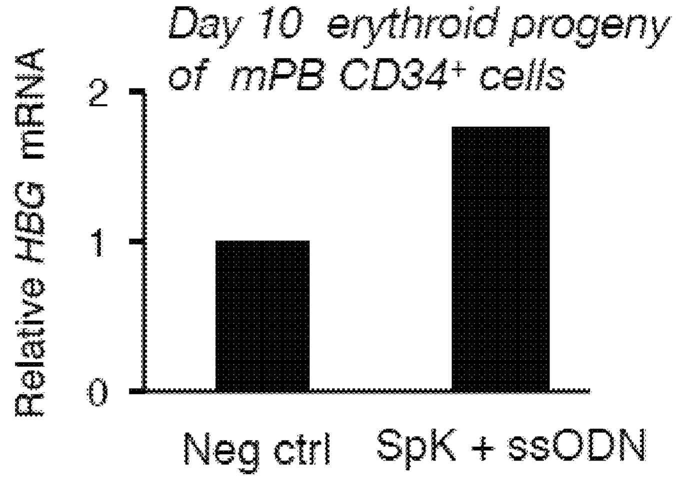
Figure 15C:
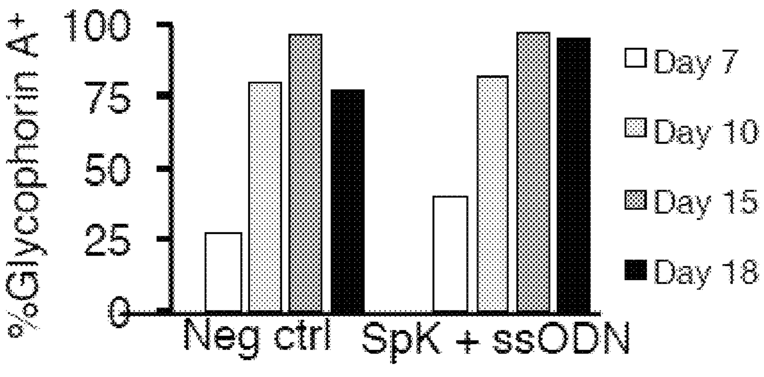

Gene editing and induction of fetal hemoglobin was also evaluated in human adult mPB CD34+ cells. Co-delivery of BCL11Ae RNP and nonspecific ssODN supported ~20% indels at the target site (FIG. 15A). To evaluate early induction of fetal hemoglobin in erythroid progeny of edited cells, mPB CD34$^+$ cells were differentiated into erythroblasts and induction of fetal hemoglobin transcription (HBG mRNA) was evaluated by qRT-PCR analysis. The erythroid progeny of BCL11Ae RNP treated CD34$^+$ cells exhibited a 2-fold induction of HBG mRNA compared to untreated controls, suggesting induction of fetal hemoglobin expression (FIG. 15B). The RNP treated marrow CD34$^+$ cells also maintained similar kinetics of differentiation (phenotype acquisition, FIG. 15C) compared to donor matched untreated control cells.

Figure 16A:
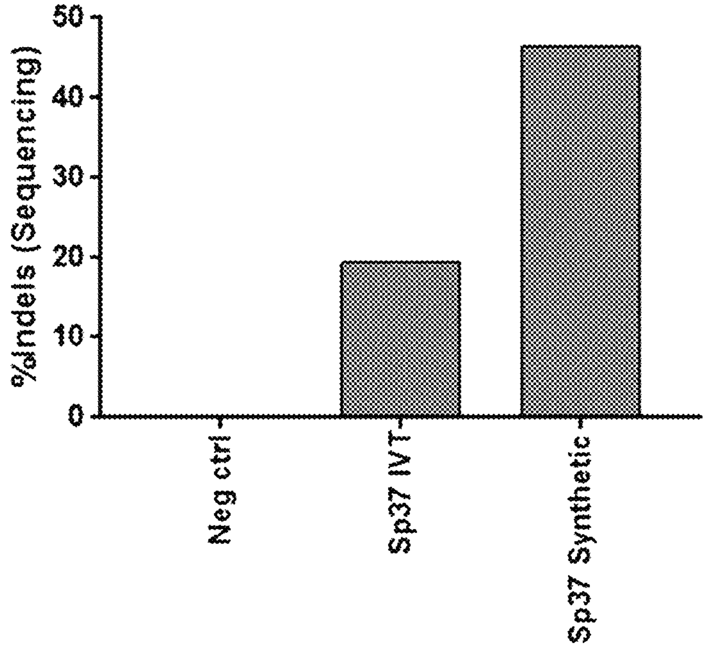
FIGS. 16A-B depict gene editing of the HBG promoter in and viability of adult human $CD34^+$ cells from mPB electroporated with Cas9 complexed with Sp37 gRNA (targeting domain set forth in SEQ ID NO:933), which was in vitro transcribed (Sp37 IVT) or chemically synthesized (Sp37 Synthetic).
Figure 16B:
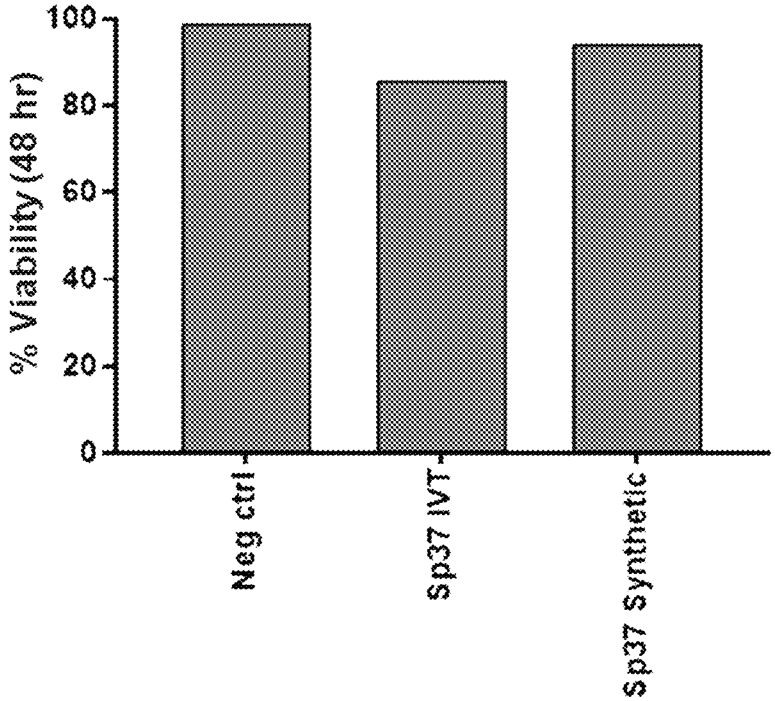

Example 8: RNP Targeting the CAAT Box have Higher Activity when Complexed with Chemically Synthesized Guide RNA than In Vitro Transcribed Synthesized gRNA To determine whether complexing Cas9 RNP with a chemically synthesized gRNA enhances editing in the promoter region of HBG, Sp37 gRNA (i.e., a gRNA that targets the 13 nt deletion associated with HPFH; targeting domain set forth in SEQ ID NO:933) was in vitro transcribed (IVT) or chemically synthesized. Human adult CD34$^+$ cells from mobilized peripheral blood (mPB) were electroporated with the RNPs. Briefly, mPB CD34$^+$ cells were prestimulated for 3 days with human cytokines and PGE2 in StemSpan SFEM and then electroporated with Cas9 protein precomplexed to Sp37 (IVT) or Sp37 (synthetic). The use of synthetic guide RNA supported an increase in indels at the HBG target of more than 2 fold (FIG. 16A) as determined by sequencing analysis of the HBG PCR product amplified from gDNA extracted 4 days after electroporation of CD34$^+$ cells. The viability of the cells at 48 hours post electroporation was not affected by the use of a chemically synthesized gRNA (FIG. 16A).

Example 9: Sequence Mismatches and End Modifications of Synthetic Guide RNAs Increase the Activity of RNP Targeting the CAAT Box To evaluate if end modifications of chemically synthesized gRNA enhance the editing of RNP in the promoter region of HBG, the Sp35 gRNA (i.e., a gRNA that targets the 13 nt deletion associated with HPFH; full length sequence set forth in SEQ ID NO:970, targeting domain sequence set forth in SEQ ID NO:339) was chemically synthesized. One or a combination of the following modifications were made at one or both of the ends of the Sp35 gRNA sequence: 3 nucleotides with a phosphorothioate (PhTx) group and 3 nucleotides with a 2'-O-methyl group (Table 10).

To evaluate if truncations of the protospacer or nucleotide mismatches enhance the editing of RNP in the HBG promoter, 5' end truncations of the Sp35 gRNA were chemically synthesized (Sp35 97mer (SEQ ID NO:976), Sp35 98mer (SEQ ID NO:977), Sp35 99mer (SEQ ID NO:978), Table 10). An Sp35 guide RNA with a C-to-A sequence substitution at the 5' end was also synthesized (Sp35-5' C->A (SEQ ID NO:979), Table 10).

TABLE 10

Sequences of chemically synthesized gRNAs targeting the CAAT box, with end modification, sequence substitution or truncations

| Name | Oli-ID | gRNA sequence (RNA) | gRNA sequence (DNA) |
|---|---|---|---|
| Sp35 unmodified | OLI7066 | CUUGUCAAGGCUAUU GGUCAGUUUUAGAGC UAGAAAUAGCAAGUU AAAAUAAGGCUAGUC CGUUAUCAACUUGAA AAAGUGGCACCGAGU CGGUGCUUUU (SEQ ID NO: 970) | CTTGTCAAGGCTATTG GTCAGTTTTAGAGCTA GAAATAGCAAGTTAAA ATAAGGCTAGTCCGTT ATCAACTTGAAAAAGT GGCACCGAGTCGGTGC TTTT (SEQ ID NO: 980) |
| Sp35 5' PS | OLI8568 | C*U*U*GUCAAGGCU AUUGGUCAGUUUUAG AGCUAGAAAUAGCAA GUUAAAAUAAGGCUA GUCCGUUAUCAACUU GAAAAAGUGGCACCG AGUCGGUGCUUUU (SEQ ID NO: 971) | C*T*T*GTCAAGGCTA TTGGTCAGTTTTAGAG CTAGAAATAGCAAGTT AAATAAGGCTAGTCCG TTATCAACTTGAAAAA GTGGCACCGAGTCGGT GCTTTT (SEQ ID NO: 981) |
| Sp35 5' OMe | OLI8569 | mCmUmUGUCAAGGCU AUUGGUCAGUUUUAG AGCUAGAAAUAGCAA GUUAAAAUAAGGCUA GUCCGUUAUCAACUU GAAAAAGUGGCACCG AGUCGGUGCUUUU (SEQ ID NO: 972) | mCmTmTGTCAAGGCTA TTGGTCAGTTTTAGAG CTAGAAATAGCAAGTT AAAATAAGGCTAGTCC GTTATCAACTTGAAAA AGTGGCACCGAGTCGG TGCTTTT (SEQ ID NO: 982) |
| Sp35 3' POSMe | OLI8396 | CUUGUCAAGGCUAUU GGUCAGUUUUAGAGC UAGAAAUAGCAAGUU AAAAUAAGGCUAGUC CGUUAUCAACUUGAA AAAGUGGCACCGAGU CGGUGCmU*mU* Mu*U (SEQ ID NO: 973) | CTTGTCAAGGCTATTG GTCAGTTTTAGAGCTA GAAATAGCAAGTTAAA ATAAGGCTAGTCCGTT ATCAACTTGAAAAAGT GGCACCGAGTCGGTGC mT*mT*mT*T (SEQ ID NO: 983) |
| Sp35 5' PSOMe | OLI8395 | mC*mU*mU*GUCAAG GCUAUUGGUCAGUUU UAGAGCUAGAAAUAG CAAGUUAAAAUAAGG CUAGUCCGUUAUCAA CUUGAAAAGUGGCAC CGAGUCGGUGCUUUU (SEQ ID NO: 974) | mC*mT*mT*GTCAAGG CTATTGGTCAGTTTTA GAGCTAGAAATAGCAA GTTAAAATAAGGCTAG TCCGTTATCAACTTGA AAAAGTGGCACCGAGT CGGTGCTTTT (SEQ ID NO: 984) |
| Sp35 5'-3' PSOMe | OLI8394 | mC*mU*mU*GUCAAG GCUAUUGGUCAGUUU UAGAGCUAGAAAUAG CAAGUUAAAAUAAGG CUAGUCCGUUAUCAA CUUGAAAAAGUGGCA CCGAGUCGGUGCmU* mU*mU*U (SEQ ID NO: 975) | mC*mT*mT*GTCAAGG CTATTGGTCAGTTTTA GAGCTAGAAATAGCAA GTTAAAATAAGGCTAG TCCGTTATCAACTTGA AAAAGTGGCACCGAGT CGGTGCmT*mT*mT*T (SEQ ID NO: 985) |
| Sp35 97mer | OLI8018 | GUCAAGGCUAUUGGU CAGUUUUAGAGCUAG AAAUAGCAAGUUAAA | GTCAAGGCTATTGGTC AGTTTTAGAGCTAGAA ATAGCAAGTTAAAATA |

TABLE 10-continued

Sequences of chemically synthesized gRNAs targeting the CAAT box, with end modification, sequence substitution or truncations

| Name | Oli-ID | gRNA sequence (RNA) | gRNA sequence (DNA) |
|---|---|---|---|
| | | AUAAGGCUAGUCCGUUAUCAACUUGAAAAAGUGGCACCGAGUCGGUGCUUUU (SEQ ID NO: 976) | AGGCTAGTCCGTTATCAACTTGAAAAAGTGGCACCGAGTCGGTGCTTTT (SEQ ID NO: 986) |
| Sp35 98mer | OLI8019 | UGUCAAGGCUAUUGGUCAGUUUUUAGAGCUAGAAAUAGCAAGUUAAAAUAAGGCUAGUCCGUUAUCAACUUGAAAAAGUGGCACCGAGUCGGUGCUUUU (SEQ ID NO: 977) | TGTCAAGGCTATTGGTCAGTTTTAGAGCTAGAAATAGCAAGTTAAAATAAGGCTAGTCCGTTATCAACTTGAAAAAGTGGCACCGAGTCGGTGCTTTT (SEQ ID NO: 987) |
| Sp35 99mer | OLI8020 | UUGUCAAGGCUAUUGGUCAGUUUUAGAGCUAGAAAUAGCAAGUUAAAAUAAGGCAGUCCGUUAUCAACUUGAAAAAGUGGCACCGAGUCGGUGCUUUU (SEQ ID NO: 978) | TTGTCAAGGCTATTGGTCAGTTTTAGAGCTAGAAATAGCAAGTTAAAATAAGGCTAGTCCGTTATCAACTTGAAAAAGTGGCACCGAGTCGGTGCTTT (SEQ ID NO: 988) |
| Sp35-5' C → A | OLI8397 | AUUGUCAAGGCUAUUGGUCAGUUUUAGAGCUAGAAAUAGCAAGUUAAAAUAAGGCUAGUCCGUUAUCAACUUGAAAAAGUGGCACCGAGUCGGUGCUUUU (SEQ ID NO: 979) | ATTGTCAAGGCTATTGGTCAGTTTTAGAGCTAGAAATAGCAAGTTAAAATAAGGCTAGTCCGTTATCAACTTGAAAAAGTGGCACCGAGTCGGTGCTTTT (SEQ ID NO: 989) |

*:Represents phosphorothioate modification.
m:Represents, 2-o-methyl modification.

Figure 17:
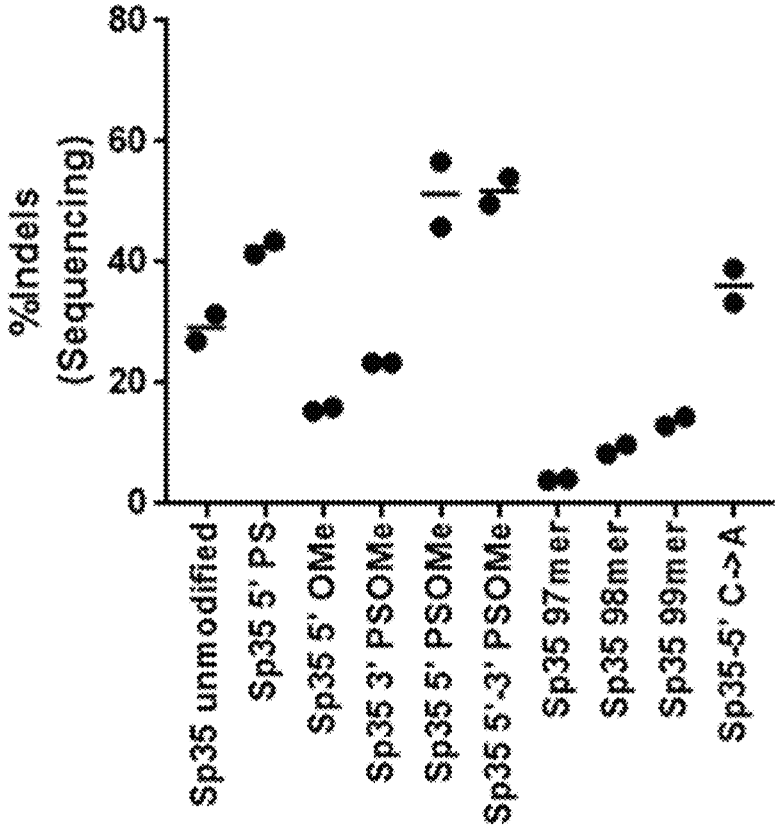
FIG. 17 depicts gene editing of the HBG promoter in adult human $CD34^+$ cells from mPB electroporated with Cas9 complexed with Sp35 gRNA (SEQ ID NO:970) and modified Sp35 gRNAs as disclosed in Table 10. The percentage of indels at the HBG promoter was determined by sequencing the HBG PCR product amplified from gDNA extracted post-electroporation with RNP.

Next, Cas9 RNP were complexed with Sp35 gRNA or modified Sp35 guide RNAs (Table 10) and 7.27 μM RNP were electroporated to human adult $CD34^+$ cells from mobilized peripheral blood (mPB). Sequence analysis of the HBG PCR product amplified from gDNA extracted post-electroporation was performed. Increased editing was observed with Sp35 guide RNAs containing 5' and 5'+3' modifications, as well as with the C-to-A substitution when compared to the unmodified Sp35 guide RNA (FIG. 17).

Example 10: Co-Delivery of Cas9 RNP Containing Chemically Synthesized Guide RNA Targeting the 13 nt Deletion Mutation with ssODN Donors Supports Precise Gene Editing in Human Hematopoietic Stem/Progenitor Cells and Increased Gamma-Globin Expression in the Erythroid Progeny To increase gene editing and the occurrence of the 13 nt deletion at the target site, single strand deoxynucleotide donor repair templates (ssODN) that encoded 90 nucleotides of homology on each side of the targeted deletion site were generated. The ssODNs were modified to contain phosphorothioates (PhTx) at the 5' and 3' ends (i.e., OLI16414 (SEQ ID NO:990), OLI16412 (SEQ ID NO:993), respectively, Table 11). The ssODNs were designed to "encode" the 13 nt deletion with sequence homology arms flanking this absent sequence to create a perfect deletion.

TABLE 11

Single strand deoxynucleotide donor repair templates used in combination with OLI7066-sp35-RNP

| Name | Oli-ID | SEQ ID NO | Sequence |
|---|---|---|---|
| PhTx ssODN 13nt-Positive strand | OLI16414 | 990 | **A*AGGGTGCTTCCTTTTATTCTTCATCCCTAGCCAGCCGCCGGCCCCTGGCCTCACTGGATACTCTAAGACTATTGGTCAAGTTTGCCTTG**TCAAGGCAAGGCTGGCCAACCCATGGGTGGAGTTTAGCCAGGGACCGTTTCAGACAGATATTTGCATTGAGATAGTGTGGGGAAGGGGC*C |
| 5' homology arm: PhTx ssODN 13nt-Positive strand | 5' homology arm OLI16414 | 991 | **A*AGGGTGCTTCCTTTTATTCTTCATCCCTAGCCAGCCGCCGGCCCCTGGCCTCACTGGATACTCTAAGACTATTGGTCAAGTTTGCCTTG** |
| 3' homology arm: PhTx ssODN 13nt-Positive strand | 3' homology arm OLI16414 | 992 | TCAAGGCAAGGCTGGCCAACCCATGGGTGGAGTTTAGCCAGGGACCGTTTCAGACAGATATTTGCATTGAGATAGTGTGGGGAAGGGGC*C |
| PhTx ssODN 13nt-Negative strand | OLI16412 | 993 | **G*GCCCCTTCCCCACACTATCTCAATGCAAATATCTGTCTGAAACGGTCCCTGGCTAAACTCCACCCATGGGTTGGCCAGCCTTGCCTTGA**CAAGGCAAACTTGACCAATAGTCTTAGAGTATCCAGTGAGGCCAGGGGCCGGCGGCTGGCTAGGGATGAAGAATAAAAGGAAGCACCCT*T |
| 5' homology arm: PhTx ssODN 13nt-Negative strand | 5' homology arm OLI16412 | 994 | **G*GCCCCTTCCCCACACTATCTCAATGCAAATATCTGTCTGAAACGGTCCCTGGCTAAACTCCACCCATGGGTTGGCCAGCCTTGCCTTGA** |
| 3' homology arm: PhTx ssODN 13nt-Negative strand | 3' homology arm OLI16412 | 995 | CAAGGCAAACTTGACCAATAGTCTTAGAGTATCCAGTGAGGCCAGGGGCCGGCGGCTGGCTAGGGATGAAGAATAAAAGGAAGCACCCT*T |

The homology arms flanking the deletion are indicated by bold [5' homology arm] and underline [3' homology arm]).
Note
the absence of the 13 bp sequence in OLI16414 and OLI16412.
*:Represents phosphorothioate modification.

OLI16414 (SEQ ID NO:990) and OLI16412 (SEQ ID NO:993) were co-delivered with RNP targeting HBG containing the chemically synthesized Sp35 gRNA (SEQ ID NO:970) ("OL17066-sp35-RNP") to human adult $CD34^+$ cells from mobilized peripheral blood (mPB). Briefly, mPB $CD34^+$ cells were prestimulated for 2 days with human cytokines in X-Vivo-10 and then electroporated with a mixture composed of an ssODN donor and Cas9 protein precomplexed to Sp35 (OL17066-sp35-RNP). Co-delivery of 2.5 μM of the ssODN donor encoding the 13 nt deletion as a positive strand donor (OLI16414 (SEQ ID NO:990)) or negative strand donor (OLI16412 (SEQ ID NO:993)) with 2 M of OL17066-sp35-RNP enhanced the editing frequency from 48.7% (without ssODN donor) to 60.11% and 70.7% respectively, as determined by sequencing analysis of the HBG PCR product from genomic DNA extracted at 72 hours post-electroporation (FIG. 18A).

Figure 18A:
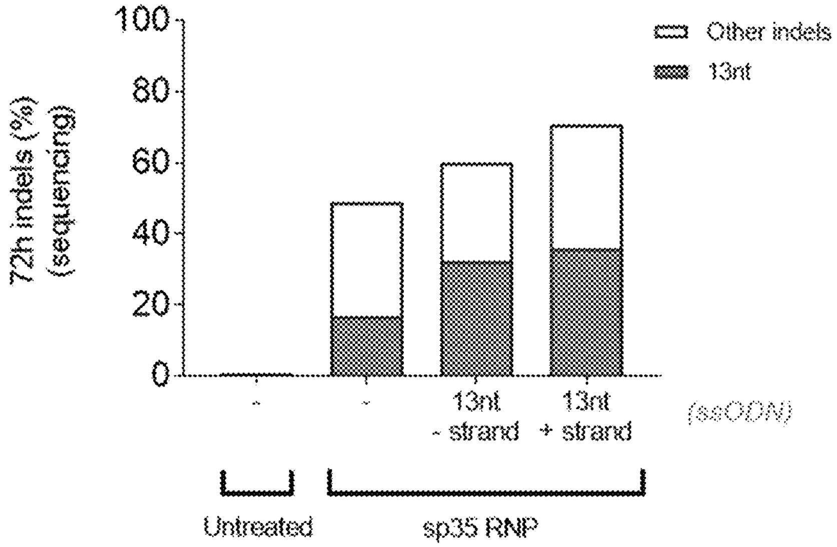
FIGS. 18A-C depict gene editing of the HBG promoter in and viability of adult human $CD34^+$ cells from mPB electroporated with ssODN "13 nt−strand" (i.e., OLI16412 (ssODN encoding the 13 nt deletion, negative (−) strand) or "13 nt+strand" (i.e., OLI16414 (ssODN encoding the 13 nt deletion, positive (+) strand) (Table 11) and RNP targeting HBG containing Sp35 gRNA (SEQ ID NO:970) (OLI7066-sp3S-RNP).
Figure 18B:
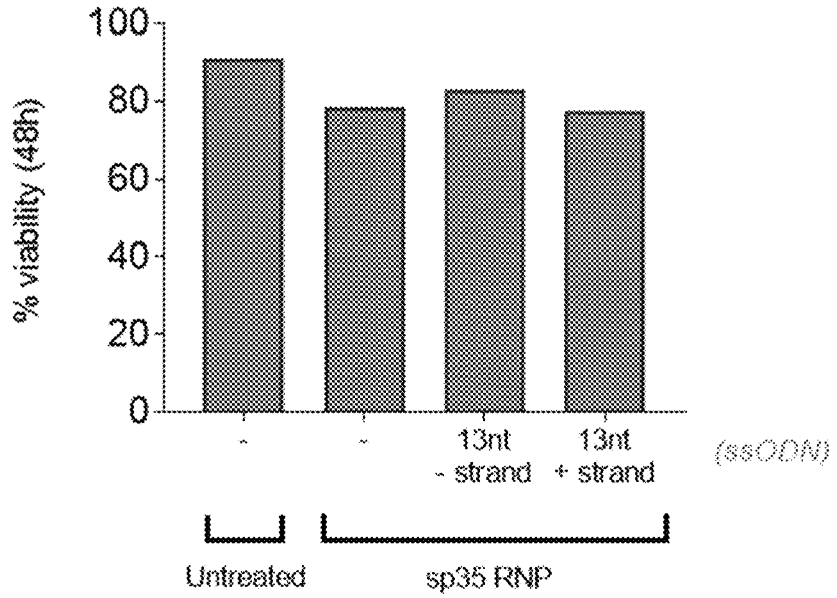

Further analysis of the specific type and size of deletions at the target site revealed that 32.6% and 36.0% of the alleles carried the precise 13 nt deletion when OL17066-sp35-RNP was co-delivered with the 13 nt positive strand donor (OLI16414 (SEQ ID NO:990)) and the 13 nt negative strand donor (OLI16412 (SEQ ID NO:993)), respectively, instead of 16.9% when OLI7066-sp35-RNP was delivered alone (FIG. 18A). No reduction in viability of CD34 cells at 48 hours post electroporation was observed when OL17066-sp35-RNP was co-delivered with the ssODNs (FIG. 18B).

Figure 18C:
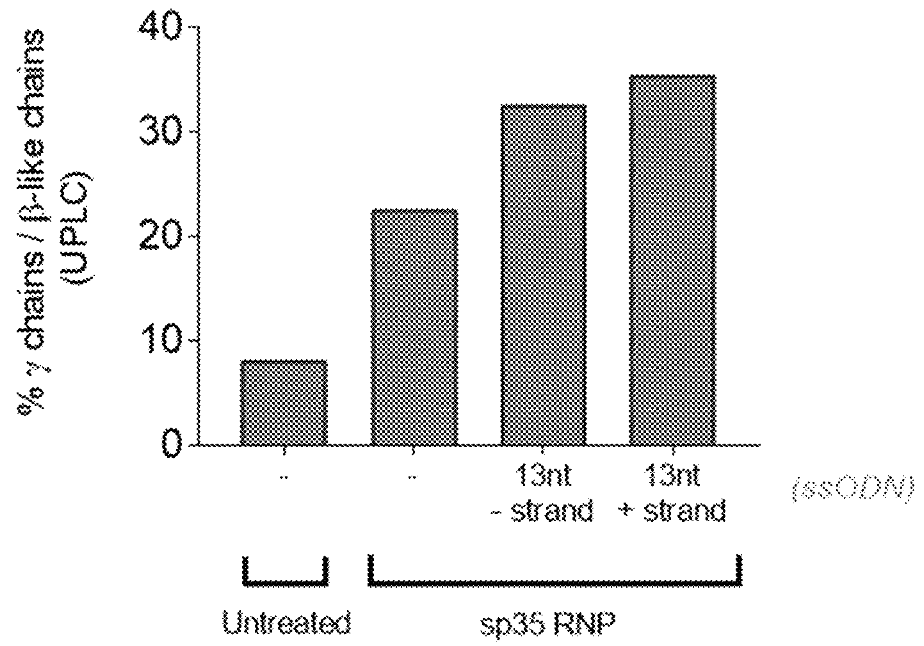

To determine whether co-delivering OL17066-sp35-RNP with ssODNs "encoding" the 13 nt deletion increased the production of fetal hemoglobin in the erythroid progeny of edited adult CD34 cells, the cells were differentiated into erythroblasts by culture for 18 days in the presence of human cytokines (erythropoietin, SCF, IL3), human plasma (Octoplas), and other supplements (hydrocortisone, heparin, transferrin, insulin). At day 18, the relative expression levels of gamma-globin chains over total beta-like globin chains (gamma chains/[gamma chains+beta chain]) was increased from 8.1% in the untreated sample to 22.6%, 32.6% and 35.4% when the CD34 cells were initially electroporated with OL17066-sp3S-RNP alone, OL17066-sp35-RNP in combination with the negative strand ssODN donor (OL116412 (SEQ ID NO:993)), and OL17066-sp35-RNP in combination with the positive strand ssODN donor (OLI16414 (SEQ ID NO:990)), respectively, as determined by ultra-performance liquid chromatography (UPLC) analysis of the cell lysates (FIG. 18C). These results demonstrate that co-delivery of a chemically synthesized guide RNA targeting the HBG distal CAAT-box with a homologous ssODN that is engineered to have a deletion supported precise gene editing (deletion) at HBG in human mPB+ CD34 cells, resulting in increased level of HBG expression.

SEQUENCES

Genome editing system components according to the present disclosure (including without limitation, RNA-guided nucleases, guide RNAs, donor template nucleic acids, nucleic acids encoding nucleases or guide RNAs, and portions or fragments of any of the foregoing), are exemplified by the nucleotide and amino acid sequences presented in the Sequence Listing. The sequences presented in the Sequence Listing are not intended to be limiting, but rather illustrative of certain principles of genome editing systems and their component parts, which, in combination with the instant disclosure, will inform those of skill in the art about additional implementations and modifications that are within the scope of this disclosure. A list of the sequences presented is provided in the following Table 12.

TABLE 12

Sequences presented in the Sequence Listing:

| SEQ ID NOS: | DESCRIPTION |
|---|---|
| 1-2, 4-6, 12, 14 | Cas9 polypeptides |
| 3, 7-11, 13 | Cas9 coding sequences |
| 15-23, 52-123 | Cas9 RuvC-like domains |
| 24-28, 124-198 | Cas9 HNH-like domains |
| 29-31, 38-51 | Full-length modular and unimolecular gRNAs |
| 32-37 | gRNA proximal and tail domains |
| 199-205 | PAM sequences |
| 251-901, 940-942, 952-955 | gRNA targeting domains (RNA)- see Tables 2, 7, 9 |
| 910-919, 943-945, 956-959 | gRNA targeting domains (DNA)- see Tables 7, 9 |
| 920-929, 946-948, 960-963 | gRNA targeting domains plus PAM (NGG) (RNA) - see Tables 7, 9 |
| 930-939, 949-951, 964-967 | gRNA targeting domains plus PAM (NGG) (DNA) - see Tables 7, 9 |
| 970-979 | Sp35 gRNA sequences (RNA)- see Table 10 |
| 980-989 | Sp35 gRNA sequences (DNA)- see Table 10 |
| 902, 903 | Human HBG1 and HBG2 promoter sequences including HPFH deletion site |
| 904-909, 990-995 | Oligonucleotide donor sequences and homology arms - see Tables 8, 11 |
| 968-969 | BCL11Ae sequences |

INCORPORATION BY REFERENCE

All publications, patents, and patent applications mentioned herein are hereby incorporated by reference in their entirety as if each individual publication, patent or patent application was specifically and individually indicated to be incorporated by reference. In case of conflict, the present application, including any definitions herein, will control.

EQUIVALENTS

Those skilled in the art will recognize, or be able to ascertain using no more than routine experimentation, many equivalents to the specific embodiments described herein. Such equivalents are intended to be encompassed by the following claims.

REFERENCES

Ahern et al., Br J Haematol 25(4):437-444 (1973)
Akinbami Hemoglobin 40:64-65 (2016)
Aliyu et al. Am J Hematol 83:63-70 (2008)
Anders et al. Nature 513(7519):569-573 (2014)
Angastiniotis & Modell Ann N Y Acad Sci 850:251-269 (1998)
Bae et al. Bioinformatics 30(10):1473-1475 (2014)
Barbosa et al. Braz J Med Bio Res 43(8):705-711 (2010)
Bouva Hematologica 91(1): 129-132 (2006)
Briner et al. Mol Cell 56(2):333-339 (2014)
Brousseau Am J Hematol 85(1):77-78 (2010)
Caldecott Nat Rev Genet 9(8):619-631 (2008)
Canvers et al. Nature 527(12): 192-197 (2015)
Chang et al. Mol Ther Methods Clin Dev 4:137-148 (2017)
Chassanidis Ann Hematol 88(6):549-555 (2009)
Chylinski et al. RNA Biol 10(5):726-737 (2013)
Cong et al. Science 399(6121):819-823 (2013)
Costa et al., Cad Saude Publica 18(5): 1469-1471 (2002)
Davis & Maizels 2 Proc Natl Acad Sci USA 111(10):E924-932 (2014)
Fine et al. Sci Rep. 5:10777 (2015)
Frit et al. DNA Repair (Amst) 17:81-97 (2014)
Fu et al. Nat Biotechnol 32(3):279-284 (2014)
Guilinger et al. Nat Biotechnol 32:577-582 (2014)
Heigwer et al. Nat Methods 11(2): 122-123 (2014)
Hsu et al. Nat Biotechnol 31(9):827-832 (2013)

Iyama & Wilson DNA Repair (Amst) 12(8):620-636 (2013)
Jiang et al. Nat Biotechnol 31(3):233-239 (2013)
Jinek et al. Science 337(6096):816-821 (2012)
Jinek et al. Science 343(6176): 1247997 (2014)
Kleinstiver et al. Nature 523(7561):481-485 (2015a)
Kleinstiver et al. Nat Biotechnol 33(12): 1293-1298 (2015b)
Kleinstiver et al. Nature 529(7587):490-495 (2016)
Komor et al. Nature 533(7603):420-424 (2016)
Lee et al. Nano Lett 12(12):6322-6327 (2012)
Lewis "Medical-Surgical Nursing: Assessment and Management of Clinical Problems" (2014)
Li Cell Res 18(1):85-98 (2008)
Maeder et al. Int'l Patent Publication No. WO 2015/138510 (2015)
Makarova et al. Nat Rev Microbiol 9(6):467-477 (2011)
Mali et al. Science 339(6121):823-826 (2013)
Mantovani et al. Nucleic Acids Res 16(16):7783-7797 (1988)
Marteijn et al. Nat Rev Mol Cell Biol 15(7):465-481 (2014)
Nishimasu et al. Cell 156(5):935-949 (2014)
Nishimasu et al. Cell 162(5): 1113-1126 (2015)
Ran & Hsu et al. Cell 154(6):1380-1389 (2013)
Richardson et al. Nat Biotechnol 34:339-344 (2016)
Shmakov et al. Molecular Cell 60(3):385-397 (2015)
Steinberg et al. Nature 507(7490):62-67 (2014)
Superti-Furga et al. EMBO J 7(10):3099-3107 (1988)
Thein Hum Mol Genet 18(R2):R216-223 (2009)
Tsai et al. Nat Biotechnol 34(5):483 (2016)
Waber et al. Blood 67(2):551-554 (1986)
Wang et al. Cell 153(4):910-918 (2013)
Xiao et al. Bioinformatics 30(8): 1180-1182 (2014)
Xu et al. Genes Dev 24(8):783-798 (2010)
Yamano et al. Cell 165(4): 949-962 (2016)
Zetsche et al. Cell 163(3):759-771 (2015a)
Zetsche et al. Nat Biotechnol 33(2): 139-42 (2015b)

The invention claimed is:

1. A genome editing system, comprising:

an RNA-guided nuclease;

a first guide RNA;

a second guide RNA, and a nucleic acid template encoding a deletion of a 13 nt region of a human HBG1 or HBG2 gene, wherein the first and second guide RNAs comprise first and second targeting domains complementary to first and second sequences on opposite sides of positions of the 13 nt target region of a human HBG1 or HBG2 gene, wherein one or both of the first and second sequences optionally overlaps the 13 nt target region of the human HBG1 or HBG2 gene, and wherein at least one of the first and second targeting domains differs by no more than 3 nucleotides from a targeting domain selected from the group consisting of SEQ ID NOs: 277, 338, 327, 299, 276, 333, 278, 339, 310, 340, 940, 941, and 942.

2. The genome editing system of claim 1, wherein the RNA-guided nuclease is an *S. pyogenes* Cas9.

3. The genome editing system of claim 1, wherein the first and second targeting domains are complementary to sequences immediately adjacent to a protospacer adjacent motif recognized by *S. pyogenes* Cas9.

4. The genome editing system of claim 3, wherein the RNA-guided nuclease is a nickase, and optionally lacks RuvC activity.

5. The genome editing system of claim 1, comprising first and second RNA-guided nucleases.

6. The genome editing system of claim 5, wherein the first and second RNA-guided nucleases are complexed with the first and second guide RNAs, respectively, forming first and second ribonucleoprotein complexes.

7. A method of altering a cell, comprising contacting a cell with the genome editing system of claim 1.

8. The method of claim 7, wherein the step of contacting the cell with the genome editing system comprises contacting the cell with a solution comprising first and second ribonucleoprotein complexes.

9. The method of claim 8, wherein the step of contacting the cell with the solution further comprises electroporating the cells, thereby introducing the first and second ribonucleoprotein complexes into the cell.

10. The method of claim 7, wherein the cell is capable of differentiating into an erythroblast or a precursor of an erythroblast.

11. The method of claim 7, wherein the cell is capable of differentiating into an erythrocyte or a precursor of an erythrocyte.

12. The method of claim 7, wherein the cell is a CD34+ cell.

* * * * *